US008444975B2

(12) United States Patent
Sooknanan et al.

(10) Patent No.: US 8,444,975 B2
(45) Date of Patent: May 21, 2013

(54) METHOD FOR INHIBITING BONE RESORPTION

(75) Inventors: Roy Rabindranauth Sooknanan, Beaconsfield (CA); Gilles Bernard Tremblay, La Prairie (CA); Mario Filion, Longueuil (CA)

(73) Assignee: Alethia Biotherapeutics Inc., Montreal, Quebec (CA)

( * ) Notice: Subject to any disclaimer, the term of this patent is extended or adjusted under 35 U.S.C. 154(b) by 0 days.

(21) Appl. No.: 13/478,556

(22) Filed: May 23, 2012

(65) Prior Publication Data

US 2012/0308561 A1 Dec. 6, 2012

Related U.S. Application Data

(62) Division of application No. 13/082,107, filed on Apr. 7, 2011, now abandoned, which is a division of application No. 11/792,932, filed as application No. PCT/CA2005/001917 on Dec. 13, 2005, now Pat. No. 7,947,436.

(60) Provisional application No. 60/634,981, filed on Dec. 13, 2004.

(51) Int. Cl.
*A61K 39/00* (2006.01)
*A61K 39/395* (2006.01)

(52) U.S. Cl.
USPC .................. 424/130.1; 424/133.1; 424/134.1; 424/135.1; 424/139.1; 424/141.1; 424/142.1

(58) Field of Classification Search ....................... None
See application file for complete search history.

(56) References Cited

U.S. PATENT DOCUMENTS

| | | | | |
|---|---|---|---|---|
| 5,742,127 | A | 4/1998 | Ahn | |
| 5,968,782 | A | 10/1999 | Stevens | |
| 5,981,830 | A | 11/1999 | Wu | |
| 6,203,979 | B1 | 3/2001 | Bandman | |
| 6,420,157 | B1 | 7/2002 | Darrow | |
| 6,426,199 | B1 | 7/2002 | Darrow | |
| 6,451,555 | B1 * | 9/2002 | Duffy | 435/69.1 |
| 6,458,564 | B1 | 10/2002 | Darrow | |
| 6,479,274 | B1 | 11/2002 | Antalis | |
| 6,482,630 | B2 | 11/2002 | Gan | |
| 6,485,957 | B1 | 11/2002 | Darrow | |
| 6,498,024 | B1 | 12/2002 | Malek et al. | |
| 6,514,741 | B1 | 2/2003 | Presnell | |
| 6,617,434 | B1 | 9/2003 | Duffy | |
| 6,649,741 | B1 | 11/2003 | O'Brien et al. | |
| 6,747,134 | B2 | 6/2004 | Darrow et al. | |
| 6,977,170 | B2 | 12/2005 | Chan | |
| 7,022,821 | B1 | 4/2006 | O'Brien et al. | |
| 7,045,603 | B2 | 5/2006 | Goddard et al. | |
| 7,049,420 | B2 | 5/2006 | Xiao | |
| 7,060,810 | B2 | 6/2006 | Xiao | |
| 7,211,425 | B2 | 5/2007 | Uemura | |
| 7,250,262 | B2 | 7/2007 | Carroll et al. | |
| 7,355,015 | B1 | 4/2008 | Dickson et al. | |
| 7,368,531 | B2 | 5/2008 | Rosen et al. | |
| 2002/0045230 | A1 | 4/2002 | Rosen et al. | |
| 2002/0090673 | A1 | 7/2002 | Rosen et al. | |
| 2003/0003530 | A1 | 1/2003 | Ashkenazi | |
| 2003/0027144 | A1 | 2/2003 | Underwood | |
| 2003/0036061 | A1 | 2/2003 | Ashkenazi | |
| 2003/0049645 | A1 | 3/2003 | Mu | |
| 2003/0068636 | A1 | 4/2003 | Veiby | |
| 2003/0077647 | A1 | 4/2003 | Weich | |
| 2003/0077808 | A1 | 4/2003 | Rosen et al. | |
| 2003/0096340 | A1 | 5/2003 | Ashkenazi | |
| 2003/0108963 | A1 | 6/2003 | Schlegel et al. | |
| 2003/0119168 | A1 | 6/2003 | Madison et al. | |
| 2003/0124706 | A1 | 7/2003 | Yang | |
| 2003/0186297 | A1 | 10/2003 | Choi | |
| 2003/0202971 | A1 | 10/2003 | Majumder | |
| 2003/0207348 | A1 * | 11/2003 | Shimkets et al. | 435/69.1 |
| 2004/0001801 | A1 | 1/2004 | Madison | |
| 2004/0009491 | A1 | 1/2004 | Birse | |
| 2004/0043930 | A1 | 3/2004 | Anderson | |
| 2004/0048255 | A1 | 3/2004 | Chan | |
| 2004/0126777 | A1 | 7/2004 | Bhatt | |
| 2004/0132156 | A1 | 7/2004 | Parry et al. | |

(Continued)

FOREIGN PATENT DOCUMENTS

| | | | |
|---|---|---|---|
| EP | 1087230 | A1 | 3/2001 |
| EP | 1132477 | | 9/2001 |

(Continued)

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Agrawal, et al. "RNA interference: biology, mechanism, and applications," Microbiol. Mol. Biol. Rev. 67(4): 657-685 (2003).
Albrecht, et al. "Structural Modeling of Ataxin-3 Reveals Distant Homology to Adaptins," Proteins 50(2):355-370 (2003).
Awaida, et al., "Jun Dimerization Protein 2 (JDP2), a member of the AP-i family of transcription factor, mediates osteoclast differentiation induced by RANKL" J. Exp. Med. 197(8): 1029-1035 (2003).

(Continued)

*Primary Examiner* — Elizabeth C Kemmerer
(74) *Attorney, Agent, or Firm* — Choate, Hall & Stewart LLP; Fangli Chen; Robert N. Sahr

(57) ABSTRACT

This invention relates, in part, to unique and newly identified genetic polynucleotides involved in the process of bone remodeling; variants and derivatives of the polynucleotides and corresponding polypeptides; uses of the polynucleotides, polypeptides, variants and derivatives; and methods and compositions for the amelioration of symptoms caused by bone remodeling disorders. Disclosed in particular are, the isolation and identification of polynucleotides, polypeptides, variants and derivatives involved in osteoclast activity, validation of the identified polynucleotides for their potential as therapeutic targets and use of the polynucleotides, polypeptides, variants and derivatives for the amelioration of disease states and research purposes.

16 Claims, 85 Drawing Sheets

U.S. PATENT DOCUMENTS

| | | | |
|---|---|---|---|
| 2004/0137623 A1 | 7/2004 | Baker et al. |
| 2004/0146907 A1 | 7/2004 | Smith |
| 2004/0253606 A1 | 12/2004 | Aziz et al. |
| 2005/0026169 A1 | 2/2005 | Cargill |
| 2005/0153305 A1 | 7/2005 | Vernet et al. |
| 2005/0153333 A1 | 7/2005 | Sooknanan |
| 2005/0176030 A1 | 8/2005 | Gan |
| 2005/0181375 A1 | 8/2005 | Aziz et al. |
| 2005/0214795 A1 | 9/2005 | Hillman et al. |
| 2005/0255114 A1 | 11/2005 | Labat |
| 2005/0272054 A1 | 12/2005 | Cargill |
| 2005/0287546 A1 | 12/2005 | Plowman |
| 2006/0046257 A1 | 3/2006 | Pollock et al. |
| 2006/0084054 A1 | 4/2006 | Alsobrook et al. |
| 2006/0084066 A1 | 4/2006 | Sah |
| 2006/0084120 A1 | 4/2006 | Kirchhofer et al. |
| 2006/0154293 A1 | 7/2006 | Xiao |
| 2006/0177875 A1 | 8/2006 | Hunt et al. |
| 2006/0188903 A1 | 8/2006 | Rancourt |
| 2006/0210570 A1 | 9/2006 | Fan et al. |
| 2007/0015145 A1 | 1/2007 | Woolf et al. |
| 2007/0042945 A1 | 2/2007 | Bodary |
| 2007/0048818 A1 | 3/2007 | Rosen et al. |
| 2007/0087004 A1 | 4/2007 | Papkoff et al. |
| 2007/0093443 A1 | 4/2007 | Madison |
| 2007/0099251 A1 | 5/2007 | Zhang et al. |
| 2007/0104647 A1 | 5/2007 | Pilkington et al. |
| 2007/0141652 A1 | 6/2007 | Zheng et al. |
| 2007/0166756 A1 | 7/2007 | Shimkets et al. |
| 2007/0224201 A1 | 9/2007 | Wu |
| 2007/0253949 A1 | 11/2007 | Golz et al. |
| 2007/0298491 A1 | 12/2007 | Rosen et al. |
| 2008/0051559 A1 | 2/2008 | Craik et al. |
| 2008/0152663 A1 | 6/2008 | Cannon |

FOREIGN PATENT DOCUMENTS

| | | |
|---|---|---|
| EP | 1792912 | 4/2006 |
| EP | 1790725 A2 | 5/2007 |
| JP | 2003/334094 A | 11/2003 |
| WO | WO9914328 | 3/1999 |
| WO | WO0018238 A1 | 4/2000 |
| WO | WO0029448 | 5/2000 |
| WO | WO0037640 | 6/2000 |
| WO | WO0105971 A2 | 1/2001 |
| WO | WO0112788 | 2/2001 |
| WO | WO0116293 A2 | 3/2001 |
| WO | WO0123547 A1 | 4/2001 |
| WO | WO0136440 A1 | 5/2001 |
| WO | WO0136645 A2 | 5/2001 |
| WO | WO0146443 | 6/2001 |
| WO | WO0166747 A2 | 9/2001 |
| WO | WO0198467 A2 | 12/2001 |
| WO | WO0198470 A2 | 12/2001 |
| WO | WO0198503 | 12/2001 |
| WO | WO02/27502 | 4/2002 |
| WO | WO0246408 A2 | 6/2002 |
| WO | WO02055704 | 7/2002 |
| WO | WO02059315 A2 | 8/2002 |
| WO | WO02064839 | 8/2002 |
| WO | WO02068647 | 9/2002 |
| WO | WO02081665 A2 | 10/2002 |
| WO | WO02095007 | 11/2002 |
| WO | WO02098917 A2 | 12/2002 |
| WO | WO03063688 | 8/2003 |
| WO | WO2004009803 | 1/2004 |
| WO | WO2004023973 | 3/2004 |
| WO | WO2004033636 | 4/2004 |
| WO | WO2004053068 | 6/2004 |
| WO | WO2004/076639 A2 | 9/2004 |
| WO | WO2004086035 A1 | 10/2004 |
| WO | WO2004093804 | 11/2004 |
| WO | WO2004106536 A2 | 12/2004 |
| WO | WO2004/076639 A3 | 5/2005 |
| WO | WO2005083125 | 9/2005 |
| WO | WO2005005647 A2 | 12/2005 |
| WO | WO2005119262 | 12/2005 |
| WO | WO2006013015 A2 | 2/2006 |
| WO | WO2006013016 A3 | 2/2006 |
| WO | WO2006131783 A2 | 12/2006 |
| WO | WO2007073478 | 6/2007 |
| WO | WO2007140907 A1 | 12/2007 |
| WO | WO2007149932 A2 | 12/2007 |
| WO | WO2007149935 A2 | 12/2007 |
| WO | WO 2008/016356 * | 2/2008 |
| WO | WO2008/016356 A2 | 2/2008 |
| WO | WO2008021290 A2 | 2/2008 |

OTHER PUBLICATIONS

Baron, "Anatomy and biology of bone matrix and cellular elements," Primer on the Metabolic Bone Diseases and Disorders of Mineral Metabolism, American Society for Bone and Mineral Research, Fifth Edition: 1-8 (2003).

Boyle, et al., "Osteoclast Differentiation and Activation," Nature 423 (6937):337-342 (2003).

Brummelkamp et al. "A System for stable expression of short interfering RNAs in mammalian cells," Science 296(5567); 550-553 (2002).

De Vernejoul, "Dynamics of bone remodeling: Biochemical and pathophysiological basis" Eur J Clin Chem Clin Biochem 34: 729-734 (1996).

Elbashir, et al. "Duplexes of 21-nucleotide RNAsmediate RNA interference in cultured mammalian cells," Nature 411(6836): 494-498 (2001).

Frost, "Dymanics of Bone Remodeling," Bone Biodynamics: 315-333 (1964).

Gee, et al., "Potential therapeutic usefulness of intermolecular triplex DNA" In: Huber BE, Cancer Therapy in the Twenty-First Century, vol. I: Molecular and Immunologic Approaches: 163-177 (1994).

Hannon, "RNA interference," Nature 418(6894): 244-251 (2002).

Hirotani, Hiroaki et al., "The Calcineurin/Nuclear Factor of Activated T Cells Signaling Pathway Regulates Osteoclastogenesis in RAW264,7 Cells," The Journal of Biological Chemistry, vol. 279, No. 14:13984-13992 (2004).

International Search Report for PCT/CA2005/001917, Dec. 13, 2005.

Ishida, et al.,"Large Scale Gene Expression Analysis of Osteoclastogenesis in Vitro and Elucidation of NFAT2 as a Key Regulator," J. Biol. Chem. 277(43):41147-41156 (2002).

Janssen, et al., "LAB: a new membrane-associated adaptor molecule in B cell activation," Nat Immunol 4(2): 117-123 (2003).

Jilka et al., "Increased Osteoclast Development After Estrogen Loss: Mediation by Interleukin-6," Science 257: 88-91 (1992).

Kawai, et al., "Functional annotation of a full-length mouse cDNA collection," Nature 409(6821): 685-690 (2001).

Kawaida, et al., "Jun Dimerization Protein 2 (JDP2), a Member of the AP-1 Family of Transcription Factor," Mediates Osteoclast Differentiation Induced by RANKL, J. Exp. Med. 197(8):1029-1035 (2003).

Ko, M.S.H., et al., "Large-Scale cDNA Analysis Reveals Phased Gene Expression Patterns During Preimplantation Mouse Development," Development, vol. 127: 1737-1749, (2000).

Kobori, Masato, "Large scale gene analysis using subtracted cDNA library and mechanisms of osteoclast function," Experimental Medicine 13: 46-52 (1995).

Kobori, Masato, "Large scale isolation of osteoclast-specific genes by an improved method involving the preparation of a subtracted cDNA library," Genes to Cells, vol. 3: 459-475 (1998).

Lee, et al., "Stable gene silencing in human monocytic cell lines using lentiviral-delivered small interference RNA. Silencing of the p110a isoform of phosphoinositide 3-kinase reveals differential regulation of adherence induced by 1a,25-dihydroxycholecalciferol and bacterial lipopolysaccharide," J. Biol Chem 279(10): 9379-9388 (2004).

Morello, et al., "cDNA cloning, characterization and chromosome mapping of Crtap encoding the mouse cartilage associated protein," Matrix Biology 18(3): 319-324 (1999).

Netzel-Arnett et al. "Membrane anchored serine proteases: A rapidly expanding group of cell surface proteolytic enzymes with potential roles in cancer," Cancer Metastasis Reviews 22(2-3): 237-258 (2003).

Nishi, T., et al. "Expression and Function of the Mouse V-ATPased Subunit isoforme," The Journal of Biological Chemistry, vol. 278(47): 46396-46402, (2003).
Nishi, T., et al. "The Vacuolar (H+)-Atpases-Nature's Most Versatile Proton Pumps," Nature Reviews, vol. 3: 94-102, (2002).
Nomura, et al., Prediction of the Coding Sequences of Unidentified Human Genes. II. The Coding Sequences of 40 New Genes (KIAA0041-KIAA0080) . . . DNA Res 1:251-262 (1994).
Nomura, et al., "Prediction of the Coding Sequences of Unidentified Human Genes. I. The Coding Sequences of 40 New Genes (KIAA0001-KIAA0040)," DNA Research 1: 27-35 (1994).
Poli, et al. "Interleukin-6 deficient mice are protected from bone loss caused by estrogen depletion" EMBO J. 13: 1189-1196 (1994).
Rubinson, et al. "A lentivirus-based system to functionally silence genes in primary mammalian cells, stem cells and transgenic mice by RNA interference" Nature Genetics 33(3): 401-406 (2003).
Shan et al. "TSP50, a possible protease in human testes, is activated in breast cancer epithelial cells" Cancer Research 62(1): 290-294 (2002).
Smith, A. N., et al. "Molecular Cloning and Characrerization fo Novel Tissue-Specific Isoforms of the Human Vacuolar H+-ATPase C, G and d Subunits, and Their Evaluation in Autosomal Recessive Distal Renal Tubular Acidosis," Gene, vol. 207: 169-177, (2002).
Smith, et al. "Mutations in ATP6N1B, encoding a new kidney vacuolar proton pump 116-kD subunit, cause recessive distal renal tubular acidosis with preserved hearing" Nature Genetics 26(1): 71-75 (2000).
Smith, et al. "Vacuolar H+-ATPase d2 subunit: molecular characterization, developmental regulation, and localization to specialized proton pumps in kidney and bone" J. Am. Soc. Nephrol 16(5): 1245-1256 (2005).
Sooknanan et al, "Identification of Osteoclast-Specific Genes Using Subtractive Transcription Amplification of mRNA (STAR)," J. Bone and Miner. Res. 19:S415 (2004).
Srivastava, et al. "Estrogen Blocks M-CSF Gene Expression and Osteoclast Formation by Regulating Phosphorylation of Egr-1 and Its Interaction with Sp-1," J. Clin. Invest. 102: 1850-1859 (1998).
Stehberger, et al. "Localization and regulation of the ATP6V0A4 (a4) vacuolar H+-ATPase subunit defective in an inherited form of distal renal tubular acidosis," J. Am. Soc. Nephrol 14(12): 3027-3038 (2003).
Strausberg, et al. "Generation and initial analysis of more than 15,000 full-length human and mouse cDNA sequences," Proc Natl Acad Sci U S A 99(26): 16899-16903 (2002).
The Riken Genome Exploration Research Group Phase II Team and the Fantom Consortium, "Functional Annotation of a Full-Length Mouse cDNA Collection," Nature, vol. 409: 685-690, (2001).
Tonachini, et al. "cDNA cloning, characterization and chromosome mapping of the gene encoding human cartilage associated protein (CRTAP)," Cytogenet Cell Genet 87(3-4): 191-194 (1999).
Tremblay et al. "Functional Validation of Osteoclast-Specific Genes in RAW264.7 Cells by RNA Interference," J. of Bone and Miner. Res. 19:S414 (2004).
Yuan, L., et al. "Isolation of a Novel Gene, *TSP50*, by a Hypomethylated DNA Fragment I Human Breast Cancer," Cancer Research, vol. 59: 3215-3221, (1999).

* cited by examiner

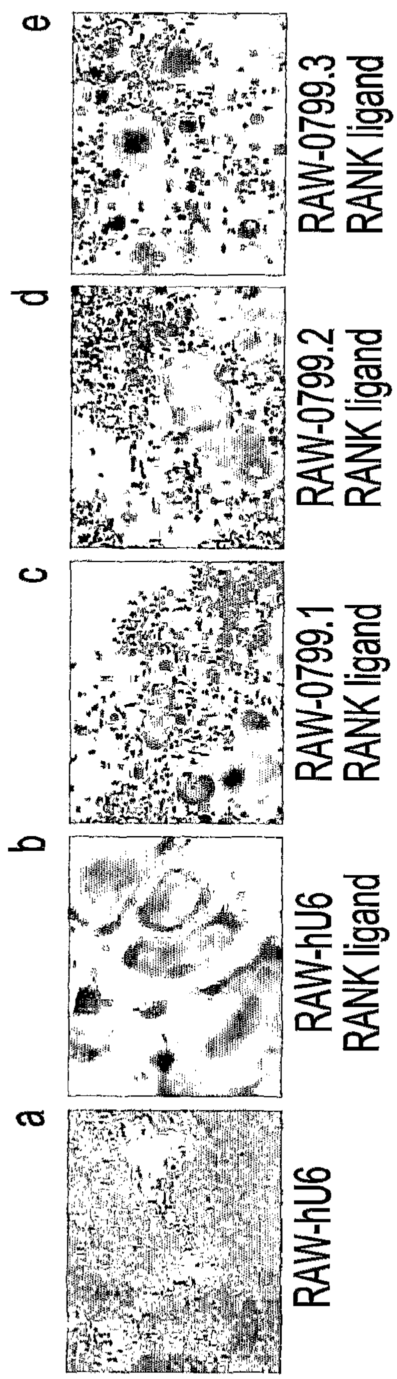
a
RAW-hU6
b
RAW-hU6
RANK ligand
c
RAW-0799.1
RANK ligand
d
RAW-0799.2
RANK ligand
e
RAW-0799.3
RANK ligand
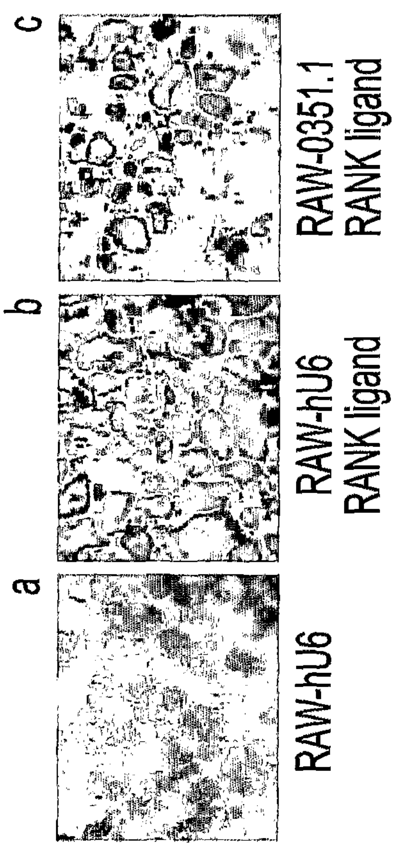
a
RAW-hU6
b
RAW-hU6
RANK ligand
c
RAW-0351.1
RANK ligand

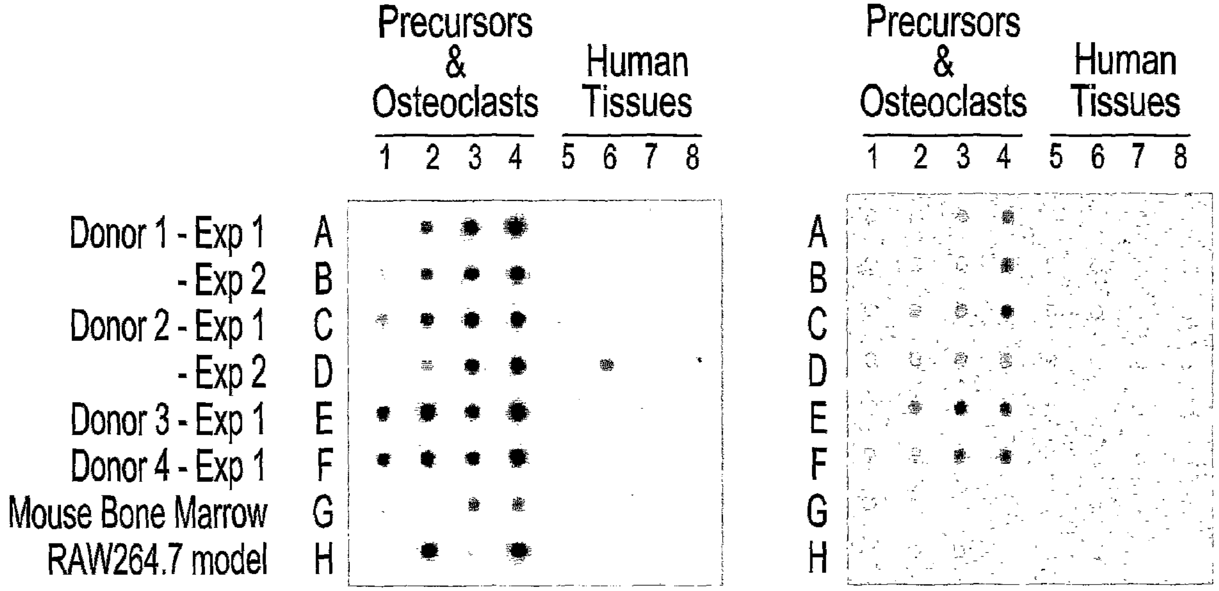

P - Precursor
OC - Osteoclast

SEQ. ID. NO. 2

SEQ. ID. NO. 4

| | | | | | | | |
|---|---|---|---|---|---|---|---|
| A1 - P | A2 - d3 OC | A3 - d7 OC | A4 - d13 OC | A5 - Adrenal | A6 - Breast | A7 - Jejunum | A8 - Trachea |
| B1 - P | B2 - d3 OC | B3 - d7 OC | B4 - d14 OC | B5 - Liver | B6 - Placenta | B7 - Aorta | B8 - Brain |
| C1 - P | C2 - d3 OC | C3 - d7 OC | C4 - d14 OC | C5 - Lung | C6 - Ad Cortex | C7 - Esophagus | C8 - Colon |
| D1 - P | D2 - d3 OC | D3 - d7 OC | D4 - d11 OC | D5 - Ovary | D6 - Kidney | D7 - Prostate | D8 - Thymus |
| E1 - P | E2 - d3 OC | E3 - d5 OC | E4 - d7 OC | E5 - Sk Muscle | E6 - Vena Cava | E7 - Stomach | E8 - Sm Intestine |
| F1 - P | F2 - d3 OC | F3 - d5 OC | F4 - d7 OC | F5 - Heart | F6 - Fa Tube | F7 - Spleen | F8 - Blader |
| G1 - P | G2 - d2 OC | G3 - d4 OC | G4 - d7 OC | G5 - Cervix | G6 - Pancreas | G7 - Ileum | G8 - Duodenum |
| H1 - P | H2 - d5 OC | H3 - P | H4 - d5 OC | H5 - Thyroid | H6 - Testicle | | |

FIG. 16A

M - DNA ladder
1 - Precursor CD34+ cells } Donor 1
2 - Osteoclasts
3 - Precursor CD34+ cells } Donor 4
4 - Osteoclasts
5 - Positive control (human breast cancer cell line - MDA231)

Control siRNA AB0440 siRNA

| Nucleotide Sequence (5'-3') | ORFs |
|---|---|
| SEQIDNO.:1<br><br>GATTGTGGAGGAACCTAGCGGCGCAATGGAGCCCTGGTGCGGGGCAGAGGTCCGTGGGCAGGGCCCTCAGGGTCCCCGTG<br>TGCCTGGGGCTTCCCGCTCCCGCTCCCGCGCCCTTCTCCTGCTGTTGCTGCTGCTGCTGCTCCTGCCTCGGCGGCCG<br>GCAGGTGAGCGCATCCGCCCCCGACGCCCTCCCCGGCACGCCCACCCGCGGCCACCTCTGACTCGCTGGAGACCTTCCAC<br>AGGCTACTTGGCCGCAGGAGCATCCCCGGGGACGCTGTCCACCACCGTCCCGACCGGACCCGGGGTCTCCTGTGGCTCCA<br>GAGGCATCTGTCCCTCAGGCAGGCTTCGCCTTCCTCGGCAAGCCCAGACTAACCAGACCACGACGGCTCCACCGAACTCA<br>CAGACCATGGCTCCACTGAAAACGGTGGGGACTCTCGGCATGATGGACACTACTGGGTCCGTTCTTAAGACGGTTCATTC<br>CAGCAACCTCCCCTTCTGTGGCTCCTCCCACGAGCCAGACCCTACTCTCAGGGACCCAGAAGCCATGACTCGGCGGTGGC<br>CCTGGATGGTCAGCGTGCAGGCTAATGGCTCACACATCTGTGCTGGCATCCTTATCGCTTCCCAGTGGGTGCTGACCGTG<br>GCCCATTGCTTGAGCCAGAACCATGTTAACTACATAGTGAGGGCGGGGAGCCCGTGGATTAATCAGACGGCAGGAACCAG<br>CTCAGATGTGCCGGTCCATCGAGTCATCATAAACCATGGCTACCAACCCAGACGGTACTGGTCATGGGTTGGCCGGGCCC<br>ATGACATCGGCCTTCTCAAGCTCAAGTGGGGGCTCAAGTACAGTAAATACGTGTGGCCCATCTGCCTGCCTGGCCTGGAT<br>TACGTGGTGGAGGACAGTTCTCTCTGCACTGTGACAGGCTGGGGATATCCCAGGGCTAACGGCATCTGGCCCCAGTTCCA<br>GTCCCTCCAGGAGAAGGAAGTCTCTATCCTGAACAGCAAGAAATGTGATCATTTCTACCACAAGTTCTCCAGAATCTCCT<br>CTCTGGTTCGGATCATCAACCCTCAGATGATCTGTGCCTCGGACAACAACAGGGAGGAGTTCTGCTATGAGATAACTGGC<br>GAGCCCCTGGTCTGCTCTTCAGATGGCACATGGTACCTGGTGGGAATGATGAGCTGGGGCCCAGGCTGCAAGAAGAGCGA<br>GGCCCCACCCATCTTTCTGCAGGTCTCCTACTACAGGCCCTGGATCTGGGACCGGCTCAGTGGGGAGCCCCTGGCCCTTC<br>CAGCCCCATCCAGGACCTTGCTCCTGGCTTTCCTTCTGCTCCTCATCCTTCTGGGCACACTGTGACACTGCCATGTCTCT<br>CCTTCCTTCCCCTCCTCCTAAGTGCTGCTGTGGGGGTGGCGCTCAGCCTGCCGGAGGCGGGGAGGAGCTAGCAGAGATTA<br>AACACTTCTTTTCCTC | SEQIDNO.:93<br><br>MEPWCGAEVRGQGPQGPRVPGAS<br>RSRSRALLLLLLLLLLLLPRRPA<br>GERIRPRRPPRHAHPRPPLTRWR<br>PSTGYLAAGASPGTLSTTVPTGP<br>GVSCGSRGICPSGRLRLPRQAQT<br>NQTTTAPPNSQTMAPLKTVGTLG<br>MMDTTGSVLKTVHSSNLPFCGSS<br>HEPDPTLRDPEAMTRRWPWMVSV<br>QANGSHICAGILIASQWVLTVAH<br>CLSQNHVNYIVRAGSPWINQTAG<br>TSSDVPVHRVIINHGYQPRRYWS<br>WVGRAHDIGLLKLKWGLKYSKYV<br>WPICLPGLDYVVEDSSLCTVTGW<br>GYPRANGIWPQFQSLQEKEVSIL<br>NSKKCDHFYHKFSRISSLVRIIN<br>PQMICASDNNREEFCYEITGEPL<br>VCSSDGTWYLVGMMSWGPGCKKS<br>EAPPIFLQVSYYRPWIWDRLSGE<br>PLALPAPSRTLLLAFLLLLILLG<br>TL |
| SEQIDNO.:2<br><br>ACACTTTCCCGGACCAGGGCCAGTGTTCAGTTGCTATCCAGGACTCGGAGCCACTTCAGCCTGAGCAGTATGCTTGAGAC<br>TGCAGAGCTGTACTTCAATGTGGACCATGGCTACCTGGAGGGCCTGGTTCGAGGATGCAAAGCCAGCCTCCTAACTCAGC<br>AGGACTATGTCAACCTAGTGCAGTGTGAGACCTTGGAAGACCTGAAAATTCATCTCCAGACCACGGACTATGGCAACTTC<br>CTGGCTAATGAAACAAATCCTCTCACTGTTTCCAAAATTGACACGGAGATGAGGAAGAAGCTCTGCAGAGAGTTTGACTA<br>TTTCCGGAATCATTCCTTGGAGCCCCTGAGCACATTTCTCACCTACATGACATGCAGCTATATGATAGACAATATAATTC<br>TACTTATGAATGGGGCCTTGCAAAAGAAATCTGTGAAAGAAGTTCTAGCCAAGTGTCACCCACTGGGCCGTTTCACAGAG<br>ATGGAAGCTGTCAACATTGCAGAGACCCCCTCAGATCTCTTCAAGGCTGTGCTGGTTGAAACACCATTAGCTCCATTCTT<br>TCAAGATTGTATGTCTGAAAACACTCTTGATGAACTGAATATTGAATTACTGCGCAATAAACTATACAAGTCTTACCTTG<br>AGGCATTCTACAAATTCTGCAAGGATCACGGTGATGTCACAGCAGACGTTATGTGTCCCATTCTTGAGTTTGAGGCCGAC | SEQIDNO.:94<br><br>MLETAELYFNVDHGYLEGLVRGC<br>KASLLTQQDYVNLVQCETLEDLK<br>IHLQTTDYGNFLANETNPLTVSK<br>IDTEMRKKLCREFDYFRNHSLEP<br>LSTFLTYMTCSYMIDNIILLMNG<br>ALQKKSVKEVLAKCHPLGRFTEM<br>EAVNIAETPSDLFKAVLVETPLA<br>PFFQDCMSENTLDELNIELLRNK<br>LYKSYLEAFYKFCKDHGDVTADV |

FIG. 22

| NucleotideSequence (5′-3′) | ORFs |
|---|---|
| AGACGCGCTTTAATCATCACTCTGAACTCATTTGGCACTGAACTAAGCAAAGAAGACAGGGAGACCCTCTTCCCCACCTG<br>CGGCAGGCTCTATCCAGAGGGGTTGCGGTTGTTAGCTCAAGCTGAAGACTTTGAGCAGATGAAGAGAGTGGCAGATAATT<br>ATGGAGTTTACAAGCCTTTGTTTGACGCTGTCGGTGGCAGTGGGGGGAAGACACTGGAAGACGTTTTCTATGAGAGAGAG<br>GTACAGATGAATGTGCTGGCATTCAACAGGCAACTCCATTATGGTGTGTTTTATGCGTATGTAAAGTTGAAGGAGCAAGA<br>GATGAGAAATATCGTGTGGATAGCAGAATGCATCTCACAGAGGCATCGAACTAAAATCAACAGCTACATTCCAATTTTAT<br>AAGCCAGTGTACAGAAGATCATACATGTTGCCATGAAGTTATTGAGGAAAGGAAGGGGATTGTGTCACATTATCTAGAT<br>TATATAAAAGTAAGTCATACCACCTTTCCATAAACTACATGTCCACTGGAAGCCCAGTAAACAGAACTTGAAACAAAATA<br>TGCCTTTCTTGTTTCCAACAAGCCCCAGTCGTTTTTCACATTTATGACTTCCTGCTCACTGGCCTCATACGTTCATTTT<br>CATTGACCCTGTGGCACTTTTTGTATTCTCATTTGGTCAGACTAAAATCATACGTAATCAGGTTCTTCACGAGTTCTTTT<br>CCGTTCTTCTCCCCAAGCTCAAACACTGCTTTGCCTTTTACGTGTTTGGTCCTTCCATGCATTCACGAAAATGCAAAGCT<br>GTGGGTAGCTAACATACACCATGCTTGGTGAAGACACGTTCCCTTCCTTTCCCCCAAGACTTTTGAGAAAGATAGATTCC<br>CCAAATGCAAGCATTGTTAAATTTATTACTAAATTAGATTATCAACGCACACATAGAGACAGAGAGAGAGAGAGAGAGAC<br>AGACAGACAGACAGACAGAAGGATGAATAACTTATATCGATATGTATACCAGTGGTTCTGTCATACTTTATTCCAGAAAA<br>TCCAACTAATTGTACTTTATTCCTTCAGAAGATGTAGATACAGCATGGTTGCTACATAAAGTTGAAACAATGCAGAGGTT<br>GCTCAGAAAAAGAAAAATAGCAAAATGTGTCTCCAATCTTTTCTTTAAATAGGAAATTTTTCTTAAATATAGTCTATGCT<br>TGCTCTGCTTCACAAATTAAATCTGTGCAGTCAACATGATGACTCAGCAGGTAAGAGCTTGAAGTCAACTCCATGAGTTC<br>GATTCCTGGAATCTCACATATGGAAGGAGGGAACTGCAAAACTACAAGATCATCTTTAATCCTTTAATCTTTACTTATGC<br>ACCCCACCACTACACACACTTACAAAAGAATTTTAAAGAAGGGCACAGAAATAATGTGAACTAATTTTACTATACACTCT<br>CTATATACACATGCTATGTAGAATAGTATGCATAAACTAAGGAGCACAACATTTTTATGTAGAATAATCATTTATAAATA<br>TAACAAAAATAATGTTTTGTTGAACTAAGAAGAAAGCCAAGTGCCTACTCCTTGACTGCAGATGCAATTTACCCAGCTGC<br>CTCCTGCCCAGACCAACACACCTTCTCAACCACCTTAGACTGTCCTCTCAAACCCTGACCCAAAAAAACCCTTCCCTTTC<br>TAAACTGTTGTTTCAGGTATTTTGTGGCAGCAACCCAACAAAGTAACTAATACAGAAAACTGATACTGCCATTGCTACAA<br>TAAACTTGATTTTGGGGATTTAAAAAAAAAAAAAAAAAAAAA | MCPILEFEADRRALIITLNSFGT<br>ELSKEDRETLFPTCGRLYPEGLR<br>LLAQAEDFEQMKRVADNYGVYKP<br>LFDAVGGSGGKTLEDVFYEREVQ<br>MNVLAFNRQLHYGVFYAYVKLKE<br>QEMRNIVWIAECISQRHRTKINS<br>YIPIL |
| SEQIDNO.3<br><br>CCCGCCTCCCTTCCTAGGCCTGCCGCGTCGCGCGTCCTCTGCTCGGGGCTCTGGTTCGTGGGCCACGCGCGATGGGGCCC<br>CGCAGCCCTGCGGCCGCGTTGCTGGTGCTGCTGTGTGTCGGGTGCGCGCCGACCCCCGGGCGCGGGCAGTACGAGCGCTA<br>CAGCTTCCGCAACTTCCCGCGGGACGAGCTGATGCCGCTCGAGTCGGCCTACCGCCACGCGCTCGACCAGTACAGCGGCG<br>AGCACTGGGCCGAGAGCGTGGGCTACCTGGAGGTGAGCCTGCGGCTGCACCGTCTGCTGCGCGACAGCGAGGCCTTCTGC<br>CACCGCAACTGCAGCGCGGCCACGCCAGCACCCGCGCCCGCCGGCCCGGCCAGCCACGCCGAACTACGCCTCTTCGGCAG<br>CGTGCTGCGCCGCGCGCAGTGCCTCAAGCGCTGCAAGCAGGGCCTGCCCGCCTTCCGCCAGTCGCAGCCCAGCCGCTCAG<br>TGCTGGCGGACTTTCAGCAGCGCGAGCCCTACAAGTTTCTGCAGTTCGCCTACTTCAAGGCCAATGACCTCCCGAAGGCC<br>ATCGCTGCGGCTCACACCTATCTCCTGAAGCATCCAGATGACGAGATGATGAAGAGAAACATGGAGTATTATAAGAGCTT | SEQIDNO.:95<br><br>MGPRSPAAALLVLLCVGCAPTPG<br>RGQYERYSFRNFPRDELMPLESA<br>YRHALDQYSGEHWAESVGYLEVS<br>LRLHRLLRDSEAFCHRNCSAATP<br>APAPAGPASHAELRLFGSVLRRA<br>QCLKRCKQGLPAFRQSQPSRSVL<br>ADFQQREPYKFLQFAYFKANDLP<br>KAIAAAHTYLLKHPDDEMMKRNM |

FIG. 23

| NucleotideSequence (5′-3′) | ORFs |
|---|---|
| GCCTGGAGCCGAGGACCACATTAAAGACTTGGAAACCAAGTCGTACGAGAGCCTGTTTGTCCGTGCGGTGCGGGCCTACA<br>ACGGGGAGAACTGGAGAACGTCCATTTCCGACATGGAGCTCGCGCTTCCCGACTTCCTCAAGGCCTTCTACGAGTGCCTG<br>GCTGCCTGCGAGGGGTCGCGGGAGATCAAGGACTTCAAGGACTTCTACCTGTCCATAGCAGATCACTATGTGGAAGTTCT<br>GGAGTGTAAGATTCGTTGTGAGGAGACCCTCACCCCAGTCATAGGAGGCTATCCCGTGGAGAAATTTGTGGCGACCATGT<br>ACCACTATTTACAGTTTGCGTATTACAAGTTGAATGATCTGAAGAATGCAGCCCCGTGTGCCGTCAGCTACCTGCTCTTT<br>GACCAGAGTGACAGGGTCATGCAACAGAACCTGGTGTACTATCAGTACCACCGGGACAAGTGGGGCCTCTCGGATGAGCA<br>CTTCCAGCCCAGACCCGAAGCAGTTCAGTTCTTTAATGTGACGACGCTCCAGAAGGAACTGTACGACTTCGCTCAGGAAC<br>ACCTAATGGATGACGATGAGGGAGAGGTTGTGGAGTATGTGGACGACTTGTTGGAGACGGAAGAGTCTGCCTAGTCCACA<br>GGGGCTAAGGAACCTCTCTTCCGAGTTCCTCTTTCTTCAAGTGCCTGGGTTGTTGATACCTCACAGCCTTTTCTTCTTAA<br>AGTAAGAAGGAAGCCACCATCTCTCCCTACCAAGGTCAAGCCTGACTTCCCCTTGTTCACACTCAGTATTCACGCTTGTC<br>TTCATGGTTACACGTCTTCATGCCTGTCTTTCCCTTCACACATGTGTTCCCGTCATCTAGTCTGTCCTCCTCAAAGTCAC<br>GTTCGTCTCCCCTCTGATCCCATGTGTCTCCCCCATGTTCAGAAAGACAGTCTTCTGTGGTCTGCTTTCTCATCCCCGGA<br>AGAAAAATCAGTATTATTTTTAAGTAAGAAAAACACTAAAAGATGATAAATATATTTGGAGAATTAAAAAAAAAAAAAA<br>AAAAA | EYYKSLPGAEDHIKDLETKSYES<br>LFVRAVRAYNGENWRTSISDMEL<br>ALPDFLKAFYECLAACEGSREIK<br>DFKDFYLSIADHYVEVLECKIRC<br>EETLTPVIGGYPVEKFVATMYHY<br>LQFAYYKLNDLKNAAPCAVSYLL<br>FDQSDRVMQQNLVYYQYHRDKWG<br>LSDEHFQPRPEAVQFFNVTTLQK<br>ELYDFAQEHLMDDDEGEVVEYVD<br>DLLETEESA |
| SEQIDNO.4<br><br>GACTCGGCCTCCGGGAGACAAAGGGCCCTGTCGTCGCCGGCCCCCGAGCTGTTCCGGGCCATGGGCAGGACAGACCGTCG<br>CGCCGGTCCCAGAGCCAGGCTCCCCAGCACAGGCTACACACTGGACACTCAAAGCCAGACAGAAGCCCCCACACCCCCTC<br>TCTGGACTGACGCAGATGAAGAGCTAGAGGTCCAGAGAGACTGACTGTGTGCCCCTGAAGTGACCCAGCCTGGAGACTGT<br>GAGCTGACCTTCAAAGTGATTGAGCAGAACTGGGTGGGCAGCCTGTGGGGACAGGTTGCAGCTCCTCGTGACCATGAAGC<br>TCAACGAGCGCAGCTTGGCCTTCTACGCAACCTGCGATGCCCCGGTGGACAACGCCGGCTTCCTGTACAAGCGTGGTGGC<br>CGTGGGACCGGCTCGCACCGGCGCTGGTTCGTGCTCCGGGGCAATATCCTCTTTTACTTCGAGGCAGAAGGCAGCCGCGA<br>GCCGCTGGGCGTCATCCTGCTGGAGGGCTGCACGGTGGAGCTGGTGGATGCCCGGGAGGAGTTCGCCTTCGCAGTGCGCT<br>TTGCCGGGGGCCGATCCCGGCCGTACGTGCTGGCCGCTGACAGCCAGGCAGCCCTGGAGGGCTGGGTGAAGGCACTGTCC<br>CGGGCCAGCTTCCACTATCTGCGCTTGGTGGTGCGGGAGCTGGAACAGCAACTGGCTGCCATGCGCGAGGGAAGCCCCGC<br>CAACGCCTTACCCGCCAACCCGAGCCCGGTTTTGACCCAGAGACCCAAGGAGAACGGCTGGGTAGTGTGGAGCACGCTGC<br>CCGAGCAGCCCTCGGTAGCCCCTCAGCGGCCGCCGCCACTGCCACCCCGCCGCAGGGCCTCAGCGGCCAACGGGCCCTTG<br>GCATCCTTCGCCCAGCTGCATGCGCGATATGGACTAGAGGTGCAGGCCCTTAGGGACCAGTGGCGCGGAGGCCAGGCTGG<br>CCTAGCCAGCTTAGAGGTCCCCTGGCATCCTGGTTCTGCTGAGACTCAGACCCAGGACCAGCCAGCCCTAAGGGGACATA<br>GTGGGTGTAAGGTATTACATGTATTCCGTTCCGTAGAATGGCCTGTTTGCAATCCAGGCTCCCAGGGGACATAGGACATA<br>TGACTCAGGAGACCTGTGCCCCTGGGGTCAGAGGCACTTACTTCTGAGAAGAATCTGGAACGTGAACCTGAGGGTGCTTC<br>TAGAGCCCAAGGAGCTGGTTTCTAGAGAACTCCGCGCCAGGGTGGCCTGTGTGACCTTGACAGCCCCGAAGCTGGCCACA<br>GGCCCATGGGGCCCAGGGTTTACCTGGTGCCTCTCAAGGATCTAAAGCTTGAACCTGGAAGCTGCTGTCTGGGCTGCTGT | SEQIDNO.:96<br><br>MKLNERSLAFYATCDAPVDNAGF<br>LYKRGGRGTGSHRRWFVLRGNIL<br>FYFEAEGSREPLGVILLEGCTVE<br>LVDAREEFAFAVRFAGGRSRPYV<br>LAADSQAALEGWVKALSRASFHY<br>LRLVVRELEQQLAAMREGSPANA<br>LPANPSPVLTQRPKENGWVVWST<br>LPEQPSVAPQRPPPLPPRRRASA<br>ANGPLASFAQLHARYGLEVQALR<br>DQWRGGQAGLASLEVPWHPGSAE<br>TQTQDQPALRGHSGCKVLHVFRS<br>VEWPVCNPGSQGT |

FIG. 24

| NucleotideSequence (5'-3') | ORFs |
|---|---|
| GGGCCTACACCAGTAGGTGGAATGTGGACTTGAACTGGATAGGTCCCCCAGGCTCCTGGCCTGGAACCAGCTAAGTCAG<br>GACTGTGTCCAGCTTTGTAGGTGAGCCCGGGCAGAAGCAGGGCCTCCCCTGACCTCGGTCCTGGCCTGGGACCCAGCTTC<br>CTCCCAGTTTCACCTGGAGGAGACAGGCCTCCGACTGATTCCATGCCTGCAGCAGGGAGAGCCCAGGCACTGTCCCTAGC<br>CACTGCAGGTGACCAGTGGGCCTCAGGACTGGGCCTACTTCTCTCTCACCACAGTGCTGGCTGTCTTCCAGAGGGTTGGG<br>CAGGACAGCCGGCCCCACCTGGGTTCTTGTTTACAGTCCTCCTCAGTGCCCTGCCCTGAGGGGACACTCCAATCGCTGCA<br>TCCTATGAACAGATTTCACCCTGGCCCCTCCCTCTCCTCTGGGGGGTGGGGTGGCTGGGTCCCATGGGTGCTTCTGTCTG<br>TCGCCAGGGCCTCTTGGCTCTCTGCTGGCTCAGGGGCCAGGGCACTTGGCTGTGGGTTTTTCTTTGAAGTACAGAGGCTA<br>CTGTCTTCCACCAGTGAAGTTAAGTAGTCCAGTCTCACCCCTGCCACTTTTGTTACTGTTGGCTGCAAGGGGTGGCATTG<br>TCTCCAGGGAGCCAGGCCCTCGCAGGAGACACACGGGCGCCTAGCTGACTTGGCCCTGACTTGGCCCTCTGTCTCCTGAG<br>CTCAGCTGTCTGCACAGGTGGTGCCTCTGGGGACTTGGTCTGTCTCCTCAACTCTCCCACTGGAGTCATACGGCTGAGGT<br>GTAGACTCTAGTCTGGGACGGGCTTACAAACTCTAAAGGTACGGGGCAGGAGGTGGGGGAGACAAGGGCAGAGTTGTTCC<br>CTCTCCCCAAAGCACAAGGTGAACACCAGCTGATTCTGGGGCTAGGAGAGTTATCAATCATGGACAGGGTATGAGGGCCA<br>AAATAAAAGCCGGTCG | |
| SEQIDNO.5<br><br>CAGCGCCCGAGCGCAGACGCGCCCGCCATGAGGGAGATTGTGCACATCCAGGCGGGCCAGTGCGGGAACCAGATCGGTAC<br>CAAGTTTTGGGAAGTGATCAGTGATGAGCACGGCATCGACCAGGCCGGAGGCTACGTGGGCGACTCAGCGCTGCAGCTGG<br>AGAGGATCAGCGTCTACTACAATGAGTCATCCTCTAAGAAGTACGTACCCAGGGCTGCCCTGGTGGACTTGGAGCCCGGC<br>ACCATGGACAGTGTGAGGTCTGGGCCTTTTGGGCAACTCTTCCGGCCTGACAACTTCATCTTCGGACAGACGGGTGCCGG<br>AAACAACTGGGCCAAGGGTCACTACACGGAGGGCGCGGAGCTGGTGGATTCGGTGCTGGATGTGGTGCGCAAGGAGTGTG<br>AGCATTGCGACTGTCTTCAGGGCTTCCAGCTCACCCACTCGCTGGGCGGTGGCACGGGCTCAGGCATGGGCACACTGCTC<br>ATCAGCAAGATCCGAGAGGAGTACCCGGACCGCATCATGAACACCTTCAGCGTCATGCCGTCACCCAAGGTCTCAGACAC<br>CGTGGTGGAGCCCTACAACGCCACATTGTCAGTGCACCAGCTGGTAGAGAACACCGACGAGACCTACTGCATCGACAACG<br>AGGCCCTCTATGACATCTGCTTCCGCACGCTCAAGCTGACCACACCCACTTACGGGGACCTCAACCACTTGGTATCCGCC<br>ACCATGAGCGGTGTCACCACATCACTGCGTTTCCCTGGCCAACTCAACGCCGACCTGCGCAAGCTGGCTGTGAACATGGT<br>GCCATTCCCACGTCTCCACTTCTTCATGCCCGGCTTTGCCCCCCTCACAGCCCGGGGCAGTCAGCAGTACCGTGCCCTGA<br>CAGTGCCTGAGCTCACACAGCAGATGTTCGATGCCAAGAACATGATGGCTGCCTGTGACCCACGCCATGGCCGCTACCTG<br>ACCGTCGCCACTGTCTTCCGGGGCCCCATGTCCATGAAGGAGGTGGACGAGCAGATGCTGGCCATCCAGAACAAGAACAG<br>CAGCTACTTTGTGGAGTGGATCCCCAACAATGTCAAGGTAGCTGTGTGCGACATCCCACCACGGGGCCTGAAGATGGCCT<br>CCACCTTCATTGGCAATAGCACTGCCATCCAGGAGCTATTCAAGCGCATCTCCGAGCAGTTCTCGGCCATGTTCCGCCGC<br>AAGGCCTTCCTGCACTGGTTCACCGGTGAGGGCATGGACGAGATGGAGTTCACCGAGGCCGAGAGTAACATGAATGACCT<br>GGTGTCCGAGTACCAGCAGTACCAGGACGCCACGGTCAATGATGGGGAAGAGGCATTTGAAGACGAGGATGAAGAAGAGA<br>TCAACGAATAGGGAGCCATAAGATGCTACAGTGAACGTCTGCTCTTTTCTTAGCCTTGATGGTGTGGGAATGGTGCCCTG | SEQIDNO.:97<br><br>MREIVHIQAGQCGNQIGTKFWEV<br>ISDEHGIDQAGGYVGDSALQLER<br>ISVYYNESSSKKYVPRAALVDLE<br>PGTMDSVRSGPFGQLFRPDNFIF<br>GQTGAGNNWAKGHYTEGAELVDS<br>VLDVVRKECEHCDCLQGFQLTHS<br>LGGGTGSGMGTLLISKIREEYPD<br>RIMNTFSVMPSPKVSDTVVEPYN<br>ATLSVHQLVENTDETYCIDNEAL<br>YDICFRTLKLTTPTYGDLNHLVS<br>ATMSGVTTSLRFPGQLNADLRKL<br>AVNMVPFPRLHFFMPGFAPLTAR<br>GSQQYRALTVPELTQQMFDAKNM<br>MAACDPRHGRYLTVATVFRGPMS<br>MKEVDEQMLAIQNKNSSYFVEWI<br>PNNVKVAVCDIPPRGLKMASTFI<br>GNSTAIQELFKRISEQFSAMFRR<br>KAFLHWFTGEGMDEMEFTEAESN |

FIG. 25

| NucleotideSequence (5'-3') | ORFs |
| --- | --- |
| GTCTAAGCATGTCACTGGCCCCTCTCAAACCAAATGCACCACACTGTTCTCCAGGTTACCTGGAACAGTCCCAGCAGACC<br>AGGGAGATCTCATATAGGAACCCTGAAAGCAAAGTAGGGGGCTCACACAGGGCTAAAGAAAGTGACCACCTTTTGTTAAG<br>CCCCCTTCCCACCCCATCAGAGTTAGAATAGGGATTTGTTTTTCATCCTCGGTGATAAAAACTAAAGCCACACAGTGCTG<br>CCTTAAGTGAATGCACACTATGGAACTTTATGACAATCCATTCATAATAAAATGCTAAACCTGAAAAAAAAAAAAAAAAA<br>AAAAAAAAAAAAAAAAAAAAAAAAAAAAAAAAAAAAAAAAAAAAA | MNDLVSEYQQYQDATVNDGEEAF<br>EDEDEEEINE |
| SEQIDNO.6<br><br>GGCCTGCTTGTCCGCGCGTGGGCCAGGTGGCGGCCCGCAAGCTCCAGGTGGCGGCGTCGGGGAGACGAACAGTCCCCGCC<br>GGGCAGGCAGCGGGAAGGAGCCCGGGACTGGCCTCACGTGACAGCAGGAGGTCGCTGCGGGGACGGTCAGCCCGGTGGGC<br>CAAGGCTGCACCGGGCGAGGCAAGGCGTCCGGCCGCACCCTCGCGGGCCAGGCGGGACCTCCCCGCGGCGGCGCCCGGGC<br>TGCCGTTCCCCTTTCCGCGGCTCCTCCCGCGCCGAGGCGAAGCGGCTCCTCCGCTGGGCCGAGTCCGCCAGTCCGCTGGC<br>GGTCATGGAGCGCTATCCCCGGAGCCCCCGCGCGGCCCGCGACCTCACGCCCTCCGATCCTCGCTAGCTCTTGGCATTGG<br>GCCTTTTCTCCGCCACCCAACCCGGTCTTCGGAGCCTGTGGTGTTGTGATTCGGACGAAATGGAAGAAAAGGAGCGATGT<br>GACCCCTTCGGTTCTGCCCTCCTGCATTGAGGCCTAGTTGGCATCTGCAGAGAGGAAAACACGGCCAGGAAAGCGTGGTG<br>TTTCTTTTTTTCCAAAGGGGGTGGAGGGGAAGGGGGGAGCCAAAGGGAGGAATCCTACGTTTATATGTTTTTTTTTTC<br>TTTGTTAATTCTACACTTTGAAAGTGTTGGCTAAATNAACTAATCCAAAAGTTATTTTTTCCTATCGAGAAGACAGAAAA<br>AGGTAGATTTTTTTTTTTGTCCCTTTTGATTCCAACCTTTCCTCCCAGTGACAAAGCATAAATCATGAACACCAGAGAA<br>TAAATAGGTGAATCTCAGGAATCCGAAGACAGGAACCTAGACTTTCCTCAGGAGGGAAGGAGCGGAGTGTTTAGCGGCTC<br>TGCCTGGAACCTAAATCGAAAAACATGAGTTGCGTGCCATGGAAAGGAGACAAGGCCAAAGCTGAATCCTCGGACCTTCC<br>CCAAGCAGCGCCCCCACAAATCTACCATGAGAAGCAGCGCAGGGAGCTCTGTGCTCTTCATGCTCTCAACAACGTCTTCC<br>AGGACAGCAACGCCTTCACGCGGGAAACGCTGCAGGAGATTTTCCAGAGGCTGTCTCCGAACACTATGGTGACGCCCCAC<br>AAGAAGAGCATGCTGGGAAATGGGAACTATGATGTGAATGTCATCATGGCAGCACTTCAAACCAAAGGCTATGAAGCTGT<br>TTGGTGGGACAAGCGAAGGGACGTGGGTGTCATTGCTCTTACTAATGTCATGGGCTTCATCATGAACCTGCCCTCCAGCC<br>TCTGCTGGGGTCCACTCAAGTTGCCTCTCAAAAGACAGCACTGGATCTGTGTTCGTGAGGTGGGAGGGGCCTACTACAAC<br>CTTGACTCCAAACTCAAGATGCCAGAGTGGATTGGAGGCGAGAGTGAGCTCAGGAAATTTCTAAAATACCATTTGCGAGG<br>TAAAAACTGTGAACTCCTACTGGTTGTACCGGAAGAAGTGGAAGCCCATCAGAGCTGGAGGGCCGACGTGTGACAGTTGT<br>TTGACCCTCTTTGTCTCAACCCTCCAGACCTCTTTGATGTGCTGTGGCCTCTACAGTCCACTTCCCCAAACATCTCATTG<br>GGTTTTCCCTTCAGATTTGCCAGTGCAATAGGACAGATGTGTGGACTGTCACAGAGCCACCCAGCAGTCTGTGCCTGGGG<br>GAAGAAGGTAGGAGCTCTGAACACTTAGGGCAAGCCATTGAACCCTTTGCTATTTCAGAGAGGGAGCCAAGAAGGGCGTC<br>CTTTGAGGGGGCTGGGTTATTTCTCCCTTTCCATAAGGTCTTGATACAGGCTCTGCTGGTAGTGTCACTGATGCTTCAGG<br>CTTACGGAAAGGCCGCCCCTTTTCTCTCCTGTGGCACCATGGGGTCTGAGGACACAGTACATGCAGAGCCAAGAAACTGT<br>CAAGACTCCAGCAGTCACACTGCATGTCACCTGCAGTTCATTAGGCCTCTTCTTGGTCCCTTTAAACCCCAGCCAGCCTT<br>GGGGTTTTATAAGAGGCTCTGCTATTCCAAAATAGGTGAATTGCACATCATTCTAGCAAGACAGTGGTGAAAGATATGCC | SEQIDNO.:98<br><br><br>MSCVPWKGDKAKAESSDLPQAAP<br>PQIYHEKQRRELCALHALNNVFQ<br>DSNAFTRETLQEIFQRLSPNTMV<br>TPHKKSMLGNGNYDVNVIMAALQ<br>TKGYEAVWWDKRRDVGVIALTNV<br>MGFIMNLPSSLCWGPLKLPLKRQ<br>HWICVREVGGAYYNLDSKLKMPE<br>WIGGESELRKFLKYHLRGKNCEL<br>LLVVPEEVEAHQSWRADV |

FIG. 26

| NucleotideSequence (5′-3′) | ORFs |
|---|---|
| TAATACCACGTGGGTAAAGCCAGAGTAGGGTAGTCACTGGTGGCTCTTCACTCTAATCGTGTCCCTATCATTTCACTACA<br>TTGACTGGGGAGGCTTTGGGACAAGACAATGAACAGGGAGAGTACTCATAGTTGGCCCATTTTTAGCAAAATCAAACACA<br>TCTACACTGACCTAAAATTCCATAGTTTGGGACAGAGTTGGGCGAGGAACTGCCATGAAGGTAAGCTTCAGGGTTTGAGC<br>CCGGTAGGCACGTCCTGAGCTCCAGAGCTGTGGCAGCAATCTCAGGTTGGCTGTATGCATCAAGCTAGAGCCTCTGAGTT<br>TGGCGTCTGTGTAGTTTCTTTGACAAACAGGGTTGGCTTGCCCCACTTCAACTAGTTCTAGATCATTTTTTTCTTGTAAT<br>TTTGGAAAATGAGGGGAAATAATTACCATACCCCCATACCAATGTGTTTGTGGTGGCCTTCAAGGCAGGTGACCTGGCCA<br>GCCCTTACCGATCCATGGTCTCTGCAGGTCTGAGAGCTGCCCCACTGGCCTGCTTCTTCTCCCTTGGCAGCAGAGCTACC<br>TGGGGCTTGCATGTTAATCCTGAGCAAGCTTGTTGGGGTGAAGGGGGGCTGTCTCCCCACTGTGACTGGAGTGCATGTTT<br>ACACCAGCACTTTTTCTGCACATGTATCTTCAATCCAACAAGGCCGTTTTTTATTCAAGTGGCAGAGGCCTCGAGTGGCT<br>ACTGCACTGCGCTCAGCCATGGTCATCTGCACCATTTTCTACACCAGATCTGCTTGGCACCATGGGGAACTCTGCCCCTG<br>CACAATGACATTCCAATCACTACCAGCCAGAAGTTACAGCCGACCTTGCTGATTGTCACAAGCAGGACCTTGGGTCCATT<br>GGCACTGTCGGTGATAGTAAGCCATTTCTTGGGAAGAGGAGACTCTTCCCTACAGATCTGCTTGGGCCTGTGCAAATGGC<br>ACTGCAAACGAGCCACACACACGTGGAGTCCATGAGCTAGTGGGATGTACAAAGACGCTTAAGCATTTCAGGGCTGGTTC<br>TGTTCATATCCAATTCTGGTGCTTAGGAACAGGGACCCATGTTAATGCCCCAGGGCAAAGCCCCACTCCTGTGAAGGAAG<br>GGGCAGCCTGACCCTGACGCCCAGCAAGGGGCAGCCCTAGGCTTTGTTTTTCTTGCTTTATTCCCTTTTCTGTTGGCCTT<br>GTGCTGGGTTTGTTTACAAAGATGTATTTTGTTTAACCAAATATTAAAAATGAAAAGCCG | |
| SEQIDNO.7<br><br>GGCATCAGCTTGGGCAGGTGTGCGGCACAAGATGAAGGGGCCATGGTGAGGAGCCCTCACCCTCAGCCTTACAGCCTCTT<br>CCCCAAGCCAACATGAGTGCCGAGCTGGAGCTGCTGTGGCCGGTGTCGGGATTATTGCTGCTGCTGTTGGGGGCCACAGC<br>CTGGCTGTGTGTCCACTGCTCCCGTCCAGGAGTGAAGAGAAATGAGAAAATCTACGAGCAGAGGAACCGGCAAGAAAATG<br>CACAGAGCTCAGCTGCGGCTCAGACATACTCCCTGGCCAGGCAGGTGTGGCCAGGACCCCAGATGGACACAGCTCCAAAC<br>AAGTCATTTGAAAGGAAGAACAAGATGCTGTTCTCCCACCTTGAGGGAAGTAACCAGGAGCCTGATGCTGCCTATGTAGA<br>CCCCATCCCTACAAACTACTACAACTGGGGATGTTTCCAGAAGCCCTCAGAAGACGACGATTCCAACTCCTACGAGAATG<br>TGCTCGTCTGCAAGCCCAGCACCCCCGAGTCAGGTGTCGAGGACTTTGAGGATTACCAGAACTCAGTATCCATCCATCAG<br>TGGCGAGAGTCCAAGAGGACTATGGGTGCACCAATGTCCCTATCAGGAAGCCCAGATGAGGAGCCAGACTATGTGAATGG<br>GGATGTGGCCGCAGCAGAGAACATCTAGGAGAGAACCAATCAATCGGAAGGAAGAAGGGCCCGAGGATGGGGGATCTGAG<br>CGGGAACTGAAGCCTTTACTGCCTGCTGAATAAAGCCTGTTCTCCAGGGATGCTCAAGTTTCACACCCTGGCCGTGGCTG<br>CTCCACAGCCTGGGAGACACTGGGCATCGCCAGAGCCCCAACCCTCAAGTGATGCCCTGGACTTCTTTGGGGGCAAAGCA<br>AGTGCCCAGAGGATATAGACTGTGCTGACTGGAAGCCCAAGACCTGAGGCAAGATGTGTCCCCAGTCTCACATCTAAAAT<br>GAGGCACAACAGTGGCATTTGTGGGTTTTGTTTTGTTTTGGCTGCAGGATCTCACTAAGTTACTCAGGCTGATCTCAAA<br>CTTGTAACCCTCAGTCCTAGTGTTGGGATTGCGGCATACCAGTTTTTTTTTTTTCCTTTCTTTGTTTGGACCTCAGATTA<br>CTTATGTCGACTTCTAGGACTGTTGCTATGACTCTTTTTGTGGTTAACTGAAGTTGCTGGAGTCGTATTTAATATTGTCA | SEQIDNO.:99<br><br>MSAELELLWPVSGLLLLLLGATA<br>WLCVHCSRPGVKRNEKIYEQRNR<br>QENAQSSAAAQTYSLARQVWPGP<br>QMDTAPNKSFERKNKMLFSHLEG<br>SNQEPDAAYVDPIPTNYYNWGCF<br>QKPSEDDDSNSYENVLVCKPSTP<br>ESGVEDFEDYQNSVSIHQWRESK<br>RTMGAPMSLSGSPDEEPDYVNGD<br>VAAAENI |

FIG. 27

| NucleotideSequence (5'-3') | ORFs |
| --- | --- |
| ATGTCAGGGGGTTCCCTGTCTCAGAGCATTATGTGTACTAACTGTAGCAGAGGAATGGGGTGTGGGGTAACCTGGGATCG<br>CTTTGGTTTCTTAGTGGGCTCCAGTTTGTTCTGATCTTTCATTCCTGCGGGGACCTTGTGCGTCGGTGATAGGGAAATAA<br>AACTGCCCCCTCACCAAACACCAATAAACCCTGTGAGTGTGAGAAAAAAAAAAAAAAAA | |
| SEQIDNO.57<br><br>GCGGGAGGGACACTCGGCGGCCGCGACGGGGGGCGCTGGCGGCAGCGGACGCTGCAGCGGCGGCGGCGGGGCTGGCGCCG<br>CGGCGGCTCCCGGGCCGGGACGGGCCTGGGCAGCGGGCGGCAGCAGCGCGGAGTGGGCACCGCGCCTGCAGCAGGGTTCT<br>GGGCCCGGGGCCGCCGCCTCCGCCAGCGGCTTCTGCACGCCCCTCCAGGCCGGCCTGCCACTCCTCCTGCTATGATGCCT<br>GGGCAGATCCCAGACCCTTCAGTGACCGCAGGCTCTCTGCCAGGGCTCGGCCCCCTCACCGGACTTCCCAGCTCTGCTCT<br>GACCACAGAGGAGCTGAAATACGCTGACATCCGCAACATTGGGGCGATGATTGCGCCCTTGCACTTCCTGGAGGTGAAAC<br>TGGGCAAGAGGCCCCAACCCGTGAAGAGTGAGCTAGACGAGGAAGAAGAGCGAAGGAAAAGGCGCCGGGAAAAGAACAAA<br>GTCGCTGCAGCCAGATGCCGGAACAAGAAGAAGGAACGCACAGAGTTTCTGCAGAGGGAGTCAGAGCGGCTGGAGCTCAT<br>GAACGCAGAGCTGAAGACGCAGATAGAGGAGCTGAAGCTGGAGCGGCAACAGCTTATCCTGATGCTCAACCGCCACCGCC<br>CCACCTGCATCGTGCGCACAGATAGCGTCAGGACGCCCGAGTCCGAAGGCAACCCACTGCTGGAGCAGCTGGACAAGAAG<br>TGACTGAAGGCCTGGAGGAGGCATCAGAGGAAGAGGAGGAAGGGGAGGAGCATAAAAGAGAAAGAGGACGAGCAAGGTGA<br>CAGAGGGCCCCTCCCAGGCACGTGACAAACTCTATGATGAGGCTTAGCATAACTAGCCTCCAGCTGGCTCTTTTTGAAA<br>CTCAGCCCTGCCGCGCAAGAGCAAGAGCGGACTGAAGAAACCAGAGGGACCAGGTGCTGAGACCAAGGTTGACCCGCAGA<br>TAGGGGCTGTCCCACTCCAGGGCCCAGCTTGAAGAGCACCTGAGCCAGAGAGGTGCCAAACCAGGTAGTAGCCTCAGGCA<br>CTCCTTTGGCCTCTCTGCCAAGACCCCCACCCAGGGGACTACTGAGCAGCCAAGAAAAGCCATGCATTGCAAACACAGTG<br>TGGCCCGCGGATGGAACTCAGCATAGACTGCAATCCACCTCCCCAGCCCTGCCCAAGCCCAGTGGAAGGGGGTGCACTGT<br>GGGGCTGCAATGGCCCAGCTGGAGTTGGCTGCGGCACAGAGGCGCGGGCGCCCTTCCAAAGCACATACTTAATCAATGAA<br>TGTTTACAGACTGGCTGTCCTGGCGGGGCTTCCAACTGCACACGGTTTTTATACTTTCTTTCTTTTTCTTTCTTTTTTTT<br>TTTAATATTTTTTACAAAAAAAAAGATTTTATACAAGCAATATATATATATATATATATATATATATATATGGATTTCTA<br>TAATCACTCGATGTGACACAGTACAAATATGCTATGGTCTGTTATGGACATCCACCCACCAGTTAAGGCCATTGTAATTC<br>CTAAGTACTGTAGGCTCTGGGTGTTGGGGGGTGGCCAGGCGGGTGAGGTACATTTCCATCCTTGTAACCCCTTCCTAGTA<br>CCCAGTCCTGTATCGTTCAGTAAACATTGCTCTTAATTACCCAAAAAAAAAAAAAAAAAAA | SEQIDNO.:100<br><br>MMPGQIPDPSVTAGSLPGLGPLT<br>GLPSSALTTEELKYADIRNIGAM<br>IAPLHFLEVKLGKRPQPVKSELD<br>EEEERRKRRREKNKVAAARCRNK<br>KKERTEFLQRESERLELMNAELK<br>TQIEELKLERQQLILMLNRHRPT<br>CIVRTDSVRTPESEGNPLLEQLD<br>KK |

FIG. 28

| Nucleotide Sequence (5'-3') | ORFs |
|---|---|
| SEQIDNO.8 | SEQIDNO.:101 |
| CAGAATTAACTCTAATTTAATGCGATGAGTATGTTTTGCTGTTACCAGTGGGGAAAAGAACACGCATTGGCCTACTCTC | MAGERPPLRGPGPGEAPGEGPG |
| CTTTTCTAGAACAACTGTGCATGACTGTTCTCTCTCCAAACCTGAACGATTCCCTTATACGGTGCACTCTCAAGACGGCC | GAGGGPGRGRPSSYRALRSAVS |
| TTGCACATTCAGCCTGCCCTCACTCCATTCCGCCGCGAGGTGGCAGGACGCTCACGGATGCCAGGAGACCTCTGCCGGGA | SLARVDDFDCAEKIGAGFFSEV |
| TCCAGTGACGTCACGCAACCCTAGCGACGATTGGCTACCTTCCCGATGACCTTGAGGGGAGGAGTCCGTGGCAGAGCCGG | YKVRHRQSGQVMVLKMNKLPSN |
| AAACATCGGCAACAGCGAAAGCCACGTCCCGAGACCGGGCGTGCGCACTCCGAGGATCCCAACCGCTGTAGAGGCCTCTG | RSNTLREVQLMNRLRHPNILRF |
| CACCTCCTCCTCTGGACTGAGGGGGCACACTGGCGTCTACCGACGTGGGGCGCAACCTGCCGAAAGGGGTCACACCGCTG | MGVCVHQGQLHALTEYMNGGTL |
| GGCGCTAGCGAGGGGAGGAGTCACCTTGAGAGGAGGGGTCACAATGACTAGCCGAGTCACTCTGCCAGGTCTCTTTTAGT | EQLLSSPEPLSWPVRLHLALDI |
| GAGAGGAACACAAAGAGGAGGGGGTGCAGCACTGAGGGGCTCGGGGAACACACGGATGTAGCAGTGTCATCCGTAGGAAA | AQGLRYLHAKGVFHRDLTSKNC |
| GGTCCCCCGAAGGAGAGCGGGCTCCGAGGGGCAGCGGCCTTTGAGGGGGCGGATCCTGCCGAGGGCGGGGCCTCCTTGC | LVRREDRGFTAVVGDFGLAEKI |
| AGGTGCAGGCGTCTCCGAAGAGAGGGTTATTAGGACAAAGAAGTAAGAGGGTGGTCACCGGATCGAGCGTCGGAATCTCA | PVYREGTRKEPLAVVGSPYWMA |
| ACTTTACTTAGGGGGATGGAGATGGAGTGAGAAGGAGTCGAGCAGGTCAGGGATGCGAAGGCCAGAGGCTCCCTACAGCC | PEVLRGELYDEKADVFAFGIVL |
| CTGGATACTGCGATCGGAGAAGACAGGTGTTAGCGAGCCCCGAGATTTAGAGTGTCGGGGTCAGAAACCCCCCTGAAATG | CELIARVPADPDYLPRTEDFGL |
| GACAGTCGGAGTCGGACGCAGACCGGGCAGGCAGCGTGGTCGATCCGTGGAGCCCAGGGCGCAGGAGAATTAGCGCCAGC | DVPAFRTLVGNDCPLPFLLLAI |
| AGTCAACCCTCAAGTCGTCCTGTGATTCACGCCCCGGCCTACGCGCGGGGACGCACCTGAGGGGGCGTGGCCGGCCGC | HCCSMEPSTRAPFTEITQHLEQ |
| AGCCCGGGCTCCAAGGAGTTAACCGCAGACCGGGCCGGGCCCCGCCCCGGGCAGGCCGCACAGCCTGAGCCCGGCGGCGA | ILEQQPEATPLAKPPLTKAPLT |
| AGCGGAGCAGCAGCCGCCCGCGGGGAGCCCGCCGCCGGCGCCCGGGAGCGCCGCCGCCGCCCGGCCCAGGCCCAGGCCCA | YNQGSVPRGGPSATLPRPDPRL |
| GGCCCCGCGCAGAGCGGAGAGCCGCGGCGTTCCACCGGGCCCAACTCGCCGGCGCGGCGGGGGCGGGCCCAGGACCTTCG | SRSRSDLFLPPSPESPPSWGDN |
| GCAGGTCCTCCAGGAGTCCACCGGGCGGGAGTCCCGGCCCCCGGGATCGGGTTGGGCCGGCGCCCATGGCGAGCGCGGCC | LTRVNPFSLREDLRGGKIKLLD |
| TGCCCGGGTCCCGGGGATCCGGCCATGTGAAGCAGGCCGGGGCTGGGGGCCCGGCCATGGCCGGGGAACGGCCGCCGCTG | TPCKPATPLPLVPPSPLTSTQL |
| CGGGGCCCCGGGCCCGGAGAGGCTCCGGGGGAGGGGCCGGGGGGCGCAGGCGGAGGCCCGGGCCGGGGCCGGCCCTCCTC | PLVTTPDILVQPETPVRRCRSL |
| CTACCGGGCCCTCCGCAGCGCCGTGTCCAGCCTTGCGCGTGTGGACGATTTCGACTGCGCAGAGAAGATCGGGGCCGGTT | PSSPELPRRMETALPGPGPSPM |
| TCTTCTCTGAGGTCTACAAGGTTCGGCACCGACAGTCGGGACAAGTCATGGTGCTGAAGATGAACAAGCTCCCCAGTAAC | GPTEERMDCEGSSPEPEPPGLA |
| CGGAGCAACACGCTAAGGGAGGTGCAGCTGATGAACCGGCTCCGGCACCCTAACATCCTCAGGTTCATGGGGGTCTGTGT | PQLPLAVATDNFISTCSSASQP |
| GCACCAAGGGCAGCTGCACGCGCTTACAGAGTATATGAATGGGGGCACCCTGGAACAGCTGCTCAGCTCCCCAGAACCCC | WSPRSGPPLNNNPPAVVVNSPQ |
| TCTCCTGGCCAGTCAGGCTCCACCTAGCCCTGGACATTGCACAAGGCCTACGGTACCTACACGCCAAAGGTGTGTTTCAC | GWAREPWNRAQHSLPRAAALEQ |
| CGAGACCTCACATCCAAGAACTGTCTGGTCCGAAGGGAAGACCGAGGCTTCACAGCTGTTGTGGGTGACTTCGGACTGGC | TEPSPPPSAPREPEEGLPCPGC |
| TGAGAAGATTCCTGTGTATAGGGAAGGGACAAGGAAGGAGCCCTTGGCTGTGGTGGGCTCCCCGTACTGGATGGCTCCAG | CLGPFSFGFLSMCPRPTPAVAR |
| AGGTGTTGCGGGGAGAGCTGTATGATGAGAAGGCCGATGTCTTCGCCTTCGGGATCGTCCTCTGTGAGCTCATCGCCCGA | YRNLNCEAGSLLCHRGHHAKPP |
| GTACCTGCAGACCCTGACTACCTACCCCGTACTGAGGACTTTGGCCTGGATGTGCCTGCTTTCCGAACTTTGGTGGAAA | TPSLQLPGARS |
| TGACTGTCCGCTACCTTTCCTGCTTCTGGCCATCCACTGCTGCAGCATGGAACCCAGCACCCGGGCCCCTTTTACTGAAA | |
| TCACCCAGCACCTGGAACAGATCCTGGAGCAGCAGCCTGAGGCCACGCCCCTCGCCAAGCCACCCCTCACCAAGGCTCCC | |
| TTGACATACAATCAGGGGTCTGTTCCAAGAGGAGGTCCCTCTGCCACACTTCCCAGGCCAGACCCCCGGCTCTCCCGAAG | |

FIG. 29

| NucleotideSequence (5′-3′) | ORFs |
|---|---|
| CCGGTCAGACCTCTTCCTGCCACCTTCGCCAGAATCACCCCCCAGCTGGGGGACAATCTAACACGAGTCAACCCCTTCT<br>CACTGCGGGAAGACCTCAGGGGTGGCAAGATCAAGCTGCTGGACACACCCTGCAAGCCGGCCACTCCACTGCCCCTGGTT<br>CCACCATCACCACTTACCTCTACCCAGCTGCCCTTAGTGACCACTCCAGACATCCTGGTCCAGCCTGAGACCCCTGTCCG<br>CCGCTGTCGCTCACTACCTTCATCCCCTGAGCTTCCCCGACGGATGGAGACTGCACTGCCAGGTCCTGGCCCTTCCCCCA<br>TGGGCCCGACTGAGGAGAGGATGGACTGCGAGGGCAGCAGCCCTGAGCCAGAGCCCCCAGGCCTGGCTCCCCAGCTGCCT<br>CTGGCTGTGGCCACTGACAACTTCATCAGTACTTGTTCCTCAGCCTCGCAGCCCTGGTCTCCTAGATCAGGACCTCCCCT<br>CAACAATAATCCCCCTGCTGTGGTGGTGAATTCCCCACAAGGGTGGGCTAGGGAGCCCTGGAACCGGGCACAGCATAGCC<br>TTCCCCGGGCAGCAGCCCTGGAGCAGACAGAGCCCTCACCGCCCCCATCAGCTCCCCGGGAGCCGGAGGAGGGGCTGCCC<br>TGCCCTGGCTGCTGCCTTGGCCCGTTCAGCTTTGGCTTTCTATCCATGTGCCCCCGCCCTACCCCAGCTGTTGCCCGCTA<br>CCGCAACTTGAACTGTGAGGCGGGCAGTCTTCTCTGCCACCGAGGGCATCATGCCAAGCCACCCACACCCAGCCTGCAGC<br>TGCCTGGGGCACGCTCTTAGCAGTGAGGCCTGTGAGCTCAGGCTTCCAACCTTGGCCTTCGGGATACCCTGTAAGGACAG<br>TGCACTTGCTGGACAATGCCAGCCCCAGATGGGCTGACTAGCTCTTCTCCCCGTATAGGGGAGCCTCAGCATGGTCTCAA<br>TGGACAGAGCACCTCCTAGCCGACCCCTGGGTTCACTGTCCCATTGGGATCACCGAACTAGACACAGCATTGCTGACACA<br>CAGGACTAACACGTGCAAAGTATTTAAAAATATTTCAATAAAACTGCCTGGCTGGCTCCGGGCCATCCATCCACTCAGCG<br>GAGCGCCCTCCCCTGACCCATCTCTAGTTTGGGAAGTTCTTAAGGAAGGTCAAGTCTTTTCTGGAGGCTTCTTTACTCTT<br>CCCAAGAGAAGTCCAGTTTCTGGAGCAGCTTTCAAGCAAGCAGCAGGTCATCCCTTAGCTGGGCATGCCCGAGAGTGAGG<br>GAGTGCTGGAGGAATAGCAGTCTTAAAAATTGGCAGGCCGTAGGTTAAGGATGTAGGTCACAAGGTCTTGTTCAAGTGTC<br>TGGAAAATAAAGCATCAGTGAGCT | |
| SEQIDNO.9<br><br>CTGAAGCCGAATCCCGGAACCAGGTAGCAGAGAGCTCGGCCGGCCTTGGAGGGAGACAAGGCTGCGACCAATCCGTCTCC<br>GTACCGTCCCACTGGACTTCACATCCGGGATCTCCTCCTGGGCGTGACCCGCGTCCCGTCTGCGGTCCTCGAACCGGTGT<br>CCTGATCTCTTTATCCAGGCCTTGCTGTTCCCGTCGTGCCTCGCGCACGACCGTAGCCCCCTCATCCGGGTTCTCTCCCG<br>GCGTTCTCCGCGTTTGCTTTGCTGTGGGGTACTTGGCGGTGCCGCCATGACTATTCTCCCCAAAAAGAAGCCGCCACCTC<br>CCGACGCCGACCCGGCCAACGAACCGCCGCCGCCCGGGCCGCTGCCCCCGGCGCCTCGGCGCGGTGCGGGTGTAGGCGTG<br>GGTGGCGGCGGCACGGGTGTGGGCGGAGGAGAGCGCGACCGTGACTCCGGCGTCGTGGGGGCCCGTCCCCGGGCTTCGCC<br>GCCACCTCAGGGCCCGCTCCCGGGGCCGCCTGGTGCTCTTCATCGTTGGGCACTGGCCGTGCCGCCTGGCGCAGTCGCGG<br>GCCCTCGGCCACAGCAGGCTTCTCCACCTCCTTGTGGGGGCCCCGGTGGCCCCGGCGGCGGTCCTGGTGACGCTCTTGGT<br>GCGACAACTGCGGGGGTGGGCGCGGCAGGGGTGGTGGTGGGCGTGGGTGGTACCGTGGGCGTGGGCGGCTGCTGCTCGGG<br>GCCCGGGCACAGCAAGCGGCGGCGTCAAGCTCCCGGCGTTGGCGCAGTTGGCGGGGCCAGTCCGGAACGTGAAGAGGTCG<br>GAGCGGGCTACAACAGTGAAGACGAGTATGAAGCTGCCGCAGCGCGAATCGAGGCCATGGATCCCGCCACTGTAGAACAG<br>CAGGAACACTGGTTTGAAAAGGCCTTGCGGGACAAGAAAGGCTTCATCATCAAGCAGATGAAGGAGGACGGTGCCTGTCT<br>ATTTCGGGCTGTAGCTGACCAGGTGTATGGAGACCAGGACATGCATGAGGTTGTTCGAAAGCATTGCATGGACTATCTGA | SEQIDNO.:102<br><br>MTILPKKKPPPPDADPANEPPP<br>PGPLPPAPRRGAGVGVGGGGTG<br>VGGGERDRDSGVVGARPRASPP<br>PQGPLPGPPGALHRWALAVPPG<br>AVAGPRPQQASPPPCGGPGGPG<br>GGPGDALGATTAGVGAAGVVVG<br>VGGTVGVGGCCSGPGHSKRRRQ<br>APGVGAVGGASPEREEVGAGYN<br>SEDEYEAAAARIEAMDPATVEQ<br>QEHWFEKALRDKKGFIIKQMKE<br>DGACLFRAVADQVYGDQDMHEV<br>VRKHCMDYLMKNADYFSNYVTE<br>DFTTYINRKRKNNCHGNHIEMQ |

FIG. 30

| NucleotideSequence (5'-3') | ORFs |
|---|---|
| TGAAGAACGCTGATTACTTCTCCAACTATGTCACAGAAGACTTCACCACCTATATCAACCGGAAGCGGAAAAACAACTGC<br>CATGGCAACCACATTGAAATGCAGGCTATGGCAGAGATGTACAACCGTCCTGTGGAGGTGTATCAATATAGCACAGAACC<br>TATCAACACATTCCATGGGATCCATCAAAATGAAGATGAACCCATCCGTGTCAGCTACCACCGGAATATCCACTATAATT<br>CAGTGGTGAATCCTAACAAGGCCACTATTGGTGTGGGGCTGGGCCTACCGTCATTTAAGCCAGGGTTTGCAGAGCAGTCC<br>CTGATGAAGAATGCCATAAAGACATCAGAAGAGTCATGGATTGAACAGCAAATGCTGGAAGACAAGAAACGAGCTACAGA<br>CTGGGAGGCCACAAATGAGGCCATAGAGGAGCAGGTGGCTCGAGAATCTTACCTTCAGTGGCTGAGGGATCAAGAGAAAC<br>AGGCCCGCCAGGTCCGGGGACCCAGCCAGCCCCGGAAAGCCAGTGCCACATGCAGTTCAGCCACAGCAGCAGCCTCCAGT<br>GGCCTGGAGGAATGGACTAGTCGGTCCCCACGGCAACGAAGTTCAGCCTCGTCACCTGAGCACCCTGAACTGCATGCCGA<br>GCTAGGCATTAAGCCCCCTTCCCCAGGCACTGTGTTAGCTCTTGCCAAACCTCCTTCACCCTGTGCACCAGGTACAAGCA<br>GTCAGTTCTCAGCAGGGGGTGATCGGGCCACCTCTCCTCTTGTGTCCCTCTACCCTGCTCTGGAGTGCCGGGCCCTCATC<br>CAGCAGATGTCCCCCTCTGCCTTTGGTCTGAATGATTGGGACGATGATGAGATCCTAGCATCGGTGCTGGCAGTGTCCCA<br>ACAGGAATACCTAGACAGTATGAAGAAAAACAAAGTGCACAGAGAGCCACCCCCAGACAAGAGTTGATGGACACCCAGGG<br>ACTGGACATCATTCCCGATCCCCCACTCCTGCCCTTTGATGCCACCCAAACTTCTTTGGCTTTCTTCCCTCTTGGCTTCC<br>TTCTTTTGTTTCCTCTTTTCCTTTTTTTTTTCCACTTCCCTCTGGCCGGCCCACCCATGCGCTCCATCCATCTCATCCCT<br>GCCACCACCATTGGTCTCTGCCAGCTGAAGTGCCCTATTGCCCCCGCACAGCACCATCTCAGCATTCCACAGGGGACTCT<br>GGAAAGGGTGCGGAAGGTAGGCAAGAGGCCCACAGAGACAGACCATCTGGCAGCCAGGCAGCCCCAGAAGAGAGACATTC<br>AGACAAAGGAAGTCTTCTGCTCACCCTTCCTTAAAGATCAGATAAACTTGTCATCCCTTCCCAGCAATGATGACAGGAAA<br>ATGGAAGTGGCAAGTTTTCCTTCTAGTATCCGAAGAATCTGAGCCTTCAATGTTAAAATTTTTCTTAATTAAAATGTGCT<br>TTATTTCACAAAAAAAAAAAAAAAA | AMAEMYNRPVEVYQYSTEPINT<br>FHGIHQNEDEPIRVSYHRNIHY<br>NSVVNPNKATIGVGLGLPSF<br>KPGFAEQSLMKNAIKTSEESWI<br>EQQMLEDKKRATDWEATNEAIE<br>EQVARESYLQWLRDQEKQARQV<br>RGPSQPRKASATCSSATAAASS<br>GLEEWTSRSPRQRSSASSPEHP<br>ELHAELGIKPPSPGTVLALAKP<br>PSPCAPGTSSQFSAGGDRATSP<br>LVSLYPALECRALIQQMSPSAF<br>GLNDWDDDEILASVLAVSQQEY<br>LDSMKKNKVHREPPPDKS |
| SEQIDNO.10<br><br>ATTTTATATGTGAGGCTTCAGTTGGTGTTGATAGAAGTTGCCCTCTGACTGTGCAAATTGACATAACTATCAGGGGGCAG<br>TTGGGCATAGCTCCGCCCAGCAGAGCCTGCACAGTGAAGATGCAGCTCATGGTACTCGCTGTGGAGTGTGGCAGCACGGA<br>CCGACAGATCAGCACTCCTCCACAGCTAAGACAGCCCAGTCCTGCGGCAACACAGCTGCTTGTAAGTGCAAAAAGGTCTG<br>CAGAGACAAGAAGTCTTCACCTAGAGCAACATCTGGGAACATCTTTGCAAGTAAGGACCTTGATAGATTGAGGAAATCAT<br>GTGAAAAAGACAAAGGCCTGATGGCAGGCGGGCACAGGAAGACAGGCAGTTAGCATTGGACATTGCCTTTGACAGGTTAG<br>GCCTTAATGTATATTAAACGATGCTCTGTGTGCTTCCCAAACACAAGCCTGTCTTGATCGGTAGATACTGTGGCGAGGCT<br>AGCTCGTGAGTATTCCTTTTGTATCACACCAGTGTTTTAAAGTTGTGTGTTCGTATGTCTGCTGTGGTATTTTTAAGTTC<br>TGGGAGAAGCCTGCTGGCCGTGTCAGCTCACGGCCATCAGTAGTTACTCAGTATTGCTGCTCCACGTTTCCCAGTGCACC<br>TTCCATGCCAGGGCAGTGGCTGCGTGCGTGCAAGCCGCGGGAGCGCCTTCCCGCTCATTTTATATGTATTTATAGAAACC<br>AAATGACCGCAGATGGCTATATGGTGTAGTGTTAAACCAGTGGAACTCTAATGGCAATAAATATATGCATATGTGTGGGA<br>GAGGGGAAAAGTGGAAATACAGGTTTACAGCCAGACATGGTGGGTGATAGCCCTTCAGTGTATTTCTCTGTCCCTTCACT<br>GACCTAGAAGGATTTGAGCTGCTGCAGCTTTAGACAGAAAATGTCCACATTTGCTGACTGTGGGCCATAAATATGCTTTT | SEQIDNO.:103<br><br>FICEASVGVDRSCPLTVQIDIT<br>IRGQLGIAPPSRACTVKMQLMV<br>LAVECGSTDRQISTPPQLRQPS<br>PAATQLLVSAKRSAETRSLHLE<br>QHLGTSLQVRTLID |

FIG. 31

| NucleotideSequence (5'-3') | ORFs |
|---|---|
| AGTACTGCTTTGCTGATGTATAAATAAGAAATCTGTAATATGTACTATATGTAATTATTTTCTTTTGACTTTATTTCAAA<br>ATGTATATTTTCTGATTATTATCATGAGCTATAAAGCAAAAAGATCAATATCTGATATTCTCCCAAATAATAAATTTTCA<br>AGATTCATTGGAAAAAAAAAAAAAAAAA | |
| SEQIDNO.11<br><br>CGACAAGAGGTAATCCTCCAGGCTCGTGATAGCACAGTGTTATCACAGATAACAGTAAGATGGCTCCTGTCCTCAGTGAA<br>GTAACTTAGAAACCATCACTCAGAGCAAGTCTTCTGCGAGGACGCTGGGCGACCTCGTCCGCAAGCTCGGGGAGAAGATC<br>CTTCCTGAGATCATCCCCATCCTGGAAGAAGGACTAAGGTCGCAGAAGAGCGACGAGAGGCAGGGCGTGTGCATCGGGCT<br>CAGCGAGATCATGAAGTCCACCAGCCGGGACGCTGTGCTCTTCTTCTCTGAGTCCCTTGTGCCCACGGCAAGGAAGGCGC<br>TGTGTGATCCCCTGGAGGAGGTCCGGGAGGCGGCAGCCAAGACCTTTGAGCAGCTGCACTCCACCATTGGCCACCAGGCT<br>TTGGAGGACATCCTCCCGTTCCTACTGAAGCAGCTGGACGACGAGGAGGTGTCGGAATTTGCCCTGGACGGTCTGAAGCA<br>GGTTATGGCCGTTAAGAGCCGTGTGGTGCTGCCCTATCTGGTGCCCAAGCTGACAACACCACCCGTCAATACCCGGGTGC<br>TGGCTTTCCTGTCCTCTGTGGCTGGTGATGCTCTGACCCGACACCTTGGCGTGATCCTCCCAGCTGTCATGTTAGCACTG<br>AAGGAGAAGCTTGGGACTCCAGACGAGCAGCTGGAGATGGCCAACTGTCAGGCTGTGATCCTCTCAGTGGAGGATGACAC<br>TGGGCACCGGATCATCATCGAGGATCTGTTGGAAGCCACGCGCAGCCCTGAAGTGGGCATGAGGCAGGCGGCGGCCATCA<br>TCCTGAACATGTACTGCTCCCGCTCCAAGGCCGACTACAGCAGCCACCTTCGCAGCCTGGTCTCGGGCTTGATCCGCCTC<br>TTCAATGACTCCAGCCCTGTGGTTCTGGAGGAGAGCTGGGACGCTCTCAATGCCATCACCAAGAAGCTGGACGCTGGTAA<br>CCAGCTGGCCCTGATCGAAGAACTCCACAAGGAAATCCGTTTCATAGGCAACGAATGCAAAGGGGAGCACGTGCCAGGCT<br>TCTGTCTTCCAAAGAGGGGAGTAACCTCCATCCTTCCAGTGCTGCGGGAAGGGGTCCTCACTGGCAGTCCTGAGCAGAAG<br>GAAGAAGCAGCCAAGGGCTTGGGCTTGGTGATCCGCCTGACCTCAGCTGATGCCCTGAGGCCCTCTGTGGTCAGCATCAC<br>TGGCCCTCTGATTCGCATCCTTGGGACCGGCTCAACTGGACTGTGAAGGCGGCTCTGCTGGAGACACTCAGCCTCTTGCT<br>GGCAAGGTTGGGATTGCCCTGAAGCCCTTCCTGCCCCAGCTTCAGACCACCTTCACCAAAGCCCTACAGGACTCCAATCG<br>GGGCGTCCGGCTGAAGGCGGCCGATGCTCTGGGGAAGCTCATTTCCATCCACGTCAAGGTGGACCCCCTCTTTACAGAGC<br>TGCTCAACGCGATCCGCGCGGTGGAGGACCCGGGCATACGAGACACCATGTTGCAGGCCCTGAGGTTTGTGATTCAGGGC<br>GCAGGCTCCAAAGTGGATGCTGCATTCGGAAAAACCTGGTCTCCGTCCTGCTGAGCATGCTGGGCCATGACGAGGACAAC<br>ACTCGGATCTCCACACTGGGTGCCTTGGGGAACTGTGTGCCTTTCTGACTGACGAAGAGCTCAACACTGTCCTTCAGCAG<br>TGCCTGCTAGCTGACGTATCTGGCATTGACTGGATGGTTCGGCACGGTCGGATCTTGGCGCTGTCCGTGGCTGTGAATGT<br>GGCTCCCAGCAGACTGTGTGCAGGCAGATACAGCAATGAGGTTCAGGACATGATCCTCAGCAACGCCGTGGCAGACAGGA<br>TCCCCATCGCCATGAGTGGGATTCGAGGCATGGGCTTCCTCATGAAGTATCACATCGAGACAGGAGGCGGGCAGCTGCCC<br>CCCAGGCTCTCCAGCCTTCTCATCAAGTGTCTGCAGAACCCATGTAGTGACATCAGGCTGGTGGCCGAGAAGATGATCTG<br>GTGGGCAAACAAGGAGCCCCGGCACCCCCTGGAGCCACAGACCATCAAGCCCATCCTGAAGGCTCTTCTCGATAACACCA<br>AGGACAAGAAACTGTCGTGCGGGCCTACAGCGACCAGGCCATCGTGAACCTGCTCAAGATGAGGCGGGGCGAGGAGCTGC<br>TCCAGTCCCTCTCCAAGATCCTGGACGTGGCCACCTGGAGGCTCTGAATGAATGCAGCGGAGGTCGCTGAGGAAGCTGGC | SEQIDNO.:104<br><br>MKSTSRDAVLFFSESLVPTARK<br>ALCDPLEEVREAAAKTFEQLHS<br>TIGHQALEDILPFLLKQLDDEE<br>VSEFALDGLKQVMAVKSRVVLP<br>YLVPKLTTPPVNTRVLAFLSSV<br>AGDALTRHLGVILPAVMLALKE<br>KLGTPDEQLEMANCQAVILSVE<br>DDTGHRIIIEDLLEATRSPEVG<br>MRQAAAIILNMYCSRSKADYSS<br>HLRSLVSGLIRLFNDSSPVVLE<br>ESWDALNAITKKLDAGNQLALI<br>EELHKEIRFIGNECKGEHVPGF<br>CLPKRGVTSILPVLREGVLTGS<br>PEQKEEAAKGLGLVIRLTSADA<br>LRPSVVSITGPLIRILGTGSTG<br>L |

FIG. 32

| NucleotideSequence (5′-3′) | ORFs |
|---|---|
| CTGCCAGGCAGACTCGGTGGAGCAGGTGGACGACACCATCCTGACGTGACAGCTGGTCCCGCCAGCCACCGCACGCTGCC<br>CCTCGTCTGTGTTCACACTGTTTTCATTTTTGAAAATACTTTTATTCCAAGGGGGAGCTCAGGAGATGGCATTCCCAGAA<br>AGTATTTTAGTACATCAAGCGACCAGAGCCAAAGCCTTAAATCCAACCCACACACAACTGAAGATCGCCTCCTCCCTCTC<br>TTGCCCTTATCTCCAGAGAAGAGAAAGAGAAGCGTGCACACCACCCTCAGCGAGCGGCAGCAAGGGGAGCCCGACTCGGC<br>TCAGCCCGGATGGACGAACTCGGGCCCTCCTTTACTTGGGAGGCCTGTGTCTGAGGGCATTGAGCGGGGCATCAGTGCTG<br>CCTGATGCTGCGCCTGGCTTTCTGGGCGGCCTGACTCTACCTGGCTTGTCTGGAGAAGAGGCTGCCCAGTCCTCCTCCTC<br>CTCAGCTCCGGGGCTTGGGGTACAGGCCATTCGAAGGAGGTTTAATAAAGGCTTTGATTTCATCTTGAAAAAAAAAAAAA<br>AAAAA | |
| SEQIDNO.12<br><br>GAAGACCCCGCAGAGAGCACGTTGTTCTCGGCCTCTCCCGGAGCTAGGCCAGCCATGGCGGCGGTAAAGACCCTAAATCC<br>GAAGGCCGAGGTGGCCCGGGCCCAGGCAGCGCTGGCGGTGAACATCAGCGCGGCTCGGGGCCTGCAGGATGTTCTGAGGA<br>CCAACTTGGGGCCTAAGGGCACCATGAAGATGCTTGTATCTGGTGCTGGAGACATCAAACTTACTAAAGATGGCAATGTG<br>CTGCTTCATGAAATGCAAATTCAACACCCAACAGCCTCTTTGATAGCAAAAGTGGCTACAGCCCAGGATGACATAACTGG<br>CGATGGCACTACATCCAATGTCCTCATCATCGGGGAGCTGCTCAAACAGGCGGACCTGTACATTTCTGAAGGTCTTCACC<br>CAAGAATAATAACTGAAGGTTTTGAAGCGGCAAAAGAAAAGGCACTCCAATTTCTGGAACAAGTCAAAGTAAGCAAAGAG<br>ATGGACAGAGAAACACTCATCGATGTGGCCAGGACATCTCTGCGGACTAAAGTTCATGCTGAACTTGCAGATGTCTTGAC<br>AGAGGCTGTAGTGGACTCCATCTTGGCCATTAGGAAAAAGGACGAGCCCATTGACCTCTTCATGGTTGAGATCATGGAGA<br>TGAAGCATAAATCTGAGACAGATACAAGCTTAATCAGAGGGCTTGTTTTGGATCATGGAGCTCGGCATCCTGATATGAAG<br>AAGAGAGTGGAAAATGCCTACATCCTCACGTGCAACGTGTCCTTAGAGTATGAGAAAACAGAAGTGAATTCTGGGTTTTT<br>TTACAAGAGTGCAGAAGAGAGAGAAAAACTAGTAAAGGCTGAAAGAAAATTCATTGAAGATAGAGTTAAAAAAATCATAG<br>AGCTGAAAAAGAAAGTCTGTGGTGACTCAGATAAAGGATTTGTCGTTATTAATCAAAAGGGGATTGACCCCTTTTCCTTA<br>GATGCCCTTGCGAAAGAAGGGATCGTAGCTCTGCGCAGAGCCAAGAGGAGAAACATGGAGAGGCTGACACTTGCTTGTGG<br>TGGGATAGCTCTGAATTCCTTTGATGACCTGAATCCTGACTGTTTGGGACATGCAGGGCTTGTCTATGAGTATACACTGG<br>GTGAGGAGAAGTTCACCTTTATTGAGAAGTGTAACAATCCCCGTTCTGTCACTTTACTGGTTAAAGGACCAAATAAGCAC<br>ACACTGACTCAAATCAAGGATGCAATAAGAGATGGCTTGAGGGCTGTCAAAAATGCTATTGATGATGGCTGTGTTGTCCC<br>AGGTGCGGGTGCAGTAGAAGTGGCACTGGCAGAAGCTCTGATTAAATACAAGCCCAGTGTGAAGGGCAGGGCGCAGCTTG<br>GAGTCCAGGCATTTGCAGATGCCTTGCTCATCATTCCCAAGGTTCTTGCGCAAAACTCTGGTTTTGACCTTCAGGAAACA<br>TTAGTTAAAGTTCAAGCTGAACATTCAGAATCGGGCCAGCTCGTAGGTGTGGATCTGAGCACAGGTGAGCCGATGGTGGC<br>CGCAGAGATGGGTGTGTGGGATAACTACTGTGTGAAGAAGCAGCTGCTACACTCCTGTACTGTGATCGCCACCAACATTC<br>TCCTGGTCGACGAGATCATGCGAGCTGGGATGTCCTCTCTGAAGGGTTGAGGCCTGCCTGTGATACTACAGGATGTTGGG<br>GGGAATGGTTATTTTTGTCCAAGCTTCAAGTGATTTGGAAAAAAATTTCTCTTCCTGATTGGAGAAAAGAAACGGACA<br>TTTGACACCTATTCAAATTATACTGTAAAATTTATTTTATTTTTGCCTTGAGTATCTGAAGACACTCAAAGCAGCTCTT | SEQIDNO.:105<br><br>MAAVKTLNPKAEVARAQAALAV<br>NISAARGLQDVLRTNLGPKGTM<br>KMLVSGAGDIKLTKDGNVLLHE<br>MQIQHPTASLIAKVATAQDDIT<br>GDGTTSNVLIIGELLKQADLYI<br>SEGLHPRIITEGFEAAKEKALQ<br>FLEQVKVSKEMDRETLIDVART<br>SLRTKVHAELADVLTEAVVDSI<br>LAIRKKDEPIDLFMVEIMEMKH<br>KSETDTSLIRGLVLDHGARHPD<br>MKKRVENAYILTCNVSLEYEKT<br>EVNSGFFYKSAEEREKLVKAER<br>KFIEDRVKKIIELKKKVCGDSD<br>KGFVVINQKGIDPFSLDALAKE<br>GIVALRRAKRRNMERLTLACGG<br>IALNSFDDLNPDCLGHAGLV<br>YEYTLGEEKFTFIEKCNNPRSV<br>TLLVKGPNKHTLTQIKDAIRDG<br>LRAVKNAIDDGCVVPGAGAVEV<br>ALAEALIKYKPSVKGRAQLGVQ<br>AFADALLIIPKVLAQNSGFDLQ<br>ETLVKVQAEHSESGQLVGVDLS<br>TGEPMVAAEMGVWDNYCVKKQL |

FIG. 33

| NucleotideSequence (5'-3') | ORFs |
|---|---|
| TTTCAACCCACTGAACAAGATGTTTTAGCTACACCGATACAAAAATTACATAATAAGATAAGCATGTTGTCTACCCTTGT<br>TCCATAAGTGTTCTTTGAAAGTTTGTAATGGTTTTCTCCTAAATAAGGCATGGTGACACATGCCTGTAAGCCTAGCCCTT<br>TGGAAATAGTCCGGAATTTCTATGCCAACTCAGGCTACAGGAGACCCCAGGTCGAAAGAATAATTTGTTGTGGATGTATT<br>TGAAATTATCCAGCCAACTCCCTGTTAAACATGTAAGATCCTTGCCAGTGTAAAACACATCTGGGTAATTTATGGGTTGC<br>ATAATGTCTAATAAATACTTAAAAGAGTG | LHSCTVIATNILLVDEIMRAGM<br>SSLKG |
| SEQIDNO.13<br><br>CAACCTCCTCCAGTGGCCAGTTTGTGCGCCCTGGGACTTACTACAGCTGGGCATGGCAGACTCTGCACAGGTGCCAACAC<br>TGGTATACCTGGTCACAGGTGGCTGCGGCTTCCTGGGGGAACATATTGTTCGGATGCTGCTGGAACGGGAGCCCAGGCTC<br>CGGGAGCTGCGTGTCTTTGACCTGCACCTGAGTTCTTGGCTGGAGGAGCTGAAAGCAGGGCCTGTGCAGGTGACTGCCAT<br>CCAGGGGGATGTGACTCAGGCCCATGAGGTGGCAGCAGCCATGTCTGGATCACATGTGGTCATCCATACAGCTGGGTTGG<br>TGGATGTGTTTGGGAAGGCCAGTCCAAAGACCATCCACAAAGTCAACGTGCAGGGCACACAGAATGTGATTGATGCTTGT<br>GTGCAGACTGGCACTCAGTACCTGGTCTACACGAGCAGCATGGAAGTGGTGGGGCCTAACATCAAGGGCCACCCCTTCTA<br>CAGGTGAGCTCAGCCCCACTTAATCTTAGAGCCCATTTCCCTCCAGCACTCAGTCTTCTTTCTCCCCTCTCCAGGGGCAA<br>TGAAGATACCCCATATGAGGCAGTCCACAGCCATCCCTACCCATGCAGTAAAGCCCTTGCTGAGCAGCTGGTCCTCGAGG<br>CCAATGGAAGGAAGGTCAATGGAGGGCTACCCCTGGTGACATGTGCCCTTCGACCCACGGGCATTTATGGTGAAGGTCAT<br>CAGGTCATGAGAGACTTCTACTACCAGGGACTGCGCTTTGGAGGTCGTCTATTTCGGGCCGTCCCAGCTTCTGTGGAGCA<br>CGGTCGGGTCTATGTTGGTAAGGACAGGGACAGCAGGGCTCGAGGAGTGGCTCTGATGGTGGCAGAGTCACGCGTGTACG<br>CCTGGCTCCACGCGAGCTCAGGCAGACAGTGGCATGTGGGCATTTTCTGCATGAGTTGAAAAACGGGGAAAGCATCCAAG<br>CAGTTGGGAGGGCTGACATAAGAACATGGCGTAGGTTATGATGAGCAACAGGAGCGACAGCTCTCCAGAGAAAGGGAGAA<br>AGCATCTACACGGGATCCAAGTAGCTGCAGGATGCCCAGGAGGGCTGGTGGCTACGGGGCCTTGGAGAAGGGCAACTTTG<br>ATTAATCAGACAGTAGAGAGGTGTGGGCAAGATCTACACGGGGCCAAGGCCAGCTTCTCTCCCTCCCTCCCTCCCTGCTG<br>GCAGGCAATGTTGCTTGGATGCACATACTGGTGGCCCGGGAGCTGGAGCAGCGGGCAGCACTCATGGGTGGCCAGGTGTA<br>TTTCTGCTATGATAAGTCACCTTATAAAAGCTACGAGGACTTCAACATGGAGTTTCTGAGTCCCTGTGGTCTTCGACTGA<br>TAGGCGCCCACCCACTGCTGCCCTACTGGCTGCTAGTGCTGCTGGCTACCCTCAATGCCCTGCTGCAGTGGCTGCTCCGC<br>CCACTGGTGCTGTACACACCCCTGCTGAATCCCTACACGCTGGCTATGGCCAACACCACCTTTACTGTCAGTACCAACAA<br>GGCACAGCGGCATTTTGGCTACAAGCCCCTCTTCTCATGGGAAGAGAGCAGGACCCGCACCATTCAGTGGGTGCAGGCGA<br>TGGAGGGTTCAGCTCGGTGATGGCAGGGCCAGGAACTGGAGACCACTGTGGCACATACTCCAGGTCCTGAGCCCCCAAAT<br>CTGGATGAAGAGAAATGGCTGCCTTTTGAAGATGAAGACTCTGCTCTACACATCATGACTCCGTGATGTGGACCCTGCCA<br>CATCTTAACTACACAGATCCTGAGACTGGTTCATATTCCAGTCTCCTAGTTCTAGGATAGGGTTTGGGGAAAGGCCTATC<br>TTTGGTGCCAACTCAGGCCTGCCAGGTAGTTGGCAAAACTGATTTCTTGAATGGTCTCACTACCTCTTCCTGTTTCCAGT<br>TTCTCAAGCAGGGAGGAACAGAGACTCCAGAGATCTTACGCTGGTCTGCTTACTTCAGCTACCATTTTCAGACCTGGCTC<br>CTGCCACATCTGGCTCTCCTTAAGGGGTTATAGTTTCACCATTTTTTAAGTGTATCTCTTTTAGACATTTATCTTTTAAT | SEQIDNO.:106<br><br>MADSAQVPTLVYLVTGGCGFLG<br>EHIVRMLLEREPRLRELRVFDL<br>HLSSWLEELKAGPVQVTAIQGD<br>VTQAHEVAAAMSGSHVVIHTAG<br>LVDVFGKASPKTIHKVNVQGTQ<br>NVIDACVQTGTQYLVYTSSMEV<br>VGPNIKGHPFYR |

FIG. 34

| NucleotideSequence (5′-3′) | ORFs |
|---|---|
| TTGCTTTAAAGAAATCTGAAGAAATCAATGATTTCCCATGTCTTGCCTCTCCTAACAAATTCACCTATGACATTGTTAGC<br>TTCCTCCCCTAGGATGCCAACCTGTATCTGGCCAAGCCTAGAATAAAATCCTTTTCCAAAAAAAAAAAAAA | |
| SEQIDNO.14<br><br>CCAAGATGGCGGCGACAGCAGCCGTGTCTGGTGTCCTCGGCCGCTTGGGCTGGAGGCTCCTGCAGCTGCGGTGCCTGCCC<br>GTGGCCCGCTGCCGACCAGCTCTGGTGCCACGTGCCTTCCACACTGCCGTGGGGTTCCGGTCTTCAGAAGAGCAGAAGCA<br>GCAGCCTCCCCACTCTTCTTCTCAGCAGCATTCTGAGACACAGGGGCCCGAGTTTTCCCGTCCACCCCCCAGGTACACAG<br>ACCAGAGTGGAGAGGAGGAAGAGGACTATGAGAGTGAGGAGCAGCTACAGCACCGCATCTTGACAGCAGCCCTAGAGTTT<br>GTGCCTGCCCATGGCTGGACTGCAGAGGCCATTGCCGAAGGAGCCCAGTCCTTGGGTCTCTCCAGCGCAGCAGCCAGCAT<br>GTTTGGGAGCGATGGCAGTGAGCTGATTCTTCACTTTGTGACCCAGTGCAATGCTCGCCTCAACCAGGTGCTGGAAGAGG<br>AGCAGAAGCTGGTGCAACTGGGCCAGGCAGAGAAGAGGAAGACAGACCAGTTCCTGAGGGATGCAGTGGAAACCAGACTG<br>AGAATGCTGATCCCCTACATTGAGCACTGGCCCCGGGCCCTCAGCATCCTCCTGCTCCCTCACAACATCCCACCCAGCCT<br>GAACTTGCTCACCAGCATGGTGGATGACATGTGGCATTACGCTGGGGACCAGTCCACTGACTTTAACTGGTACACCCGCC<br>GTGCAGTGCTGGCTGGCATCTACAACACAACAGAGCTGGTGATGATGCAGGATTCCTCCCCAGACTTTGAAGATACTTGG<br>CGCTTCCTGGAAAACCGGATTAATGATGCAATGAACATGGGCCACACGGCTAAGCAGGTGAAGTCCACGGGAGAGGCACT<br>GGTGCAAGGACTGATGGGTGCAGCGGTCACGCTCAAGAACCTGACGGGTCTAAACCAGCGTCGGTGAGAGAAGGGAACCC<br>GTGTGCTGGGAGGAGCAGCAGTAGATATGAAGGGCTTTGACAAGATGTGCCACCCATTGAACAGGATGTTAATGAGAACA<br>CACTGAAGAACTTGGAGTCGTATGACAGCCACAAGGCTGGAAATCACAATGCACTTGCTGCCGTTCTGACCTGGAACTGG<br>GCCACTTCTTCAGTTCCTAATGCCAGGCCTGGCCTCCTGATGCCTTTTGCATTGCAGCTGTGTGTTTGAAAACTGAGGCT<br>CACATCCAAGGTTTCAAACCACAAAACCTTGGCATGACTCTGCCATGGTGTCACAGGCATCTTGATCATGTCTTGACCAT<br>AGAATTGCTCTCTAGGAGCTGGGCATGGTGACCTACGTCTGTATTCTCAGCACTCAGGAGACTGCTACAGCAAGATTGAG<br>AGATCAGAGGCAGGCTTGTCTTTGTAGAGAATTACAAGCCTGCTTGAGCTACAGAGTGTGATCCTGTCAAAATCCCCTGA<br>GAAATATTCTTAGGGGCTCACAACCAAGGTCCGGAGGCAACACATAGTGGGAGCTCTTCCCCAGCACAGGGCAGACAGTG<br>CTCACAAACATTTGCCACTGGCCATTGCCTCTGGATCCCCTCAGAAAGCTGCCTCCCCTAGGCAGGTGCCTTTTGGACAG<br>TCGTGCTGAGCCTGGCATCACAGACACCAGCATGCACTTCAGGATCATTAGTGTATTTAGAATCTGTAAAAATAATAAAT<br>ATGTTTGAAACAAAAAAAAAAAAAAAAAAAAAAAAA | SEQIDNO.:107<br><br>MAATAAVSGVLGRLGWRLLQLR<br>CLPVARCRPALVPRAFHTAVGF<br>RSSEEQKQQPPHSSSQQHSETQ<br>GPEFSRPPPRYTDQSGEEEEDY<br>ESEEQLQHRILTAALEFVPAHG<br>WTAEAIAEGAQSLGLSSAAASM<br>FGSDGSELILHFVTQCNARLNQ<br>VLEEEQKLVQLGQAEKRKTDQF<br>LRDAVETRLRMLIPYIEHWPRA<br>LSILLLPHNIPPSLNLLTSMVD<br>DMWHYAGDQSTDFNWYTRRAVL<br>AGIYNTTELVMMQDSSPDFEDT<br>WRFLENRINDAMNMGHTAKQVK<br>STGEALVQGLMGAAVTLKNLTG<br>LNQRR |
| SEQIDNO.15<br><br>CCGGGCAGGTCTAGAATTCAGCGGCCGCTGAATTCTATCCAGCGGTCGGTGCCTCTGCCCGCGTGTGTGTCCCGGGTGCC<br>GGGGGACCTGTGTCAGTTAGCGCTTCTGAGATCACACAGCTGCCTAGGGGCCGTGTGATGCCCAGGGCAATTCTTGGCTT<br>TGATTTTTATTATTATTACTATTATTTTGCGTTCAGCTTTCGGGAAACCCTCGTGATGTTGTAGGATAAAGGAAATGACA<br>CTTTGAGGAACTGGAGAGAACATACACGCGTTTGGGTTTGAAGAGGAAACCGGTCTCCGCTTCCTTAGCTTGCTCCCTCT | SEQIDNO.:108<br><br>MDMFPLTWVFLALYFSGHEVRS<br>QQDPPCGGRPNSKDAGYITSPG<br>YPQDYPSHQNCEWIVYAPEPNQ<br>KIVLNFNPHFEIEKHDCKYDFI |

FIG. 35

| NucleotideSequence (5'-3') | ORFs |
|---|---|
| TTGCTGATTTCAAGAGCTATCTCCTATGAGGTGGAGATATTCCAGCAAGAATAAAGGTGAAGACAGACTGACTGCCAGGA | EIRDGDSESADLLGKHCGNIAP |
| CCCAGGAGGAAAACGTTGATCGTTAGAGACCTTTGCAGAAGACACCACCAGGAGGAAAATTAGAGAGGAAAAACACAAAG | PTIISSGSVLYIKFTSDYARQG |
| ACATAATTATAGGAGATCCCACAAACCTAGCCCGGGAGAGAGCCTCTCTGTCAAAAATGGATATGTTTCCTCTTACCTGG | AGFSLRYEIFKTGSEDCSKNFT |
| GTTTTCTTAGCTCTGTACTTTTCAGGACACGAAGTGAGAAGCCAGCAAGATCCACCCTGCGGAGGTCGGCCGAATTCCAA | SPNGTIESPGFPEKYPHNLDCT |
| AGATGCTGGCTACATCACTTCCCCAGGCTACCCCCAGGACTATCCCTCCCACCAGAACTGTGAGTGGATTGTCTACGCCC | FTILAKPRMEIILQFLTFDLEH |
| CCGAACCCAACCAGAAGATTGTTCTCAACTTCAACCCTCACTTTGAAATCGAGAAACACGACTGCAAGTATGACTTCATT | DPLQVGEGDCKYDWLDIWDGIP |
| GAGATTCGGGATGGGGACAGTGAGTCAGCTGACCTCCTGGGCAAGCACTGTGGGAACATCGCCCCGCCCACCATCATCTC | HVGPLIGKYCGTKTPSKLRSST |
| CTCAGGCTCCGTGTTATACATCAAGTTCACCTCAGACTACGCCCGGCAGGGGGCAGGTTTCTCTCTACGCTATGAGATCT | GILSLTFHTDMAVAKDGFSARY |
| TCAAAACAGGCTCTGAAGATTGTTCCAAGAACTTTACAAGCCCCAATGGGACCATTGAATCTCCAGGGTTTCCAGAGAAG | YLIHQEPPENFQCNVPLGMESG |
| TATCCACACAATCTGGACTGTACCTTCACCATCCTGGCCAAACCCAGGATGGAGATCATCCTACAGTTCCTGACCTTTGA | RIANEQISASSTFSDGRWTPQQ |
| CCTGGAGCATGACCCTCTACAAGTGGGGGAAGGAGACTGTAAATATGACTGGCTGGACATCTGGGATGGCATTCCACATG | SRLHGDDNGWTPNLDSNKEYLQ |
| TTGGACCTCTGATTGGCAAGTACTGTGGGACGAAAACACCCTCCAAACTCCGCTCGTCCACGGGGATCCTCTCCTTGACC | VDLRFLTMLTAIATQGAISRET |
| TTTCACACGGACATGGCAGTGGCCAAGGATGGCTTCTCCGCACGTTACTATTTGATCCACCAGGAGCCACCTGAGAATTT | QKGYYVKSYKLEVSTNGEDWMV |
| TCAGTGCAATGTCCCTTTGGGAATGGAGTCTGGCCGGATTGCTAATGAACAGATCAGTGCCTCCTCCACCTTCTCTGATG | YRHGKNHKIFQANNDATEVVLN |
| GGAGGTGGACTCCTCAACAGAGCCGGCTCCATGGTGATGACAATGGCTGGACACCCAATTTGGATTCCAACAAGGAGTAT | KLHMPLLTRFIRIRPQTWHLGI |
| CTCCAGGTGGACCTGCGCTTCCTAACCATGCTCACAGCCATTGCAACACAGGGAGCCATTTCCAGGGAAACCCAGAAAGG | ALRLELFGCRVTDAPCSNMLGM |
| CTACTACGTCAAATCGTACAAGCTGGAAGTCAGCACAAATGGTGAAGATTGGATGGTCTACCGGCATGGCAAAAACCACA | LSGLIADTQISASSTREYLWSP |
| AGATATTCCAAGCGAACAATGATGCGACCGAGGTGGTGCTAAACAAGCTCCACATGCCACTGCTGACTCGGTTCATCAGG | SAARLVSSRSGWFPRNPQAQPG |
| ATCCGCCCGCAGACGTGGCATTTGGGCATTGCCCTTCGCCTGGAGCTCTTTGGCTGCCGGGTCACAGATGCACCCTGCTC | EEWLQVDLGTPKTVKGVIIQGA |
| CAACATGCTGGGGATGCTCTCGGGCCTCATTGCTGATACCCAGATCTCTGCCTCCTCCACCCGAGAGTACCTCTGGAGCC | RGGDSITAVEARAFVRKFKVSY |
| CCAGTGCTGCCCGCCTGGTTAGTAGCCGCTCTGGCTGGTTTCCTCGGAACCCTCAAGCCCAGCCAGGTGAAGAATGGCTT | SLNGKDWEYIQDPRTQQTKLFE |
| CAGGTAGACCTGGGGACACCCAAGACAGTGAAAGGGGTCATCATCCAGGGAGCCCGAGGAGGAGACAGCATCACTGCCGT | GNMHYDTPDIRRFDPVPAQYVR |
| GGAAGCCAGGGCGTTTGTACGCAAGTTCAAAGTCTCCTACAGCCTAAATGGCAAGGACTGGGAATATATCCAGGACCCCA | VYPERWSPAGIGMRLEVLGCDW |
| GGACTCAGCAGACAAAGCTGTTTGAAGGGAACATGCACTATGACACCCCTGACATCCGAAGGTTCGATCCTGTTCCAGCG | TDSKPTVETLGPTVKSEETTTP |
| CAGTATGTGCGGGTGTACCCAGAGAGGTGGTCGCCAGCAGGCATCGGGATGAGGCTGGAGGTGCTGGGCTGTGACTGGAC | YPMDEDATECGENCSFEDDKDL |
| AGACTCAAAGCCCACAGTGGAGACGCTGGGACCCACCGTGAAGAGTGAAGAGACTACCACCCCATATCCCATGGATGAGG | QLPSGFNCNFDFPEETCGWVYD |
| ATGCCACCGAGTGTGGGGAAAACTGCAGCTTTGAGGATGACAAAGATTTGCAACTTCCTTCAGGATTCAACTGCAACTTT | HAKWLRSTWISSANPNDRTFPD |
| GATTTTCCGGAAGAGACCTGTGGTTGGGTGTACGACCATGCCAAGTGGCTCCGGAGCACGTGGATCAGCAGCGCTAACCC | DKNFLKLQSDGRREGQYGRLIS |
| CAATGACAGAACATTTCCAGATGACAAGAACTTCTTGAAACTGCAGAGTGATGGCCGACGAGAGGGCCAGTACGGGCGGC | PPVHLPRSPVCMEFQYQAMGGH |
| TCATCAGCCCACCGGTGCACCTGCCCCGAAGCCCTGTGTGCATGGAGTTCCAGTACCAAGCCATGGGCGGCCACGGGGTG | GVALQVVREASQESKLLWVIRE |
| GCACTGCAGGTGGTTCGGGAAGCCAGCCAGGAAAGCAAACTCCTTTGGGTCATCCGTGAGGACCAGGGCAGCGAGTGGAA | DQGSEWKHGRIILPSYDMEYQI |
| GCACGGGCGCATTATCCTGCCCAGCTATGACATGGAGTATCAGATCGTGTTCGAGGGAGTGATAGGGAAGGGACGATCGG | VFEGVIGKGRSGEISGDDIRIS |
| GAGAGATTTCCGGCGATGACATTCGGATAAGCACTGATGTCCCACTGGAGAACTGCATGGAACCCATATCAGCTTTTGCA | TDVPLENCMEPISAFAGEDFKD |
| GGTGAGGATTTTAAAGATGAATATGAAGGAGATTGGAGCAACTCTTCTTCCTCTACCTCAGGGGCTGGTGACCCCTCATC | EYEGDWSNSSSSTSGAGDPSSG |

FIG. 36

| Nucleotide Sequence (5'-3') | ORFs |
|---|---|
| TGGCAAAGAAAAGAGCTGGCTGTACACCCTAGATCCCATTCTGATCACCATCATCGCCATGAGCTCGCTGGGGGTCCTGC<br>TGGGGGCCACCTGTGCGGGCCTCCTCCTTTACTGCACCTGCTCCTATTCGGGTCTGAGTTCGAGGAGCTGCACCACACTG<br>GAGAACTACAACTTTGAGCTCTACGATGGCCTCAAGCACAAGGTCAAGATCAATCATCAGAAGTGCTGCTCGGAGGCATG<br>ACCGATTGTGTCTGGATCGCTTCTGGCGTTTCATTCCAGTGAGAGGGGCTAGCGAAGATTACAGTTTTGTTTTGTTTTGT<br>TTTGTTTTCCCTTTGGAAACTGAATGCCATAATCTGGATCAAAGTGTTCCAGAATACTGAAGGTATGGACAGGACAGACA<br>GGCCAGTCTAGGGAGAAAGGGAGATGCAGCTGTGAAGGGGATCGTTGCCCACCAGGACTGTGGTGGCCAAGTGAATGCAG<br>GAACCGGGCCCGGAATTCCGGCTCTCGGCTAAAATCTCAGCTGCCTCTGGAAAGGCTCAACCATACTCAGTGCCAACTCA<br>GACTCTGTTGCTGTGGTGTCAACATGGATGGATCATCTGTACCTTGTATTTTTAGCAGAATTCATGCTCAGATTTCTTTG<br>TTCTGAATCCTTGCTTTGTGCTAGACACAAAGCATACATGTCCTTCTAAAATTAATATGATCACTATAATCTCCTGTGTG<br>CAGAATTCAGAAATAGACCTTTGAAACCATTTGCATTGTGAGTGCAGATCCATGACTGGGGCTAGTGCAGCAATGAAACA<br>GAATTCCAGAAACAGTGTGTTCTTTTTATTATGGAAAATACAGATAAAAATGGCCACTGATGAACATGAAAGTTAGCAC<br>TTTCCCAACACAGTGTACACTTGCAACCTTGTTTTGGATTTCTCATACACCAAGACTGTGAAACACAAATTTCAAGAATG<br>TGTTCAAATGTGTGTGTGTGTGTGTGTGTGTGTGTGTGTGTGTGTATGTGTGTGTGTGTGTGTGCTTGTGTGTTTC<br>TGTCAGTGGTATGAGTGATATGTATGCATGTGTGTATGTATATGTATGTATGTATGTATGTATGTACGTACATATGTATG<br>TATGTATGTATGTATGTATGTATGTATATGTGTGTGTGTGTTTGTGTGTGTGTGTTTGTGTGTGTGTGTGGTAAGT<br>GTGGTATGTGTGTATGCATTTGTCTATATGTGTATCTGTGTGTCTATGTGTTTCTGTCAGTGGAATGAGTGGCATGTGTG<br>CATGTGTATGTATGTGGATATGTGTGTTGTGTTTATGTGCTTGTGTATAAGAGGTAAGTGTGGTGTGTGTGCATGTGTCT<br>CTGTGTGTGTTTGTCTGTGTACCTCTTTGTATAAGTACCTGTGTTTGTATGTGGAATATGTATATTGAGGCATTGCTGT<br>GTTAGTATGTTTATAGAAAAGAAGACAGTCTGAGATGTCTTCCTCAATACCTCTCCACTTATATCTTGGATAGACAAAAG<br>TAATGACAAAAAATTGCTGGTGTGTATATGGAAAAGGGGGACACATATCCATGGATGGTAGAAGTGTAAACTGTGCAGTC<br>ACTGTGGACATCAATATGCAGGTTCTTCACAAATGTAGATATAAAGCTACTATAGTTATACCC | KEKSWLYTLDPILITIIAMSSL<br>GVLLGATCAGLLLYCTCSYSGL<br>SSRSCTTLENYNFELYDGLKHK<br>VKINHQKCCSEA |
| SEQIDNO.16<br><br>GGGGAGCGCGGCGCAGAGCAGGGGCCCGGCCGAGGCAGCGCTGCGCGGGCCACCATGGCCACGGACGAGTTGGCCAGCAA<br>GCTGAGCCGGAGGCTGCAGATGGAGGGCGAAGGCGGCGAGGCGACGGAGCAGCCGGGGCTCAACGGGGCGGCGGCGGCGG<br>CGGCGGCCGAGGCTCCCGACGAGACTGCCCAGGCGTTGGGCAGCGCGGACGACGAGCTGAGCGCCAAGCTGCTGCGGCGC<br>GCGGACCTCAACCAGGGCATCGGCGAGCCACAGTCGCCCAGCCGCCGCGTCTTCAACCCCTACACCGAGTTCAAGGAGTT<br>CTCCAGGAAGCAGATCAAAGACATGGAGAAGATGTTCAAGCAGTATGATGCCGGCAGGGATGGCTTCATCGACCTGATGG<br>AGCTGAAACTCATGATGGAGAAGCTGGGGGCCCCCCAGACACACTTGGGCCTCAAGAGTATGATCCAGGAGGTGGACGAG<br>GATTTCGACAGCAAACTCAGCTTCCGGGAGTTCCTTCTGATCTTCCGCAAGGCAGCAGCAGGGGAGTTGCAGGAAGACAG<br>CGGCTTGCACGTCCTGGCCCGCCTGTCCGAGATCGATGTCTCCACAGAGGGCGTTAAGGGTGCCAAGAACTTCTTCGAGG<br>CCAAGGTACAGGCCATCAACGTGTCCAGCCGCTTTGAGGAAGAGATCAAAGCTGAGCAAGAGGAAAGGAAGAAGCAGGCT<br>GAGGAGGTGAAGCAGCGGAAAGCGGCCTTTAAGGAGCTGCAGTCCACGTTCAAGTAGCCAGAGCCAAGGCCGAGACCTGG | SEQIDNO.:109<br><br>MATDELASKLSRRLQMEGEGGE<br>ATEQPGLNGAAAAAAAEAPDET<br>AQALGSADDELSAKLLRRADLN<br>QGIGEPQSPSRRVFNPYTEFKE<br>FSRKQIKDMEKMFKQYDAGRDG<br>FIDLMELKLMMEKLGAPQTHLG<br>LKSMIQEVDEDFDSKLSFREFL<br>LIFRKAAAGELQEDSGLHVLAR<br>LSEIDVSTEGVKGAKNFFEAKV<br>QAINVSSRFEEEIKAEQEERKK |

FIG. 37

| NucleotideSequence (5'-3') | ORFs |
|---|---|
| CCCTGCCCCGTGTGCGGTCTGGGGGCACGGGTGGGTACAGGGGATCTGTGGGAGACTAGCTCCCAGGTCCTGCTCTCTGT<br>GCCCGGACCACTACTAAAAACCGCAAACGATATGTGACCCGATCTCATTCAGGAGTCTCCTCGGTGGTTGGTCCCTGCCC<br>TGCCCTCTCCTGCGGTTCATGCGGCTGTGATGCCAGCCAGCAGCATCCTCTCTGGCCATCCCTACGTGTCTTGTTCTCTG<br>GCCACCTTGCTGCCTGCTCTAGCCCAACTTCAGCCCATTCACGCCCCTGCCTTTGGTACCAGCTACTTTCTCCACCCACC<br>CAACTCCCCTTAACTATAGGCCGCCCTGCCATGGTCCAGCAGAGAGTGAGACCCTCCCCAGGACGCTTCCTTTCAGATCA<br>GGCCCCATCTCTGATGGAAGTGGAGAGACTCTTCTATTAGTGAGGAGATCCGGGGACTCCTACATTAGTGAGGAGATCCA<br>GGCCCTAGCACTCTAAGCTGATTTCAATGGGGCCCAGCCAGGCAGGGTGAAGGCCACTGTGCGAATCTACCTCACAGGCT<br>ACACTCTGCCAGGCATGCCTTGGGGATGTGAGTGATAGGGTTCCGAGGGGAGGGGCAGAAATGTCACCCTCTGACAGCCT<br>ACCCCCGCAGCAAGCTGAGGGTCCCAAGGGGCTGTGGAGAGAGGGGTGGGGTCCCTAAGGGATTGGCCTTTTCAGGGTGG<br>ACCTCAGCACTCTGCCTTGACTCCCCAAGGAGTGCCTGACGTGTTTATGTTCACTGGCAGTAGGACTCGGGGCCGGCACC<br>CCTTTCACACTCTCCTTCCTTGGGTTTGTCACCCGTGATGGCACCAGCCTGTCGTGCCCACCCGTAGACTCGCATGGGGA<br>CTCCCCAGGCCACAGTGAAACCCGTGCCGTTCCTCTATAGCTCCATGTGCTTGCTCACGTGTGTGTATGTGCGTGTCCGT<br>TGCTGTGTTGTGAAACTGTGACGTCACCCAGTCTAAGTGAATGGCCACCGGGGCCACCGTTATGCAATGTTCAGCGTGTC<br>ACTGCTTGTGAAGCTCGATAACTCTTTATTTTACTACAATGTCCCCAGAGTCCCTGGGACCCCTGTGGGACTTGCAAAGG<br>TTTTATTTTTTCGGTCTTAGAACCTATGAGAATCGGAGGGGCCGAGCCAAGCCCAGCCCAGCCCAGCTGCCGTGGCCTTG<br>GCTTGCGTTTGCCTCAGCGGATATGTTTATACAGATGAATATAAATTCTCTTTACTTTTGGCTGTTTGCATTTTATTTTT<br>GGTTCCCCCTCTCAGTACCTCCCAAAAAAAGAAAAAAAGAAAAAAACTACTTCTTCATTCGGTGGTACGATTATTTTTTT<br>TAACTAAAATGAGATAAAATTCTATATTCTTATGTGTGTGTGGTTTTTGATGACTAACTAGAAACAAAGGTGGACAGGAT<br>CAGGATGAGGTCGCTGGATCTGGGCCGTCACATCAGGAGCCTGGGGAGGAAGGCACTCCTGCTGGAGAGCTCTGTCCCTT<br>AGCATCTACAAACACTCCTGATCTAAGCACTACCTGTATTAAACTCATTTCATCCTTAAAGG | QAEEVKQRKAAFKELQSTFK |
| SEQIDNO.17<br><br>CCCACGCGTCCGGCCAGCAGCAGAGTCAGAAAGAAGGCGGCTGCTGTCTGAGGTGGCCTTGGGTGGCTTCTGAGCGTTCC<br>TGTCCCTCGCCCGCTACCTTCCTTGGGTTCCCACCATGCCGATGTACCAGGAAACATCCGAGCCTTCTTTGCAAGCCCTT<br>GAATCTCGCCAAGATGATATTTTAAAACGCTTGTATGAGTTGAAGGCAGCAGTCGATGGCCTTTCAAAGATGATTCACAC<br>CCCAGATGCAGACTTGGACGTAACCAACATCCTGCAAGCTGATGAGCCCACAACTTTAGCCACAAACACATTGGACTTGA<br>ATTCCGTGCTTGGAAAGGACTATGGGGCGCTGAAAGACATTGTGATCAACGCAAACCCAGCCTCCCCACCACTGTCCCTG<br>CTTGTGCTGCACAGGCTGCTCTGTGAACGCTACAGGGTCCTGTCCACTGTGCACACACATTCGTCTGTCAAGAATGTGCC<br>CGAGAATCTTGTCAAGTGCTTCGGGGAGCAGGCTAGGAAGCAGTCCCGCCACGAGTATCAGCTGGGCTTCACTCTGATTT<br>GGAAGAATGTGCCCAAGACACAGATGAAGTTCAGTGTACAAACCATGTGCCCCATTGAAGGAGAAGGGAACATCGCACGT<br>TTCCTGTTCTCTCTGTTTGGCCAGAAGCATAATGCTGTCACCCTCACCCTCATCGATAGCTGGGTGGATATCGCCATGTT<br>TCAGCTTCGAGAAGGCAGCAGTAAAGAAAAAGCGGCCGTGTTCCGCTCTATGAACTCCGCTTTGGGGAGGAGCCCGTGGC<br>TGGTTGGAAATGAGCTCACTGTGGCAGATGTGGTGCTGTGGTCTGTGCTCCAGCAGACTGGGGGCAGCAGTGGGGCAGCA | SEQIDNO.:110<br><br>MPMYQETSEPSLQALESRQDDI<br>LKRLYELKAAVDGLSKMIHTPD<br>ADLDVTNILQADEPTTLATNTL<br>DLNSVLGKDYGALKDIVINANP<br>ASPPLSLLVLHRLLCERYRVLS<br>TVHTHSSVKNVPENLVKCFGEQ<br>ARKQSRHEYQLGFTLIWKNVPK<br>TQMKFSVQTMCPIEGEGNIARF<br>LFSLFGQKHNAVTLTLIDSWVD<br>IAMFQLREGSSKEKAAVFRSMN<br>SALGRSPWLVGNELTVADVVLW |

FIG. 38

| NucleotideSequence (5′-3′) | ORFs |
|---|---|
| CCCACCAATGTGCAGCGGTGGCTTAAGTCCTGTGAAAACCTGGCCCCCTTCAGCACTGCCCTTCAGCTCCTTAAGTGAAT<br>TCGAGCAGCTTGTCTTGCAGGGTTCAACAGAAGAATGGTACGGCTTCCAGTCTGTTGTCAGAAAGGGACTTGTCCAATAA<br>AGTACCATATCATCTAAAAAAAAAAAAAAAAA | SVLQQTGGSSGAAPTNVQRWLK<br>SCENLAPFSTALQLLK |
| SEQIDNO.18<br><br>TTCGGAGAGGGCCGCTATAAAGGCTTGTTTTGCTCAGGGTCCGATGTTCGCGAGCGTGCCCGGGCTGTTTGCTCTCGTGT<br>GGGGAGGCTGGGGTGCAGAATTTCTGAAGTGAAAGGAGGAGTCTGCACCCTGGTCCTCTGTGTGGTGAAGATGAAAGATA<br>TTGACATGGGAAAAGAATATATCATCCCCAGCCCTGGGTACAGAAGTGACAGGGACAGAAGCGCTGTACCAGGGCAACAC<br>AGAGACCCCGAGGAACCCAGGTTCCGGAGAACAAGATCGTTGGAATGCCAAGATGCTCTCGAAACAGCAGCCCGAGTTGA<br>GGGGCTTTCCCTGGATATCTCTGTGCATTCTCATCTCCAAATTCTGGACGAGGAGCATTCTAAGGGAAAATACCACCATG<br>GTTTAAGTGTCCTGAAGCCCTTCCGGACCACTACCAAGCACCAGCACCCAGTGGACAATGCTGGACTTTTCTCCTACATG<br>ACCTTTTCATGGCTCTCTCCTCTGGCCCGAGTGGTTCACAAGAAGGGGGAGCTGTTAATGGAGGATGTGTGGCCTTTGTC<br>CAAGTATGAGTCTTCTGATGTGAACTGCAGAAGACTAGAGAGACTGTGGCAAGAAGAGCTGAATGAAGTTGGGCCAGACG<br>CTGCTTCCCTGCGAAGGGTTGTGTGGATCTTCTGCCGCACCAGGCTCATCCTGTCCATCGTGTGCCTGATGATCACGCAG<br>CTGGCTGGCTTCAGTGGACCAGCCTTCATGGTGAAACACCTCTTGGAGTATACCCAGGCAACAGAGTCTAACCTGCAGTG<br>CAGCTTGTTGTTAGTGCTGGGCCTCCTCCTGACGGAAATCGTGCGGTCTTGGTCGCTTGCACTGACTTGGGCATTGAATT<br>ACCGAACCGGTGTCCGCTTGCGGGGGGCCATCCTAACCATGGCATTTAAGAAGATCCTTAAGTTAAAGAACATTAAAGAG<br>AAATCCCTGGGTGAGCTCATCAACATTTGCTCCAACGATGGGCAGAGAATGTTTGAGGCAGCAGCCGTTGGCAGCCTGCT<br>GGCTGGAGGACCTGTTGTTGCCATCTTGGGCATGATTTATAATGTAATCATCCTAGGACCCACGGGCTTCCTGGGATCAG<br>CGGTTTTTATCCTCTTTTATCCAGCAATGATGTTCGTGTCACGGCTAACTGCATATTTCAGGAGAAAGCGTGTAGCTGCC<br>ACAGATGACCGTGTCCAGAAGATGAATGAAGTTCTTACCTACATTAAATTCATTAAAATGTATGCCTGGGTCAAAGCGTT<br>TTCTCAGTGTGTGCAAAAAATCCGAGAGGAGGAACGTCGGATATTGGAGAAAGCCGGGTACTTTCAGAGCATCACTGTTG<br>GAGTGGCTCCTATTGTGGTAGTGATCGCCAGTGTGGTGACGTTCTCCGTTCACATGACCCTGGGCTTCCATCTGACTGCG<br>GCACAGGCCTTCACAGTGGTGACTGTCTTCAATTCCATGACTTTTGCTTTGAAAGTAACACCATTCTCAGTGAAGTCCCT<br>CTCTGAAGCATCAGTGGCTGTTGACAGATTTAAGAGTTTGTTTCTAATGGAAGAGGTTCACATGATAAAGAACAAACCGG<br>CCAGTCCTCACATCAAGATAGAGATGAAAAATGCCACCTTGGCATGGGACTCCTCCCACTCCAGTATACAGAACTCGCCC<br>AAGCTGACCCCCAAAATGAAAAAAGACAAGAGGGCTACCAGGGGCAAGAAAGAGAAGTCGAGGCAGCTGCAACACACTGA<br>GCACCAGGCGGTGCTGGCAGAACAGAAAGGACACCTCCTCCTGGACAGCGACGAGCGGCCCAGCCCGGAAGAGGAAGAAG<br>GCAAGCAGATCCACACAGGGAGCCTGCGCCTGCAGAGGACACTGTACAACATTGACTTAGAAATTGAAGAGGGCAAACTG<br>GTTGGAATCTGCGGCAGTGTGGGAAGTGGAAAAACCTCTCTCGTTTCAGCCATTTTAGGCCAGATGACGCTTTTGGAGGG<br>CAGCATTGCCGTCAGTGGGACCTTTGCTTATGTGGCCCAACAGGCCTGGATTCTCAATGCCACTCTGAGAGACAACATTC<br>TCTTTGGGAAGGAATTTGATGAAGAGAGATACAACTCAGTGCTGAATAGCTGCTGCCTGCGGCCTGACTTGGCCATTCTC<br>CCCAACAGCGACCTGACTGAGATTGGAGAGCGAGGAGCCAACCTGAGTGGTGGACAGCGCCAGAGAATCAGCCTTGCTAG | SEQIDNO.:111<br><br>MKDIDMGKEYIIPSPGYRSDRD<br>RSAVPGQHRDPEEPRFRRTRSL<br>ECQDALETAARVEGLSLDISVH<br>SHLQILDEEHSKGKYHHGLSVL<br>KPFRTTTKHQHPVDNAGLFSYM<br>TFSWLSPLARVVHKKGELLMED<br>VWPLSKYESSDVNSRRLERLWQ<br>EELNEVGPDAASLRRVVWIFCR<br>TRLILSIVCLMITQLAGFSGPA<br>FVVKHLLEYTQATESNLQYSLL<br>LVLGLLLTEVVRSWSLALTWAL<br>NYRTGVRLRGAILTMAFKKILK<br>LKNIKEKSLGELINICSNDGQR<br>MFEAAAVGSLLAGGPVVAILGM<br>IYNVIILGPTGFLGSAVFILFY<br>PAMMFVSRLTAYFRRKCVAA<br>TDDRVQKMNEVLTYIKFIKMYA<br>WVKAFSQCVQKIREEERRILEK<br>AGYFQSITVGVAPIVVVIASVV<br>TFSVHMTLGFHLTAAQAFTVVT<br>VFNSMTFALKVTPFSVKSLSEA<br>SVAVDRFKSLFLMEEVHMIKNK<br>PASPHIKIEMKNATLAWDSSHS<br>SIQNSPKLTPKMKKDKRATRGK<br>KEKSRQLQHTEHQAVLAEQKGH<br>LLLDSDERPSPEEEEGKQIHTG<br>SLRLQRTLYNIDLEIEEGKLVG<br>ICGSVGSGKTSLVSAILGQMTL |

FIG. 39

| NucleotideSequence (5'-3') | ORFs |
|---|---|
| AGCCTTGTACAGTGATAGAAGCATCTACATCCTGGATGACCCCCTCAGTGCCTTAGATGCCCATGTGGGCAACCACATCT | LEGSIAVSGTFAYVAQQAWILN |
| TCAACAGTGCTATCCGGAAGCGCCTCAAGTCTAAGACGGTTCTGTTTGTTACACACCAGTTACAGTATCTGGTCGATTGT | ATLRDNILFGKEFDEERYNSVL |
| GATGAGGTGATCTTCATGAAGGAAGGCTGTATCACAGAGAGAGGTACCCATGAGGAGCTGATGAACTTAAATGGGGATTA | NSCCLRPDLAILPNSDLTEIGE |
| CGCTACGATTTTTAATAACCTGTTGCTGGGAGAGACACCCCCAGTTGAGATTAATTCGAAAAAGGAAGCTACTGGTTCAC | RGANLSGGQRQRISLARALY |
| AAAAATCACAAGACAAGGGCCCTAAGCCAGGGTCAGTGAAGAAGGAGAAGGCGGTGAAGTCGGAGGAAGGGCAGCTTGTG | SDRSIYILDDPLSALDAHVGNH |
| CAGGTGGAGGAGAAAGGGCAAGGTTCTGTGCCTTGGTCAGTCTACTGGGTCTACATCCAGGCTGCAGGGGGCCCCTTGGC | IFNSAIRKRLKSKTVLFVTHQL |
| TTTCCTGGTCATCATGGTCCTCTTCATGCTGAATGTGGGCAGCACTGCCTTCAGCACCTGGTGGCTTAGCTACTGGATCA | QYLVDCDEVIFMKEGCITERGT |
| AGCAAGGAAGCGGGAACAGCACAGTGTATCAAGGGAACAGAAGCTTCGTGAGTGACAGCATGAAGGACAACCCCTTCATG | HEELMNLNGDYATIFNNLLLGE |
| CAGTACTACGCCAGCATCTACGCCCTCTCCATGGCAGTCATGCTGATCTTGAAAGCCATTCGAGGAGTTGTCTTCGTCAA | TPPVEINSKKEATGSQKSQDKG |
| GGGCACACTGAGAGCCTCCTCCCGGCTCCATGATGAGCTATTCCGAAGGATCCTTAGGAGCCCCATGAAGTTTTTTGATA | PKPGSVKKEKAVKSEEGQLVQV |
| CTACCCCAACAGGAAGGATTCTCAACAGGTTTTCCAAAGACATGGATGAAGTGGATGTGCGGCTGCCGTTCCAGGCTGAG | EEKGQGSVPWSVYWVYIQAAGG |
| ATGTTTATTCAGAATGTAATCCTGGTGTTCTTCTGTGTTGGAATGATTGCTGGAGTCTTCCCATGGTTCCTCGTGGCGGT | PLAFLVIMVLFMLNVGSTAFST |
| GGGGCCTCTCCTCATCCTCTTCTCACTTCTCCACATTGTCTCCAGGGTCCTGATTCGTGAGCTAAAGCGGTTGGACAATA | WWLSYWIKQGSGNSTVYQGNRS |
| TCACGCAGTCTCCTTTCCTCTCCCACATCACGTCTAGCATTCAGGGCCTGGCCACCATCCATGCCTACAACAAAAGGCAG | FVSDSMKDNPFMQYYASIYALS |
| GAGTTTTTACACAGGTATCAGGAGCTCCTGGATGACAACCAGGCTCCCTTTTTCCTGTTCACCTGTGCAATGAGGTGGCT | MAVMLILKAIRGVVFVKGTLRA |
| GCCAGTGCGGCTGGACATCATCAGCATTGCCTTGATTACCAGCACTGGCCTGATGATTGTCTCAGGCATGGCCAGATCCC | SSRLHDELFRRILRSPMKFFDT |
| TTTCAGCCTATGCGGGGCTTGCCATTTCCTACGCTGTGCAGTTAATTGGACTATTCCAGTTCACCGTCAGACTGGCATCG | TPTGRILNRFSKDMDEVDVRLP |
| GAGACAGAAGCACGGTTCACTTCCGTGGAGAGGATCAACCACTATATCAAGACTCTCTCTTTGGAAGCACCTGCCAGAAT | FQAEMFIQNVILVFFCVGMIAG |
| CAAGAACAAGGCTCCTCCCCATGACTGGCCCCAGGAGGGAGAAGTAACCTTTGAGAATGCAGAAATGAGATACCGGGAAA | VFPWFLVAVGPLLILFSLLHIV |
| ATCTCCCTCTGGTCCTTAAGAAAGTGTCCTTCACCATCAAGCCCAAGGAAAAGATAGGCATTGTGGGACGAACAGGGTCA | SRVLIRELKRLDNITQSPFL |
| GGGAAGTCCTCTTTGGGGATGGCCCTCTTCCGTCTGGTGGAGCTATCTGGAGGCTGCATCAAGATTGATGGAATAAGAAT | SHITSSIQGLATIHAYNKRQEF |
| CAGTGACATCGGCCTGGCCGACCTCCGAAGCAAACTGGCCATCATTCCTCAGGAGCCAGTGCTGTTCAGTGGCACTGTCA | LHRYQELLDDNQAPFFLFTCAM |
| GATCAAACCTGGACCCTTTCAACCAGTACACGGAAGACCAGATCTGGGATGCTCTAGAGAGAACGCACATGAAGGAATGT | RWLAVRLDLISIALITTTGLMI |
| ATTGCCCAGCTACCTCTGAAACTTGAGTCTGAAGTAATGGAGAACGGGGACAACTTCTCTGTTGGGGAACGGCAGCTGTT | VLMHGQIPSAYAGLAISYAVQL |
| GTGCATAGCAAGAGCCCTGCTGCGTCACTGTAAGATTCTGATTTTAGATGAAGCTACAGCCGCTATGGACACAGAGACAG | TGLFQFTVRLASETEARFTSVE |
| ACTTACTGATCCAGGAGACCATCCGGGAAGCATTTGCGGACTGCACCATGCTGACCATTGCCCATCGCCTGCACACAGTT | RINHYIKTLSLEAPARIKNKAP |
| CTGGGCTCTGACAGGATCATGGTGCTGGCCCAGGGACAGGTGGTGGAGTTTGACACCCCATCGGTCCTTCTGTCTAATGA | PHDWPQEGEVTFENAEMRYREN |
| CAGTTCAAGATTCTATGCCATGTTTGCTGCTGCAGAGAACAAGGTGGCTGTCAAGGGCTGAGTCCTCCCGTCCTCGAAGT | LPLVLKKVSFTIKPKEKIGIVG |
| CTCTTCCTCAGAGCATTGCCATTCTCTTCCTGGTTTGGGCCCCTCATCCTGTCCTGCTGAAACTTCGCCTTTCCCAGTTT | RTGSGKSSLGMALFRLVELSGG |
| TATCTCTCACACAACCATTCAGGATTAGCTGTGTGTTTCACTTTTAAGGAAAGTCATATTTTGATTATTGTATTTATTCC | CIKIDGIRISDIGLADLRSKLA |
| CTATTCACTTAAATGAAATTTAGTTTTTGTTCTTAATTGCACTCTTAAGAGGTTCAGGGAACCATTACTATAAATGTTAT | IIPQEPVLFSGTVRSNLDPFNQ |
| CAGTGGCCTATAATGAAGCTTTATATGTGTAGCTATGTCTATATATAATTCTGTACATAGCCTATATTTACAGTAAAATG | YTEDQIWDALERTHMKECIAQL |
| TAAGCGGCCCGGAATTCTCAGGGCTCCTGCTTTCCTGTCTTGGTGTCAGCTGCTGTTTATGTTAGAGCAGTGGGCAAAGC | PLKLESEVMENGDNFSVGERQL |
| CAGCCCCCACCCAGTCTGCTCCCAGTGTTCCATGCTTCAGGTTCCTGAGGCTGGTCGCCACAGAGTTGTCGAGTTCCCTG | LCIARALLRHCKILILDEATAA |

FIG. 40

| NucleotideSequence (5'-3') | ORFs |
|---|---|
| GCCAGCTGGTTCCCAGCCCCAGGGTCCACTGCTGCTGTTGTAGGTGGCATTTTCATTTGCCTGACCCCAAGGCTCCAGAG<br>CTCAGCAACAGGGCTCAGGATGGTGGGGTCCGTTCTTCCTCACTTTAGTCTCCTCTGCAAAGTCTGCACCCACCCCTCAG<br>CAGCTCTTGCTAATCAGTGTCTCACACTGGTGTAGAAGTTTTTTGTACTGTAAAGAGACCTACCTCAGGTTGCTGATTGC<br>TGTGTGGTTTGGTGCGCTCTTGCAGACCCCCTTGTGCTCTGGGGCTCGTAGCTTGGGTGGGTGTGGTTGCCACTGTCACC<br>AGTCGAGTGGTCAGCGTCGCATGTCGTGACCAACTAGACATTCTGTCGCCTTAGCATGTTTGCTAAATACCTTATAAAAG<br>CAAAAATATGAAAAAGTGAATAAAATTATTTTGGATTTGT | MDTETDLLIQETIREAFADCTM<br>LTIAHRLHTVLGSDRIMVLA<br>QGQVVEFDTPSVLLSNDSSRFY<br>AMFAAAENKVAVKG |
| SEQIDNO.19<br><br>CTGGAGAGGAGCGCGTCCTGACGGGACTACGTTTCCCGGCATGCGCTGAACAGCTACCGTCGTGCCCTGCTTCTCCTAGA<br>CCGCTTGCCGGGTTCTAGAGGACCGCCTCTGAGTAGGGCGGCGAGGAGAGTCGAGGCGGAGCTGATGGCTGCGCTGAAA<br>GCGGGGCGGGGTGCAAACTGGAGCCTTCGGGCATGGCGGGCTTTGGGGGGCATCTTCTGGAGGAAGCCTCCCCTGTTAGC<br>TCCTGACCTCCGGGCTCTGCTGACGTCAGGAACTCCTGACTCTCAGATCTGGATGACTTATGGGACCCCCAGTCTCCCGG<br>CCCAGGTGCCTGAGGGGTTCCTTGCATCACGGGCAGATCTGACGTCTAGGACCCCGGATCTCTGGGCACGATTGAATGTG<br>GGGACTTCAGGCTCCAGTGACCAGGAGGCCCGCAGGAGCCCTGGAAGCCGTCGGCGCGAATGGCTGGCGGTGGCGGTGGG<br>CGCAGGAGGTGCAGTGGTGCTGCTGTTGTGGGGTTGGGGTCGGGGTCTTTCCACGGTGCTGGCTGCTGTTCCTGCTCCGC<br>CACCCACTTCTCCCCGGAGCCAGTACAATTTCATCGCAGATGTGGTGGAGAAGACAGCCCCTGCTGTGGTCTATATCGAG<br>ATCCTAGACCGGCACCCTTTCTCCGGCCGTGAAGTCCCCATCTCAAACGGATCAGGATTCGTAGTGGCTTCAGATGGGCT<br>CATCGTTACCAACGCCCACGTGGTGGCTGATCGGCGCCGAGTACGAGTGAGGCTGCCTAGCGGGGATACTTATGAGGCCA<br>TGGTCACAGCTGTGGATCCCGTAGCAGACATTGCCACACTGAGGATTCAAACCAAGGAGCCTCCTCCCACACTGCCCCTC<br>GGCCGCTCTGCTGATGTCCGGCAAGGGGAGTTTGTTGTTGCCATGGGAAGCCCCTTTGCACTGCAGAACACGATCACATC<br>TGGTATTGTCAGCTCTGCTCAGCGCCCAGCCAGGGACCTGGGACTCCCTCAAAACAACGTGGAATACATTCAGACCGATG<br>CAGCTATTGATTTTGGAAATTCTGGTGGTCCCCTGGTTAACCTGGATGGGGAGGTGATTGGAGTGAACACCATGAAGGTG<br>ACAGCTGGAATCTCCTTTGCCATCCCTTCTGATCGCCTTAGGGAGTTTCTGCATCGCGGGGAAAAGAAAAATTCCTGGTT<br>TGGAACCAGTGGGTCCCAGCGCCGCTACATTGGAGTGATGATGCTGACCCTGACTCCCAGCATCCTTATTGAACTACAGC<br>TCCGTGAGCCAAGCTTCCCTGATGTTCAGCATGGTGTCCTCATTCATAAAGTTATCCTGGGCTCCCCCGCACACAGGGCT<br>GGTCTGCGGCCTGGTGATGTGATCTTGGCCATTGGGGAGAAATTGGCACAAAATGCTGAAGATGTTTATGAAGCTGTTCG<br>AACCCAATCACAGCTGGCAGTGCGGATCCGGCGCGGATCAGAGACACTGATCTTATATGTGACCCCCGAGGTCACAGAAT<br>GAATGACTGGACCGGCAAGAGTGTGAAGCTCTTGCCCTGATCTCCTCCTTGCTTTCCTAGCCTAGGTTCTGAGTGCATGT<br>GGGTAGAGGAGGAGTCAGTGAACCTGCGGAGGGCAAGTCCCTCTAACCGCTGCATCAGTCCTGGGCTCCGAAGAACACAT<br>TTTATATAAAATAAAATTATACCTAGCAAAAAAAAAAAAAAA | SEQIDNO.:112<br><br>MAALKAGRGANWSLRAWRALGG<br>IFWRKPPLLAPDLRALLTSGTP<br>DSQIWMTYGTPSLPAQVPEGFL<br>ASRADLTSRTPDLWARLNVGTS<br>GSSDQEARRSPGSRRREWLAVA<br>VGAGGAVVLLLWGWGRGLSTVL<br>AAVPAPPPTSPRSQYNFIADVV<br>EKTAPAVVYIEILDRHPFSGRE<br>VPISNGSGFVVASDGLIVTNAH<br>VVADRRRVRVRLPSGDTYEAMV<br>TAVDPVADIATLRIQTKEPPPT<br>LPLGRSADVRQGEFVVAMGSPF<br>ALQNTITSGIVSSAQRPARDLG<br>LPQNNVEYIQTDAAIDFGNSGG<br>PLVNLDGEVIGVNTMKVTAGIS<br>FAIPSDRLREFLHRGEKKNSWF<br>GTSGSQRRYIGVMMLTLTPSIL<br>IELQLREPSFPDVQHGVLIHKV<br>ILGSPAHRAGLRPGDVILAIGE<br>KLAQNAEDVYEAVRTQSQLAVR<br>IRRGSETLILYVTPEVTE |
| SEQIDNO.20 | SEQIDNO.:113 |

FIG. 41

| NucleotideSequence (5′-3′) | ORFs |
|---|---|
| GGAATTCCTAGCATGTTGGGTGTTATGTAGTCAAAGGAGGGCATTATGAGCTGTACCCCAGGGACTTCCTGATCCTCTTA<br>CATGTATAAATAGCAAGACCGGGCCAGGAACAGCAAGCAGTCTGAAGGCCAGCTGGGTCTGCCCACTAAGAAGATGAAGC<br>CTTTTCATACTGCCCTCTCCTTCCTCATTCTTACAACTGCTCTTGGAATCTGGGCCCAGATCACACATGCAACAGAGACA<br>AAAGAAGTCCAGAGCAGTCTGAAGGCACAGCAAGGGCTTGAAATTGAAATGTTTCACATGGGCTTTCAAGACTCTTCAGA<br>TTGCTGCCTGTCCTATAACTCACGGATTCAGTGTTCAAGATTTATAGGTTATTTTCCCACCAGTGGTGGGTGTACCAGGC<br>CGGGCATCATCTTTATCAGCAAGAGGGGGTTCCAGGTCTGTGCCAACCCCAGTGATCGGAGAGTTCAGAGATGCATTGAA<br>AGATTGGAGCAAAACTCACAACCACGGACCTACAAACAATAACATTTGCTTGAAGAGAAGGGTGTGAACTGCCAGCTACT<br>TTCTTTGGTCTTCCCCAGTGACCACCTAAGTGGCTCTAAGTGTTTATTTTTATAGGTATATAAACATTTTTTTTTCTGT<br>TCCACTTTAAAGTGGCATATCTGGCTTTGTCACAGAGGGGAACTTGTCTGTGCCAACCCCAGTCATCTGAAAACTCAGAT<br>GCCTGGAAGGTCTGAAGCTGACCTCAATGACTACACATAATATTTGATTGAGATAAATGGGCAAGGTCTGGAGAGATGGC<br>TTGGTGGTTAAGAGCACTGCTGCTCAACCAGAGGACCTGGGTTCAATTTCCACTTAGATGGCAGCTCAAACTATCTATAA<br>TTCCAATTCCAAAGAAAACTGATTGCCCTATTTTGCCCTTTAGTTAGTAGTATTTACAGTATTCTTTATAAATTCACCTT<br>GACATGACCATCTTGAGCTACAGCCATCCTAACTGCCTCAGAATCACTCAAGTTCTTGCACTTTCGGTTTCCCAGCGGAT<br>TTTAAGTGGATAAACTGTGAGAGTGGTCTGTGGGACTTTGGAATGTGTCTGGTTCTGATAGTCACTTATGGCAACCCAGG<br>TACATTCAACTAGGATGAAATAAATTCTGCCTTAGCCCAGTAGTATGTCTGTGTTTGTAAGGACCCAGCTGATTTTCCCA<br>CCACCCCTCCATCTGTAAGCCACTAATAAAGTGCATCTATGCAGCCACAAAAAAA | <br>MKPFHTALSFLILTTALGIWAQ<br>ITHATETKEVQSSLKAQQGLEI<br>EMFHMGFQDSSDCCLSYNSRIQ<br>CSRFIGYFPTSGGCTRPGIIFI<br>SKRGFQVCANPSDRRVQRCIER<br>LEQNSQPRTYKQ |
| SEQIDNO.21<br><br>CCCGAGTGTCGCTGCCTCCTGTCTGCCTTGGTTAGGGGACATCCCGGGAGCGAAAAGCCCAGCCCGTGGCCGGGCCGGTG<br>GACCAGCGAGCGCGCAGCAGACTGTGCGCGGCCGCGGCGAGGGCGGGGAAGAAAACCACCCTGTTTCCTCTCCGGCCCCC<br>ACCGCGGATCATGTACCAGGATTATCCCGGGAACTTTGACACCTCGTCCCGGGGCAGCAGCGGCTCTCCTGCGCACGCCG<br>AGTCCTACTCCAGCGGTGGCGGCGGCCAGCAGAAGTTCCGGGTAGATATGCCTGGCTCGGGCAGTGCCTTCATCCCCACA<br>ATCAACGCCATCACCACCAGCCAGGACCTGCAGTGGATGGTACAGCCCACAGTGATCACCTCCATGTCCAATCCCTATCC<br>ACGCTCACATCCCTACAGTCCCCTGCCAGGCCTGGCTTCAGTCCCTGGGCACATGGCTCTCCCCAGACCTGGAGTGATCA<br>AGACCATCGGTACCACCGTGGGCCGCAGAAGGAGAGATGAGCAGCTGTCTCCTGAGGAGGAGGAGAAGCGTCGAATCCGG<br>AGGGAGAGAAACAAGCTAGCTGCAGCCAAGTGTCGGAACCGTCGCCGGGAGCTGACAGAGAAGCTGCAGGCGGAGACCGA<br>GGAGCTGGAAGAGGAGAAGTCTGGGCTGCAGAAAGAGATTGCTGAGCTGCAGAAGGAGAAGGAGAAGCTAGAGTTCATGT<br>TGGTGGCTCACGGCCCCGTGTGCAAAATCAGCCCCGAGGAACGCCGATCGCCCCCCACCTCCGGGCTGCAGTCCTTGCGC<br>GGTACGGGCAGTGCCGTTGGCCCCGTGGTGGTGAAGCAGGAGCCTCCCGAAGAGGACAGCCCCTCTTCCTCAGCAGGGAT<br>GGACAAGACCCAGCGCTCTGTCATCAAGCCCATCAGCATCGCCGGGGGTGGTTTCTACGGGGAAGAGCCTCTGCACACCC<br>CCATCGTGGTGACCTCCACGCCTGCCATCACTCCCGGCACTTCAAACCTTGTCTTCACCTACCCCAATGTCCTGGAGCAG<br>GAGTCGCCTTCGTCGCCCTCAGAGTCCTGCTCCAAGGCTCACCGCAGAAGCAGTAGCAGTGGGGACCAGTCATCAGACTC<br>CTTGAACTCCCCCACACTTCTAGCCCTGTAACCCTGTGCTCCTCTGGCCAGCTCTGGAGGAATCCTCATCCATCATTACC | SEQIDNO.:114<br><br><br>MYQDYPGNFDTSSRGSSGSPAH<br>AESYSSGGGGQQKFRVDMPGSG<br>SAFIPTINAITTSQDLQWMVQP<br>TVITSMSNPYPRSHPYSPLPGL<br>ASVPGHMALPRPGVIKTIGTTV<br>GRRRRDEQLSPEEEEKRRIRRE<br>RNKLAAAKCRNRRRELTEKLQA<br>ETEELEEEKSGLQKEIAELQKE<br>KEKLEFMLVAHGPVCKISPEER<br>RSPPTSGLQSLRGTGSAVGPVV<br>VKQEPPEEDSPSSSAGMDKTQR<br>SVIKPISIAGGGFYGEEPLHTP<br>IVVTSTPAITPGTSNLVFTYPN<br>VLEQESPSSPSESCSKAHRRSS |

FIG. 42

| NucleotideSequence (5'-3') | ORFs |
|---|---|
| ACACCCTTCCCAGGGACCAGCACCTTTAAGCACTCCAGGGCCTTGAGGGAATAAGGGGCCCCTGGCTCTGGGGACCCACC<br>CGGTGGGACTTAGTGGTGAGACACTGGTTGATCTCTTAGAAGCCCTGGGACACGCCCTCCCTCATTCATCTTGCAAGCGA<br>AGCGAATCCTTTTTCTTGAGAAGCCTCAGAGAACTTGGTTTGTGGACTCAGACGCGCCTGCGGCTACCCCCACCTCACCC<br>CACCCCCCCCTCTTCTGAAGCCCCGCCCCCTGGAGCTGGCCCGGATGGTTTCTGTCCCTTTGTTATCCGTTGTCTCTGAA<br>GTGGACAGTATCCTTTCCTGCCCCGCCAAGCATGCTCAGTGCCTTTTGGTTTCCCCTCCTTCCCCTAGATTCAGTTTTGC<br>TCCCTCTGGGTTTTTATAAGATTTGCCATGACATTTCATCTGGGTGGTCCAGATAGTAAAGCGCTTTTATTTCTGGAGCT<br>GGGGAAGCAGATGACTCTTCCACTGGGGCGGAAGGGGCACCCACTGTGTCCCGAAGGGGCAGTCAAAGTGCAATATTATT<br>GAAACTTCCCTCCCTACACACCCAGTGCGCTGTGGTTACAGACCGTGGGCTCCCTGAGTTCTGCCGGTGAGCTGCCGTCA<br>CTGGGATGCGCCAAGGACCTTTCCTCCCCGGTCTCAGAGATGCACATCTCTTTGAGGATCGGCTTGGCTGGAAGACAGGG<br>TGTGAGTGCGACAACAGGGGCACAGGTTGGGTTTGCCAAACGTCTAATTACCAAGCCAGGATTTGTGCCAACAAAGCCAC<br>ATGGCTGTCCTAGTGAGCTTCCTTTCTTACCTGTCTTGAGCTGGGCGTCTCTTTAATTACTGCCTCTGCCCCGGACCCTT<br>CTCTCTAGACTTGGGAAGCACTCCTTCCTAGAAGCCACACATCACTCCAAGGCTCAGCTGGGCGCTGCTCATCCCCAACT<br>CTCATAGTGACATCACCTGTGGATATTTAATGAGTGTGGGATGCGGGGTCTGCGGTAGAGATGGTTTCTGGCAGCCGCAG<br>CAGCCCCAGGTACCTAGCCTCCCCTGGCTGCTCTCCTGTCAGTGAGATGCAGGAGCCGCCCTCTGCTCTCAGTGGTCTCT<br>GCTACTGATGAATCCAGTGGGTTTCCTTTCATATTCTCCTGGCCAACTCCAGAGTGGCCTCCTAACCCAGCAGGCCCACC<br>CCTCTGGGAGTCGTTGGTCTCCACCAGTTTTGTTAGGCTTTGAGTGTCTATTCGGTTCCTATCAAAGCTAGTGTGTATTC<br>CTTTCCACTACAGAAGAACCATCACTCTCATGGGTGTCCCAGCCTCCAGCAAGGGCACAGCTCTGTCCCCTGCCTTTCTC<br>TCCCTTTGTCCCCACTGCATGTTGACACAAGTATGGAAGTGGAGCCTGGTTAGAACTTGTTTCTAGTGCTAATGCTCTGA<br>CCTAGTATTTCCATTGGAGATCACTGTCCAGCCATCTAAAGCCCTGTTATTCGAGTCAAGCTTATCCCCATTTTTGAGAG<br>AGAAGGGGTACCTTCACAGACCGATGCCCTTCTTACCCCAAGTTCCCATAAACACTTGCATGCAGAAGCACACAGGACAC<br>AGGGACCATGTGGGAAGCATGCTCAGCCTAGCAGAGCTGAAAGGAGCAGGCTTGGCTTGGTAGAGAGGGGGGCAGAAAGG<br>AGATAATCTCAATGTGTTCTTTCCTGTATGCCTTGGCTCTAACTCTGCTGCTCTGGTCTCCCAGAGCCTCTAGGGGCAGG<br>GGAGTGCTCCACAAGGTGGTTTGCTGGCTTCAGAGCCCTAGAAGCACAAGACAGTGGAGCCAGCGGAGCCGGGACTAGAG<br>GAGTTGGGCAGTCTCAGTTGAGAAGCTTTATCGCCTCAAGCCAAGTGGGAGCTCTCTCCCTCATGCCTGTGGGTATTTCT<br>GAAATGAAGCTGCGCCCTGTTCTGTCCTTTCCCAAAGCCCCCTTCTGCCCATAGCATGGATCCAACCCAGGTCACAGGCC<br>TGGGACTTGGTACCCTGGTTGGACACTCCTGAGACTCCAAGTCTGGCTTTCAGTTCAGTTTTCATCTGTGTTGACATCGG<br>GGCCAGAAAGCACAGCCAGCTAAATGGGCCTCTGAGGTCACCTTCCCTTCCGGCCTGCTTGCTTTGTCTTACAAGACTTC<br>TTGGCTTTTCCAAAGACAGAGATTTCTGGGGGGAAGCCGAATATTTCTACCTAAACTCTGGGTGTGACCTCAGCTCGCTT<br>TCCTCTGATCCACTGTCCAAGTTGGGTCACAAACATGTCACTCATGCATGCCTGCACTCCAGAGTCAGGTGCCAAGCTTG<br>CTTGTCCTTCCCTGCCTCCAGGTCAGGGAGCAGCTGCAGTGAGGGTGGGGAGGTGAGGGCTTTGTACACGTGTGTCCTCT<br>GCTGTCATGAACTTGGGCTGGACTGTGAGCAGCTCTGGGTTAATACAGGGCAGGCAATCCTTAAACAGCTAGCATGAAAC<br>AGTTTTGTCGTGGCCACCAGGCTTCTGTGGGAACAGTCCTTCTCTGGCTGGCTAGCTAGGCACAGCTACGGCACTGGAAA<br>GAGTAGAGCCCAGGTGAAGCTTAGGAAATTGGGAGCTAACACCAAGCAACTGGTTCCGTGGGGGAAGGTTTTAGGGAGCT<br>CAGACTGCTGCTTTCATAGGCAAAGTGTGCCCATGGGGGCCAGTCATGGAACATGTCAAAGCCAACAGGAAGCAGAACC | SSGDQSSDSLNSPTLLAL |

FIG. 43

| NucleotideSequence (5'-3') | ORFs |
|---|---|
| TGTAGCTTTCTCTGGCATTAGGGAGAGAGAACCCTGCTTGCTTCCACTTAACTCCTGGTGGAAGAGGGGCAGGCACGTTC<br>GAAGCTTCTGGATTCATTTTTCCTCCACTTTCCTGAGAGACCAAAAGTGTTCCTTGAGATGTCACCATTTGTCTTTCACA<br>GTGACTTCCTTCCCTGAGCAAACATTCATGTGGCTTCGCTGGGGAGGAAAAAAATAAGCACCTACTGTGTGCCAGGCACT<br>ATGAGGCACTTTTCTATTTATCCTCTTTTAAGATAGGACTAAGAGTTCATCTCCTTCTAGAAGGCCCCCAGGTTAAATAA<br>AAACACTTGGGGGTAAGAGGGCTTTCTTCAGAGACTCCCAGGTGGGAGTGCCTCTAGTCTGGTGGTCCTCAAAGACTCAT<br>CCACAGCAGCATCTGCCCATCCCAGGCTCCTCTCTCCTCAGACTCCTCCTATCTGGCTTGTGCTCCTCAGGTGGCTGAAG<br>GGGCCACCTTAGTTCTCATAGAAATTGTGGACCAATAGGATATGTGCTGTGTATAACTTTCTTTTTAAACTGTAAGTAAA<br>GGGTCTTGCAGCTTTGTGCTTGTGTTATCTTAGCATTTATCTTCAAACCAGCATCTCACTATTTATTGACAGTGGTGTGT<br>GTGTGTGTGTGTGTGTGTTTCTGCGTGTGCACATATGTGTGCACACATGTGCGTGTGTGTGTTCATGTGTGTGCATGCTT<br>GTGTCTTTCCACAGCTTTTTTTTTTTTTTTAAGGATCATCCTACTGCTAAGTCCGTGTCTCTTCTTGCTTCTAGTGTTT<br>TGGCCACGCCTCACCAAATGTCTGTAATGACCCAGTACTCACAACATGTTCAGGAGGAGCTGGGTCAGATTTTGACAGAG<br>GGTATGGGAAGGGAAAGGGGAGAAGAAATTGACATTTATTTTATTATTTATTTTAAATGTTTACATTTCTTTGTGTTGTT<br>CCAAGCCTGAATAGAAACAGATAGCATTAAAGTACTTCCTTCCCACTCCTTTCTCTGGCTCTCTCTCCCCCACTTGTTCT<br>GACTTAGGATAATGATCTCTATTTTGTTTGTTTCTCAAGTGACTTGTGGACTTGTGCTGTATAAACTGTATTAAAAAGGC<br>TCTGTTTTTAAAGATCAATTGTCATTCCTGTGGGGACAGTGGCTACTGAGAAATCTACATTGTAAGAGAAGACAATGAAA<br>GACCCTGGCCCTGTCTCTCAAAACTTAACTTTCTCTGTATGATTTTTTTTTTAAAAAAATATTCCATTTATTTTACTTTG<br>TGGTTACTTGATTTTGAGGAAGAAAATATTCAGCTTTGTATAAAGACTAGGTATCAGATTCCTTTTGCAGTGGGAGGTGT<br>ATATATCGTATTTTGGTATAGAGTAGGACCCAAGCTTCATGCATCTGTATTTGGTATATGTCAATGACGTGGAGTGAAAT<br>TTGCTATTAGATCCTGGAGGCAAATGGGTTGTACAAGGTTTTATGGCTCCGCGGGGAATTTAATTTCCTTTCTGGGCACC<br>TTTTGTCCCCTACTTTTAAATTAACGGTGAAACGGCCCTAGGAGGGTCGCTCTAGTTGAACTCTCCAGGCAGGACCTTAT<br>GCTCAGAAATCTTTGTATAGTTTTAAATTTTTGAGGAGTATCTCTGCTCGGAAGCATCTGTGGTGGTGTGATGTGTTGTT<br>CTGTGTACTGTATGTGACACAAGCCTACAGGATTTGCACTAAGAAAAGCTTGGTAGGAGCTTGCTGCTATGGAGGAAAGA<br>ACATATTAAAAACTTATTTTCCCTCGGGTTTGTTCTCGTTTTATGTTTTGTTGTTGTTGTTTTGTTAGCTTTCCTACTT<br>CCACTGAGTAGCATTTTGTAGAATAAAATTAATCAAGAACAAAAAAAAAAAAAAAAAAAAAAAA | |
| SEQIDNO.22<br><br>GGTTTCACCCGGCTGGGCGCTGTGGCCGTAGTGGCCCTGGGTGTGCGGCCGGCGCCCGTGACAGCAGCGTCGCGGAGCCG<br>GCTACCCCGACCTGGGGCCACTGCGGATCTTGGTGGCAGAGCGACATCGCCTGGCGGAATGGAGGCGAGGCGGGAGCGA<br>ATGGTCCTCGGGGCCGTGTCAAGAGCTTGGGGCTAGTGTTCGAAGATGAGAGCAAGGGCTGCTACTCAAGCGGCGAGACA<br>GTGGCCGGGCACGTGCTGCTGGAGGCGGCAGAGCCGGTGGCCCTGCGCGGACTGCGCCTGGAGGCCCAGGGCCGTGCCAC<br>CTCTGCCTGGGGCCCGAGCGCTGGGGCCAGGGTCTGCATCGGTGGGGGCTCTCCCGCAGCCTCCTCAGAAGTGGAATACT<br>TGAACCTGCGGTTGAGTCTGCTGGAGGCCCCAGCTGGTGAAGGTGTCACCTTGTTACAACCAGGAAAACACGAGTTTCCC<br>TTTCGCTTTCAGCTTCGGTCTGAACCTTTGGCAACATCGTTTACTGGGAAGTATGGCAGTATTCAGTACTGTGTGAGGGC | SEQIDNO.:115<br><br><br>MGGEAGANGPRGRVKSLGLVFE<br>DESKGCYSSGETVAGHVLLEAA<br>EPVALRGLRLEAQGRATSAWGP<br>SAGARVCIGGGSPAASSEVEYL<br>NLRLSLLEAPAGEGVTLLQPGK<br>HEFPFRFQLRSEPLATSFTGKY |

FIG. 44

| Nucleotide Sequence (5'-3') | ORFs |
|---|---|
| TGTTTTGGAACGACCCCAAGTTCCAGATCAGAGCGTCAGACGAGAGCTCCAGGTTGTCAGTCACGTGGATGTCAACACAC CGCCCTTATTGACTCCTATGCTGAAGACGCAGGAGAAAATGGTTGGCTGTTGGCTTTTCACCTCTGGTCCTGTGTCACTG AGCGTCAAGATCGAGAGAAAGGGCTACTGTAACGGAGAAGCTATCCCTATCTATGCAGAAATAGAAAATTGTTCATCTCG GCTGGTTGTTCCCAAGGCAGCCATATTCCAAACCCAGACGTACTTGGCTAGTGGAAAGACAAAGACAGTCCGGCACATGG TTGCCAATGTTCGAGGAAACCACATTGGTTCTGGGAGTACGGACACCTGGAATGGGAAGATGCTGAAGATCCCACCTGTC ACCCCATCCATCCTGGATTGCTGCATCATCAGAGTGGACTACTCCTTAGCTGTAATCCAAGCTTCTTGAATCATTAAAAA TACAT | GSIQYCVRAVLERPQVPDQSVR RELQVVSHVDVNTPPLLTPMLK TQEKMVGCWLFTSGPVSLSVKI ERKGYCNGEAIPIYAEIENCSS RLVVPKAAIFQTQTYLASGKTK TVRHMVANVRGNHIGSGSTDTW NGKMLKIPPVTPSILDCCIIRV DYSLAVIQAS |
| SEQIDNO.23 | SEQIDNO.:116 |
| GCTCCTTCCTCATTTCGCTGCTGATTCTAGCCCCAAACAAAACAGGTTGAGCCTTTTTCCTCCTCCGGCAGTTGCCTCTG GCTTGTGGCTGCCTTCTGAGCGTTTCAGACGGCGCCGGCTGGGAGTGGGAGGGAGGGCCTGGGCTAGCCGCGCTGGGACT GGGACGTGCTCCTGGCTCCTGGCCCATGCTCAGCCCTGCTTGAAGCAGGAGTGCTAGCATTTGACACAACGCCCTTGGAG GATGATGGCCCAGCTGCAGTTCCGAGATGCCTTCTGGTGCAGGGACTTCACGGCCCACACAGGGTATGAGGTGCTACTGC AGAGGCTGCTGGACGGCAGGAAGATGTGCAAGGATGTGGAGGAGCTGCTCAGACAGAGGGCCCAGGCGGAGGAGAGGTAC GGGAAGGAGCTGGTGCAGATTGCACGCAAGGCTGGTGGCCAGACAGAGATGAATTCCCTGAGGACCTCCTTTGACTCCCT GAAGCAGCAAACAGAGAATGTGGGCAGTGCACACATCCAGCTGGCCCTGGCCCTGCGTGAGGAGCTGCGGAGCCTGGAGG AGTTCCGAGAGAGACAGAAAGAGCAGCGGAAGAAGTATGAGGCCATCATGGACCGTGTCCAGAAGAGCAAGTTGTCGCTC TACAAGAAGACCATGGAGTCCAAGAAGGCATATGACCAGAAGTGCAGGGATGCAGATGATGCTGAGCAGGCCTTCGAGCG TGTGAGTGCCAATGGCCACCAGAAGCAAGTAGAAAAGAGCCAGAACAAAGCCAAGCAGTGCAAGGAGTCAGCCACAGAGG CAGAAAGAGTGTACAGGCAAAATATCGAACAACTGGAGAGAGCGAGGACCGAGTGGGAGCAGGAGCACCGGACTACCTGT GAGGCCTTCCAGTTGCAGGAGTTTGACCGGCTCACCATCCTCCGCAATGCCCTGTGGGTGCACTGTAACCAGCTCTCCAT GCAGTGTGTCAAGGATGATGAGCTCTATGAGGAAGTGCGGCTGACCCTTGAGGGCTGTGATGTGGAAGGTGACATCAATG GCTTCATCCAGTCCAAGAGCACTGGCAGAGAGCCCCCAGCTCCGGTGCCTTATCAGAACTACTATGACAGGGAGGTGACC CCACTGATTGGCAGCCCTAGCATCCAGCCCTCCTGCGGTGTGATAAAGAGGTTCTCTGGGCTGCTACATGGAAGTCCCAA GACCACACCTTCTGCTCCTGCTGCTTCCACAGAGACTCTGACTCCCACCCCTGAGCGGAATGAGTTGGTCTACGCATCCA TCGAAGTGCAGGCGACCCAGGGAAACCTTAACTCATCAGCCCAGGACTACCGGGCACTCTACGACTACACTGCACAGAAT TCTGATGAGCTGGACATTTCCGCGGGAGACATCCTGGCGGTCATCCTGGAAGGGGAGGATGGCTGGTGGACTGTGGAGCG GAACGGACAACGTGGCTTTGTCCCTGGGTCGTACTTGGAGAAGCTCTGAGGAAAGGCTAGCAGTCTCCACATACCTCCGC CCTGACTGTGAGGTCAGGACTGTTTCTTTCCATCACCGCCCAGGCCTCACGGGGCCAGAACCAAGCCCGGTGGTGCTGGG CATGGGCTGGGTGCTGGCTACTCTCAATAAATGTCTCCCAGAAGGAAAAAAAAAAAAAAA | MMAQLQFRDAFWCRDFTAHTGY EVLLQRLLDGRKMCKDVEELLR QRAQAEERYGKELVQIARKAGG QTEMNSLRTSFDSLKQQTENVG SAHIQLALALREELRSLEEFRE RQKEQRKKYEAIMDRVQKSKLS LYKKTMESKKAYDQKCRDADDA EQAFERVSANGHQKQVEKSQNK AKQCKESATEAERVYRQNIEQL ERARTEWEQEHRTTCEAFQLQE FDRLTILRNALWVHCNQLSMQC VKDDELYEEVRLTLEGCDVEGD INGFIQSKSTGREPPAPVPYQN YYDREVTPLIGSPSIQPSCGVI KRFSGLLHGSPKTTPSAPAAST ETLTPTPERNELVYASIEVQ ATQGNLNSSAQDYRALYDYTAQ NSDELDISAGDILAVILEGEDG WWTVERNGQRGFVPGSYLEKL |
| SEQIDNO.24 | SEQIDNO.:117 |

FIG. 45

| NucleotideSequence<br>(5'-3') | ORFs |
|---|---|
| ATGGTTAGGGGTGGAGGACCTGTGATGAGTGCAGCCTCCAATCGCAGCAAAAGGACGAAGGTCCTTCGCC<br>ACCTGCCAGCAGAAGACGCTGCAAGCGCCCGCGGCGCCGCAGTAGCCTCTCTCCTGCTGCAGTCCCGACA<br>GAGTTTCAGATCCAAATCCATAGGGCTAGCGCTCCTCTTCCCCTCGCCCCGCTCCCCTGCCTTCGACCTC<br>CTCTGGAGGCCCGGAGGAAGGAAGCAGGGCACTTTGCCACTTCTAAGGAAGGGGAGGAGAGGCGGCGACA<br>GAGACTCCCACAGAAGGAGCCCCAAGCCCTGTATCCTTCTCCCCACTCCCCGCCCGCACACCCGCGCAGG<br>TCCGATGCTGGCGAGTGGGCCACTTGCCAAGGTGTCGGTGCTCACTCCGGGTGCCGGGATTCAGGCGGGA<br>CTGCCTTCCCTCCGGGTGCGTTCGCCTCCCGCCCCGCTCCCCGCCTGGACGTCTGCGGAAAAAGAAGATA<br>AAAGAGTACCTGGAGCGAACACCATGACTTCCTTCAGCCGCTACACCCTTGGGTTTCTAGAGGTGGACAG<br>ACAGAGGGCGGGAGCCGACGGGGGACCGGGGAACCGCGGGGCCGGGAGCAGACGGGCGCGCAGGGTGCGG<br>GCGGGACGGTCAGCACCTCGGACAGCTCCCTGCGCGCGGTCCCGGGCCGCGGCTCAGCGCTGGGCGCGCG<br>CTGCCTCCACAATGCACCGCTCCGCCGGCGGGAGGAGGAGAGGCAACCCGGCTCAGCTCCTCCTCGGTCC<br>CCGCGCCAGCTTGGCGATTCACCGCCGAAGGAGCAGGGCGCTTCTACCGCTTCCACCGAAGCAGGAAGGA<br>CGGAAGGGGAAGCCAGACAGAAAGGGAGCTGGCTGCCAATATAAAGTCTGTCTTCCGCTCTGCCCGCCTA<br>TACGAAATGCTCCCAGAGACAATGTGAGAAGGCCTGCAATTTTCTGTGCTTCTGGCAATGGTAGAAAGGA<br>GAAGTAGATAAGGAAAGATCCCCCTCCAGATGATGAATGCTACCCGAGCTCATATCGGTGAAGGGAACCT<br>GTGCTATTCGGTCGAATGCAACCGCCCTTGCAAGACGTGGCTTGTCAGCGCTACTCATCGAAGTGTAAAC<br>CCATCTCTGAAGACCTGGCAGGCAGAAGTACTCTCCCCACCCCAACCCCACCCACGGACTTTGCAGCATC<br>AGTCCATTTGTACACTCGGATCTCTAAGGAAAACAGCATCATCGACGTGAATGACAGCTGCAGCGGGAGC<br>CGGGGAGCGGGCGGTCAGATGCTCCGCCGGGGCTGTCCACTCCGCGGGCACTGAAAACGTCAGGGAAGGT<br>CTCTCTTGGAGCCAACGCGGACTTGACAAAACAGTTGACAATTAGGGCAAAGCACGTACGGCAGAATCAT<br>TAGAACCCACAGAAGCCCCGGCCCCAGCGGCGACACCGCGGCGTGGCGATGCCCC | MVRGGGPVMSAASNRSKRTKVL<br>RHLPAEDAASARGAAVASLLLQ<br>SRQSFRSKSIGLALLFPSPRSP<br>AFDLLWRPGGRKQGTLPLLRKG<br>RRGGDRDSHRRSPKPCILLPTP<br>RPHTRAGPMLASGPLAKVSVLT<br>PGAGIQAGLPSLRVRSPPAPLP<br>AWTSAEKEDKRVPGANTMTSFS<br>RYTLGFLEVDRQRAGADGGPGN<br>RGAGSRRARRVRAGRSAPRTAP<br>CARSRAAAQRWARAASTMHRSA<br>GGRRRGNPAQLLLGPRASLAIH<br>RRRSRALLPLPPKQEGRKGKPD<br>RKGAGCQYKVCLPLCPPIRNAP<br>RDNVRRPAIFCASGNGRKEK |
| SEQIDNO.25<br><br>CCTCGATTCAGTTTTGGTGAAATGGCGGCCATTCTCATCTTCTCGGAGCCCTTCTCTTTGCTCACACTCGCGATTCTGCC<br>CCCGCAAGAGTACTCTGGGGACGTCCTTATCGCTGGGAGAGAGCGGTCGCATCTCATTCCTGAACCTGTTGGCTCGCTG<br>GGCGCGTCACCTGGCTAGCAGCTTGGGCCAGCTCCGCAGGCTAACTTTCCTGGACGCCTACTGAAGAGTCTGCTCCTCTC<br>TGTGTTCTTTCCAGTGTCTCGTTCGATCCAGTTTTCTGGTGGTCTCCAGCGAAGACAGGCGACAAAGCCGTTGTTGAGTG<br>GGATGGGCCGGCGACCGCCCGGTAGTGTCTCTATTGCAAGAACTCTGAGAGAAATGAAGAGAGTCCTCAGCAATGATGTT<br>GGCTTCTCGTGGTTCCCAGAGCCCTGCTTAATGGATGGAGACTGGACGAGAACCTGGCTGCTGTGGTTCTGAACATGGCC<br>CAGAGCCCTGTGTCTGCCGAGGTCATTCACCAGGTGGAAGAGTGTCTTGATGAAGACGAGAAGGAGATGATGCTCTTCCT<br>GTGTAGAGATGTGACTGAGAACCTGGCTGCACCTAACGTCAGGGACCTCCTGGATAGCTTAAGTGAGAGAGGCCAGCTCT<br>CTTTTGCTACCTTGGCTGAATTGCTCTACAGAGTGAGGCGGTTTGACCTTCTCAAGAGGATCTTGAAGACAGACAAAGCA | SEQIDNO.:118<br><br><br>MAQSPVSAEVIHQVEECLDEDE<br>KEMMLFLCRDVTENLAAPNVRD<br>LLDSLSERGQLSFATLAELLYR<br>VRRFDLLKRILKTDKATVEDHL<br>RRNPHLVSDYRVLLMEIGESLD<br>QNDVSSLVFLTRDYTGRGKIAK<br>DKSFLDLVIELEKLNLIASDQL<br>NLLEKCLKNIHRIDLNTKIQKY |

FIG. 46

| NucleotideSequence (5′-3′) | ORFs |
|---|---|
| ACCGTGGAGGACCACCTGCGCAGAAACCCTCACCTGGTTTCTGATTATAGGGTCCTGCTGATGGAGATTGGTGAGAGCTT<br>AGATCAGAACGATGTATCCTCCTTAGTTTTCCTTACAAGGGATTACACAGGCAGAGGCAAGATAGCCAAGGACAAGAGTT<br>TCTTGGATCTGGTGATTGAATTGGAGAAACTGAATCTAATTGCTTCAGACCAATTGAATTTGTTAGAAAAATGCCTGAAG<br>AACATCCACAGAATAGACTTGAACACAAAGATCCAGAAGTACACCCAGTCCAGCCAAGGAGCAAGATCAAATATGAATAC<br>TCTCCAGGCTTCGCTCCCAAAATTGAGTATCAAGTATAACTCAAGGCTCCAGAATGGGCGAAGTAAAGAGCCAAGATTTG<br>TGGAATACCGTGACAGTCAAAGAACACTGGTGAAGACATCCATCCAGGAATCAGGAGCTTTTTTACCTCCGCACATCCGT<br>GAAGAGACTTACAGGATGCAGAGCAAGCCCCTAGGAATCTGCTTGATCATTGATTGTATTGGCAACGACACAAAATATCT<br>TCAAGAGACCTTCACTTCCCTGGGCTATCATATCCAGCTTTTCTTGTTTCCCAAGTCACATGACATAACCCAGATTGTTC<br>GCCGATATGCAAGTATGGCCCAACATCAAGACTATGACAGCTTTGCATGTGTTCTGGTGAGCCTAGGAGGCTCCCAAAGC<br>ATGATGGGCAGAGATCAAGTTCACTCAGGGTTCTCCTTGGATCATGTCAAGAACATGTTCACGGGGACACGTGCCCTTC<br>TCTCAGAGGGAAGCCAAAGCTCTTTTTTATTCAGAACTATGAGTCGTTAGGTAGCCAGTTGGAAGATAGCAGCCTGGAGG<br>TAGATGGGCCATCAATAAAAAATGTGGACTCTAAGCCCCTGCAACCCAGACACTGCACAACTCACCCAGAAGCTGATATC<br>TTTTGGAGCCTGTGCACAGCAGACGTATCTCACTTGGAGAAGCCCTCCAGCTCATCCTCTGTGTATCTGCAGAAGCTCTC<br>CCAGCAGCTGAAGCAAGGCAGGAGACGCCCACTCGTGGACCTCCACGTTGAACTCATGGACAAAGTGTATGCGTGGAACA<br>GTGGTGTTTCGTCTAAGGAGAAATACAGCCTCAGCCTGCAGCACACTCTGAGGAAGAAACTCATCCTGGCTCCTACGTGA<br>GAACCCCAGACCGTTGGTGTTCTTGGTATATCATCCAGGGTGGCGGCTTGGAGCAGAGCTTGGCGGTTACGGCTGCTTCT<br>GGCTGCTTCTGGCTCTGCCGTGAGTCCTGGCCTAGGGTTCTCCTGTGCACAGGCATGAGCCGTAACCCTGTGCCTGGGAA<br>ACGTCTCACTCCCGCCGCCGTGCCTTTACCTCTCTAAACTTCCCTACTTACATTCCTTAGTCGGATGTTTTGCCAGAGTG<br>TGGAGAACAGTAAGACATAAACCTATTGTTTGTTTGTTTTTTTGGGGGGGAGGTTATCTACCAAGTTATACCAAGTTATT<br>GTATGGGTGTATAGTGTATAGTGGTTCAAGATTTGACACTGAATGTAACTTGAGACTTACCTGAGTTTGTCATGCGACTG<br>GGTAAATTGTTTCTATGGCACATCTAATCATTTAATAAGTAATTACCTCATTAAGTACCCATTGCTTCAGGACTTTCACA<br>TTGGCCACCAATTTCTGTGACCCAGCTCCACATTTATATTCTCTTTCTGCAAAACCAAATTTCATTATGTCTGTTTAATA<br>TCTACAGTCTAATGCTTTGTAAGACATCTAGATAGAAAAATAGTTACCCATGAGCACAGGAGGGCTGGCCTGACCCTCAC<br>CAGCTGTGCAGTGGCTTCGGTGAAGGAGAATGAGCCCTACTCCTTGAAGGTTGTAGTGCTTGGGAGAGCAGTCTGTACCT<br>TGCCTGGGCAGCACAGTAGAGCCAGCCCCAAGAACACAACAGTGAGTGGGGGAGCTTGCCCTGGTTGGCTCAGGATCAGG<br>AACAGGAGGGATGACCAACTTGGGGCTTTGAGGTGGCCCACCCCAGCATCCATATCATCTGTGAACTGCCAGAGCCTGTG<br>AAGGGGCGGGTCCTGTAGAACTAAGGCTGCAGGATCTCCATGACACAGGGCAACAACAGGGTATCTGAGAAGGGTCCCCG<br>TGAGGGTCCAGTATTTATAGTGCACCAGAAGCCAGAGGCCTCGGATCAGACAATGACCCATTGCACTGAGTAAAGATGTA<br>AGTGAATGAGTGAAGATGTGTGGGCACACGGAAATACTGAGGGACACACACAAGCTTTTATGGAGATGTTTGTTTGTTTG<br>TTTGTTTGTTTTTTGTTTCTTTGGCAGGAACAGATTGCAAGGGCAGAGAGTAGATAAGGAAGCTGGAGACATGAGTGGGG<br>TTGGGTGCATGATATAGAATTCACAAAGAATCAAAAAAAAAAAAAAAA | TQSSQGARSNMNTLQASLPKLS<br>IKYNSRLQNGRSKEPRFVEYRD<br>SQRTLVKTSIQESGAFLPPHIR<br>EETYRMQSKPLGICLIIDCIGN<br>DTKYLQETFTSLGYHIQLFLFP<br>KSHDITQIVRRYASMAQHQDYD<br>SFACVLVSLGGSQSMMGRDQVH<br>SGFSLDHVKNMFTGDTCPSL<br>RGKPKLFFIQNYESLGSQLEDS<br>SLEVDGPSIKNVDSKPLQPRHC<br>TTHPEADIFWSLCTADVSHLEK<br>PSSSSSVYLQKLSQQLKQGRRR<br>PLVDLHVELMDKVYAWNSGVSS<br>KEKYSLSLQHTLRKKLILAPT |
| SEQIDNO.26 | SEQIDNO.:119 |

FIG. 47

| Nucleotide Sequence (5′-3′) | ORFs |
|---|---|
| CCTTTGAACAACTTTGTTGATGAGAGCTCTCCAGGATTGCCTATAGAAGAAGCTTTGGATGGAGTGCATGGAAGCGTAGC<br>TCTGGAGACGCTGAGGCAGCAGCAGGCGCGGCTACAGCAGTGAGGGCAGAGTGGAAAGTCGCCGGCAGGGCTGACGATGA<br>AACAGAGACAACATTCTCAAGGTTTCAAGACTTACTCAGAGAGCTGTCCCATCGGGATCAAGGTGACACTCGAGAACTAG<br>CTGAAATGCCACCACCTCAGTCAAGACTTCTGCAGTACAGACAAGTTCAGCCTAGAAGTCCGCCAGCGGTCCCGTCTCCC<br>CCTTCCTCCACAGACCACAGTAGCCAGTTTGCTAACTTTAATGACAGCAGCAGAGACATTGAAGTAGCCAACAGCCCAGC<br>ATTCCCGCAGCGCCTCCCGCCTCAGCTATTTGGCTCCCCTTTCTCGTTGCCATCTGAACACCTTGCCCCTCCTCCTCTGA<br>AATACCTGGCTCCGGAAGGAGCATGGAATTTTGCTAACTTGCAGCAGAATCACTTAATAGGGCCGGGCTTTCCCTATGGC<br>CTACCTCCATTGCCTCCCAGGCCACCACAGAACCCTTTTATACACATCCAGAACCATCAACACGCTGCTGGTCAAGAGCC<br>ATTTCACCCACTGTCATCTCGAACAGTGTCTGCTTCTTCGCTCCCCAGCCTAGAAGAGTATGAGCCCAGAGGACCTGGTC<br>GGCCCTTGTACCAAAGAAGAATCTCATCTAGCTCAGCCCAGCCTTGTGTGGAAGAGGCAAGCGCTCCCCAAGACAGCCTG<br>GCTCAGGGCAAAGAATCGCAGGGCCACAGCAACCCACCTGCCTTCAACTTCCCGGCCCCCGAGTCCTGGGCCAACACCAC<br>CTCATCTGCCCCCTACCAGAACATTCCGTGCAATGGATCCAGCAGGACGAGTCAGCCCAGAGAGTTGATAGCTCCACCCA<br>AGACTGTCAAACCCCCTGAGGATCAGCTGAAGCCCGAGAGCGGGGAGGTGTCCAGTTCCTTCAACTACTCGATGCTGCAG<br>CACCTTGGCCAGTTCCCACCCCTCATGCCCAACAAGCAGATCGCAGAGTCCGCCAACTGCAGCAGCCAGCAGAGCCCGGC<br>AGGGAGCAAGCCCGCCATGTCCTACGCCAGTGCGCTGCGGGCCCCGCCCAAGCCCAGGCCGCCACCCGAGCAGGCCAAGA<br>AGGGCAGCGACCCGCTGTCCCTGCTCCAGGAGCTCAGTCTGGGCAGCAGCCCGGGCAGCAATGGCTTCTACTCCTACTTC<br>AAGTGACCCCGCTCGCGCTGTCCTCAGAGAATATGCGGTTCCTGTCCAGTCTGCAGGATGGAGGTGGCGGCTCTGTGTGC<br>GTGCAGCCCTCCATTACGTTCACTGCGCTCTCAGCCCCCTTGCTGCTAGACCTGCGCCTACGTTTAAAAGTATATTCCAT<br>TATTTTGCATTTTTGATGTGAGTCAGAATTTTGACAGCTTTTATGTAGAATAAAAATATTTTTAAATTTGAAAAAAAAAA<br>AAAAAAAAAAAAAA | MPPPQSRLLQYRQVQPRSPPAV<br>PSPPSSTDHSSQFANFNDSSRD<br>IEVANSPAFPQRLPPQLFGSPF<br>SLPSEHLAPPPLKYLAPEGAWN<br>FANLQQNHLIGPGFPYGLPPLP<br>PRPPQNPFIHIQNHQHAAGQEP<br>FHPLSSRTVSASSLPSLEEYEP<br>RGPGRPLYQRRISSSSAQPCVE<br>EASAPQDSLAQGKESQGHSNPP<br>AFNFPAPESWANTTSSAPYQNI<br>PCNGSSRTSQPRELIAPPKTVK<br>PPEDQLKPESGEVSSSFNYSML<br>QHLGQFPPLMPNKQIAESANCS<br>SQQSPAGSKPAMSYASALRAPP<br>KPRPPPEQAKKGSDPLSLLQEL<br>SLGSSPGSNGFYSYFK |
| SEQIDNO.27<br><br>CGGCGCGTTGAGGGGCGGGGTGAAAGGTCACAGCGCGGCGGCGGGTCTGGCTGGCGGCAGCTGCGGGCGGGAGCCGAGTG<br>TCCCGAGTGCACGTGTGGAGGAGCGGCGGCGGCGGCAGCGCGGCGGCAGATTTCCCCGCGTCTCCCGGAGCCTCAGGGCC<br>TGGCTTGGCTTCTCAGCCAAAAGACCGGCGTGTGGGGTTGAGTGGTCTGAGCTCAGGGCGCGGGCGGAGAGCTCCGGGCG<br>ACGAGGACGACGGCGTTGGCGGCGGCTGTAACGACGGCCTCAGCAGACGGGGAAGATGAAAGGCCGGATCGAGCTGGGAG<br>ATGTGACGCCACACAATATTAAACAGTTGAAGAGACTGAACCAGGTCATCTTTCCAGTCAGCTATAATGATAAATTCTAC<br>AAGGATGTGCTAGAGGTTGGCGAGCTAGCAAAACTTGCATATTTCAATGATATAGCTGTAGGTGCAGTGTGCTGCAGGGT<br>GGATCATTCACAGAATCAAAAGAGACTTTACATCATGACACTAGGATGCCTTGCACCTTACCGAAGACTAGGAATAGGAA<br>CTAAAATGTTAAATCATGTCCTAAACATCTGTGAGAAGGATGGCACTTTTGACAATATCTATCTGCATGTCCAGATCAGC<br>AATGAGTCAGCGATTGACTTTTACCGGAAGTTTGGCTTTGAGATTATCGAGACAAAGAAGAACTACTATAAGAGGATAGA<br>GCCTGCAGACGCGCATGTGCTTCAGAAAAACCTCAAAGTCCCATCTGGTCAGAATGCAGAGACACAGAAGACAGACAACT<br>GAACAAATCACAAATGAACTTTCTTGCACTTGCTTGTCGCCAAATAAAAGAAAGACCCATTGGTTCCCTTCCCCCCTTTC | SEQIDNO.:120<br><br>MKGRIELGDVTPHNIKQLKRLN<br>QVIFPVSYNDKFYKDVLEVGEL<br>AKLAYFNDIAVGAVCCRVDHSQ<br>NQKRLYIMTLGCLAPYRRLGIG<br>TKMLNHVLNICEKDGTFDNIYL<br>HVQISNESAIDFYRKFGFEIIE<br>TKKNYYKRIEPADAHVLQKNLK<br>VPSGQNAETQKTDN |

FIG. 4B

| NucleotideSequence (5'-3') | ORFs |
|---|---|
| TTCCACTTTCCTCCTTTGTTATTCCTTTTTTTTTTCTTTCCTCTTAAAGTTTTAATACTTTCATGGACTCTTAAAAATG<br>ATCATGTGTTGGATTGTTTTAGTTCTCTTACTTTTGTGAGGTGGTTGGATTGAAGGAGGAGAAGATAGATCTGTATAGTT<br>TCACAGTTAAGATGTCCCGAAAATTGGGTGGCAGATGATTTCAAATTTTTAGCTGAATTTTTTTAAAAAATAAAAACAAA<br>CCAACATCCTGCTTTCACATTGAAGGGCAGAGCCTACTATATTGTTTATTTCAAAAGACAAAAAGCAGCAGCAATACCTT<br>GCTCTCTAATTCATAGACAAGCTTAGTGTATCTGTGGTACTTTGAGTTATACAGACTGTCTGTGGGGTGCTAATCCCCAG<br>CATTGCCTTCACTCTACCCTTAGTCCTTTGAGCACTCTCAGGAGTTGGACCATTGTTATCCTTGTGAGAAAATACCAAGC<br>TTATTTAGGTTTTTAAAGCAATTTTTTTCTATTTGCTGATTGGCGGGGCAGTTTGTGTAGGTAGTAAGTATTAAACTTTG<br>GTCAAAGTATTTCAGTTAAACTGCTTTTTTTGCTGAGGAATGGACTTCTTGTTAGCAGGTTTTTTTTGTTTTTTCCTTCT<br>TTCCTGCTGTTAATCTTGTTACTAGAGGCATTAACTGGTAGAGTGTGGGCTGGTGAAATTAACTGTTTTAATATCCCAGC<br>TAGAGATATGGCCTTTAACTGACCTAAAGAAGATTGTTATAATTGATTTTTTTTCCTCTTGTTTTTCAGTAAGCCCAATA<br>ATAGTGTAACCTTATAAATGGAGTTATGCCCTTATAAGTCAATATCCCTAAATAAACCTGAAGCAAGTGTTTTCTCTTGG<br>ACGAACAGAATTGCATTACGTAAAAGGCTTAGATGGACTTGTAACACATTAAGTGTATTTAATGTCAACTAATACAGATT<br>GTTAAAAGTGTGGTCATTGAGTGTTTAATAATATATGAAAGAATTTCTAGACAGTATTTTTGAAAAGAACATTGTTATGC<br>TATTGCTTATCTGTTGGAGAACATCCCAGGTTAGCTTCCACTCTGTGCCTACAATGTTGAGTTTAAAGATTTGGAATAAG<br>AGGAATCAGTAGAAAAATTCCTTCTATTCTTGGAACAATAGACGTATAAAGTATTAATACAAATATCACTGTGACCTTCA<br>GCTGACAGGTTTGGTTAAGACCAGACCATCTTCAGGCACACTGGGAGTGGCTCTGATGGATTGAGAACTGTAATGTGGAG<br>ACATGTGAGATACGTTTTGCTCACATTGTCCTGTCTCAAATATATGGAATTTCTTAGATTGTTAGTAGTCATCAGTGGCT<br>CAAGAAATGTTCTTGTTAGACTTTAAAACAGTACAGATTGTGTGTTTTCTTTCATTTGACTTTAAAAGGAAGTTTAATAC<br>ATCATATTAGTAAAATTGTGGTATGAAAGTATCATTTCCAAATAGGTTGAATGATAAAATTATCTCACAAGATGATAAAA<br>CACCTTATAACTCTTACGTTTTTATTTGAGAATGTGAAAGTATGTAAAATGGACTTGAGTAGTCTTGAGTGCCAAGAATA<br>TAGATAAGGGGTGGGATGGATGGATGGATGGATGGATGGATGGATGGATGGATGGATGGGCGGGCTAGTGAAATTGTAGA<br>AATACCATGCTTGTTTCTTGGGTATCAGTTTCCTAAACAGTCCAAATCTAAGCTCAGAAGTTTAGTGTTAAGCACCCTTA<br>CTTTAATGGATAAGCTTCAGCGTGCTCTTGCCAAGAGAAGAGGGCATAAATAATAGTAAAATTAGTTTGAAAAACGTCAG<br>CAATTTTGTAAACTTCCTGATAGCAAAATAGATTTTGATATATAAAAGAGTTTTCTGAGATGACACTGCCTCTATTTCTA<br>TAACCATTTCACTTGGACTAAGTAGTCCTATGAATGTATCCCTAAATGTGGTTTTTGAAAACCGAATAGCTGCCTCACAA<br>CAATTAAGTACATGTTATTTAAAGAGGAAGAACAAATAATAAAGATTGATTTGAATGTGTAGGCTCCCTATTATAGCTTC<br>TTTTTCCACACTAGTCAGTGATTTAACCTAAAATTTAAATGTATGGGTCAATTGTCCTGTATCAAAGTTACAGTAAATAA<br>TTCCATCCACTTACATAAGGAGAAGATGTGGAAAATGTAGAAACTGGGACTAGTCCATGTACCTGTGAGTCAAGAAATAC<br>TAAAGTAATGCCCCAGTTGAGTTTGTGGGTTTGGGTTTTGATTTGTTTGGGCTTTCTCTTTGTTTTTAACATTATAAAAA<br>TAATCTTTGAGGTAAAACTAATTCTATTAACTGGAAGATACCCAGCTATCTTCATCATTTTTTCAGGAAAGATCATTTTT<br>ATTGTGGGGTAAATAGGTTAAAATTATTCTGTATGCTATTTGAATTTAGGTTCTAAAGTAAAGAATCCGTAGAGGAATCT<br>ATGCAATATGTAATTTGTCAAGATTAATTTTCATCTGGGGAAAGAAGTTGCTAAGTGTCTCCAAAGCAGGTCACTCAATA<br>ACTGAAAGTCCTCCAAAAAGAGAACTAGTGGGAAGCATGGTGTGTGGTGGTGGAAAAGAAAAACTCCCTCAGTTTTTGGA<br>GGGAATAACTTTAAAGATACTTAAGTGGCTACGTTTACTTGGTGCAGTTAAGAATTAAACTTGTCAATTTTAATGTTGCT | |

FIG. 49

| Nucleotide Sequence (5′-3′) | ORFs |
|---|---|
| GTTACATCTAAAATAAACTTATGTGATGTTCTGGTAGTGATCTGTCTGTAACTGTCATGAAATCATTATTGTGCTGAATT<br>TTACAGTCTGCAACTATGTCATTGTTGTGTACTGTGATCCATACATCCATATTTCACTAGGGCCTAATTTAAAACTCATG<br>AATAATCAAAGTATGCTAATTCAGACCTCTTGGAATTGGGAAAAGACACCAGGCAATATATCTGAATTTAATCTAGGTGA<br>AAAAAAGATCCCCAGGAATGCCTTATTGCCATATTTTAAATATAGTTACTATAAATAGAACTTTAGGCTTTATTCTAGTG<br>AGTATGAACTGTAAATGTGCATATTCTGATCTATTACTTTTTGTAGTGAAGATTTTAGTTGAGTGAGTGGATTTTATGTT<br>AAGTACTTCGAAATTTTTGACAGTGTTTAATATATCTAGTCACAATGGTCTGAATTAGTATTTTGCTTATTACCCAAGAA<br>ACAAAGGATGGCCTTTGTCTTATTTACCATATCACTACAAAATTTAGCAGTTTAAAATAACAGATTTGTTGTATCCTATA<br>GTTTCCCAATCAAGCAGTGTGTGACATAACCAGTTAGGTCTGACAAAGGATCTTATATCAGGTATCAGCCAAGGCTGCAA<br>ATTGATGAAGGCTTGACCGCAGCTACTTCATTTCACTCACATGGCTGTTCTGGAAACCATTTGGGACAGAACACTAACAT<br>AAGACTTGCTTAACAAAGCCTAGTATTAGTCTTAAAAAGTTATGGTCTTTTTGTTATATTGTAATGAAAGCTTAAATCTA<br>ACAATTGGAAAGTGGTATTGTTGGATAGGATATTTTGTAAATTTACGAACATTCAGTGAACTCATTTACTGTCCTCAACA<br>ATTCAAGACATATGAGTTAAGTATGGATTAAAACATGTTGATACT | |
| SEQIDNO.28<br><br>GGCAAAGGCGCGCGTTCTCTGCTCTGCGCCCCGGGCGGAGAAGGCATCATGTCAGACAACGAGGACAATTTCGACGGCGA<br>CGACTTTGATGACGTTGAGGAGGACGAAGGACTTGACGACTTGGAAAATGCTGAGGAGGAGGGCCAGGAAAATGTCGAGA<br>TTCTCCCATCTGGTGAGCGACCACAGGCCAACCAGAAGCGGATCACCACTCCTTACATGACCAAGTATGAGCGTGCCCGA<br>GTGCTGGGCACCCGGGCTCTTCAGATCGCGATGTGTGCCCCGGTGATGGTGGAGCTGGAGGGGGAGACAGACCCTTTGCT<br>CATCGCCATGAAGGAACTCAAGGCGCGGAAGATCCCCATCATCATTCGCCGGTACCTGCCAGACGGCAGCTATGAGGACT<br>GGGGCGTGGACGAGCTTATCATCAGCGACTGAGCCGGGCGCGCTCGGCCTGCACCAGCTCTGCTGGGCACCCTCTCTGTG<br>CCCGTTTTATATGTGTAAATAATAAACCTCACCCTTTCCAAAAAAAAAAAAAAAAAAAAAAAAAAAAAAAAAAAAAAAAA | SEQIDNO.:121<br><br>MSDNEDNFDGDDFDDVEEDEGL<br>DDLENAEEEGQENVEILPSGER<br>PQANQKRITTPYMTKYERARVL<br>GTRALQIAMCAPVMVELEGETD<br>PLLIAMKELKARKIPIIIRRYL<br>PDGSYEDWGVDELIISD |
| SEQIDNO.29<br><br>CCACGCGTCCGCGGACGCGTGGGCGGGCACAGGAGAGCTCTCGGCACCTCCGGGAAAGCCACCTCGGCCTCCCCCGCGCC<br>CGGGCTCCAGCCGCGGCCGGCCCAGCCTCGACCTCAGCAGCGACCAGCTGCTCCTGCGAGGAGCCGAGCGAGCCCGGTCG<br>CGGGCGGGGAGCGTGCGTCGGTTCGCACAGGCTGCGAGAGGAGGGGCGGCGCGAGTCATGGCCGGGGACAGCGAGCAGAC<br>CCTGCAGAACCACCAGCAGCCCAACGGCGGCGAGCCCTTCCTGATCGGCGTGAGCGGGGGCACGGCCAGCGGGAAGTCTT<br>CCGTTTGTGCTAAGATCGTCCAGCTTTTGGGGCAGAATGAGGTGGATTACCACCAGAAGCAGGTGGTGATCCTGAGCCAG<br>GATAGCTTCTACCGAGTCCTCACCTCAGAGCAGAAGGCCAAAGCCCTCAAGGGCCAATTCAACTTTGATCACCCGGATGC<br>CTTTGACAACGAACTCATCTTCAAAACACTCAAAGAAATCACCGAAGGAAAAACCGTCCAGATCCCCGTATACGACTTTG<br>TCTCCCACTCACGGAAAGAGGAGACGGTCACCATCTACCCCGCCGACGTGGTGCTCTTCGAAGGGATCCTAGCCTTCTAT<br>TCCCAGGAGGTCCGAGACCTGTTCCAGATGAAGCTTTTCGTGGACACAGATGCGGATACCCGTCTGTCTCGCCGAGTATT | SEQIDNO.:122<br><br>MAGDSEQTLQNHQQPNGGEPFL<br>IGVSGGTASGKSSVCAKIVQLL<br>GQNEVDYHQKQVVILSQDSFYR<br>VLTSEQKAKALKGQFNFDHPDA<br>FDNELIFKTLKEITEGKTVQIP<br>VYDFVSHSRKEETVTIYPADVV<br>LFEGILAFYSQEVRDLFQMKLF<br>VDTDADTRLSRRVLRDISERGR |

FIG. 50

| NucleotideSequence (5′-3′) | ORFs |
| --- | --- |
| GAGGGACATCAGCGAAAGAGGGAGGGACCTTGAGCAGATTTTATCACAGTACATTACGTTTGTGAAGCCTGCCTTTGAGG | DLEQILSQYITFVKPAFEEFCL |
| AATTCTGCTTGCCAACAAAGAAATACGCCGATGTGATCATTCCTAGAGGTGCCGACAATCTCGTGGCCATCAACCTCATC | PTKKYADVIIPRGADNLVAINL |
| GTGCAACACATCCAGGACATCCTCAACGGGGGCTCTCCAAGCGGCAGACGAACGGCTATCTCAACGGCTACACCCCTTC | IVQHIQDILNGGLSKRQTNGYL |
| CCGCAAGAGGCAGGCGTCAGAGTCCAGCAGCCGACCACATTGACTCCCGTGCCCCTGACTCCAAACCCCAGCCCCCCAGC | NGYTPSRKRQASESSSRPH |
| TCCAAGACACAGGAGGGGTCGAGAGGCTCTGGTCACCTGTACATACGCCTCCTCAGAAAATTACTGTATTTAAGAAAACA | |
| CCACGGAGATGAAATGCCTTGATTTCCCTTTCTGCCTTTTTGTACTTTGGAACAGCAAATCTTGATGGAACTTGACCCTG | |
| AGCTTAAGTGACAAACTGTGCCAACTAGTACTGGTGATGCCTAATTATGAACCCAACGTGTAACCAGTTATAAATACACA | |
| CATACATACGTCTATATAAAAAAAAAAAAAAA | |
| SEQIDNO.30 | SEQIDNO.:123 |
| CTGCGCTCCGCCGCGCGGAGTAGAATGAACTGTAACAAAACAAGCCGAGCCTTTGTATCTGCTTAAAGGGGCCGCGGCCA | |
| CTTCCCTCGCGTCCCCTCACCCCCGCCCCGCGCCGTCGCGTCTCCAGGGCTCCCGGCAACTAGCTTGGAAAGGGCTTCCC | MSKVIQKKNHWTGRVHECTVKR |
| TCGCGCTGAGGAGCGGCCGGCCGGCGCGGAGCAGGCGCGGCGTGTGTGGAGAGAGCCGCGGAGCGGAGAGCGGGCCCGGG | GPQGELGVTVLGGAEHGEFPYV |
| CGGCGCCGGAGTGGACTCTGGTCCCGGGAGCGCGGTCGGCGCCGGAACGCGGACCCGGAGGCACCGGAATGCAAACAAAG | GAVAAAEAAGLPGGGEGPKLAE |
| CTCGCGGGCGCCCGTGCAGGGCTCTTCACGGAGCCCGGAAAGTTTGTTTTATGATGGCTTGAGAGCGCGAGAGAGTCGGG | GELLLEVQGVRVSGLPRYDVLG |
| CGAGGAGGCTCGAGTAGCTCGCTCCCGCGCTCCGAGAGATGCTTCTCCCGTGAGCCCGCCGCTCCGGGGGCTCGTGCTGT | VIDSCKEAVTFKAVRQGGRLNK |
| GGGGGCACCTGTCTCTCGTTTTAGCAGTTTTCTTTTCTTTTTCTTTTTTTCTTTAATTTGAATTTTGTTTTCGAGGAGGG | DLRHFLNQRFQKGSPDHELQQT |
| GCTGTAACTCATCATGTCGAAAGTGATCCAGAAGAAGAACCACTGGACTGGCCGCGTTCACGAGTGCACCGTGAAGCGGG | IRDNLYRHAVPCTTRSPREGEV |
| GACCCCAGGGCGAGCTGGGGGTGACGGTCCTGGGGGGCGCGGAGCATGGGGAGTTTCCGTACGTGGGGGCGGTGGCGGCG | PGVDYSFLTVKEFLDLEQSGTL |
| GCCGAGGCGGCGGGGCTTCCCGGCGGTGGCGAGGGGCCGAAGCTGGCCGAAGGTGAGCTGCTGCTGGAGGTGCAGGGGGT | LEVGTYEGNYYGTPKPPSQPVS |
| CCGGGTGTCCGGCTTGCCCCGCTATGACGTGCTGGGAGTCATCGACAGCTGCAAGGAGGCCGTCACCTTCAAAGCCGTCA | GKVITTDALHSLQSGSKQSTPK |
| GACAAGGAGGAAGGCTCAACAAGGACCTACGACATTTCCTCAACCAACGGTTCCAGAAGGGGTCTCCAGATCATGAGCTC | RTKSYNDMQNAGIVHPENEEEE |
| CAGCAGACCATAAGGGACAACCTCTACCGCCATGCTGTGCCTTGCACAACCCGGTCTCCCAGAGAAGGAGAAGTGCCTGG | DVPEMNSSFTADSGDQDEHTLQ |
| CGTGGATTACAGCTTTCTGACTGTGAAGGAGTTCTTGGACCTCGAGCAGAGCGGGACCCTGTTGGAAGTCGGCACCTATG | EATLPPVNSSILAAPITDPSQK |
| AAGGAAACTATTATGGACACCCAAACCTCCCAGCCAGCCAGTCAGTGGAAAGTGATCACGACGGATGCCTTGCACAGC | FPQYLPLSAEDNLGPLPENWEM |
| CTGCAGTCTGGCTCCAAACAGTCGACCCCTAAGCGAACAAAGTCCTACAATGATATGCAAAATGCTGGCATAGTCCACCC | AYTENGEVYFIDHNTKTTSWLD |
| GGAGAATGAGGAGGAGGAGGATGTCCCTGAAATGAACAGTAGCTTTACAGCCGACTCTGGAGACCAGGACGAGCACACTC | PRCLNKQQKPLEECEDDEGVHT |
| TCCAAGAAGCAACGCTCCCACCTGTGAATAGTAGCATCCTCGCTGCTCCCATCACGGACCCTTCTCAGAAGTTCCCTCAG | EELDSELELPAGWEKIEDPVYG |
| TACCTACCTCTTTCTGCAGAGGATAATTTAGGTCCTCTACCTGAAAACTGGGAGATGGCCTATACTGAAAATGGAGAAGT | VYYVDHINRKTQYENPVLEAKR |
| CTATTTCATAGACCACAACACGAAAACAACATCATGGTTAGACCCTCGGTGCCTGAACAAACAGCAGAAGCCTCTGGAAG | KKQLEQQQQQQPQPPQPEEWT |
| AATGTGAAGATGATGAAGGGGTACACACCGAGGAGCTGGACAGTGAACTAGAGTTGCCTGCTGGCTGGGAAAAGATTGAA | EDHASVVPPVAPSHPPSNPEPA |
| GACCCTGTCTACGGTGTCTACTATGTAGACCACATCAACAGGAAGACGCAATATGAAAACCCAGTCCTAGAAGCCAAACG | RETPLQGKPFFTRNPSELKGKF |
| GAAGAAACAGCTTGAACAGCAGCAGCAACAGCAGCAGCCTCAGCCACCGCAGCCAGAAGAGTGGACAGAGGATCATGCAT | IHTKLRKSSRGFGFTVVGGDEP |

FIG. 51

| NucleotideSequence (5'-3') | ORFs |
|---|---|
| CTGTTGTGCCTCCTGTTGCTCCTTCCCATCCCCCGAGCAATCCGGAGCCAGCCAGGGAAACTCCACTTCAGGGCAAACCT | DEFLQIKSLVLDGPAALDGKME |
| TTTTTTACAAGAAACCCCTCTGAGCTGAAAGGCAAGTTCATTCACACGAAGCTACGGAAAAGCAGCCGAGGCTTTGGCTT | TGDVIVSVNDTCVLGHTHAQVV |
| CACGGTGGTTGGAGGAGACGAGCCTGATGAGTTCCTGCAGATCAAGAGCCTCGTCCTCGATGGTCCTGCCGCACTGGATG | KIFQSIPIGASVDLELCRGYPL |
| GCAAGATGGAGACAGGGGATGTAATTGTGAGTGTGAATGACACCTGTGTTTTGGGACACACACATGCTCAAGTTGTGAAA | PFDPDDPNTSLVTSVAILDKEP |
| ATCTTCCAGTCCATTCCCATTGGTGCCAGTGTGGACCTTGAACTCTGCAGAGGTTATCCATTGCCTTTTGACCCGGATGA | IIVNGQETYDSPASHSSKTGKV |
| CCCTAATACAAGTTTAGTGACCTCGGTGGCCATTTTGGACAAAGAACCAATTATTGTAAATGGACAAGAGACCTACGATT | SSMKDARPSSPADVASNSSHGY |
| CACCAGCGAGCCACAGTAGTAAAACAGGCAAAGTCAGCAGCATGAAGGACGCCAGGCCAAGCAGCCCTGCTGATGTGGCT | PNDTVSLASSIATQPELITVHI |
| TCCAACAGCTCTCATGGTTACCCCAACGACACAGTCTCCTTGGCTTCCTCCATAGCCACCCAGCCAGAGCTAATAACTGT | VKGPMGFGFTIADSPGGGGQRV |
| TCACATAGTCAAAGGGCCAATGGGATTTGGCTTTACGATCGCAGACAGTCCCGGTGGGGGTGGCCAAAGAGTGAAACAGA | KQIVDSPRCRGLKEGDLIVEVN |
| TTGTTGACAGTCCACGCTGCAGAGGCCTCAAAGAAGGGGATCTTATCGTGGAGGTGAATAAGAAGAACGTGCAGGCCCTG | KKNVQALTHNQVVDMLIECPKG |
| ACGCACAATCAAGTCGTGGATATGCTGATTGAATGTCCCAAGGGAAGTGAGGTCACACTGTTGGTGCAGCGAGGAGGGCT | SEVTLLVQRGGLPVPKKSPKSP |
| ACCAGTTCCCAAGAAGAGCCCAAAGTCGCCACTGGAGAGGAAAGACAGCCAGAATAGCTCCCAGCACAGCGTCTCCAGCC | LERKDSQNSSQHSVSSHRSLHT |
| ACCGGAGCCTGCACACTGCGTCCCCGAGCCACGGCATACAGGTGCTCCCTGAGTACCTACCTGCAGACGCCCCTGCTCCA | ASPSHGIQVLPEYLPADAPAPD |
| GATCAGACCGACAGCTCTGGGCAGAAAAAGCCAGATCCTTTTAAAATCTGGGCCCAGTCCAGGAGCATGTATGAAAACCG | QTDSSGQKKPDPFKIWAQSRSM |
| ACTTCCAGATTACCAGGAACAGGACATCTTCCTCTGGAGAAAAGAAACCGGATTTGGATTTAGGATTCTGGGTGGAAATG | YENRLPDYQEQDIFLWRKETGF |
| AACCAGGGGAACCCATTTATATCGGTCACATCGTACCGCTGGGTGCTGCTGACACAGACGGCCGCCTGAGGTCTGGAGAT | GFRILGGNEPGEPIYIGHIVPL |
| GAATTAATCTGTGTGGATGGGACACCAGTAATTGGGAAATCACACCAGCTCGTGGTCCAGCTTATGCAACAAGCTGCCAA | GAADTDGRLRSGDELICVDGTP |
| GCAAGGCCATGTCAATCTCACAGTGAGGCGGAAAGTGGTCTTTGCCGTCCCCAAAGCAGAGAATGAGGTGCCCTCACCAG | VIGKSHQLVVQLMQQAAKQGHV |
| CCTCATCACACCACAGTAGCAACCAGCCCGCGTCCCTGACGGAGGAGAAACGCACACCGCAAGGCAGCCAGAACTCTCTG | NLTVRRKVVFAVPKAENEVPSP |
| AACACTGTGAGCTCTGGCAGCGGCAGCACCAGTGGCATTGGCAGTGGTGGCGGCGGGGGCAGCGGTGTGGTGAGCGCTGT | ASSHHSSNQPASLTEEKRTPQG |
| GCTGCAGCCCTATGATGTGGAGATTCGGCGTGGGGAGAACGAGGGCTTTGGGTTTGTCATCGTGTCCTCCGTGAGCAGGC | SQNSLNTVSSGSGSTSGIGSGG |
| CCGAAGCGGGCACAACCTTCGAGTCCTCAAATGCCACGCTGCTGACTAATGCTGAGAAGATTGCCACCATCACCACCACT | GGGSGVVSAVLQPYDVEIRRGE |
| CATGCCCCCTCTCAGCAGGGGACCCAGGAAACAAGGACCACCACCAAACCAAAGCAGGATTCTCAGTTTGAGTTCAAAGG | NEGFGFVIVSSVSRPEAGTTFE |
| ACCGCAGGCTGCACAGGAGCAAGATTTCTACACTGTGGAATTGGAAAGAGGGGCCAAGGGATTTGGCTTTAGTCTTCGAG | SSNATLLTNAEKIATITTTHAP |
| GGGGCCGAGAATATAACATGGATCTTTATGTTCTGCGCTTGGCAGAGGATGGTCCTGCAGAAAGATGTGGGAAGATGAGG | SQQGTQETRTTTKPKQDSQFEF |
| ATTGGCGATGAAATTCTAGAGATCAATGGTGAGACCACCAAAAACATGAAACACTCTCGGGCCATAGAACTGATCAAGAA | KGPQAAQEQDFYTVELERGAKG |
| | FGFSLRGGREYNMDLYVLRLAE |
| | DGPAERCGKMRIGDEILEINGE |
| | TTKNMKHSRAIELIK |
| SEQIDNO.31 | SEQIDNO.:124 |
| GGAAATCCTGGAAGGATTTATATCTCCTCCTGTGGTTCTGGTGGGGAAGGACTCGTGCCGAATTCGGCACGAGTGGAGCT | |
| GGCCTGAACTTTGGACCTTGTCTTCCAGTAGGAAATCAGTCTCTCAGAAGGCGATCATGGCCTCCAAGCCTGAGAAAAGG | MASKPEKRVASSVFITLAPPRR |

FIG. 52

| Nucleotide Sequence (5'-3') | ORFs |
|---|---|
| GTGGCCTCCTCTGTCTTCATCACCCTGGCACCGCCACGCCGAGATGTAGCCGTGAGTGAGGAAGTGGGCCAGGCAGCTTG | DVAVSEEVGQAACEARRARPWE |
| TGAAGCCAGACGCGCTCGGCCCTGGGAGATGCTTCCCACAAAGACACCTGGGGCCGCAGTGGGCAGGAGCCCCAAGACCT | MLPTKTPGAAVGRSPKTWTPSG |
| GGACGCCCTCTGGCAAGACCAATGCCTCACTCTCTGGAGTCACACCTCAGCTCTCCAATGGAGGATGCTCTCTCCCACCT | KTNASLSGVTPQLSNGGCSLPP |
| CCTTCCCTGAATGAGGAGGACCTAGACCTCCCGCCTCCTCCACCGCCCCCTTCTGCCTACCTGCCTCTCCCAGAAGAGGA | PSLNEEDLDLPPPPPPPSAYLP |
| GCCTCCTGTCTTACCAGGGAAGTCGCTCATTTCCGACTTGGAGCAACTGCACCTGCCCCCACCCCCGCCTCCACCCCCGC | LPEEEPPVLPGKSLISDLEQLH |
| CACAGGCTCCATCAAAGGGATCGTCTGTCCACCCTCCGCCTGGTCACGCCAGACCCTCGGAAGAGGAGCTTCCTCCTCCT | LPPPPPPPPPQAPSKGSSVHPP |
| CCAGAAGAGCCTGTCACACTTCCAGAGAGAGAAGTGTCTACGGATGTCTGTGGTTTCTGTCACAAGCCTGTGTCTCCTCG | PGHARPSEEELPPPPEEPVTLP |
| AGAGCTGGCTGTTGAGGCCATGAAGAGGCAGTACCACGCCCAGTGCTTCACCTGTCGTACCTGCCGCCGCCAGTTGGCTG | EREVSTDVCGFCHKPVSPRELA |
| GACAGAGATTCTACCAGAAGGATGGGCGCCCCCTGTGCGAACCCTGCTACCAGGATACTCTGGAGAAGTGTGGCAAGTGC | VEAMKRQYHAQCFTCRTCRRQL |
| GGAGAGGTGGTCCAAGAGCACGTGATCCGGGCCCTGGGCAAGGCCTTCCACCCACCCTGCTTCACCTGCGTGACCTGTGC | AGQRFYQKDGRPLCEPCYQDTL |
| CCGCTGCATCAGCGACGAGAGCTTTGCGCTGGACAGCCAGAACCAGGTGTACTGTGTGGCTGATTTCTACAGGAAATTTG | EKCGKCGEVVQEHVIRALGKAF |
| CCCCCGTGTGCAGCATCTGCGAGAATCCCATCATCCCCCGAGACGGGAAGGACGCCTTCAAAATCGAGTGCATGGGAAGG | HPPCFTCVTCARCISDESFALD |
| AATTTCCACGAGAACTGTTACCGCTGTGAGGACTGCAGCGTGCTCCTGTCTGTGGAACCTACCGACCAAGGCTGCTACCC | SQNQVYCVADFYRKFAPVCSIC |
| ACTGAATGACCACCTCTTCTGCAAGCCCTGTCACCTGAAGCGGAGTGCTGCTGGTTGCTGCTGAAGAGTCCCGATAGCTG | ENPIIPRDGKDAFKIECMGRNF |
| GCCCTTCCCTGACTTGGTTTCCCCTCCTGACTTTTCTTGAGTACTTTCTTTTTGAACCTCACTGGGCACCAGCACACTGC | HENCYRCEDCSVLLSVEPTDQG |
| TCAGCCCATAGTGTCTAAATGCACAGACAGGCTTGAGACACTGGGCTTTGGCCTCCTAGTACACAGCACCCCCCACCCCC | CYPLNDHLFCKPCHLKRSAAGC |
| AGACTTTCTACTCCTCTCCCTTCATTGACCAGGAGGCCTCACCACCAGACTGCAACCCTGGTCCATCTCTAGTGCTGCCC | C |
| TGACATGTTTATGGGGACAGGTCTCAGGATGATACCTGTGTCTCTGACCATGATGCTTAGCTGCCTAGCAGAAGGCGCTG | |
| AGACCTCAGCTTAGATTGTAGAGCTAAGTTGTTTGAAGTGCGCCTTCTCAGCCACTCCAAAAAGTATTTTTTGAGAATAT | |
| AAGTGTGTAGTAGACATGATAGCACACACCTTTAATCCCAGCACTTGGGAGGCAGAGGCAGGTGGATTTCTATGTTCAAT | |
| CTAGTCTGATCTACTAAAAGATTCAAAACAATATTCTTTGGATTTGGGGGAGAGAAATCTTTGAATTTTTCTCTTTTTCT | |
| TTTTTTGGTGGGGTAAAATCAGTAAACATCTTCCCTTGGTTCAGGGGCTGCGAAGATGGCTCGGTGATGAAGAGCGAGCT | |
| CTTGCTCCTCTTGCGGAGGACCAGAGTTCATTTCCCAGCATCCCTCATGGAGGCTCATAACTACCTGTCCTGCAACTCCA | |
| GTTTCCGGAGAGCTGGCGCCCTCTGCTGGCCTCCTTGGAACCTTAATGCATGTGGTGTACACGCTTACACTCAGGCACAC | |
| ACACATACATTAAAAAAAAAAACAATTTAGCCTGTCTAATGGCAAACACATTTAATCTCAGTACTTGGGAGGCAGAGACA | |
| SEQIDNO.32 | SEQIDNO.:125 |
| GACACTTCCTGTCACCCGGGGCTTTGGGAAGCTGAACTCCAGTAAAACCAGCTTCCCCGAAGAATGGACTCCATGCGGAC | |
| CATGGCCTTTTCCCTTTGTAATCTGCTGCCAGCCGTGGAACTGCACTTTGACATCTTACACTGATGCAGAAGAAGACTCA | MERPHQDASLSKKDACTQTYPP |
| GCTCTACCTCAGCCTTAAGGTCCAGCTTGCCGGGTCCAGCTGAGCCGCAGATAGCTGTCCATTTTCTCTGGCTGGATGGA | RRRIRHAQVQDAGQLKLSIDAQ |
| GAGGCCACATCAGGATGCTTCCTTGTCCAAAAAAGATGCCTGCACCCAGACTTACCCACCTAGGAGGAGGATCAGGCATG | DRVLLPHIIEGKGLMSREPGIC |
| CCCAAGTGCAGGATGCAGGTCAACTGAAGCTGTCCATTGATGCCCAGGATCGGGTTCTGCTGCCGCACATCATAGAAGGC | DPYVKVSLIPEDSQLPCQTTQI |
| AAAGGCCTGATGAGCAGGGAGCCTGGCATCTGCGATCCCTATGTGAAGGTTTCTTTGATCCCAGAAGACAGCCAGCTCCC | IPDCRDPAFHEHFFFPVPEEGD |

FIG. 53

| NucleotideSequence (5'-3') | ORFs |
|---|---|
| CTGCCAGACCACACAGATCATTCCAGACTGCCGAGACCCAGCTTTCCACGAGCACTTCTTCTTTCCTGTCCCAGAGGAGG | QKRLLVTVWNRASETRQHTLIG |
| GTGATCAGAAGCGTCTTCTGGTGACAGTGTGGAACCGGGCCAGTGAGACCAGGCAGCATACGCTTATTGGCTGCATGAGC | CMSFGVRSLLTPDKEISGWYYL |
| TTTGGGGTGAGGTCTCTCTTGACTCCGGACAAGGAGATCAGTGGCTGGTACTATCTGCTAGGGGAGGACCTGGGTCGGAC | LGEDLGRTKHLKVARRRLQPLR |
| CAAGCACCTCAAGGTGGCTAGGCGGCGGCTCCAGCCCCTGAGAGACATGCTGTTGAGAATGCCAGGAGAGGGGGACCCTG | DMLLRMPGEGDPENGEKLQITI |
| AGAACGGGGAGAAACTCCAGATCACCATCCGGAGGGGCAAAGACGGCTTTGGCTTCACCATCTGCTGTGACTCTCCGGTC | RRGKDGFGFTICCDSPVRVQAV |
| CGAGTCCAGGCTGTGGATTCTGGGGGCCCGGCAGAGAGGGCGGGACTGCAGCAGCTGGACACAGTGCTACAACTGAATGA | DSGGPAERAGLQQLDTVLQLNE |
| GAGACCCGTGGAGCACTGGAAATGTGTGGAGCTGGCACATGAGATCCGGAGCTGTCCTAGCGAGATCATCCTGCTCGTGT | RPVEHWKCVELAHEIRSCPSEI |
| GGCGTGTGGTCCCCCAGATCAAGCCGGGGCCAGATGGCGGAGTCTTGCGGCGGGCCTCCTGCAAGTCCACACATGACCTC | ILLVWRVVPQIKPGPDGGVLRR |
| CTGTCACCCCCTAACAAGAGGGAGAAGAACTGTACTCATGGGGCCCCAGTTCGTCCTGAGCAGCGCCACAGCTGCCACCT | ASCKSTHDLLSPPNKREKNCTH |
| GGTGTGTGACAGCTCTGATGGTCTACTGCTTGGTGGCTGGGAGCGCTACACTGAGGTGGGCAAGCGCAGTGGCCAGCACA | GAPVRPEQRHSCHLVCDSSDGL |
| CCCTGCCTGCACTGTCCCGGACCACCACCCCTACTGACCCCAACTACATCATCCTGGCCCCACTGAATCCTGGAAGCCAG | LLGGWERYTEVGKRSGQHTLPA |
| TTGCTGCGGCCTGTGTACCAGGAGGATACAATCCCTGAAGAACCGGGGACTACTACTAAAGGGAAATCGTACACCGGCCT | LSRTTTPTDPNYIILAPLNPGS |
| GGGCAAGAAGTCTCGGCTCATGAAGACAGTGCAGACCATGAAGGGCCACAGTAACTACCAAGACTGCTCAGCCCTGAGAC | QLLRPVYQEDTIPEEPGTTTKG |
| CGCACATCCCGCATTCCAGTTACGGCACCTATGTCACCCTGGCCCCTAAAGTCCTGGTGTTCCCTGTCTTTGTGCAGCCC | KSYTGLGKKSRLMKTVQTMKGH |
| CTAGATCTCTGTAACCCTGCCCGGACTCTCCTGCTGTCGGAGGAGCTGCTGCTGTATGAGGGGAGGAACAAGACTTCCCA | SNYQDCSALRPHIPHSSYGTYV |
| GGTGACACTGTTTGCCTACTCGGACCTGCTGCTGTTCACTAAGGAGGAGGAGCCAGGCCGCTGCGACGTCCTGAGAAATC | TLAPKVLVFPVFVQPLDLCNPA |
| CCCTCTACCTCCAGAGCGTGAAGCTACAGGAGGGCTCTTCAGAAGACTTGAAATTCTGTGTGCTGTACCTGGCAGAGAAG | RTLLLSEELLLYEGRNKTSQVT |
| GCAGAGTGCTTATTCACTTTGGAGGCACACTCGCAGGAGCAGAAGAAGAGAGTGTGCTGGTGCCTGTCGGAGAACATCGC | LFAYSDLLLFTKEEEPGRCDVL |
| CAAGCAGCAACAGCTGGCCGCACCACCTACAGAGAGGAAGAAACTTCACCCTTACGGCTCTCTCCAGCAGGAGATGGGGC | RNPLYLQSVKLQEGSSEDLKFC |
| CAGTCACCTCCATCAGTGCCACCCAGGATAGAAGCTTTACCTCATCAGGACAGACCCTGATTGGCTGAGCAAGTCCAAGG | VLYLAEKAECLFTLEAHSQEQK |
| GCAGGACTATGCTTCTGGCAACTCTGGGGCTTCCCCTATCACACAGTAACCTCATCTCAACTGGACCCAAAACAGAAGAC | KRVCWCLSENIAKQQQLAAPPT |
| CAAGATGGTGGGCCTAGGGTCACCTGGAGGGAGTGGTCCCAAGGGTGTGTGTGGACCTGGCAACAGGAGGAACAGTGGTA | ERKKLHPYGSLQQEMGPVTSIS |
| TGAGGGACCCTGTGGGTTTGTGCAGACTGGTACCAGGAAGTCCTGGATGGAGAAGACGCCAAAACAGGAGGCTAAGTGGC | ATQDRSFTSSGQTLIG |
| ACCTGGGCACCTTCCTGGGCACAGCAGGAAAGAGGGAGAGGGCACTCGAACGGAAGATGGTGCCTGTGACCCATTCCTGC | |
| TGGAAGACATCTCTCCTTCCCACTCCTATTTCAAATGGACACATTTACTTCCTCAGTCAGTGGGTACTGGGGGACATCTC | |
| CTTTGTGCTAGGGTGTGTGCTAGAAGATGCTGTGCTCCCATCAAGATCCCAGCCCTCCCCGTCCCAACAGGGAGAGAACA | |
| CCAAATAAATCAACACTGATACACACATACACTGCAAGGGTCTGTACAGAAACATCACAGATGTCTTCAGACAGGGCATT | |
| ATGTCTCCTTGCTACGTGTGGGCTATGAAGGGGAACCATACAGCTTGAGCTGGAGAGGAGCTAGCCAGCCAAGGACTTTG | |
| AAGAGAGCGTTCCAGGCAGTGGAAGAAGCTTGAGGAAAGGTGTCACAGACTCCTCCCGGTGCATATCTACAAGATCAGAT | |
| TGCAGTTAGGAGGGGCCCAAGTGGCTGTGAGACTGGTTAGGGCTCCCCTTCAGGCCTCCAGGGTGAGGGGTGATGGTGGT | |
| TTGTTCTAGAGGGCGCTGCGATGGTAGGTATTGGAAGGGTAGGCTCTGGGATAAGGAGTGATGCTAGCTCACCCTTGCCT | |
| GCCCTCGTGCTCCGTTGGGTCTTGCTATCTTGGTGGCGTGAGGTTTGAGGCCTCCCTCCTAGGGATTCCTCTACTCAGAC | |
| CAGAGTTGAGCTTTTGGGAATGCCCATGAGCACCGAAACAGTAAAGCTTAATTTTCCCAAGATGGAAAGTTCATGTCTC | |
| CCCTGCTTCCAGGCTCCGTAGAGATCACCTGTATCTGCTCTACCTGTCATGCTAAGAGAAGGAAGCTAGGGCCTTGCACT | |

FIG. 54

| NucleotideSequence (5′-3′) | ORFs |
|---|---|
| CTGAGAACTCCCGTTTTTTGCTTTCTGTAGGGCTTCTAAGGAGCAGCAGCCGGTGGCCAGGACCAAGTGTAGCTCAGCAA<br>CCTTTACAGAGACAACATGAAAGGAATCTTGCCCAGGTCCAGTAATGAGAGCTGGGTCCACTCCCATGCTCTGGGCTAGG<br>TAGCTCACCCTTTTCTAACTGTAGAGACCCAGCAGGACAGAATCTCAAGGCTGTGGATTGGAAGGACGAGGGCCATATGC<br>TAGAGAGTATTTGTCGGGTTAGGTACTGAGCACGCAGAGGCAGAAAGCTGCAGTGATGGCTAAGGCCAGAGAAGCCCCAG<br>ACCTGAGTCTTAAGTACCTTAAGGACGATTCTTGTGCTCTTTTGAGTTTGCTAAACTACCAGAGCCACCTGAGCCCCTAA<br>ATGGTGGCCCAGGAGAGTGCATGTCCCTTATTTTCCTTCCAACTTTGGAAAAATGAGCCATGCTGAGTTATCAGTCTAAC<br>AGGGAATGGGGTGACTCTGCAGGAATCAGGCTAACACCCAGCCCAGCAAGGAAAGATTGGCTTGGTTCAAGGGTTGTGTA<br>GCACCACACTGCCAGCCAGTGATCAGCCCACGGGGTAAATCCGAACAGCCGGGTCTGTGCAGACAGCAAACCACACTTTG<br>ATTTCACTTGATTCTCTCACCTAATGATTGATCGTGAGGTCATGAAGCCCAGGAGGACCACCTGCGTGGGAAATCAGCTA<br>TCTTGTTTCGCTTGCATCTGGGCACAGACCTCTGTCCAACAGATGGGCACAGAAGACAAGAAGAGGATCTGAACATAACA<br>CCCACCCCGGGGACGAGCCGTTCTCCCTGATCAGCAACTTCTGAGTGGAACAGATTCTCCCATCAAGCTCCCAGGCCTAC<br>TGGCTGATGGGGAAGAGGAAGGTACTCCTGGCAAGTCCTGGGCTAGCTTGCTCCATGACTGTGGTGAGCCACGGCACCAT<br>GGCCATCTTGCTTCATAAATCAATGTGACAATTAATTTGGTGTCGTGGGCCCGAGAGGATGAAATATGACCCGGTGGCCT<br>CCGCTCTTCAGTCCATCCCAGCTGTTCAAGAGGAGGAGGAGCTCTCAGCGTGGCCTCTGAGAGTCATAATCACGGGAACC<br>ACGCCGGCCCCCTCCCTGCCACATAAATCACGCTAAGAAGCACACAACGACTTCTTTCCTGATGGGCTAATTGTCTTGGG<br>TGGTGTCTCCGGCCCCAGGAGCGGGGAGGTCGGGAGCACAGCCACTTTATTGTTGAAAGGCCATCTGTGAGATTTGAATA<br>CAAAGTGCCTCTTTGAGTCTCCTACCCGTTCTGGGATCCCATTTCTGTGTCTCCCACTCTGAGTCCTTTGAAGCTCATCT<br>CTCATAGAAGCCCTCATTGCCTGAGTCCTTTGGCCCTTTGGGAGCTGGAATTATACAGACCTTCTGAGAATGGTGATTCT<br>TATTTGTACATGTCTTATTATTATTACTATTATAATAATAATTATTATTATTAAAAAAAAAAAAAAAAATAAA | |
| SEQIDNO.33<br><br>GGCACGAGAAGGAGAGCAACTTCTAGGAGCCGGTGAGGTCTTTGCCATCAGGCCCTTGCAGCTCTATGCTATCACAGAAC<br>AGCTGCAACAGGGAAAGCCTACTTGTGCCAGTGGTGATGCCAAGACTGACCTTGGACACATCCTAGACTTCACCTGTCGC<br>CTTAAGTATCTTAAGGTTTCAGGCACAGAAGGACCTTTTGGGACCAGCAATATTAAGGAGCAGCTCTTGCCCTTTGATCT<br>TTCAATATTCAAGTCTCTTCACCAGGTGGAGATAAGTCATTGTGATGCCAAGCATATCCGAGGGCTGGTCACCTCCAAGC<br>CCACTTTAGCCACGATGAGTGTTAGATTCTCAGCAACCTCAATGAAGGAAGTGCTTGCTCCTGAAGCCTCAGAATTTGAT<br>GAGTGGGAGCCTGAAGGCACTGCTACCCTCGGAGGCCCTGTGACTGCTATCATCCCAACATGGCAAGCACTGACTACTCT<br>AGACCTGAGCCACAACAGCATCTGTGAGATCGACGAATCTGTGAAACTGATCCCAAAGATAGAGTACCTGGACCTGAGTC<br>ACAATGGACTGCGAGTTGTGGATAACCTGCAGCACCTATACAACCTCGTGCACCTTGACCTGTCATACAACAAGCTCTCC<br>TCCCTGGAAGGCGTGCACACTAAACTGGGCAATGTCAAAACCCTAAACCTGGCAGGCAACTTCTTAGAGAGTCTGAGCGG<br>TCTGCACAAACTCTACTCCTTGGTTAATGTGGACCTACGAGACAACCGGATTGAGCAGTTGGATGAGGTCAAGAGCATTG<br>GCAGCCTGCCATGTCTGGAGCGTTTGACCTTGCTGAACAACCCTTTGAGCATCATCCCTGACTACCGGACCAAGGTGCTT<br>TCCCAGTTTGGAGAACGAGCCTCTGAGATTTGTCTAGATGATGTCGCAACCACAGAGAAAGAGCTGGACACTGTGGAAGT | SEQIDNO.:126<br><br><br>MSVRFSATSMKEVLAPEASEFD<br>EWEPEGTATLGGPVTAIIPTWQ<br>ALTTLDLSHNSICEIDESVKLI<br>PKIEYLDLSHNGLRVVDNLQHL<br>YNLVHLDLSYNKLSSLEGVHTK<br>LGNVKTLNLAGNFLESLSGLHK<br>LYSLVNVDLRDNRIEQLDEVKS<br>IGSLPCLERLTLLNNPLSIIPD<br>YRTKVLSQFGERASEICLDDVA<br>TTEKELDTVEVLKAIQKAKDVK<br>SKLSNTEKKAGEDFRLPPAPCI |

FIG. 55

| Nucleotide Sequence (5'-3') | ORFs |
|---|---|
| GCTGAAGGCAATTCAGAAAGCCAAAGATGTCAAGTCCAAACTGAGCAACACAGAAAAGAAGGCTGGTGAGGACTTCCGGC | RPGGSPPAAPASASLPQPILSN |
| TCCCGCCTGCACCCTGCATCAGACCCGGCGGCTCCCCTCCTGCAGCTCCCGCCTCAGCCTCCCTGCCTCAGCCGATCCTC | QGIMFVQEEALASSLSSTDSLP |
| TCCAACCAAGGTATCATGTTTGTACAGGAAGAGGCCCTGGCCAGCAGCCTCTCATCCACGGATAGTCTGCCACCCGAGGA | PEDHRPIARACSDSLESIPAGQ |
| CCACCGGCCCATTGCCCGAGCCTGCTCTGACTCCTTGGAATCTATCCCTGCAGGACAGGTGGCCTCTGATGATCTGAGGG | VASDDLRDVPGAVGGVSPDHAE |
| ATGTGCCAGGAGCTGTTGGCGGCGTGAGCCCAGATCATGCAGAGCCAGAGGTTCAGGTGGTGCCTGGGTCCGGCCAGATC | PEVQVVPGSGQIIFLPFTCIGY |
| ATCTTCCTGCCCTTCACTTGCATTGGCTACACAGCCACCAACCAGGACTTTATCCAGCGCCTCAGCACACTGATCCGCCA | TATNQDFIQRLSTLIRQAIERQ |
| GGCCATTGAACGGCAACTCCCTGCCTGGATTGAGGCTGCCAACCAGCGCGAGGAAGCCCATGGTGAGCAGGGCGAGGAGG | LPAWIEAANQREEAHGEQGEEE |
| AAGAAGAGGAAGAGGAAGAGGAGGATGTTGCTGAGAACCGCTACTTTGAAATGGGACCCCCAGACGCAGAGGAAGAGGAG | EEEEEEEDVAENRYFEMGPPDA |
| GGGAGTGGCCAGGGAGAAGAGGATGAGGAAGACGAGGACGAGGAGGCGGAGGAGGAGCGCCTGGCTCTGGAGTGGGCCCT | EEEEGSGQGEEDEEDEDEEAEE |
| GGGCGCCGATGAGGACTTCCTGCTGGAGCACATCCGCATCCTCAAGGTGCTCTGGTGCTTCCTGATCCACGTGCAAGGCA | ERLALEWALGADEDFLLEHIRI |
| GCATCCGCCAGTTCGCTGCCTGCCTTGTGCTCACTGACTTCGGCATCGCAGTCTTTGAGATCCCACACCAAGAGTCAAGA | LKVLWCFLIHVQGSIRQFAACL |
| GGCAGCAGCCAGCACATCCTCTCATCCCTGCGTTTTGTCTTCTGCTTCCCACATGGCGACCTCACGGAGTTTGGCTTCCT | VLTDFGIAVFEIPHQESRGSSQ |
| CATGCCCGAGCTGTGTCTGGTGCTCAAGGTGCGGCACAGTGAGAACACGCTCTTCATCATCTCGGATGCTGCCAACTTAC | HILSSLRFVFCFPHGDLTEFGF |
| ACGAGTTCCATGCTGATCTACGCTCCTGCTTTGCACCGCAGCACATGGCCATGCTGTGCAGCCCCATCCTCTACGGCAGC | LMPELCLVLKVRHSENTLFIIS |
| CACACCACCCTGCAGGAGTTCTTGCGCCAGCTGCTCACCTTCTACAAGGTGGCCGGGGGCTCTCAGGAGCGCAGCCAGGG | DAANLHEFHADLRSCFAPQHMA |
| CTGCTTCCCTGTCTACCTGGTCTACAGTGACAAGCGCATGGTCCAGACCCCTGCCGGGGACTATTCAGGCAATATCGAAT | MLCSPILYGSHTTLQEFLRQLL |
| GGGCCAGCTGCACGCTGTGCTCGGCGGTGCGGCGCTCCTGCTGCGCGCCCTCGGAGGCCGTCAAGTCCGCTGCCATCCCC | TFYKVAGGSQERSQGCFPVYLV |
| TACTGGCTGCTGCTCACATCCCAGCATCTCAACGTCATCAAGGCCGACTTCAACCCCATGCCCAATCGAGGCACCCACAA | YSDKRMVQTPAGDYSGNIEWAS |
| CTGCCGCAACCGCAACAGCTTCAAGCTTAGCCGCGTCCCGCTCTCTACCGTGCTGCTAGACCCCACTCGCAGCTGCACCC | CTLCSAVRRSCCAPSEAVKSAA |
| AGCCACGGGGTGCCTTCGCTGATGGCCATGTGCTCGAGCTGCTCGTGGGCTACCGCTTCGTTACCGCCATCTTTGTGCTG | IPYWLLLTSQHLNVIKADFNPM |
| CCCCACGAGAAATTCCACTTCCTGCGAGTCTACAATCAGCTACGCGCCTCACTGCAGGACCTGAAGACTGTGGTCATCTC | PNRGTHNCRNRNSFKLSRVPLS |
| CAAGAATCCTTCAGCTAAGCCAAGAAATCAGCCTGCCAAGAGCAGGGCCAGTGCTGAGCAGCGGCTACAGGAGACCCCAG | TVLLDPTRSCTQPRGAFADGHV |
| CAGACGCTCCGGCTCCAGCTGCAGTCCCACCAACAGCTTCAGCTCCAGCCCCCGCAGAGGCCTTGGCTCCAGATCTGGCT | LELLVGYRFVTAIFVLPHEKFH |
| CCTGTACAGGCCCCAGGAGAGGACCGAGGTCTAACTTCAGCAGAGGCTCCAGCCGCAGCAGAGGCTCCAGCCGCAGCAGA | FLRVYNQLRASLQDLKTVVISK |
| GGCTCCAGCCGCAGCAGAGGCTCCAGCCGCAGCAGAGGCTCCAGCCGCAGCAGAGGCTCCAGCCGCAGCAGAGGCTCCGG | NPSAKPRNQPAKSRASAEQRLQ |
| CCCCAGCAGAGGCTCCAGCCGCAGCAGAGGCTCCGGCCGCAGCAGAGGCTCCAGCTGCAGCAGAGGCTCCAGCCGCAGCA | ETPADAPAPAAVPPTASAPAPA |
| GAGGCTCCAGCTTCAGCAGAGGCTCCAGCTCCAAACCAGGCTCCTGCTCCAGCAAGGGGTCCCGCTCCAGCAAGGGGTCC | EALAPDLAPVQAPGEDRGLTSA |
| CGCTCCAGCAGGGGGTCCCGCTCCAGCAGGGGGTCCAGCTCCAGCAGAGGCCCTGGCACAAGCAGAAGTCCCTGCCCAGT | EAPAAAEAPAAAEAPAAAEAPA |
| ACCCAAGTGAGCGCCTAATCCAGTCCACATCTGAAGAGAATCAGATCCCTTCTCACTTGCCAGTATGCCCATCACTCCAG | AAEAPAAAEAPAAAEAPAPAEA |
| CACATTGCCCGTCTTCGGGGGAGAGCCATCATTGACCTCTTCCACAACAGCATTGCTGAGGTTGAAAATGAGGAGCTGAG | PAAAEAPAAAEAPAAAEAPAAA |
| GCACCTCCTGTGGTCATCAGTGGTGTTCTACCAGACCCCGGGGCTAGAAGTGACCGCCTGTGTGCTGCTCTCTAGCAAGG | EAPASAEAPAPNQAPAPARGPA |
| CTGTGTACTTCATACTGCATGATGGTCTCCGCCGCTACTTCTCTGAACCACTGCAGGATTTCTGGCACCAGAAAAACACC | PARGPAPAGGPAPAGGPAPAEA |
| GACTATAACAACAGTCCTTTCCACGTCTCTCAGTGCTTTGTGTTGAAACTCAGTGACCTGCAGTCAGTCAACGTCGGCCT | LAQAEVPAQYPSERLIQSTSEE |
| TTTCGACCAGTACTTCCGGCTGACGGCTCCTCCCCGACGCAGGTGGTCACGTGCTTGACTCGCGACAGCTACCTGACGC | NQIPSHLPVCPSLQHIARLRGR |

FIG. 56

| Nucleotide Sequence (5'-3') | ORFs |
|---|---|
| ACTGCTTCCTCCAGCATCTGATGCTTGTGCTGTCCTCCCTGGAGCGCACACCCTCGCCTGAGCCTGTTGACAAGGACTTC<br>TACTCAGAATTTGGGGACAAGAATACAGGGAAAATGGAGAACTATGAGCTGATCCATTCCAGCCGCGTCAAGTTCACCTA<br>CCCCAGTGAGGAAGAGGTTGGGGACCTGACCTATATTGTCGCACAGAAGATGGCTGATCCTGCAAAGAATCCAGCCCTCA<br>GCATCTTACTGTACATCCAGGCCTTCCAGGTGGTCACACCACACCTTGGGCGGGGCAGGGGCCCACTGCGCCCTAAGACG<br>CTGCTCCTGACCAGCGCCGAGATCTTCCTCCTGGATGAGGACTACATCCACTATCCATTGCCTGAATTTGCCAAAGAGCC<br>ACCGCAGAGGGACAGATACCGGCTAGACGATGGCCGCCGGGTCCGGGATTTGGACCGGGTGCTCATGGGCTACTATCCCT<br>ACCCACAGGCCCTCACTCTTGTTTTTGATGACACACAGGGTCACGACCTCATGGGGAGTGTCACCCTGGACCACTTTGGG<br>GAGATGCCAGGTGGTCCTGGCAGGGTTGGCCAGGGCCGAGAGGTACAGTGGCAGGTGTTTGTCCCCAGTGCCGAGAGCCG<br>AGAAAAGCTCATCTCACTGCTCGCACGACAGTGGGAAGCTCTTTGTGGCAGGGAGCTGCCTGTGGAGCTCACTGGCTAGT<br>GCACGCCATAGCAGCCCTGGCCTCCTGCCATGCCCAGCCTAGCCTGGTGCCCGTGAAGGCAGGGAAGCGGCCTTCTGCGT<br>TCTTTTTAAGGTCTTTCTCCTCTCCCTTGGTTCCTACATTGTTTTGTCTGTGATTGATGCTGTTGTTAGCGTGGCGCTGT<br>GGACCTGATAACCCCCACGTCCTTTTCTGAAGTGTTAAGTCCAGTCCTTCGTTGCTGTTTGCTGTCATTGTGGGCGTGCC<br>GCTGCTAATTACAAAGCTGGTAGCAGAGTTACACAGGCAAGCTCCCACGTTGTGGGCTTTTCCAAAATGGAGGCCTCCTC<br>AAGTCCAGAGCAGAGGAGGCCCTATGGGGAGTTCCCAGGTCATGGGTCCAAGAGGAGCCAGTACAGGGGACCTAGAGCTG<br>CCAGCACCAAGTATAATTCCTGTTGCCTACGTTCTCTATTCTAATAAAATGGAGTTTGACACAAAAAAAAAAAAAAAAAA<br>CTCGTGCCGAATTCGGCACGAGGAAA | AIIDLFHNSIAEVENEELRHLL<br>WSSVVFYQTPGLEVTACVLLSS<br>KAVYFILHDGLRRYFSEPLQDF<br>WHQKNTDYNNSPFHVSQCFVLK<br>LSDLQSVNVGLFDQYFRLTGSS<br>PTQVVTCLTRDSYLTHCFLQHL<br>MLVLSSLERTPSPEPVDKDFYS<br>EFGDKNTGKMENYELIHSSRVK<br>FTYPSEEEVGDLTYIVAQKMAD<br>PAKNPALSILLYIQAFQVVTPH<br>LGRGRGPLRPKTLLLTSAEIFL<br>LDEDYIHYPLPEFAKEPPQRDR<br>YRLDDGRRVRDLDRVLMGYYPY<br>PQALTLVFDDTQGHDLMGSVTL<br>DHFGEMPGGPGRVGQGREVQWQ<br>VFVPSAESREKLISLLARQWEA<br>LCGRELPVELTG |
| SEQIDNO.34<br><br>GCGTCAGCTCTGAGCCGACTTTACTGTCCCAGAGCCTAGACTGCCCGCCCCGGAGGACGTGGAGGACGAGGCAGCCCGCG<br>GGAGAGACAGCTGTGGGGGCCCTGGCAGCGACCTCGCGCAGCTCGTACCCTGTCACTCAGCATCCCAATCGGTGTTGCGC<br>CCGCGCCCGCCCCCTGCCCGAGGGGCGGGGCTGGTCTTGTGGTACCCAGAGTCTGCGCACGCTGAGGTGTGCCCCTGCCC<br>AGTGAGGACCTGGGACTGGGCCATGCCAGCCCCAGACCATCAAGGTGGGAAGAGGACCGCATCCCAGAGCCGGTGAGCAA<br>CCCGCAGCTTTGGCCGCTCCAGAGAAGTTCCGCACCCTCCAGGAGTGAAGATGAAAGAGATTTGCAGGATCTGTGCCCGG<br>GAGCTGTGTGGAAACCAGCGGCGTTGGATCTTTCATACCGCGTCCAAGCTCAACCTCCAGGTTCTGCTTTCGCACGTCCT<br>AGGCAAAGATGTCTCTCGTGATGGCAAAGCCGAGTTTGCTTGTAGCAAGTGCGCTTTCATGCTCGATCGCATCTATCGAT<br>TCGATACTGTCATTGCCAGGATCGAAGCCCTTTCTCTTGAGCGCTTACAGAAGCTGCTCCTGGAAAAGGATCGCCTCAAG<br>TTCTGCATTGCCAGTATGTATCGGAAGAATAATGATGACTCTGGCGAGGAGAACAAGGCGGGGAGTGGGACAGTAGACAT<br>TTCCGGCTTGCCAGATATGAGGTACGCTGCGCTGCTCCAAGAAGACTTTGCCTATTCGGGATTTGAGTGTTGGGTAGAAA<br>ATGAGGATCAGATTAACGACTCACACAGCTGTCATGCTTCCGAAGGGCCCGGAAACCGACCCAGGAGATGTCGCGGTTGT<br>GCAGCTCTGCGGGTTGCGGATTCCGACTATGAAGCCATTTGTAAGGTGCCTCGAAAAGTGGCCCGAAGTATTTCTTATGC<br>CCCCTCTAGCAGGTGGTCTACCAGCATTTGCACTGAAGAACCGGCATTGTCAGAGGTTGGGCCACCAGACTTAGCAAGCA<br>CAAAAGTACCCCCGGATGGAGAAAGCATGGAGGAAGGACACCAGGTTCCTCCGTGGAGTCTCTGGATGCTAGTGTCCAG | SEQIDNO.:127<br><br><br>MKEICRICARELCGNQRRWIFH<br>TASKLNLQVLLSHVLGKDVSRD<br>GKAEFACSKCAFMLDRIYRFDT<br>VIARIEALSLERLQKLLLEKDR<br>LKFCIASMYRKNNDDSGEENKA<br>GSGTVDISGLPDMRYAALLQED<br>FAYSGFECWVENEDQINDSHSC<br>HASEGPGNRPRRCRGCAALRVA<br>DSDYEAICKVPRKVARSISYAP<br>SSRWSTSICTEEPALSEVGPPD<br>LASTKVPPDGESMEEGTPGSSV<br>ESLDASVQASPPQQKDEETERS<br>AKELVKCDYCSDEQAPQHLCNH |

FIG. 57

| NucleotideSequence (5′-3′) | ORFs |
|---|---|
| GCTAGTCCTCCACAACAGAAAGACGAGGAAACGGAGAGAAGTGCGAAAGAACTTGTAAAGTGTGACTACTGTTCTGACGA | KLELALSMIKGLDYKPIQSPRG |
| ACAGGCTCCACAGCATTTGTGTAACCACAAACTGGAGCTAGCTCTTAGCATGATTAAAGGTCTTGATTATAAGCCCATTC | SKLPIPVKSILPGAKPGHILTN |
| AGAGTCCCAGAGGGAGCAAGCTTCCTATTCCAGTGAAATCCATCCTACCTGGAGCCAAGCCTGGCCATATCCTGACAAAC | GVSSSFLNRPLKPLYRTPVSYP |
| GGAGTTAGTTCCAGTTTCCTTAACAGGCCTTTGAAACCCCTTTACAGGACGCCTGTGAGCTATCCTTGGGAGATTTCAGA | WEISDGQELWDDLCDEYLPIGF |
| CGGACAGGAGCTGTGGGATGATCTCTGTGATGAGTATTTGCCGATCGGGTTCCAGCCCGTGCCTAAAGGGTTACCCACGC | QPVPKGLPTQQKPDLHETPTTQ |
| AACAGAAGCCGGACTTGCATGAGACCCCTACAACCCAGCCACCTGTGTCTGAGTCCCACCTGGCAGAACTCCAGGACAAA | PPVSESHLAELQDKIQQTEATN |
| ATCCAGCAAACAGAGGCCACCAACAAGATTCTTCAAGAGAAACTGAATGACCTGAGCTGTGAGCTGAAATCTGCACAGGA | KILQEKLNDLSCELKSAQESSQ |
| GTCATCTCAGAAGCAAGATACGACAATCCAGAGCCTCAAGGAAATGCTTAAAAGCAGGGAAAGTGAGACTGAGGAGCTGT | KQDTTIQSLKEMLKSRESETEE |
| ACCAGGTGATCGAAGGACAAAATGACACAATGGCAAAGCTTCGGGAAATGCTGCACCAGAGCCAGCTCGGACAGCTCCAC | LYQVIEGQNDTMAKLREMLHQS |
| AGCTCAGAGGGCATTGCCCCTGCTCAGCAACAGGTAGCCCTGCTTGACCTTCAGAGCGCTCTATTCTGCAGCCAGCTTGA | QLGQLHSSEGIAPAQQQVALLD |
| AATACAGAGGCTCCAGAGGCTGGTCCGGCAGAAAGAACGCCAGCTGGCGGATGGCAAGCGATGTGTGCAGTTAGTGGAGG | LQSALFCSQLEIQRLQRLVRQK |
| CTGCAGCCCAGGAGAGAGAGCACCAGAAGGAAGCTGCTTGGAAACATAACCAGGAATTACGAAAGGCTTTACAGCACCTC | ERQLADGKRCVQLVEAAAQERE |
| CAAGGAGAACTGCACAGCAAGAGCCAGCAGCTCCATGTTCTGGAGGCGGAAAAATACAATGAGATTCGAACCCAGGGACA | HQKEAAWKHNQELRKALQHLQG |
| AAACATCCAACACCTAAGTCACAGTCTGAGTCACAAAGAGCAGCTAATTCAGGAACTCCAGGAGCTCCTACAGTATCGTG | ELHSKSQQLHVLEAEKYNEIRT |
| ACAACGCAGACAAAACTCTAGACACAAACGAAGTGTTTCTTGAGAAATTGCGGCAACGAATACAAGACCGAGCTGTTGCT | QGQNIQHLSHSLSHKEQLIQEL |
| CTAGAGCGGGTCATAGATGAGAAGTTCTCTGCTCTAGAAGAAAAGGACAAGGAACTGCGGCAGCTTCGCCTAGCTGTGAG | QELLQYRDNADKTLDTNEVFLE |
| GGACCGAGACCATGACTTAGAGAGACTGCGTTGTGTCCTGTCCGCCAATGAAGCTACCATGCAGAGCATGGAGAGTCTCC | KLRQRIQDRAVALERVIDEKFS |
| TGAGGGCCAGAGGCCTGGAAGTGGAGCAGTTAACTGCCACCTGCCAAAACCTCCAGTGGCTGAAAGAAGAACTGGAAACC | ALEEKDKELRQLRLAVRDRDHD |
| AAATTTGGCCATTGGCAGAAGGAACAGGAGAGCATCATTCAGCAATTGCAGACATCTCTACACGACAGGAACAAAGAAGT | LERLRCVLSANEATMQSMESLL |
| AGAGGATCTCAGCGCAACTCTGCTCTGTAAACTTGGACCGGGTCAGAGTGAAGTAGCTGAGGAACTGTGCCAGCGCTTGC | RARGLEVEQLTATCQNLQWLKE |
| AGCGAAAGGAACGGATGCTGCAGGACCTTCTGAGCGATCGGAACAAACAAGCCGTGGAGCACGAGATGGAGATCCAGGGG | ELETKFGHWQKEQESIIQQLQT |
| CTGCTCCAGTCGATGGGCACCAGGGAGCAGGAAAGACAGGCTGCTGCAGAAAAAATGGTCCAGGCCTTCATGGAAAGGAA | SLHDRNKEVEDLSATLLCKLGP |
| CTCAGAACTGCAGGCCCTGCGCCAGTATTTAGGGGGGAAGGAACTAATGACATCGTCTCAGACGTTCATCTCTAACCAGC | GQSEVAEELCQRLQRKERMLQD |
| CAGCTGGAGTGACGTCCATCGGGCCTCACCACGGAGAGCAAACCGATCAAGGTTCTATGCAGATGCCCTCTCGAGATGAT | LLSDRNKQAVEHEMEIQGLLQS |
| AGCACCTCACTGACTGCTAGAGAGGAGGCCAGCATACCCCGGTCCACATTAGGAGACTCGGACACAGTTGCAGGGCTGGA | MGTREQERQAAAEKMVQAFMER |
| GAAAGAACTGAGCAACGCCAAGGAGGAGCTCGAGCTCATGGCCAAAAAAGAAAGAGAAAGCCAGATGGAACTGTCTGCCC | NSELQALRQYLGGKELMTSSQT |
| TGCAGTCCATGATGGCCATGCAAGAGGAAGAGCTGCAGGTGCAGGCTGCTGACTTGGAGTCCCTGACCAGGAATGTGCAG | FISNQPAGVTSIGPHHGEQTDQ |
| ATAAAAGAAGATCTCATAAAGGACCTGCAGATGCAACTGGTCGACCCTGAAGATATACCAGCCATGGAGCGTCTTACCCA | GSMQMPSRDDSTSLTAREEASI |
| AGAGGTCTTACTTCTTCGGGAAAAAGTTGCTTCCGTGGAACCCCAGGGTCAGGAAGTATCAGGGAACAAGAGACAGCAGT | PRSTLGDSDTVAGLEKELSNAK |
| TGCTGCTGATGTTAGAAGGACTAGTGGATGAACGGAGTCGGCTCAACGAGGCCCTGCAAGCTGAGAGGCAACTCTACAGC | EELELMAKKERESQMELSALQS |
| AGCCTGGTCAAGTTCCATGCCCAGCCAGAGAACTCTGAGAGAGACGGAACTCTGCAGGTGGAACTGGAAGGGGCCCAGGT | MMAMQEEELQVQAADLESLTRN |
| GTTACGCACTCGACTAGAAGAAGTTCTTGGAAGAAGCCTGGAGCGTTTAAGCAGGCTGGAGAGCCTGGCCGCCATTGGAG | VQIKEDLIKDLQMQLVDPEDIP |
| GTGGGGAACTGGAAAGTGTGCAAGCCCGTCACAAGCATGCCTTCTGAGCACTGGCGGGTCACACTGCGACCCAGGATGGA | AMERLTQEVLLLREKVASVEPQ |
| AACCCTGTTTATACTAACCAGAAAGCTGTGTCGGACTTGACAACCAAGTGTGGCTTACTAATGGTAACGGTAGGACTGCT | GQEVSGNKRQQLLLMLEGLVDE |

FIG. 58

| NucleotideSequence (5′-3′) | ORFs |
|---|---|
| GTCAGTAGCAGCAAAGGGAAGCAGCTGGAGTCTTCCTTACTCCCTGCACGGACCTAGTTCTTAGCTAACTGAGGTCTTGA<br>AGCATACTGCACATCTTAAATCATTCCATTTTAATTTCCCATTCATACTGCTCTTCTCCCTGGCCTGTCCTCATTCCTTT<br>ACCCCTTCCATGGGCCAATAAAGTTTACTCCCCCATCTTACCACCCCCGCCACAAGTCCCACGTCATGTCATCAAATGCA<br>TGTGTGTGTATTATTTTTGCCATCCAATCAAATCCTGTTCTTTGAAAGCAATTTTTAATCAAATAAAGGAATCAAGTATG<br>AGTTTTAGGTTTAGAAAGAAAGGTAGAGAGTCCCGTGAGAGTGAGTCTGGGGAGGGGTATAAAACCCTACTAAGGATAAT<br>CAGAACTAGACAGGAGGGTGTGGGCTGAGCTCAGGAGCAGAGACCGTTAGTGTTCCAATAAAATTTGCCCTCGAAGGCCT<br>CTTCAGAGTTGACTGTCTAGGGAAAGATGAAGTCAGATCAGTGGACAGCATGGTCTAGTCCATAAAAGCCTATACAACTC<br>ATGTTCTTCACTGGCCTAGGGTTTCTTCAAGCCTCAGGCATGGCCTTTAGTCAGAACATGACTTTAAAAACCGGTTTCCC<br>AAATCAGAATCCTCTAGATAAAAAATCATCTTCTATGTGATATTTCCCACCCTCCTTTTTTTTATTATTTTGGTTTTGTT<br>TTTTTGGTATTTTATTTGTTTGTTTGAGACAGGATATCACTGTGGCTGGCCTGAAATGCACTGGGTAAACCAGACTGGCA<br>TTGAACTCACAGAGATGAGCCTGCTTCTACCTTTGGGTGCTGGGATTAGAGGCATGGCTGCCACCCCTGCCTGTCAGCAT<br>CCCCCTTAAGAGCAATAGTTTCCAGGATCCCCAGATCAGGGGAAGTATAATTCCTGGATGCTCATTAGGAGGTGAAGCGG<br>GTGGCGTCCTTCATTGACCTCTGCTTTGGTGGGAGTAATTCTTGATAGTGGAGTAAGAAGACGATGTGAGATGCTGTCAT<br>GTTCAGGTCACTCAGAAGGAGGCCTTAGATCTCATGTAGGTTTTACTCACCCTCTCTGCTTTCTTGGGACAACCCGACAG<br>GTGGGGAGGTGGTAGATTGTTCATTTCTAGCATCTTAAATGTCAAGAATAGGAAAAGTAACAGGTTACTTGCAAGGGGCT<br>GTGGATTCTGCCCCAGAACCTTTCCTAGTGCTGAAGGGTATGAGTAACGTAATCCATGCTTTCCAGCACCCTGAGAAAGA<br>CTGAGCCCCCTTCCCGAGCTACACTGAGCTTTCCTTTCCTCTTCTTATTTATTTTTATTTTTTATTTTTTGACAAGGC<br>ACACTACATCCATGTGTTGACATGGCATGTGTTCTAAATTCTATTCAAGATTCTGTAACCTCAGCTGTGTGACACACTTT<br>AACTGATGTGTATCCATCAGCTTGAAGTGGACAGGAGGAAAATATTCTACCAGAGAAGCACTTGAAATCTTCTGATGAAG<br>TAGTTCACAAAGATTGATAGCCATGGCCTTCCTTATAATGGATGTGCTATTACAGTTTTACAACCTTTAGGGGGGAAAGG<br>ACTCATTTAATATTAAAGATAGAAGATGTAGAAGCAGAGCCATCCAATGTTCTTAGTAACCCCATTCTAAGATACTCTAA<br>GGCCTGCCTGAACAAACCTTATGTAACTAACAAGGAAGAGCATAATAGAGTTGAGCTATAGACATGTCAAACAATTAAAG<br>ACCAGCCTGTTAGTCATTACAAGGCAATTAGGAAATGTGTTTACTCAACTTTACCAATAGACAACAAAGTTCTGCAAAGC<br>TGCTATTAAGTTTCAACTCTAGTAATCTCTAGGGTTCTGAGGGCTCACAGTGATTATAATAATGAAGGTTAATAATTAGT<br>GCAACTGCCAACCTCTAACAAGAGTAGGTTGATAGACAAGTAAATTAAGAGTTTGTTATCAATTCCATAAATGTGACTAT<br>AAAATCTGGTACTGACTTTCTGGTCCTGATGCTAGAATGAAGGTGGAGACCTTGCTGCCTGGAGGGAATGTGCTTGGCCC<br>ACAAGCTTGTGCAATAATTTGACACCTAGCTACCGAACACAGTTCTGATGAATTGTACAGCGTGAGCCACAGGTGGATGG<br>TACTATGATTACACGTCATTCATATCATATAATTGGATTTAGCATGCTGTAATCTTCATTTCTCTGTAGGAGTATGGACT<br>ATGTTAGAATGTGTCTGCCTTTGTTTGGATTTTTTAATATTATAATAAAATAAACTTAGTTTAAAACAAAAAAAAAAA<br>AAAAAAAAAAAAAAAAAAA | RSRLNEALQAERQLYSSLVKFH<br>AQPENSERDGTLQVELEGAQVL<br>RTRLEEVLGRSLERLSRLESLA<br>AIGGGELESVQARHKHAF |
| SEQIDNO.35 | SEQIDNO.:128 |

FIG. 59

| NucleotideSequence (5'-3') | ORFs |
|---|---|
| GGCAGCGAGTGAGCACCCCGGTTCCACTGTGCCGCACCCGCAGCCTGAAGCCAGCATGGAGAAGGACAGCCTGAGTCGCG<br>CCGATCAGCAGTATGAGTGCGTGGCGGAGATCGGCGAAGGCGCCTATGGGAAGGTGTTCAAGGCCCGCGACCTGAAGAAC<br>GGCGGCCGCTTCGTGGCTCTGAAGCGCGTGCGAGTGCAGACCAGTGAGGAGGGCATGCCGCTCTCCACCATCCGCGAGGT<br>GGCGGTGCTGAGGCACCTGGAGACCTTCGAGCACCCCAACGTGGTCAGGTTGTTTGATGTGTGCACAGTGTCACGGACGG<br>ACAGAGAAACCAAGCTTACACTAGTGTTTGAGCATGTTGATCAAGACTTGACCACTTACTTGGATAAAGTTCCAGAGCCC<br>GGCGTACCCACAGAAACCATAAAGGATATGATGTTTCAGCTTCTCCGAGGTCTGGACTTTCTTCATTCTCACAGAGTAGT<br>GCATCGTGATCTGAAACCGCAGAACATTCTGGTGACCAGCAGTGGACAGATAAAGCTGGCTGACTTTGGCCTTGCCCGCA<br>TCTATAGTTTTCAGATGGCCCTTACCTCGGTGGTCGTCACGCTGTGGTACCGAGCCCCAGAAGTCCTGCTCCAGTCCAGC<br>TATGCCACCCCTGTGGACCTCTGGAGTGTCGGTTGCATCTTTGCAGAAATGTTTCGCAGAAAGCCTCTTTTTCGTGGAAG<br>TTCAGACGTGGATCAACTAGGAAAAATCTTGGACATCATTGGACTCCCAGGAGAGGAAGACTGGCCTAGGGACGTGGCCC<br>TTCCCCGGCAGGCTTTTCATTCCAAATCTGCTCAACCCATCGAGAAGTTTGTGACAGATATTGACGAACTAGGCAAAGAC<br>CTACTTCTGAAATGCCTGACGTTTAATCCAGCTAAAAGGATATCCGCCTACGGCGCCCTGAATCACCCGTACTTCCAAGA<br>TCTGGAGAGATACAAGGACAACCTGAACTCTCACCTGCCATCCAACCAGAGCACCTCGGAGCTGAACACAGCCTGAGGTT<br>CCACGGGGATGCCCATGAGCTCGTCATCTGAACACATTGGCGGCTGCGAGTCCCCTAAGCAAGCCTCTCAGAGCAGTTGA<br>AGATTGCTGGCTGCCAACCTTCTGGCTGCCAGCTTCTGGGTGGGCTCTGCCTTACCAAGGAAACCACCTAGTTTACTGTT<br>CAGAGATCAATGCAAGGGTGATTGCAGCTTTATGTTCGTTTGTACACTTGTTTGTTTTGTCTGTTTGTTTCAAGAACCTG<br>GAAAACTTCCAGAAGAAGAGAAGCTGCTGACCAATTGTGCTGCCATTTCGTTTTCTAACCTTGAATGCTGCCAGTGTAGG<br>GTGGGAATCCAGGCCCAGCTGAGTTATGATGTAATCCGCCTGCAGCTGCTGGGCCTGCTTTGGTACTTGTGAGTGTGTGT<br>GCATGCGTATGTGTGTGTAAGAGAGAAGAGGAGGGGAGAGAAAGACCCCTGATCTCGTCAAGTGTTACTTTTTTTTTGTA<br>GAAAACAAGAATAATTGAGTTTTAAAGAGTAGAGGTGACTGATAGTAAGAAGGGCTTGCTCAGTGAAAGGTGATTCACAA<br>TGGAGTCTTGTTAGGAAGGTTGGACCTAAGTCCTCAGAGTTGCCTTCCTGTCCAAAAGCTTTTGCTAGCAGTAAACAATA<br>AAGGTTTAGATGCCACAAAAAATGGGGGAACCGCAATATTTTTAAGAGACTTTTAAGGCATACATCTTCTATTTACT<br>CTTTGGAAAGCTGAACTTAATGTGTCCCAGGCCCTATATATAGTACAGTATGTACTTAATTGTTTCTTTGGGGAAAGATG<br>CTATAAGTATCTTATTACTTGCAATACATTTAAGGAGTGAGTGTACCTCAGATAGGTTTAAAGATAGAGAGCACCTGTT<br>TTCTGGTGTGAGATGTTATCATTTTCTTCACGTCTCTTGATACCTTGATACCTTGTCACCTTAGGGAATCACTTCCTGCT<br>CTGACTAGAGGCGGGAATACCATCTAGCTGTCTCCACCACCCACCATGGCGCATCTGCCTTGTGCTGCCTTGTGTAGTGC<br>GAAGCTCTCAACCACCAGCACTTCTAATTCATTTTCCTGCCACTGCCTGGCTAACGACAGATGGCCCAGCTGCCCCAATC<br>CCACACCCGCTTGCACGCTTACCGTCTTTCACCGAATGCTTTGGGCGTAGGCTCCCATTCCGAAACCCTAACAGTATCCC<br>CTTGTGCCTTTGTAATACAGTCTTCCCCCTGCCGCAGCTGAGGTCACCTAGGCAGTGAAGAGTGCTTGTTCTGTGTGTGT<br>ATAGACTACTACCGACTGTCACTTGGTGTTTCCTATCTTTAAGTGTATGTTGTCAGTGTAATGTCTGAGGAAATGTCTTT<br>TCCTCTCTTCTAGAGATAACTACTTACTCTCTAAAGTGATCTCTCTGTCTGTCCGCAGGATGTGTTTCTG | MEKDSLSRADQQYECVAEIGEG<br>AYGKVFKARDLKNGGRFVALKR<br>VRVQTSEEGMPLSTIREVAVLR<br>HLETFEHPNVVRLFDVCTVSRT<br>DRETKLTLVFEHVDQDLTTYLD<br>KVPEPGVPTETIKDMMFQLLRG<br>LDFLHSHRVVHRDLKPQNILVT<br>SSGQIKLADFGLARIYSFQMAL<br>TSVVVTLWYRAPEVLLQSSYAT<br>PVDLWSVGCIFAEMFRRKPLFR<br>GSSDVDQLGKILDIIGLPGEED<br>WPRDVALPRQAFHSKSAQPIEK<br>FVTDIDELGKDLLLKCLTFNPA<br>KRISAYGALNHPYFQDLERYKD<br>NLNSHLPSNQSTSELNTA |
| SEQIDNO.36 | SEQIDNO.:129 |

FIG. 60

| NucleotideSequence (5′-3′) | ORFs |
|---|---|
| CGACAGGGCGGCGGCGGCGGGGGTGAGGTGCGAGGCGAAGCGCAGAGCGCGCAACTCTGGAGGAGCGGATGTTAAGTCAG<br>AGTACAACAGAAAATGTCCACTGAACGAACTTCATGGACAAACCTGTCCACTATTCAGAAAATAGCCCTGGGCCTAGGAA<br>TTCCAGCAAGTGCAACAGTTGCCTACATTCTGTATCGTCGATATAGGGAAAGCAGAGAAGAGAGATTGACATTTGTTGGA<br>GAAGATGACATTGAGATAGAGATGCGAGTCCCCCAGGAGGCTGTGAAGCTCATCATTGGTCGACAAGGAGCCAATATTAA<br>ACAGTTGCGGAAACAGACAGGCGCGCGGATTGATGTGGACACAGAGGATGTAGGCGATGAGCGAGTGCTGCTTATCAGTG<br>GGTTTCCTGTTCAGGTGTGCAAGGCCAAAGCAGCAATCCATCAGATTCTGACAGAAAACACCCCAGTGTTTGAGCAACTC<br>TCAGTCCCTCAGAGATCTGTGGGCAGAATCATAGGGAGAGGCGGTGAGACGATTCGTTCTATCTGTAAGGCTTCTGGAGC<br>CAAAATCACTTGCGACAAAGAATCAGAGGGAACGTTACTACTCTCACGACTTATAAAAATCTCAGGAACACAGAAGGAAG<br>TGGCAGCAGCTAAGCATCTGATACTGGAGAAAGTTTCAGAAGATGAAGAACTTCGGAAGAGAATTGCCCATTCTGCAGAA<br>ACCAGAGTCCCACGAAAGCAGCCAATCAGTGTGAGAAGAGAGGAAGTGACAGAGCCTGGTGGAGCTGGAGAAGCAGCTTT<br>ATGGAAAAATACCAATTCTAGCATGGGACCAGCTACACCCCTGGAAGTTCCTCTCCGCAAAGGAGGTGGTGATATGGTTG<br>TTGTAGGACCAAAAGAAGGTTCCTGGGAGAAACCTAATGATGACAGCTTTCAGAATTCTGGTGCCCAGAGCAGTCCAGAG<br>ACGTCCATGTTTGAAATTCCCAGTCCTGACTTCAGTTTCCATGCTGATGAGTACCTAGAAGTCTACGTTTCTTCCTCTGA<br>ACACCCTAATCACTTCTGGATCCAAATCATTGGTTCCCGCAGCCTGCAGTTGGATAAACTTGTCAGTGAGATGACCCAGC<br>ACTATGAGAATAGTCTGCCTGAAGACTTGACTGTGCATGTAGGAGACATTGTAGCAGCACCTTTATCTACAAATGGTTCC<br>TGGTATCGAGCCCGGGTTCTTGGAACCTTGGAAAATGGAAACTTGGACCTCTACTTTGTTGACTTTGGAGATAATGGAGA<br>TTGTGCACTAAAGGATCTCAGGGCTCTCAGGAGTGACTTTCTAAGCCTCCCATTTCAAGCAATAGAATGCAGTCTGGCAC<br>GGATTGCCCCCACAGGTGAAGAGTGGGAAGAGGAAGCTCTAGATGAGTTTGACAGACTCACTCACTGTGCTGACTGGAAG<br>CCCCTGGTGGCCAAGATTTCTAGCTATGTCCAGACTGGAATCTCAACTTGGCCAAAGATCTATTTGTATGATACCAGTGA<br>TGAGAAGAAACTTGATATTGGGCTAGAATTAGTTCGTAAAGGGTATGCAGTTGAACTTCCTGAAGACATGGAAGAAAACA<br>GAACTGTCCCAAATATGTTGAAGGACATGGCCACAGAAACAGATGATTCTCTTGCAAGCATACTCACTGAAACAAAAAAG<br>AGCCCTGAAGAGATGCCACATACCCTGTCCTGCCTCAGCTTGTCAGAAGCTGCCTCTATGTCTGGTGATGATAACCTTGA<br>AGACGACTTATTCTGAAATCTGGGCTTCAGCTGCTGGATCAGCCATCTGCTTTGCTGTGATGTGGTGCCGAGAGAGGAGT<br>CTATGATAGAGAGATCCATGAAGTCCTTTACTTCACATGGTGTGGCTTGCTGTGAATCAAATCCATTTTTTGTTTCATTG<br>GATCTACCAGAAAGTAACAGACGGAGGCAAATGGAGACAGATTTCTCCACTCCACTCCTCTGGTTCCTCCCCTATCTTTC<br>AATGTTTGAATGCTGTATAATTCCCAGCCTCTCCATATCAGGTTCAGTTCCCTCTGCCAGTAATATTTTGCATTACTGCT<br>GGGCTATGTTTTTGAGGCTGAGAAACAGCCAAGGTTTGGGCATTGGAAGTGATGATTCTGCAGATTTCTGACTCGACTTA<br>TCAGGTGACTGTAGTTATAGGAAGTATTTGGTGGACTCAGAAGACTGCAGTTATCAGGAGATAAGGCAAAATCAGCATAA<br>CTATATTTAAAAGCCTCATAAAAGGGGAAGAGTGTACTACCTCTCACCCACAGTTGCCGAGGTTATTGGAGATGGGTCCT<br>CCAGCTATTTCTTTGTGAACTTCAGTTAAAATACAACTAGAAGGGAGAAGTATCTTAGGAAATGTGTAAACGTGTTACAA<br>ATATGTGTCTGTATACACACAACTAGAGAGAAAGAATGAATATATATAGTTCTGCTTAAATAATTTGGGGAATGTTTGCT<br>AATAAAGTTCTCAAAAATTATCTAAAAACACATACTCAGTCACAACGTGGGAGTAGGCCTGTGGGTAAAGTCTCTTCTGA<br>GTAAGCCTTGGTAGTAATTGCCAGCACCTCACATACGGAAGCATCTTGAGACAAATGTCCTTCCCATACAAGTATTCACA<br>CTCTTCCCGTAAAGTCACTGCAGAAGTCCACTACTCCCTCAGAACCATAACCAGTTTTAGCTATATACACAAACCTACTT | MSTERTSWTNLSTIQKIALGLG<br>IPASATVAYILYRRYRESREER<br>LTFVGEDDIEIEMRVPQEAVKL<br>IIGRQGANIKQLRKQTGARIDV<br>DTEDVGDERVLLISGFPVQVCK<br>AKAAIHQILTENTPVFEQLSVP<br>QRSVGRIIGRGGETIRSICKAS<br>GAKITCDKESEGTLLLSRLIKI<br>SGTQKEVAAAKHLILEKVSEDE<br>ELRKRIAHSAETRVPRKQPISV<br>RREEVTEPGGAGEAALWKNTNS<br>SMGPATPLEVPLRKGGGDMVVV<br>GPKEGSWEKPNDDSFQNSGAQS<br>SPETSMFEIPSPDFSFHADEYL<br>EVYVSSSEHPNHFWIQIIGSRS<br>LQLDKLVSEMTQHYENSLPEDL<br>TVHVGDIVAAPLSTNGSWYRAR<br>VLGTLENGNLDLYFVDFGDNGD<br>CALKDLRALRSDFLSLPFQAIE<br>CSLARIAPTGEEWEEEALDEFD<br>RLTHCADWKPLVAKISSYVQTG<br>ISTWPKIYLYDTSDEKKLDIGL<br>ELVRKGYAVELPEDMEENRTVP<br>NMLKDMATETDDSLASILTETK<br>KSPEEMPHTLSCLSLSEAASMS<br>GDDNLEDDLF |

FIG. 61

| NucleotideSequence (5'-3') | ORFs |
|---|---|
| ACACTGTAAGAGAAGGCCTGTACTAGGGTTCTAGAAGTAGGTCTTCACTATAAACTTACTTTACTTCTAGTGTCTTTTCA<br>TTACTGACAGTAGTGCAAGACACCACTGAGACTTGTGACAGTACTTAGAATTAAATACAAAATGCATAGTGATTTAACGA<br>ACTTTAGGAAACAAGGCAAGGTGAACTGGGAAATCTAAACTGAACACATGGATGCCTTATATAGGCTTCTCTAAACTCTA<br>GTATTAGTAGCCATGCCTGGTGTCCCAGACCTATACCCAGCCTTTGAGGCTAGTGAGAGAGAGTGAAAGTTAAAGGCCAT<br>GCCTAAGCAACTTAGTAAGATGCTATCTCAAAAAGAGGCTAGGGGTGTAGCTAGTGGTATAGTGTAGCACTTGTGTCATT<br>TGCAGCATGCCAAGTTAGCAGAAAGACATCAAGGAAGGAGCAGTTTGAGCATCTCTTTACTCTAGAGAAACCTAGACAGG<br>CCCCTATTAATGTTCCAGGTTCTGACTGTAGTGAACCATTTAAGTGTGTTCAGCCAGGCATTGGAGTTACTACACAACAG<br>ACTCTGGAGGCCATTTTGTCTCTAGTTTCCTCGGTGCTCTTTTCCCTCAGTTAGAGGTCATAAGACCTGTAGTTAATTGT<br>GTAAAAAGCCTATTTAAACCAATTGTGTGGGACTGGAAAGATGCTCAAAGGTTAAGAACACTGACTGCTCTTGTAGAAAA<br>CCCAGGTTCAATTCTCACCACCCACATGGTGACTCACAACCATCTTTTAATTCTAGTTCTAGGGGACCTAGTTCTCTCTT<br>CTAACTTCTAACCAGGTATGCATATGGTATACATATATACATGTAGGCAAAACATTCATCTACATGTCTAAAATTTGAGA<br>ATAAAATTTTGAAATAAAATATGGTACATACCTAAAAAAAAAAAAAAAAAAAAAAAAAAAAAAAA | |
| SEQIDNO.37<br><br>GGCCTCCGGAGCTTTGCTTTGTCTTCCGTAGGTCAAGGCGTTGGTTCTCTCTCTCTCTTTTTTTTTAATAAATAAAGTGG<br>AACCTGACTCACGACTCACGAGACGCTATGACTTGCTCAGTACCTTCAGGGTCTCCATGGCAACGGAGCCATCCAGAAAG<br>CTGACAGTCCCAACTCAGACCTTGGAGTCAGAGAAATCACTGTCTTCAAGACAGCAAAAAGAGAAAGAAAAGTTCTGAGC<br>CAGTATTAAAAGGGCACAAAACCGGGGCTGAAGAGATGGCTCAGCGCTTTGGAGTGACTGCTGTTCTTCCAGGGGATCCT<br>GGTTGGTCTCCCAGTACCCACATGGTGGCTCACAAGCATCTGTAAGTACAGTTTAACAGGATCTGACCCCTGGGAGCATC<br>ATGTACATATGTGGTACTACATCTATGCAGGCAAGACACTCATACATAAAAAATAATAAAATAAATAAGGCAAAAGAAAG<br>CACCACAATCAAATGTCTTAAAAATAACCACACTTTTGGAATTGATCCCAAGGAAATAACCTGGGCTAAACTTAAAGACT<br>TATCCATAGGAATATTAACCTCAGCATTGATTATAGCAATTAAAAAACCCCAGGAATGTCTGATCAGTGGGGCTGATTAA<br>AGCTGACCTGAGAACTTATGCAGCATCCTTCTGTGGTGGATGTCATGGAGACGTTAGAATGGTATTGTCATATCAAGGCT<br>CTCAGCCAGGGTCTAGGGCTCCTGGAATCTCTGAAATCATGTGCATAATTGTGTGGGAGTGTGTGTATTTCTGGAAGGAA<br>GATTCTTTGGGATTCTCAAATAGGTACATGACCCAAGAGAGTAAAACAGTCACTTCTGTAGAAAATAATCAAAGCAGAAA<br>CATGTTGACAGCATATTATTAAGGGAGAGAGTGGGAAAGATAAGTTGAAAGCAACTATGATATGATCTTATTTTATTAAA<br>AATAAAAGTCTTATGTATACACCTGTATAGGGAAAACATGAAAGTGTTACTCACCAAAGCAGTAATCATAGTGGGGCGGC<br>CATTGTAGTGGGGAGGCATGGCGGCTGAGTGACTCATTGTGGGGAGCCTGTACATCTCGGTGAGTCAGGAGGCAGAGAAA<br>TGAGCCCAGAAAAGGGGACCAGGCTACAGCTCTCTGCTAGCCAACCCAGCTCTCTGCTCTCTGCTGCCGGGCCCGAAACC<br>AGCATGGAAGGGGACGTTCTGGACACCTTGGAGGCGCTGGGGTATAAGGGGCCACTGTTAGAGGAACAGGCACTCTCCAA<br>GGCAGCAGAGGGTGGACTGTCTTCACCTGAGTTTCAGAGCTCTGCATTTGGTTAGGCTCCCAGATAAAGTCCTTATGCA<br>ACCTGGAAGAAAGCATCACTTCAGCTGGGAGAGATGACCTAGAGAGCTTCCAGCTTGAGATAAGTGGGTTTTAAAAGAG<br>ATGGCCTGTCCATACTCGGTACTCGTCTCAGGAGACATTAAAGAGCGCCTCACAAAGAAGGATGACTGCTTAAACTTCTG | SEQIDNO.:130<br><br><br>MRGPELGPETSMEGDVLDTLEA<br>LGYKGPLLEEQALSKAAEGGLS<br>SPEFSELCIWLGSQIKSLCNLE<br>ESITSAGRDDLESFQLEISGFL<br>KEMACPYSVLVSGDIKERLTKK<br>DDCLKLLLFLSTELQALQILQK<br>KKHKNSQLDKNSEICQEVQAVC<br>DALGVPKSDTSDIPLLLSQVES<br>KVKDILCRVQKNHVGKPLLKVD<br>LSSEQAEKLERINDALSCEYEC<br>RRRMLMKRLDVTVQSFGWSDRA<br>KAKTDNIARIYQPKRYALSPKT<br>TVTLAHLLAAREDLSKIIRTSS<br>GISREKTACAINKVLMGRVPDR<br>GGRPNEIEPPPPEMPPWQKRQE<br>GGGRGGWGGGGGRGGGGGGRG<br>GWGGGGGWGGGGGSGGGWGGSG<br>GGGGGRGGFQGRGDYGGRGDYG |

FIG. 62

| NucleotideSequence (5'-3') | ORFs |
| --- | --- |
| TTGTTTTTAAGTACAGAACTTCAAGCTTTACAAATATT | GRGGYGGRGGYGGRGYGDPYGG<br>GGGGGGGYRRY |
| SEQIDNO.38<br><br>GCCTGCCCACCTCTTGTGCAGCTGCCTATCTGCTGAGGACTACCTGGTCCACTCCTCCCCTGCTGGAGGTCCACAGAAGG<br>ACCGAGATATGTCCACATGGGACAGGCAGGAATGAAAGTGGTATCCTGGCAAGCAATGACTATGATTAGCCAAGGCCCAC<br>TGGGCCCAACACTAAGCAAAACTCACGTAGACTGTGTAGAAGCCCTCTTGGCACTGCTTCTAGACAGCCTCTGCAGCACG<br>GTGCCCACCTTGTTACAGTTCTCACCTCACCATCTGCCCTCAAGATAGCCAACTCAGGGGAACTAGGACTTCACCGCCCA<br>CAAACAGGATGTGTGGTCCCAATGCCAACGCTCCTCAGACAACTGTAAAAGCACACACCATTGAGTGGCACTGCCCTGCC<br>GGACATTGTTGGCACCCAACAAACTCCCCTCACAGACCCACTCTTGAGCCAGGCCAGTCCTATGGGCCAAGCCTGGTAGT<br>ATGTTGGTCTCTACCACCACACCAGAGGTCTTTGAGTCTACACAGTGAACGGAATGTGGTAACTTCTAGGTGCCCCGCAC<br>TTAGCCTAGCACCTTTCTTACATGATCTCAAGTTGAACCGACTTCCTTAACTCTGCTGTCCCCTGTAATCCTAACTTCCC<br>TTAGGGGAATTGGGGGCTACTGGTGGCCACATCATGCCTATTGAATGTCTAGCGTACAGCACAACAGTGCCTCTTTTAAT<br>AGCATGGGCAAGGTCTGTTCTGTACTGAAGACTCTGTCTCCACAGTGCTCATCGGATGTGGGTGTGTGTATAAATGTATA<br>ATATAGATTTATATATGTTGCTATGGCTATATGTTGAAGGCCAACATGATGTGCAGACTGATGGGTGAGAAGACGCTGAG<br>CAGTCTTTCTGATGGCTATTAAAGCAAACTGTGTATAAAAAAAAAAAAAAAAAAAAAAAAAAAAAAAAAAAAAAAAAAAA<br>AAAAAAAAAAAAAAAAA | SEQIDNO.:131<br><br>MCGPNANAPQTTVKAHTIEWHC<br>PAGHCWHPTNSPHRPTLEPGQS<br>YGPSLVVCWSLPPHQRSLSLHS<br>ERNVVTSRCPALSLAPFLHDLK<br>LNRLP |
| SEQIDNO.39<br><br>CCACGCGTCCGGGCACACGCCGGTAGGATCTGCCTCCCAGGTGCTGAGATTAGACACCATGCCCGGCTTTGGTACTTTGT<br>GGTTTTGCTGTGGTTTTGTTTGTCTTGTGCTTCTTTACTAACTATCATTTGGAGGTTGTCAAAAGCCTCCATGGCCGTGT<br>GTTTCCTCTCTGCCCTCAGCTAAGCACAAGAGAGACCTGCAGAATGCAAGACCTTGAGAAGTTAAACCATGTGGGAAGC<br>CCGTGGTTTTCTGTGCTGAGTGGTGTCTGAGCTGATGACAGGTGACAGTGCTGAGGCCACACCGACAGGGACAGGGTCCG<br>AGGAACGGCCCTCTCCTCAGTCCCTTCTCACTTTAGCATCCGAGTTTGTCCTTAGTTCTCATTCTTCATCCAGTTGCTCC<br>TCAGCTTTTGTAGGGCATCCAGAATTCAAGCCATGGCTGGGAGAGAGAAAGCCATGTCCTGCCAAGCACGGTGCCCCTGC<br>CTATGACTTCAGCTATTCTGGAGATGGAAGCAGGAGAGTCAGCTGAGCCTGGGGATTTGGTACTAGTCTGGCAAAAGAGA<br>CCCTGAGAGGGAATGGGGCTGTCCCAAAGCAATTGGCCTTCTAGCAGTAATGACTATCTGGAGTATTCTCTTCCCATCTC<br>CCACGAGCACCAGACACATGCCAGTCTCACTGGCCAGTAGAAATGGAGAACTGAGACCCTTAGAGACAAACCCACTCACC<br>AAATCTAGCAGTTTCTAAGTATCCCAGTTAGAGATGCACCACTACCAACACAAATGAAAGCGGGAACCACCAGCCATCTG<br>AAGAGAAGTGTTCCCAGCACCCACTTACGGCCCTGGACATCTAGCCCTCTGATTGAGGTTGGAGTTCTGGGACACCCTGA<br>GTAGCTCACTGACTATCACTACATTAGTTGAATGCACTTGATACATTGTGGCCTCCTTTCTGTCAAGAGCACACTAGATA<br>GCACCAAGCACTGCCCAAGTGTGACATACTATTCGAGGTGAACAGAGCTCATAATGGAAGTGTAAGGTGTGCCGCTGTGT | |

FIG. 63

| NucleotideSequence (5'-3') | ORFs |
|---|---|
| AATATTTCTAATAAATATATTTTGTTTCTGCCTCAAAAAAAAAAAAAA | |
| SEQIDNO.40<br><br>CGCTGCTACAGGTCCAAAGTGACGAGGCCAGACGAGACTGAACCAAGACAAGTCTTTCATTTCCTTAGCATATTTATCCC<br>AGTGTGGAAGGCTAGCTCTGGGGCAGCGATTCCTTCGGAACCATGGTGGCGTGGCTGTGGAAGGTGCTGATGGGCGTCGG<br>TCTCTTCGCCCTCACCCACGCGGCCTTCTCAGCTGCTCAGCATCGCTCTCATGCGCGACTGACAGAAAAGAAGTATGAGC<br>CGCTGCCGGCGGATATAGTTCTCCAGACCCTTTTGGCCTTTGCGCTTACCTGTTACGGCGTGGTTCATACTGCAGGGGAC<br>TTTAGAGACAGGGATGCCACTTCGGAACTAAAGGATATGACATTTGACACCTTAAGGAATCGCCCGTCTTTTTACGTGTT<br>TCACCGTTCTGGCTACCGACTGTTCCAGCGTCCGGATTCAACCCATTCTTCAAACCTCAGCGCGTCATCTTCTGACTTAC<br>CGTTGAAGTTTTGAAAGCTCAAATCACCGCACCATTCAGCTTTTTAACGAGTTAAGTAACAGGACAGACGCAGAATTAAG<br>TACCGGGATTTGGGATGTGAAACACCCCCAACACATCAGTATTTTTACTGATATTTCAGACTTAATTAAAAAAAAAAAAA<br>AAAA | SEQIDNO.:132<br><br><br>QHRSHARLTEKKYEPLPADIVL<br>QTLLAFALTCYGVVHTAGDFRD<br>RDATSELKDMTFDTLRNRPSFY<br>VFHRSGYRLFQRPDSTHSSNLS<br>ASSSDLPLKF |
| SEQIDNO.41<br><br>CCACGCGTCCGCTTGAAGTCTAGCTTCTCGGGGGAAGATAAGGGGGAGTCAAAACTCTCAAATCCGGGCGGAGGAGAGCC<br>AGACGAGGTCACCGAATGTAAAAGTCGCCGGGGTTCGGCTCAGCCCGGCGAATCGGCTGGGCGGGGTGGGGCCGCGAAGC<br>CGCAAATCACCAGTTGAGGGCCAGAGAGCGCGCTGCCGGCTCAGAGCTGAGCCTGCAGCCGCCCGGCCAGGCAGCAGCCG<br>GAGCGGGACAGCCGTGCACACCCGCCAGCCGCACCAGCCTCTTGGCGGACGCCCGCGGACCATGAGCCGCCCGAGCTCCG<br>AGAGCAGCTGCGGTGAGGTGAGAGCAGCCCGGCGCTGAACCGCAATCCCGGACTCCGAACGCGGCGCGGGGAGAGTTAAG<br>AATCATGGCTGCGGGAAAGTTTGCAAGCCTTCCCAGAAACATGCCTGTGAATCACCAGTTCCCCTTGGCCTCGTCCATGG<br>ACCTCCTGAGCAGCAAGTCCCCTCTTGCTGAGCGTCGCACAGATGCCTATCAAGACGTGTCTATACATGGCACTCTTCCA<br>CGGAAGAAAAAGGGCCCTCCTTCCATACGGTCCTGTGACAATGCTGGCCACTCCAAATCCCCACGACAGAGCTCACCTCT<br>GACCCAGGACATCATCCAGGAAAACCCACTGCAAGACCGGAAAGGGGAAAACTTCATCTTCAGGGATCCATATCTTCTGG<br>ACCCAACTCTGGAATACGTGAAGTTCTCCAAGGAGAGGCACATCATGGACAGGACCCCTGAGAGGCTGAAAAAGGAATTG<br>GAGGAGGAGCTGCTGCTGAGCAGCGAAGACCTACGCAGCCACGCCTGGTACCACGGCCGGATCCCCCGACAGGTGTCTGA<br>AAACCTTGTGCAGCGGGATGGGGACTTCCTGGTTCGCGACTCCCTGTCGAGCCCCGGAAACTTTGTCCTGACCTGTCAGT<br>GGAAGAACCTCGCTCAGCACTTTAAGATCAACCGGACTGTCCTGCGGCTCAGCGAGGCCTACAGCCGTGTGCAGTACCAA<br>TTCGAGATGGAGAGCTTTGACTCCATCCCGGGGCTGGTCCGCTGCTACGTGGGCAACCGGCGGCCCATCTCCCAACAGAG<br>TGGTGCCATCATCTTCCAGCCCATCAATAGGACAGTGCCCCTCTGGTGTCTGGAGGAGCGTTATGGCACCTCCCCGGGCC<br>GAGGCCGGGAGGGCAGCCTGGCTGAGGGAAGGCCAGACGTGGTGAAGAGGCTGAGCCTCACCACAGGCAGCAGCATCCAG<br>GCTCGGGAACACAGCCTGCCCCGAGGAAACCTCCTCAGGAATAAAGAGAAGAGTGGCAGCCAGCCCGCCTGCCTGGATCA<br>CGTGCAGGACAGGAAGGCCTTAACCCTCAAAGCTCACCAGTCGGAGAGTCACCTGCCAATAGGCTGCAAGCTGCCCCCCC | SEQIDNO.:133<br><br><br>MAAGKFASLPRNMPVNHQFPLA<br>SSMDLLSSKSPLAERRTDAYQD<br>VSIHGTLPRKKKGPPSIRSCDN<br>AGHSKSPRQSSPLTQDIIQENP<br>LQDRKGENFIFRDPYLLDPTLE<br>YVKFSKERHIMDRTPERLKKEL<br>EEELLLSSEDLRSHAWYHGRIP<br>RQVSENLVQRDGDFLVRDSLSS<br>PGNFVLTCQWKNLAQHFKINRT<br>VLRLSEAYSRVQYQFEMESFDS<br>IPGLVRCYVGNRRPISQQSGAI<br>IFQPINRTVPLWCLEERYGTSP<br>GRGREGSLAEGRPDVVKRLSLT<br>TGSSIQAREHSLPRGNLLRNKE<br>KSGSQPACLDHVQDRKALTLKA<br>HQSESHLPIGCKLPPQSPSMDT<br>SPCPSSPVFRTGSEPTLSPALV |

FIG. 64

| NucleotideSequence (5'-3') | ORFs |
|---|---|
| AGTCTCCGAGTATGGACACAAGCCCTTGCCCCAGCTCTCCCGTGTTCAGGACTGGCAGCGAGCCCACTCTGAGTCCAGCA | RRFSSDARTGEALRGSDSQLCP |
| CTGGTACGAAGGTTCTCTTCAGATGCTAGGACAGGGGAGGCGCTTCGGGGATCAGACAGCCAGCTGTGCCCCAAGCCACC | KPPPKPCKVPFLKTPPSPSPWL |
| CCCGAAGCCCTGCAAGGTGCCCTTCCTCAAGACTCCCCCCTCTCCATCTCCCTGGCTCACCTCAGAGGCCAACTACTGTG | TSEANYCELNPAFAVGCDRGAK |
| AACTGAACCCTGCTTTTGCTGTGGGCTGTGACAGGGGAGCCAAGCTTCCCATGCAAGCCCACGACAGCCACGAGATGCTG | LPMQAHDSHEMLLTAKQNGPSG |
| CTGACAGCCAAACAGAATGGGCCATCGGGTCCCCGGAACTCTGGCATCAACTACATGATCCTTGATGGGGATGACCAGGC | PRNSGINYMILDGDDQARHWDP |
| GAGACATTGGGATCCACTGGCAGTGCAGACGGATGAAGGTCAGGAGGACAAGACCAAGTTTGTGCCACCTCTCATGGAGA | LAVQTDEGQEDKTKFVPPLMET |
| CCGTGTCGTCATTCAGACCCAATGACTTTGAGTCCAAGCTTCTTCCTCCAGAGAACAAACCCCTGGAAACGGCCATGCTG | VSSFRPNDFESKLLPPENKPLE |
| AAGCACGCGAAAGAACTGTTCACCAACCACGATGCCAGGGTCATTGCGCAGCACATGCTGAGCGTGGACTGCAAGGTTGC | TAMLKHAKELFTNHDARVIAQH |
| TAGGATACTCGAAGTCTCTGAAGACAGGAAGAGGAGCATGGGTGTGAGCTCTGGGTTGGAGCTCATTACTTTACCTCATG | MLSVDCKVARILEVSEDRKRSM |
| GACGGCAGCTGCGCCTGGACATCATCGAGAGGCACAACACCATGGCCATTGGCATTGCTGTGGACATTCTGGGCTGCACA | GVSSGLELITLPHGRQLRLDII |
| GGCACACTGGAGAACCGAGCGGGTACCCTCAATAAGATCATCCAGGTGGCGGTGGAACTGAAGGATGCCATGGGAGACCT | ERHNTMAIGIAVDILGCTGTLE |
| CTATGCTTTCTCTGCCATCATGAAAGCCCTGGAGATGCCTCAGATCACAAGGTTAGAGAAAACATGGACGGCTCTGAGGC | NRAGTLNKIIQVAVELKDAMGD |
| ACCACTACACGCAGACAGCCATCCTCTATGAGAAGCAGTTGAAGCCCTTTAGCAAAATCCTGCATGAAGGCAGAGAGTCT | LYAFSAIMKALEMPQITRLEKT |
| ACATATGTCCCAGCAAGCAATGTGTCAGTCCCTCTGCTGATGCCACTGGTGACCTTAATGGAACGCCAGGCTGTCACTTT | WTALRHHYTQTAILYEKQLKPF |
| TGAAGGGACCGACATGTGGGAAAACAATGACGAGAGCTGTGAAATTCTGCTGAATCACTTGGCAACAGCCAGGTTCATGG | SKILHEGRESTYVPASNVSVPL |
| CTGAGGCTTCTGAGAGCTACAGGATGAATGCTGAGAGGATCCTGGCAGATTTCCAACCAGATGAAGAAATGACTGAGATC | LMPLVTLMERQAVTFEGTDMWE |
| TTAAGGACTGAGTTCCAGATGAGATTGTTATGGGGCAGCAAGGGCGCCGAAGTCAACCAGAACGAGAGATACGACAAGTT | NNDESCEILLNHLATARFMAEA |
| CAACCAGATCCTAACAGCCCTCTCACGGAAACTAGAACCTCCCTCTGGAAAGCAGGCCGAGCTGTGAGAACCAGCTGGAG | SESYRMNAERILADFQPDEEMT |
| GGCCTTGGGGCACTCCAGTCCCACTGGGCATGCCTGTCAACTCTAAGTAATAACGAGCAGATCTAACAGGATACAAGCCG | EILRTEFQMRLLWGSKGAEVNQ |
| CTAACATCCACAGGATAGTAAATGTGTAAACTGCACAGAGCACACTTATTTATGAATTGTTTAAAATTACTACTGATTTT | NERYDKFNQILTALSRKLEPPS |
| TAAATGAATGGTAATTTATTATTAAGATAACTATTGCTAATGTTGATCAGCAAACTTAAGACATAGCTATGTTGCTGGTT | GKQAEL |
| GTTTAGTATCATGGCATTTGACCATCTTAGTTTTAATTCCTTGTCAGATAAATGTAAATAGAGGCATTTAAAAGAAAAGC | |
| ATGAAACATGGAAGAAGGTATCAGTTATATGATATTCTTTGAATATGAAACTGTAAATAGTTATGAATGGAAATATATCT | |
| TTTTGTGAAAAAAAAAAAAAAAAAAA | |
| SEQIDNO.42 | SEQIDNO.:134 |
| GGCACGAGCTGAGCAGAAGAGGTTCTCGCCGCACCTAGCCTTTGCCTGGGCGCCCGATTCTTCTTTGCCGCTGGGCCTCG | |
| GCCAGAAGCCACAACGGGCGACACGGAGCCGCCAGTGCTGGAGGGGGAGCCATGGGTGCGGGGCAGCGTGGGGGCAGAGG | MHKHQHCCKCPECYEVTRLAAL |
| CCCAGGACGCCCGCCCGGCCCCAGGCCCCGCTCAGCCAGGGCACCCCCACGGGTGCCCTCCTTCTTGGTCTGAGCAGTGC | RRLEPPGYGDWQVPDPYGPSGG |
| GAGTGTGCTAGGGAGCCCGGCGGCGGCGGCGGCGGCGTGGAAACTGGCGTGGGCTGGGGGGTCCGAGCCGCGGGGGGCAG | NGASSGYGGYSSQTLPSQAGAT |
| TGCCATGCACAAGCACCAGCACTGCTGTAAGTGCCCCGAGTGCTATGAGGTGACCCGCCTGGCCGCCCTGCGCCGTCTTG | PTPRTKAKLIPTGRDVGPVPPK |
| AGCCTCCTGGCTACGGGGACTGGCAGGTGCCGGACCCCTATGGGCCAAGTGGGGGCAATGGGGCTAGCTCCGGTTATGGA | PVPGKSTPKLNGSGPGWWPECT |
| GGCTACAGCTCGCAGACCCTGCCTTCACAGGCAGGGGCTACCCCCACCCCTCGCACCAAGGCCAAGCTCATCCCCACAGG | CTNRDWYEQASPAPLLVNPEAL |

FIG. 65

| NucleotideSequence (5′-3′) | ORFs |
|---|---|
| CCGAGATGTGGGGCCAGTGCCCCCTAAGCCAGTCCCCGGCAAGAGCACCCCAAAACTCAACGGCAGTGGCCCCGGCTGGT | EPSLSVNGSDGMFKYEEIVLER |
| GGCCCGAGTGCACCTGTACCAACCGGGACTGGTATGAGCAGGCCAGCCCTGCACCCCTCCTAGTGAACCCCGAGGCCCTG | GNSGLGFSIAGGIDNPHVPDDP |
| GAGCCCAGCCTATCGGTGAATGGCAGTGATGGCATGTTCAAGTATGAGGAGATAGTACTGGAACGGGGCAACTCTGGCCT | GIFITKIIPGGAAAMDGRLGVN |
| TGGCTTCAGTATCGCAGGTGGCATCGACAACCCTCATGTCCCTGATGACCCTGGCATCTTTATTACCAAGATCATTCCTG | DCVLRVNEVDVSEVVHSRAVEA |
| GTGGAGCAGCTGCCATGGATGGGAGGCTGGGGGTGAATGACTGTGTGCTACGGGTGAATGAGGTGGACGTGTCCGAGGTG | LKEAGPVVRLVVRRRQPPPETI |
| GTGCACAGCCGGGCCGTGGAGGCACTGAAGGAGGCAGGCCCTGTGGTGCGGTTGGTGGTGCGGAGGCGACAGCCCCCACC | MEVNLLKGPKGLGFSIAGGIGN |
| TGAGACTATCATGGAGGTCAACCTGCTCAAAGGGCCAAAAGGCCTAGGTTTCAGCATTGCTGGGGGCATTGGCAACCAGC | QHIPGDNSIYITKIIEGGAAQK |
| ACATCCCAGGAGACAACAGCATCTATATCACCAAGATCATTGAAGGAGGAGCTGCTCAGAAGGATGGACGCCTACAGATT | DGRLQIGDRLLAVNNTNLQDVR |
| GGGGACCGGCTGCTTGCGGTGAACAATACCAATCTGCAGGATGTGAGGCATGAGGAAGCTGTGGCCTCACTCAAGAACAC | HEEAVASLKNTSDMVYLKVAKP |
| ATCAGACATGGTCTATCTGAAGGTGGCCAAGCCAGGCAGCATCCACCTCAACGATATGTATGCTCCCCCTGACTATGCCA | GSIHLNDMYAPPDYASTFTALA |
| GCACTTTCACTGCCTTGGCTGACAATCACATAAGCCATAATTCCAGCCTGGGTTATCTTGGGGCAGTGGAGAGCAAGGTC | DNHISHNSSLGYLGAVESKVTY |
| ACCTACCCTGCTCCACCTCAGGTGCCCCCTACTCGTTACTCTCCTATTCCCAGACACATGCTGGCTGAGGAAGACTTTAC | PAPPQVPPTRYSPIPRHMLAEE |
| CAGAGAGCCCCGCAAGATCATCCTGCACAAAGGTTCTACAGGCCTGGGCTTCAACATTGTAGGAGGAGAAGATGGAGAAG | DFTREPRKIILHKGSTGLGFNI |
| GCATTTTTGTTTCCTTCATCCTGGCGGGAGGCCCAGCAGACCTAAGTGGGGAGTTGCGAAGGGGAGACCGGATCTTATCG | VGGEDGEGIFVSFILAGGPADL |
| GTAAATGGAGTCAACCTGAGGAATGCTACCCACGAGCAAGCAGCGGCTGCTCTGAAACGGGCTGGCCAGTCAGTCACCAT | SGELRRGDRILSVNGVNLRNAT |
| TGTGGCCCAGTATAGACCTGAAGAGTACAGTCGCTTTGAATCCAAGATCCATGACTTGCGGGAACAAATGATGAACAGCA | HEQAAAALKRAGQSVTIVAQYR |
| GCATGAGTTCTGGGTCTGGGTCTCTCCGAACCAGTGAGAAGAGGTCCTTGTATGTCAGGGCCCTGTTTGATTATGATCGG | PEEYSRFESKIHDLREQMMNSS |
| ACTCGTGACAGCTGTCTACCAAGCCAGGGACTCAGTTTCTCTTATGGTGACATTCTGCACGTCATTAACGCCTCTGATGA | MSSGSGSLRTSEKRSLYVRALF |
| TGAGTGGTGGCAAGCAAGGCTGGTGACTCCTCATGGAGAGAGTGAACAGATCGGTGTGATCCCTAGTAAAAAGAGGGTGG | DYDRTRDSCLPSQGLSFSYGDI |
| AAAAGAAAGAGCGAGCTCGATTGAAAACTGTGAAGTTCCATGCCAGGACAGGGATGATTGAGTCTAATCGGGACTTCCCT | LHVINASDDEWWQARLVTPHGE |
| GGGTTAAGTGACGATTATTATGGAGCAAAGAACCTGAAGGGAGTGACATCCAACACCAGTGACAGCGAAAGCAGTTCCAA | SEQIGVIPSKKRVEKKERARLK |
| AGGACAAGAGGATGCTATTTTGTCATATGAGCCAGTGACACGACAAGAAATTCACTATGCCAGGCCTGTGATCATCTTGG | TVKFHARTGMIESNRDFPGLSD |
| GCCCAATGAAGGACCGAGTCAACGATGACCTCATCTCTGAGTTCCCGCATAAATTTGGATCCTGTGTGCCACATACCACC | DYYGAKNLKGVTSNTSDSESSS |
| CGGCCTCGGCGTGATAACGAGGTAGATGGACAGGATTACCACTTTGTGGTTTCCCGGGAACAAATGGAGAAGGATATTCA | KGQEDAILSYEPVTRQEIHYAR |
| GGACAACAAGTTCATTGAGGCGGGCCAGTTCAATGATAATCTCTATGGGACCAGCATCCAGTCTGTGCGGGCAGTTGCAG | PVIILGPMKDRVNDDLISEFPH |
| AGAGGGGCAAGCACTGCATCTTAGATGTCTCCGGCAACGCCATAAAGAGACTGCAGCAAGCACAACTTTATCCCATTGCC | KFGSCVPHTTRPRRDNEVDGQD |
| ATTTTCATCAAGCCCAAGTCCATTGAAGCACTTATGGAAATGAACCGACGGCAGACATACGAACAAGCAAATAAGATCTT | YHFVVSREQMEKDIQDNKFIEA |
| TGATAAAGCCATGAAACTGGAGCAAGAATTTGGAGAATACTTTACAGCCATTGTACAGGGTGACTCACTGGAAGAGATTT | GQFNDNLYGTSIQSVRAVAERG |
| ATAACAAAATCAAACAAATCATTGAGGACCAGTCTGGGCACTACATTTGGGTCCCATCCCCTGAAAAACTCTGAAGAATC | KHCILDVSGNAIKRLQQAQLYP |
| CCCTCCAAGCATTCTCTTGTGAACAGAAGAAATGAAGCCCCTCTTCCCTCCTTCCTCTTCATTCCTGTCCCCACGGGGAG | IAIFIKPKSIEALMEMNRRQTY |
| AACAAATGACTACTGTTCTTGTCCCCCTTTTTAGATATGTCAAAAATTGAGTTTTCTAGTCCTGTTCTTTTTTAAAAAAT | EQANKIFDKAMKLEQEFGEYFT |
| GTTGTTTTGTTTTGGTTTCTCTTTCGGGATGATGCCATCTCACTCATCACGTGACCGTGCCCATTCCTGCATGGACCTTT | AIVQGDSLEEIYNKIKQIIEDQ |
| CCCACGCGCTAGCACAGGTGCAAATCCATCAGAGTTGTTGTTCTCATAAACACCCAGCAGAAGCGAAGAGAAGAGAGGAG | SGHYIWVPSPEKL |
| GACTGATGGAAAGACAGACTCTGGACAACTGCACAGCTTGTGAAGTGAGCGAAACAGCCCACGTGAGGAGGCGCTCCCGG | |

FIG. 66

| NucleotideSequence (5′-3′) | ORFs |
|---|---|
| GCATTCCTACCCTGTACTGCGGCTTGCAGCTCTGAACGGTGCAACGTAACGGCTACAGAAAGGATCTTATTTATATATAG<br>ATATATATATGTAATTTATATAAAATATATAGAAATTATTATATATATATATTATACACTCTTCTATAATATATATATAT<br>ATATTCACATACATTGGGACTAGAAAATCTATGGAGACGTCCATCAACGGTACTATGTTATTAGAGAAATGCTTTAATTT<br>TCATATTCCAATCAGATGACATCTTTTGTTCCACCTGGTTGGGAAGGGGTTGACAACAGTAGTAAGTGCTATACCAAAGC<br>ACTCGAATTTGGTCATTCTCTTCAGAGCTAAGGCTTGCTCCAGGTGGGGCCAACCTACAGCATAAGAGAAGGGGCTTTGG<br>CTGGGAGCTGGAGATTGGAGACGTGACTAAAGCAGTTGCTGCCCCTGCAGGGCAGTCGTTCCTGTGCAGAAAGAGAGAAT<br>GAATGGCTAATGATGCTCCGGATGAAATTGCCTATTGTTTTATGCCGCCTGATGTGTCTGCATGAGAGGTTTCCTTTTTG<br>TTCATTTTTAAGCTGCTGTTAAACCAAAACCATGTTGTGCTACTGTGTCAGCCTTTTCATTATTCCAGATTTTACTTTTA<br>CTATTTAAGTGAATGCGTAGAATCCTATTTGCCAGTGTTCTAAAGGCTTGTGAGGTTCTGAAGGAGCCAGGCCTGGGATA<br>CAGCGGTAACTTAGGCCTGGCCATCCAGTCAACAGAGGGAAAGCAGGGGCTGGTGAGGGCAGAGAGTACAAGCTGGGGCT<br>CGGAGTTACCATGCTGGACTTAGCTAGGGGTTCCTTCACGGGGCCACTGACAGGCATAGGGAGGTGCTTGCCTTCTGGCT<br>CGGTGCTGGGACAGTGGAAGAGCACCAGGCTTGGCCAGCCGTGTAGTGAGTTGGATTTGGATTCTTTTCTTTTGCAACTG<br>CTCCATTTGCCCTACCCCAGCCCCCTCACCAACAGCTGGTAGCTTACTGTTTCTTCAAGAAGAAAGTAGACTTTAACGCT<br>GTAAATTTGAGCTGTAGAGCTAAGACTCGCTTACTGGTGAGCTGTGAAATCTTGTTGCTTTTTTCCCAGAGTCTGATGGC<br>AGTGACTGGTCCAGGTAGTTTCCCTCCCGCAGCCAGTGCAGGCAGCAGGTGTGGTCCAGGCCCTACCCCACCCCACTATG<br>CTCCTTTGAAGCCAACGTGCCTCCCTCACCTCCACACTGGAGGGATGACGCAGGGGAGAACATAGAATTGCTTGGCCCTC<br>AACTGGGTTAGGACCATCGCAGGTGATGCAGGGTTGACACTTTAAAGCACTACCAGCCACATTCAGGAACTCTGTTCACA<br>GGTATCCTACCAGCATAATGAGGCTAACTGTGACTCGTGGGGCCCAGAGTTAGAAGAAAGAAAAGGCAGCAGCTTTCTCT<br>TGGGCAGTACACTGGATTGAAGGCAAAGAGGGATAAAGTGACAGATGATTGTGACTCTCGCGAGGGGGGGTGAGCGGGAA<br>GTGTTGATTCTCTGATGGTAACTGACAGCAGTGGACAGTGCTCAATCCTCCCTCCCAGGGAAGAAAAGCAAAGATTCGAA<br>GTAAGCATGATAATAGTTGGTTTACCAGTGTTCCTTCCAAGGAGACATATATTTTTTAATAAATGATAGTTGCAATG | |
| SEQIDNO.43<br><br>CCCACGCGTCCGCACCACCTTCTCTTCTTTACGGAATAACTCAGGTCACGCTGACTGGAAATCAGTTGACTGACATCAGT<br>GAAGCAGTGGTTCCTGAGTTTGAAGAAAAGAGGTCTCCTGCCTGGACAGAGGAGTGTGTGCCTTTCTCCAAGCCGTCTCT<br>GGACATATCTTCCCAGCATCCTCTAACAAAGATGCGTCAACTCAAAGGGAAGCCAAAGAAAGAGACCTCCAAGGACAAGA<br>AGGAGCGGAAGCAGGCCATGCAGGAGGCGCGGCAGCAGATCACCACTGTGGTGCTGCCCACCCTGGCTGTGGTGGTGCTC<br>CTCATTGTCGTGTTTGTGTATGTGGCCACACGCCCCGCCGTCACCGAGTGAGCACGTCCATTCTGCTTTCCTCTGCAGAG<br>ATGTCCGAAATGCCAAGCTCTGAGCAGGAGTGCCCTGTCTCCTCTGGTCTTTGACTTGATCAATATTTCTCTACTTTTTT<br>GGGGGGTGGGGTGGGGTGGGGATAGGGAACATTTTATCAGTGAATGTGCCATTTACTTGATGGTCCACTTCATGTGCCTT<br>TCAGACTTCAAAGCTGTGTGTGTGTGTGTGTGTGTGTGTGTGTGTGTGGCCCTTTTTCTCCTGAAATCGATGCATCGCTG<br>CCCCTGAGGAGAGCCTCTCTGGGTGATGCTGTTGGGATCAGAGTCGCCCTCCCATCCAGCAGCATGCTTCCCGGCTCCAC<br>TTCACAACTTTCTAAGGGGACAGCCTTTCTTCTCTGTGCTTGATGGGATTTGAAATATGTTGACTCAAAGTGAAATATTT | SEQIDNO.:135<br><br><br>MRQLKGKPKKETSKDKKERKQA<br>MQEARQQITTVVLPTLAVVVLL<br>IVVFVYVATRPAVTE |

FIG. 67

| NucleotideSequence (5′-3′) | ORFs |
|---|---|
| ATTTTTTGAATAAAGGAGATAATAGTCTTAAAAAAAAAAAAAAAAA | |
| SEQIDNO.44 | SEQIDNO.:136 |
| ACATCCTCTTTTGGCTTCCAGGGGTGACTGCAGGGTTTTTCTCTCTCTTTCACAGTGAGGGGCCTGGGGTGGGCTCTGTC | MTMQPAIQVWFGEDLPLSPRCP |
| TGAAAGACTTCTGCTTTGGACGGGTCCCTGCTGGGTTGGTTTGTGTTTCTGGAAACCTCAGTGCCCCTCCGGATGGATGT | LTPRHGPGLADVCQYDEWIAVR |
| AAGCAGATTTTAGGGTTGGAAGGAGCTCAAAGTCCTGGGAAGAGCAACATTCCAGGGCGCTCTGAAGCAGCCTTGAGAGG | HEATLLPMQEDLSIWLSGLLGV |
| CGGGCTTCACACACTCTCCTGAACGACGGGACAAATAGGAGGGGTTGTCACTGCCACTGATAGAGACTGGACTGGAAAAG | DIKAERLLEELDNGVLLCQLIN |
| GTCGCTACGAATTCTTCGTGCGGTAGAAAGTCTCCGGAGGCGTGGCGCCCAGACCACGCCTCCGGTTCTGATTGGCTCCT | VLQNMVKGCHSDEPGNFPMRKV |
| TCGAAACAGGCGGCCGCGCTGGGCGACGAACTGCGGCGGCGGCGGCGGTTGGTTGCAGGCTTGCTGGCACGCACAGATTG | PCKKDAASGSFFARDNTANFLH |
| AGCCCGAGTCGCCCGGAGAAGTGATCTCGCTCCCGGGCTGGTTCCGAGAAGTTAGCACCGTTGTGCCCGTATAGATGGTT | WCRHIGVDETYLFESEGLVLHK |
| TACGCTGGAGCAGGAGTTGAACCCAGATGAATCCCGTGCTTTGTACTACCATAGTGCTGTTTTGATGATTCCAAGAGCAG | DPRQVYLCLLEIGRIVSRYGVE |
| AGCTTTGGAGCCAACGCTGCCGCCTCTTTTGGGTTTTGACGGATTATCACGGGGAGGTACATAGAAGTTTCATCTCAGTG | PPVLVKLEKEIELEETLLNASG |
| TAGATGACCATGCAGCCTGCAATCCAAGTGTGGTTTGGGGAAGATCTGCCTCTAAGTCCCAGGTGTCCCCTGACTCCCAG | LEESISIPKSCCQQEELHEAVK |
| ACATGGCCCGGGACTGGCTGACGTTTGCCAGTATGACGAGTGGATAGCCGTGAGACATGAAGCCACCCTGCTGCCTATGC | HIAEDPPCSCSHRFSIEYLSEG |
| AGGAAGATCTCTCTATTTGGTTATCTGGCTTACTAGGTGTTGACATCAAGGCAGAAAGATTATTGGAAGAGCTCGATAAT | RYRLGEKILFIRMLHGKHVMVR |
| GGAGTGCTGTTGTGTCAGCTAATCAATGTTCTTCAGAACATGGTGAAAGGCTGCCACTCTGACGAGCCAGGGAACTTTCC | VGGGWDTLQGFLLKYDPCRILQ |
| AATGAGAAAGGTGCCTTGTAAGAAAGATGCTGCTTCGGGCTCATTCTTTGCCAGAGACAACACCGCCAACTTTCTTCACT | FATLEQKILAFQKGVSNESVPD |
| GGTGCCGACACATCGGTGTTGACGAGACTTACCTCTTTGAGTCGGAAGGTTTAGTTTTACATAAAGATCCCAGACAGGTG | SPARTPQPPEMNPLSAVNMFQK |
| TACCTTTGTCTTCTTGAGATTGGTCGGATTGTGTCAAGATACGGAGTTGAGCCACCAGTATTAGTAAAACTTGAGAAAGA | QNLRPGTPVSVPKNKEKQVRLP |
| AATTGAGTTGGAAGAGACCTTGCTTAATGCCTCGGGGCTTGAAGAGTCCATCAGCATCCCCAAATCCTGCTGTCAGCAAG | GARLPASSVKGNLASPSTRAKR |
| AAGAACTACATGAAGCTGTTAAACACATTGCGGAGGACCCTCCTTGTAGCTGCTCTCATCGGTTTTCTATTGAATACTTA | PDSPASFPHPKVTSLKDAAKKT |
| TCCGAAGGGCGGTACCGGCTAGGGGAGAAAATTCTCTTTATAAGGATGCTTCATGGAAAACACGTTATGGTCCGCGTCGG | TAPSNSVSQSLASPNPGSKPST |
| TGGAGGCTGGGATACTCTACAGGGATTTTTGCTGAAGTATGACCCCTGTCGAATACTGCAGTTTGCTACACTAGAACAAA | AQCASESSRKCVTFPKTAQTKA |
| AAATTTTAGCATTTCAAAAAGGAGTTTCTAATGAAAGCGTGCCAGATTCGCCTGCCAGAACGCCTCAGCCTCCAGAAATG | IPAQNSRDLSKSRLLPSKSPGK |
| AACCCTTTGTCAGCAGTTAATATGTTTCAGAAACAAAATTTAAGACCTGGCACACCAGTGAGTGTTCCGAAGAACAAGGA | MEPKHLKHNHLSSRDESRINLS |
| GAAACAGGTACGTCTACCAGGTGCACGTCTGCCTGCATCGTCAGTAAAAGGTAATTTGGCTTCCCCGTCTACCCGGGCTA | SKSPKLPKGAMHGRPNPSPFQP |
| AACGGCCAGATTCTCCAGCATCATTTCCACATCCCAAGGTGACATCTTTGAAGGACGCAGCAAAAAAGACGACTGCTCCT | PAKVTKPSSKTGAIGLGTQSQP |
| TCCAACAGTGTATCGCAGTCCCTGGCTTCTCCAAATCCAGGGTCTAAACCAAGCACTGCACAGTGTGCCTCAGAGTCATC | PTRTPRSGAVSAQRLQSTLNLN |
| GCGAAAATGTGTCACCTTCCCCAAGACTGCACAGACCAAGGCTATTCCAGCCCAGAATTCAAGAGATCTGTCTAAGTCCA | SPASVCSGSSAKATQGSKGKNT |
| GACTTTTACCAAGTAAATCTCCTGGAAAAATGGAACCAAAGCATTTGAAACACAATCATCTTTCTTCTAGGGATGAGTCA | VSVAKKQPQSKGVCRNPGPGSS |
| CGTATAAACTTATCATCCAAGTCCCCAAAGCTACCTAAAGGAGCCATGCACGGAAGGCCTAACCCTTCTCCTTTCCAGCC | KSPGRTPLSIVTVPQSATKTET |
| ACCTGCCAAAGTGACCAAGCCCAGTTCTAAAACCGGAGCCATAGGTCTAGGGACACAGTCTCAGCCACCCACTAGAACGC | VSKSAKTAMKGQYSAKGPPKSS |
| CGAGGTCAGGAGCAGTCTCAGCACAAAGACTTCAGTCTACATTGAATTTAAACAGTCCAGCTTCTGTGTGCTCAGGGTCC | KPPTSFRDPPSSGKGADSGDKM |

FIG. 6B

| NucleotideSequence (5′-3′) | ORFs |
| --- | --- |
| TCTGCAAAAGCTACTCAGGGATCGAAAGGTAAGAATACAGTTTCAGTTGCCAAAAAGCAACCTCAGAGTAAGGGTGTCTG<br>CCGGAATCCGGGACCTGGCTCTTCAAAGTCTCCTGGCCGTACCCCGCTGTCTATTGTGACTGTTCCCCAATCTGCTACCA<br>AGACAGAAACTGTCTCGAAGTCAGCCAAGACTGCCATGAAGGGCCAGTACTCAGCTAAAGGGCCTCCCAAAAGCAGCAAG<br>CCACCAACTTCCTTCAGGGACCCACCCTCATCTGGTAAGGGGGCAGACAGCGGAGATAAAATGCCCACTGCCAGGAAGAA<br>GGAAGAAGATGACCATTATTTTGTTATGACCGGAAATAAGAAGCTTAGGAAATAAATACACTTGTATCGTTTCAGCAAAT<br>CAGGGTGATCAATGAATGGCGAGCCACAAGGATCACCAAAGATCTTCCTATTTGTGTCTGTCCGGAGAGCTGCAGACATG<br>AAGTCAAGATGGGATGAAGCTGGGTCAGGGAAAGGACCCATGCATTTTGTGTATCAATGGACAAATGTGTGAGTTTTGAC<br>CTGTATCATCTTGCTAATGATGTCTGCTGTTTGAGGGAAGTGTAAAAGTCCAAGAACACTACTAGAATTTTAACTATTGG<br>TGGTATATTTTTGAACACAGGTTAACTGTGGAGGTTATCTGCTAATAGCAACTCCGATACTCTTAAACACTAGTTACTGT<br>GCTCAGCCACAAAGCAATGGTTTGCTTGGCGCTAGTGTGTGCCTGTAATCCCAGCTCCGAAGGCTGAGGCAGGGGTACAC<br>AGTAGAAGCCAGCAAGGTTTTGAAATGTGCTGTAATAGGCACCTAATTTATTGGTCAGGAATCCTGGTCCAGCAATCCTA<br>AGTACCAATGGCTCCTGCTGTTTACTTTGATATTATTCTGGATTAAATGGAATTCTTACTATTTAAATCTCTATAATATT<br>TCCGTATCAGAAGGGACTATTTGGTTTTTTAATTAAACTTGGCTTTTTAATACTGTATCATTTTATAACCAATATTTTTG<br>ATAAAAAGAAAAAAAAACTCAACCAAGTAAGTTAACTTATTGAATCATAAGCTGAAATTTAGTAAGAATTAAGTTTTTTA<br>AAAAAAAAAAATATATATATATATAATCTAGACACTTTGTATCTTATATTTTTAGATGAAGTCTGTGCAGTGTGACAGGG<br>AAACATTTAATAGCTTTTAGCATACTAAGATATTTTAAATAGACATTTCCTATATGTACATATAAATTTTTTCATTAAAA<br>TAATGTGTTTTGATACCAGAATTAGGTTTTAATGATCTTAAAATTAAAAGGGATGGGGGGTGGCTCAATGGATAAGTCAT<br>GTCTAGTACAGGCATGGGGATTGGAGTTTGTGTCCCCATACCTACATACAAATCTGGGTGGGCTTGATGGTCTGCCTGTA<br>GTCCCAGCACTCAGGAGGAAGAGACAGGATTTCCTGGGACAAGCTGGCTGGCGAGAGGAGCCGATGGATGAGAGGCAGCT<br>CTTTTGAGAGACCACCCCTACCTTAGTAAAAAAGGAAGATTCCCAAAGTCAATGTCTGTTCTCTCTATGTACAGACTCAT<br>ACATATATCCTGTTCACATATGCACACACACACACACACACACACACACACGCACACACACCTATGAATGCATATATACA<br>CACAGACTCACATACATGCATGCACACCACATATATTGACGCGTACAAAAGATTAAGATGGTATTAAGAGAACCTTTGTG<br>TGATGCTATGCACACATCTCATCAGGTGACTTGTATTTCTTTTGCTAGCACACTGTCGATTTTAATTAGTCTCCAGATTA<br>TGTTCATCTTCATTAGTAAGGCCATGTTGTGCTCAGTTTTCCAGTGCCCAGCAGACAGTGTACCTTCTGTTCTGTAGGCA<br>GATTCTCGTCAGGAATATCCAATGATTTCATGACAGCATAAACACCTTCCACCCACAGGGATACTTGTAAATGATTTATG<br>TACAGGCTTGTCACTATTTAAAGTTTATTAATGTACTTTGGGAACTTTTAAGGGTGTTAAGTAACTATGGTATTACCAGT<br>TATCCTAAGTTGTAGGAAGGAAAAGCAGGTCTAAGAGGTACACGCTTGTAATTCCATTACTTGGAAAGTGGAGGCAGGAG<br>GATCAGAAATTCAAGGTCATGTTCAGCTATGCACTAGAGACACGCCTCAAAAAAAATTGTCACTTTGACTCCTCTTTTAT<br>AACTCAGATGCCCTCCCTTTAAAATCTGCTTTCCATCCTCCTCCTCTTCCTTTCTTTTCTTTGTGAGACTGAGGATCTAT<br>GGTGTCTTACATTGATAGATAAGCATTGCGACTGAGCTTCCTCCTCGGCCCCTTCAAATACGGTTTCTAACACAAACAAA<br>ATAGTTGACCCAGACCTGCCATCATTGAATGAGTGAGCATCGTGGCTGGCTGCTGGCATTCTCTAGACCTACATACAGCA<br>AGAGAACCTTGGGTAAAGACCACTGGATCTTTACCCAAGCAGTATGCATAAAATCAAAGATCTACTCAGGATCCCTTACA<br>ACAGAAAACCACCAAAAACTTGCCAAACGTTCCGGTTCTGAGCATCACTAATGGCAATATGTACATCTTTGAAAGCACCT<br>CTTAGCACTCAAAAGAGATGCCAGGGGCATTTCTGTAATCAGGAATATCTAACACACCTTTCAGAGAGGAAGGATTGTAG | PTARKKEEDDHYFVMTGNKKLR<br>K |

FIG. 69

| NucleotideSequence (5'-3') | ORFs |
|---|---|
| CTTTAGAGAGGCTATTCCCTCATAGAGAGGGCCGCCGAAACTATTTCTAGATCAGTAACTTCTGAGAATTAAAAGAAAAA<br>TATAAATTACACTATAGGCAGACTAAACCTATGACTCAGTACATTGTACAGTTTTATAAACATTATCTTTTGTGCTGGGT<br>AATCAAGAATAAAGATATTCTCAGACACCTGGCACAAATTCCCGAATTAACTTTAGGATTATTTATTTAAGATAAAGATT<br>GGGTTTTTTGTTTTTGTCTGCTGTTCAGTAGCATTTCTCCAACTGTAGTCATATAGGGTGAATTTCTTTGTGTGTGTACC<br>TTGTCTTTCCTAAGCATAGGTTGTATGTGAATAAGTAATTCAGTTCCATGGGAACTGAGAGAACACTCAGCAACTCAGAA<br>CACTTGGTATTCTTGCAGAGAACCTGAGTTCTATTTCCAGCACTCCCGGGGTGGCTCACAAGCATCCAGAACTCTTGTTT<br>CAGGGTATCTGATGCTCGCTTCTGGCCTCCAGAACACAGGCACCAGGCATTCATATTGCACACATACAGGCAAAACATTC<br>ATACATGCAATCAATCAATTAGTAAATATCTTTCCCTCCCAAATTAAAAAAGTTAAATTCTTTCTGATGTATTTTGGTAT<br>TTTCTAAAGGAGCTGATAAATCTTTGCCACAATTTAAAAAACAAGTATAATGCAGTTGTACTCACTTCTTTTTACTACTA<br>GTGTGAAATTACATAAGGTCTTTTTGTGTTTAATATTTAATAAACCAAATATTAAGCATAAAATGCTGATGTACCTGGAA<br>GACACATGTGTGGTTTCTTAAAAATAGAATGTTTTTGTTTTGGAATGCTTTGCTAATGTGTAATTATATAAAGCTGAACA<br>GGGACGGGAAGGGATTTTTTTTTTTTTTTTTTTTTAAGATTTATTTATTATTTTATGTAAGTACACTGTAGCTGTCTTC<br>AGACACACCAGAAGAGGGAGTCAGATCTTGTTACGGATGGTTGTGAGCCACCATGTGGTTGCTGGGATTTGAACTCTGGA<br>CCTTCGGAAGAGCAGTCGGGTGCTCTTACCCACTGAGCCATCTCACCAGCCCATGAAGGGATTCTTTTTACACTCTGCTT<br>CTGGGGAGGTGTTTGAAGAGAGCACCTTCCCAATGTATGGACTTTTAGTGCCCTTGGCCTGTCATCTCCACAAAGTCTCA<br>TCACGCAGATGCAGCTTGCCTGGCATTCTCTAGGTAGCCCAGGCTGGCCTTGAGCTCATAGCAATCCTCCTGCCTCAGTC<br>TCCTGAGTACTGGGTTTGCAGGTTTCGGGTACCACATCAGCTTGATTTCATAATGGATAAAGGAATAGTTTGGAGAAAAT<br>AATTTCTTCTGCAGTCTTTTTTATTTCTGTCTAATTTAAAAATCTGTTACTTCCTTAAAAGGAGCTAATAAAGGTTTTGA<br>TGTATTCTTACATCCAAGTTTCATGCCATCTCTGTGTCAGTTTGGATTTGTATATATTCTGTTGTTTTTTAATTGTTGTT<br>GTTGTTTCATGTCAGCAGTATTTGTATCCAACTTAACTTATATTTTCTCAAGTATTAAAATGTCAGCATAAACCCACTCT<br>GTTTGCTTTTTTAATGTATTTTAACTGTGTTTTGATTATTTGACCCATGTTGGAAATTGCATATATGAAACTGATAAATT<br>AAGAGTTTTAAATATTATGTTATTTTAAACATTTTTTTATTGTATTGTTTCTCGATATTGTTTCAGAAAGACCAGACTCG<br>TGGCTAATTATCTTTGAGATAATGGAAATGATCAGTTATTAAAGTCAAATTTTATAGGACACACCAACACTGTGCTTACA<br>GAAAGTCACTGATAATAGAATTTCAAACTTCCTTTTCCCATAGTCCTGTTTCAGGGTCACACTTTGATACACCGTAAATG<br>TATTTGAAATCCTTTTTTTAATGTTCTTTTATGACCAGAGCAATTATTAAAATGGAGTTAACCTACTATGTATTTCCTGG<br>GCTGTTTCTAAGAATAAAATCCCAAATGAAGTTTTATGTTTGCCTAACTTTATAAGTGTAAAAAAATTTAAGTGTAAGTGT<br>ATTTTATGACATTCTGGAAAAGATGAGGCACACTTAAAACCTTTTTTGGGTAAATATGAAAACACAGACAAATCTTAAGT<br>GGTTTTACAATATCTATACTGTTAATGTAGAAAACCCACAATCTTGAAGGAATAATGCAAAGATAATGTTTTCTCTTTCT<br>ACATTAGGTGGGAACAATTTAAGCACTGGTTGGAGATATAGCCTCAGTACACACCAATTAAAATTAACCTCT | |
| SEQIDNO.45<br><br>AAGAGGACTCGCGGCGGGCCGCTTCGGCTTCTTCTCGGGCCTGCTCCCTCGGCGGCTTCCCGCGCCTTCAGCCGGCCACC<br>ATGGGGAAACGGGATAATCGCGTGGCCTACATGAATCCAATAGCAATGGCTCGATCAAGGGGTCCAATCCAGTCTTCAGG<br>ACCAACAATCCAGGATTATCTGAATCGACCAAGGCCTACCTGGAGGAAGTCAAGGAACAGCTGGAAAAGAAAAAGAAGG | SEQIDNO.:137<br><br><br>MGKRDNRVAYMNPIAMARSRGP<br>IQSSGPTIQDYLNRPRPTWEEV |

FIG. 70

| NucleotideSequence (5'-3') | ORFs |
|---|---|
| GCTCCAAGGCTTTGGCTGAGTTTGAAGAAAAAATGAATGAGAATTGGAAGAAAGAACTAGAAAAACATAGAGAAAAATTA<br>TTAAGTGGAAATGAGAGCTCATCCAAAAAAAGACAGAAAAAGAAAAAAGAAAAGAAGAAATCTGGTAGGGTGAGCAAAAG<br>TTTTCTATTTTCTAAATGTTACAGCTAAGGGCCTGTAAAGCAAAGTAAGAATGATTGGGTTTTCCTTGTATGCGAACGCT<br>AACTTAGACTGTGGGTTCACCACGCAGCCCACAGGTCTCTCTCTCTCTGACATGAAAGACGTGACAATGTCCTCATAG<br>CCTGGTAACGTCTCTGCTGCTGCTACTGAGGACAGTGTTGTCATTGCTGCACTTGTTGTTTTGTTGAGCTTTTGGGGGAG<br>GGAGGAGACTTTTATATTTTAGCTTCTAAATCCTATGAATATGGCATCTGTTTCTTAGACACTAGATTGAGTTCACTAAG<br>TGCTTGAGAGACTTAGTAAAAGAAACCAATTCCTGCATCTCACAAGCTTTAATTGTTTTGTGCTTGGTCAAGTATTCATC<br>TTCTTCTTCATCGAGCTCTGATTCTTCCAGCAGTTCTTCAGATTCCGAAGATGAGGATAAAAAACAAACAAAAAGAAGGA<br>AGAAAAAGAAGAGCCGTTGCCATAAGTCTCCTGAGAGCTCGGGGTCGGATTCGGCTTCAGACAGCAAGGATGGTTCAAAA<br>AAGAAAAAGAAGTCCAAGGATGTAACTGAAAGAGAAAAGGACACTAAAGGTCTCAGCAAAAAGAGAAAGATGTACGAAGA<br>TAAACCGTTGTCATCTGAGTCGCTGTCAGAGTCAGACTGTGGAGAGGTGCAAGCAAAAAGGAAGAAAAGCGGTGAAGAGC<br>GTGAGAGAACAACAGACAAAGCCAAAAAGAGAAGGAAGCATAAGAAGCACAGCAAGAAGAAGAAAAAGAAGGCCGCCAGC<br>TCCAGCTCAGACTCGCCGTAGCGTCCATGAAGACCAGGACCCTTACCCAGTGCAGTGTCAAAGGAGCTCAACTGTGAAGA<br>TTGCGACACACTTAGTAACGTGCATGAATTCCCTTGTTCTTAGACTTGTCCTGGACTAGTCAGTAGCCACTTGGATTCTG<br>CTGTGTGAAGGGCCATGATTGTTGCCTGCTGCTTCAACACCTTTTCCTCTTCCAGTGCTTGGTGACTCTGGGAGATAGTA<br>CTTTGCAGTCATACTAGTGATTAAGATATCTGGAATAAAGCTAATATTTTTACTAGAAGTACTTAAGAATAAATCAACA<br>GAAACTGAATCTGGATTCATCTTTTAAGATGTAACCAGAAAAAATGAGATGACTCTAGTAAAAATTTTCAAAGTAGGGAT<br>TACATTAATATTTCAGAATCCTTACTCTGTAGATAAGTATATTTTAATTTTCCCCATGTATACTTTGATTTACTTGGGGA<br>AGGAGCTTTTAAAGGGGGTGGTTTGCTATCTCTTTAGCTACCAGAACAGTGTGCCTTTGATCTCACACATCCTACTTTTA<br>TGGACACAGTAGCCATGCTTCCTGGGAGGACAGAGCTGGGCACCGTCATTCCTGCCCGACTGAGGTTATGACATCCTTAG<br>ACTTTGTTGTATGCTGCTTCGAATGAACCAGAGATACCCGGCCCTTTGCAGCATGAGAAAGCCCCCAAAGCTCTGGAATT<br>TACCTCCACATCAATAATAAGTGAATGTTTTCAGGGTTAAAAAAAAAAAAAAAAAAAAAAAAAAAAAAAAAAAAAAAAAA<br>AAAAAAAAAAAAAAAAAAAAAAAA | KEQLEKKKKGSKALAEFEEKMN<br>ENWKKELEKHREKLLSGNESSS<br>KKRQKKKKEKKKSGRVSKSFLF<br>SKCYS |
| SEQIDNO.46<br><br>GCAGCCGAGGCCGCGAACTGCATCATGGAGGTTTCCTGTGGCCAAGCAGAAAGTAGTGAGAAGCCCAACGCTGAGGACAT<br>GACATCCAAAGACTACTACTTTGACTCCTATGCCCACTTTGGCATCCACGAGGAGATGCTGAAGGATGAGGTGCGCACCC<br>TCACATACCGCAACTCCATGTTTCACAATCGGCATCTCTTCAAAGACAAGGTGGTGCTGGACGTGGGCTCAGGCACTGGC<br>ATCCTCTGCATGTTTGCTGCCAAGGCGGGGGCCCGCAAGGTTATTGGGATTGAGTGTTCCAGTATCTCCGATTATGCTGT<br>GAAGATTGTCAAAGCCAACAAGTTAGACCATGTGGTGACCATCATCAAGGGCAAGGTGGAGGAGGTGGAGCTGCCCGTGG<br>AGAAGGTGGACATCATCATCAGCGAGTGGATGGGTTACTGCCTCTTCTACGAGTCCATGCTCAACACCGTGCTGCATGCT<br>CGGGACAAGTGGCTGGCACCCGATGGCCTCATCTTCCCAGACCGGGCCACCTTGTATGTGACAGCCATTGAGGACCGACA<br>ATATAAAGACTACAAGATCCACTGGTGGGAGAACGTGTATGGCTTTGATATGTCCTGCATTAAAGACGTGGCCATCAAGG | SEQIDNO.:138<br><br><br>MEVSCGQAESSEKPNAEDMTSK<br>DYYFDSYAHFGIHEEMLKDEVR<br>TLTYRNSMFHNRHLFKDKVVLD<br>VGSGTGILCMFAAKAGARKVIG<br>IECSSISDYAVKIVKANKLDHV<br>VTIIKGKVEEVELPVEKVDIII<br>SEWMGYCLFYESMLNTVLHARD |

FIG. 71

| Nucleotide Sequence (5'-3') | ORFs |
|---|---|
| AGCCCCTGGTGGACGTGGTGGACCCAAAGCAGCTGGTCACCAATGCCTGCCTCATAAAGGAGGTGGACATCTACACAGTC<br>AAGGTGGAGGACCTGACCTTCACCTCCCCCTTCTGCCTGCAAGTGAAGAGGAACGACTACGTGCATGCGTTGGTGGCTTA<br>CTTCAACATCGAGTTCACCCGATGCCACAAGAGGACCGGCTTCTCCACCAGTCCTGAGTCCCCGTACACACACTGGAAGC<br>AGACTGTGTTCTACATGGAGGACTACCTAACAGTGAAGACTGGCGAGGAGATCTTTGGCACCATTGGAATGAGGCCCAAT<br>GCCAAAAACAATCGTGACTTGGACTTTACCATCGACCTGGACTTCAAGGGTCAGCTGTGTGAGCTCTCTTGTTCCACCGA<br>CTACCGGATGCGCTGAGGAGGTGCCAGGCTGGCCCTCCTGCAGAAGGGGGCTCGGGGGGATGGCTTGGGGGATGGGGGG<br>GTACATCGTGACTGTGTTTTTCATAACTTATGTTTTATATGGTTGCGTTTATGCCAATAAATCCTCAGCTGACCATGAA<br>AAAAAAAAAAAAA | KWLAPDGLIFPDRATLYVTAIE<br>DRQYKDYKIHWWENVYGFDMSC<br>IKDVAIKEPLVDVVDPKQLVTN<br>ACLIKEVDIYTVKVEDLTFTSP<br>FCLQVKRNDYVHALVAYFNIEF<br>TRCHKRTGFSTSPESPYTHWKQ<br>TVFYMEDYLTVKTGEEIFGTIG<br>MRPNAKNNRDLDFTIDLDFKGQ<br>LCELSCSTDYRMR |
| SEQIDNO.47<br><br>GGCGTCCGAGCTGAAGCTTCCCCGGCTTCCCAATTGCCCAAGGTAATAATCTTCAGTAGCCAAGATGTCTTCAGCACCTG<br>ATCCTCCAACAGTTAAAAAAGAACCATTAAAAGAGAAAAACTTTGAAAACCCAGGCCTCCGAGGGGCGCACACAACCACC<br>TTATTTCGAGCTGTGAATCCCGAGCTCTTCATTAAACCCAACAAACCTGTGATGGCTTTTGGATTGGTAACCCTTTCACT<br>TTGTGTGGCTTACATTGGTTATCTGCATGCAACTCAAGAGAACAGAAAGGACCTCTATGAAGCCATTGACAGTGAAGGGC<br>ATCGGTACATGAGGAGAAAAACATCTAAGTGGGACTAACTGCTGCTTCCTTCAGGTGGAGTGTTATTATAGGCTCCGACA<br>CCTTTGAAAGAAAGACTGTTAGTGCACAGAATTGTTTCTTGTTCCATAATATGTTAACAAGGGAGAATATAAAATTGAAA<br>GCAGTCCACTGTGGTGAGTTTAGTCTCATTACAGCTGAAGGCATTAAATTCTGTATAATAAAAGTACCCAGTACTCTTCC<br>ATTTGCATGGAGTTTCTAACGTTTTAGAGTGGATTGTGCCTTTGCAGCAATGCTTTACTGTTTAGGAGAGAAGACAACCC<br>CTTCAGTTACTAAAATCATAATTAAATGAAAGAATAAAAAAAAAAAAAAAAAAAAAAA | SEQIDNO.:139<br><br>MSSAPDPPTVKKEPLKEKNFEN<br>PGLRGAHTTTLFRAVNPELFIK<br>PNKPVMAFGLVTLSLCVAYIGY<br>LHATQENRKDLYEAIDSEGHRY<br>MRRKTSKWD |
| SEQIDNO.48<br><br>GCTCCCACCCCCTCCCCGCCTCCGGGCCGTGGCACTCTGGGGCTCTGCCGTCGACATGGGCGCCGCCGCGTGGGCACCGC<br>CACACCTGCTGCTGCGGGCGTCTTTCCTGCTTCTGCTGCTGTTGCTGCCGCTCCGCGGGCGGTCAGCGGGCTCCTGGGAC<br>CTGGCCGGTTACCTGCTCTACTGTCCCTGCATGGGGCGCTTTGGGAACCAGGCTGATCACTTCTTGGGCTCCCTGGCATT<br>TGCGAAGCTGCTGAACCGCACCTTGGCTGTACCTCCATGGATTGAATACCAACATCACAAGCCTCCTTTCACCAACCTCC<br>ATGTGTCCTACCAAAAGTACTTCAAACTGGAGCCTCTCCAAGCCTACCATCGGGTTGTCAGCCTGGAGGACTTCATGGAA<br>AATCTGGCACCCTCCCACTGGCCCCCTGAGAAGCGAGTGGCATACTGCTTTGAGGTGGCAGCCCAGCGAAGTCCTGATAA<br>GAAGACATGTCCCATGAAGGAAGGAAATCCTTTTGGGCCATTCTGGGACCAGTTTCATGTGAGTTTCAATAAGTCAGAAC<br>TGTTCACAGGCATTTCCTTCAGCGCCTCCTACAAAGAACAATGGACCCAGAGATTTCCTGCAAAAGAGCATCCTGTGCTC<br>GCACTGCCTGGGGCCCCAGCACAGTTCCCTGTCCTGGAGGAACACAGGGAGCTCCAGAAGTACATGGTGTGGTCAGATGA | SEQIDNO.:140<br><br>MGAAAWAPPHLLLRASFLLLLL<br>LLPLRGRSAGSWDLAGYLLYCP<br>CMGRFGNQADHFLGSLAFAKLL<br>NRTLAVPPWIEYQHHKPPFTNL<br>HVSYQKYFKLEPLQAYHRVVSL<br>EDFMENLAPSHWPPEKRVAYCF<br>EVAAQRSPDKKTCPMKEGNPFG<br>PFWDQFHVSFNKSELFTGISFS |

FIG. 72

| Nucleotide Sequence (5'-3') | ORFs |
|---|---|
| GATGGTGAGGACGGGAGAGGCCCTGATCAGTGCCCACCTCGTCCGGCCCTATGTGGGCATTCATCTGCGCATTGGCTCCG<br>ACTGGAAGAATGCCTGTGCCATGCTGAAGGATGGAACTGCAGGGTCACACTTCATGGCTTCCCCTCAGTGTGTGGGCTAT<br>AGCCGCAGCACAGCGACCCCTCTCACCATGACCATGTGCCTCCCTGACCTGAAGGAAATCCAGCGGGCTGTGACGCTTTG<br>GGTGAGAGCACTGAATGCCAGATCGGTCTACATCGCCACAGACTCTGAGAGCTACGTGTCAGAGATCCAGCAGCTCTTCA<br>AAGACAAGGTGAGGGTGGTGAGCCTGAAACCCGAGGTGGCCCAGATCGACCTGTACATCCTCGGCCAGGCTGACCACTTC<br>ATTGGAAACTGTGTCTCCTCGTTCACTGCCTTCGTGAAGCGGGAGCGGGACCTCCATGGGAGGCAGTCGTCCTTCTTTGG<br>CATGGACAGACCCTCCCAGCTTCGGGATGAATTTTGATCCCATCTGAAGCCCCCACCTCCCACCCTCAACCAGGCTTGGC<br>TGCTAAGGATGCTCCTGGGATTACACATCCCTTTTCTTTTCTGCCAGAGGTGGAGAACAGTACCAAGGACGTCCTGGAAG<br>AGAAGGCATTCCATCCCAGGCATTGGCTCCCATGGTCCCCAGCCAGGGCTGCTCTGGGCTGCATGATCATGCACATACAA<br>AGCAGCCCACCTCCAGCCTGGGCACACCCTGATATATACACATACATACACATAATATATATCATATATATATAAAAAAA<br>AAAAAAAAA | ASYKEQWTQRFPAKEHPVLALP<br>GAPAQFPVLEEHRELQKYMVWS<br>DEMVRTGEALISAHLVRPYVGI<br>HLRIGSDWKNACAMLKDGTAGS<br>HFMASPQCVGYSRSTATPLTMT<br>MCLPDLKEIQRAVTLWVRALNA<br>RSVYIATDSESYVSEIQQLFKD<br>KVRVVSLKPEVAQIDLYILGQA<br>DHFIGNCVSSFTAFVKRERDLH<br>GRQSSFFGMDRPSQLRDEF |
| SEQIDNO.49<br><br>TTCCTGCGGAGGCCGCGGCCGCCATGTTGTTGTGGGGCTGAGGCGGCGCCGGCTGAGAGCCCAGCAGCCGTGACAGGCTG<br>CGCAACAGGTTCGCTGCGGCCGGCCTGACGACTGACCCGGCGGCGGCCGCGGCACGGCAGGGTCTTCCCGGAGCTTG<br>GCCGCGCCCACGCGCCGGTGTCGAGGAGCGCGCGGGGTCGCGCCGGGACGTGCGCGAGGCGCCAGATGGCTGAGAGCTGC<br>AAGAAGAAGTCAGGATCATGATGGCTCAGTTTCCCACAGCGATGAATGGAGGGCCAAATATGTGGGCTATTACATCTGAA<br>GAACGTACTAAGCATGATAAACAGTTTGATAACCTCAAACCTTCAGGAGGTTACATAACAGGTGATCAAGCCCGTACTTT<br>TTTCCTACAGTCAGGTCTGCCGGCCCCGGTTTTAGCTGAAATATGGGCCTTATCAGATCTGAACAAGGATGGGAAGATGG<br>ACCAGCAAGAGTTCTCTATAGCTATGAAACTCATCAAGTTAAAGTTGCAGGGCCAACAGCTGCCTGTAGTCCTCCCTCCT<br>ATCATGAAACAACCCCCTATGTTCTCTCCACTAATCTCTGCTCGTTTTGGGATGGGAAGCATGCCCAATCTGTCCATTCA<br>TCAGCCATTGCCTCCAGTTGCACCTATAGCAACACCCTTGTCTTCTGCTACTTCAGGGACCAGTATTCCTCCCCTAATGA<br>TGCCTGCTCCCCTAGTGCCTTCTGTTAGTACATCCTCATTACCAAATGGAACTGCCAGTCTCATTCAGCCTTTATCCATT<br>CCTTATTCTTCTTCAACATTGCCTCATGCATCATCTTACAGCCTGATGATGGGAGGATTTGGTGGTGCTAGTATCCAGAA<br>GGCCCAGTCTCTGATTGATTTAGGATCTAGTAGCTCAACTTCCTCAACTGCTTCCCTCTCAGGGAACTCACCTAAGACAG<br>GGACCTCAGAGTGGGCAGTTCCTCAGCCTTCAAGATTAAAGTATCGGCAAAAATTTAATAGTCTAGACAAAGGCATGAGC<br>GGATACCTCTCAGGTTTTCAAGCTAGAAATGCCCTTCTTCAGTCAAATCTCTCTCAAACTCAGCTAGCTACTATTTGGAC<br>TCTGGCTGACATCGATGGTGACGGACAGTTGAAAGCTGAAGAATTTATTCTGGCGATGCACCTCACTGACATGGCCAAAG<br>CTGGACAGCCACTACCACTGACGTTGCCTCCCGAGCTTGTCCCTCCATCTTTCAGAGGGGGAAAGCAAGTTGATTCTGTT<br>AATGGAACTCTGCCTTCATATCAGAAAACACAAGAAGAAGAGCCTCAGAAGAAACTGCCAGTTACTTTTGAGGACAAACG<br>GAAAGCCAACTATGAACGAGGAAACATGGAGCTGGAGAAGCGACGCCAAGTGTTGATGGAGCAGCAGCAGAGGGAGGCTG<br>AACGCAAAGCCCAGAAAGAGAAGGAAGAGTGGGAGCGGAAACAGAGAGAACTGCAAGAGCAAGAATGGAAGAAGCAGCTG<br>GAGTTGGAGAAACGCTTGGAGAAACAGAGAGAGCTGGAGAGACAGCGGGAGGAAGAGAGGAGAAAGGAGATAGAAAGACG | SEQIDNO.:141<br><br>MMAQFPTAMNGGPNMWAITSEE<br>RTKHDKQFDNLKPSGGYITGDQ<br>ARTFFLQSGLPAPVLAEIWALS<br>DLNKDGKMDQQEFSIAMKLIKL<br>KLQGQQLPVVLPPIMKQPPMFS<br>PLISARFGMGSMPNLSIHQPLP<br>PVAPIATPLSSATSGTSIPPLM<br>MPAPLVPSVSTSSLPNGTASLI<br>QPLSIPYSSSTLPHASSYSLMM<br>GGFGGASIQKAQSLIDLGSSSS<br>TSSTASLSGNSPKTGTSEWAVP<br>QPSRLKYRQKFNSLDKGMSGYL<br>SGFQARNALLQSNLSQTQLATI<br>WTLADIDGDGQLKAEEFILAMH<br>LTDMAKAGQPLPLTLPPELVPP<br>SFRGGKQVDSVNGTLPSYQKTQ<br>EEEPQKKLPVTFEDKRKANYER<br>GNMELEKRRQVLMEQQQREAER<br>KAQKEKEEWERKQRELQEQEWK<br>KQLELEKRLEKQRELERQREEE |

FIG. 73

| Nucleotide Sequence (5′-3′) | ORFs |
|---|---|
| AGAGGCAGCAAAACAGGAGCTTGAGAGACAACGCCGTTTAGAATGGGAAAGACTCCGTCGGCAGGAGCTGCTCAGTCAGA | RRKEIERREAAKQELERQRRLE |
| AGACCAGGGAACAAGAAGACATTGTCAGGCTGAGCTCCAGAAAGAAAAGTCTCCACCTGGAACTGGAAGCAGTGAATGGA | WERLRRQELLSQKTREQEDIVR |
| AAACATCAGCAGATCTCAGGCAGACTACAAGATGTCCAAATCAGAAAGCAAACACAAAAGACTGAGCTAGAAGTTTTGGA | LSSRKKSLHLELEAVNGKHQQI |
| TAAACAGTGTGACCTGGAAATTATGGAAATCAAACAACTTCAACAAGAGCTTAAGGAATATCAAAATAAGCTTATCTATC | SGRLQDVQIRKQTQKTELEVLD |
| TGGTCCCTGAGAAGCAGCTATTAAACGAAAGAATTAAAAACATGCAGCTCAGTAACACACCTGATTCAGGGATCAGTTTA | KQCDLEIMEIKQLQQELKEYQN |
| CTTCATAAAAAGTCATCAGAAAAGGAAGAATTATGCCAAAGACTTAAAGAACAATTAGATGCTCTTGAAAAAGAAACTGC | KLIYLVPEKQLLNERIKNMQLS |
| ATCTAAGCTCTCAGAAATGGATTCATTTAACAATCAGCTGAAGGAACTCAGAGAAAGCTATAATACACAGCAGTTAGCCC | NTPDSGISLLHKKSSEKEELCQ |
| TTGAACAACTTCATAAAATCAAACGTGACAAATTGAAGGAAATCGAAAGAAAAAGATTAGAGCAAATTCAAAAAAAGAAA | RLKEQLDALEKETASKLSEMDS |
| CTAGAAGATGAGGCTGCAAGGAAAGCAAAGCAAGGAAAAGAAAACTTGTGGAGAGAAAGTATTAGAAAGGAAGAAGAGGA | FNNQLKELRESYNTQQLALEQL |
| AAAGCAAAAACGACTCCAGGAAGAAAAGTCACAGGACAAAACTCAAGAAGAGGAACGAAAAGCTGAGGCAAAACAAAGTG | HKIKRDKLKEIERKRLEQIQKK |
| AGACAGCCAGTGCTTTGGTGAATTACAGAGCACTGTACCCTTTTGAAGCAAGAAACCATGATGAGATGAGTTTTAGTTCT | KLEDEAARKAKQGKENLWRESI |
| GGGGATATAATTCAGGTTGATGAAAAAACTGTAGGAGAGCCTGGTTGGCTTTATGGTAGTTTTCAGGGAAAGTTTGGCTG | RKEEEEKQKRLQEEKSQDKTQE |
| GTTCCCGTGCAACTATGTAGAAAAAGTGCTGTCAAGTGAAAAAGCTCTGTCTCCTAAGAAGGCCTTACTTCCTCCTACAG | EERKAEAKQSETASALVNYRAL |
| TGTCTCTCTCTGCTACCTCAACTTCTTCCCAGCCACCAGCATCAGTGACTGATTATCACAATGTATCCTTCTCAAACCTT | YPFEARNHDEMSFSSGDIIQVD |
| ACTGTTAATACAACATGGCAGCAGAAGTCAGCTTTTACCCGCACTGTGTCCCCTGGATCTGTGTCCCCCATTCACGGACA | EKTVGEPGWLYGSFQGKFGWFP |
| GGGGCAGGCTGTAGAAAACCTGAAAGCCCAGGCCCTTTGTTCCTGGACGGCAAAGAAGGAGAACCACCTGAACTTCTCAA | CNYVEKVLSSEKALSPKKALLP |
| AGCACGACGTCATCACTGTCCTGGAGCAGCAGGAAAACTGGTGGTTTGGGGAGGTGCACGGAGGAAGAGGATGGTTCCCC | PTVSLSATSTSSQPPASVTDYH |
| AAGTCTTATGTCAAGCTCATTCCTGGGAATGAAGTACAGCGAGGAGAGCCAGAAGCTTTGTATGCAGCTGTGACTAAGAA | NVSFSNLTVNTTWQQKSAFTRT |
| ACCTACCTCCACAGCCTATCCAGTTACCTCCACAGCCTATCCAGTTGGAGAAGACTACATTGCACTTTATTCATACTCAA | VSPGSVSPIHGQGQAVENLKAQ |
| GTGTAGAGCCCGGGGATTTGACTTTCACTGAAGGTGAAGAAATTCTAGTGACCCAGAAAGATGGAGAGTGGTGGACAGGA | ALCSWTAKKENHLNFSKHDVIT |
| AGTATTGGAGAGAGAACTGGAATCTTCCCGTCCAACTACGTCAGACCAAAGGATCAAGAGAATTTTGGGAATGCTAGCAA | VLEQQENWWFGEVHGGRGWFPK |
| ATCTGGAGCATCAAACAAAAAACCCGAGATCGCTCAAGTAACTTCAGCATATGCTGCTTCAGGGACTGAGCAGCTCAGCC | SYVKLIPGNEVQRGEPEALYAA |
| TTGCGCCAGGACAGTTAATATTAATCTTAAAGAAAAACACAAGCGGGTGGTGGCAAGGAGAGCTACAGGCCAGAGGGAAG | VTKKPTSTAYPVTSTAYPVGED |
| AAACGACAGAAGGGATGGTTTCCTGCCAGCCATGTAAAGCTGCTAGGTCCAAGCAGTGAAAGAACCATGCCTACTTTTCA | YIALYSYSSVEPGDLTFTEGEE |
| CGCTGTATGTCAAGTGATTGCTATGTATGACTACATGGCGAATAACGAAGATGAGCTCAATTTCTCCAAAGGACAGCTGA | ILVTQKDGEWWTGSIGERTGIF |
| TTAATGTTATGAACAAAGATGACCCTGACTGGTGGCAAGGAGAAACCAATGGTCTGACTGGTCTCTTTCCTTCAAACTAT | PSNYVRPKDQENFGNASKSGAS |
| GTTAAGATGACAACAGACTCAGATCCAAGTCAACAGTGGTGTGCTGACCTCCAAGCCCTGGACACAATGCAGCCTACGGA | NKKPEIAQVTSAYAASGTEQLS |
| GAGGAAGCGACAGGGCTACATTCACGAGCTCATTCAGACAGAGGAGCGGTACATGGACGACCTGCAGCTGGTCATCGAGG | LAPGQLILILKKNTSGWWQGEL |
| TCTTCCAGAAACGGATGGCTGAGTCAGGCTTCCTCACTGAAGCAGACATGGCTCTGATCTTTGTGAACTGGAAAGAGCTC | QARGKKRQKGWFPASHVKLLGP |
| ATCATGTCCAACACGAAGCTGCTGAGGGCCTTGCGGGTGAGGAAGAAGACTGGGGGTGAGAAGATGCCAGTTCAGATGAT | SSERTMPTFHAVCQVIAMYDYM |
| TGGAGACATCCTGGCGGCAGAGCTGTCCCACATGCAGGCCTACATCCGCTTCTGCAGCTGTCAGCTTAATGGGGCAACCC | ANNEDELNFSKGQLINVMNKDD |
| TGTTACAGCAGAAGACAGACGAGGACACGGACTTCAAGGAATTTCTAAAGAAGTTGGCATCAGACCCACGATGCAAAGGG | PDWWQGETNGLTGLFPSNYVKM |
| ATGCCCCTCTCCAGCTTCCTGCTGAAGCCCATGCAGAGGATCACTCGCTACCCGCTGCTCATCCGAAGTATCCTGGAGAA | TTDSDPSQQWCADLQALDTMQP |
| CACTCCACAGAGTCATGTTGACCACTCCTCCCTGAAGCTGGCCCTAGAACGTGCTGAGGAGCTGTGCTCTCAGGTGAACG | TERKRQGYIHELIQTEERYMDD |

FIG. 74

| NucleotideSequence (5'-3') | ORFs |
|---|---|
| AGGGAGTCCGGGAGAAGGAAAATTCAGACCGGCTGGAGTGGATCCAGGCACACGTGCAGTGCGAAGGCTTGGCAGAGCAA | LQLVIEVFQKRMAESGFLTEAD |
| CTTATTTTCAACTCCCTCACCAACTGCCTGGGCCCCCGGAAGCTTCTGCACAGCGGGAAGCTGTACAAGACCAAGAGCAA | MALIFVNWKELIMSNTKLLRAL |
| TAAGGAGCTGCACGCCTTCCTCTTCAACGACTTCCTGCTGCTCACCTACCTGGTCAGGCAGTTTGCCGCCGCCTCTGGCC | RVRKKTGGEKMPVQMIGDILAA |
| ACGAGAAGCTCTTCAACTCCAAGTCCAGTGCTCAGTTCCGGATGTACAAAACGCCCATTTTCCTGAATGAAGTGTTGGTG | ELSHMQAYIRFCSCQLNGATLL |
| AAACTTCCCACAGACCCTTCCAGCGATGAGCCCGTCTTCCACATTTCCCACATTGATCGTGTGTACACACTCCGAACAGA | QQKTDEDTDFKEFLKKLASDPR |
| CAACATCAACGAGAGGACGGCCTGGGTCCAGAAGATCAAGGGTGCCTCAGAGCAGTACATCGACACTGAGAAGAAGAAAC | CKGMPLSSFLLKPMQRITRYPL |
| GGGAAAAGGCTTACCAAGCCCGTTCTCAAAAGACTTCAGGTATTGGGCGTCTGATGGTGCATGTCATTGAAGCTACAGAA | LIRSILENTPQSHVDHSSLKLA |
| TTAAAAGCCTGCAAACCAAACGGGAAAAGTAATCCATACTGTGAAGTCAGCATGGGCTCCCAAAGCTATACCACCAGGAC | LERAEELCSQVNEGVREKENSD |
| CCTGCAGGACACACTAAACCCCAAGTGGAACTTCAACTGCCAGTTCTTCATCAAGGATCTTTACCAGGACGTTCTGTGTC | RLEWIQAHVQCEGLAEQLIFNS |
| TCACTATGTTTGACAGAGACCAGTTTTCTCCAGATGACTTCTTGGGTCGTACTGAAGTTCCAGTGGCAAAAATCCGAACA | LTNCLGPRKLLHSGKLYKTKSN |
| GAACAGGAAAGCAAAGGCCCCACCACCCGCCGACTACTACTGCACGAAGTCCCCACTGGAGAAGTCTGGGTCCGCTTTGA | KELHAFLFNDFLLLTYLVRQFA |
| CCTGCAACTTTTTGAACAAAAAACTCTCCTTTGAGGGCCTGGGGAAGCCAGAACCAGGGGAGCTGCCCACAAGGCTGGGT | AASGHEKLFNSKSSAQFRMYKT |
| CTAAAGACAGATTTTGCTCTCCCAGGACAGAGGAGCATCACATGGCTTCATCCATCAAACAGCCACACTCGCTGGGCCTG | PIFLNEVLVKLPTDPSSDEPVF |
| TATTTTATTGCACACTAAATTGCTAGCAATCTATGCAAACATGATCTTTTAAACAAACGCCACAGCACAGTGCCTTGTAC | HISHIDRVYTLRTDNINERTAW |
| TAGTGTTAACCTGTTCAGCTGTGTTAGATGCCAGGGTTTCCATTTTCAGGGCTATAAAAGTATTATGTGGAAATGAGGCA | VQKIKGASEQYIDTEKKKREKA |
| TCAGACCACCGGACGTTACCACTTGGCAAATCTGTCCACTGTGGAGTTGGTGATGTTGGAACCATTCCACACTATGTGAC | YQARSQKTSGIGRLMVHVIEAT |
| CTCTGCTGGGTCACACACTCAGGAGGTGAAGGGCTGAGATGAAATGCTGCAGCCTTGGGGCTTGTGCAGCCTGATACTGA | ELKACKPNGKSNPYCEVSMGSQ |
| AATAGCATCCACTTGTGCACTGAATAAATAGAAACTTGATCGTTTTATTCTGACTAGATATTATCATTCTCTGCTAAGAC | SYTTRTLQDTLNPKWNFNCQFF |
| AATATAGTTTGAAATATTATAGTTTGAATATAAGGAGGAAAGCTTGATGTACTTTAAATATACTGTGAACTCTAATAATG | IKDLYQDVLCLTMFDRDQFSPD |
| TGGGGATATTTTTCAACTTTAATTTTCTTAAGTATAAATTATTTATGTAAATTCTTTGTTTTGCATATTTCATAGAACAT | DFLGRTEVPVAKIRTEQESKGP |
| GCATCTTTAAGCTTTATCATTGCCAACAATGTACAGAAAGAGAATAAAAGTATAAGTTTATGAATGTAAAAAAAAAAAAA | TTRRLLLHEVPTGEVWVRFDLQ |
| A | LFEQKTLL |
| SEQIDNO.50 | SEQIDNO.:142 |
| CAAGTGGGTGTAGAGGAGGCTGAGCGTGAGCCTCCTCGTCTCTCTGGGGCAGTCGCCTGCACGCAGAGACCTTTCGCTGA | MTQSCTMASTKPLSRFWEWGKN |
| CCTCAGCGTCCCGCTGCTGCGCAAGGAAGGGCGGGGCCGCTCCGGCCTGGACAGCGTCCTAAGCCAGTCCTCTGGAGGCC | IVCVGRNYADHVKEMRSTVLSE |
| GCCGTAGTCCGGGGGAGTCGGTGGTCACATGACCCAAAGCTGTACTATGGCTTCCACCAAACCGCTGTCTCGTTTCTGGG | PVLFLKPSTAYAPEGSPVLMPA |
| AGTGGGGCAAGAATATCGTCTGCGTGGGGAGGAACTATGCAGATCACGTCAAAGAGATGCGCAGCACCGTGCTGAGTGAG | YCRNLHHEVELGVLLGKRGEAI |
| CCTGTGCTTTTCCTGAAGCCGTCCACCGCGTATGCTCCCGAGGGCTCACCGGTGTTAATGCCCGCTTACTGCCGCAACCT | PEAAAMDYVAGYALCLDMTARD |
| CCACCACGAGGTGGAGTTGGGAGTGCTTCTGGGCAAGCGTGGTGAAGCGATCCCGGAGGCTGCAGCCATGGACTACGTGG | VQEECKKKGLPWTLAKSFTSSC |
| CCGGCTATGCCCTGTGCCTGGACATGACTGCCAGAGATGTGCAGGAGGAGTGCAAGAAGAAGGGGCTGCCGTGGACCCTG | PVSAFVPKEKIPDPHALRLWLK |
| GCTAAGAGCTTTACGTCCTCCTGCCCGGTCAGTGCCTTCGTGCCCAAGGAGAAGATTCCTGACCCTCATGCCCTAAGACT | VNGELRQEGKTSSMIFSIPYII |
| GTGGCTCAAGGTCAACGGAGAGCTCAGGCAGGAGGGCAAAACATCATCTATGATCTTTTCCATCCCCTACATCATCAGCT | SYVSKIITLEEGDLILTGTPKG |

FIG. 75

| NucleotideSequence (5'-3') | ORFs |
|---|---|
| ATGTTTCTAAGATAATAACCTTGGAAGAAGGAGATCTTATCTTGACCGGGACTCCAAAGGGAGTTGGGCCAGTTAAAGAA<br>AACGATGAGATCGAGGCCGGCATAGATGGGGTGGTTAGTATGAGGTTCAAGGTGAAAAGATCAGAATACTGAGAGTAGAG<br>TGCCAAAGGGGAAGGGAGACAGAAGCAAGGGAAATAAATGACACTAATAATGAAAATCTAAAAATTATGCTAGACATGTC<br>AAAAAAGATGAATCCTTAAAAAATAACGTGATCTAAAAGAGCTGGGACAGAAATAGAAACAGGAACAACGAAGCTAAAGG<br>ATATAGAATGCTTCCCAAGAGGGCAATGTTAAACTAAACTTTGAGAAGTTGTAGTTTTCTTTTCTAAAACTGAACTGAAT<br>AGACTTTTCAATAAATCATTCTGAAGTCTAAAAAAAAAAAAAAAAAAAAAAAAAAAAAAAA | VGPVKENDEIEAGIDGVVSMRF<br>KVKRSEY |
| SEQIDNO.51<br><br>GCTGGAGACCCGGCCCTAGTCGCCGGCCCCACCGCCCCGGGGCGCCAATCGAGACGACGCGGCCCCGCGCGGCGCGAGGA<br>GGAGCCATGGGCAAGTGCAGCGGCCGCTGCACGCTGGTCGCCTTCTGCTGCCTGCAGCTGGTGGCTGCACTCCAGCGGCA<br>GATCTTCGATTTCCTGGGCTACCAGTGGGCTCCTATCCTGGCCNACTTCCTGCATATCATGGCTGTCATCCTGGGCATCT<br>TTGGTACCGTGCAGTATCGGTCCCGGTATCTCATCCTGTATGCAGCCTGGCTTGTACTCTGGGTTGGCTGGAACGCCTTC<br>ATCATCTGCTTCTACCTGGAAGTTGGACAGCTATCCCAGGACCGGGACTTCATCATGACCTTCAACACATCCCTGCATCG<br>CTCCTGGTGGATGGAGAATGGTCCAGGCTGCCTGGTGACTCCTGTTCTGAACTCTCGCCTGGCCCTGGAGGACCACCACG<br>TCATCTCGGTCACTGGCTGCCTGCTTGATTATCCTTACATTGAAGCCCTCAGTAGTGCCCTGCAGATCTTCCTAGCTCTG<br>TTCGGCTTCGTGTTTGCCTGTTATGTGAGCAAAGTATTCCTGGAAGAGGAGGACAGCTTTGACTTCATCGGTGGCTTTGA<br>CTCCTATGGATACCAGGCGCCGCAGAAGACGTCGCATTTACAGCTGCAGCCTCTGTACACGTCCGGATAGCTTCTGTCCC<br>ACCCGCGTACAGTTTTCCCTGGACCACTGGAGCCTGAAGCAGTGCTGTCCGGAGGCGCGGATCACGATAGGCAGGCGCGC<br>CCCTGGTGGCGCTTAGGCTAACTGCAGCTTGTGCAGCCTCCTGGATCTGCAGCCCCTGGAGAAAATGCGGACTCTCAAGA<br>CTTGAACTTGGACCTGACCCTAGCTCTAGCAGGACTTCAGGGTTGGGGCAGGACGGGCAGGGGGGGAGGGGGAATCACTG<br>GGTTTGTATTTTTTTAATCTCAGCCTTGGTACGTGCCGGGGTCTTCCTCTTTCTTCAGCTCTACTCCTTACCTAGTATC<br>TTGCCCTCAGTCCAAACAGCAAGACAGACCGAACTCACCCCATCTCACCTCTCATTCACCTGCCCTGGGGAAAGATACTG<br>TGAACTAGAAGCAGGAGTCCTGGGCTCCAGCTACGGCACCATCACTGACATCCGGTGTGACATCGGGCCGAGTCTTTGCT<br>TCCTCCGGGCCTCAGTTTCCCCACATCAAATAATTAAAATTATCCCTTAGTTG | SEQIDNO.:143<br><br>MGKCSGRCTLVAFCCLQLVAAL<br>QRQIFDFLGYQWAPILAXFLHI<br>MAVILGIFGTVQYRSRYLILYA<br>AWLVLWVGWNAFIICFYLEVGQ<br>LSQDRDFIMTFNTSLHRSWWME<br>NGPGCLVTPVLNSRLALEDHHV<br>ISVTGCLLDYPYIEALSSALQI<br>FLALFGFVFACYVSKVFLEEED<br>SFDFIGGFDSYGYQAPQKTSHL<br>QLQPLYTSG |
| SEQIDNO.52<br><br>ACGATCGAACGGCTCAACTTTGCGAGGTGAGGTGTCAAAAAGGGAAAAGTGAATGTGGCTTTCGCTCCACGGGGTGTGCT<br>GTCGTCTGGGGCCGTCAGGGAGCTCAGCCCTTGTGTTGTGCCAGGGTGGGGTCCAGGGTCTGGCACTGAGGAGGGTAGCC<br>TGCTGGCTGAAGTGGCAGAGCAGTGGCCTTGATTTGTCTTGTGGAAGATTTAAAAACAAAAAAGCATAAATATTCTGGTC<br>CTTCAGCAATGCTTTCTCTGAAGAAATATTTAACGGAAGGACTTCTCCAGTTCACCATCCTGCTGAGTCTGATTGGGGTT<br>CGGGTGGACGTGGATACTTACCTGACCTCACAGCTCCCCCCTCTCCGGGAGATCATCCTGGGGCCCAGCTCTGCCTATAC<br>CCAGACCCAGTTCCACAACCTGAGGAATACCTTGGATGGCTATGGGATCCACCCCAAGAGCATAGACCTGGACAATTACT | SEQIDNO.:144<br><br>MLSLKKYLTEGLLQFTILLSLI<br>GVRVDVDTYLTSQLPPLREIIL<br>GPSSAYTQTQFHNLRNTLDGYG<br>IHPKSIDLDNYFTARRLLSQVR<br>ALDRFQVPTTEVNAWLVHRDPE<br>GSVSGSQPNSGLALESSSGLQD |

FIG. 76

| NucleotideSequence (5'-3') | ORFs |
|---|---|
| TCACTGCCCGGCGGCTCCTTAGTCAGGTGAGGGCCCTGGATAGGTTCCAGGTGCCTACCACTGAGGTCAATGCTTGGCTG | VTGPDNGVRESETEQGFGEDLE |
| GTCCACCGAGACCCGGAGGGGTCTGTCTCTGGCAGCCAGCCCAACTCAGGCCTCGCCCTCGAGAGTTCCAGTGGCCTCCA | DLGAVAPPVSGDLTKEDIDLID |
| AGATGTGACAGGCCCAGACAACGGGGTGAGAGAAAGCGAAACGGAGCAGGGATTCGGTGAAGATTTGGAGGACCTGGGGG | ILWRQDIDLGAGREVFDYSHRQ |
| CTGTAGCCCCTCCTGTCAGTGGAGACTTAACCAAAGAGGATATAGATCTGATTGACATCCTTTGGCGACAGGATATTGAT | KEQDVDKELQDGRERED TWSGE |
| CTGGGGGCTGGGCGTGAGGTTTTTGACTACAGTCATCGCCAGAAGGAGCAGGATGTGGATAAGGAACTGCAAGATGGACG | GAEALARDLLVDGETGESFPAQ |
| AGAACGAGAGGACACCTGGTCAGGCGAGGGTGCGGAAGCTCTGGCCCGAGACCTGCTAGTAGATGGAGAGACTGGGGAGA | FPADVSSIPEAVPSESESPALQ |
| GCTTCCCTGCACAGTTCCCAGCTGACGTTTCCAGCATCCCAGAAGCAGTGCCTAGTGAGAGTGAGTCCCCCGCCCTTCAG | NSLLSPLLTGTESPFDLEQQWQ |
| AACAGCCTTCTATCTCCTCTTCTGACGGGGACAGAATCACCATTTGATTTGGAACAGCAGTGGCAAGATCTCATGTCCAT | DLMSIMEMQAMEVNTSASEILY |
| CATGGAAATGCAGGCTATGGAAGTAAATACATCAGCAAGTGAGATTCTGTACAATGCCCCTCCTGGAGACCCTCTTAGCA | NAPPGDPLSTNYSLAPNTPINQ |
| CCAACTACAGCCTTGCACCCAACACTCCCATCAATCAGAATGTCAGCCTGCATCAGGCGTCCCTGGGGGGCTGCAGTCAG | NVSLHQASLGGCSQDFSLFSPE |
| GACTTCTCCCTCTTCAGCCCCGAGGTGGAGAGCCTGCCTGTGGCTAGCAGCTCCACACTGCTTCCACTCGTCCCCAGCAA | VESLPVASSSTLLPLVPSNSTS |
| CTCCACCAGTCTCAACTCCACCTTTGGCTCTACCAACCTAGCAGGGCTTTTCTTTCCATCCCAGCTCAATGGCACAGCCA | LNSTFGSTNLAGLFFPSQLNGT |
| ATGACACATCAGGCCCTGAGCTACCTGACCCCCTTGGGGGCCTGTTAGACGAAGCTATGCTGGATGAGATCAGCCTGATG | ANDTSGPELPDPLGGLLDEAML |
| GACCTGGCCATTGAGGAGGGCTTCAACCCGGTGCAGGCTTCCCAGCTCGAAGAGGAGTTTGACTCTGACTCAGGCCTCTC | DEISLMDLAIEEGFNPVQASQL |
| CTTGGACTCCAGCCATAGCCCTTCCTCTCTGAGCAGCTCTGAAGGGAGCTCTTCTTCTTCCTCCTCCTCCTCTTCCTCTT | EEEFDSDSGLSLDSSHSPSSLS |
| CTGCTTCCTCCTCTGCCTCTTCTTCCTTCTCTGAGGAGGGTGCTGTTGGTTACAGCTCTGACTCTGAGACCCTAGACCTA | SSEGSSSSSSSSSSSASSSAS |
| GAAGAGGCTGAGGGTGCAGTGGGCTACCAGCCGGAATACTCCAAGTTCTGCCGCATGAGCTATCAGGATCCTTCTCAGCT | SSFSEEGAVGYSSDSETLDLEE |
| CTCTTGCCTTCCCTACTTAGAGCATGTGGGCCACAATCATACATACAATATGGCACCCAGTGCCCTTGACTCTGCTGATC | AEGAVGYQPEYSKFCRMSYQDP |
| TACCACCACCCAGCACCCTCAAGAAAGGTAGCAAGGAAAAGCAGGCTGACTTCCTGGACAAGCAGATGAGCCGAGATGAG | SQLSCLPYLEHVGHNHTYNMAP |
| CACAGAGCCCGAGCCATGAAGATCCCATTCACCAATGACAAGATCATCAACCTGCCTGTAGAAGAATTCAATGAGCTGCT | SALDSADLPPPSTLKKGSKEKQ |
| GTCCAAATACCAGCTGAGCGAGGCCCAGCTCAGCCTCATCCGGGATATCCGGCGCCGGGGCAAAAACAAGATGGCTGCAC | ADFLDKQMSRDEHRARAMKIPF |
| AGAACTGCCGCAAGCGCAAGTTGGACACCATCCTAAACCTAGAACGTGATGTGGAGGACTTGCAGCGAGATAAGGCCCGA | TNDKIINLPVEEFNELLSKYQL |
| TTGCTTCGAGAAAAGGTAGAGTTCCTTCGGTCTCTGCGACAGATGAAGCAGAAGGTCCAAAGCTTATACCAGGAGGTGTT | SEAQLSLIRDIRRRGKNKMAAQ |
| TGGGCGGCTGCGGGATGAGCATGGGAGGCCCTACTCACCCAGTCAGTATGCCCTTCAGTATGCTGGGGATGGCAGTGTCC | NCRKRKLDTILNLERDVEDLQR |
| TCCTCATTCCTCGCACGATGGCTGACCAGCAGGCTCGGCGACAGGAGAGAAAGCCAAAGGACCGGAGGAAGTGAGCCTGG | DKARLLREKVEFLRSLRQMKQK |
| GGAGGCAGGGGGTGGACGCTCACTAAGACCGAAACTGGAGAAGGGCTGGGCCTGGACCTAACATTGGGGACTTAAATGCC | VQSLYQEVFGRLRDEHGRPYSP |
| TTCTTATCCAATATATCTTCTCAGATGGGATGACTGCGGGTCAGTGCACCGAAGAGGCGGGCGCAGGCGCTGTCTGGCTC | SQYALQYAGDGSVLLIPRTMAD |
| AGCTGCCCCCTTGGGGTGGGCAGGGAGGACCAGACTGCTTGGGTGATTGGGGTCCCCAGCCTATTCCCTTTCTCTTGAGG | QQARRQERKPKDRRK |
| GGAGGGTAGTGTCGGCATGCTGGAAGTAGAGGAGCTGTGTGGAGTGAAGGAGAGAAAGTGTGGGAGATCTCATTGCTGGA | |
| AGGAGAAAAGGAAGGAATCCCCCGAAAATCAAAGCAGTCAGAAAAACCAGAGCGACTGTTAAGGGCTTTGGCCAGCTTTC | |
| TAGGCAGCGAGTGCAGGTGACAACGGTGGTCTAGGGAGAGTTACTGGTATGGAACACAGACATGGCGGGGCCCCAGAAGG | |
| CCTTTGTAACTGTTTCTTCAACTCTTGCATCCCTGAAGGGAAGATGCTCTTGGATGCACCTGTAATATCTTAGTTACTGA | |
| ATGGGAAGCTGTAGGGGCCGAGGAGGGCAGAGGGTATAGGAAGTGAGAACGAGGCCTGTGTCGCAGCAGCCCAGCATCAA | |
| GCATGTCACACACTGCCCTGCCACAGCCACCTCCCTCCCTGGCCATCCCAGAGCCGAGGCTCCCACTGTCCTCAGAGAGC | |

FIG. 77

| NucleotideSequence (5′-3′) | ORFs |
|---|---|
| CTGCATGGAAATGCTGTCCTCTTCCACTCTCCTCCTCTTTTTGATACCCACCCTCACTAGCTGCCTCCAGCTCTGGAGTG<br>GGGTGCTATTCTGGCAGTATCTGGAACTTGGCCTACAGCTTCCTCTGCAGGGTCTAAACAGGGAAGGCACGTGTGGAGGA<br>GTGGTCCCAGTGACATCCAGGCACCATTCAGCACAACACTGGGAAGTGATTCTTCCCTCAGGCCCCTCTGCCTACCAACA<br>CCTGGGCTCCTCACTGGGGAAACAAAAGCCTATAAACCCCAGCAACAAAACCTAGTCCTCTTAGACGTTCTTGCGCTTT<br>GATTTTTTTAGGGCGTGTGCCCTGTTACACTTATAGGGCCTAGGATGCTTGTGTTGAGTAAAAAGGAGATGCCCCAATAT<br>TCAAAGCTGCTAAATGTTCTCTTTGCCATAAAGACTCCGTGTTAACTGTGTAAACACTTGGGATTTTTCTCCTATGTCCC<br>GAGGTCTGGTCTTGATTTCTTTTTTGGGTTTCTTTCTAGGAAAATGAGAAGTGCATGCAAGGGGCAGGAGATGACCCTCC<br>CCTAGGCTTTCAGCTTCAGGCAGCTTCTTCACAGCCTGTTCAGCCTGGGCTCCTGGAGGACAGCCCTGGGGGAGGCAGTG<br>AGGGGCAGCGCCAAGATAGCCAGGTGGTTGGTTCCAGGACCACAGTGTCTTTTTTTTTGTTGTTGGTTTTTTGTTGTTGTT<br>GTTTGTTTGTTTGTTTTTTAACTGCCACTGCCGCCCCCTGACCCCCAATCTTGGTCAGCTCTGGAGTACTGCCTGCCCCA<br>GACGAGCAGGGGTTGGGGGGGAGCACTGATCCTCCTCCCTGGGCAGGGCAGAGGGCTTTCCTAACCGAGCAGTAGGGATA<br>GAAAGCGTGAGCCTGGGAGTGCTTTTTATAAATTATTTTCCTTGTAGATTTTATTTTTAATTTATCTCTGTGACCTGCCA<br>GGGAGAGGAGAGAAAGAAATGCTGTGAGCACATGACAAAATAAAATCAAATAAAATGGAAAAAAAAAAAAAAAAAAAAA<br>AAAAAAAAAAAAAAAAAAAA | |
| SEQIDNO.53<br><br>CCCACGCGTCCGCGCGTTTACCCGGAGCATGGCGGATACCGGCTTGCGCCGCGTGGTTCCCAGCGACCTTTATCCCCTT<br>GTGCTCAGATTTCTGCGGGATAGCCAACTCTCGGAGGTGGCCAGTAAATTTGCAAAAGCGACCGGCGCTACACAGCAGGA<br>CGCCAATGCCTCGTCCCTCTTGGACATCTATAGCTTCTGGCTCAAGTCCACCAAAGCCCCAAAGGTGAAGTTACAGTCAA<br>ATGGACCAGTGACCAAGAAGGCTAAGAAAGAGACTTCATCCAGTGACAGCAGTGAGGACAGCAGTGAGGACGAGGACAAA<br>AAAGCCCAGGGACTTCCCACACAGAAGGCTGCCGCACAGGTCAAGCGAGCCAGTGTGCCTCAGCATGCTGGAAAGGCAGC<br>AGCCAAAGCTTCAGAGAGCAGCAGTAGTGAAGAATCCAGTGAGGAAGAGGAAGAGGACAAAAAGAAAAAGCCTGTCCAGA<br>AGGCAGCTAAGCCCCAAGCCAAGGCAGTCAGACCTCCTGCGAAGAAGGCAGAGAGCTCTGAGTCGGACTCAGACTCGGAT<br>TCGGACTCCAGCTCAGAGGAAGAAACACCACAGACCCAGAAGCCAAAGGCAGCTGTGGCAGCAAAAGCTCAGACTAAAGC<br>CGAAGCCAAACCAGGTACACCAGCGAAAGCACAGCCTAAGGTAGCCAATGGCAAAGCAGCCGCCAGCAGCAGCAGCAGCA<br>GCAGCAGCAGCAGCAGCGATGACTCAGAGGAAGAGAAGAAGGCAGCTGCACCTCCCAAGAAGACTGTACCAAAAAAGCAA<br>GTCGTGGCCAAGGCCCCAGTGAAAGTAGCTGCCGCCCCCACCCAGAAGAGCTCCAGCAGTGAGGATTCTTCCAGTGAAGA<br>GGAGGAGGGACAGAGACAACCCATGAAGAAAAAAGCAGGTCCCTACAGTTCAGTTCCACCACCCTCTGTTCCTTTACCAA<br>AGAAGTCCCCGGGAACCCAGGCTCCAAAGAAAGCTGCTGCGCAGACACAGCCTGCAGACAGCAGTGACGACAGCAGTGAC<br>GATTCTGATTCAAGTTCTGAGGAAGAGAAAAAACCTCCAGCTAAGACGGTCGTCTCCAAGACACCCGCCAAAGCAGCTCC<br>AGTGAAGAAGAAAGCAGAAAGCTCTTCAGACAGCTCGGGTAACGCTGCCCAGAGCTCTGGGCTGCTGGGGTACTCACTGC<br>CTTGGGCTGCTCTTACAGGGCTCCCCTGAGGTTGATTTTGGGGAGCTGTTCATTCTGTCTCCTCTCTCTAGATTCTGACA<br>GTTCTGAGGATGAAGCTCCTGCCAAGCCAGTCAGTACAACCAAGAGTCCCAAGCCAGCTGTCACTCCGAAGCCATCTGCA | SEQIDNO.:145<br><br>MADTGLRRVVPSDLYPLVLRFL<br>RDSQLSEVASKFAKATGATQQD<br>ANASSLLDIYSFWLKSTKAPKV<br>KLQSNGPVTKKAKKETSSSDSS<br>EDSSEDEDKKAQGLPTQKAAAQ<br>VKRASVPQHAGKAAAKASESSS<br>SEESSEEEEEDKKKKPVQKAAK<br>PQAKAVRPPAKKAESSESDSDS<br>DSDSSSEEETPQTQKPKAAVAA<br>KAQTKAEAKPGTPAKAQPKVAN<br>GKAAASSSSSSSSSSDDSEEE<br>KKAAAPPKKTVPKKQVVAKAPV<br>KVAAAPTQKSSSSEDSSSEEEE<br>GQRQPMKKKAGPYSSVPPPSVP<br>LPKKSPGTQAPKKAAAQTQPAD<br>SSDDSSDDSDSSSEEEKKPPAK<br>TVVSKTPAKAAPVKKKAESSSD |

FIG. 7B

| NucleotideSequence (5'-3') | ORFs |
|---|---|
| GCAAAGGCAGTGACAACTCCTAAGCAACCTGCAGGCAGTAACCAGAAACCTCAGAGCAGGAAGGCTGACAGCAGCTCCAG<br>CGAGGAGGAAAGCAGCTCCAGCGAGGAGGAGGAGGCCTCCAAGAAAAGTGCCACAACCCCCAAGGCCAAGGTGACTGCTA<br>AAGCAGCACCCGCCAAACAGGCCCCTCAGGCTGCTGGGGACAGCAGCTCTGACTCAGATAGTTCCAGCAGTGAAGAGGAG<br>GAGAAGACTCCTAAGCCCCCAGCTAAGAAGAAGGCAGCAGGTGGAGCCGTTTCTACACCAGCCCCTGGGAAGAAAGCAGA<br>GGCCGAGAGCAGCAGCAGCAGCAGCAGCAGCTCTGAAGATTCCAGTGAAGAGGAGAAAAAAAAGAAGCCCAAAGCTACTA<br>CCCCTAAAATACAGGCAAGCAAGGCCAATGGCACTCCAGCTTCTCTGAATGGAAAAGCAGCCAAGGAAAGTGAGGAGGAA<br>GAGGAGGAGGAAGAAACAAAAAAAAAAAAAA | SSGNAAQSSGLLGYSLPWAALT<br>GLP |
| SEQIDNO.54<br><br>AAGCAGAGCCTGAAGTGCGAGTGTGGGAGCCGGGGCCCGGGAGGGAAAGGTCGCCACGATGAACACCGTCCTGTCGCGCG<br>CGAACTCCCTGTTCGCCTTCTCGCTGAGCGTGATGGCGGCGCTCACCTTCGGCTGCTTCATCACCACCGCCTTCAAAGAC<br>AGGAGCGTCCCAGTGCGGCTGCACGTCTCGCGGATCATGCTAAAAAATGTAGAAGACTTCACGGGCCCTAGAGAAAGAAG<br>TGACCTGGGATTCATCACATTTGATATAACAGCTGATCTAGAGAATATATTTGATTGGAATGTTAAGCAGTTATTTCTTT<br>ATTTATCTGCAGAGTATTCAACAAAAAATAATGCTCTGAACCAAGTTGTCCTTTGGGACAAAATTGTTTTGAGAGGTGAT<br>AATCCGAAGCTACTTTTGAAAGATATGAAGACAAAGTATTTCTTCTTTGACGATGGAAATGGCCTCAAGGGAAACAGGAA<br>TGTCACTCTGACGCTCTCCTGGAACGTTGTACCAAACGCTGGAATTCTACCTCTTGTGACAGGATCGGGACATGTGTCTG<br>TGCCATTTCCAGATACATACGAAATAACCAAGAGTTACTAAATTATTCTGAATTTGAAGCATATTTTTATACATGTTGAA<br>TTGCATCTCATCTCTTCCCGGTTTCTTCATTGATTTTTTTTTTTCTTTTTTTTTTTCCTTTTTTGTTTGGATGTAAGAAA<br>AACTCACGTCAGAAGACGCAGTTGAAGTGAAAGGTTCTGAGCTGCTTAAGCTTAGCTTTGTAAACAGACAGAAAAAGCCT<br>CCCAGAGGAGAGTAGTTATGAAGAACGAGGCAACTGCATAGGAAGAATCTATCAGCAGTGTAGGGTTGAAACACGTATTT<br>ATATTATCTTACGGAATACAAAATGATCATAAAGGGCTGTTAGACATTCAGGTGTCATAAGAATTCTGAATTGTATCCTT<br>TGTGTTCATGCAAGGCAGTTGTGACTTACTCATGGGCATTCTCTTATATCTCTAAGTGTATACACTTAGAGATCCTAAGT<br>GTAGATGACTGGAAACTAGATGAATGTGGTTCTTTGAAGTCTGGTTTACAAACGAGCAGAGTGGTATAATTGTATCCCAT<br>TTCTTTTACAAAGCCCAATCATGCTTGCTTTTCTTAGGTGAGTAGCAGCTTCTCCAAATGAAGAGGAAGAACCTGTTTGT<br>ATGCTGAAAAATCTAGCAGGCTCATTTTAAAGTTTCAACCCAGCCAAATGTGTATCTTTCAGTCTTTTCAGAGTGTTTCT<br>TTGTGTATTTCTTTAAAATTTTACCTTTGCCATGCAAAGTTGAAAATGTTTGCATGGATTTCCTCCTGAACTGAATTGGT<br>CCCACTGAGCTTGCCTCTGTGGTTAAGTACAGTTTGCATAGCTCCATACTTTTACAGTTGGAACAGTAGGGACAGCTGTC<br>AGTGCTTTTCCACCCACAGGTTTCTCTCCTGTGTTGAGTGTTGTCTTGAGTGATCCTAATGAGGTAGAGAGTACAAATGT<br>TAGCTCTTTGCAGGTGAAGAAACTGAAACCCAGAAACTTACTGACTTGCACCCAAATTAAAAAGCAAGCAGTGGTCTTGT<br>TTTATACCTCAGTTTACACATTGGTCACATTCATATAATTTTATTGTAGTTCATTACTCTCATTTTCCTTCTGGGAATGA<br>GAGTTTGAAACTAATTTTCTAGCAGCCAACAACTTACACAGTGATATCTTTGTGTATATTCATTTTTACCCATATTAAAA<br>TAACTATATAGATTTGTAAAATAATTTAGAGATTAAATATGTTGTATATGATTGAATATGTAATTGTATTTGACATGAAA<br>TTTATTTTCCTCATTGATAAATACTCTCAGAATTAGCATCTGCATCTTGGCTACTCTTAAATGCAAGAGTAGACACTACG | SEQIDNO.:146<br><br>MNTVLSRANSLFAFSLSVMAAL<br>TFGCFITTAFKDRSVPVRLHVS<br>RIMLKNVEDFTGPRERSDLGFI<br>TFDITADLENIFDWNVKQLFLY<br>LSAEYSTKNNALNQVVLWDKIV<br>LRGDNPKLLLKDMKTKYFFFDD<br>GNGLKGNRNVTLTLSWNVVPNA<br>GILPLVTGSGHVSVPFPDTYEI<br>TKSY |

FIG. 79

| NucleotideSequence (5'-3') | ORFs |
|---|---|
| CACATTCTAAAGTAACCTAAAAGGGCTGTTTACTAGCAATAGCATAAATTAGCATTTGTTCTGTTTACCTCATGTGCTTA<br>GTGACATTCATCAAACAGCTCTTGTATGTGGTGGTACAGTTCTTACAAATGCATGTGTTTGAGGTTTTCTTACCAGCAGA<br>AAGGTCAGAGGCGCACCTTGAGATTGGCACCAGCACGTTCCTTAAACATTTCGGGGTCTCTGTTTCTTTGTCTATAAAAG<br>GATCCTTTACTAGGATAGAAAGTTGTGATATGTTTTCTGTTCAGCAGATTTCGAACAGGAAACCACCTTAGTGATCTGAA<br>GTCAGAAAAGTGATGGAAAGATTAACAGAGTTCATAAGGATCTGAGCTTCTGCTACATTTTACACCTACAAAAGTGAGCT<br>TTATACATCGATGAGATAGTAGATGTGTAAAGTCTGCAAGCGTCAGAGTTAGAGGGTCTGGGTGTGTCCTAGCTAAGGAA<br>GCCCTCCCAAGCCTAGGGCATTAAAGCCACACCTCAGTTCAGTTAACAGTTCACTGTACCTTTGTGATGAGTGGCTATGT<br>TGGTTGAGCACAGACTATCTAACACTGACATTTATGTATCTGAAAAGCCCAGTTCAGGTGTTTGGTAAGGAAAGCCCAAT<br>ATGGCAAATGGCCTTTGTTTTTAGCAGCTGAGGGAGCAGCTGCTCCGGCATGCCACTAGCCCTGTCTCTCAGGAACTCCA<br>TTGCGTGCGTGCACGGCTTTATCAGTCTGTGATGATGCTGTAACTTGCAAAGTTCGTATGTGTGATAAGCATCTCTGGTC<br>TCAGTGTTTAGAGAAGACTCAGTGCTTCAGTGGCTGAGCCCAGAGGTGATTCTATGAAAAGAAGATGATTGCAAGAGTG<br>TTAGTAAAGAGGTTGCAGTTAGAAATGAACTTGAACATGTAGCACCCAGCGTATCCCTCTCAGTCTTAACTAGACAACTG<br>TGTGCTTTTGTGTCTGGCCCTATTGCATTTACTGTGCTCATGCTGAAAGGAAAGTAACAGCTTTAGAAACTGTTGAAAAT<br>AAAATAGGAAAACAGGCTGGGTTGAATTCCTTTGCTGGGAATTGTTTTACAGCTCTTCAGTGGTCTTTCTAGCCAGTTAT<br>TCCTGTGAAGAATTGGACTTTGAGGAGCTAAAGCTTTGAATGGGGGCTGGTGCAGGGGCCTGGGAGTGGAGAGTCTGCTT<br>TCAGATACTTTAACCTCGGAGCTGTGACCTTTGATTGTAGCAAACATCGATTTCAAAAGCTTCTTTTGCTTTCAGTCACA<br>AGCCTGCGTACCTTACTGCGAGACTGCCAATGCTTCAAAGATGTATGTTTGAAAAAGTTCTTTCATAGTTTTTATGAAAT<br>TTGGGAAGTTGTTTACTTAAACAAATGCACAAGAAAATAATTCATAAAAATACTGAATATATATGTGCAAAATTTTTCTT<br>AGCTACAATAAATGTTCAACATTTTTCTAATAAAGATTTTTTTTCTGAGTAAAAAAAAAAAAAAAAAAAAAAAAA | |
| SEQIDNO.55<br><br>CAGGTTTTGAAATCACCTGGGGATTTCTTGGGTGCGGGGTGGACCTTAGGGAGAACAGAAAGCAGAGCTGGCTGCAGCCA<br>TTACTGGCCTCGGGCGGGCGGCCACAGAGGCAGTTGAAGTGAAAGTGAAAGAGAAACGATAAGAGAACGGAGACCACAGG<br>TGCTAAGTGAGGGTGCTCACAGAACCCCCTCTTCAGCCAGAGATCACTAGCAGGGGAACTGTGGAGAAGGCAGCCAGCAA<br>GGAAGAGCCTGAGAGTAGCCTCCATGGGCTTGGAGCCCAGCTGGTATCTGCTGCTCTGTTTGGCTGTCTCTGGGGCAGCA<br>GGGACTGACCCTCCCACAGCGCCCACCACAGCAGAAAGACAGCGGCAGCCCACGGACATCATCTTAGACTGCTTCTTGGT<br>GACAGAAGACAGGCACCGCGGGGCTTTTGCCAGCAGTGGGGACAGGGAGAGGGCCTTGCTTGTGCTGAAGCAGGTACCAG<br>TGCTGGATGATGGCTCCCTGGAAGGCATCACAGATTTCCAGGGGAGCACTGAGACCAAACAGGATTCACCTGTTATCTTT<br>GAGGCCTCATTGGACTTGGTACAGATTCCCCAGGCAGAGGCGTTGCTCCATGCTGACTGCAGCGGGAAGGCAGTGACCTG<br>CGAGATCTCCAAGTATTTCCTCCAGGCCAGACAAGAGGCCACTTTTGAGAAAGCACATTGGTTCATCAGCAACATGCAGG<br>TTTCTAGAGGTGGCCCCAGTGTCTCCATGGTGATGAAGACTCTAAGAGATGCTGAAGTTGGAGCTGTCCGGCACCCTACA<br>CTGAACCTACCTCTGAGTGCCCAGGGCACAGTGAAGACTCAAGTGGAGTTCCAGGTGACATCAGAGACCCAAACCCTGAA<br>CCACCTGCTGGGGTCCTCTGTCTCCCTGCACTGCAGTTTCTCCATGGCACCAGACCTGGACCTCACTGGCGTGGAGTGGC | SEQIDNO.:147<br><br>MGLEPSWYLLLCLAVSGAAGTD<br>PPTAPTTAERQRQPTDIILDCF<br>LVTEDRHRGAFASSGDRERALL<br>VLKQVPVLDDGSLEGITDFQGS<br>TETKQDSPVIFEASLDLVQIPQ<br>AEALLHADCSGKAVTCEISKYF<br>LQARQEATFEKAHWFISNMQVS<br>RGGPSVSMVMKTLRDAEVGAVR<br>HPTLNLPLSAQGTVKTQVEFQV<br>TSETQTLNHLLGSSVSLHCSFS<br>MAPDLDLTGVEWRLQHKGSGQL<br>VYSWKTGQGQAKRKGATLEPEE |

FIG. 80

| NucleotideSequence (5'-3') | ORFs |
|---|---|
| GGCTGCAGCATAAAGGCAGCGGCCAGCTGGTGTACAGCTGGAAGACAGGGCAGGGGCAGGCCAAGCGCAAGGGCGCTACA<br>CTGGAGCCTGAGGAGCTACTCAGGGCTGGAAACGCCTCTCTCACCTTACCCAACCTCACTCTAAAGGATGAGGGGACCTA<br>CATCTGCCAGATCTCCACCTCTCTGTATCAAGCTCAACAGATCATGCCACTTAACATCCTGGCTCCCCCCAAAGTACAAC<br>TGCACTTGGCAAACAAGGATCCTCTGCCTTCCCTCGTCTGCAGCATTGCCGGCTACTATCCTCTGGATGTGGGAGTGACG<br>TGGATTCGAGAGGAGCTGGGTGGAATTCCAGCCCAAGTCTCTGGTGCCTCCTTCTCCAGCCTCAGGCAGAGCACGATGGG<br>AACCTACAGCATTTCTTCCACGGTGATGGCTGACCCAGGCCCCACAGGTGCCACTTATACCTGCCAAGTCGCCCACGTCT<br>CCCTGGAGGAGCCCCTTACAACCAGCATGAGGGTTTTGCCAAATCCAGAGCAGAGAGGAACCTTGGGAGTCATCTTTGCC<br>AGCATCATCTTCCTTTCTGCGCTGTTGTTGTTTCTGGGACTTCACAGACAGCAAGCTTCTTCGTCAAGGTCCACCAGGCC<br>TATGAGGCATTCTGGGTAGCCGCCTGCCTGCCTCCGAATACAAAGTAAAGTACTCCACATCCTGGCTACTTAAAGGACCC<br>CGTGTGAGGTGTGGGGCTGAGCTGGGCCTGAAGGTGCCAGCACATTGGGAGTGCAGTACTGGCCCTGGACTGTACAAGTC<br>TCTGCTTTCTGTGCTATTGAGAAGAGAGCCCTGGGCTGATGAAAAGGGACAGGACAAGAGGATGGCAGAATTATCAAAGT<br>GGAAGCTAACACCATCTATGTGAGGTATTAAGAAATTGGGGGTGGGGGCTGGTGAGATGGCTCAGTGGTAAGAGCACCC<br>GACTGCTCTTCCGAAGATCTGGAGTTCAAATCCCAGCAACCACATGGTGGCTCACAACCATCTGTAACGAGATCTGACTC<br>CCTCTTCTGGAGTGTCTGAAGACAGCTACAGTGTACTTACATATAATAAATAAATAAATCTAATAAAAAAGAAAAAAAAA<br>AAAAAA | LLRAGNASLTLPNLTLKDEGTY<br>ICQISTSLYQAQQIMPLNILAP<br>PKVQLHLANKDPLPSLVCSIAG<br>YYPLDVGVTWIREELGGIPAQV<br>SGASFSSLRQSTMGTYSISSTV<br>MADPGPTGATYTCQVAHVSLEE<br>PLTTSMRVLPNPEQRGTLGVIF<br>ASIIFLSALLLFLGLHRQQASS<br>SRSTRPMRHSG |
| SEQIDNO.56<br><br>GTGCTTTGTGCTTGTGGAGGAACCTAAGCGGAACTTAGACACAGGGAGAATGAGGCTCTGGACCTTGGGCACCAGTATTT<br>TCCTGAGGCTTTGGGGGACTTATGTGTTTCCACGAAGCCCTAGCTGGCTGGACTTCATCCAGCATTTGGGAGTCTGTTGC<br>TTTGTGGCCTTCCTTTCGGTGAGCCTCTTCTCTGCAGCCTTTTACTGGATCCTGCCACCCGTTGCCCTGCTCTCTTCTGT<br>CTGGATGATCACCTGTGTTTTCCTATGCTGTTCCAAGCGCGCACGATGCTTCATTCTTCTGGCCGTTCTGTCGTGTGGCC<br>TCCGTGAAGGTAGGAACGCTTTGATTGCGGCTGGCACTGGGGTAGTGATCTTTGGACATGTGGAAAATATTTTTTATAAC<br>TTCAGAGGTCTCCTAGACAGCATGACTTGCAACCTAAGGGCAAAGAGCTTTTCAGTACATTTCCCACTTTTAAAACGGTA<br>TACTGAAGCCATCCAGTGGATTTACGGCCTTGCCACTCCGCTGAATCTATTTGATGACCTTGTTTCTTGGAACCAGACTC<br>TGGTGGTCTCTCTTTTTAGTCCCAGCCATGCCCTGGAGGCTCATATGAATGACACTAGAGGAGAAGTCCTGGGAGTCCTG<br>CACCATATGGTGGTCACGACAGAGCTGTTGACTTCCGTGGGCCAGAAGTTGCTTGCCCTTGCCGGGCTTCTGCTCATCCT<br>AGTCAGCACTGGCCTCTTCCTGAAGCGATTCCTGGGCCCTTGTGGCTGGAAGTATGAGAATGTCTACATCACCAAACAAT<br>TTGTTCGGTTTGATGAAAAGGAGAGGCACCAACAGCGGCCCTGTGTCCTCCCGCTGAATAAGAAGGAAAGGAAGAAATAT<br>GTCATCGTCCCATCTTTGCAGCTGACTCCTAAGGAGAAGAAAACCCTTGGGCTGTTCTTCCTTCCTGTCCTGACCTATCT<br>CTACATGTGGGTGCTGTTTGCCGCTGTGGACTATCTGCTGTATCGGCTCATCTCCTCCATGAACAAACAGTTCCAAAGCT<br>TGCCAGGGCTGGAAGTTCACTTGAAACTACGTGGAGAGCTTAAAATTCTCGTGTCAGTCTCCTTCTACCCCAAAGTGGAG<br>AGGGAGAGAATTGAATACCTGCATGCGAAGCTCCTTGAGAAACGATCAAAGCAGCCATTGAGAGAGGCTGACGGGAAACC<br>GAGCCTGTACTTTAAAAAGATTCATTTCTGGTTTCCAGTCCTGAAAATGATTAGGAAGAAGCAGACAATCCCTGCAAATG | SEQIDNO.:148<br><br>MRLWTLGTSIFLRLWGTYVFPR<br>SPSWLDFIQHLGVCCFVAFLSV<br>SLFSAAFYWILPPVALLSSVWM<br>ITCVFLCCSKRARCFILLAVLS<br>CGLREGRNALIAAGTGVVIFGH<br>VENIFYNFRGLLDSMTCNLRAK<br>SFSVHFPLLKRYTEAIQWIYGL<br>ATPLNLFDDLVSWNQTLVVSLF<br>SPSHALEAHMNDTRGEVLGVLH<br>HMVVTTELLTSVGQKLLALAGL<br>LLILVSTGLFLKRFLGPCGWKY<br>ENVYITKQFVRFDEKERHQQRP<br>CVLPLNKKERKKYVIVPSLQLT<br>PKEKKTLGLFFLPVLTYLYMWV<br>LFAAVDYLLYRLISSMNKQFQS<br>LPGLEVHLKLRGELKILVSVSF |

FIG. 81

| NucleotideSequence (5′-3′) | ORFs |
|---|---|
| AAGATGATCTATGAGCAACACAGTCCCTCTTTCTGGGCCAACTGCTGCTTCTGTCTACTCAACAAGAGGGGGCTATCTGA<br>GAAGGTCTACAGATGTTTGAGTTTGCAAGGCTGCCTTTCTCTTTGGTGATCCTTCAAGATACATGTCGATCATAATGCCA<br>AATAGCCCCTAGGTAAATAGTTTCAGAGTCTGTCTTCCAAACAAAACACAGTATCTAAACTGTGTCATAGTTAAAGCTAT<br>GGTGATGGCTGGCATGGAAATGTCCTCCAAAGGCTTAGATATTTGAAAACTTGGTCCCCAGTTAGTGCATCTTGGGGGAG<br>GCTTATAAGGTGTCATGTTGCTGGACAAAGTGTGACTCCAGAGGAGTGTTTTGCAGTTTTAAAAGTCATGTGCTACTCCT<br>GTTCACTCTACTCAGCCTGTGGCTGGAGATGTGGGCTCTCAGCTGTCCCTGCCTCCATGTCTGTCTGTAATAGAGTTCCC<br>AACTGTGATATTGATGGAGTCTTACCTCTCTGAAACCTTAAGCCCAAATAAATCCTTCCTTCTAT | YPKVERERIEYLHAKLLEKRSK<br>QPLREADGKPSLYFKKIHFWFP<br>VLKMIRKKQTIPANEDDL |

FIG. 82

| Nucleotide Sequence (5'-3') | ORFs |
|---|---|
| SEQ ID NO. 83<br><br>TGGAGGAACCTAGCGGCGCAATGGAGCCCTGGTGCGGGGCAGAGGTCCGTGGGCAGGGCCCTCAGGGTCCCCGTGTGCCT<br>GGGGCTTCCCGCTCCCGCTCCCGCGCCCTTCTCCTGCTGTTGCTGCTGCTGCTGCTGCTCCTGCCTCGGCGGCCGGCAGG<br>TGAGCGCATCCGCCCCCGACGCCCTCCCCGGCACGCCCACCCGCGGCCACCTCTGACTCGCTGGAGACCTTCCACAGGCT<br>ACTTGGCCGCAGGAGCATCCCCGGGGACGCTGTCCACCACCGTCCCGACCGGACCCGGGGTCTCCTGTGGCTCCAGAGGC<br>ACCTGTCCCTCAGGCAGGCTTCGCCTTCCTCGGCAAGCCCAGACTAACCAGACCACGACGGCTCCACCGAACTCACAGAC<br>CATGGCTCCACTGAAAACGGTGGGGACTCTCGGCATGATGGACACTACTGGGTCCGTTCTTAAGACGGTTCATTCCAGCA<br>ACCTCCCCTTCTGTGGCTCCTCCCACGAGCCAGACCCTACTCTCAGGGACCCAGAAGCCATGACTCGGCGGTGGCCCTGG<br>ATGGTCAGCGTGCAGGCTAACGGCTCACACGTCTGTGCTGGCATCCTTATCGCTTCCCAGTGGGTGCTGACCGTGGCCCA<br>TTGCTTGAGCCAGAACCATGTTAACTACATAGTGAGGGCGGGGAGCCCGTGGATTAATCAGACGGCAGGAACCAGCTCAG<br>ATGTGCCGGTCCATCGAGTCATCATAAACCATGGCTACCAACCCAGACGGTACTGGTCATGGGTTGGCCGGGCCCATGAC<br>ATCGGCCTTCTCAAGCTCAAGTGGGGGCTCAAGTACAGTAAATACGTGTGGCCCATCTGCCTGCCTGGCCTGGATTACAT<br>GGTGGAGGACAGTTCTCTCTGCACTGTGACAGGCTGGGGATATCCCAGGGCTAACGGAGATAACTGGCGAGCCCCTGGTC<br>TGCTCTTCAGATGGCACATGGTACCTGGTGGGAATGATGAGCTGGGGCCCAGGCTGCAAGAAGAGCGAGGCCCCACCCAT<br>CTTTCTGCAGGTCTCCTACTACAGGCCCTGGATCTGGGACCGGCTCAGTGGGGAGCCCCTGGCCCTTCCAGCCCCATCCA<br>GGACCTTGCTCCTGGCTTTCCTTCTGCTCCTCATCCTTCTGGGCACACTGTGACACTGCCATGTCTCTCCTTCCTTCCCT<br>TCCTTCTAAGTGCTGCTGTGGGGGTGGCGCTCAGCCTGCCGGAGGCGGGGAGGAGCTAGCAGAGATTAAACACTTCTTTT<br>CCCCAAAAAAAAAA | SEQ ID NO. 149<br><br>MEPWCGAEVRGQGPQGPRVPGA<br>SRSRSRALLLLLLLLLLLLPRR<br>PAGERIRPRRPPRHAHPRPPLT<br>RWRPSTGYLAAGASPGTLSTTV<br>PTGPGVSCGSRGTCPSGRLRLP<br>RQAQTNQTTTAPPNSQTMAPLK<br>TVGTLGMMDTTGSVLKTVHSSN<br>LPFCGSSHEPDPTLRDPEAMTR<br>RWPWMVSVQANGSHVCAGILIA<br>SQWVLTVAHCLSQNHVNYIVRA<br>GSPWINQTAGTSSDVPVHRVII<br>NHGYQPRRYWSWVGRAHDIGLL<br>KLKWGLKYSKYVWPICLPGLDY<br>MVEDSSLCTVTGWGYPRANGDN<br>WRAPGLLFRWHMVPGGNDELGP<br>RLQEERGPTHLSAGLLLQALDL<br>GPAQWGAPGPSSPIQDLAPGFP<br>SAPHPSGHTVTLPCLSFLPFLL<br>SAAVGVALSLPEAGRS |
| SEQ ID NO. 84<br><br>GAGCTGTTTCACCCTACCTTGGCTTCAATCTCTTCCCCCATGCTCGAAGGTGCGGAGCTGTACTTCAACGTGGACCATGG<br>CTACCTGGAGGGCCTGGTTCGAGGATGCAAGGCCAGCCTCCTGACCCAGCAAGACTATATCAACCTGGTCCAGTGTGAGA<br>CCCTAGAAGACCTGAAAATTCATCTCCAGACTACTGATTATGGTAACTTTTTGGCTAATCACACAAATCCTCTTACTGTT<br>TCCAAAATTGACACTGAGATGAGGAAAAGACTATGTGGAGAATTTGAGTATTTCCGGAATCATTCCCTGGAGCCCCTCAG<br>CACATTTCTCACCTATATGACGTGCAGTTATATGATAGACAATGTGATTCTGCTGATGAATGGTGCATTGCAGAAAAAAT<br>CTGTGAAAGAAATTCTGGGGAAGTGCCACCCCTTGGGCCGTTTCACAGAAATGGAAGCTGTCAACATTGCAGAGACACCT<br>TCAGATCTCTTTAATGCCATTCTGATCGAAACGCCATTAGCTCCATTCTTCCAAGACTGCATGTCTGAAAATGCTCTAGA<br>TGAACTGAATATTGAATTGCTACGCAATAAACTATACAAGTCTTACCTTGAGGCATTCTATAAATTCTGTAAGAATCATG<br>GTGATGTCACAGCAGAAGTTATGTGTCCCATTCTTGAGTTTGAGGCCGACAGACGTGCTTTTATCATCACTCTTAACTCC<br>TTTGGCACTGAATTGAGCAAAGAAGACCGAGAGACCCTCTATCCAACCTTCGGCAAACTCTATCCTGAGGGGTTGCGGCT<br>GTTGGCTCAAGCAGAAGACTTTGACCAGATGAAGAACGTAGCGGATCATTACGGAGTATACAAACCTTTATTTGAAGCTG | SEQ ID NO. 150<br><br>MLEGAELYFNVDHGYLEGLVRG<br>CKASLLTQQDYINLVQCETLED<br>LKIHLQTTDYGNFLANHTNPLT<br>VSKIDTEMRKRLCGEFEYFRNH<br>SLEPLSTFLTYMTCSYMIDNVI<br>LLMNGALQKKSVKEILGKCHPL<br>GRFTEMEAVNIAETPSDLFNAI<br>LIETPLAPFFQDCMSENALDEL<br>NIELLRNKLYKSYLEAFYKFCK<br>NHGDVTAEVMCPILEFEADRRA<br>FIITLNSFGTELSKEDRETLYP |

FIG. 83

| Nucleotide Sequence (5'-3') | ORFs |
| --- | --- |
| TAGGTGGCAGTGGGGGAAAGACATTGGAGGACGTGTTTTACGAGCGTGAGGTACAAATGAATGTGCTGGCATTCAACAGA<br>CAGTTCCACTACGGTGTGTTTTATGCATATGTAAAGCTGAAGGAACAGGAAATTAGAAATATTGTGTGGATAGCAGAATG<br>TATTTCACAGAGGCATCGAACTAAAATCAACAGTTACATTCCAATTTTATAACCCAAGCTAGAGTGCAATGGCGTGATCT<br>CGGCTCACTGCAACCTCCACCTCCCAGATTCAAGCAACTCTCTGCCTCAGCCTCCCGAGTAGCTGGGATTACAAGCACCC<br>ACCACTACACTCAGCTAATTTTTTGTATTTTTAGTAGAGCCGGGGTTTCACCATCTTGGCCAGGCTGATCTTGAACTCCT<br>GAGCTCATGATCCACCCGCCTCAGCCTCCCAAAGTGCTGGGATTACAGGCCCCTTGTTCAGCCACTGCACCTGGCCCCTT<br>ATTTTGTTTTTGTTTTCTAATATACTTTGATGTAATCAGCTTGAGAAAGCAACACAATTTCAAATCCTATCTTCTAGATG<br>CAAGCAG | TFGKLYPEGLRLLAQAEDFDQM<br>KNVADHYGVYKPLFEAVGGSGG<br>KTLEDVFYEREVQMNVLAFNRQ<br>FHYGVFYAYVKLKEQEIRNIVW<br>IAECISQRHRTKINSYIPIL |
| SEQ ID NO. 85<br><br>GAGCTGTTTCACCCTACCTTGGCTTCAATCTCTTCCCCCATGCTCGAAGGTGCGGAGCTGTACTTCAACGTGGACCATGG<br>CTACCTGGAGGGCCTGGTTCGAGGATGCAAGGCCAGCCTCCTGACCCAGCAAGACTATATCAACCTGGTCCAGTGTGAGA<br>CCCTAGAAGACCTGAAAATTCATCTCCAGACTACTGATTATGGTAACTTTTTGGCTAATCACACAAATCCTCTTACTGTT<br>TCCAAAATTGACACTGAGATGAGGAAAAGACTATGTGGAGAATTTGAGTATTTCCGGAATCATTCCCTGGAGCCCCTCAG<br>CACATTTCTCACCTATATGACGTGCAGTTATATGATAGGCAATGTGATTCTGCTGATGAATGGTGCATTGCAGAAAAAAT<br>CTGTGAAAGAAATTCTGGGGAAGTGCCACCCCTTGGGCCGTTTCACAGAAATGGAAGCTGTCAACATTGCAGAGACACCT<br>TCAGATCTCTTTAATGCCATTCTGATCGAAACGCCATTAGCTCCATTCTTCCAAGACTGCATGTCTGAAAATGCTCTAGA<br>TGAACTGAATATTGAATTGCTACGCAATAAACTATACAAGTCTTACCTTGAGGCATTCTATAAATTCTGTAAGAATCATG<br>GTGATGTCACAGCAGAAGTTATGTGTCCCATTCTTGAGTTTGAGGCCGACAGACGTGCTTTTATCATCACTCTTAACTCC<br>TTTGGCACTGAATTGAGCAAAGAAGACCGAGAGACCCTCTATCCAACCTTCGGCAAACTCTATCCTGAGGGGTTGCGGCT<br>GTTGGCTCAAGCAGAAGACTTTGACCAGATGAAGAACGTAGCGGATCATTACGGAGTATACAAACCTTTATTTGAAGCTG<br>TAGGTGGCAGTGGGGGAAAGACATTGGAGGACGTGTTTTACGAGCGTGAGGTACAAATGAATGTGCTGGCATTCAACAGA<br>CAGTTCCACTACGGCTAGAGTGCAATGGCGTGATCTCGGCTCACTGCAACCTCCACCTCCCAGATTCAAGCAACTCTCTG<br>CCTCAGCCTCCCGAGTAGCTGGGATTACAAGCACCCACCACTACACTCAGCTAATTTTTTGTATTTTTAGTAGAGCCGGG<br>GTTTCACCATCTTGGCCAGGCTGATCTTGAACTCCTGAGCTCATGATCCACCCGCCTCAGCCTCCCAAAGTGCTGGGATT<br>ACAGGCCCCTTGTTCAGCCACTGCACCTGGCCCCTTATTTTGTTTTTGTTTTCTAATATACTTTGATGTAATCAGCTTGA<br>GAAAGCAACACAATTTCAAATCCTATCTTCTAGATGCAAGCAG | SEQ ID NO.:155<br><br>MLEGAELYFNVDHGYLEGLVRG<br>CKASLLTQQDYINLVQCETLED<br>LKIHLQTTDYGNFLANHTNPLT<br>VSKIDTEMRKRLCGEFEYFRNH<br>SLEPLSTFLTYMTCSYMIGNVI<br>LLMNGALQKKSVKEILGKCHPL<br>GRFTEMEAVNIAETPSDLFNAI<br>LIETPLAPFFQDCMSENALDEL<br>NIELLRNKLYKSYLEAFYKFCK<br>NHGDVTAEVMCPILEFEADRRA<br>FIITLNSFGTELSKEDRETLYP<br>TFGKLYPEGLRLLAQAEDFDQM<br>KNVADHYGVYKPLFEAVGGSGG<br>KTLEDVFYEREVQMNVLAFNRQ<br>FHYG |
| SEQ ID NO. 86<br><br>ATTAAGACAGTTGTTTATAGAAGCGTGCAGGGGTACACACGGGATCTTCTAATCCCTAGCACTAGGGCCACTCAGGGGTA<br>CCCAGCCCTTGGCCAGAAGGAGCAGGGGAGCCAATGACCTCCCGAAGGCCATCGCTGCGGCTCACACCTATCTCCTGAAG<br>CATCCAGATGACGAGATGATGAAGAGAAACATGGAGTATTATAAGAGCTTGCCTGGAGCCGAGGACCACATTAAAGACTT<br>GGAAACCAAGTCGTACGAGAGCCTGTTTGTCCGTGCGGTGCGGGCCTACAACGGGGAGAACTGGAGAACGTCCATTTCCG<br>ACATGGAGCTCGCGCTTCCCGACTTCCTCAAGGCCTTCTACGAGTGCCTGGCTGCCTGCGAGGGGTCGCGGGAGATCAAG<br>GACTTCAAGGACTTCTACCTGTCCATAGCAGATCACTATGTGGAAGTTCTGGAGTGTAAGATTCGTTGTGAGGAGACCCT | SEQ ID NO. 151<br><br>MLEGAELYFNVDHGYLEGLVRG<br>CKASLLTQQDYINLVQCETLED<br>LKIHLQTTDYGNFLANHTNPLT<br>VSKIDTEMRKRLCGEFEYFRNH<br>SLEPLSTFLTYMTCSYMIGNVI<br>LLMNGALQKKSVKEILGKCHPL |

FIG. 84

| Nucleotide Sequence (5′-3′) | ORFs |
|---|---|
| CACCCCAGTCATAGGAGGCTATCCCGTGGAGAAATTTGTGGCGACCATGTACCACTATTTACAGTTTGCGTATTACAAGT<br>TGAATGATCTGAAGAATGCAGCCCCGTGTGCCGTCAGCTACCTGCTCTTTGACCAGAGTGACAGGGTCATGCAACAGAAC<br>CTGGTGTACTATCAGTACCACCGGGACAAGTGGGGCCTCTCGGATGAGCACTTCCAGCCCAGACCCGAAGCAGTTCAGTT<br>CTTTAATGTGACGACGCTCCAGAAGGAACTGTACGACTTCGCTCAGGAACACCTAATGGATGACGATGAGGGAGAGGTTG<br>TGGAGTATGTGGACGACTTGTTGGAGACGGAAGAGTCTGCCTAGTCCACAGGGGCTAAGGAACCTCTCTTCCGAGTTCCT<br>CTTTCTTCAAGTGCCTGGGTTGTTGATACCTCACAGCCTTTTCTTCTTAAAGTAAGAAGGAAGCCACCATCTCTCCCTAC<br>CAAGGTCAAGCCTGACTTCCCCTTGTTCACACTCAGTATTCACGCTTGTCTTCATGGTTACACGTCTTCATGCCTGTCTT<br>TCCCTTCACACATGTGTTCCCGTCATCTAGTCTGTCCTCCTCAAAGTCACGTTCGTCTCCCCTCTGATCCCATGTGTCTC<br>CCCCCATGTTC | GRFTEMEAVNIAETPSDLFNAI<br>LIETPLAPFFQDCMSENALDEL<br>NIELLRNKLYKSYLEAFYKFCK<br>NHGDVTAEVMCPILEFEADRRA<br>FIITLNSFGTELSKEDRETLYP<br>TFGKLYPEGLRLLAQAEDFDQM<br>KNVADHYGVYKPLFEAVGGSGG<br>KTLEDVFYEREVQMNVLAFNRQ<br>FHYG |
| SEQ ID NO. 87<br><br>ATTTGGAGTTGAACTGAAGAGGACATGTGGTCATTTGGGCTGGGGGGTGTAGCTCAGTGGTAGAGGGTTTGCATACCCGC<br>ACAGCGCCCTGGGTTCATTCCCCAGCACTGTATAAAACTGGGCATGATGGTGCATACCCGAGAGTCCAGCACACAGCAGT<br>TCAAGAGCCTGTTTGTCCGTGCGGTGCGGGCCTACAACGGGGAGAACTGGAGAACGTCCATTTCCGACATGGAGCTCGCG<br>CTTCCCGACTTCCTCAAGGCCTTCTACGAGTGCCTGGCTGCCTGCGAGGGGTCGCGGGAGATCAAGGACTTCAAGGACTT<br>CTACCTGTCCATAGCAGATCACTATGTGGAAGTTCTGGAGTGTAAGATTCGTTGTGAGGAGACCCTCACCCCAGTCATAG<br>GAGGCTATCCCGTGGAGAAATTTGTGGCGACCATGTACCACTATTTACAGTTTGCGTATTACAAGTTGAATGATCTGAAG<br>AATGCAGCCCCGTGTGCCGTCAGCTACCTGCTCTTTGACCAGAGTGACAGGGTCATGCAACAGAACCTGGTGTACTATCA<br>GTACCACCGGGACAAGTGGGGCCTCTCGGATGAGCACTTCCAGCCCAGACCCGAAGCAGTTCAGTTCTTTAATGTGACGA<br>CGCTCCAGAAGGAACTGTACGACTTCGCTCAGGAACACCTAATGGATGACGATGAGGGAGAGGTTGTGGAGTATGTGGAC<br>GACTTGTTGGAGACGGAAGAGTCTGCCTAGTCCACAGGGGCTAAGGAACCTCTCTTCCGAGTTCCTCTTTCTTCAAGTGC<br>CTGGGTTGTTGATACCTCACAGCCTTTTCTTCTTAAAGTAAGAAGGAAGCCACCATCTCTCCCTACCAAGGTCAAGCCTG<br>ACTTCCCCTTGTTCACACTCAGTATTCACGCTTGTCTTCATGGTTACACGTCTTCATGCCTGCCTTTCCCTTCACACATG<br>TGTTCCCGTCATCTAGTCTGTCCTCCTCAAAGTCACGTTCGTCTCCCCTCTGATCCCATGTGTCTCCCCCATGTTCA | SEQ ID NO. 152<br><br>MMVHTRESSTQQFKSLFVRAVR<br>AYNGENWRTSISDMELALPDFL<br>KAFYECLAACEGSREIKDFKDF<br>YLSIADHYVEVLECKIRCEETL<br>TPVIGGYPVEKFVATMYHYLQF<br>AYYKLNDLKNAAPCAVSYLLFD<br>QSDRVMQQNLVYYQYHRDKWGL<br>SDEHFQPRPEAVQFFNVTTLQK<br>ELYDFAQEHLMDDDEGEVVEYV<br>DDLLETEESA |

FIG. 85

| Nucleotide Sequence (5'-3') | ORFs |
|---|---|
| SEQ ID NO. 88<br><br>AGCGGACTGGGAGCGCCTTCCGGAGAGACGCAGTCGGCTGCCACCCCGGGATGGGTCGCTGGTGCCAGACCGTCGCGCGC<br>GGGCAGCGCCCCCGGACGTCTGCCCCCTCCCGCGCCGGTGCCCTGCTGCTGCTGCTTCTGTTGCTGAGGTCTGCAGGTTG<br>CTGGGGCGCAGGGGAAGCCCCGGGGGCGCTGTCCACTGCTGATCCCGCCGACCAGAGCGTCCAGTGTGTCCCCAAGGCCA<br>CCTGTCCTTCCAGCCGGCCTCGCCTTCTCTGGCAGACCCCGACCACCCAGACACTGCCCTCGACCACCATGGAGACCCAA<br>TTCCCAGTTTCTGAAGGCAAAGTCGACCCATACCGCTCCTGTGGCTTTTCCTACGAGCAGGACCCCACCCTCAGGGACCC<br>AGAAGCCGTGGCTCGGCGGTGGCCCTGGATGGTCAGCGTGCGGGCCAATGGCACACACATCTGTGCCGGCACCATCATTG<br>CCTCCCAGTGGGTGCTGACTGTGGCCCACTGCCTGATCTGGCGTGATGTTATCTACTCAGTGAGGGTGGGGAGTCCGTGG<br>ATTGACCAGATGACGCAGACCGCCTCCGATGTCCCGGTGCTCCAGGTCATCATGCATAGCAGGTACCGGGCCCAGCGGTT<br>CTGGTCCTGGGTGGGCCAGGCCAACGACATCGGCCTCCTCAAGCTCAAGCAGGAACTCAAGTACAGCAATTACGTGCGGC<br>CCATCTGCCTGCCTGGCACGGACTATGTGTTGAAGGACCATTCCCGCTGCACTGTGACGGGCTGGGGACTTTCCAAGGCT<br>GACGGCATGTGGCCTCAGTTCCGGACCATTCAGGAGAAGGAAGTCATCATCCTGAACAACAAAGAGTGTGACAATTTCTA<br>CCACAACTTCACCAAAATCCCCACTCTGGTTCAGATCATCAAGTCCCAGATGATGTGTGCGGAGGACACCCACAGGGAGA<br>AGTTCTGCTATGAGCTAACTGGAGAGCCCTTGGTCTGCTCCATGGAGGGCACGTGGTACCTGGTGGGATTGGTGAGCTGG<br>GGTGCAGGCTGCCAGAAGAGCGAGGCCCCACCCATCTACCTACAGGTCTCCTCCTACCAACACTGGATCTGGGACTGCCT<br>CAACGGGCAGGCCCTGGCCCTGCCAGCCCCATCCAGGACCCTGCTCCTGGCACTCCCACTGCCCCTCAGCCTCCTTGCTG<br>CCCTCTGACTCTGTGTGCCCTCCCTCACTTGTGGCCCCCCTTGCCTCCGTGCCCAGGTTGCTGTAGGTGCAGCTGTCAC<br>AGCCCTGAGAGTCAGGGTGGAGATGAGGTGCTCAATTAAACATTACTGTTTTCCATGCAAAAAAAAAAAAAAA | SEQ ID NO.:153<br><br>MGRWCQTVARGQRPRTSAPSRA<br>GALLLLLLLLRSAGCWGAGEAP<br>GALSTADPADQSVQCVPKATCP<br>SSRPRLLWQTPTTQTLPSTTME<br>TQFPVSEGKVDPYRSCGFSYEQ<br>DPTLRDPEAVARRWPWMVSVRA<br>NGTHICAGTIIASQWVLTVAHC<br>LIWRDVIYSVRVGSPWIDQMTQ<br>TASDVPVLQVIMHSRYRAQRFW<br>SWVGQANDIGLLKLKQELKYSN<br>YVRPICLPGTDYVLKDHSRCTV<br>TGWGLSKADGMWPQFRTIQEKE<br>VIILNNKECDNFYHNFTKIPTL<br>VQIIKSQMMCAEDTHREKFCYE<br>LTGEPLVCSMEGTWYLVGLVSW<br>GAGCQKSEAPPIYLQVSSYQHW<br>IWDCLNGQALALPAPSRTLLLA<br>LPLPLSLLAAL |
| SEQ ID NO. 89<br><br>GCAAATCTTCAGGGGCCGTCCAGGACTACAGAGCTGTTTCACCCTACCTTGGCTTCAATCTCTTCCCCCATGCTCGAAGG<br>TGCGGAGCTGTACTTCAACGTGGACCATGGCTACCTGGAGGGCCTGGTTCGAGGATGCAAGGCCAGCCTCCTGACCCAGC<br>AAGACTATATCAACCTGGTCCAGTGTGAGACCCTAGAAGACCTGAAAATTCATCTCCAGACTACTGATTATGGTAACTTT<br>TTGGCTAATCACACAAATCCTCTTACTGTTTCCAAAATTGACACTGAGATGAGGAAAAGACTATGTGGAGAATTTGAGTA<br>TTTCCGGAATCATTCCCTGGAGCCCCTCAGCACATTTCTCACCTATATGACGTGCAGTTATATGATAGACAATGTGATTC<br>TGCTGATGAATGGTGCATTGCAGAAAAAATCTGTGAAAGAAATTCTGGGGAAGTGCCACCCCTTGGGCCGTTTCACAGAA<br>ATGGAAGCTGTCAACATTGCAGAGACACCTTCAGATCTCTTTAATGCCATTCTGATCGAAACGCCATTAGCTCCATTCTT<br>CCAAGACTGCATGTCTGAAAATGCTCTAGATGAACTGAATATTGAATTGCTACGCAATAAACTATACAAGTCTTACCTTG<br>AGGCATTCTATAAATTCTGTAAGAATCATGGTGATGTCACAGCAGAAGTTATGTGTCCCATTCTTGAGTTTGAGGCCGAC<br>AGACGTGCTTTTATCATCACTCTTAACTCCTTTGGCACTGAATTGAGCAAAGAAGACCGAGAGACCCTCTATCCAACCTT<br>CGGCAAACTCTATCCTGAGGGGTTGCGGCTGTTGGCTCAAGCAGAAGACTTTGACCAGATGAAGAACGTAGCGGATCATT | SEQ ID NO.:154<br><br>MLEGAELYFNVDHGYLEGLVRG<br>CKASLLTQQDYINLVQCETLED<br>LKIHLQTTDYGNFLANHTNPLT<br>VSKIDTEMRKRLCGEFEYFRNH<br>SLEPLSTFLTYMTCSYMIDNVI<br>LLMNGALQKKSVKEILGKCHPL<br>GRFTEMEAVNIAETPSDLFNAI<br>LIETPLAPFFQDCMSENALDEL<br>NIELLRNKLYKSYLEAFYKFCK<br>NHGDVTAEVMCPILEFEADRRA<br>FIITLNSFGTELSKEDRETLYP |

FIG. 86

| Nucleotide Sequence (5'-3') | ORFs |
|---|---|
| ACGGAGTATACAAACCTTTATTTGAAGCTGTAGGTGGCAGTGGGGGAAAGACATTGGAGGACGTGTTTTACGAGCGTGAG<br>GTACAAATGAATGTGCTGGCATTCAACAGACAGTTCCACTACGGTGTGTTTTATGCATATGTAAAGCTGAAGGAACAGGA<br>AATTAGAAATATTGTGTGGATAGCAGAATGTATTTCACAGAGGCATCGAACTAAAATCAACAGTTACATTCCAATTTTAT<br>AACCCAAGTAAGGTTCTCAAATGTAGAAAATTATAAATGTTAAAAGGAAGTTATTGAAGAAAATAAAAGAAATTATGTTA<br>TATTATCTAGACTACACAAAAGTAAGCCACACTATATCTTCATGAGTTGCAAATCCATGGAAACACAGTAAACCAGCCCT<br>GAAACAAAGCATTTCCTTGTTTTCAGTGGTATTAGATCTTGTTTCCACATGTCTGTCTCATTCTTCACTGGGCCTTACAG<br>GTTAGTTTTAATTAACTCTATGGTATTTTTCTTATTCTTGTTTGATCATGTTAAAAATTGGACCTAATAAAAGTATTTTA<br>TTCTTGCTTTTCCATGCTTCTCTACAGGTCCAAATACTGAATGTCTCCTTTACTTTTTCTCTTTTAAATTTTTTTCTAGA<br>CAGGGTCTCACTCTGTCACCTAGGCTACAGTGCAGTGGTGTGATCACAGCTCACTGCAGCCTCGACTTCCCAGGCTCAAG<br>TGATCCTCCCAGCTCTCAGCCTCCAAAGTAGCTGGCACTACAAGTGTACACCCCCACACAAGGCTAAGTTTTGTATTTTT<br>TGTAGAGACAGGGTTTCAACATATTATCCAGGCTGGTGTCGAATTCCTGGGCTCCAGGGATCCACAGTCCCCCTTGGCCT<br>CCCAAAGTGTTGGGATTACATGCATGAGCCACTGTGCTGGGCTTCATTTACATTTTAACTGTCTGTTCCTTGCCTAGATT<br>CACAGAAATCCAAAGCTGTATGTAGTCAACATGGTTCACAAGTGTTGGAAAATGTGTTTTTTGTTTTGTTTTGTTTTGTT<br>TCGTTTTGTTTTGAGACAGAGTTTCCCTCTGTCGCCCAGGCTAGAGTGCAATGGCGTGATCTCGGCTCACTGCAACCTCC<br>ACCTCCCAGATTCAAGCAACTCTCTGCCTCAGCCTCCCGAGTAGCTGGGATTACAAGCACCCACCACTACACTCAGCTAA<br>TTTTTTGTATTTTTAGTAGAGCCGGGGTTTCACCATCTTGGCCAGGCTGATCTTGAACTCCTGAGCTCATGATCCACCCG<br>CCTCAGCCTCCCAAAGTGCTGGGATTACAGGCCCCTTGTTCAGCCACTGCACCTGGCCCCTTATTTTGTTTTTGTTTTCT<br>AATATACTTTGATGTAATCAGCTTGAGAAAGCAACACAATTTCAAATCCTATCTTCTAGATGCAAGCAGTGTTAAATTTG<br>TTAATAAATTTGCTTTTCACACCTTTCTTTAAATAAAAGGTATATCTCTC | TFGKLYPEGLRLLAQAEDFDQM<br>KNVADHYGVYKPLFEAVGGSGG<br>KTLEDVFYEREVQMNVLAFNRQ<br>FHYGVFYAYVKLKEQEIRNIVW<br>IAECISQRHRTKINSYIPIL |

FIG. 87

SEQUENCE LISTING

```
<160> NUMBER OF SEQ ID NOS: 155

<210> SEQ ID NO 1
<211> LENGTH: 1456
<212> TYPE: DNA
<213> ORGANISM: Mus musculus

<400> SEQUENCE: 1

gattgtggag gaacctagcg gcgcaatgga gccctggtgc ggggcagagg tccgtgggca      60

gggccctcag ggtccccgtg tgcctggggc ttcccgctcc cgctcccgcg cccttctcct     120

gctgttgctg ctgctgctgc tgctcctgcc tcggcggccg gcaggtgagc gcatccgccc     180

ccgacgccct ccccggcacg cccacccgcg gccacctctg actcgctgga gaccttccac     240

aggctacttg gccgcaggag catccccggg gacgctgtcc accaccgtcc cgaccggacc     300

cggggtctcc tgtggctcca gaggcatctg tccctcaggc aggcttcgcc ttcctcggca     360

agcccagact aaccagacca cgacggctcc accgaactca cagaccatgg ctccactgaa     420

aacggtgggg actctcggca tgatggacac tactgggtcc gttcttaaga cggttcattc     480

cagcaacctc cccttctgtg gctcctccca cgagccagac cctactctca gggacccaga     540

agccatgact cggcggtggc cctggatggt cagcgtgcag gctaatggct cacacatctg     600

tgctggcatc cttatcgctt cccagtgggt gctgaccgtg gcccattgct tgagccagaa     660

ccatgttaac tacatagtga gggcggggag cccgtggatt aatcagacgg caggaaccag     720
```

```
ctcagatgtg ccggtccatc gagtcatcat aaaccatggc taccaaccca gacggtactg    780
gtcatgggtt ggccgggccc atgacatcgg ccttctcaag ctcaagtggg ggctcaagta    840
cagtaaatac gtgtggccca tctgcctgcc tggcctggat tacgtggtgg aggacagttc    900
tctctgcact gtgacaggct ggggatatcc cagggctaac ggcatctggc cccagttcca    960
gtccctccag gagaaggaag tctctatcct gaacagcaag aaatgtgatc atttctacca   1020
caagttctcc agaatctcct ctctggttcg gatcatcaac cctcagatga tctgtgcctc   1080
ggacaacaac agggaggagt tctgctatga gataactggc gagcccctgg tctgctcttc   1140
agatggcaca tggtacctgg tgggaatgat gagctggggc ccaggctgca agaagagcga   1200
ggccccaccc atctttctgc aggtctccta ctacaggccc tggatctggg accggctcag   1260
tggggagccc ctggcccttc cagccccatc caggaccttg ctcctggctt tccttctgct   1320
cctcatcctt ctgggcacac tgtgacactg ccatgtctct ccttccttcc cctcctccta   1380
agtgctgctg tgggggtggc gctcagcctg ccggaggcgg ggaggagcta gcagagatta   1440
aacacttctt ttcctc                                                   1456
```

<210> SEQ ID NO 2
<211> LENGTH: 2523
<212> TYPE: DNA
<213> ORGANISM: Mus musculus

<400> SEQUENCE: 2

```
acactttccc ggaccagggc cagtgttcag ttgctatcca ggactcggag ccacttcagc     60
ctgagcagta tgcttgagac tgcagagctg tacttcaatg tggaccatgg ctacctggag    120
ggcctggttc gaggatgcaa agccagcctc ctaactcagc aggactatgt caacctagtg    180
cagtgtgaga ccttggaaga cctgaaaatt catctccaga ccacggacta tggcaacttc    240
ctggctaatg aaacaaatcc tctcactgtt tccaaaattg acacggagat gaggaagaag    300
ctctgcagag agtttgacta tttccggaat cattccttgg agcccctgag cacatttctc    360
acctacatga catgcagcta tatgatagac aatataattc tacttatgaa tggggccttg    420
caaaagaaat ctgtgaaaga agttctagcc aagtgtcacc cactgggccg tttcacagag    480
atggaagctg tcaacattgc agagaccccc tcagatctct tcaaggctgt gctggttgaa    540
acaccattag ctccattctt tcaagattgt atgtctgaaa acactcttga tgaactgaat    600
attgaattac tgcgcaataa actatacaag tcttaccttg aggcattcta caaattctgc    660
aaggatcacg gtgatgtcac agcagacgtt atgtgtccca ttcttgagtt tgaggccgac    720
agacgcgctt taatcatcac tctgaactca tttggcactg aactaagcaa agaagacagg    780
gagaccctct tccccacctg cggcaggctc tatccagagg ggttgcggtt gttagctcaa    840
gctgaagact ttgagcagat gaagagagtg gcagataatt atggagttta caagcctttg    900
tttgacgctg tcggtggcag tgggggggaag acactggaag acgttttcta tgagagagag    960
gtacagatga atgtgctggc attcaacagg caactccatt atggtgtgtt ttatgcgtat   1020
gtaaagttga aggagcaaga gatgagaaat atcgtgtgga tagcagaatg catctcacag   1080
aggcatcgaa ctaaaatcaa cagctacatt ccaattttat aagccagtgt acagaagatc   1140
atacatgttg ccatgaagtt attgaggaaa ggaaggggga ttgtgtcaca ttatctagat   1200
tatataaaag taagtcatac cacctttcca taaactacat gtccactgga agcccagtaa   1260
acagaacttg aaacaaaata tgcctttctt gtttccaaca agccccagtc gttttttcac   1320
atttatgact tcctgctcac tggcctcata cgttcatttt cattgaccct gtggcacttt   1380
```

ttgtattctc atttggtcag actaaaatca tacgtaatca ggttcttcac gagttctttt 1440
ccgttcttct ccccaagctc aaacactgct ttgcctttta cgtgtttggt ccttccatgc 1500
attcacgaaa atgcaaagct gtgggtagct aacatacacc atgcttggtg aagacacgtt 1560
cccttccttt cccccaagac ttttgagaaa gatagattcc ccaaatgcaa gcattgttaa 1620
atttattact aaattagatt atcaacgcac acatagagac agagagagag agagagagac 1680
agacagacag acagacagaa ggatgaataa cttatatcga tatgtatacc agtggttctg 1740
tcatacttta ttccagaaaa tccaactaat tgtactttat tccttcagaa gatgtagata 1800
cagcatggtt gctacataaa gttgaaacaa tgcagaggtt gctcagaaaa agaaaaatag 1860
caaaatgtgt ctccaatctt ttctttaaat aggaaatttt tcttaaatat agtctatgct 1920
tgctctgctt cacaaattaa atctgtgcag tcaacatgat gactcagcag gtaagagctt 1980
gaagtcaact ccatgagttc gattcctgga atctcacata tggaaggagg gaactgcaaa 2040
actacaagat catctttaat cctttaatct ttacttatgc accccaccac tacacacact 2100
tacaaaagaa ttttaaagaa gggcacagaa ataatgtgaa ctaattttac tatacactct 2160
ctatatacac atgctatgta gaatagtatg cataaactaa ggagcacaac atttttatgt 2220
agaataatca tttataaata taacaaaaat aatgttttgt tgaactaaga agaaagccaa 2280
gtgcctactc cttgactgca gatgcaattt acccagctgc ctcctgccca gaccaacaca 2340
ccttctcaac caccttagac tgtcctctca aaccctgacc caaaaaaacc cttccctttc 2400
taaactgttg tttcaggtat tttgtggcag caacccaaca aagtaactaa tacagaaaac 2460
tgatactgcc attgctacaa taaacttgat tttggggatt taaaaaaaaa aaaaaaaaaa 2520
aaa 2523

<210> SEQ ID NO 3
<211> LENGTH: 1685
<212> TYPE: DNA
<213> ORGANISM: Mus musculus

<400> SEQUENCE: 3
cccgcctccc ttcctaggcc tgccgcgtcg cgcgtcctct gctcggggct ctggttcgtg 60
ggccacgcgc gatggggccc cgcagccctg cggccgcgtt gctggtgctg ctgtgtgtcg 120
ggtgcgcgcc gacccccggg cgcgggcagt acgagcgcta cagcttccgc aacttcccgc 180
gggacgagct gatgccgctc gagtcggcct accgccacgc gctcgaccag tacagcggcg 240
agcactgggc cgagagcgtg ggctacctgg aggtgagcct gcggctgcac cgtctgctgc 300
gcgacagcga ggccttctgc caccgcaact gcagcgcggc cacgccagca cccgcgcccg 360
ccggcccggc cagccacgcc gaactacgcc tcttcggcag cgtgctgcgc cgcgcgcagt 420
gcctcaagcg ctgcaagcag ggcctgcccg ccttccgcca gtcgcagccc agccgctcag 480
tgctggcgga ctttcagcag cgcgagccct acaagtttct gcagttcgcc tacttcaagg 540
ccaatgacct cccgaaggcc atcgctgcgg ctcacaccta tctcctgaag catccagatg 600
acgagatgat gaagagaaac atggagtatt ataagagctt gcctggagcc gaggaccaca 660
ttaaagactt ggaaaccaag tcgtacgaga gcctgtttgt ccgtgcggtg cgggcctaca 720
acggggagaa ctggagaacg tccatttccg acatggagct cgcgcttccc gacttcctca 780
aggccttcta cgagtgcctg gctgcctgcg aggggtcgcg ggagatcaag gacttcaagg 840
acttctacct gtccatagca gatcactatg tggaagttct ggagtgtaag attcgttgtg 900
aggagaccct caccccagtc ataggaggct atcccgtgga gaaatttgtg gcgaccatgt 960
accactattt acagtttgcg tattacaagt tgaatgatct gaagaatgca gccccgtgtg 1020
ccgtcagcta cctgctcttt gaccagagtg acagggtcat gcaacagaac ctggtgtact 1080
atcagtacca ccgggacaag tggggcctct cggatgagca cttccagccc agacccgaag 1140
cagttcagtt ctttaatgtg acgacgctcc agaaggaact gtacgacttc gctcaggaac 1200
acctaatgga tgacgatgag ggagaggttg tggagtatgt ggacgacttg ttggagacgg 1260
aagagtctgc ctagtccaca ggggctaagg aacctctctt ccgagttcct ctttcttcaa 1320
gtgcctgggt tgttgatacc tcacagcctt ttcttcttaa agtaagaagg aagccaccat 1380
ctctccctac caaggtcaag cctgacttcc ccttgttcac actcagtatt cacgcttgtc 1440
ttcatggtta cacgtcttca tgcctgtctt tcccttcaca catgtgttcc cgtcatctag 1500
tctgtcctcc tcaaagtcac gttcgtctcc cctctgatcc catgtgtctc ccccatgttc 1560
agaaagacag tcttctgtgg tctgctttct catccccgga agaaaaatca gtattatttt 1620
ttaagtaaga aaaacactaa aagatgataa atatatttgg agaattaaaa aaaaaaaaaa 1680
aaaaa 1685

<210> SEQ ID NO 4
<211> LENGTH: 2336
<212> TYPE: DNA
<213> ORGANISM: Mus musculus

<400> SEQUENCE: 4
gactcggcct ccgggagaca aagggccctg tcgtcgccgg cccccgagct gttccgggcc 60
atgggcagga cagaccgtcg cgccggtccc agagccaggc tccccagcac aggctacaca 120
ctggacactc aaagccagac agaagccccc acaccccctc tctggactga cgcagatgaa 180
gagctagagg tccagagaga ctgactgtgt gcccctgaag tgacccagcc tggagactgt 240
gagctgacct tcaaagtgat tgagcagaac tgggtgggca gcctgtgggg acaggttgca 300
gctcctcgtg accatgaagc tcaacgagcg cagcttggcc ttctacgcaa cctgcgatgc 360
cccggtggac aacgccggct tcctgtacaa gcgtggtggc cgtgggaccg gctcgcaccg 420
gcgctggttc gtgctccggg gcaatatcct cttttacttc gaggcagaag gcagccgcga 480
gccgctgggc gtcatcctgc tggagggctg cacggtggag ctggtggatg cccgggagga 540
gttcgccttc gcagtgcgct ttgccggggg ccgatcccgg ccgtacgtgc tggccgctga 600
cagccaggca gccctggagg gctgggtgaa ggcactgtcc cgggccagct tccactatct 660
gcgcttggtg gtgcgggagc tggaacagca actggctgcc atgcgcgagg gaagccccgc 720
caacgcctta cccgccaacc cgagcccggt tttgacccag agacccaagg agaacggctg 780
ggtagtgtgg agcacgctgc ccgagcagcc ctcggtagcc cctcagcggc cgccgccact 840
gccaccccgc cgcagggcct cagcggccaa cgggcccttg gcatccttcg cccagctgca 900
tgcgcgatat ggactagagg tgcaggccct tagggaccag tggcgcggag gccaggctgg 960
cctagccagc ttagaggtcc cctggcatcc tggttctgct gagactcaga cccaggacca 1020
gccagcccta aggggacata gtgggtgtaa ggtattacat gtattccgtt ccgtagaatg 1080
gcctgtttgc aatccaggct cccaggggac ataggacata tgactcagga gacctgtgcc 1140
cctggggtca gaggcactta cttctgagaa gaatctggaa cgtgaacctg agggtgcttc 1200
tagagcccaa ggagctggtt tctagagaac tccgcgccag ggtggcctgt gtgaccttga 1260
cagccccgaa gctggccaca ggcccatggg gcccagggtt tacctggtgc ctctcaagga 1320
tctaaagctt gaacctggaa gctgctgtct gggctgctgt gggcctacac cagtaggtgg 1380

-continued aatgtgggac ttgaactgga taggtccccc aggctcctgg cctggaacca gctaagtcag 1440
gactgtgtcc agctttgtag gtgagcccgg gcagaagcag ggcctcccct gacctcggtc 1500
ctggcctggg acccagcttc ctcccagttt cacctggagg agacaggcct ccgactgatt 1560
ccatgcctgc agcagggaga gcccaggcac tgtccctagc cactgcaggt gaccagtggg 1620
cctcaggact gggcctactt ctctctcacc acagtgctgg ctgtcttcca gagggttggg 1680
caggacagcc ggccccacct gggttcttgt ttacagtcct cctcagtgcc ctgccctgag 1740
gggacactcc aatcgctgca tcctatgaac agatttcacc ctggcccctc cctctcctct 1800
ggggggtggg gtggctgggt cccatgggtg cttctgtctg tcgccagggc ctcttggctc 1860
tctgctggct caggggccag ggcacttggc tgtgggtttt tctttgaagt acagaggcta 1920
ctgtcttcca ccagtgaagt taagtagtcc agtctcaccc ctgccacttt tgttactgtt 1980
ggctgcaagg ggtggcattg tctccaggga gccaggccct cgcaggagac acacgggcgc 2040
ctagctgact tggccctgac ttggccctct gtctcctgag ctcagctgtc tgcacaggtg 2100
gtgcctctgg ggacttggtc tgtctcctca actctcccac tggagtcata cggctgaggt 2160
gtagactcta gtctgggacg ggcttacaaa ctctaaaggt acggggcagg aggtggggga 2220
gacaagggca gagttgttcc ctctccccaa agcacaaggt gaacaccagc tgattctggg 2280
gctaggagag ttatcaatca tggacagggt atgagggcca aaataaaagc cggtcg 2336

<210> SEQ ID NO 5
<211> LENGTH: 1807
<212> TYPE: DNA
<213> ORGANISM: Mus musculus

<400> SEQUENCE: 5
cagcgcccga gcgcagacgc gcccgccatg agggagattg tgcacatcca ggcgggccag 60
tgcgggaacc agatcggtac caagttttgg gaagtgatca gtgatgagca cggcatcgac 120
caggccggag gctacgtggg cgactcagcg ctgcagctgg agaggatcag cgtctactac 180
aatgagtcat cctctaagaa gtacgtaccc agggctgccc tggtggactt ggagcccggc 240
accatggaca gtgtgaggtc tgggcctttt gggcaactct tccggcctga caacttcatc 300
ttcggacaga cgggtgccgg aaacaactgg gccaagggtc actacacgga gggcgcggag 360
ctggtggatt cggtgctgga tgtggtgcgc aaggagtgtg agcattgcga ctgtcttcag 420
ggcttccagc tcacccactc gctgggcggt ggcacgggct caggcatggg cacactgctc 480
atcagcaaga tccgagagga gtacccggac cgcatcatga acaccttcag cgtcatgccg 540
tcacccaagg tctcagacac cgtggtggag ccctacaacg ccacattgtc agtgcaccag 600
ctggtagaga acaccgacga gacctactgc atcgacaacg aggccctcta tgacatctgc 660
ttccgcacgc tcaagctgac cacacccact tacggggacc tcaaccactt ggtatccgcc 720
accatgagcg gtgtcaccac atcactgcgt ttccctggcc aactcaacgc cgacctgcgc 780
aagctggctg tgaacatggt gccattccca cgtctccact tcttcatgcc cggctttgcc 840
cccctcacag cccggggcag tcagcagtac cgtgccctga cagtgcctga gctcacacag 900
cagatgttcg atgccaagaa catgatggct gcctgtgacc cacgccatgg ccgctacctg 960
accgtcgcca ctgtcttccg gggccccatg tccatgaagg aggtggacga gcagatgctg 1020
gccatccaga acaagaacag cagctacttt gtggagtgga tccccaacaa tgtcaaggta 1080
gctgtgtgcg acatcccacc acggggcctg aagatggcct ccaccttcat tggcaatagc 1140
actgccatcc aggagctatt caagcgcatc tccgagcagt tctcggccat gttccgccgc 1200
aaggccttcc tgcactggtt caccggtgag ggcatggacg agatggagtt caccgaggcc 1260
gagagtaaca tgaatgacct ggtgtccgag taccagcagt accaggacgc cacggtcaat 1320
gatggggaag aggcatttga agacgaggat gaagaagaga tcaacgaata gggagccata 1380
agatgctaca gtgaacgtct gctcttttct tagccttgat ggtgtgggaa tggtgccctg 1440
gtctaagcat gtcactggcc cctctcaaac caaatgcacc acactgttct ccaggttacc 1500
tggaacagtc ccagcagacc agggagatct catataggaa ccctgaaagc aaagtagggg 1560
gctcacacag ggctaaagaa agtgaccacc ttttgttaag ccccccttccc accccatcag 1620
agttagaata gggatttgtt tttcatcctc ggtgataaaa actaaagcca cacagtgctg 1680
ccttaagtga atgcacacta tggaacttta tgacaatcca ttcataataa aatgctaaac 1740
ctgaaaaaaa aaaaaaaaaa aaaaaaaaaa aaaaaaaaaa aaaaaaaaaa aaaaaaaaaa 1800
aaaaaaa 1807

<210> SEQ ID NO 6
<211> LENGTH: 3340
<212> TYPE: DNA
<213> ORGANISM: Mus musculus
<220> FEATURE:
<221> NAME/KEY: misc_feature
<222> LOCATION: (677)..(677)
<223> OTHER INFORMATION: n is a, c, g, or t

<400> SEQUENCE: 6
ggcctgcttg tccgcgcgtg ggccaggtgg cggcccgcaa gctccaggtg gcggcgtcgg 60
ggagacgaac agtccccgcc gggcaggcag cgggaaggag cccgggactg gcctcacgtg 120
acagcaggag gtcgctgcgg ggacggtcag cccggtgggc caaggctgca ccgggcgagg 180
caaggcgtcc ggccgcaccc tcgcgggcca ggcgggacct ccccgcggcg gcgcccgggc 240
tgccgttccc ctttccgcgg ctcctcccgc gccgaggcga agcggctcct ccgctgggcc 300
gagtccgcca gtccgctggc ggtcatggag cgctatcccc ggagccccccg cgcggcccgc 360
gacctcacgc cctccgatcc tcgctagctc ttggcattgg gccttttctc cgccacccaa 420
cccggtcttc ggagcctgtg gtgttgtgat tcggacgaaa tggaagaaaa ggagcgatgt 480
gacccccttcg gttctgccct cctgcattga ggcctagttg gcatctgcag agaggaaaac 540
acggccagga aagcgtggtg tttctttttt tccaaagggg gtgggagggg aagggggggag 600
ccaaagggag gaatcctacg ttttatatgt ttttttttttc tttgttaatt ctacactttg 660
aaagtgttgg ctaaatnaac taatccaaaa gttatttttt cctatcgaga agacagaaaa 720
aggtagattt tttttttttg tccctttga ttccaacctt tcctcccagt gacaaagcat 780
aaatcatgaa caccagagaa taaataggtg aatctcagga atccgaagac aggaacctag 840
actttcctca ggagggaagg agcggagtgt ttagcggctc tgcctggaac ctaaatcgaa 900
aaacatgagt tgcgtgccat ggaaaggaga caaggccaaa gctgaatcct cggaccttcc 960
ccaagcagcg cccccacaaa tctaccatga gaagcagcgc agggagctct gtgctcttca 1020
tgctctcaac aacgtcttcc aggacagcaa cgccttcacg cgggaaacgc tgcaggagat 1080
tttccagagg ctgtctccga acactatggt gacgccccac aagaagagca tgctgggaaa 1140
tgggaactat gatgtgaatg tcatcatggc agcacttcaa accaaaggct atgaagctgt 1200
ttggtgggac aagcgaaggg acgtgggtgt cattgctctt actaatgtca tgggcttcat 1260
catgaacctg ccctccagcc tctgctgggg tccactcaag ttgcctctca aaagacagca 1320
ctggatctgt gttcgtgagg tgggaggggc ctactacaac cttgactcca aactcaagat 1380

-continued gccagagtgg attggaggcg agagtgagct caggaaattt ctaaaatacc atttgcgagg 1440
taaaaactgt gaactcctac tggttgtacc ggaagaagtg gaagcccatc agagctggag 1500
ggccgacgtg tgacagttgt ttgaccctct ttgtctcaac cctccagacc tctttgatgt 1560
gctgtggcct ctacagtcca cttccccaaa catctcattg ggttttccct tcagatttgc 1620
cagtgcaata ggacagatgt gtggactgtc acagagccac ccagcagtct gtgcctgggg 1680
gaagaaggta ggagctctga acacttaggg caagccattg aaccctttgc tatttcagag 1740
agggagccaa gaagggcgtc ctttgagggg gctgggttat ttctcccttt ccataaggtc 1800
ttgatacagg ctctgctggt agtgtcactg atgcttcagg cttacggaaa ggccgcccct 1860
tttctctcct gtggcaccat ggggtctgag gacacagtac atgcagagcc aagaaactgt 1920
caagactcca gcagtcacac tgcatgtcac ctgcagttca ttaggcctct tcttggtccc 1980
tttaaacccc agccagcctt ggggttttat aagaggctct gctattccaa aataggtgaa 2040
ttgcacatca ttctagcaag acagtggtga aagatatgcc taataccacg tgggtaaagc 2100
cagagtaggg tagtcactgg tggctcttca ctctaatcgt gtccctatca tttcactaca 2160
ttgactgggg aggctttggg acaagacaat gaacagggag agtactcata gttggcccat 2220
ttttagcaaa atcaaacaca tctacactga cctaaaattc catagtttgg gacagagttg 2280
ggcgaggaac tgccatgaag gtaagcttca gggtttgagc ccggtaggca cgtcctgagc 2340
tccagagctg tggcagcaat ctcaggttgg ctgtatgcat caagctagag cctctgagtt 2400
tggcgtctgt gtagtttctt tgacaaacag ggttggcttg ccccacttca actagttcta 2460
gatcattttt ttcttgtaat tttggaaaat gaggggaaat aattaccata cccccatacc 2520
aatgtgtttg tggtggcctt caaggcaggt gacctggcca gcccttaccg atccatggtc 2580
tctgcaggtc tgagagctgc cccactggcc tgcttcttct cccttggcag cagagctacc 2640
tggggcttgc atgttaatcc tgagcaagct tgttggggtg aagggggggct gtctccccac 2700 tgtgactgga gtgcatgttt acaccagcac tttttctgca catgtatctt caatccaaca 2760
aggccgtttt ttattcaagt ggcagaggcc tcgagtggct actgcactgc gctcagccat 2820
ggtcatctgc accattttct acaccagatc tgcttggcac catggggaac tctgcccctg 2880
cacaatgaca ttccaatcac taccagccag aagttacagc cgaccttgct gattgtcaca 2940
agcaggacct tgggtccatt ggcactgtcg gtgatagtaa gccatttctt gggaagagga 3000
gactcttccc tacagatctg cttgggcctg tgcaaatggc actgcaaacg agccacacac 3060
acgtggagtc catgagctag tgggatgtac aaagacgctt aagcatttca gggctggttc 3120
tgttcatatc caattctggt gcttaggaac agggacccat gttaatgccc cagggcaaag 3180
ccccactcct gtgaaggaag gggcagcctg accctgacgc ccagcaaggg gcagccctag 3240
gctttgtttt tcttgcttta ttccctttc tgttggcctt gtgctgggtt tgtttacaaa 3300
gatgtatttt gtttaaccaa atattaaaaa tgaaaagccg 3340

<210> SEQ ID NO 7
<211> LENGTH: 1419
<212> TYPE: DNA
<213> ORGANISM: Mus musculus

<400> SEQUENCE: 7
ggcatcagct tgggcaggtg tgcggcacaa gatgaagggg ccatggtgag gagccctcac 60
cctcagcctt acagcctctt ccccaagcca acatgagtgc cgagctggag ctgctgtggc 120
cggtgtcggg attattgctg ctgctgttgg gggccacagc ctggctgtgt gtccactgct 180

```
cccgtccagg agtgaagaga aatgagaaaa tctacgagca gaggaaccgg caagaaaatg    240

cacagagctc agctgcggct cagacatact ccctggccag gcaggtgtgg ccaggacccc    300

agatggacac agctccaaac aagtcatttg aaaggaagaa caagatgctg ttctcccacc    360

ttgagggaag taaccaggag cctgatgctg cctatgtaga ccccatccct acaaactact    420

acaactgggg atgtttccag aagccctcag aagacgacga ttccaactcc tacgagaatg    480

tgctcgtctg caagcccagc acccccgagt caggtgtcga ggactttgag gattaccaga    540

actcagtatc catccatcag tggcgagagt ccaagaggac tatgggtgca ccaatgtccc    600

tatcaggaag cccagatgag gagccagact atgtgaatgg ggatgtggcc gcagcagaga    660

acatctagga gagaaccaat caatcggaag gaagaagggc ccgaggatgg gggatctgag    720

cgggaactga agcctttact gcctgctgaa taaagcctgt tctccaggga tgctcaagtt    780

tcacaccctg gccgtggctg ctccacagcc tgggagacac tgggcatcgc cagagcccca    840

accctcaagt gatgccctgg acttctttgg gggcaaagca agtgcccaga ggatatagac    900

tgtgctgact ggaagcccaa gacctgaggc aagatgtgtc cccagtctca catctaaaat    960

gaggcacaac agtggcattt gtgggttttg tttttgtttt ggctgcagga tctcactaag   1020

ttactcaggc tgatctcaaa cttgtaaccc tcagtcctag tgttgggatt gcggcatacc   1080

agtttttttt ttttcctttc tttgtttgga cctcagatta cttatgtcga cttctaggac   1140

tgttgctatg actctttttg tggttaactg aagttgctgg agtcgtattt aatattgtca   1200

atgtcagggg gttccctgtc tcagagcatt atgtgtacta actgtagcag aggaatgggg   1260

tgtggggtaa cctgggatcg ctttggtttc ttagtgggct ccagtttgtt ctgatctttc   1320

attcctgcgg ggaccttgtg cgtcggtgat agggaaataa aactgccccc tcaccaaaca   1380

ccaataaacc ctgtgagtgt gagaaaaaaa aaaaaaaaa                          1419
```

<210> SEQ ID NO 8
<211> LENGTH: 3944
<212> TYPE: DNA
<213> ORGANISM: Mus musculus

<400> SEQUENCE: 8

```
cagaattaac tctaatttaa tgcgatgagt atgttttgct gttaccagtg ggggaaaaga     60

acacgcattg gcctactctc cttttctaga acaactgtgc atgactgttc tctctccaaa    120

cctgaacgat tcccttatac ggtgcactct caagacggcc ttgcacattc agcctgccct    180

cactccattc cgccgcgagg tggcaggacg ctcacggatg ccaggagacc tctgccggga    240

tccagtgacg tcacgcaacc ctagcgacga ttggctacct tcccgatgac cttgagggga    300

ggagtccgtg gcagagccgg aaacatcggc aacagcgaaa gccacgtccc gagaccgggc    360

gtgcgcactc cgaggatccc aaccgctgta gaggcctctg cacctcctcc tctggactga    420

gggggcacac tggcgtctac cgacgtgggg cgcaacctgc cgaaaggggt cacaccgctg    480

ggcgctagcg aggggaggag tcaccttgag aggaggggtc acaatgacta gccgagtcac    540

tctgccaggt ctcttttagt gagaggaaca caaagaggag ggggtgcagc actgaggggc    600

tcggggaaca cacggatgta gcagtgtcat ccgtaggaaa ggtcccccga aggagagcgg    660

gctccgaggg gcagcggcct ttgagggggc gggatcctgc cgagggcggg gcctccttgc    720

aggtgcaggc gtctccgaag agagggttat taggacaaag aagtaagagg gtggtcaccg    780

gatcgagcgt cggaatctca actttactta gggggatgga gatggagtga gaaggagtcg    840

agcaggtcag ggatgcgaag gccagaggct ccctacagcc ctggatactg cgatcggaga    900
```

-continued

```
agacaggtgt tagcgagccc cgagatttag agtgtcgggg tcagaaaccc ccctgaaatg    960
gacagtcgga gtcggacgca gaccgggcag gcagcgtggt cgatccgtgg agcccagggc   1020
gcaggagaat tagcgccagc agtcaaccct caagtcgtcc tgtgattcac gccccggcct   1080
acgcgcgggg gacgcacctg agggggcgtg gccgggccgc agcccgggct ccaaggagtt   1140
aaccgcagac cgggccgggc cccgccccgg gcaggccgca cagcctgagc ccggcggcga   1200
agcggagcag cagccgcccg cggggagccc gccgccggcg cccgggagcg ccgccgccgc   1260
ccggcccagg cccaggccca ggccccgcgc agagcggaga gccgcggcgt tccaccgggc   1320
ccaactcgcc ggcgcggcgg gggcgggccc aggaccttcg gcaggtcctc caggagtcca   1380
ccgggcggga gtcccggccc ccgggatcgg gttgggccgg cgcccatggc gagcgcggcc   1440
tgcccgggtc ccggggatcc ggccatgtga agcaggccgg ggctgggggc ccggccatgg   1500
ccggggaacg gccgccgctg cggggccccg ggcccggaga ggctccgggg gaggggccgg   1560
ggggcgcagg cggaggcccg ggccggggcc ggccctcctc ctaccgggcc ctccgcagcg   1620
ccgtgtccag ccttgcgcgt gtggacgatt tcgactgcgc agagaagatc ggggccggtt   1680
tcttctctga ggtctacaag gttcggcacc gacagtcggg acaagtcatg gtgctgaaga   1740
tgaacaagct ccccagtaac cggagcaaca cgctaaggga ggtgcagctg atgaaccggc   1800
tccggcaccc taacatcctc aggttcatgg gggtctgtgt gcaccaaggg cagctgcacg   1860
cgcttacaga gtatatgaat gggggcaccc tggaacagct gctcagctcc ccagaacccc   1920
tctcctggcc agtcaggctc cacctagccc tggacattgc acaaggccta cggtacctac   1980
acgccaaagg tgtgtttcac cgagacctca catccaagaa ctgtctggtc cgaagggaag   2040
accgaggctt cacagctgtt gtgggtgact tcggactggc tgagaagatt cctgtgtata   2100
gggaagggac aaggaaggag cccttggctg tggtgggctc ccccgtactgg atggctccag   2160
aggtgttgcg gggagagctg tatgatgaga aggccgatgt cttcgccttc gggatcgtcc   2220
tctgtgagct catcgcccga gtacctgcag accctgacta cctaccccgt actgaggact   2280
ttggcctgga tgtgcctgct ttccgaactt tggtgggaaa tgactgtccg ctacctttcc   2340
tgcttctggc catccactgc tgcagcatgg aacccagcac ccgggcccct tttactgaaa   2400
tcacccagca cctggaacag atcctggagc agcagcctga ggccacgccc ctcgccaagc   2460
cacccctcac caaggctccc ttgacataca atcaggggtc tgttccaaga ggaggtccct   2520
ctgccacact tcccaggcca gacccccggc tctcccgaag ccggtcagac ctcttcctgc   2580
caccttcgcc agaatcaccc cccagctggg gggacaatct aacacgagtc aacccccttct   2640
cactgcggga agacctcagg ggtggcaaga tcaagctgct ggacacaccc tgcaagccgg   2700
ccactccact gcccctggtt ccaccatcac cacttacctc tacccagctg cccttagtga   2760
ccactccaga catcctggtc cagcctgaga cccctgtccg ccgctgtcgc tcactacctt   2820
catcccctga gcttccccga cggatggaga ctgcactgcc aggtcctggc ccttccccca   2880
tgggcccgac tgaggagagg atggactgcg agggcagcag ccctgagcca gagcccccag   2940
gcctggctcc ccagctgcct ctggctgtgg ccactgacaa cttcatcagt acttgttcct   3000
cagcctcgca gccctggtct cctagatcag gacctcccct caacaataat ccccctgctg   3060
tggtggtgaa ttccccacaa gggtgggcta gggagccctg gaaccgggca cagcatagcc   3120
ttccccgggc agcagccctg gagcagacag agccctcacc gcccccatca gctccccggg   3180
agccggagga ggggctgccc tgccctggct gctgccttgg cccgttcagc tttggctttc   3240
tatccatgtg cccccgccct accccagctg ttgcccgcta ccgcaacttg aactgtgagg   3300
```

cgggcagtct tctctgccac cgagggcatc atgccaagcc acccacaccc agcctgcagc 3360
tgcctggggc acgctcttag cagtgaggcc tgtgagctca ggcttccaac cttggccttc 3420
gggataccct gtaaggacag tgcacttgct ggacaatgcc agccccagat gggctgacta 3480
gctcttctcc ccgtataggg gagcctcagc atggtctcaa tggacagagc acctcctagc 3540
cgacccctgg gttcactgtc ccattgggat caccgaacta gacacagcat tgctgacaca 3600
caggactaac acgtgcaaag tatttaaaaa tatttcaata aaactgcctg gctggctccg 3660
ggccatccat ccactcagcg gagcgccctc ccctgaccca tctctagttt gggaagttct 3720
taaggaaggt caagtctttt ctggaggctt ctttactctt cccaagagaa gtccagtttc 3780
tggagcagct ttcaagcaag cagcaggtca tcccttagct gggcatgccc gagagtgagg 3840
gagtgctgga ggaatagcag tcttaaaaat tggcaggccg taggttaagg atgtaggtca 3900
caaggtcttg ttcaagtgtc tggaaaataa agcatcagtg agct 3944

<210> SEQ ID NO 9
<211> LENGTH: 2505
<212> TYPE: DNA
<213> ORGANISM: Mus musculus

<400> SEQUENCE: 9
ctgaagccga atcccggaac caggtagcag agagctcggc cggccttgga gggagacaag 60
gctgcgacca atccgtctcc gtaccgtccc actggacttc acatccggga tctcctcctg 120
ggcgtgaccc gcgtcccgtc tgcggtcctc gaaccggtgt cctgatctct ttatccaggc 180
cttgctgttc ccgtcgtgcc tcgcgcacga ccgtagcccc ctcatccggg ttctctcccg 240
gcgttctccg cgtttgcttt gctgtggggt acttggcggt gccgccatga ctattctccc 300
caaaaagaag ccgccacctc ccgacgccga cccggccaac gaaccgccgc cgcccgggcc 360 gctgccccccg gcgcctcggc gcggtgcggg tgtaggcgtg ggtggcggcg gcacgggtgt 420
gggcggagga gagcgcgacc gtgactccgg cgtcgtgggg gcccgtcccc gggcttcgcc 480
gccacctcag ggcccgctcc cggggccgcc tggtgctctt catcgttggg cactggccgt 540
gccgcctggc gcagtcgcgg gccctcggcc acagcaggct tctccacctc cttgtggggg 600
ccccggtggc cccggcggcg gtcctggtga cgctcttggt gcgacaactg cgggggtggg 660
cgcggcaggg gtggtggtgg gcgtgggtgg taccgtgggc gtgggcggct gctgctcggg 720
gcccgggcac agcaagcggc ggcgtcaagc tcccggcgtt ggcgcagttg gcggggccag 780
tccggaacgt gaagaggtcg gagcgggcta caacagtgaa gacgagtatg aagctgccgc 840
agcgcgaatc gaggccatgg atcccgccac tgtagaacag caggaacact ggtttgaaaa 900
ggccttgcgg gacaagaaag gcttcatcat caagcagatg aaggaggacg gtgcctgtct 960
atttcgggct gtagctgacc aggtgtatgg agaccaggac atgcatgagg ttgttcgaaa 1020
gcattgcatg gactatctga tgaagaacgc tgattacttc tccaactatg tcacagaaga 1080
cttcaccacc tatatcaacc ggaagcggaa aaacaactgc catggcaacc acattgaaat 1140
gcaggctatg gcagagatgt acaaccgtcc tgtggaggtg tatcaatata gcacagaacc 1200
tatcaacaca ttccatggga tccatcaaaa tgaagatgaa cccatccgtg tcagctacca 1260
ccggaatatc cactataatt cagtggtgaa tcctaacaag gccactattg gtgtggggct 1320
gggcctaccg tcatttaagc cagggtttgc agagcagtcc ctgatgaaga atgccataaa 1380
gacatcagaa gagtcatgga ttgaacagca aatgctggaa gacaagaaac gagctacaga 1440
ctgggaggcc acaaatgagg ccatagagga gcaggtggct cgagaatctt accttcagtg 1500

```
gctgagggat caagagaaac aggcccgcca ggtccgggga cccagccagc cccggaaagc   1560
cagtgccaca tgcagttcag ccacagcagc agcctccagt ggcctggagg aatggactag   1620
tcggtcccca cggcaacgaa gttcagcctc gtcacctgag caccctgaac tgcatgccga   1680
gctaggcatt aagccccctt ccccaggcac tgtgttagct cttgccaaac ctccttcacc   1740
ctgtgcacca ggtacaagca gtcagttctc agcagggggt gatcgggcca cctctcctct   1800
tgtgtccctc taccctgctc tggagtgccg ggccctcatc cagcagatgt ccccctctgc   1860
ctttggtctg aatgattggg acgatgatga gatcctagca tcggtgctgg cagtgtccca   1920
acaggaatac ctagacagta tgaagaaaaa caaagtgcac agagagccac ccccagacaa   1980
gagttgatgg acacccaggg actggacatc attcccgatc cccccactcct gccctttgat   2040
gccacccaaa cttctttggc tttcttccct cttggcttcc ttcttttgtt tcctcttttc   2100
cttttttttt tccacttccc tctggccggc ccacccatgc gctccatcca tctcatccct   2160
gccaccacca ttggtctctg ccagctgaag tgccctattg cccccgcaca gcaccatctc   2220
agcattccac aggggactct ggaaagggtg cggaaggtag gcaagaggcc cacagagaca   2280
gaccatctgg cagccaggca gccccagaag agagacattc agacaaagga agtcttctgc   2340
tcacccttcc ttaaagatca gataaacttg tcatcccttc ccagcaatga tgacaggaaa   2400
atggaagtgg caagtttttcc ttctagtatc cgaagaatct gagccttcaa tgttaaaatt   2460
tttcttaatt aaaatgtgct ttatttcaca aaaaaaaaaa aaaaa                    2505
```

<210> SEQ ID NO 10
<211> LENGTH: 1148
<212> TYPE: DNA
<213> ORGANISM: Mus musculus

<400> SEQUENCE: 10

```
attttatatg tgaggcttca gttggtgttg atagaagttg ccctctgact gtgcaaattg     60
acataactat cagggggcag ttgggcatag ctccgcccag cagagcctgc acagtgaaga    120
tgcagctcat ggtactcgct gtggagtgtg gcagcacgga ccgacagatc agcactcctc    180
cacagctaag acagcccagt cctgcggcaa cacagctgct tgtaagtgca aaaaggtctg    240
cagagacaag aagtcttcac ctagagcaac atctgggaac atctttgcaa gtaaggacct    300
tgatagattg aggaaatcat gtgaaaaaga caaaggcctg atggcaggcg ggcacaggaa    360
gacaggcagt tagcattgga cattgccttt gacaggttag gccttaatgt atattaaacg    420
atgctctgtg tgcttcccaa acacaagcct gtcttgatcg gtagatactg tggcgaggct    480
agctcgtgag tattcctttt gtatcacacc agtgttttaa agttgtgtgt tcgtatgtct    540
gctgtggtat ttttaagttc tgggagaagc ctgctggccg tgtcagctca cggccatcag    600
tagttactca gtattgctgc tccacgtttc ccagtgcacc ttccatgcca gggcagtggc    660
tgcgtgcgtg caagccgcgg gagcgccttc ccgctcattt tatatgtatt tatagaaacc    720
aaatgaccgc agatggctat atggtgtagt gttaaaccag tggaactcta atggcaataa    780
atatatgcat atgtgtggga gaggggaaaa gtggaaatac aggtttacag ccagacatgg    840
tgggtgatag cccttcagtg tatttctctg tcccttcact gacctagaag gatttgagct    900
gctgcagctt tagacagaaa atgtccacat ttgctgactg tgggccataa atatgctttt    960
agtactgctt tgctgatgta taaataagaa atctgtaata tgtactatat gtaattattt   1020
tcttttgact ttatttcaaa atgtatattt tctgattatt atcatgagct ataaagcaaa   1080
aagatcaata tctgatattc tcccaaataa taaattttca agattcattg gaaaaaaaaa   1140
```

aaaaaaaa 1148

<210> SEQ ID NO 11
<211> LENGTH: 2805
<212> TYPE: DNA
<213> ORGANISM: Mus musculus

<400> SEQUENCE: 11
cgacaagagg taatcctcca ggctcgtgat agcacagtgt tatcacagat aacagtaaga 60
tggctcctgt cctcagtgaa gtaacttaga aaccatcact cagagcaagt cttctgcgag 120
gacgctgggc gacctcgtcc gcaagctcgg ggagaagatc cttcctgaga tcatccccat 180
cctggaagaa ggactaaggt cgcagaagag cgacgagagg cagggcgtgt gcatcgggct 240
cagcgagatc atgaagtcca ccagccggga cgctgtgctc ttcttctctg agtcccttgt 300
gcccacggca aggaaggcgc tgtgtgatcc cctggaggag gtccgggagg cggcagccaa 360
gacctttgag cagctgcact ccaccattgg ccaccaggct ttggaggaca tcctcccgtt 420
cctactgaag cagctggacg acgaggaggt gtcggaattt gccctggacg gtctgaagca 480
ggttatggcc gttaagagcc gtgtggtgct gccctatctg gtgcccaagc tgacaacacc 540
acccgtcaat acccgggtgc tggctttcct gtcctctgtg gctggtgatg ctctgacccg 600
acaccttggc gtgatcctcc cagctgtcat gttagcactg aaggagaagc ttgggactcc 660
agacgagcag ctggagatgg ccaactgtca ggctgtgatc ctctcagtgg aggatgacac 720
tgggcaccgg atcatcatcg aggatctgtt ggaagccacg cgcagccctg aagtgggcat 780
gaggcaggcg gcggccatca tcctgaacat gtactgctcc cgctccaagg ccgactacag 840
cagccacctt cgcagcctgg tctcgggctt gatccgcctc ttcaatgact ccagccctgt 900
ggttctggag gagagctggg acgctctcaa tgccatcacc aagaagctgg acgctggtaa 960
ccagctggcc ctgatcgaag aactccacaa ggaaatccgt ttcataggca acgaatgcaa 1020
aggggagcac gtgccaggct tctgtcttcc aaagagggga gtaacctcca tccttccagt 1080
gctgcgggaa ggggtcctca ctggcagtcc tgagcagaag gaagaagcag ccaagggctt 1140
gggcttggtg atccgcctga cctcagctga tgccctgagg ccctctgtgg tcagcatcac 1200
tggccctctg attcgcatcc ttgggaccgg ctcaactgga ctgtgaaggc ggctctgctg 1260
gagacactca gcctcttgct ggcaaggttg ggattgccct gaagcccttc ctgccccagc 1320
ttcagaccac cttcaccaaa gccctacagg actccaatcg ggcgtccggg ctgaaggcgg 1380
ccgatgctct ggggaagctc atttccatcc acgtcaaggt ggaccccctc tttacagagc 1440
tgctcaacgc gatccgcgcg gtggaggacc cgggcatacg agacaccatg ttgcaggccc 1500
tgaggtttgt gattcagggc gcaggctcca aagtggatgc tgcattcgga aaaacctggt 1560
ctccgtcctg ctgagcatgc tgggccatga cgaggacaac actcggatct ccacactggg 1620
tgccttgggg aactgtgtgc ctttctgact gacgaagagc tcaacactgt ccttcagcag 1680
tgcctgctag ctgacgtatc tggcattgac tggatggttc ggcacggtcg gatcttggcg 1740
ctgtccgtgg ctgtgaatgt ggctcccagc agactgtgtg caggcagata cagcaatgag 1800
gttcaggaca tgatcctcag caacgccgtg gcagacagga tccccatcgc catgagtggg 1860
attcgaggca tgggcttcct catgaagtat cacatcgaga caggaggcgg gcagctgccc 1920
cccaggctct ccagccttct catcaagtgt ctgcagaacc catgtagtga catcaggctg 1980
gtggccgaga agatgatctg gtgggcaaac aaggagcccc ggcaccccct ggagccacag 2040
accatcaagc ccatcctgaa ggctcttctc gataacacca aggacaagaa actgtcgtgc 2100
gggcctacag cgaccaggcc atcgtgaacc tgctcaagat gaggcggggc gaggagctgc 2160
tccagtccct ctccaagatc ctggacgtgg ccacctggag gctctgaatg aatgcagcgg 2220
aggtcgctga ggaagctggc ctgccaggca gactcggtgg agcaggtgga cgacaccatc 2280
ctgacgtgac agctggtccc gccagccacc gcacgctgcc cctcgtctgt gttcacactg 2340
ttttcatttt tgaaaatact tttattccaa gggggagctc aggagatggc attcccagaa 2400
agtattttag tacatcaagc gaccagagcc aaagccttaa atccaaccca cacacaactg 2460
aagatcgcct cctccctctc ttgcccttat ctccagagaa gagaaagaga agcgtgcaca 2520
ccaccctcag cgagcggcag caaggggagc ccgactcggc tcagcccgga tggacgaact 2580
cgggccctcc tttacttggg aggcctgtgt ctgagggcat tgagcggggc atcagtgctg 2640
cctgatgctg cgcctggctt tctgggcggc ctgactctac ctggcttgtc tggagaagag 2700
gctgcccagt cctcctcctc ctcagctccg gggcttgggg tacaggccat tcgaaggagg 2760
tttaataaag gctttgattt catcttgaaa aaaaaaaaaa aaaaa 2805

<210> SEQ ID NO 12
<211> LENGTH: 2189
<212> TYPE: DNA
<213> ORGANISM: Mus musculus

<400> SEQUENCE: 12
gaagaccccg cagagagcac gttgttctcg gcctctcccg gagctaggcc agccatggcg 60
gcggtaaaga ccctaaatcc gaaggccgag gtggcccggg cccaggcagc gctggcggtg 120
aacatcagcg cggctcgggg cctgcaggat gttctgagga ccaacttggg gcctaagggc 180
accatgaaga tgcttgtatc tggtgctgga gacatcaaac ttactaaaga tggcaatgtg 240
ctgcttcatg aaatgcaaat tcaacaccca acagcctctt tgatagcaaa agtggctaca 300
gcccaggatg acataactgg cgatggcact acatccaatg tcctcatcat cggggagctg 360
ctcaaacagg cggacctgta catttctgaa ggtcttcacc caagaataat aactgaaggt 420
tttgaagcgg caaaagaaaa ggcactccaa tttctggaac aagtcaaagt aagcaaagag 480
atggacagag aaacactcat cgatgtggcc aggacatctc tgcggactaa agttcatgct 540
gaacttgcag atgtcttgac agaggctgta gtggactcca tcttggccat taggaaaaag 600
gacgagccca ttgacctctt catggttgag atcatggaga tgaagcataa atctgagaca 660
gatacaagct taatcagagg gcttgttttg gatcatggag ctcggcatcc tgatatgaag 720
aagagagtgg aaaatgccta catcctcacg tgcaacgtgt ccttagagta tgagaaaaca 780
gaagtgaatt ctgggttttt ttacaagagt gcagaagaga gagaaaaact agtaaaggct 840
gaaagaaaat tcattgaaga tagagttaaa aaaatcatag agctgaaaaa gaaagtctgt 900
ggtgactcag ataaaggatt tgtcgttatt aatcaaaagg ggattgaccc cttttcctta 960
gatgcccttg cgaaagaagg gatcgtagct ctgcgcagag ccaagaggag aaacatggag 1020
aggctgacac ttgcttgtgg tgggatagct ctgaattcct ttgatgacct gaatcctgac 1080
tgtttgggac atgcagggct tgtctatgag tatacactgg gtgaggagaa gttcaccttt 1140
attgagaagt gtaacaatcc ccgttctgtc actttactgg ttaaaggacc aaataagcac 1200
acactgactc aaatcaagga tgcaataaga gatggcttga gggctgtcaa aaatgctatt 1260
gatgatggct gtgttgtccc aggtgcgggt gcagtagaag tggcactggc agaagctctg 1320
attaaataca agcccagtgt gaagggcagg gcgcagcttg gagtccaggc atttgcagat 1380
gccttgctca tcattcccaa ggttcttgcg caaaactctg gttttgacct tcaggaaaca 1440
ttagttaaag ttcaagctga acattcagaa tcgggccagc tcgtaggtgt ggatctgagc 1500
acaggtgagc cgatggtggc cgcagagatg ggtgtgtggg ataactactg tgtgaagaag 1560
cagctgctac actcctgtac tgtgatcgcc accaacattc tcctggtcga cgagatcatg 1620
cgagctggga tgtcctctct gaagggttga ggcctgcctg tgatactaca ggatgttggg 1680
gggaatggtt atttttgtcc aagcttcaag tgatttggaa aaaaattttc tcttcctgat 1740
tggagaaaag aaacgggaca tttgacacct attcaaatta tactgtaaaa ttttatttta 1800
tttttgcctt gagtatctga agacactcaa agcagctctt tttcaaccca ctgaacaaga 1860
tgttttagct acaccgatac aaaaattaca taataagata agcatgttgt ctacccttgt 1920
tccataagtg ttctttgaaa gtttgtaatg gttttctcct aaataaggca tggtgacaca 1980
tgcctgtaag cctagccctt tggaaatagt ccggaatttc tatgccaact caggctacag 2040
gagaccccag gtcgaaagaa taatttgttg tggatgtatt tgaaattatc cagccaactc 2100
cctgttaaac atgtaagatc cttgccagtg taaaacacat ctgggtaatt tatgggttgc 2160
ataatgtcta ataaatactt aaaagagtg 2189

<210> SEQ ID NO 13
<211> LENGTH: 2232
<212> TYPE: DNA
<213> ORGANISM: Mus musculus

<400> SEQUENCE: 13
caacctcctc cagtggccag tttgtgcgcc ctgggactta ctacagctgg gcatggcaga 60
ctctgcacag gtgccaacac tggtatacct ggtcacaggt ggctgcggct tcctggggga 120
acatattgtt cggatgctgc tggaacggga gcccaggctc cgggagctgc gtgtctttga 180
cctgcacctg agttcttggc tggaggagct gaaagcaggg cctgtgcagg tgactgccat 240
ccagggggat gtgactcagg cccatgaggt ggcagcagcc atgtctggat cacatgtggt 300
catccataca gctgggttgg tggatgtgtt tgggaaggcc agtccaaaga ccatccacaa 360
agtcaacgtg cagggcacac agaatgtgat tgatgcttgt gtgcagactg gcactcagta 420
cctggtctac acgagcagca tggaagtggt ggggcctaac atcaagggcc accccttcta 480
caggtgagct cagccccact taatcttaga gcccatttcc ctccagcact cagtcttctt 540
tctcccctct ccaggggcaa tgaagatacc ccatatgagg cagtccacag ccatccctac 600
ccatgcagta aagcccttgc tgagcagctg gtcctcgagg ccaatggaag gaaggtcaat 660
ggagggctac ccctggtgac atgtgccctt cgacccacgg gcatttatgg tgaaggtcat 720
caggtcatga gagacttcta ctaccaggga ctgcgctttg gaggtcgtct atttcgggcc 780
gtcccagctt ctgtggagca cggtcgggtc tatgttggta aggacaggga cagcagggct 840
cgaggagtgg ctctgatggt ggcagagtca cgcgtgtacg cctggctcca cgcgagctca 900
ggcagacagt ggcatgtggg cattttctgc atgagttgaa aaacggggaa agcatccaag 960
cagttgggag ggctgacata agaacatggc gtaggttatg atgagcaaca ggagcgacag 1020
ctctccagag aaagggagaa agcatctaca cgggatccaa gtagctgcag gatgcccagg 1080
agggctggtg gctacggggc cttggagaag ggcaactttg attaatcaga cagtagagag 1140
gtgtgggcaa gatctacacg gggccaaggc cagcttctct ccctccctcc ctccctgctg 1200
gcaggcaatg ttgcttggat gcacatactg gtggcccggg agctggagca gcgggcagca 1260
ctcatgggtg gccaggtgta tttctgctat gataagtcac cttataaaag ctacgaggac 1320
ttcaacatgg agtttctgag tccctgtggt cttcgactga taggcgccca cccactgctg 1380

-continued

```
ccctactggc tgctagtgct gctggctacc ctcaatgccc tgctgcagtg gctgctccgc   1440

ccactggtgc tgtacacacc cctgctgaat ccctacacgc tggctatggc caacaccacc   1500

tttactgtca gtaccaacaa ggcacagcgg cattttggct acaagcccct cttctcatgg   1560

gaagagagca ggacccgcac cattcagtgg gtgcaggcga tggagggttc agctcggtga   1620

tggcagggcc aggaactgga gaccactgtg gcacatactc caggtcctga gcccccaaat   1680

ctggatgaag agaaatggct gccttttgaa gatgaagact ctgctctaca catcatgact   1740

ccgtgatgtg gaccctgcca catcttaact acacagatcc tgagactggt tcatattcca   1800

gtctcctagt tctaggatag ggtttgggga aaggcctatc tttggtgcca actcaggcct   1860

gccaggtagt tggcaaaact gatttcttga atggtctcac tacctcttcc tgtttccagt   1920

ttctcaagca gggaggaaca gagactccag agatcttacg ctggtctgct tacttcagct   1980

accattttca gacctggctc ctgccacatc tggctctcct taaggggtta tagtttcacc   2040

attttttaag tgtatctctt ttagacattt atcttttaat ttgctttaaa gaaatctgaa   2100

gaaatcaatg atttcccatg tcttgcctct cctaacaaat tcacctatga cattgttagc   2160

ttcctcccct aggatgccaa cctgtatctg gccaagccta gaataaaatc cttttccaaa   2220

aaaaaaaaaa aa                                                        2232
```

<210> SEQ ID NO 14
<211> LENGTH: 1717
<212> TYPE: DNA
<213> ORGANISM: Mus musculus

<400> SEQUENCE: 14

```
ccaagatggc ggcgacagca gccgtgtctg gtgtcctcgg ccgcttgggc tggaggctcc     60

tgcagctgcg gtgcctgccc gtggcccgct gccgaccagc tctggtgcca cgtgccttcc    120

acactgccgt ggggttccgg tcttcagaag agcagaagca gcagcctccc cactcttctt    180

ctcagcagca ttctgagaca caggggcccg agttttcccg tccacccccc aggtacacag    240

accagagtgg agaggaggaa gaggactatg agagtgagga gcagctacag caccgcatct    300

tgacagcagc cctagagttt gtgcctgccc atggctggac tgcagaggcc attgccgaag    360

gagcccagtc cttgggtctc tccagcgcag cagccagcat gtttgggagc gatggcagtg    420

agctgattct tcactttgtg acccagtgca atgctcgcct caaccaggtg ctggaagagg    480

agcagaagct ggtgcaactg ggccaggcag agaagaggaa gacagaccag ttcctgaggg    540

atgcagtgga aaccagactg agaatgctga tcccctacat tgagcactgg ccccgggccc    600

tcagcatcct cctgctccct cacaacatcc cacccagcct gaacttgctc accagcatgg    660

tggatgacat gtggcattac gctggggacc agtccactga ctttaactgg tacacccgcc    720

gtgcagtgct ggctggcatc tacaacacaa cagagctggt gatgatgcag gattcctccc    780

cagactttga agatacttgg cgcttcctgg aaaaccggat taatgatgca atgaacatgg    840

gccacacggc taagcaggtg aagtccacgg gagaggcact ggtgcaagga ctgatgggtg    900

cagcggtcac gctcaagaac ctgacgggtc taaaccagcg tcggtgagag aagggaaccc    960

gtgtgctggg aggagcagca gtagatatga agggctttga caagatgtgc cacccattga   1020

acaggatgtt aatgagaaca cactgaagaa cttggagtcg tatgacagcc acaaggctgg   1080

aaatcacaat gcacttgctg ccgttctgac ctggaactgg gccacttctt cagttcctaa   1140

tgccaggcct ggcctcctga tgccttttgc attgcagctg tgtgtttgaa aactgaggct   1200

cacatccaag gtttcaaacc acaaaacctt ggcatgactc tgccatggtg tcacaggcat   1260
```

-continued

```
cttgatcatg tcttgaccat agaattgctc tctaggagct gggcatggtg acctacgtct   1320

gtattctcag cactcaggag actgctacag caagattgag agatcagagg caggcttgtc   1380

tttgtagaga attacaagcc tgcttgagct acagagtgtg atcctgtcaa aatcccctga   1440

gaaatattct taggggctca caaccaaggt ccggaggcaa cacatagtgg gagctcttcc   1500

ccagcacagg gcagacagtg ctcacaaaca tttgccactg gccattgcct ctggatcccc   1560

tcagaaagct gcctccccta ggcaggtgcc ttttggacag tcgtgctgag cctggcatca   1620

cagacaccag catgcacttc aggatcatta gtgtatttag aatctgtaaa aataataaat   1680

atgtttgaaa caaaaaaaaa aaaaaaaaaa aaaaaaa                            1717


<210> SEQ ID NO 15
<211> LENGTH: 4703
<212> TYPE: DNA
<213> ORGANISM: Mus musculus

<400> SEQUENCE: 15

ccgggcaggt ctagaattca gcggccgctg aattctatcc agcggtcggt gcctctgccc     60

gcgtgtgtgt cccgggtgcc gggggacctg tgtcagttag cgcttctgag atcacacagc    120

tgcctagggg ccgtgtgatg cccagggcaa ttcttggctt tgatttttat tattattact    180

attattttgc gttcagcttt cgggaaaccc tcgtgatgtt gtaggataaa ggaaatgaca    240

ctttgaggaa ctggagagaa catacacgcg tttgggtttg aagaggaaac cggtctccgc    300

ttccttagct tgctccctct ttgctgattt caagagctat ctcctatgag gtggagatat    360

tccagcaaga ataaaggtga agacagactg actgccagga cccaggagga aaacgttgat    420

cgttagagac ctttgcagaa gacaccacca ggaggaaaat tagagaggaa aaacacaaag    480

acataattat aggagatccc acaaacctag cccgggagag agcctctctg tcaaaaatgg    540

atatgtttcc tcttacctgg gttttcttag ctctgtactt ttcaggacac gaagtgagaa    600

gccagcaaga tccaccctgc ggaggtcggc cgaattccaa agatgctggc tacatcactt    660

ccccaggcta cccccaggac tatccctccc accagaactg tgagtggatt gtctacgccc    720

ccgaacccaa ccagaagatt gttctcaact tcaaccctca ctttgaaatc gagaaacacg    780

actgcaagta tgacttcatt gagattcggg atggggacag tgagtcagct gacctcctgg    840

gcaagcactg tgggaacatc gccccgccca ccatcatctc ctcaggctcc gtgttataca    900

tcaagttcac ctcagactac gcccggcagg gggcaggttt ctctctacgc tatgagatct    960

tcaaaacagg ctctgaagat tgttccaaga actttacaag ccccaatggg accattgaat   1020

ctccagggtt tccagagaag tatccacaca atctggactg taccttcacc atcctggcca   1080

aacccaggat ggagatcatc ctacagttcc tgacctttga cctggagcat gaccctctac   1140

aagtggggga aggagactgt aaatatgact ggctggacat ctgggatggc attccacatg   1200

ttggacctct gattggcaag tactgtggga cgaaaacacc ctccaaactc cgctcgtcca   1260

cggggatcct ctccttgacc tttcacacgg acatggcagt ggccaaggat ggcttctccg   1320

cacgttacta tttgatccac caggagccac ctgagaattt tcagtgcaat gtccctttgg   1380

gaatggagtc tggccggatt gctaatgaac agatcagtgc ctcctccacc ttctctgatg   1440

ggaggtggac tcctcaacag agccggctcc atggtgatga caatggctgg acacccaatt   1500

tggattccaa caaggagtat ctccaggtgg acctgcgctt cctaaccatg ctcacagcca   1560

ttgcaacaca gggagccatt tccagggaaa cccagaaagg ctactacgtc aaatcgtaca   1620

agctggaagt cagcacaaat ggtgaagatt ggatggtcta ccggcatggc aaaaaccaca   1680
```

```
agatattcca agcgaacaat gatgcgaccg aggtggtgct aaacaagctc cacatgccac   1740
tgctgactcg gttcatcagg atccgcccgc agacgtggca tttgggcatt gcccttcgcc   1800
tggagctctt tggctgccgg gtcacagatg caccctgctc caacatgctg ggatgctct    1860
cgggcctcat tgctgatacc cagatctctg cctcctccac ccgagagtac ctctggagcc   1920
ccagtgctgc ccgcctggtt agtagccgct ctggctggtt tcctcggaac cctcaagccc   1980
agccaggtga agaatggctt caggtagacc tggggacacc caagacagtg aaaggggtca   2040
tcatccaggg agcccgagga ggagacagca tcactgccgt ggaagccagg gcgtttgtac   2100
gcaagttcaa agtctcctac agcctaaatg gcaaggactg ggaatatatc caggacccca   2160
ggactcagca gacaaagctg tttgaaggga acatgcacta tgacacccct gacatccgaa   2220
ggttcgatcc tgttccagcg cagtatgtgc gggtgtaccc agagaggtgg tcgccagcag   2280
gcatcgggat gaggctggag gtgctgggct gtgactggac agactcaaag cccacagtgg   2340
agacgctggg acccaccgtg aagagtgaag agactaccac cccatatccc atggatgagg   2400
atgccaccga gtgtggggaa aactgcagct ttgaggatga caaagatttg caacttcctt   2460
caggattcaa ctgcaacttt gattttccgg aagagacctg tggttgggtg tacgaccatg   2520
ccaagtggct ccggagcacg tggatcagca gcgctaaccc caatgacaga acatttccag   2580
atgacaagaa cttcttgaaa ctgcagagtg atggccgacg agagggccag tacgggcggc   2640
tcatcagccc accggtgcac ctgccccgaa gccctgtgtg catggagttc cagtaccaag   2700
ccatgggcgg ccacggggtg gcactgcagg tggttcggga agccagccag gaaagcaaac   2760
tcctttgggt catccgtgag gaccaggcca gcgagtggaa gcacgggcgc attatcctgc   2820
ccagctatga catggagtat cagatcgtgt tcgagggagt gatagggaag ggacgatcgg   2880
gagagatttc cggcgatgac attcggataa gcactgatgt cccactggag aactgcatgg   2940
aacccatatc agcttttgca ggtgaggatt ttaaagatga atatgaagga gattggagca   3000
actcttcttc ctctacctca ggggctggtg acccctcatc tggcaaagaa aagagctggc   3060
tgtacaccct agatcccatt ctgatcacca tcatcgccat gagctcgctg gggtcctgc    3120
tgggggccac ctgtgcgggc ctcctccttt actgcacctg ctcctattcg ggtctgagtt   3180
cgaggagctg caccacactg gagaactaca actttgagct ctacgatggc ctcaagcaca   3240
aggtcaagat caatcatcag aagtgctgct cggaggcatg accgattgtg tctggatcgc   3300
ttctggcgtt tcattccagt gagaggggct agcgaagatt acagttttgt tttgttttgt   3360
tttgttttcc ctttggaaac tgaatgccat aatctggatc aaagtgttcc agaatactga   3420
aggtatggac aggacagaca ggccagtcta gggagaaagg gagatgcagc tgtgaagggg   3480
atcgttgccc accaggactg tggtggccaa gtgaatgcag gaaccgggcc cggaattccg   3540
gctctcggct aaaatctcag ctgcctctgg aaaggctcaa ccatactcag tgccaactca   3600
gactctgttg ctgtggtgtc aacatggatg gatcatctgt accttgtatt tttagcagaa   3660
ttcatgctca gatttctttg ttctgaatcc ttgctttgtg ctagacacaa agcatacatg   3720
tccttctaaa attaatatga tcactataat ctcctgtgtg cagaattcag aaatagacct   3780
ttgaaaccat ttgcattgtg agtgcagatc catgactggg gctagtgcag caatgaaaca   3840
gaattccaga aacagtgtgt tctttttatt atgggaaaat acagataaaa atggccactg   3900
atgaacatga aagttagcac tttcccaaca cagtgtacac ttgcaacctt gttttggatt   3960
tctcatacac caagactgtg aaacacaaat ttcaagaatg tgttcaaatg tgtgtgtgtg   4020
tgtgtgtgtg tgtgtgtgtg tgtgtgtatg tgtgtgtgtg tgtgtgtgct tgtgtgtttc   4080
```

```
tgtcagtggt atgagtgata tgtatgcatg tgtgtatgta tatgtatgta tgtatgtatg   4140

tatgtacgta catatgtatg tatgtatgta tgtatgtatg tatgtatatg tgtgtgtgtg   4200

tttgtgtgtg tgtgtgtttg tgtgtgtgtg tgtggtaagt gtggtatgtg tgtatgcatt   4260

tgtctatatg tgtatctgtg tgtctatgtg tttctgtcag tggaatgagt ggcatgtgtg   4320

catgtgtatg tatgtggata tgtgtgttgt gtttatgtgc ttgtgtataa gaggtaagtg   4380

tggtgtgtgt gcatgtgtct ctgtgtgtgt ttgtctgtgt acctctttgt ataagtacct   4440

gtgtttgtat gtgggaatat gtatattgag gcattgctgt gttagtatgt ttatagaaaa   4500

gaagacagtc tgagatgtct tcctcaatac ctctccactt atatcttgga tagacaaaag   4560

taatgacaaa aaattgctgg tgtgtatatg gaaaaggggg acacatatcc atggatggta   4620

gaagtgtaaa ctgtgcagtc actgtggaca tcaatatgca ggttcttcac aaatgtagat   4680

ataaagctac tatagttata ccc                                           4703
```

<210> SEQ ID NO 16
<211> LENGTH: 2382
<212> TYPE: DNA
<213> ORGANISM: Mus musculus

<400> SEQUENCE: 16

```
ggggagcgcg gcgcagagca ggggcccggc cgaggcagcg ctgcgcgggc caccatggcc     60

acggacgagt tggccagcaa gctgagccgg aggctgcaga tggagggcga aggcggcgag    120

gcgacggagc agccggggct caacggggcg gcggcggcgg cggcggccga ggctcccgac    180

gagactgccc aggcgttggg cagcgcggac gacgagctga gcgccaagct gctgcggcgc    240

gcggacctca accagggcat cggcgagcca cagtcgccca gccgccgcgt cttcaacccc    300

tacaccgagt tcaaggagtt ctccaggaag cagatcaaag acatggagaa gatgttcaag    360

cagtatgatg ccggcaggga tggcttcatc gacctgatgg agctgaaact catgatggag    420

aagctggggg ccccccagac acacttgggc ctcaagagta tgatccagga ggtggacgag    480

gatttcgaca gcaaactcag cttccgggag ttccttctga tcttccgcaa ggcagcagca    540

ggggagttgc aggaagacag cggcttgcac gtcctggccc gcctgtccga gatcgatgtc    600

tccacagagg gcgttaaggg tgccaagaac ttcttcgagg ccaaggtaca ggccatcaac    660

gtgtccagcc gctttgagga agagatcaaa gctgagcaag aggaaaggaa gaagcaggct    720

gaggaggtga agcagcggaa agcggccttt aaggagctgc agtccacgtt caagtagcca    780

gagccaaggc cgagacctgg ccctgccccg tgtgcggtct gggggcacgg gtgggtacag    840

gggatctgtg ggagactagc tcccaggtcc tgctctctgt gcccggacca ctactaaaaa    900

ccgcaaacga tatgtgaccc gatctcattc aggagtctcc tcggtggttg gtccctgccc    960

tgccctctcc tgcggttcat gcggctgtga tgccagccag cagcatcctc tctggccatc   1020

cctacgtgtc ttgttctctg gccaccttgc tgcctgctct agcccaactt cagcccattc   1080

acgcccctgc ctttggtacc agctactttc tccacccacc caactcccct taactatagg   1140

ccgccctgcc atggtccagc agagagtgag accctcccca ggacgcttcc tttcagatca   1200

ggccccatct ctgatggaag tggagagact cttctattag tgaggagatc cggggactcc   1260

tacattagtg aggagatcca ggccctagca ctctaagctg atttcaatgg ggcccagcca   1320

ggcagggtga aggccactgt gcgaatctac ctcacaggct acactctgcc aggcatgcct   1380

tggggatgtg agtgataggg ttccgagggg aggggcagaa atgtcaccct ctgacagcct   1440

acccccgcag caagctgagg gtcccaaggg gctgtggaga gaggggtggg gtccctaagg   1500
```

```
gattggcctt ttcagggtgg acctcagcac tctgccttga ctccccaagg agtgcctgac   1560

gtgtttatgt tcactggcag taggactcgg ggccggcacc cctttcacac tctccttcct   1620

tgggtttgtc acccgtgatg gcaccagcct gtcgtgccca cccgtagact cgcatgggga   1680

ctccccaggc cacagtgaaa cccgtgccgt tcctctatag ctccatgtgc ttgctcacgt   1740

gtgtgtatgt gcgtgtccgt tgctgtgttg tgaaactgtg acgtcaccca gtctaagtga   1800

atggccaccg gggccaccgt tatgcaatgt tcagcgtgtc actgcttgtg aagctcgata   1860

actctttatt ttactacaat gtccccagag tccctgggac ccctgtggga cttgcaaagg   1920

ttttattttt tcggtcttag aacctatgag aatcggaggg gccgagccaa gcccagccca   1980

gcccagctgc cgtggccttg gcttgcgttt gcctcagcgg atatgtttat acagatgaat   2040

ataaattctc tttacttttg gctgtttgca ttttattttt ggttcccccct ctcagtacct  2100

cccaaaaaaa gaaaaaaaga aaaaaactac ttcttcattc ggtggtacga ttattttttt   2160

taactaaaat gagataaaat tctatattct tatgtgtgtg tggtttttga tgactaacta   2220

gaaacaaagg tggacaggat caggatgagg tcgctggatc tgggccgtca catcaggagc   2280

ctggggagga aggcactcct gctggagagc tctgtccctt agcatctaca aacactcctg   2340

atctaagcac tacctgtatt aaactcattt catccttaaa gg                      2382
```

<210> SEQ ID NO 17
<211> LENGTH: 1072
<212> TYPE: DNA
<213> ORGANISM: Mus musculus

<400> SEQUENCE: 17

```
cccacgcgtc cggccagcag cagagtcaga aagaaggcgg ctgctgtctg aggtggcctt     60

gggtggcttc tgagcgttcc tgtccctcgc ccgctacctt ccttgggttc ccaccatgcc    120

gatgtaccag gaaacatccg agccttcttt gcaagccctt gaatctcgcc aagatgatat    180

tttaaaacgc ttgtatgagt tgaaggcagc agtcgatggc ctttcaaaga tgattcacac    240

cccagatgca gacttggacg taaccaacat cctgcaagct gatgagccca caactttagc    300

cacaaacaca ttggacttga attccgtgct tggaaaggac tatggggcgc tgaaagacat    360

tgtgatcaac gcaaacccag cctccccacc actgtccctg cttgtgctgc acaggctgct    420

ctgtgaacgc tacagggtcc tgtccactgt gcacacacat tcgtctgtca agaatgtgcc    480

cgagaatctt gtcaagtgct tcggggagca ggctaggaag cagtcccgcc acgagtatca    540

gctgggcttc actctgattt ggaagaatgt gcccaagaca cagatgaagt tcagtgtaca    600

aaccatgtgc cccattgaag gagaagggaa catcgcacgt ttcctgttct ctctgtttgg    660

ccagaagcat aatgctgtca ccctcaccct catcgatagc tgggtggata tcgccatgtt    720

tcagcttcga gaaggcagca gtaaagaaaa agcggccgtg ttccgctcta tgaactccgc    780

tttggggagg agcccgtggc tggttggaaa tgagctcact gtggcagatg tggtgctgtg    840

gtctgtgctc cagcagactg gggcagcag tggggcagca cccaccaatg tgcagcggtg     900

gcttaagtcc tgtgaaaacc tggccccctt cagcactgcc cttcagctcc ttaagtgaat    960

tcgagcagct tgtcttgcag ggttcaacag aagaatggta cggcttccag tctgttgtca   1020

gaaagggact tgtccaataa agtaccatat catctaaaaa aaaaaaaaaa aa           1072
```

<210> SEQ ID NO 18
<211> LENGTH: 5400
<212> TYPE: DNA
<213> ORGANISM: Mus musculus

<400> SEQUENCE: 18

```
ttcggagagg gccgctataa aggcttgttt tgctcagggt ccgatgttcg cgagcgtgcc     60
cgggctgttt gctctcgtgt ggggaggctg gggtgcagaa tttctgaagt gaaaggagga    120
gtctgcaccc tggtcctctg tgtggtgaag atgaaagata ttgacatggg aaaagaatat    180
atcatcccca gccctgggta cagaagtgac agggacagaa gcgctgtacc agggcaacac    240
agagaccccg aggaacccag gttccggaga acaagatcgt tggaatgcca agatgctctc    300
gaaacagcag cccgagttga ggggctttcc ctggatatct ctgtgcattc tcatctccaa    360
attctggacg aggagcattc taagggaaaa taccaccatg gtttaagtgt cctgaagccc    420
ttccggacca ctaccaagca ccagcaccca gtggacaatg ctggactttt ctcctacatg    480
accttttcat ggctctctcc tctggcccga gtggttcaca agaaggggga gctgttaatg    540
gaggatgtgt ggcctttgtc caagtatgag tcttctgatg tgaactgcag aagactagag    600
agactgtggc aagaagagct gaatgaagtt gggccagacg ctgcttccct gcgaagggtt    660
gtgtggatct tctgccgcac caggctcatc ctgtccatcg tgtgcctgat gatcacgcag    720
ctggctggct tcagtggacc agccttcatg gtgaaacacc tcttggagta tacccaggca    780
acagagtcta acctgcagtg cagcttgttg ttagtgctgg gcctcctcct gacggaaatc    840
gtgcggtctt ggtcgcttgc actgacttgg gcattgaatt accgaaccgg tgtccgcttg    900
cggggggcca tcctaaccat ggcatttaag aagatcctta agttaaagaa cattaaagag    960
aaatccctgg gtgagctcat caacatttgc tccaacgatg ggcagagaat gtttgaggca   1020
gcagccgttg gcagcctgct ggctggagga cctgttgttg ccatcttggg catgatttat   1080
aatgtaatca tcctaggacc cacgggcttc ctgggatcag cggtttttat cctcttttat   1140
ccagcaatga tgttcgtgtc acggctaact gcatatttca ggagaaagcg tgtagctgcc   1200
acagatgacc gtgtccagaa gatgaatgaa gttcttacct acattaaatt cattaaaatg   1260
tatgcctggg tcaaagcgtt ttctcagtgt gtgcaaaaaa tccgagagga ggaacgtcgg   1320
atattggaga aagccgggta ctttcagagc atcactgttg gagtggctcc tattgtggta   1380
gtgatcgcca gtgtggtgac gttctccgtt cacatgaccc tgggcttcca tctgactgcg   1440
gcacaggcct tcacagtggt gactgtcttc aattccatga cttttgcttt gaaagtaaca   1500
ccattctcag tgaagtccct ctctgaagca tcagtggctg ttgacagatt taagagtttg   1560
tttctaatgg aagaggttca catgataaag aacaaaccgg ccagtcctca catcaagata   1620
gagatgaaaa atgccacctt ggcatgggac tcctcccact ccagtataca gaactcgccc   1680
aagctgaccc ccaaaatgaa aaaagacaag agggctacca ggggcaagaa agagaagtcg   1740
aggcagctgc aacacactga gcaccaggcg gtgctggcag aacagaaagg acacctcctc   1800
ctggacagcg acgagcggcc cagcccggaa gaggaagaag gcaagcagat ccacacaggg   1860
agcctgcgcc tgcagaggac actgtacaac attgacttag aaattgaaga gggcaaactg   1920
gttggaatct gcggcagtgt gggaagtgga aaaacctctc tcgtttcagc cattttaggc   1980
cagatgacgc ttttggaggg cagcattgcc gtcagtggga cctttgctta tgtggcccaa   2040
caggcctgga ttctcaatgc cactctgaga gacaacattc tctttgggaa ggaatttgat   2100
gaagagagat acaactcagt gctgaatagc tgctgcctgc ggcctgactt ggccattctc   2160
cccaacagcg acctgactga gattggagag cgaggagcca acctgagtgg tggacagcgc   2220
cagagaatca gccttgctag agccttgtac agtgatagaa gcatctacat cctggatgac   2280
cccctcagtg ccttagatgc ccatgtgggc aaccacatct tcaacagtgc tatccggaag   2340
```

-continued

```
cgcctcaagt ctaagacggt tctgtttgtt acacaccagt tacagtatct ggtcgattgt   2400
gatgaggtga tcttcatgaa ggaaggctgt atcacagaga gaggtaccca tgaggagctg   2460
atgaacttaa atggggatta cgctacgatt tttaataacc tgttgctggg agagacaccc   2520
ccagttgaga ttaattcgaa aaaggaagct actggttcac aaaaatcaca agacaagggc   2580
cctaagccag ggtcagtgaa gaaggagaag gcggtgaagt cggaggaagg gcagcttgtg   2640
caggtggagg agaaagggca aggttctgtg ccttggtcag tctactgggt ctacatccag   2700
gctgcagggg gccccttggc tttcctggtc atcatggtcc tcttcatgct gaatgtgggc   2760
agcactgcct tcagcacctg gtggcttagc tactggatca agcaaggaag cgggaacagc   2820
acagtgtatc aagggaacag aagcttcgtg agtgacagca tgaaggacaa ccccttcatg   2880
cagtactacg ccagcatcta cgccctctcc atggcagtca tgctgatctt gaaagccatt   2940
cgaggagttg tcttcgtcaa gggcacactg agagcctcct cccggctcca tgatgagcta   3000
ttccgaagga tccttaggag ccccatgaag ttttttgata ctaccccaac aggaaggatt   3060
ctcaacaggt tttccaaaga catggatgaa gtggatgtgc ggctgccgtt ccaggctgag   3120
atgtttattc agaatgtaat cctggtgttc ttctgtgttg gaatgattgc tggagtcttc   3180
ccatggttcc tcgtggcggt ggggcctctc ctcatcctct tctcacttct ccacattgtc   3240
tccagggtcc tgattcgtga gctaaagcgg ttggacaata tcacgcagtc tcctttcctc   3300
tcccacatca cgtctagcat tcagggcctg gccaccatcc atgcctacaa caaaaggcag   3360
gagtttttac acaggtatca ggagctcctg gatgacaacc aggctccctt tttcctgttc   3420
acctgtgcaa tgaggtggct gccagtgcgg ctggacatca tcagcattgc cttgattacc   3480
agcactggcc tgatgattgt ctcaggcatg gccagatccc tttcagccta tgcggggctt   3540
gccatttcct acgctgtgca gttaattgga ctattccagt tcaccgtcag actggcatcg   3600
gagacagaag cacggttcac ttccgtggag aggatcaacc actatatcaa gactctctct   3660
ttggaagcac ctgccagaat caagaacaag gctcctcccc atgactggcc ccaggaggga   3720
gaagtaacct ttgagaatgc agaaatgaga taccgggaaa atctccctct ggtccttaag   3780
aaagtgtcct tcaccatcaa gcccaaggaa aagataggca ttgtgggacg aacagggtca   3840
gggaagtcct ctttggggat ggccctcttc cgtctggtgg agctatctgg aggctgcatc   3900
aagattgatg gaataagaat cagtgacatc ggcctggccg acctccgaag caaactggcc   3960
atcattcctc aggagccagt gctgttcagt ggcactgtca gatcaaacct ggaccctttc   4020
aaccagtaca cggaagacca gatctgggat gctctagaga gaacgcacat gaaggaatgt   4080
attgcccagc tacctctgaa acttgagtct gaagtaatgg agaacgggga caacttctct   4140
gttggggaac ggcagctgtt gtgcatagca agagccctgc tgcgtcactg taagattctg   4200
attttagatg aagctacagc cgctatggac acagagacag acttactgat ccaggagacc   4260
atccgggaag catttgcgga ctgcaccatg ctgaccattg cccatcgcct gcacacagtt   4320
ctgggctctg acaggatcat ggtgctggcc cagggacagg tggtggagtt tgacacccca   4380
tcggtccttc tgtctaatga cagttcaaga ttctatgcca tgtttgctgc tgcagagaac   4440
aaggtggctg tcaagggctg agtcctcccg tcctcgaagt ctcttcctca gagcattgcc   4500
attctcttcc tggtttgggc ccctcatcct gtcctgctga aacttcgcct ttcccagttt   4560
tatctctcac acaaccattc aggattagct gtgtgtttca cttttaagga aagtcatatt   4620
ttgattattg tatttattcc ctattcactt aaatgaaatt tagtttttgt tcttaattgc   4680
actcttaaga ggttcaggga accattacta taaatgttat cagtggccta taatgaagct   4740
```

ttatatgtgt agctatgtct atatataatt ctgtacatag cctatattta cagtaaaatg 4800
taagcggccc ggaattctca gggctcctgc tttcctgtct tggtgtcagc tgctgtttat 4860
gttagagcag tgggcaaagc cagcccccac ccagtctgct cccagtgttc catgcttcag 4920
gttcctgagg ctggtcgcca cagagttgtc gagttccctg gccagctggt tcccagcccc 4980
agggtccact gctgctgttg taggtggcat tttcatttgc ctgaccccaa ggctccagag 5040
ctcagcaaca gggctcagga tggtggggtc cgttcttcct cactttagtc tcctctgcaa 5100
agtctgcacc cacccctcag cagctcttgc taatcagtgt ctcacactgg tgtagaagtt 5160
ttttgtactg taaagagacc tacctcaggt tgctgattgc tgtgtggttt ggtgcgctct 5220
tgcagacccc cttgtgctct ggggctcgta gcttgggtgg gtgtggttgc cactgtcacc 5280
agtcgagtgg tcagcgtcgc atgtcgtgac caactagaca ttctgtcgcc ttagcatgtt 5340
tgctaaatac cttataaaag caaaaatatg aaaaagtgaa taaaattatt ttggatttgt 5400

<210> SEQ ID NO 19
<211> LENGTH: 1722
<212> TYPE: DNA
<213> ORGANISM: Mus musculus

<400> SEQUENCE: 19
ctggagagga gcgcgtcctg acgggactac gtttcccggc atgcgctgaa cagctaccgt 60
cgtgccctgc ttctcctaga ccgcttgccg ggttctagag gaccgcctct gagtagggcg 120
ggcgaggaga gtcgaggcgg agctgatggc tgcgctgaaa gcggggcggg gtgcaaactg 180
gagccttcgg gcatggcggg ctttgggggg catcttctgg aggaagcctc ccctgttagc 240
tcctgacctc cgggctctgc tgacgtcagg aactcctgac tctcagatct ggatgactta 300
tgggaccccc agtctcccgg cccaggtgcc tgaggggttc cttgcatcac gggcagatct 360
gacgtctagg accccggatc tctgggcacg attgaatgtg gggacttcag gctccagtga 420
ccaggaggcc cgcaggagcc ctggaagccg tcggcgcgaa tggctggcgg tggcggtggg 480
cgcaggaggt gcagtggtgc tgctgttgtg gggttggggt cggggtcttt ccacggtgct 540
ggctgctgtt cctgctccgc cacccacttc tccccggagc cagtacaatt tcatcgcaga 600
tgtggtggag aagacagccc ctgctgtggt ctatatcgag atcctagacc ggcacccttt 660
ctccggccgt gaagtcccca tctcaaacgg atcaggattc gtagtggctt cagatgggct 720
catcgttacc aacgcccacg tggtggctga tcggcgccga gtacgagtga ggctgcctag 780
cggggatact tatgaggcca tggtcacagc tgtggatccc gtagcagaca ttgccacact 840
gaggattcaa accaaggagc ctcctcccac actgcccctc ggccgctctg ctgatgtccg 900
gcaaggggag tttgttgttg ccatgggaag cccctttgca ctgcagaaca cgatcacatc 960
tggtattgtc agctctgctc agcgcccagc cagggacctg ggactccctc aaaacaacgt 1020
ggaatacatt cagaccgatg cagctattga ttttggaaat tctggtggtc ccctggttaa 1080
cctggatggg gaggtgattg gagtgaacac catgaaggtg acagctggaa tctcctttgc 1140
catcccttct gatcgcctta gggagtttct gcatcgcggg gaaaagaaaa attcctggtt 1200
tggaaccagt gggtcccagc gccgctacat tggagtgatg atgctgaccc tgactcccag 1260
catccttatt gaactacagc tccgtgagcc aagcttccct gatgttcagc atggtgtcct 1320
cattcataaa gttatcctgg gctcccccgc acacagggct ggtctgcggc ctggtgatgt 1380
gatcttggcc attggggaga aattggcaca aaatgctgaa gatgtttatg aagctgttcg 1440
aacccaatca cagctggcag tgcggatccg gcgcggatca gagacactga tcttatatgt 1500
gacccccgag gtcacagaat gaatgactgg accggcaaga gtgtgaagct cttgccctga 1560
tctcctcctt gctttcctag cctaggttct gagtgcatgt gggtagagga ggagtcagtg 1620
aacctgcgga gggcaagtcc ctctaaccgc tgcatcagtc ctgggctccg aagaacacat 1680
tttatataaa ataaaattat acctagcaaa aaaaaaaaaa aa 1722

<210> SEQ ID NO 20
<211> LENGTH: 1255
<212> TYPE: DNA
<213> ORGANISM: Mus musculus

<400> SEQUENCE: 20
ggaattccta gcatgttggg tgttatgtag tcaaaggagg gcattatgag ctgtacccca 60
gggacttcct gatcctctta catgtataaa tagcaagacc gggccaggaa cagcaagcag 120
tctgaaggcc agctgggtct gcccactaag aagatgaagc cttttcatac tgccctctcc 180
ttcctcattc ttacaactgc tcttggaatc tgggcccaga tcacacatgc aacagagaca 240
aaagaagtcc agagcagtct gaaggcacag caagggcttg aaattgaaat gtttcacatg 300
ggctttcaag actcttcaga ttgctgcctg tcctataact cacggattca gtgttcaaga 360
tttataggtt attttcccac cagtggtggg tgtaccaggc cgggcatcat ctttatcagc 420
aagagggggt tccaggtctg tgccaacccc agtgatcgga gagttcagag atgcattgaa 480
agattggagc aaaactcaca accacggacc tacaaacaat aacatttgct tgaagagaag 540
ggtgtgaact gccagctact ttctttggtc ttccccagtg accacctaag tggctctaag 600
tgtttatttt tataggtata taaacatttt ttttttctgt tccactttaa agtggcatat 660
ctggctttgt cacagagggg aacttgtctg tgccaacccc agtcatctga aaactcagat 720
gcctggaagg tctgaagctg acctcaatga ctacacataa tatttgattg agataaatgg 780
gcaaggtctg gagagatggc ttggtggtta agagcactgc tgctcaacca gaggacctgg 840
gttcaatttc cacttagatg gcagctcaaa ctatctataa ttccaattcc aaagaaaact 900
gattgcccta ttttgccctt tagttagtag tatttacagt attctttata aattcacctt 960
gacatgacca tcttgagcta cagccatcct aactgcctca gaatcactca agttcttgca 1020
ctttcggttt cccagcggat tttaagtgga taaactgtga gagtggtctg tgggactttg 1080
gaatgtgtct ggttctgata gtcacttatg gcaacccagg tacattcaac taggatgaaa 1140
taaattctgc cttagcccag tagtatgtct gtgtttgtaa ggacccagct gatttcccca 1200
ccacccctcc atctgtaagc cactaataaa gtgcatctat gcagccacaa aaaaa 1255

<210> SEQ ID NO 21
<211> LENGTH: 5825
<212> TYPE: DNA
<213> ORGANISM: Mus musculus

<400> SEQUENCE: 21
cccgagtgtc gctgcctcct gtctgccttg gttaggggac atcccgggag cgaaaagccc 60
agcccgtggc cgggccggtg gaccagcgag cgcgcagcag actgtgcgcg gccgcggcga 120
gggcggggaa gaaaaccacc ctgtttcctc tccggccccc accgcggatc atgtaccagg 180
attatcccgg gaactttgac acctcgtccc ggggcagcag cggctctcct gcgcacgccg 240
agtcctactc cagcggtggc ggcggccagc agaagttccg ggtagatatg cctggctcgg 300
gcagtgcctt catccccaca atcaacgcca tcaccaccag ccaggacctg cagtggatgg 360
tacagcccac agtgatcacc tccatgtcca atccctatcc acgctcacat ccctacagtc 420

-continued

```
ccctgccagg cctggcttca gtccctgggc acatggctct ccccagacct ggagtgatca    480
agaccatcgg taccaccgtg ggccgcagaa ggagagatga gcagctgtct cctgaggagg    540
aggagaagcg tcgaatccgg agggagagaa acaagctagc tgcagccaag tgtcggaacc    600
gtcgccggga gctgacagag aagctgcagg cggagaccga ggagctggaa gaggagaagt    660
ctgggctgca gaaagagatt gctgagctgc agaaggagaa ggagaagcta gagttcatgt    720
tggtggctca cggccccgtg tgcaaaatca gccccgagga acgccgatcg ccccccacct    780
ccgggctgca gtccttgcgc ggtacgggca gtgccgttgg ccccgtggtg gtgaagcagg    840
agcctcccga agaggacagc ccctcttcct cagcagggat ggacaagacc cagcgctctg    900
tcatcaagcc catcagcatc gccgggggtg gtttctacgg ggaagagcct ctgcacaccc    960
ccatcgtggt gacctccacg cctgccatca ctcccggcac ttcaaacctt gtcttcacct   1020
accccaatgt cctggagcag gagtcgcctt cgtcgccctc agagtcctgc tccaaggctc   1080
accgcagaag cagtagcagt ggggaccagt catcagactc cttgaactcc cccacacttc   1140
tagccctgta accctgtgct cctctggcca gctctggagg aatcctcatc catcattacc   1200
acacccttcc cagggaccag caccttaag cactccaggg ccttgaggga ataaggggcc    1260
cctggctctg gggacccacc cggtgggact tagtggtgag acactggttg atctcttaga   1320
agccctggga cacgccctcc ctcattcatc ttgcaagcga agcgaatcct ttttcttgag   1380
aagcctcaga gaacttggtt tgtggactca gacgcgcctg cggctacccc cacctcaccc   1440
caccccccc tcttctgaag ccccgccccc tggagctggc ccggatggtt tctgtccctt    1500
tgttatccgt tgtctctgaa gtggacagta tcctttcctg ccccgccaag catgctcagt   1560
gccttttggt ttcccctcct tcccctagat tcagttttgc tccctctggg tttttataag   1620
atttgccatg acatttcatc tgggtggtcc agatagtaaa gcgcttttat ttctggagct   1680
ggggaagcag atgactcttc cactggggcg gaaggggcac ccactgtgtc ccgaaggggc   1740
agtcaaagtg caatattatt gaaacttccc tccctacaca cccagtgcgc tgtggttaca   1800
gaccgtgggc tccctgagtt ctgccggtga gctgccgtca ctgggatgcg ccaaggacct   1860
ttcctccccg gtctcagaga tgcacatctc tttgaggatc ggcttggctg gaagacaggg   1920
tgtgagtgcg acaacagggg cacaggttgg gtttgccaaa cgtctaatta ccaagccagg   1980
atttgtgcca acaaagccac atggctgtcc tagtgagctt cctttcttac ctgtcttgag   2040
ctgggcgtct ctttaattac tgcctctgcc ccggaccctt ctctctagac ttgggaagca   2100
ctccttccta gaagccacac atcactccaa ggctcagctg ggcgctgctc atccccaact   2160
ctcatagtga catcacctgt ggatatttaa tgagtgtggg atgcggggtc tgcggtagag   2220
atggtttctg gcagccgcag cagccccagg tacctagcct cccctggctg ctctcctgtc   2280
agtgagatgc aggagccgcc ctctgctctc agtggtctct gctactgatg aatccagtgg   2340
gtttcctttc atattctcct ggccaactcc agagtggcct cctaacccag caggcccacc   2400
cctctgggag tcgttggtct ccaccagttt tgttaggctt tgagtgtcta ttcggttcct   2460
atcaaagcta gtgtgtattc ctttccacta cagaagaacc atcactctca tgggtgtccc   2520
agcctccagc aagggcacag ctctgtcccc tgcctttctc tccctttgtc cccactgcat   2580
gttgacacaa gtatggaagt ggagcctggt tagaacttgt ttctagtgct aatgctctga   2640
cctagtattt ccattggaga tcactgtcca gccatctaaa gccctgttat tcgagtcaag   2700
cttatcccca tttttgagag agaaggggta ccttcacaga ccgatgccct tcttacccca   2760
agttcccata aacacttgca tgcagaagca cacaggacac agggaccatg tgggaagcat   2820
```

```
gctcagccta gcagagctga aaggagcagg cttggcttgg tagagagggg ggcagaaagg   2880

agataatctc aatgtgttct ttcctgtatg ccttggctct aactctgctg ctctggtctc   2940

ccagagcctc taggggcagg ggagtgctcc acaaggtggt ttgctggctt cagagcccta   3000

gaagcacaag acagtggagc cagcggagcc gggactagag gagttgggca gtctcagttg   3060

agaagcttta tcgcctcaag ccaagtggga gctctctccc tcatgcctgt gggtatttct   3120

gaaatgaagc tgcgccctgt tctgtccttt cccaaagccc ccttctgccc atagcatgga   3180

tccaacccag gtcacaggcc tggacttgg taccctggtt ggacactcct gagactccaa   3240

gtctggcttt cagttcagtt ttcatctgtg ttgacatcgg ggccagaaag cacagccagc   3300

taaatgggcc tctgaggtca ccttcccttc cggcctgctt gctttgtctt acaagacttc   3360

ttggcttttc caaagacaga gatttctggg gggaagccga atatttctac ctaaactctg   3420

ggtgtgacct cagctcgctt tcctctgatc cactgtccaa gttgggtcac aaacatgtca   3480

ctcatgcatg cctgcactcc agagtcaggt gccaagcttg cttgtccttc cctgcctcca   3540

ggtcagggag cagctgcagt gagggtgggg aggtgagggc tttgtacacg tgtgtcctct   3600

gctgtcatga acttgggctg gactgtgagc agctctgggt taatacaggg caggcaatcc   3660

ttaaacagct agcatgaaac agttttgtcg tggccaccag gcttctgtgg gaacagtcct   3720

tctctggctg gctagctagg cacagctacg gcactggaaa gagtagagcc caggtgaagc   3780

ttaggaaatt gggagctaac accaagcaac tggttccgtg ggggaaggtt ttagggagct   3840

cagactgctg ctttcatagg caaagtgtgc ccatgggggc cagtcatggg aacatgtcaa   3900

agccaacagg aagcagaacc tgtagctttc tctggcatta gggagagaga accctgcttg   3960

cttccactta actcctggtg gaagaggggc aggcacgttc gaagcttctg gattcatttt   4020

tcctccactt tcctgagaga ccaaaagtgt tccttgagat gtcaccattt gtctttcaca   4080

gtgacttcct tccctgagca aacattcatg tggcttcgct ggggaggaaa aaaataagca   4140

cctactgtgt gccaggcact atgaggcact tttctattta tcctctttta agataggact   4200

aagagttcat ctccttctag aaggccccca ggttaaataa aaacacttgg gggtaagagg   4260

gctttcttca gagactccca ggtgggagtg cctctagtct ggtggtcctc aaagactcat   4320

ccacagcagc atctgcccat cccaggctcc tctctcctca gactcctcct atctggcttg   4380

tgctcctcag gtggctgaag gggccacctt agttctcata gaaattgtgg accaatagga   4440

tatgtgctgt gtataacttt ctttttaaac tgtaagtaaa gggtcttgca gctttgtgct   4500

tgtgttatct tagcatttat cttcaaacca gcatctcact atttattgac agtggtgtgt   4560

gtgtgtgtgt gtgtgtgttt ctgcgtgtgc acatatgtgt gcacacatgt gcgtgtgtgt   4620

gttcatgtgt gtgcatgctt gtgtctttcc acagcttttt tttttttttt taaggatcat   4680

cctactgcta agtccgtgtc tcttcttgct tctagtgttt tggccacgcc tcaccaaatg   4740

tctgtaatga cccagtactc acaacatgtt caggaggagc tgggtcagat tttgacagag   4800

ggtatgggaa gggaaagggg agaagaaatt gacatttatt ttattattta ttttaaatgt   4860

ttacatttct ttgtgttgtt ccaagcctga atagaaacag atagcattaa agtacttcct   4920

tcccactcct ttctctggct ctctctcccc cacttgttct gacttaggat aatgatctct   4980

attttgtttg tttctcaagt gacttgtgga cttgtgctgt ataaactgta ttaaaaaggc   5040

tctgttttta aagatcaatt gtcattcctg tggggacagt ggctactgag aaatctacat   5100

tgtaagagaa gacaatgaaa gaccctggcc ctgtctctca aaacttaact ttctctgtat   5160

gatttttttt ttaaaaaaat attccattta ttttactttg tggttacttg attttgagga   5220
```

agaaaatatt cagctttgta taaagactag gtatcagatt ccttttgcag tgggaggtgt 5280
atatatcgta ttttggtata gagtaggacc caagcttcat gcatctgtat ttggtatatg 5340
tcaatgacgt ggagtgaaat ttgctattag atcctggagg caaatgggtt gtacaaggtt 5400
ttatggctcc gcggggaatt taatttcctt tctgggcacc ttttgtcccc tacttttaaa 5460
ttaacggtga aacggcccta ggagggtcgc tctagttgaa ctctccaggc aggaccttat 5520
gctcagaaat ctttgtatag ttttaaattt ttgaggagta tctctgctcg gaagcatctg 5580
tggtggtgtg atgtgttgtt ctgtgtactg tatgtgacac aagcctacag gatttgcact 5640
aagaaaagct tggtaggagc ttgctgctat ggaggaaaga acatattaaa aacttatttt 5700
ccctcgggtt tgttctcgtt ttatgttttt gttgttgttg ttttgttagc tttcctactt 5760
ccactgagta gcattttgta gaataaaatt aatcaagaac aaaaaaaaaa aaaaaaaaaa 5820
aaaaa 5825

<210> SEQ ID NO 22
<211> LENGTH: 1045
<212> TYPE: DNA
<213> ORGANISM: Mus musculus

<400> SEQUENCE: 22
ggtttcaccc ggctgggcgc tgtggccgta gtggccctgg gtgtgcggcc ggcgcccgtg 60
acagcagcgt cgcggagccg gctaccccga cctggggcca ctgcggatct tggtggcaga 120
gcgacatcgc ctggcggaat gggaggcgag gcgggagcga atggtcctcg gggccgtgtc 180
aagagcttgg ggctagtgtt cgaagatgag agcaagggct gctactcaag cggcgagaca 240
gtggccgggc acgtgctgct ggaggcggca gagccggtgg ccctgcgcgg actgcgcctg 300
gaggcccagg gccgtgccac ctctgcctgg ggcccgagcg ctggggccag ggtctgcatc 360
ggtgggggct ctcccgcagc ctcctcagaa gtggaatact tgaacctgcg gttgagtctg 420
ctggaggccc cagctggtga aggtgtcacc ttgttacaac caggaaaaca cgagtttccc 480
tttcgctttc agcttcggtc tgaacctttg gcaacatcgt ttactgggaa gtatggcagt 540
attcagtact gtgtgagggc tgttttggaa cgaccccaag ttccagatca gagcgtcaga 600
cgagagctcc aggttgtcag tcacgtggat gtcaacacac cgcccttatt gactcctatg 660
ctgaagacgc aggagaaaat ggttggctgt tggcttttca cctctggtcc tgtgtcactg 720
agcgtcaaga tcgagagaaa gggctactgt aacggagaag ctatccctat ctatgcagaa 780
atagaaaatt gttcatctcg gctggttgtt cccaaggcag ccatattcca aacccagacg 840
tacttggcta gtggaaagac aaagacagtc cggcacatgg ttgccaatgt tcgaggaaac 900
cacattggtt ctgggagtac ggacacctgg aatgggaaga tgctgaagat cccacctgtc 960
accccatcca tcctggattg ctgcatcatc agagtggact actccttagc tgtaatccaa 1020
gcttcttgaa tcattaaaaa tacat 1045

<210> SEQ ID NO 23
<211> LENGTH: 1660
<212> TYPE: DNA
<213> ORGANISM: Mus musculus

<400> SEQUENCE: 23
gctccttcct catttcgctg ctgattctag ccccaaacaa aacaggttga gccttttttcc 60 tcctccggca gttgcctctg gcttgtggct gccttctgag cgtttcagac ggcgccggct 120
gggagtggga gggagggcct gggctagccg cgctgggact gggacgtgct cctggctcct 180

-continued

```
ggcccatgct cagccctgct tgaagcagga gtgctagcat ttgacacaac gcccttggag    240
gatgatggcc cagctgcagt tccgagatgc cttctggtgc agggacttca cggcccacac    300
agggtatgag gtgctactgc agaggctgct ggacggcagg aagatgtgca aggatgtgga    360
ggagctgctc agacagaggg cccaggcgga ggagaggtac gggaaggagc tggtgcagat    420
tgcacgcaag gctggtggcc agacagagat gaattccctg aggacctcct ttgactccct    480
gaagcagcaa acagagaatg tgggcagtgc acacatccag ctggccctgg ccctgcgtga    540
ggagctgcgg agcctggagg agttccgaga gagacagaaa gagcagcgga agaagtatga    600
ggccatcatg gaccgtgtcc agaagagcaa gttgtcgctc tacaagaaga ccatggagtc    660
caagaaggca tatgaccaga agtgcaggga tgcagatgat gctgagcagg ccttcgagcg    720
tgtgagtgcc aatggccacc agaagcaagt agaaaagagc cagaacaaag ccaagcagtg    780
caaggagtca gccacagagg cagaaagagt gtacaggcaa aatatcgaac aactggagag    840
agcgaggacc gagtgggagc aggagcaccg gactacctgt gaggccttcc agttgcagga    900
gtttgaccgg ctcaccatcc tccgcaatgc cctgtgggtg cactgtaacc agctctccat    960
gcagtgtgtc aaggatgatg agctctatga ggaagtgcgg ctgacccttg agggctgtga   1020
tgtggaaggt gacatcaatg gcttcatcca gtccaagagc actggcagag agcccccagc   1080
tccggtgcct tatcagaact actatgacag ggaggtgacc ccactgattg gcagccctag   1140
catccagccc tcctgcggtg tgataaagag gttctctggg ctgctacatg gaagtcccaa   1200
gaccacacct tctgctcctg ctgcttccac agagactctg actcccaccc ctgagcggaa   1260
tgagttggtc tacgcatcca tcgaagtgca ggcgacccag ggaaacctta actcatcagc   1320
ccaggactac cgggcactct acgactacac tgcacagaat tctgatgagc tggacatttc   1380
cgcgggagac atcctggcgg tcatcctgga aggggaggat ggctggtgga ctgtggagcg   1440
gaacggacaa cgtggctttg tccctgggtc gtacttggag aagctctgag gaaaggctag   1500
cagtctccac atacctccgc cctgactgtg aggtcaggac tgtttctttc catcaccgcc   1560
caggcctcac ggggccagaa ccaagcccgg tggtgctggg catgggctgg gtgctggcta   1620
ctctcaataa atgtctccca gaaggaaaaa aaaaaaaaaa                         1660
```

<210> SEQ ID NO 24
<211> LENGTH: 1455
<212> TYPE: DNA
<213> ORGANISM: Mus musculus

<400> SEQUENCE: 24

```
atggttaggg gtggaggacc tgtgatgagt gcagcctcca atcgcagcaa aaggacgaag     60
gtccttcgcc acctgccagc agaagacgct gcaagcgccc gcggcgccgc agtagcctct    120
ctcctgctgc agtcccgaca gagtttcaga tccaaatcca tagggctagc gctcctcttc    180
ccctcgcccc gctcccctgc cttcgacctc ctctggaggc ccggaggaag gaagcagggc    240
actttgccac ttctaaggaa ggggaggaga ggcggcgaca gagactccca cagaaggagc    300
cccaagccct gtatccttct ccccactccc cgcccgcaca cccgcgcagg tccgatgctg    360
gcgagtgggc cacttgccaa ggtgtcggtg ctcactccgg gtgccgggat tcaggcggga    420
ctgccttccc tccgggtgcg ttcgcctccc gccccgctcc ccgcctggac gtctgcggaa    480
aaagaagata aaagagtacc tggagcgaac accatgactt ccttcagccg ctacaccctt    540
gggtttctag aggtggacag acagagggcg ggagccgacg ggggaccggg gaaccgcggg    600
gccgggagca gacgggcgcg cagggtgcgg gcgggacggt cagcacctcg gacagctccc    660
```

```
tgcgcgcggt cccgggccgc ggctcagcgc tgggcgcgcg ctgcctccac aatgcaccgc    720

tccgccggcg ggaggaggag aggcaacccg gctcagctcc tcctcggtcc ccgcgccagc    780

ttggcgattc accgccgaag gagcagggcg cttctaccgc ttccaccgaa gcaggaagga    840

cggaagggga agccagacag aaagggagct ggctgccaat ataaagtctg tcttccgctc    900

tgcccgccta tacgaaatgc tcccagagac aatgtgagaa ggcctgcaat tttctgtgct    960

tctggcaatg gtagaaagga gaagtagata aggaaagatc cccctccaga tgatgaatgc   1020

tacccgagct catatcggtg aagggaacct gtgctattcg gtcgaatgca accgcccttg   1080

caagacgtgg cttgtcagcg ctactcatcg aagtgtaaac ccatctctga agacctggca   1140

ggcagaagta ctctccccac cccaacccca cccacggact ttgcagcatc agtccatttg   1200

tacactcgga tctctaagga aaacagcatc atcgacgtga atgacagctg cagcgggagc   1260

cggggagcgg gcggtcagat gctccgccgg ggctgtccac tccgcgggca ctgaaaacgt   1320

cagggaaggt ctctcttgga gccaacgcgg acttgacaaa acagttgaca attagggcaa   1380

agcacgtacg gcagaatcat tagaacccac agaagccccg gccccagcgg cgacaccgcg   1440

gcgtggcgat gcccc                                                    1455
```

<210> SEQ ID NO 25
<211> LENGTH: 3168
<212> TYPE: DNA
<213> ORGANISM: Mus musculus

<400> SEQUENCE: 25

```
cctcgattca gttttggtga aatggcggcc attctcatct tctcggagcc cttctctttg     60

ctcacactcg cgattctgcc cccgcaagag tactctgggg acgtccttat cgctgggaga    120

gagcggtcgc atctcattcc tgaacctgtt gggctcgctg ggcgcgtcac ctggctagca    180

gcttgggcca gctccgcagg ctaactttcc tggacgccta ctgaagagtc tgctcctctc    240

tgtgttcttt ccagtgtctc gttcgatcca gttttctggt ggtctccagc gaagacaggc    300

gacaaagccg ttgttgagtg ggatgggccg gcgaccgccc ggtagtgtct ctattgcaag    360

aactctgaga gaaatgaaga gagtcctcag caatgatgtt ggcttctcgt ggttcccaga    420

gccctgctta atggatggag actggacgag aacctggctg ctgtggttct gaacatggcc    480

cagagccctg tgtctgccga ggtcattcac caggtggaag agtgtcttga tgaagacgag    540

aaggagatga tgctcttcct gtgtagagat gtgactgaga acctggctgc acctaacgtc    600

agggacctcc tggatagctt aagtgagaga ggccagctct cttttgctac cttggctgaa    660

ttgctctaca gagtgaggcg gtttgacctt ctcaagagga tcttgaagac agacaaagca    720

accgtggagg accacctgcg cagaaaccct cacctggttt ctgattatag ggtcctgctg    780

atggagattg gtgagagctt agatcagaac gatgtatcct ccttagtttt ccttacaagg    840

gattacacag gcagaggcaa gatagccaag gacaagagtt tcttggatct ggtgattgaa    900

ttggagaaac tgaatctaat tgcttcagac caattgaatt tgttagaaaa atgcctgaag    960

aacatccaca gaatagactt gaacacaaag atccagaagt acacccagtc cagccaagga   1020

gcaagatcaa atatgaatac tctccaggct tcgctcccaa aattgagtat caagtataac   1080

tcaaggctcc agaatgggcg aagtaaagag ccaagatttg tggaataccg tgacagtcaa   1140

agaacactgg tgaagacatc catccaggaa tcaggagctt ttttacctcc gcacatccgt   1200

gaagagactt acaggatgca gagcaagccc ctaggaatct gcttgatcat tgattgtatt   1260

ggcaacgaca caaaatatct tcaagagacc ttcacttccc tgggctatca tatccagctt   1320
```

```
ttcttgtttc ccaagtcaca tgacataacc cagattgttc gccgatatgc aagtatggcc   1380

caacatcaag actatgacag ctttgcatgt gttctggtga gcctaggagg ctcccaaagc   1440

atgatgggca gagatcaagt tcactcaggg ttctccttgg atcatgtcaa gaacatgttc   1500

acgggggaca cgtgcccttc tctcagaggg aagccaaagc tctttttat tcagaactat    1560

gagtcgttag gtagccagtt ggaagatagc agcctggagg tagatgggcc atcaataaaa   1620

aatgtggact ctaagcccct gcaacccaga cactgcacaa ctcacccaga agctgatatc   1680

ttttggagcc tgtgcacagc agacgtatct cacttggaga agccctccag ctcatcctct   1740

gtgtatctgc agaagctctc ccagcagctg aagcaaggca ggagacgccc actcgtggac   1800

ctccacgttg aactcatgga caaagtgtat gcgtggaaca gtggtgtttc gtctaaggag   1860

aaatacagcc tcagcctgca gcacactctg aggaagaaac tcatcctggc tcctacgtga   1920

gaaccccaga ccgttggtgt tcttggtata tcatccaggg tggcggcttg gagcagagct   1980

tggcggttac ggctgcttct ggctgcttct ggctctgccg tgagtcctgg cctagggttc   2040

tcctgtgcac aggcatgagc cgtaaccctg tgcctgggaa acgtctcact cccgccgccg   2100

tgcctttacc tctctaaact tccctactta cattccttag tcggatgttt tgccagagtg   2160

tggagaacag taagacataa acctattgtt tgtttgtttt tttgggggg aggttatcta    2220

ccaagttata ccaagttatt gtatgggtgt atagtgtata gtggttcaag atttgacact   2280

gaatgtaact tgagacttac ctgagtttgt catgcgactg ggtaaattgt ttctatggca   2340

catctaatca tttaataagt aattacctca ttaagtaccc attgcttcag gactttcaca   2400

ttggccacca atttctgtga cccagctcca catttatatt ctctttctgc aaaaccaaat   2460

ttcattatgt ctgtttaata tctacagtct aatgctttgt aagacatcta gatagaaaaa   2520

tagttaccca tgagcacagg agggctggcc tgaccctcac cagctgtgca gtggcttcgg   2580

tgaaggagaa tgagccctac tccttgaagg ttgtagtgct tgggagagca gtctgtacct   2640

tgcctgggca gcacagtaga gccagcccca agaacacaac agtgagtggg ggagcttgcc   2700

ctggttggct caggatcagg aacaggaggg atgaccaact tggggctttg aggtggccca   2760

ccccagcatc catatcatct gtgaactgcc agagcctgtg aaggggcggg tcctgtagaa   2820

ctaaggctgc aggatctcca tgacacaggg caacaacagg gtatctgaga agggtccccg   2880

tgagggtcca gtatttatag tgcaccagaa gccagaggcc tcggatcaga caatgaccca   2940

ttgcactgag taaagatgta agtgaatgag tgaagatgtg tgggcacacg gaaatactga   3000

gggacacaca caagctttta tggagatgtt tgtttgtttg tttgtttgtt ttttgtttct   3060

ttggcaggaa cagattgcaa gggcagagag tagataagga agctggagac atgagtgggg   3120

ttgggtgcat gatatagaat tcacaaagaa tcaaaaaaaa aaaaaaaa                3168
```

<210> SEQ ID NO 26
<211> LENGTH: 1534
<212> TYPE: DNA
<213> ORGANISM: Mus musculus

<400> SEQUENCE: 26

```
cctttgaaca actttgttga tgagagctct ccaggattgc ctatagaaga agctttggat     60

ggagtgcatg gaagcgtagc tctggagacg ctgaggcagc agcaggcgcg gctacagcag    120

tgagggcaga gtggaaagtc gccggcaggg ctgacgatga aacagagaca acattctcaa    180

ggtttcaaga cttactcaga gagctgtccc atcgggatca aggtgacact ggagaactag    240

ctgaaatgcc accacctcag tcaagacttc tgcagtacag acaagttcag cctagaagtc    300
```

```
cgccagcggt cccgtctccc ccttcctcca cagaccacag tagccagttt gctaacttta    360
atgacagcag cagagacatt gaagtagcca acagcccagc attcccgcag cgcctcccgc    420
ctcagctatt tggctcccct ttctcgttgc catctgaaca ccttgcccct cctcctctga    480
aatacctggc tccggaagga gcatggaatt ttgctaactt gcagcagaat cacttaatag    540
ggccgggctt tccctatggc ctacctccat tgcctcccag gccaccacag aacccttta    600
tacacatcca gaaccatcaa cacgctgctg gtcaagagcc atttcaccca ctgtcatctc    660
gaacagtgtc tgcttcttcg ctccccagcc tagaagagta tgagcccaga ggacctggtc    720
ggcccttgta ccaaagaaga atctcatcta gctcagccca gccttgtgtg gaagaggcaa    780
gcgctcccca agacagcctg gctcagggca aagaatcgca gggccacagc aacccacctg    840
ccttcaactt cccggccccc gagtcctggg ccaacaccac ctcatctgcc ccctaccaga    900
acattccgtg caatggatcc agcaggacga gtcagcccag agagttgata gctccaccca    960
agactgtcaa accccctgag gatcagctga agcccgagag cggggaggtg tccagttcct   1020
tcaactactc gatgctgcag caccttggcc agttcccacc cctcatgccc aacaagcaga   1080
tcgcagagtc cgccaactgc agcagccagc agagcccggc agggagcaag cccgccatgt   1140
cctacgccag tgcgctgcgg gccccgccca agcccaggcc gccacccgag caggccaaga   1200
agggcagcga cccgctgtcc ctgctccagg agctcagtct gggcagcagc ccgggcagca   1260
atggcttcta ctcctacttc aagtgacccc gctcgcgctg tcctcagaga atatgcggtt   1320
cctgtccagt ctgcaggatg gaggtggcgg ctctgtgtgc gtgcagccct ccattacgtt   1380
cactgcgctc tcagcccccct tgctgctaga cctgcgccta cgtttaaaag tatattccat   1440
tattttgcat ttttgatgtg agtcagaatt ttgacagctt ttatgtagaa taaaaatatt   1500
tttaaatttg aaaaaaaaaa aaaaaaaaaa aaaa                                1534
```

<210> SEQ ID NO 27
<211> LENGTH: 4525
<212> TYPE: DNA
<213> ORGANISM: Mus musculus

<400> SEQUENCE: 27

```
cggcgcgttg aggggcgggg tgaaaggtca cagcgcggcg gcgggtctgg ctggcggcag     60
ctgcgggcgg gagccgagtg tcccgagtgc acgtgtggag gagcggcggc ggcggcagcg    120
cggcggcaga tttccccgcg tctcccggag cctcagggcc tggcttggct tctcagccaa    180
aagaccggcg tgtggggttg agtggtctga gctcagggcg cgggcggaga gctccgggcg    240
acgaggacga cggcgttggc ggcggctgta acgacggcct cagcagacgg ggaagatgaa    300
aggccggatc gagctgggag atgtgacgcc acacaatatt aaacagttga agagactgaa    360
ccaggtcatc tttccagtca gctataatga taaattctac aaggatgtgc tagaggttgg    420
cgagctagca aaacttgcat atttcaatga tatagctgta ggtgcagtgt gctgcagggt    480
ggatcattca cagaatcaaa agagacttta catcatgaca ctaggatgcc ttgcacctta    540
ccgaagacta ggaataggaa ctaaaatgtt aaatcatgtc ctaaacatct gtgagaagga    600
tggcactttt gacaatatct atctgcatgt ccagatcagc aatgagtcag cgattgactt    660
ttaccggaag tttggctttg agattatcga gacaaagaag aactactata agaggataga    720
gcctgcagac gcgcatgtgc ttcagaaaaa cctcaaagtc ccatctggtc agaatgcaga    780
gacacagaag acagacaact gaacaaatca caaatgaact ttcttgcact tgcttgtcgc    840
caaataaaag aaagacccat tggttccctt ccccccttc ttccactttc ctcctttgtt    900
```

-continued

```
attccttttt tttttctttc ctcttaaagt ttttaatact ttcatggact cttaaaaatg    960
atcatgtgtt ggattgtttt agttctctta cttttgtgag gtggttggat tgaaggagga   1020
gaagatagat ctgtatagtt tcacagttaa gatgtcccga aaattgggtg gcagatgatt   1080
tcaaattttt agctgaattt ttttaaaaaa taaaaacaaa ccaacatcct gctttcacat   1140
tgaagggcag agcctactat attgtttatt tcaaaagaca aaaagcagca gcaatacctt   1200
gctctctaat tcatagacaa gcttagtgta tctgtggtac tttgagttat acagactgtc   1260
tgtggggtgc taatccccag cattgccttc actctaccct tagtcctttg agcactctca   1320
ggagttggac cattgttatc cttgtgagaa aataccaagc ttatttaggt ttttaaagca   1380
atttttttct atttgctgat tggcggggca gtttgtgtag gtagtaagta ttaaactttg   1440
gtcaaagtat ttcagttaaa ctgctttttt tgctgaggaa tggacttctt gttagcaggt   1500
tttttttgtt ttttccttct ttcctgctgt taatcttgtt actagaggca ttaactggta   1560
gagtgtgggc tggtgaaatt aactgtttta atatcccagc tagagatatg gcctttaact   1620
gacctaaaga agattgttat aattgatttt ttttcctctt gtttttcagt aagcccaata   1680
atagtgtaac cttataaatg gagttatgcc cttataagtc aatatcccta aataaacctg   1740
aagcaagtgt tttctcttgg acgaacagaa ttgcattacg taaaaggctt agatggactt   1800
gtaacacatt aagtgtattt aatgtcaact aatacagatt gttaaaagtg tggtcattga   1860
gtgtttaata atatatgaaa gaatttctag acagtatttt tgaaaagaac attgttatgc   1920
tattgcttat ctgttggaga acatcccagg ttagcttcca ctctgtgcct acaatgttga   1980
gtttaaagat ttggaataag aggaatcagt agaaaaattc cttctattct tggaacaata   2040
gacgtataaa gtattaatac aaatatcact gtgaccttca gctgacaggt ttggttaaga   2100
ccagaccatc ttcaggcaca ctgggagtgg ctctgatgga ttgagaactg taatgtggag   2160
acatgtgaga tacgttttgc tcacattgtc ctgtctcaaa tatatggaat ttcttagatt   2220
gttagtagtc atcagtggct caagaaatgt tcttgttaga ctttaaaaca gtacagattg   2280
tgtgtttttct ttcatttgac tttaaaagga agtttaatac atcatattag taaaattgtg   2340
gtatgaaagt atcatttcca aataggttga atgataaaat tatctcacaa gatgataaaa   2400
caccttataa ctcttacgtt tttatttgag aatgtgaaag tatgtaaaat ggacttgagt   2460
agtcttgagt gccaagaata tagataaggg gtgggatgga tggatggatg gatggatgga   2520
tggatggatg gatggatggg cgggctagtg aaattgtaga aataccatgc ttgtttcttg   2580
ggtatcagtt tcctaaacag tccaaatcta agctcagaag tttagtgtta agcaccctta   2640
ctttaatgga taagcttcag cgtgctcttg ccaagagaag agggcataaa taatagtaaa   2700
attagtttga aaaacgtcag caattttgta aacttcctga tagcaaaata gatttgata   2760
tataaaagag ttttctgaga tgacactgcc tctatttcta taaccatttc acttggacta   2820
agtagtccta tgaatgtatc cctaaatgtg gtttttgaaa accgaatagc tgcctcacaa   2880
caattaagta catgttattt aaagaggaag aacaaataat aaagattgat ttgaatgtgt   2940
aggctcccta ttatagcttc tttttccaca ctagtcagtg atttaaccta aaatttaaat   3000
gtatgggtca attgtcctgt atcaaagtta cagtaaataa ttccatccac ttacataagg   3060
agaagatgtg gaaaatgtag aaactgggac tagtccatgt acctgtgagt caagaaatac   3120
taaagtaatg ccccagttga gtttgtgggt ttgggttttg atttgtttgg gctttctctt   3180
tgtttttaac attataaaaa taatctttga ggtaaaacta attctattaa ctggaagata   3240
cccagctatc ttcatcattt tttcaggaaa gatcattttt attgtggggt aaataggtta   3300
```

aaattattct gtatgctatt tgaatttagg ttctaaagta aagaatccgt agaggaatct 3360
atgcaatatg taatttgtca agattaattt tcatctgggg aaagaagttg ctaagtgtct 3420
ccaaagcagg tcactcaata actgaaagtc ctccaaaaag agaactagtg ggaagcatgg 3480
tgtgtggtgg tggaaaagaa aaactccctc agtttttgga gggaataact ttaaagatac 3540
ttaagtggct acgtttactt ggtgcagtta agaattaaac ttgtcaattt taatgttgct 3600
gttacatcta aaataaactt atgtgatgtt ctggtagtga tctgtctgta actgtcatga 3660
aatcattatt gtgctgaatt ttacagtctg caactatgtc attgttgtgt actgtgatcc 3720
atacatccat atttcactag ggcctaattt aaaactcatg aataatcaaa gtatgctaat 3780
tcagacctct tggaattggg aaaagacacc aggcaatata tctgaattta atctaggtga 3840
aaaaaagatc cccaggaatg ccttattgcc atattttaaa tatagttact ataaatagaa 3900
ctttaggctt tattctagtg agtatgaact gtaaatgtgc atattctgat ctattacttt 3960
ttgtagtgaa gatttagtt gagtgagtgg attttatgtt aagtacttcg aaatttttga 4020
cagtgtttaa tatatctagt cacaatggtc tgaattagta ttttgcttat tacccaagaa 4080
acaaaggatg gcctttgtct tatttaccat atcactacaa aatttagcag tttaaaataa 4140
cagatttgtt gtatcctata gtttcccaat caagcagtgt gtgacataac cagttaggtc 4200
tgacaaagga tcttatatca ggtatcagcc aaggctgcaa attgatgaag gcttgaccgc 4260
agctacttca tttcactcac atggctgttc tggaaaccat ttgggacaga acactaacat 4320
aagacttgct taacaaagcc tagtattagt cttaaaaagt tatggtcttt ttgttatatt 4380
gtaatgaaag cttaaatcta acaattggaa agtggtattg ttggatagga tattttgtaa 4440
atttacgaac attcagtgaa ctcatttact gtcctcaaca attcaagaca tatgagttaa 4500
gtatggatta aaacatgttg atact 4525

<210> SEQ ID NO 28
<211> LENGTH: 560
<212> TYPE: DNA
<213> ORGANISM: Mus musculus

<400> SEQUENCE: 28
ggcaaaggcg cgcgttctct gctctgcgcc ccgggcggag aaggcatcat gtcagacaac 60
gaggacaatt tcgacggcga cgactttgat gacgttgagg aggacgaagg acttgacgac 120
ttggaaaatg ctgaggagga gggccaggaa aatgtcgaga ttctcccatc tggtgagcga 180
ccacaggcca accagaagcg gatcaccact ccttacatga ccaagtatga gcgtgcccga 240
gtgctgggca cccgggctct tcagatcgcg atgtgtgccc cggtgatggt ggagctggag 300
ggggagacag accctttgct catcgccatg aaggaactca aggcgcggaa gatccccatc 360
atcattcgcc ggtacctgcc agacggcagc tatgaggact ggggcgtgga cgagcttatc 420
atcagcgact gagccgggcg cgctcggcct gcaccagctc tgctgggcac cctctctgtg 480
cccgttttat atgtgtaaat aataaacctc accctttcca aaaaaaaaaa aaaaaaaaaa 540
aaaaaaaaaa aaaaaaaaaa 560

<210> SEQ ID NO 29
<211> LENGTH: 1312
<212> TYPE: DNA
<213> ORGANISM: Mus musculus

<400> SEQUENCE: 29
ccacgcgtcc gcggacgcgt gggcgggcac aggagagctc tcggcacctc cgggaaagcc 60

-continued

```
acctcggcct cccccgcgcc cgggctccag ccgcggccgg cccagcctcg acctcagcag    120

cgaccagctg ctcctgcgag gagccgagcg agcccggtcg cgggcgggga gcgtgcgtcg    180

gttcgcacag gctgcgagag gaggggcggc gcgagtcatg gccggggaca gcgagcagac    240

cctgcagaac caccagcagc ccaacggcgg cgagcccttc ctgatcggcg tgagcggggg    300

cacggccagc gggaagtctt ccgtttgtgc taagatcgtc cagcttttgg ggcagaatga    360

ggtggattac caccagaagc aggtggtgat cctgagccag gatagcttct accgagtcct    420

cacctcagag cagaaggcca aagccctcaa gggccaattc aactttgatc acccggatgc    480

ctttgacaac gaactcatct tcaaaacact caaagaaatc accgaaggaa aaaccgtcca    540

gatccccgta tacgactttg tctcccactc acggaaagag gagacggtca ccatctaccc    600

cgccgacgtg gtgctcttcg aagggatcct agccttctat tcccaggagg tccgagacct    660

gttccagatg aagcttttcg tggacacaga tgcggatacc cgtctgtctc gccgagtatt    720

gagggacatc agcgaaagag ggagggacct tgagcagatt ttatcacagt acattacgtt    780

tgtgaagcct gcctttgagg aattctgctt gccaacaaag aaatacgccg atgtgatcat    840

tcctagaggt gccgacaatc tcgtggccat caacctcatc gtgcaacaca tccaggacat    900

cctcaacggg gggctctcca agcggcagac gaacggctat ctcaacggct acacccccttc    960

ccgcaagagg caggcgtcag agtccagcag ccgaccacat tgactcccgt gcccctgact   1020

ccaaaccccca gccccccagc tccaagacac aggaggggtc gagaggctct ggtcacctgt   1080

acatacgcct cctcagaaaa ttactgtatt taagaaaaca ccacggagat gaaatgcctt   1140

gatttccctt tctgcctttt tgtactttgg aacagcaaat cttgatggaa cttgaccctg   1200

agcttaagtg acaaactgtg ccaactagta ctggtgatgc ctaattatga acccaacgtg   1260

taaccagtta taaatacaca catacatacg tctatataaa aaaaaaaaaa aa           1312
```

<210> SEQ ID NO 30
<211> LENGTH: 3920
<212> TYPE: DNA
<213> ORGANISM: Mus musculus

<400> SEQUENCE: 30

```
ctgcgctccg ccgcgcggag tagaatgaac tgtaacaaaa caagccgagc ctttgtatct     60

gcttaaaggg gccgcggcca cttccctcgc gtcccctcac ccccgccccg cgccgtcgcg    120

tctccagggc tcccggcaac tagcttggaa agggcttccc tcgcgctgag gagcggccgg    180

ccggcgcgga gcaggcgcgg cgtgtgtgga gagagccgcg gagcggagag cgggcccggg    240

cggcgccgga gtggactctg gtcccgggag cgcggtcggc gccggaacgc ggacccggag    300

gcaccggaat gcaaacaaag ctcgcgggcg cccgtgcagg gctcttcacg gagcccggaa    360

agtttgtttt atgatggctt gagagcgcga gagagtcggg cgaggaggct cgagtagctc    420

gctcccgcgc tccgagagat gcttctcccg tgagcccgcc gctccggggg ctcgtgctgt    480

gggggcacct gtctctcgtt ttagcagttt tcttttcttt ttcttttttt ctttaatttg    540

aattttgttt tcgaggaggg gctgtaactc atcatgtcga aagtgatcca gaagaagaac    600

cactggactg gccgcgttca cgagtgcacc gtgaagcggg gaccccaggg cgagctgggg    660

gtgacggtcc tgggggggcgc ggagcatggg gagtttccgt acgtgggggc ggtggcggcg    720

gccgaggcgg cggggcttcc cggcggtggc gaggggccga agctggccga aggtgagctg    780

ctgctggagg tgcagggggt ccgggtgtcc ggcttgcccc gctatgacgt gctgggagtc    840

atcgacagct gcaaggaggc cgtcaccttc aaagccgtca gacaaggagg aaggctcaac    900
```

-continued

```
aaggacctac gacatttcct caaccaacgg ttccagaagg ggtctccaga tcatgagctc    960
cagcagacca taagggacaa cctctaccgc catgctgtgc cttgcacaac ccggtctccc   1020
agagaaggag aagtgcctgg cgtggattac agctttctga ctgtgaagga gttcttggac   1080
ctcgagcaga gcgggaccct gttggaagtc ggcacctatg aaggaaacta ttatgggaca   1140
cccaaacctc ccagccagcc agtcagtggg aaagtgatca cgacggatgc cttgcacagc   1200
ctgcagtctg gctccaaaca gtcgacccct aagcgaacaa agtcctacaa tgatatgcaa   1260
aatgctggca tagtccaccc ggagaatgag gaggaggagg atgtccctga aatgaacagt   1320
agctttacag ccgactctgg agaccaggac gagcacactc tccaagaagc aacgctccca   1380
cctgtgaata gtagcatcct cgctgctccc atcacggacc cttctcagaa gttccctcag   1440
tacctacctc tttctgcaga ggataattta ggtcctctac ctgaaaactg ggagatggcc   1500
tatactgaaa atggagaagt ctatttcata gaccacaaca cgaaaacaac atcatggtta   1560
gaccctcggt gcctgaacaa acagcagaag cctctggaag aatgtgaaga tgatgaaggg   1620
gtacacaccg aggagctgga cagtgaacta gagttgcctg ctggctggga aaagattgaa   1680
gaccctgtct acggtgtcta ctatgtagac cacatcaaca ggaagacgca atatgaaaac   1740
ccagtcctag aagccaaacg gaagaaacag cttgaacagc agcagcaaca gcagcagcct   1800
cagccaccgc agccagaaga gtggacagag gatcatgcat ctgttgtgcc tcctgttgct   1860
ccttcccatc ccccgagcaa tccggagcca gccagggaaa ctccacttca gggcaaacct   1920
ttttttacaa gaaacccctc tgagctgaaa ggcaagttca ttcacacgaa gctacggaaa   1980
agcagccgag gctttggctt cacggtggtt ggaggagacg agcctgatga gttcctgcag   2040
atcaagagcc tcgtcctcga tggtcctgcc gcactggatg gcaagatgga gacaggggat   2100
gtaattgtga gtgtgaatga cacctgtgtt ttgggacaca cacatgctca agttgtgaaa   2160
atcttccagt ccattcccat tggtgccagt gtggaccttg aactctgcag aggttatcca   2220
ttgccttttg acccggatga ccctaataca agtttagtga cctcggtggc cattttggac   2280
aaagaaccaa ttattgtaaa tggacaagag acctacgatt caccagcgag ccacagtagt   2340
aaaacaggca aagtcagcag catgaaggac gccaggccaa gcagccctgc tgatgtggct   2400
tccaacagct ctcatggtta ccccaacgac acagtctcct tggcttcctc catagccacc   2460
cagccagagc taataactgt tcacatagtc aaagggccaa tgggatttgg ctttacgatc   2520
gcagacagtc ccggtggggg tggccaaaga gtgaaacaga ttgttgacag tccacgctgc   2580
agaggcctca aagaagggga tcttatcgtg gaggtgaata agaagaacgt gcaggccctg   2640
acgcacaatc aagtcgtgga tatgctgatt gaatgtccca agggaagtga ggtcacactg   2700
ttggtgcagc gaggagggct accagttccc aagaagagcc caaagtcgcc actggagagg   2760
aaagacagcc agaatagctc ccagcacagc gtctccagcc accggagcct gcacactgcg   2820
tccccgagcc acggcataca ggtgctccct gagtacctac ctgcagacgc ccctgctcca   2880
gatcagaccg acagctctgg gcagaaaaag ccagatcctt ttaaaatctg ggcccagtcc   2940
aggagcatgt atgaaaaccg acttccagat taccaggaac aggacatctt cctctggaga   3000
aaagaaaccg gatttggatt taggattctg ggtggaaatg aaccagggga acccatttat   3060
atcggtcaca tcgtaccgct gggtgctgct gacacagacg gccgcctgag gtctggagat   3120
gaattaatct gtgtggatgg gacaccagta attgggaaat cacaccagct cgtggtccag   3180
cttatgcaac aagctgccaa gcaaggccat gtcaatctca cagtgaggcg gaaagtggtc   3240
tttgccgtcc ccaaagcaga gaatgaggtg ccctcaccag cctcatcaca ccacagtagc   3300
```

-continued

```
aaccagcccg cgtccctgac ggaggagaaa cgcacaccgc aaggcagcca gaactctctg   3360

aacactgtga gctctggcag cggcagcacc agtggcattg gcagtggtgg cggcgggggc   3420

agcggtgtgg tgagcgctgt gctgcagccc tatgatgtgg agattcggcg tggggagaac   3480

gagggctttg ggtttgtcat cgtgtcctcc gtgagcaggc ccgaagcggg cacaaccttc   3540

gagtcctcaa atgccacgct gctgactaat gctgagaaga ttgccaccat caccaccact   3600

catgcccccct ctcagcaggg gacccaggaa acaaggacca ccaccaaacc aaagcaggat   3660

tctcagtttg agttcaaagg accgcaggct gcacaggagc aagatttcta cactgtggaa   3720

ttggaaagag gggccaaggg atttggcttt agtcttcgag gggccgaga atataacatg    3780

gatctttatg ttctgcgctt ggcagaggat ggtcctgcag aaagatgtgg gaagatgagg   3840

attggcgatg aaattctaga gatcaatggt gagaccacca aaaacatgaa acactctcgg   3900

gccatagaac tgatcaagaa                                               3920
```

<210> SEQ ID NO 31
<211> LENGTH: 2160
<212> TYPE: DNA
<213> ORGANISM: Mus musculus

<400> SEQUENCE: 31

```
ggaaatcctg gaaggattta tatctcctcc tgtggttctg gtggggaagg actcgtgccg     60

aattcggcac gagtggagct ggcctgaact ttggaccttg tcttccagta ggaaatcagt    120

ctctcagaag gcgatcatgg cctccaagcc tgagaaaagg gtggcctcct ctgtcttcat    180

caccctggca ccgccacgcc gagatgtagc cgtgagtgag gaagtgggcc aggcagcttg    240

tgaagccaga cgcgctcggc cctgggagat gcttcccaca aagacacctg gggccgcagt    300

gggcaggagc cccaagacct ggacgccctc tggcaagacc aatgcctcac tctctggagt    360

cacacctcag ctctccaatg gaggatgctc tctcccacct ccttccctga atgaggagga    420

cctagacctc ccgcctcctc caccgccccc ttctgcctac ctgcctctcc cagaagagga    480

gcctcctgtc ttaccaggga agtcgctcat ttccgacttg gagcaactgc acctgccccc    540

acccccgcct ccacccccgc cacaggctcc atcaaaggga tcgtctgtcc accctccgcc    600

tggtcacgcc agaccctcgg aagaggagct tcctcctcct ccagaagagc ctgtcacact    660

tccagagaga gaagtgtcta cggatgtctg tggtttctgt cacaagcctg tgtctcctcg    720

agagctggct gttgaggcca tgaagaggca gtaccacgcc cagtgcttca cctgtcgtac    780

ctgccgccgc cagttggctg gacagagatt ctaccagaag gatgggcgcc ccctgtgcga    840

accctgctac caggatactc tggagaagtg tggcaagtgc ggagaggtgg tccaagagca    900

cgtgatccgg gccctgggca aggccttcca cccacccctgc ttcacctgcg tgacctgtgc   960

ccgctgcatc agcgacgaga gctttgcgct ggacagccag aaccaggtgt actgtgtggc   1020

tgatttctac aggaaatttg cccccgtgtg cagcatctgc gagaatccca tcatcccccg   1080

agacgggaag gacgccttca aaatcgagtg catgggaagg aatttccacg agaactgtta   1140

ccgctgtgag gactgcagcg tgctcctgtc tgtggaacct accgaccaag gctgctaccc   1200

actgaatgac cacctcttct gcaagccctg tcacctgaag cggagtgctg ctggttgctg   1260

ctgaagagtc ccgatagctg gcccttccct gacttggttt cccctcctga cttttcttga   1320

gtactttctt tttgaacctc actgggcacc agcacactgc tcagcccata gtgtctaaat   1380

gcacagacag gcttgagaca ctgggctttg gcctcctagt acacagcacc ccccaccccc   1440

agactttcta ctcctctccc ttcattgacc aggaggcctc accaccagac tgcaaccctg   1500
```

gtccatctct agtgctgccc tgacatgttt atggggacag gtctcaggat gatacctgtg 1560
tctctgacca tgatgcttag ctgcctagca gaaggcgctg agacctcagc ttagattgta 1620
gagctaagtt gtttgaagtg cgccttctca gccactccaa aaagtatttt ttgagaatat 1680
aagtgtgtag tagacatgat agcacacacc tttaatccca gcacttggga ggcagaggca 1740
ggtggatttc tatgttcaat ctagtctgat ctactaaaag attcaaaaca atattctttg 1800
gatttggggg agagaaatct ttgaattttt ctctttttct ttttttggtg gggtaaaatc 1860
agtaaacatc ttcccttggt tcaggggctg cgaagatggc tcggtgatga agagcgagct 1920
cttgctcctc ttgcggagga ccagagttca tttcccagca tccctcatgg aggctcataa 1980
ctacctgtcc tgcaactcca gtttccggag agctggcgcc ctctgctggc ctccttggaa 2040
ccttaatgca tgtggtgtac acgcttacac tcaggcacac acacatacat taaaaaaaaa 2100
aacaatttag cctgtctaat ggcaaacaca tttaatctca gtacttggga ggcagagaca 2160

<210> SEQ ID NO 32
<211> LENGTH: 4712
<212> TYPE: DNA
<213> ORGANISM: Mus musculus

<400> SEQUENCE: 32
gacacttcct gtcacccggg gctttgggaa gctgaactcc agtaaaacca gcttccccga 60
agaatggact ccatgcggac catggccttt tccctttgta atctgctgcc agccgtggaa 120
ctgcactttg acatcttaca ctgatgcaga agaagactca gctctacctc agccttaagg 180
tccagcttgc cgggtccagc tgagccgcag atagctgtcc attttctctg gctggatgga 240
gaggccacat caggatgctt ccttgtccaa aaaagatgcc tgcacccaga cttacccacc 300
taggaggagg atcaggcatg cccaagtgca ggatgcaggt caactgaagc tgtccattga 360
tgcccaggat cgggttctgc tgccgcacat catagaaggc aaaggcctga tgagcaggga 420
gcctggcatc tgcgatccct atgtgaaggt ttctttgatc ccagaagaca gccagctccc 480
ctgccagacc acacagatca ttccagactg ccgagaccca gctttccacg agcacttctt 540
ctttcctgtc ccagaggagg gtgatcagaa gcgtcttctg gtgacagtgt ggaaccgggc 600
cagtgagacc aggcagcata cgcttattgg ctgcatgagc tttggggtga ggtctctctt 660
gactccggac aaggagatca gtggctggta ctatctgcta ggggaggacc tgggtcggac 720
caagcacctc aaggtggcta ggcggcggct ccagcccctg agagacatgc tgttgagaat 780
gccaggagag ggggaccctg agaacgggga gaaactccag atcaccatcc ggaggggcaa 840
agacggcttt ggcttcacca tctgctgtga ctctccggtc cgagtccagg ctgtggattc 900
tgggggcccg gcagagaggg cgggactgca gcagctggac acagtgctac aactgaatga 960
gagacccgtg gagcactgga aatgtgtgga gctggcacat gagatccgga gctgtcctag 1020
cgagatcatc ctgctcgtgt ggcgtgtggt cccccagatc aagccggggc cagatggcgg 1080
agtcttgcgg cgggcctcct gcaagtccac acatgacctc ctgtcacccc ctaacaagag 1140
ggagaagaac tgtactcatg ggccccagt tcgtcctgag cagcgccaca gctgccacct 1200
ggtgtgtgac agctctgatg gtctactgct tggtggctgg gagcgctaca ctgaggtggg 1260
caagcgcagt ggccagcaca ccctgcctgc actgtcccgg accaccaccc ctactgaccc 1320
caactacatc atcctggccc cactgaatcc tggaagccag ttgctgcggc ctgtgtacca 1380
ggaggataca atccctgaag aaccggggac tactactaaa gggaaatcgt acaccggcct 1440
gggcaagaag tctcggctca tgaagacagt gcagaccatg aagggccaca gtaactacca 1500

```
agactgctca gccctgagac cgcacatccc gcattccagt tacggcacct atgtcaccct   1560
ggcccctaaa gtcctggtgt tccctgtctt tgtgcagccc ctagatctct gtaaccctgc   1620
ccggactctc ctgctgtcgg aggagctgct gctgtatgag gggaggaaca agacttccca   1680
ggtgacactg tttgcctact cggacctgct gctgttcact aaggaggagg agccaggccg   1740
ctgcgacgtc ctgagaaatc ccctctacct ccagagcgtg aagctacagg agggctcttc   1800
agaagacttg aaattctgtg tgctgtacct ggcagagaag gcagagtgct tattcacttt   1860
ggaggcacac tcgcaggagc agaagaagag agtgtgctgg tgcctgtcgg agaacatcgc   1920
caagcagcaa cagctggccg caccacctac agagaggaag aaacttcacc cttacggctc   1980
tctccagcag gagatggggc cagtcacctc catcagtgcc acccaggata gaagctttac   2040
ctcatcagga cagaccctga ttggctgagc aagtccaagg gcaggactat gcttctggca   2100
actctggggc ttcccctatc acacagtaac ctcatctcaa ctggacccaa aacagaagac   2160
caagatggtg ggcctagggt cacctggagg gagtggtccc aagggtgtgt gtggacctgg   2220
caacaggagg aacagtggta tgagggaccc tgtgggtttg tgcagactgg taccaggaag   2280
tcctggatgg agaagacgcc aaaacaggag gctaagtggc acctgggcac cttcctgggc   2340
acagcaggaa agagggagag ggcactcgaa cggaagatgg tgcctgtgac ccattcctgc   2400
tggaagacat ctctccttcc cactcctatt tcaaatggac acatttactt cctcagtcag   2460
tgggtactgg gggacatctc ctttgtgcta gggtgtgtgc tagaagatgc tgtgctccca   2520
tcaagatccc agccctcccc gtcccaacag ggagagaaca ccaaataaat caacactgat   2580
acacacatac actgcaaggg tctgtacaga aacatcacag atgtcttcag acagggcatt   2640
atgtctcctt gctacgtgtg ggctatgaag gggaaccata cagcttgagc tggagaggag   2700
ctagccagcc aaggactttg aagagagcgt tccaggcagt ggaagaagct tgaggaaagg   2760
tgtcacagac tcctcccggt gcatatctac aagatcagat tgcagttagg aggggcccaa   2820
gtggctgtga gactggttag ggctcccctt caggcctcca gggtgagggg tgatggtggt   2880
ttgttctaga gggcgctgcg atggtaggta ttggaagggt aggctctggg ataaggagtg   2940
atgctagctc acccttgcct gccctcgtgc tccgttgggt cttgctatct tggtggcgtg   3000
aggtttgagg cctccctcct agggattcct ctactcagac cagagttgag cttttgggaa   3060
tgcccatgag caccgaaaca gtaaagctta attttcccaa gatgggaaag ttcatgtctc   3120
ccctgcttcc aggctccgta gagatcacct gtatctgctc tacctgtcat gctaagagaa   3180
ggaagctagg gccttgcact ctgagaactc ccgtttttg ctttctgtag ggcttctaag    3240
gagcagcagc cggtggccag gaccaagtgt agctcagcaa cctttacaga gacaacatga   3300
aaggaatctt gcccaggtcc agtaatgaga gctgggtcca ctcccatgct ctgggctagg   3360
tagctcaccc ttttctaact gtagagaccc agcaggacag aatctcaagg ctgtggattg   3420
gaaggacgag ggccatatgc tagagagtat ttgtcgggtt aggtactgag cacgcagagg   3480
cagaaagctg cagtgatggc taaggccaga gaagccccag acctgagtct taagtacctt   3540
aaggacgatt cttgtgctct tttgagtttg ctaaactacc agagccacct gagcccctaa   3600
atggtggccc aggagagtgc atgtccctta ttttccttcc aactttggaa aaatgagcca   3660
tgctgagtta tcagtctaac agggaatggg gtgactctgc aggaatcagg ctaacaccca   3720
gcccagcaag gaaagattgg cttggttcaa gggttgtgta gcaccacact gccagccagt   3780
gatcagccca cggggtaaat ccgaacagcc gggtctgtgc agacagcaaa ccacactttg   3840
atttcacttg attctctcac ctaatgattg atcgtgaggt catgaagccc aggaggacca   3900
```

-continued

```
cctgcgtggg aaatcagcta tcttgtttcg cttgcatctg ggcacagacc tctgtccaac   3960

agatgggcac agaagacaag aagaggatct gaacataaca cccaccccgg ggacgagccg   4020

ttctccctga tcagcaactt ctgagtggaa cagattctcc catcaagctc ccaggcctac   4080

tggctgatgg ggaagaggaa ggtactcctg gcaagtcctg ggctagcttg ctccatgact   4140

gtggtgagcc acggcaccat ggccatcttg cttcataaat caatgtgaca attaatttgg   4200

tgtcgtgggc ccgagaggat gaaatatgac ccggtggcct ccgctcttca gtccatccca   4260

gctgttcaag aggaggagga gctctcagcg tggcctctga gagtcataat cacgggaacc   4320

acgccggccc cctccctgcc acataaatca cgctaagaag cacacaacga cttctttcct   4380

gatgggctaa ttgtcttggg tggtgtctcc ggccccagga gcggggaggt cgggagcaca   4440

gccactttat tgttgaaagg ccatctgtga gatttgaata caaagtgcct ctttgagtct   4500

cctacccgtt ctgggatccc atttctgtgt ctcccactct gagtcctttg aagctcatct   4560

ctcatagaag ccctcattgc ctgagtcctt tggccctttg ggagctggaa ttatacagac   4620

cttctgagaa tggtgattct tatttgtaca tgtcttatta ttattactat tataataata   4680

attattatta ttaaaaaaaa aaaaaaaata aa                                 4712
```

```
<210> SEQ ID NO 33
<211> LENGTH: 4906
<212> TYPE: DNA
<213> ORGANISM: Mus musculus

<400> SEQUENCE: 33

ggcacgagaa ggagagcaac ttctaggagc cggtgaggtc tttgccatca ggcccttgca     60

gctctatgct atcacagaac agctgcaaca gggaaagcct acttgtgcca gtggtgatgc    120

caagactgac cttggacaca tcctagactt cacctgtcgc cttaagtatc ttaaggtttc    180

aggcacagaa ggaccttttg ggaccagcaa tattaaggag cagctcttgc cctttgatct    240

ttcaatattc aagtctcttc accaggtgga gataagtcat tgtgatgcca agcatatccg    300

agggctggtc acctccaagc ccactttagc cacgatgagt gttagattct cagcaacctc    360

aatgaaggaa gtgcttgctc ctgaagcctc agaatttgat gagtgggagc ctgaaggcac    420

tgctaccctc ggaggccctg tgactgctat catcccaaca tggcaagcac tgactactct    480

agacctgagc cacaacagca tctgtgagat cgacgaatct gtgaaactga tcccaaagat    540

agagtacctg gacctgagtc acaatggact gcgagttgtg gataacctgc agcacctata    600

caacctcgtg caccttgacc tgtcatacaa caagctctcc tccctggaag gcgtgcacac    660

taaactgggc aatgtcaaaa ccctaaacct ggcaggcaac ttcttagaga gtctgagcgg    720

tctgcacaaa ctctactcct tggttaatgt ggacctacga gacaaccgga ttgagcagtt    780

ggatgaggtc aagagcattg gcagcctgcc atgtctggag cgtttgacct tgctgaacaa    840

ccctttgagc atcatccctg actaccggac caaggtgctt tcccagtttg gagaacgagc    900

ctctgagatt tgtctagatg atgtcgcaac cacagagaaa gagctggaca ctgtggaagt    960

gctgaaggca attcagaaag ccaaagatgt caagtccaaa ctgagcaaca cagaaaagaa   1020

ggctggtgag gacttccggc tcccgcctgc accctgcatc agacccggcg gctcccctcc   1080

tgcagctccc gcctcagcct ccctgcctca gccgatcctc tccaaccaag gtatcatgtt   1140

tgtacaggaa gaggccctgg ccagcagcct ctcatccacg gatagtctgc cacccgagga   1200

ccaccggccc attgcccgag cctgctctga ctccttggaa tctatccctg caggacaggt   1260

ggcctctgat gatctgaggg atgtgccagg agctgttggc ggcgtgagcc cagatcatgc   1320
```

agagccagag gttcaggtgg tgcctgggtc cggccagatc atcttcctgc ccttcacttg 1380
cattggctac acagccacca accaggactt tatccagcgc ctcagcacac tgatccgcca 1440
ggccattgaa cggcaactcc ctgcctggat tgaggctgcc aaccagcgcg aggaagccca 1500
tggtgagcag ggcgaggagg aagaagagga agaggaagag gaggatgttg ctgagaaccg 1560
ctactttgaa atgggacccc cagacgcaga ggaagaggag gggagtggcc agggagaaga 1620
ggatgaggaa gacgaggacg aggaggcgga ggaggagcgc ctggctctgg agtgggccct 1680
gggcgccgat gaggacttcc tgctggagca catccgcatc ctcaaggtgc tctggtgctt 1740
cctgatccac gtgcaaggca gcatccgcca gttcgctgcc tgccttgtgc tcactgactt 1800
cggcatcgca gtctttgaga tcccacacca agagtcaaga ggcagcagcc agcacatcct 1860
ctcatccctg cgttttgtct tctgcttccc acatggcgac ctcacggagt ttggcttcct 1920
catgcccgag ctgtgtctgg tgctcaaggt gcggcacagt gagaacacgc tcttcatcat 1980
ctcggatgct gccaacttac acgagttcca tgctgatcta cgctcctgct ttgcaccgca 2040
gcacatggcc atgctgtgca gccccatcct ctacggcagc cacaccaccc tgcaggagtt 2100
cttgcgccag ctgctcacct tctacaaggt ggccgggggc tctcaggagc gcagccaggg 2160
ctgcttccct gtctacctgg tctacagtga caagcgcatg gtccagaccc ctgccgggga 2220
ctattcaggc aatatcgaat gggccagctg cacgctgtgc tcggcggtgc ggcgctcctg 2280
ctgcgcgccc tcggaggccg tcaagtccgc tgccatcccc tactggctgc tgctcacatc 2340
ccagcatctc aacgtcatca aggccgactt caaccccatg cccaatcgag gcacccacaa 2400
ctgccgcaac cgcaacagct tcaagcttag ccgcgtcccg ctctctaccg tgctgctaga 2460
ccccactcgc agctgcaccc agccacgggg tgccttcgct gatggccatg tgctcgagct 2520
gctcgtgggc taccgcttcg ttaccgccat ctttgtgctg ccccacgaga aattccactt 2580
cctgcgagtc tacaatcagc tacgcgcctc actgcaggac ctgaagactg tggtcatctc 2640
caagaatcct tcagctaagc caagaaatca gcctgccaag agcagggcca gtgctgagca 2700
gcggctacag gagaccccag cagacgctcc ggctccagct gcagtcccac caacagcttc 2760
agctccagcc cccgcagagg ccttggctcc agatctggct cctgtacagg ccccaggaga 2820
ggaccgaggt ctaacttcag cagaggctcc agccgcagca gaggctccag ccgcagcaga 2880
ggctccagcc gcagcagagg ctccagccgc agcagaggct ccagccgcag cagaggctcc 2940
agccgcagca gaggctccgg ccccagcaga ggctccagcc gcagcagagg ctccggccgc 3000
agcagaggct ccagctgcag cagaggctcc agccgcagca gaggctccag cttcagcaga 3060
ggctccagct ccaaaccagg ctcctgctcc agcaaggggt cccgctccag caaggggtcc 3120
cgctccagca gggggtcccg ctccagcagg gggtccagct ccagcagagg ccctggcaca 3180
agcagaagtc cctgcccagt acccaagtga gcgcctaatc cagtccacat ctgaagagaa 3240
tcagatccct tctcacttgc cagtatgccc atcactccag cacattgccc gtcttcgggg 3300
gagagccatc attgacctct tccacaacag cattgctgag gttgaaaatg aggagctgag 3360
gcacctcctg tggtcatcag tggtgttcta ccagaccccg gggctagaag tgaccgcctg 3420
tgtgctgctc tctagcaagg ctgtgtactt catactgcat gatggtctcc gccgctactt 3480
ctctgaacca ctgcaggatt tctggcacca gaaaaacacc gactataaca acagtccttt 3540
ccacgtctct cagtgctttg tgttgaaact cagtgacctg cagtcagtca acgtcggcct 3600
tttcgaccag tacttccggc tgacgggctc ctccccgacg caggtggtca cgtgcttgac 3660
tcgcgacagc tacctgacgc actgcttcct ccagcatctg atgcttgtgc tgtcctccct 3720

```
ggagcgcaca ccctcgcctg agcctgttga caaggacttc tactcagaat ttggggacaa   3780
gaatacaggg aaaatggaga actatgagct gatccattcc agccgcgtca agttcaccta   3840
ccccagtgag gaagaggttg gggacctgac ctatattgtc gcacagaaga tggctgatcc   3900
tgcaaagaat ccagccctca gcatcttact gtacatccag gccttccagg tggtcacacc   3960
acaccttggg cggggcaggg gcccactgcg ccctaagacg ctgctcctga ccagcgccga   4020
gatcttcctc ctggatgagg actacatcca ctatccattg cctgaatttg ccaaagagcc   4080
accgcagagg gacagatacc ggctagacga tggccgccgg gtccgggatt tggaccgggt   4140
gctcatgggc tactatccct acccacaggc cctcactctt gtttttgatg acacacaggg   4200
tcacgacctc atggggagtg tcaccctgga ccactttggg gagatgccag gtggtcctgg   4260
cagggttggc cagggccgag aggtacagtg gcaggtgttt gtccccagtg ccgagagccg   4320
agaaaagctc atctcactgc tcgcacgaca gtgggaagct ctttgtggca gggagctgcc   4380
tgtggagctc actggctagt gcacgccata gcagccctgg cctcctgcca tgcccagcct   4440
agcctggtgc ccgtgaaggc agggaagcgg ccttctgcgt tctttttaag gtctttctcc   4500
tctcccttgg ttcctacatt gttttgtctg tgattgatgc tgttgttagc gtggcgctgt   4560
ggacctgata acccccacgt ccttttctga agtgttaagt ccagtccttc gttgctgttt   4620
gctgtcattg tgggcgtgcc gctgctaatt acaaagctgg tagcagagtt acacaggcaa   4680
gctcccacgt tgtgggcttt tccaaaatgg aggcctcctc aagtccagag cagaggaggc   4740
cctatgggga gttcccaggt catgggtcca agaggagcca gtacagggga cctagagctg   4800
ccagcaccaa gtataattcc tgttgcctac gttctctatt ctaataaaat ggagtttgac   4860
acaaaaaaaa aaaaaaaaaa ctcgtgccga attcggcacg aggaaa                  4906
```

<210> SEQ ID NO 34
<211> LENGTH: 6179
<212> TYPE: DNA
<213> ORGANISM: Mus musculus

<400> SEQUENCE: 34

```
gcgtcagctc tgagccgact ttactgtccc agagcctaga ctgcccgccc cggaggacgt     60
ggaggacgag gcagcccgcg ggagagacag ctgtgggggc cctggcagcg acctcgcgca    120
gctcgtaccc tgtcactcag catcccaatc ggtgttgcgc ccgcgcccgc cccctgcccg    180
aggggcgggg ctggtcttgt ggtacccaga gtctgcgcac gctgaggtgt gcccctgccc    240
agtgaggacc tgggactggg ccatgccagc cccagaccat caaggtggga agaggaccgc    300
atcccagagc cggtgagcaa cccgcagctt tggccgctcc agagaagttc cgcaccctcc    360
aggagtgaag atgaaagaga tttgcaggat ctgtgcccgg gagctgtgtg gaaaccagcg    420
gcgttggatc tttcataccg cgtccaagct caacctccag gttctgcttt cgcacgtcct    480
aggcaaagat gtctctcgtg atggcaaagc cgagtttgct tgtagcaagt gcgctttcat    540
gctcgatcgc atctatcgat tcgatactgt cattgccagg atcgaagccc tttctcttga    600
gcgcttacag aagctgctcc tggaaaagga tcgcctcaag ttctgcattg ccagtatgta    660
tcggaagaat aatgatgact ctggcgagga gaacaaggcg gggagtggga cagtagacat    720
ttccggcttg ccagatatga ggtacgctgc gctgctccaa gaagactttg cctattcggg    780
atttgagtgt tgggtagaaa atgaggatca gattaacgac tcacacagct gtcatgcttc    840
cgaagggccc ggaaaccgac ccaggagatg tcgcggttgt gcagctctgc gggttgcgga    900
ttccgactat gaagccattt gtaaggtgcc tcgaaaagtg gcccgaagta tttcttatgc    960
```

-continued

```
ccccctctagc aggtggtcta ccagcatttg cactgaagaa ccggcattgt cagaggttgg   1020
gccaccagac ttagcaagca caaaagtacc cccggatgga gaaagcatgg aggaagggac   1080
accaggttcc tccgtggagt ctctggatgc tagtgtccag gctagtcctc cacaacagaa   1140
agacgaggaa acggagagaa gtgcgaaaga acttgtaaag tgtgactact gttctgacga   1200
acaggctcca cagcatttgt gtaaccacaa actggagcta gctcttagca tgattaaagg   1260
tcttgattat aagcccattc agagtcccag agggagcaag cttcctattc cagtgaaatc   1320
catcctacct ggagccaagc ctggccatat cctgacaaac ggagttagtt ccagtttcct   1380
taacaggcct ttgaaacccc tttacaggac gcctgtgagc tatccttggg agatttcaga   1440
cggacaggag ctgtgggatg atctctgtga tgagtatttg ccgatcgggt tccagcccgt   1500
gcctaaaggg ttacccacgc aacagaagcc ggacttgcat gagacccccta caacccagcc   1560
acctgtgtct gagtcccacc tggcagaact ccaggacaaa atccagcaaa cagaggccac   1620
caacaagatt cttcaagaga aactgaatga cctgagctgt gagctgaaat ctgcacagga   1680
gtcatctcag aagcaagata cgacaatcca gagcctcaag gaaatgctta aaagcaggga   1740
aagtgagact gaggagctgt accaggtgat cgaaggacaa aatgacacaa tggcaaagct   1800
tcgggaaatg ctgcaccaga gccagctcgg acagctccac agctcagagg gcattgcccc   1860
tgctcagcaa caggtagccc tgcttgacct tcagagcgct ctattctgca gccagcttga   1920
aatacagagg ctccagaggc tggtccggca gaaagaacgc cagctggcgg atggcaagcg   1980
atgtgtgcag ttagtggagg ctgcagccca ggagagagag caccagaagg aagctgcttg   2040
gaaacataac caggaattac gaaaggcttt acagcacctc caaggagaac tgcacagcaa   2100
gagccagcag ctccatgttc tggaggcgga aaaatacaat gagattcgaa cccagggaca   2160
aaacatccaa cacctaagtc acagtctgag tcacaaagag cagctaattc aggaactcca   2220
ggagctccta cagtatcgtg acaacgcaga caaaactcta gacacaaacg aagtgtttct   2280
tgagaaattg cggcaacgaa tacaagaccg agctgttgct ctagagcggg tcatagatga   2340
gaagttctct gctctagaag aaaaggacaa ggaactgcgg cagcttcgcc tagctgtgag   2400
ggaccgagac catgacttag agagactgcg ttgtgtcctg tccgccaatg aagctaccat   2460
gcagagcatg gagagtctcc tgagggccag aggcctggaa gtggagcagt taactgccac   2520
ctgccaaaac ctccagtggc tgaaagaaga actggaaacc aaatttggcc attggcagaa   2580
ggaacaggag agcatcattc agcaattgca gacatctcta cacgacagga acaaagaagt   2640
agaggatctc agcgcaactc tgctctgtaa acttggaccg ggtcagagtg aagtagctga   2700
ggaactgtgc cagcgcttgc agcgaaagga acggatgctg caggaccttc tgagcgatcg   2760
gaacaaacaa gccgtggagc acgagatgga gatccagggg ctgctccagt cgatgggcac   2820
cagggagcag gaaagacagg ctgctgcaga aaaaatggtc caggccttca tggaaaggaa   2880
ctcagaactg caggccctgc gccagtattt aggggggaag gaactaatga catcgtctca   2940
gacgttcatc tctaaccagc cagctggagt gacgtccatc gggcctcacc acggagagca   3000
aaccgatcaa ggttctatgc agatgccctc tcgagatgat agcacctcac tgactgctag   3060
agaggaggcc agcatacccc ggtccacatt aggagactcg gacacagttg cagggctgga   3120
gaaagaactg agcaacgcca aggaggagct cgagctcatg gccaaaaaag aaagagaaag   3180
ccagatggaa ctgtctgccc tgcagtccat gatggccatg caagaggaag agctgcaggt   3240
gcaggctgct gacttggagt ccctgaccag gaatgtgcag ataaaagaag atctcataaa   3300
ggacctgcag atgcaactgg tcgaccctga agatatacca gccatggagc gtcttaccca   3360
```

-continued

```
agaggtctta cttcttcggg aaaaagttgc ttccgtggaa ccccagggtc aggaagtatc   3420
agggaacaag agacagcagt tgctgctgat gttagaagga ctagtggatg aacggagtcg   3480
gctcaacgag gccctgcaag ctgagaggca actctacagc agcctggtca agttccatgc   3540
ccagccagag aactctgaga gagacggaac tctgcaggtg gaactggaag gggcccaggt   3600
gttacgcact cgactagaag aagttcttgg aagaagcctg gagcgtttaa gcaggctgga   3660
gagcctggcc gccattggag gtggggaact ggaaagtgtg caagcccgtc acaagcatgc   3720
cttctgagca ctggcgggtc acactgcgac ccaggatgga aaccctgttt atactaacca   3780
gaaagctgtg tcggacttga caaccaagtg tggcttacta atggtaacgg taggactgct   3840
gtcagtagca gcaaagggaa gcagctggag tcttccttac tccctgcacg gacctagttc   3900
ttagctaact gaggtcttga agcatactgc acatcttaaa tcattccatt ttaatttccc   3960
attcatactg ctcttctccc tggcctgtcc tcattccttt accccttcca tgggccaata   4020
aagtttactc ccccatctta ccacccccgc cacaagtccc acgtcatgtc atcaaatgca   4080
tgtgtgtgta ttatttttgc catccaatca aatcctgttc tttgaaagca atttttaatc   4140
aaataaagga atcaagtatg agttttaggt ttagaaagaa aggtagagag tcccgtgaga   4200
gtgagtctgg ggaggggtat aaaaccctac taaggataat cagaactaga caggagggtg   4260
tgggctgagc tcaggagcag agaccgttag tgttccaata aaatttgccc tcgaaggcct   4320
cttcagagtt gactgtctag ggaaagatga agtcagatca gtggacagca tggtctagtc   4380
cataaaagcc tatacaactc atgttcttca ctggcctagg gtttcttcaa gcctcaggca   4440
tggcctttag tcagaacatg actttaaaaa ccggtttccc aaatcagaat cctctagata   4500
aaaaatcatc ttctatgtga tatttcccac cctccttttt tttattattt tggttttgtt   4560
tttttggtat tttatttgtt tgtttgagac aggatatcac tgtggctggc ctgaaatgca   4620
ctgggtaaac cagactggca ttgaactcac agagatgagc ctgcttctac ctttgggtgc   4680
tgggattaga ggcatggctg ccacccctgc ctgtcagcat ccccccttaag agcaatagtt   4740
tccaggatcc ccagatcagg ggaagtataa ttcctggatg ctcattagga ggtgaagcgg   4800
gtggcgtcct tcattgacct ctgctttggt gggagtaatt cttgatagtg gagtaagaag   4860
acgatgtgag atgctgtcat gttcaggtca ctcagaagga ggccttagat ctcatgtagg   4920
ttttactcac cctctctgct ttcttgggac aacccgacag gtggggaggt ggtagattgt   4980
tcatttctag catcttaaat gtcaagaata ggaaaagtaa caggttactt gcaaggggct   5040
gtggattctg ccccagaacc tttcctagtg ctgaagggta tgagtaacgt aatccatgct   5100
ttccagcacc ctgagaaaga ctgagccccc ttcccgagct acactgagct ttcctttcct   5160
cttcttattt atttttattt ttttattttt ttgacaaggc acactacatc catgtgttga   5220
catggcatgt gttctaaatt ctattcaaga ttctgtaacc tcagctgtgt gacacacttt   5280
aactgatgtg tatccatcag cttgaagtgg acaggaggaa aatattctac cagagaagca   5340
cttgaaatct tctgatgaag tagttcacaa agattgatag ccatggcctt ccttataatg   5400
gatgtgctat tacagtttta caacctttag gggggaaagg actcatttaa tattaaagat   5460
agaagatgta gaagcagagc catccaatgt tcttagtaac cccattctaa gatactctaa   5520
ggcctgcctg aacaaacctt atgtaactaa caaggaagag cataatagag ttgagctata   5580
gacatgtcaa acaattaaag accagcctgt tagtcattac aaggcaatta ggaaatgtgt   5640
ttactcaact ttaccaatag acaacaaagt tctgcaaagc tgctattaag tttcaactct   5700
agtaatctct agggttctga gggctcacag tgattataat aatgaaggtt aataattagt   5760
```

gcaactgcca acctctaaca agagtaggtt gatagacaag taaattaaga gtttgttatc 5820
aattccataa atgtgactat aaaatctggt actgactttc tggtcctgat gctagaatga 5880
aggtggagac cttgctgcct ggagggaatg tgcttggccc acaagcttgt gcaataattt 5940
gacacctagc taccgaacac agttctgatg aattgtacag cgtgagccac aggtggatgg 6000
tactatgatt acacgtcatt catatcatat aattggattt agcatgctgt aatcttcatt 6060
tctctgtagg agtatggact atgttagaat gtgtctgcct ttgtttggat ttttttaata 6120
ttataataaa ataaacttag ttttaaaaca aaaaaaaaaa aaaaaaaaaa aaaaaaaaa 6179

<210> SEQ ID NO 35
<211> LENGTH: 2470
<212> TYPE: DNA
<213> ORGANISM: Mus musculus

<400> SEQUENCE: 35
ggcagcgagt gagcaccccg gttccactgt gccgcacccg cagcctgaag ccagcatgga 60
gaaggacagc ctgagtcgcg ccgatcagca gtatgagtgc gtggcggaga tcggcgaagg 120
cgcctatggg aaggtgttca aggcccgcga cctgaagaac ggcggccgct tcgtggctct 180
gaagcgcgtg cgagtgcaga ccagtgagga gggcatgccg ctctccacca tccgcgaggt 240
ggcggtgctg aggcacctgg agaccttcga gcaccccaac gtggtcaggt tgtttgatgt 300
gtgcacagtg tcacggacgg acagagaaac caagcttaca ctagtgtttg agcatgttga 360
tcaagacttg accacttact tggataaagt tccagagccc ggcgtaccca cagaaaccat 420
aaaggatatg atgtttcagc ttctccgagg tctggacttt cttcattctc acagagtagt 480
gcatcgtgat ctgaaaccgc agaacattct ggtgaccagc agtggacaga taaagctggc 540
tgactttggc cttgcccgca tctatagttt tcagatggcc cttacctcgg tggtcgtcac 600
gctgtggtac cgagccccag aagtcctgct ccagtccagc tatgccaccc ctgtggacct 660
ctggagtgtc ggttgcatct ttgcagaaat gtttcgcaga aagcctcttt ttcgtggaag 720
ttcagacgtg gatcaactag gaaaaatctt ggacatcatt ggactcccag gagaggaaga 780
ctggcctagg gacgtggccc ttccccggca ggcttttcat tccaaatctg ctcaacccat 840
cgagaagttt gtgacagata ttgacgaact aggcaaagac ctacttctga aatgcctgac 900
gtttaatcca gctaaaagga tatccgccta cggcgccctg aatcacccgt acttccaaga 960
tctggagaga tacaaggaca acctgaactc tcacctgcca tccaaccaga gcacctcgga 1020
gctgaacaca gcctgaggtt ccacggggat gcccatgagc tcgtcatctg aacacattgg 1080
cggctgcgag tcccctaagc aagcctctca gagcagttga agattgctgg ctgccaacct 1140
tctggctgcc agcttctggg tgggctctgc cttaccaagg aaaccaccta gtttactgtt 1200
cagagatcaa tgcaagggtg attgcagctt tatgttcgtt tgtacacttg tttgttttgt 1260
ctgtttgttt caagaacctg gaaaacttcc agaagaagag aagctgctga ccaattgtgc 1320
tgccatttcg ttttctaacc ttgaatgctg ccagtgtagg gtgggaatcc aggcccagct 1380
gagttatgat gtaatccgcc tgcagctgct gggcctgctt tggtacttgt gagtgtgtgt 1440
gcatgcgtat gtgtgtgtaa gagagaagag gaggggagag aaagacccct gatctcgtca 1500
agtgttactt ttttttgta gaaaacaaga ataattgagt tttaaagagt agaggtgact 1560
gatagtaaga agggcttgct cagtgaaagg tgattcacaa tggagtcttg ttaggaaggt 1620
tggacctaag tcctcagagt tgccttcctg tccaaaagct tttgctagca gtaaacaata 1680
aaggtttaga tgccacaaaa aatgggggga accgcaatat tttttaagag actttttaag 1740
gcatacatct tctatttact ctttggaaag ctgaacttaa tgtgtcccag gccctatata 1800
tagtacagta tgtacttaat tgtttctttg gggaaagatg ctataagtat cttattactt 1860
gcaatacatt taaggagtga gtgtacctca gataggtttt aaagatagag agcacctgtt 1920
ttctggtgtg agatgttatc attttcttca cgtctcttga taccttgata ccttgtcacc 1980
ttagggaatc acttcctgct ctgactagag gcgggaatac catctagctg tctccaccac 2040
ccaccatggc gcatctgcct tgtgctgcct tgtgtagtgc gaagctctca accaccagca 2100
cttctaattc attttcctgc cactgcctgg ctaacgacag atggcccagc tgccccaatc 2160
ccacacccgc ttgcacgctt accgtctttc accgaatgct ttgggcgtag gctcccattc 2220
cgaaacccta acagtatccc cttgtgcctt tgtaatacag tcttccccct gccgcagctg 2280
aggtcaccta ggcagtgaag agtgcttgtt ctgtgtgtgt atagactact accgactgtc 2340
acttggtgtt tcctatcttt aagtgtatgt tgtcagtgta atgtctgagg aaatgtcttt 2400
tcctctcttc tagagataac tacttactct ctaaagtgat ctctctgtct gtccgcagga 2460
tgtgtttctg 2470

<210> SEQ ID NO 36
<211> LENGTH: 3664
<212> TYPE: DNA
<213> ORGANISM: Mus musculus

<400> SEQUENCE: 36
cgacagggcg gcggcggcgg gggtgaggtg cgaggcgaag cgcagagcgc gcaactctgg 60
aggagcggat gttaagtcag agtacaacag aaaatgtcca ctgaacgaac ttcatggaca 120
aacctgtcca ctattcagaa aatagccctg ggcctaggaa ttccagcaag tgcaacagtt 180
gcctacattc tgtatcgtcg atatagggaa agcagagaag agagattgac atttgttgga 240
gaagatgaca ttgagataga gatgcgagtc ccccaggagg ctgtgaagct catcattggt 300
cgacaaggag ccaatattaa acagttgcgg aaacagacag gcgcgcggat tgatgtggac 360
acagaggatg taggcgatga gcgagtgctg cttatcagtg ggtttcctgt tcaggtgtgc 420
aaggccaaag cagcaatcca tcagattctg acagaaaaca ccccagtgtt tgagcaactc 480
tcagtccctc agagatctgt gggcagaatc atagggagag gcggtgagac gattcgttct 540
atctgtaagg cttctggagc caaaatcact tgcgacaaag aatcagaggg aacgttacta 600
ctctcacgac ttataaaaat ctcaggaaca cagaaggaag tggcagcagc taagcatctg 660
atactggaga aagtttcaga agatgaagaa cttcggaaga gaattgccca ttctgcagaa 720
accagagtcc cacgaaagca gccaatcagt gtgagaagag aggaagtgac agagcctggt 780
ggagctggag aagcagcttt atggaaaaat accaattcta gcatgggacc agctacaccc 840
ctggaagttc ctctccgcaa aggaggtggt gatatggttg ttgtaggacc aaaagaaggt 900
tcctgggaga aacctaatga tgacagcttt cagaattctg gtgcccagag cagtccagag 960
acgtccatgt ttgaaattcc cagtcctgac ttcagtttcc atgctgatga gtacctagaa 1020
gtctacgttt cttcctctga acaccctaat cacttctgga tccaaatcat tggttcccgc 1080
agcctgcagt tggataaact tgtcagtgag atgacccagc actatgagaa tagtctgcct 1140
gaagacttga ctgtgcatgt aggagacatt gtagcagcac ctttatctac aaatggttcc 1200
tggtatcgag cccgggttct tggaaccttg gaaaatggaa acttggacct ctactttgtt 1260
gactttggag ataatggaga ttgtgcacta aaggatctca gggctctcag gagtgacttt 1320
ctaagcctcc catttcaagc aatagaatgc agtctggcac ggattgcccc cacaggtgaa 1380

-continued

```
gagtgggaag aggaagctct agatgagttt gacagactca ctcactgtgc tgactggaag   1440
cccctggtgg ccaagatttc tagctatgtc cagactggaa tctcaacttg gccaaagatc   1500
tatttgtatg ataccagtga tgagaagaaa cttgatattg ggctagaatt agttcgtaaa   1560
gggtatgcag ttgaacttcc tgaagacatg gaagaaaaca gaactgtccc aaatatgttg   1620
aaggacatgg ccacagaaac agatgattct cttgcaagca tactcactga aacaaaaaag   1680
agccctgaag agatgccaca taccctgtcc tgcctcagct tgtcagaagc tgcctctatg   1740
tctggtgatg ataaccttga agacgactta ttctgaaatc tgggcttcag ctgctggatc   1800
agccatctgc tttgctgtga tgtggtgccg agagaggagt ctatgataga gagatccatg   1860
aagtccttta cttcacatgg tgtggcttgc tgtgaatcaa atccattttt tgtttcattg   1920
gatctaccag aaagtaacag acggaggcaa atggagacag atttctccac tccactcctc   1980
tggttcctcc cctatctttc aatgtttgaa tgctgtataa ttcccagcct ctccatatca   2040
ggttcagttc cctctgccag taatattttg cattactgct gggctatgtt tttgaggctg   2100
agaaacagcc aaggtttggg cattggaagt gatgattctg cagatttctg actcgactta   2160
tcaggtgact gtagttatag gaagtatttg gtggactcag aagactgcag ttatcaggag   2220
ataaggcaaa atcagcataa ctatatttaa aagcctcata aaaggggaag agtgtactac   2280
ctctcaccca cagttgccga ggttattgga gatgggtcct ccagctattt ctttgtgaac   2340
ttcagttaaa atacaactag aagggagaag tatcttagga aatgtgtaaa cgtgttacaa   2400
atatgtgtct gtatacacac aactagagag aaagaatgaa tatatatagt tctgcttaaa   2460
taatttgggg aatgtttgct aataaagttc tcaaaaatta tctaaaaaca catactcagt   2520
cacaacgtgg gagtaggcct gtgggtaaag tctcttctga gtaagccttg gtagtaattg   2580
ccagcacctc acatacggaa gcatcttgag acaaatgtcc ttcccataca agtattcaca   2640
ctcttcccgt aaagtcactg cagaagtcca ctactccctc agaaccataa ccagttttag   2700
ctatatacac aaacctactt acactgtaag agaaggcctg tactagggtt ctagaagtag   2760
gtcttcacta taaacttact ttacttctag tgtcttttca ttactgacag tagtgcaaga   2820
caccactgag acttgtgaca gtacttagaa ttaaatacaa aatgcatagt gatttaacga   2880
actttaggaa acaaggcaag gtgaactggg aaatctaaac tgaacacatg gatgccttat   2940
ataggcttct ctaaactcta gtattagtag ccatgcctgg tgtcccagac ctatacccag   3000
cctttgaggc tagtgagaga gagtgaaagt taaaggccat gcctaagcaa cttagtaaga   3060
tgctatctca aaaagaggct aggggtgtag ctagtggtat agtgtagcac ttgtgtcatt   3120
tgcagcatgc caagttagca gaaagacatc aaggaaggag cagtttgagc atctctttac   3180
tctagagaaa cctagacagg cccctattaa tgttccaggt tctgactgta gtgaaccatt   3240
taagtgtgtt cagccaggca ttggagttac tacacaacag actctggagg ccattttgtc   3300
tctagtttcc tcggtgctct tttccctcag ttagaggtca taagacctgt agttaattgt   3360
gtaaaaagcc tatttaaacc aattgtgtgg gactggaaag atgctcaaag gttaagaaca   3420
ctgactgctc ttgtagaaaa cccaggttca attctcacca cccacatggt gactcacaac   3480
catcttttaa ttctagttct aggggaccta gttctctctt ctaacttcta accaggtatg   3540
catatggtat acatatatac atgtaggcaa aacattcatc tacatgtcta aaatttgaga   3600
ataaaatttt gaaataaaat atggtacata cctaaaaaaa aaaaaaaaaa aaaaaaaaaa   3660
aaaa                                                                3664
```

<210> SEQ ID NO 37
<211> LENGTH: 1558
<212> TYPE: DNA
<213> ORGANISM: Mus musculus

<400> SEQUENCE: 37
ggcctccgga gctttgcttt gtcttccgta ggtcaaggcg ttggttctct ctctctcttt 60 tttttaata aataaagtgg aacctgactc acgactcacg agacgctatg acttgctcag 120
taccttcagg gtctccatgg caacggagcc atccagaaag ctgacagtcc caactcagac 180
cttggagtca gagaaatcac tgtcttcaag acagcaaaaa gagaaagaaa agttctgagc 240
cagtattaaa agggcacaaa accggggctg aagagatggc tcagcgcttt ggagtgactg 300
ctgttcttcc aggggatcct ggttggtctc ccagtaccca catggtggct cacaagcatc 360
tgtaagtaca gtttaacagg atctgacccc tgggagcatc atgtacatat gtggtactac 420
atctatgcag gcaagacact catacataaa aaataataaa ataaataagg caaaagaaag 480
caccacaatc aaatgtctta aaaataacca cacttttgga attgatccca aggaaataac 540
ctgggctaaa cttaaagact tatccatagg aatattaacc tcagcattga ttatagcaat 600
taaaaaaccc caggaatgtc tgatcagtgg ggctgattaa agctgacctg agaacttatg 660
cagcatcctt ctgtggtgga tgtcatggag acgttagaat ggtattgtca tatcaaggct 720
ctcagccagg gtctagggct cctggaatct ctgaaatcat gtgcataatt gtgtgggagt 780
gtgtgtattt ctggaaggaa gattctttgg gattctcaaa taggtacatg acccaagaga 840
gtaaaacagt cacttctgta gaaaataatc aaagcagaaa catgttgaca gcatattatt 900
aagggagaga gtgggaaaga taagttgaaa gcaactatga tatgatctta ttttattaaa 960
aataaaagtc ttatgtatac acctgtatag ggaaaacatg aaagtgttac tcaccaaagc 1020
agtaatcata gtggggcggc cattgtagtg gggaggcatg gcggctgagt gactcattgt 1080
ggggagcctg tacatctcgg tgagtcagga ggcagagaaa tgagcccaga aaaggggacc 1140
aggctacagc tctctgctag ccaacccagc tctctgctct ctgctgccgg gcccgaaacc 1200
agcatggaag gggacgttct ggacaccttg gaggcgctgg ggtataaggg gccactgtta 1260
gaggaacagg cactctccaa ggcagcagag ggtggactgt cttcacctga gttttcagag 1320
ctctgcattt ggttaggctc ccagataaag tccttatgca acctggaaga aagcatcact 1380
tcagctggga gagatgacct agagagcttc cagcttgaga taagtgggtt tttaaaagag 1440
atggcctgtc catactcggt actcgtctca ggagacatta aagagcgcct cacaaagaag 1500
gatgactgct taaacttctg ttgtttttaa gtacagaact tcaagcttta caaatatt 1558

<210> SEQ ID NO 38
<211> LENGTH: 977
<212> TYPE: DNA
<213> ORGANISM: Mus musculus

<400> SEQUENCE: 38
gcctgcccac ctcttgtgca gctgcctatc tgctgaggac tacctggtcc actcctcccc 60
tgctggaggt ccacagaagg accgagatat gtccacatgg gacaggcagg aatgaaagtg 120
gtatcctggc aagcaatgac tatgattagc caaggcccac tgggcccaac actaagcaaa 180
actcacgtag actgtgtaga agccctcttg gcactgcttc tagacagcct ctgcagcacg 240
gtgcccacct tgttacagtt ctcacctcac catctgccct caagatagcc aactcagggg 300
aactaggact tcaccgccca caaacaggat gtgtggtccc aatgccaacg ctcctcagac 360
aactgtaaaa gcacacacca ttgagtggca ctgccctgcc ggacattgtt ggcacccaac 420

-continued

```
aaactcccct cacagaccca ctcttgagcc aggccagtcc tatgggccaa gcctggtagt    480

atgttggtct ctaccaccac accagaggtc tttgagtcta cacagtgaac ggaatgtggt    540

aacttctagg tgccccgcac ttagcctagc acctttctta catgatctca agttgaaccg    600

acttccttaa ctctgctgtc ccctgtaatc ctaacttccc ttaggggaat tgggggctac    660

tggtggccac atcatgccta ttgaatgtct agcgtacagc acaacagtgc ctcttttaat    720

agcatgggca aggtctgttc tgtactgaag actctgtctc cacagtgctc atcggatgtg    780

ggtgtgtgta taaatgtata atatagattt atatatgttg ctatggctat atgttgaagg    840

ccaacatgat gtgcagactg atgggtgaga agacgctgag cagtctttct gatggctatt    900

aaagcaaact gtgtataaaa aaaaaaaaaa aaaaaaaaaa aaaaaaaaaa aaaaaaaaaa    960

aaaaaaaaaa aaaaaaa                                                   977
```

<210> SEQ ID NO 39
<211> LENGTH: 1089
<212> TYPE: DNA
<213> ORGANISM: Mus musculus

<400> SEQUENCE: 39

```
ccacgcgtcc gggcacacgc cggtaggatc tgcctcccag gtgctgagat tagacaccat     60

gcccggcttt ggtactttgt ggttttgctg tggttttgtt tgtcttgtgc ttctttacta    120

actatcattt ggaggttgtc aaaagcctcc atggccgtgt gtttcctctc tgccctcagc    180

taagcacaag agagacctgc agaatgcaag accttgagaa gttaaaccat gtggggaagc    240

ccgtggtttt ctgtgctgag tggtgtctga gctgatgaca ggtgacagtg ctgaggccac    300

accgacaggg acagggtccg aggaacggcc ctctcctcag tcccttctca ctttagcatc    360

cgagtttgtc cttagttctc attcttcatc cagttgctcc tcagcttttg tagggcatcc    420

agaattcaag ccatggctgg gagagagaaa gccatgtcct gccaagcacg gtgcccctgc    480

ctatgacttc agctattctg gagatggaag caggagagtc agctgagcct ggggatttgg    540

tactagtctg gcaaaagaga ccctgagagg gaatggggct gtcccaaagc aattggcctt    600

ctagcagtaa tgactatctg gagtattctc ttcccatctc ccacgagcac cagacacatg    660

ccagtctcac tggccagtag aaatggagaa ctgagaccct tagagacaaa cccactcacc    720

aaatctagca gtttctaagt atcccagtta gagatgcacc actaccaaca caaatgaaag    780

cgggaaccac cagccatctg aagagaagtg ttcccagcac ccacttacgg ccctggacat    840

ctagccctct gattgaggtt ggagttctgg gacaccctga gtagctcact gactatcact    900

acattagttg aatgcacttg atacattgtg gcctcctttc tgtcaagagc acactagata    960

gcaccaagca ctgcccaagt gtgacatact attcgaggtg aacagagctc ataatggaag   1020

tgtaaggtgt gccgctgtgt aatatttcta ataaatatat tttgtttctg cctcaaaaaa   1080

aaaaaaaaa                                                           1089
```

<210> SEQ ID NO 40
<211> LENGTH: 644
<212> TYPE: DNA
<213> ORGANISM: Mus musculus

<400> SEQUENCE: 40

```
cgctgctaca ggtccaaagt gacgaggcca gacgagactg aaccaagaca agtctttcat     60

ttccttagca tatttatccc agtgtggaag gctagctctg gggcagcgat tccttcggaa    120

ccatggtggc gtggctgtgg aaggtgctga tggcgtcgg tctcttcgcc ctcacccacg    180
```

cggccttctc agctgctcag catcgctctc atgcgcgact gacagaaaag aagtatgagc 240
cgctgccggc ggatatagtt ctccagaccc ttttggcctt tgcgcttacc tgttacggcg 300
tggttcatac tgcaggggac tttagagaca gggatgccac ttcggaacta aaggatatga 360
catttgacac cttaaggaat cgcccgtctt tttacgtgtt tcaccgttct ggctaccgac 420
tgttccagcg tccggattca acccattctt caaacctcag cgcgtcatct tctgacttac 480
cgttgaagtt ttgaaagctc aaatcaccgc accattcagc tttttaacga gttaagtaac 540
aggacagacg cagaattaag taccgggatt tgggatgtga aacaccccca acacatcagt 600
atttttactg atatttcaga cttaattaaa aaaaaaaaaa aaaa 644

<210> SEQ ID NO 41
<211> LENGTH: 3306
<212> TYPE: DNA
<213> ORGANISM: Mus musculus

<400> SEQUENCE: 41
ccacgcgtcc gcttgaagtc tagcttctcg ggggaagata agggggagtc aaaactctca 60
aatccgggcg gaggagagcc agacgaggtc accgaatgta aaagtcgccg gggttcggct 120
cagcccggcg aatcggctgg gcggggtggg gccgcgaagc cgcaaatcac cagttgaggg 180
ccagagagcg cgctgccggc tcagagctga gcctgcagcc gcccggccag gcagcagccg 240
gagcgggaca gccgtgcaca cccgccagcc gcaccagcct cttggcggac gcccgcggac 300
catgagccgc ccgagctccg agagcagctg cggtgaggtg agagcagccc ggcgctgaac 360
cgcaatcccg gactccgaac gcggcgcggg gagagttaag aatcatggct gcgggaaagt 420
ttgcaagcct tcccagaaac atgcctgtga atcaccagtt ccccttggcc tcgtccatgg 480
acctcctgag cagcaagtcc cctcttgctg agcgtcgcac agatgcctat caagacgtgt 540
ctatacatgg cactcttcca cggaagaaaa agggccctcc ttccatacgg tcctgtgaca 600
atgctggcca ctccaaatcc ccacgacaga gctcacctct gacccaggac atcatccagg 660
aaaacccact gcaagaccgg aaaggggaaa acttcatctt cagggatcca tatcttctgg 720
acccaactct ggaatacgtg aagttctcca aggagaggca catcatggac aggacccctg 780
agaggctgaa aaaggaattg gaggaggagc tgctgctgag cagcgaagac ctacgcagcc 840
acgcctggta ccacggccgg atcccccgac aggtgtctga aaaccttgtg cagcgggatg 900
gggacttcct ggttcgcgac tccctgtcga gccccggaaa ctttgtcctg acctgtcagt 960
ggaagaacct cgctcagcac tttaagatca accggactgt cctgcggctc agcgaggcct 1020
acagccgtgt gcagtaccaa ttcgagatgg agagctttga ctccatcccg gggctggtcc 1080
gctgctacgt gggcaaccgg cggcccatct cccaacagag tggtgccatc atcttccagc 1140
ccatcaatag gacagtgccc ctctggtgtc tggaggagcg ttatggcacc tccccgggcc 1200
gaggccggga gggcagcctg gctgagggaa ggccagacgt ggtgaagagg ctgagcctca 1260
ccacaggcag cagcatccag gctcgggaac acagcctgcc ccgaggaaac ctcctcagga 1320
ataaagagaa gagtggcagc cagcccgcct gcctggatca cgtgcaggac aggaaggcct 1380
taaccctcaa agctcaccag tcggagagtc acctgccaat aggctgcaag ctgccccccc 1440
agtctccgag tatggacaca agcccttgcc ccagctctcc cgtgttcagg actggcagcg 1500
agcccactct gagtccagca ctggtacgaa ggttctcttc agatgctagg acaggggagg 1560
cgcttcgggg atcagacagc cagctgtgcc ccaagccacc cccgaagccc tgcaaggtgc 1620
ccttcctcaa gactcccccc tctccatctc cctggctcac ctcagaggcc aactactgtg 1680

```
aactgaaccc tgcttttgct gtgggctgtg acaggggagc caagcttccc atgcaagccc   1740

acgacagcca cgagatgctg ctgacagcca aacagaatgg gccatcgggt ccccggaact   1800

ctggcatcaa ctacatgatc cttgatgggg atgaccaggc gagacattgg gatccactgg   1860

cagtgcagac ggatgaaggt caggaggaca agaccaagtt tgtgccacct ctcatggaga   1920

ccgtgtcgtc attcagaccc aatgactttg agtccaagct tcttcctcca gagaacaaac   1980

ccctggaaac ggccatgctg aagcacgcga aagaactgtt caccaaccac gatgccaggg   2040

tcattgcgca gcacatgctg agcgtggact gcaaggttgc taggatactc gaagtctctg   2100

aagacaggaa gaggagcatg ggtgtgagct ctgggttgga gctcattact ttacctcatg   2160

gacggcagct gcgcctggac atcatcgaga ggcacaacac catggccatt ggcattgctg   2220

tggacattct gggctgcaca ggcacactgg agaaccgagc gggtaccctc aataagatca   2280

tccaggtggc ggtggaactg aaggatgcca tgggagacct ctatgctttc tctgccatca   2340

tgaaagccct ggagatgcct cagatcacaa ggttagagaa aacatggacg gctctgaggc   2400

accactacac gcagacagcc atcctctatg agaagcagtt gaagcccttt agcaaaatcc   2460

tgcatgaagg cagagagtct acatatgtcc cagcaagcaa tgtgtcagtc cctctgctga   2520

tgccactggt gaccttaatg gaacgccagg ctgtcacttt tgaagggacc gacatgtggg   2580

aaaacaatga cgagagctgt gaaattctgc tgaatcactt ggcaacagcc aggttcatgg   2640

ctgaggcttc tgagagctac aggatgaatg ctgagaggat cctggcagat ttccaaccag   2700

atgaagaaat gactgagatc ttaaggactg agttccagat gagattgtta tggggcagca   2760

agggcgccga agtcaaccag aacgagagat acgacaagtt caaccagatc ctaacagccc   2820

tctcacggaa actagaacct ccctctggaa agcaggccga gctgtgagaa ccagctggag   2880

ggccttgggg cactccagtc ccactgggca tgcctgtcaa ctctaagtaa taacgagcag   2940

atctaacagg atacaagccg ctaacatcca caggatagta aatgtgtaaa ctgcacagag   3000

cacacttatt tatgaattgt ttaaaattac tactgatttt taaatgaatg gtaatttatt   3060

attaagataa ctattgctaa tgttgatcag caaacttaag acatagctat gttgctggtt   3120

gtttagtatc atggcatttg accatcttag ttttaattcc ttgtcagata aatgtaaata   3180

gaggcattta aaagaaaagc atgaaacatg gaagaaggta tcagttatat gatattcttt   3240

gaatatgaaa ctgtaaatag ttatgaatgg aaatatatct tttgtgaaa aaaaaaaaaa   3300

aaaaaa                                                              3306
```

<210> SEQ ID NO 42
<211> LENGTH: 4957
<212> TYPE: DNA
<213> ORGANISM: Mus musculus

<400> SEQUENCE: 42

```
ggcacgagct gagcagaaga ggttctcgcc gcacctagcc tttgcctggg cgcccgattc     60

ttctttgccg ctgggcctcg gccagaagcc acaacgggcg acacggagcc gccagtgctg    120

gagggggagc catgggtgcg gggcagcgtg ggggcagagg cccaggacgc ccgcccggcc    180

ccaggccccg ctcagccagg gcacccccac gggtgccctc cttcttggtc tgagcagtgc    240

gagtgtgcta gggagcccgg cggcggcggc ggcggcgtgg aaactggcgt gggctggggg    300

gtccgagccg cggggggcag tgccatgcac aagcaccagc actgctgtaa gtgccccgag    360

tgctatgagg tgacccgcct ggccgccctg cgccgtcttg agcctcctgg ctacggggac    420

tggcaggtgc cggaccccta tggccaagt gggggcaatg ggctagctc cggttatgga     480
```

-continued

```
ggctacagct cgcagaccct gccttcacag gcaggggcta cccccacccc tcgcaccaag    540
gccaagctca tccccacagg ccgagatgtg gggccagtgc cccctaagcc agtccccggc    600
aagagcaccc caaaactcaa cggcagtggc cccggctggt ggcccgagtg cacctgtacc    660
aaccgggact ggtatgagca ggccagccct gcacccctcc tagtgaaccc cgaggccctg    720
gagcccagcc tatcggtgaa tggcagtgat ggcatgttca agtatgagga gatagtactg    780
gaacggggca actctggcct tggcttcagt atcgcaggtg gcatcgacaa ccctcatgtc    840
cctgatgacc ctggcatctt tattaccaag atcattcctg gtggagcagc tgccatggat    900
gggaggctgg gggtgaatga ctgtgtgcta cgggtgaatg aggtggacgt gtccgaggtg    960
gtgcacagcc gggccgtgga ggcactgaag gaggcaggcc ctgtggtgcg gttggtggtg   1020
cggaggcgac agcccccacc tgagactatc atggaggtca acctgctcaa agggccaaaa   1080
ggcctaggtt tcagcattgc tgggggcatt ggcaaccagc acatcccagg agacaacagc   1140
atctatatca ccaagatcat tgaaggagga gctgctcaga aggatggacg cctacagatt   1200
ggggaccggc tgcttgcggt gaacaatacc aatctgcagg atgtgaggca tgaggaagct   1260
gtggcctcac tcaagaacac atcagacatg gtctatctga aggtggccaa gccaggcagc   1320
atccacctca acgatatgta tgctcccccct gactatgcca gcactttcac tgccttggct   1380
gacaatcaca taagccataa ttccagcctg ggttatcttg ggcagtgga gagcaaggtc   1440
acctaccctg ctccacctca ggtgcccccct actcgttact ctcctattcc cagacacatg   1500
ctggctgagg aagactttac cagagagccc cgcaagatca tcctgcacaa aggttctaca   1560
ggcctgggct tcaacattgt aggaggagaa gatggagaag gcatttttgt ttccttcatc   1620
ctggcgggag gcccagcaga cctaagtggg gagttgcgaa ggggagaccg gatcttatcg   1680
gtaaatggag tcaacctgag gaatgctacc cacgagcaag cagcggctgc tctgaaacgg   1740
gctggccagt cagtcaccat tgtggcccag tatagacctg aagagtacag tcgctttgaa   1800
tccaagatcc atgacttgcg ggaacaaatg atgaacagca gcatgagttc tgggtctggg   1860
tctctccgaa ccagtgagaa gaggtccttg tatgtcaggg ccctgtttga ttatgatcgg   1920
actcgtgaca gctgtctacc aagccaggga ctcagtttct cttatggtga cattctgcac   1980
gtcattaacg cctctgatga tgagtggtgg caagcaaggc tggtgactcc tcatggagag   2040
agtgaacaga tcggtgtgat ccctagtaaa aagagggtgg aaaagaaaga gcgagctcga   2100
ttgaaaactg tgaagttcca tgccaggaca gggatgattg agtctaatcg ggacttccct   2160
gggttaagtg acgattatta tggagcaaag aacctgaagg gagtgacatc caacaccagt   2220
gacagcgaaa gcagttccaa aggacaagag gatgctattt tgtcatatga gccagtgaca   2280
cgacaagaaa ttcactatgc caggcctgtg atcatcttgg gcccaatgaa ggaccgagtc   2340
aacgatgacc tcatctctga gttcccgcat aaatttggat cctgtgtgcc acataccacc   2400
cggcctcggc gtgataacga ggtagatgga caggattacc actttgtggt ttcccgggaa   2460
caaatggaga aggatattca ggacaacaag ttcattgagg cgggccagtt caatgataat   2520
ctctatggga ccagcatcca gtctgtgcgg gcagttgcag agaggggcaa gcactgcatc   2580
ttagatgtct ccggcaacgc cataaagaga ctgcagcaag cacaacttta tcccattgcc   2640
attttcatca agcccaagtc cattgaagca cttatggaaa tgaaccgacg gcagacatac   2700
gaacaagcaa ataagatctt tgataaagcc atgaaactgg agcaagaatt tggagaatac   2760
tttacagcca ttgtacaggg tgactcactg gaagagattt ataacaaaat caaacaaatc   2820
attgaggacc agtctgggca ctacatttgg gtcccatccc ctgaaaaact ctgaagaatc   2880
```

```
ccctccaagc attctcttgt gaacagaaga aatgaagccc ctcttccctc cttcctcttc   2940

attcctgtcc ccacggggag aacaaatgac tactgttctt gtcccccttt ttagatatgt   3000

caaaaattga gttttctagt cctgttcttt tttaaaaaat gttgttttgt tttggtttct   3060

ctttcgggat gatgccatct cactcatcac gtgaccgtgc ccattcctgc atggaccttt   3120

cccacgcgct agcacaggtg caaatccatc agagttgttg ttctcataaa cacccagcag   3180

aagcgaagag aagagaggag gactgatgga aagacagact ctggacaact gcacagcttg   3240

tgaagtgagc gaaacagccc acgtgaggag gcgctcccgg gcattcctac cctgtactgc   3300

ggcttgcagc tctgaacggt gcaacgtaac ggctacagaa aggatcttat ttatatatag   3360

atatatatat gtaatttata taaaatatat agaaattatt atatatatat attatacact   3420

cttctataat atatatatat atattcacat acattgggac tagaaaatct atggagacgt   3480

ccatcaacgg tactatgtta ttagagaaat gctttaattt tcatattcca atcagatgac   3540

atcttttgtt ccacctggtt gggaaggggt tgacaacagt agtaagtgct ataccaaagc   3600

actcgaattt ggtcattctc ttcagagcta aggcttgctc caggtggggc caacctacag   3660

cataagagaa ggggctttgg ctgggagctg gagattggag acgtgactaa agcagttgct   3720

gcccctgcag ggcagtcgtt cctgtgcaga aagagagaat gaatggctaa tgatgctccg   3780

gatgaaattg cctattgttt tatgccgcct gatgtgtctg catgagaggt ttccttttttg   3840

ttcattttta agctgctgtt aaaccaaaac catgttgtgc tactgtgtca gccttttcat   3900

tattccagat tttactttta ctatttaagt gaatgcgtag aatcctattt gccagtgttc   3960

taaaggcttg tgaggttctg aaggagccag gcctgggata cagcggtaac ttaggcctgg   4020

ccatccagtc aacagaggga aagcaggggc tggtgagggc agagagtaca agctggggct   4080

cggagttacc atgctggact tagctagggg ttccttcacg gggccactga caggcatagg   4140

gaggtgcttg ccttctggct cggtgctggg acagtggaag agcaccaggc ttggccagcc   4200

gtgtagtgag ttggatttgg attcttttct tttgcaactg ctccatttgc cctaccccag   4260

ccccctcacc aacagctggt agcttactgt ttcttcaaga agaaagtaga ctttaacgct   4320

gtaaatttga gctgtagagc taagactcgc ttactggtga gctgtgaaat cttgttgctt   4380

ttttcccaga gtctgatggc agtgactggt ccaggtagtt tccctcccgc agccagtgca   4440

ggcagcaggt gtggtccagg ccctacccca ccccactatg ctcctttgaa gccaacgtgc   4500

ctccctcacc tccacactgg agggatgacg caggggagaa catagaattg cttggccctc   4560

aactgggtta ggaccatcgc aggtgatgca gggttgacac tttaaagcac taccagccac   4620

attcaggaac tctgttcaca ggtatcctac cagcataatg aggctaactg tgactcgtgg   4680

ggcccagagt tagaagaaag aaaaggcagc agctttctct tgggcagtac actggattga   4740

aggcaaagag ggataaagtg acagatgatt gtgactctcg cgaggggggg tgagcgggaa   4800

gtgttgattc tctgatggta actgacagca gtggacagtg ctcaatcctc cctcccaggg   4860

aagaaaagca aagattcgaa gtaagcatga taatagttgg tttaccagtg ttccttccaa   4920

ggagacatat attttttaat aaatgatagt tgcaatg                           4957
```

<210> SEQ ID NO 43
<211> LENGTH: 847
<212> TYPE: DNA
<213> ORGANISM: Mus musculus

<400> SEQUENCE: 43

```
cccacgcgtc cgcaccacct tctcttcttt acggaataac tcaggtcacg ctgactggaa     60
```

```
atcagttgac tgacatcagt gaagcagtgg ttcctgagtt tgaagaaaag aggtctcctg    120
cctggacaga ggagtgtgtg cctttctcca agccgtctct ggacatatct tcccagcatc    180
ctctaacaaa gatgcgtcaa ctcaaaggga agccaaagaa agagacctcc aaggacaaga    240
aggagcggaa gcaggccatg caggaggcgc ggcagcagat caccactgtg gtgctgccca    300
ccctggctgt ggtggtgctc ctcattgtcg tgtttgtgta tgtggccaca cgccccgccg    360
tcaccgagtg agcacgtcca ttctgctttc ctctgcagag atgtccgaaa tgccaagctc    420
tgagcaggag tgccctgtct cctctggtct ttgacttgat caatatttct ctactttttt    480
ggggggtggg gtggggtggg gatagggaac attttatcag tgaatgtgcc atttacttga    540
tggtccactt catgtgcctt tcagacttca aagctgtgtg tgtgtgtgtg tgtgtgtgtg    600
tgtgtgtggc ccttttctc ctgaaatcga tgcatcgctg cccctgagga gagcctctct    660
gggtgatgct gttgggatca gagtcgccct cccatccagc agcatgcttc ccggctccac    720
ttcacaactt tctaagggga cagcctttct tctctgtgct tgatgggatt tgaaatatgt    780
tgactcaaag tgaaatattt attttttgaa taaaggagat aatagtctta aaaaaaaaaa    840
aaaaaaa                                                                847
```

<210> SEQ ID NO 44
<211> LENGTH: 7432
<212> TYPE: DNA
<213> ORGANISM: Mus musculus

<400> SEQUENCE: 44

```
acatcctctt ttggcttcca ggggtgactg cagggttttt ctctctcttt cacagtgagg     60
ggcctggggt gggctctgtc tgaaagactt ctgctttgga cgggtccctg ctgggttggt    120
ttgtgtttct ggaaacctca gtgcccctcc ggatggatgt aagcagattt tagggttgga    180
aggagctcaa agtcctggga agagcaacat tccagggcgc tctgaagcag ccttgagagg    240
cgggcttcac acactctcct gaacgacggg acaaatagga ggggttgtca ctgccactga    300
tagagactgg actggaaaag gtcgctacga attcttcgtg cggtagaaag tctccggagg    360
cgtggcgccc agaccacgcc tccggttctg attggctcct tcgaaacagg cggccgcgct    420
gggcgacgaa ctgcggcggc ggcggcggtt ggttgcaggc ttgctggcac gcacagattg    480
agcccgagtc gcccggagaa gtgatctcgc tcccgggctg gttccgagaa gttagcaccg    540
ttgtgcccgt atagatggtt tacgctggag caggagttga acccagatga atcccgtgct    600
ttgtactacc atagtgctgt tttgatgatt ccaagagcag agctttggag ccaacgctgc    660
cgcctctttt gggttttgac ggattatcac ggggaggtac atagaagttt catctcagtg    720
tagatgacca tgcagcctgc aatccaagtg tggtttgggg aagatctgcc tctaagtccc    780
aggtgtcccc tgactcccag acatggcccg ggactggctg acgtttgcca gtatgacgag    840
tggatagccg tgagacatga agccaccctg ctgcctatgc aggaagatct ctctatttgg    900
ttatctggct tactaggtgt tgacatcaag gcagaaagat tattggaaga gctcgataat    960
ggagtgctgt tgtgtcagct aatcaatgtt cttcagaaca tggtgaaagg ctgccactct   1020
gacgagccag ggaactttcc aatgagaaag gtgccttgta agaaagatgc tgcttcgggc   1080
tcattctttg ccagagacaa caccgccaac tttcttcact ggtgccgaca catcggtgtt   1140
gacgagactt acctctttga gtcggaaggt ttagttttac ataaagatcc cagacaggtg   1200
tacctttgtc ttcttgagat tggtcggatt gtgtcaagat acggagttga gccaccagta   1260
ttagtaaaac ttgagaaaga aattgagttg gaagagacct tgcttaatgc ctcggggctt   1320
```

```
gaagagtcca tcagcatccc caaatcctgc tgtcagcaag aagaactaca tgaagctgtt   1380
aaacacattg cggaggaccc tccttgtagc tgctctcatc ggttttctat tgaatactta   1440
tccgaagggc ggtaccggct aggggagaaa attctcttta taaggatgct tcatggaaaa   1500
cacgttatgg tccgcgtcgg tggaggctgg gatactctac agggattttt gctgaagtat   1560
gacccctgtc gaatactgca gtttgctaca ctagaacaaa aaattttagc atttcaaaaa   1620
ggagtttcta atgaaagcgt gccagattcg cctgccagaa cgcctcagcc tccagaaatg   1680
aacccctttgt cagcagttaa tatgtttcag aaacaaaatt taagacctgg cacaccagtg   1740
agtgttccga agaacaagga gaaacaggta cgtctaccag gtgcacgtct gcctgcatcg   1800
tcagtaaaag gtaatttggc ttccccgtct acccgggcta aacggccaga ttctccagca   1860
tcatttccac atcccaaggt gacatctttg aaggacgcag caaaaaagac gactgctcct   1920
tccaacagtg tatcgcagtc cctggcttct ccaaatccag ggtctaaacc aagcactgca   1980
cagtgtgcct cagagtcatc gcgaaaatgt gtcaccttcc ccaagactgc acagaccaag   2040
gctattccag cccagaattc aagagatctg tctaagtcca gacttttacc aagtaaatct   2100
cctggaaaaa tggaaccaaa gcatttgaaa cacaatcatc tttcttctag ggatgagtca   2160
cgtataaact tatcatccaa gtccccaaag ctacctaaag gagccatgca cggaaggcct   2220
aacccttctc ctttccagcc acctgccaaa gtgaccaagc ccagttctaa aaccggagcc   2280
ataggtctag ggacacagtc tcagccaccc actagaacgc cgaggtcagg agcagtctca   2340
gcacaaagac ttcagtctac attgaattta aacagtccag cttctgtgtg ctcagggtcc   2400
tctgcaaaag ctactcaggg atcgaaaggt aagaatacag tttcagttgc caaaaagcaa   2460
cctcagagta agggtgtctg ccggaatccg ggacctggct cttcaaagtc tcctggccgt   2520
accccgctgt ctattgtgac tgttccccaa tctgctacca agacagaaac tgtctcgaag   2580
tcagccaaga ctgccatgaa gggccagtac tcagctaaag ggcctcccaa aagcagcaag   2640
ccaccaactt ccttcaggga cccaccctca tctggtaagg gggcagacag cggagataaa   2700
atgcccactg ccaggaagaa ggaagaagat gaccattatt ttgttatgac cggaaataag   2760
aagcttagga aataaataca cttgtatcgt ttcagcaaat cagggtgatc aatgaatggc   2820
gagccacaag gatcaccaaa gatcttccta tttgtgtctg tccggagagc tgcagacatg   2880
aagtcaagat gggatgaagc tgggtcaggg aaaggaccca tgcattttgt gtatcaatgg   2940
acaaatgtgt gagttttgac ctgtatcatc ttgctaatga tgtctgctgt ttgagggaag   3000
tgtaaaagtc caagaacact actagaattt taactattgg tggtatattt ttgaacacag   3060
gttaactgtg gaggttatct gctaatagca actccgatac tcttaaacac tagttactgt   3120
gctcagccac aaagcaatgg tttgcttggc gctagtgtgt gcctgtaatc ccagctccga   3180
aggctgaggc aggggtacac agtagaagcc agcaaggttt tgaaatgtgc tgtaataggc   3240
acctaattta ttggtcagga atcctggtcc agcaatccta agtaccaatg gctcctgctg   3300
tttactttga tattattctg gattaaatgg aattcttact atttaaatct ctataatatt   3360
tccgtatcag aagggactat ttggtttttt aattaaactt ggctttttaa tactgtatca   3420
ttttataacc aatatttttg ataaaaagaa aaaaaaactc aaccaagtaa gttaacttat   3480
tgaatcataa gctgaaattt agtaagaatt aagtttttta aaaaaaaaaa atatatatat   3540
atataatcta gacactttgt atcttatatt tttagatgaa gtctgtgcag tgtgacaggg   3600
aaacatttaa tagcttttag catactaaga tattttaaat agacatttcc tatatgtaca   3660
tataaatttt ttcattaaaa taatgtgttt tgataccaga attaggtttt aatgatctta   3720
```

-continued aaattaaaag ggatgggggg tggctcaatg gataagtcat gtctagtaca ggcatgggga 3780
ttggagtttg tgtccccata cctacataca aatctgggtg ggcttgatgg tctgcctgta 3840
gtcccagcac tcaggaggaa gagacaggat ttcctgggac aagctggctg gcgagaggag 3900
ccgatggatg agaggcagct cttttgagag accaccccta ccttagtaaa aaaggaagat 3960
tcccaaagtc aatgtctgtt ctctctatgt acagactcat acatatatcc tgttcacata 4020
tgcacacaca cacacacaca cacacacaca cgcacacaca cctatgaatg catatataca 4080
cacagactca catacatgca tgcacaccac atatattgac gcgtacaaaa gattaagatg 4140
gtattaagag aacctttgtg tgatgctatg cacacatctc atcaggtgac ttgtatttct 4200
tttgctagca cactgtcgat tttaattagt ctccagatta tgttcatctt cattagtaag 4260
gccatgttgt gctcagtttt ccagtgccca gcagacagtg taccttctgt tctgtaggca 4320
gattctcgtc aggaatatcc aatgatttca tgacagcata aacaccttcc acccacaggg 4380
atacttgtaa atgatttatg tacaggcttg tcactattta aagtttatta atgtactttg 4440
ggaactttta agggtgttaa gtaactatgg tattaccagt tatcctaagt tgtaggaagg 4500
aaaagcaggt ctaagaggta cacgcttgta attccattac ttggaaagtg gaggcaggag 4560
gatcagaaat tcaaggtcat gttcagctat gcactagaga cacgcctcaa aaaaaattgt 4620
cactttgact cctcttttat aactcagatg ccctcccttt aaaatctgct ttccatcctc 4680
ctcctcttcc tttcttttct ttgtgagact gaggatctat ggtgtcttac attgatagat 4740
aagcattgcg actgagcttc ctcctcggcc ccttcaaata cggtttctaa cacaaacaaa 4800
atagttgacc cagacctgcc atcattgaat gagtgagcat cgtggctggc tgctggcatt 4860
ctctagacct acatacagca agagaacctt gggtaaagac cactggatct ttacccaagc 4920
agtatgcata aaatcaaaga tctactcagg atcccttaca acagaaaacc accaaaaact 4980
tgccaaacgt tccggttctg agcatcacta atggcaatat gtacatcttt gaaagcacct 5040
cttagcactc aaaagagatg ccaggggcat ttctgtaatc aggaatatct aacacacctt 5100
tcagagagga aggattgtag ctttagagag gctattccct catagagagg gccgccgaaa 5160
ctatttctag atcagtaact tctgagaatt aaaagaaaaa tataaattac actataggca 5220
gactaaacct atgactcagt acattgtaca gttttataaa cattatcttt tgtgctgggt 5280
aatcaagaat aaagatattc tcagacacct ggcacaaatt cccgaattaa ctttaggatt 5340
atttatttaa gataaagatt gggttttttg tttttgtctg ctgttcagta gcatttctcc 5400
aactgtagtc atatagggtg aatttctttg tgtgtgtacc ttgtctttcc taagcatagg 5460
ttgtatgtga ataagtaatt cagttccatg ggaactgaga gaacactcag caactcagaa 5520
cacttggtat tcttgcagag aacctgagtt ctatttccag cactcccggg gtggctcaca 5580
agcatccaga actcttgttt cagggtatct gatgctcgct tctggcctcc agaacacagg 5640
caccaggcat tcatattgca cacatacagg caaaacattc atacatgcaa tcaatcaatt 5700
agtaaatatc tttccctccc aaattaaaaa agttaaattc tttctgatgt attttggtat 5760
tttctaaagg agctgataaa tctttgccac aatttaaaaa acaagtataa tgcagttgta 5820
ctcacttctt tttactacta gtgtgaaatt acataaggtc tttttgtgtt taatatttaa 5880
taaaccaaat attaagcata aaatgctgat gtacctggaa gacacatgtg tggtttctta 5940
aaaatagaat gtttttgttt tggaatgctt tgctaatgtg taattatata aagctgaaca 6000
gggacgggaa gggatttttt tttttttttt ttttttaaga tttatttatt attttatgta 6060
agtacactgt agctgtcttc agacacacca gaagagggag tcagatcttg ttacggatgg 6120
ttgtgagcca ccatgtggtt gctgggattt gaactctgga ccttcggaag agcagtcggg 6180
tgctcttacc cactgagcca tctcaccagc ccatgaaggg attcttttta cactctgctt 6240
ctggggaggt gtttgaagag agcaccttcc caatgtatgg acttttagtg cccttggcct 6300
gtcatctcca caaagtctca tcacgcagat gcagcttgcc tggcattctc taggtagccc 6360
aggctggcct tgagctcata gcaatcctcc tgcctcagtc tcctgagtac tgggtttgca 6420
ggtttcgggt accacatcag cttgatttca taatggataa aggaatagtt tggagaaaat 6480
aatttcttct gcagtctttt ttatttctgt ctaatttaaa aatctgttac ttccttaaaa 6540
ggagctaata aaggttttga tgtattctta catccaagtt tcatgccatc tctgtgtcag 6600
tttggatttg tatatattct gttgtttttt aattgttgtt gttgtttcat gtcagcagta 6660
tttgtatcca acttaactta tattttctca agtattaaaa tgtcagcata aacccactct 6720
gtttgctttt ttaatgtatt ttaactgtgt tttgattatt tgacccatgt tggaaattgc 6780
atatatgaaa ctgataaatt aagagtttta aatattatgt tattttaaac atttttttat 6840
tgtattgttt ctcgatattg tttcagaaag accagactcg tggctaatta tctttgagat 6900
aatggaaatg atcagttatt aaagtcaaat tttataggac acaccaacac tgtgcttaca 6960
gaaagtcact gataatagaa tttcaaactt ccttttccca tagtcctgtt tcagggtcac 7020
actttgatac accgtaaatg tatttgaaat cctttttta atgttctttt atgaccagag 7080
caattattaa aatggagtta acctactatg tatttcctgg gctgtttcta agaataaaat 7140
cccaaatgaa gttttatgtt tgcctaactt tataagtgta aaaaatttaa gtgtaagtgt 7200
attttatgac attctggaaa agatgaggca cacttaaaac ctttttgggg taaatatgaa 7260
aacacagaca aatcttaagt ggttttacaa tatctatact gttaatgtag aaaacccaca 7320
atcttgaagg aataatgcaa agataatgtt ttctctttct acattaggtg ggaacaattt 7380
aagcactggt tggagatata gcctcagtac acaccaatta aaattaacct ct 7432

<210> SEQ ID NO 45
<211> LENGTH: 2024
<212> TYPE: DNA
<213> ORGANISM: Mus musculus

<400> SEQUENCE: 45
aagaggactc gcggcgggcc gcttcggctt cttctcgggc ctgctccctc ggcggcttcc 60
cgcgccttca gccggccacc atggggaaac gggataatcg cgtggcctac atgaatccaa 120
tagcaatggc tcgatcaagg ggtccaatcc agtcttcagg accaacaatc caggattatc 180
tgaatcgacc aaggcctacc tgggaggaag tcaaggaaca gctggaaaag aaaaagaagg 240
gctccaaggc tttggctgag tttgaagaaa aaatgaatga gaattggaag aaagaactag 300
aaaaacatag agaaaaatta ttaagtggaa atgagagctc atccaaaaaa agacagaaaa 360
agaaaaaaga aaagaagaaa tctggtaggg tgagcaaaag ttttctattt tctaaatgtt 420
acagctaagg gcctgtaaag caaagtaaga atgattgggt tttccttgta tgcgaacgct 480
aacttagact gtgggttcac cacgcagccc acaggtctct ctctctctct gacatgaaag 540
acgtgacaat gtcctcatag cctggtaacg tctctgctgc tgctactgag gacagtgttg 600
tcattgctgc acttgttgtt ttgttgagct tttgggggag ggaggagact tttatatttt 660
agcttctaaa tcctatgaat atggcatctg tttcttagac actagattga gttcactaag 720
tgcttgagag acttagtaaa agaaaccaat tcctgcatct cacaagcttt aattgttttg 780
tgcttggtca agtattcatc ttcttcttca tcgagctctg attcttccag cagttcttca 840

-continued

```
gattccgaag atgaggataa aaaacaaaca aaaagaagga agaaaaagaa gagccgttgc    900
cataagtctc ctgagagctc ggggtcggat tcggcttcag acagcaagga tggttcaaaa    960
aagaaaaaga agtccaagga tgtaactgaa agagaaaagg acactaaagg tctcagcaaa   1020
aagagaaaga tgtacgaaga taaaccgttg tcatctgagt cgctgtcaga gtcagactgt   1080
ggagaggtgc aagcaaaaag gaagaaaagc ggtgaagagc gtgagagaac aacagacaaa   1140
gccaaaaaga gaaggaagca taagaagcac agcaagaaga agaaaaagaa ggccgccagc   1200
tccagctcag actcgccgta gcgtccatga agaccaggac ccttacccag tgcagtgtca   1260
aaggagctca actgtgaaga ttgcgacaca cttagtaacg tgcatgaatt cccttgttct   1320
tagacttgtc ctggactagt cagtagccac ttggattctg ctgtgtgaag ggccatgatt   1380
gttgcctgct gcttcaacac cttttcctct tccagtgctt ggtgactctg ggagatagta   1440
ctttgcagtc atactagtga ttaagatatc tggaataaag ctaatatttt ttactagaag   1500
tacttaagaa taaatcaaca gaaactgaat ctggattcat cttttaagat gtaaccagaa   1560
aaaatgagat gactctagta aaaattttca aagtagggat tacattaata tttcagaatc   1620
cttactctgt agataagtat attttaattt tccccatgta tactttgatt tacttgggga   1680
aggagctttt aaagggggtg gtttgctatc tctttagcta ccagaacagt gtgcctttga   1740
tctcacacat cctactttta tggacacagt agccatgctt cctgggagga cagagctggg   1800
caccgtcatt cctgcccgac tgaggttatg acatccttag actttgttgt atgctgcttc   1860
gaatgaacca gagatacccg gccctttgca gcatgagaaa gcccccaaag ctctggaatt   1920
tacctccaca tcaataataa gtgaatgttt tcagggttaa aaaaaaaaaa aaaaaaaaaa   1980
aaaaaaaaaa aaaaaaaaaa aaaaaaaaaa aaaaaaaaaa aaaa                    2024
```

<210> SEQ ID NO 46
<211> LENGTH: 1213
<212> TYPE: DNA
<213> ORGANISM: Mus musculus

<400> SEQUENCE: 46

```
gcagccgagg ccgcgaactg catcatggag gtttcctgtg gccaagcaga aagtagtgag     60
aagcccaacg ctgaggacat gacatccaaa gactactact ttgactccta tgcccacttt    120
ggcatccacg aggagatgct gaaggatgag gtgcgcaccc tcacataccg caactccatg    180
tttcacaatc ggcatctctt caaagacaag gtggtgctgg acgtgggctc aggcactggc    240
atcctctgca tgtttgctgc caaggcgggg gcccgcaagg ttattgggat tgagtgttcc    300
agtatctccg attatgctgt gaagattgtc aaagccaaca agttagacca tgtggtgacc    360
atcatcaagg gcaaggtgga ggaggtggag ctgcccgtgg agaaggtgga catcatcatc    420
agcgagtgga tgggttactg cctcttctac gagtccatgc tcaacaccgt gctgcatgct    480
cgggacaagt ggctggcacc cgatggcctc atcttcccag accgggccac cttgtatgtg    540
acagccattg aggaccgaca atataaagac tacaagatcc actggtggga gaacgtgtat    600
ggctttgata tgtcctgcat taaagacgtg gccatcaagg agcccctggt ggacgtggtg    660
gacccaaagc agctggtcac caatgcctgc ctcataaagg aggtggacat ctacacagtc    720
aaggtggagg acctgacctt cacctccccc ttctgcctgc aagtgaagag gaacgactac    780
gtgcatgcgt tggtggctta cttcaacatc gagttcaccc gatgccacaa gaggaccggc    840
ttctccacca gtcctgagtc ccgtacacac cactggaagc agactgtgtt ctacatggag    900
gactacctaa cagtgaagac tggcgaggag atctttggca ccattggaat gaggcccaat    960
```

gccaaaaaca atcgtgactt ggactttacc atcgacctgg acttcaaggg tcagctgtgt 1020
gagctctctt gttccaccga ctaccggatg cgctgaggag gtgccaggct ggccctcctg 1080
cagaaggggg ctcgggggga tgggcttggg ggatgggggg gtacatcgtg actgtgtttt 1140
tcataactta tgtttttata tggttgcgtt tatgccaata aatcctcagc tgaccatgaa 1200
aaaaaaaaaa aaa 1213

<210> SEQ ID NO 47
<211> LENGTH: 700
<212> TYPE: DNA
<213> ORGANISM: Mus musculus

<400> SEQUENCE: 47
ggcgtccgag ctgaagcttc cccggcttcc caattgccca aggtaataat cttcagtagc 60
caagatgtct tcagcacctg atcctccaac agttaaaaaa gaaccattaa aagagaaaaa 120
ctttgaaaac ccaggcctcc gaggggcgca cacaaccacc ttatttcgag ctgtgaatcc 180
cgagctcttc attaaaccca acaaacctgt gatggctttt ggattggtaa ccctttcact 240
ttgtgtggct tacattggtt atctgcatgc aactcaagag aacagaaagg acctctatga 300
agccattgac agtgaagggc atcggtacat gaggagaaaa acatctaagt gggactaact 360
gctgcttcct tcaggtggag tgttattata ggctccgaca cctttgaaag aaagactgtt 420
agtgcacaga attgtttctt gttccataat atgttaacaa gggagaatat aaaattgaaa 480
gcagtccact gtggtgagtt tagtctcatt acagctgaag gcattaaatt ctgtataata 540
aaagtaccca gtactcttcc atttgcatgg agtttctaac gttttagagt ggattgtgcc 600
tttgcagcaa tgctttactg tttaggagag aagacaaccc cttcagttac taaaatcata 660
attaaatgaa agaataaaaa aaaaaaaaaa aaaaaaaaaa 700

<210> SEQ ID NO 48
<211> LENGTH: 1529
<212> TYPE: DNA
<213> ORGANISM: Mus musculus

<400> SEQUENCE: 48
gctcccaccc cctccccgcc tccgggccgt ggcactctgg ggctctgccg tcgacatggg 60
cgccgccgcg tgggcaccgc cacacctgct gctgcgggcg tctttcctgc ttctgctgct 120
gttgctgccg ctccgcgggc ggtcagcggg ctcctgggac ctggccggtt acctgctcta 180
ctgtccctgc atggggcgct ttgggaacca ggctgatcac ttcttgggct ccctggcatt 240
tgcgaagctg ctgaaccgca ccttggctgt acctccatgg attgaatacc aacatcacaa 300
gcctcctttc accaacctcc atgtgtccta ccaaaagtac ttcaaactgg agcctctcca 360
agcctaccat cgggttgtca gcctggagga cttcatggaa aatctggcac cctcccactg 420
gccccctgag aagcgagtgg catactgctt tgaggtggca gcccagcgaa gtcctgataa 480
gaagacatgt cccatgaagg aaggaaatcc ttttgggcca ttctgggacc agtttcatgt 540
gagtttcaat aagtcagaac tgttcacagg catttccttc agcgcctcct acaaagaaca 600
atggacccag agatttcctg caaaagagca tcctgtgctc gcactgcctg ggcccccagc 660
acagttccct gtcctggagg aacacaggga gctccagaag tacatggtgt ggtcagatga 720
gatggtgagg acgggagagg ccctgatcag tgcccacctc gtccggccct atgtgggcat 780
tcatctgcgc attggctccg actggaagaa tgcctgtgcc atgctgaagg atggaactgc 840
agggtcacac ttcatggctt cccctcagtg tgtgggctat agccgcagca cagcgacccc 900

-continued

```
tctcaccatg accatgtgcc tccctgacct gaaggaaatc cagcgggctg tgacgctttg    960
ggtgagagca ctgaatgcca gatcggtcta catcgccaca gactctgaga gctacgtgtc   1020
agagatccag cagctcttca aagacaaggt gagggtggtg agcctgaaac ccgaggtggc   1080
ccagatcgac ctgtacatcc tcggccaggc tgaccacttc attggaaact gtgtctcctc   1140
gttcactgcc ttcgtgaagc gggagcggga cctccatggg aggcagtcgt ccttctttgg   1200
catggacaga ccctcccagc ttcgggatga attttgatcc catctgaagc cccccacctcc  1260
caccctcaac caggcttggc tgctaaggat gctcctggga ttacacatcc cttttctttt   1320
ctgccagagg tggagaacag taccaaggac gtcctggaag agaaggcatt ccatcccagg   1380
cattggctcc catggtcccc agccagggct gctctgggct gcatgatcat gcacatacaa   1440
agcagcccac ctccagcctg ggcacaccct gatatataca catacataca cataatatat   1500
atcatatata tataaaaaaa aaaaaaaaa                                     1529
```

<210> SEQ ID NO 49
<211> LENGTH: 6001
<212> TYPE: DNA
<213> ORGANISM: Mus musculus

<400> SEQUENCE: 49

```
ttcctgcgga ggccgcggcc gccatgttgt tgtggggctg aggcggcgcc ggctgagagc     60
ccagcagccg tgacaggctg cgcaacaggt tcgctgcggc cggcctgacg actgacccgg    120
cggcggcggc cgcggcacgg cagggtcttc ccggagcttg gccgcgccca cgcgccggtg    180
tcgaggagcg cgcggggtcg cgccgggacg tgcgcgaggc gccagatggc tgagagctgc    240
aagaagaagt caggatcatg atggctcagt ttcccacagc gatgaatgga gggccaaata    300
tgtgggctat tacatctgaa gaacgtacta agcatgataa acagtttgat aacctcaaac    360
cttcaggagg ttacataaca ggtgatcaag cccgtacttt tttcctacag tcaggtctgc    420
cggccccggt tttagctgaa atatgggcct tatcagatct gaacaaggat gggaagatgg    480
accagcaaga gttctctata gctatgaaac tcatcaagtt aaagttgcag ggccaacagc    540
tgcctgtagt cctccctcct atcatgaaac aaccccctat gttctctcca ctaatctctg    600
ctcgttttgg gatgggaagc atgcccaatc tgtccattca tcagccattg cctccagttg    660
cacctatagc aacacccttg tcttctgcta cttcagggac cagtattcct cccctaatga    720
tgcctgctcc cctagtgcct tctgttagta catcctcatt accaaatgga actgccagtc    780
tcattcagcc tttatccatt ccttattctt cttcaacatt gcctcatgca tcatcttaca    840
gcctgatgat gggaggattt ggtggtgcta gtatccagaa ggcccagtct ctgattgatt    900
taggatctag tagctcaact tcctcaactg cttccctctc agggaactca cctaagacag    960
ggacctcaga gtgggcagtt cctcagcctt caagattaaa gtatcggcaa aaatttaata   1020
gtctagacaa aggcatgagc ggatacctct caggttttca agctagaaat gcccttcttc   1080
agtcaaatct ctctcaaact cagctagcta ctatttggac tctggctgac atcgatggtg   1140
acggacagtt gaaagctgaa gaatttattc tggcgatgca cctcactgac atggccaaag   1200
ctggacagcc actaccactg acgttgcctc ccgagcttgt ccctccatct ttcagagggg   1260
gaaagcaagt tgattctgtt aatggaactc tgccttcata tcagaaaaca caagaagaag   1320
agcctcagaa gaaactgcca gttacttttg aggacaaacg gaaagccaac tatgaacgag   1380
gaaacatgga gctggagaag cgacgccaag tgttgatgga gcagcagcag agggaggctg   1440
aacgcaaagc ccagaaagag aaggaagagt gggagcggaa acagagagaa ctgcaagagc   1500
```

-continued

```
aagaatggaa gaagcagctg gagttggaga aacgcttgga gaaacagaga gagctggaga   1560
gacagcggga ggaagagagg agaaaggaga tagaaagacg agaggcagca aaacaggagc   1620
ttgagagaca acgccgttta gaatgggaaa gactccgtcg gcaggagctg ctcagtcaga   1680
agaccaggga acaagaagac attgtcaggc tgagctccag aaagaaaagt ctccacctgg   1740
aactggaagc agtgaatgga aaacatcagc agatctcagg cagactacaa gatgtccaaa   1800
tcagaaagca aacacaaaag actgagctag aagttttgga taaacagtgt gacctggaaa   1860
ttatggaaat caaacaactt caacaagagc ttaaggaata tcaaaataag cttatctatc   1920
tggtccctga gaagcagcta ttaaacgaaa gaattaaaaa catgcagctc agtaacacac   1980
ctgattcagg gatcagttta cttcataaaa agtcatcaga aaaggaagaa ttatgccaaa   2040
gacttaaaga acaattagat gctcttgaaa aagaaactgc atctaagctc tcagaaatgg   2100
attcatttaa caatcagctg aaggaactca gagaaagcta taatacacag cagttagccc   2160
ttgaacaact tcataaaatc aaacgtgaca aattgaagga aatcgaaaga aaaagattag   2220
agcaaattca aaaaaagaaa ctagaagatg aggctgcaag gaaagcaaag caaggaaaag   2280
aaaacttgtg gagagaaagt attagaaagg aagaagagga aaagcaaaaa cgactccagg   2340
aagaaaagtc acaggacaaa actcaagaag aggaacgaaa agctgaggca aaacaaagtg   2400
agacagccag tgctttggtg aattacagag cactgtaccc ttttgaagca agaaaccatg   2460
atgagatgag ttttagttct ggggatataa ttcaggttga tgaaaaaact gtaggagagc   2520
ctggttggct ttatggtagt tttcagggaa agtttggctg gttcccgtgc aactatgtag   2580
aaaaagtgct gtcaagtgaa aaagctctgt ctcctaagaa ggccttactt cctcctacag   2640
tgtctctctc tgctacctca acttcttccc agccaccagc atcagtgact gattatcaca   2700
atgtatcctt ctcaaacctt actgttaata caacatggca gcagaagtca gcttttaccc   2760
gcactgtgtc ccctggatct gtgtccccca ttcacggaca ggggcaggct gtagaaaacc   2820
tgaaagccca ggccctttgt tcctggacgg caaagaagga gaaccacctg aacttctcaa   2880
agcacgacgt catcactgtc ctggagcagc aggaaaactg gtggtttggg gaggtgcacg   2940
gaggaagagg atggttcccc aagtcttatg tcaagctcat tcctgggaat gaagtacagc   3000
gaggagagcc agaagctttg tatgcagctg tgactaagaa acctacctcc acagcctatc   3060
cagttacctc cacagcctat ccagttggag aagactacat tgcactttat tcatactcaa   3120
gtgtagagcc cggggatttg actttcactg aaggtgaaga aattctagtg acccagaaag   3180
atggagagtg gtggacagga agtattggag agagaactgg aatcttcccg tccaactacg   3240
tcagaccaaa ggatcaagag aattttggga atgctagcaa atctggagca tcaaacaaaa   3300
aacccgagat cgctcaagta acttcagcat atgctgcttc agggactgag cagctcagcc   3360
ttgcgccagg acagttaata ttaatcttaa agaaaaacac aagcgggtgg tggcaaggag   3420
agctacaggc cagagggaag aaacgacaga agggatggtt tcctgccagc catgtaaagc   3480
tgctaggtcc aagcagtgaa agaaccatgc ctacttttca cgctgtatgt caagtgattg   3540
ctatgtatga ctacatggcg aataacgaag atgagctcaa tttctccaaa ggacagctga   3600
ttaatgttat gaacaaagat gaccctgact ggtggcaagg agaaaccaat ggtctgactg   3660
gtctctttcc ttcaaactat gttaagatga caacagactc agatccaagt caacagtggt   3720
gtgctgacct ccaagccctg gacacaatgc agcctacgga gaggaagcga cagggctaca   3780
ttcacgagct cattcagaca gaggagcggt acatggacga cctgcagctg gtcatcgagg   3840
tcttccagaa acggatggct gagtcaggct tcctcactga agcagacatg gctctgatct   3900
```

ttgtgaactg gaaagagctc atcatgtcca acacgaagct gctgagggcc ttgcgggtga 3960
ggaagaagac tgggggtgag aagatgccag ttcagatgat tggagacatc ctggcggcag 4020
agctgtccca catgcaggcc tacatccgct tctgcagctg tcagcttaat ggggcaaccc 4080
tgttacagca gaagacagac gaggacacgg acttcaagga atttctaaag aagttggcat 4140
cagacccacg atgcaaaggg atgcccctct ccagcttcct gctgaagccc atgcagagga 4200
tcactcgcta cccgctgctc atccgaagta tcctggagaa cactccacag agtcatgttg 4260
accactcctc cctgaagctg gccctagaac gtgctgagga gctgtgctct caggtgaacg 4320
agggagtccg ggagaaggaa aattcagacc ggctggagtg gatccaggca cacgtgcagt 4380
gcgaaggctt ggcagagcaa cttattttca actccctcac caactgcctg ggcccccgga 4440
agcttctgca cagcgggaag ctgtacaaga ccaagagcaa taaggagctg cacgccttcc 4500
tcttcaacga cttcctgctg ctcacctacc tggtcaggca gtttgccgcc gcctctggcc 4560
acgagaagct cttcaactcc aagtccagtg ctcagttccg gatgtacaaa acgcccattt 4620
tcctgaatga agtgttggtg aaacttccca cagacccttc cagcgatgag cccgtcttcc 4680
acatttccca cattgatcgt gtgtacacac tccgaacaga caacatcaac gagaggacgg 4740
cctgggtcca gaagatcaag ggtgcctcag agcagtacat cgacactgag aagaagaaac 4800
gggaaaaggc ttaccaagcc cgttctcaaa agacttcagg tattgggcgt ctgatggtgc 4860
atgtcattga agctacagaa ttaaaagcct gcaaaccaaa cgggaaaagt aatccatact 4920
gtgaagtcag catgggctcc caaagctata ccaccaggac cctgcaggac acactaaacc 4980
ccaagtggaa cttcaactgc cagttcttca tcaaggatct ttaccaggac gttctgtgtc 5040
tcactatgtt tgacagagac cagttttctc cagatgactt cttgggtcgt actgaagttc 5100
cagtggcaaa aatccgaaca gaacaggaaa gcaaaggccc caccacccgc cgactactac 5160
tgcacgaagt ccccactgga gaagtctggg tccgctttga cctgcaactt tttgaacaaa 5220
aaactctcct ttgagggcct ggggaagcca gaaccagggg agctgcccac aaggctgggt 5280
ctaaagacag attttgctct cccaggacag aggagcatca catggcttca tccatcaaac 5340
agccacactc gctgggcctg tattttattg cacactaaat tgctagcaat ctatgcaaac 5400
atgatctttt aaacaaacgc cacagcacag tgccttgtac tagtgttaac ctgttcagct 5460
gtgttagatg ccagggtttc cattttcagg gctataaaag tattatgtgg aaatgaggca 5520
tcagaccacc ggacgttacc acttggcaaa tctgtccact gtggagttgg tgatgttgga 5580
accattccac actatgtgac ctctgctggg tcacacactc aggaggtgaa gggctgagat 5640
gaaatgctgc agccttgggg cttgtgcagc ctgatactga aatagcatcc acttgtgcac 5700
tgaataaata gaaacttgat cgttttattc tgactagata ttatcattct ctgctaagac 5760
aatatagttt gaaatattat agtttgaata taaggaggaa agcttgatgt actttaaata 5820
tactgtgaac tctaataatg tggggatatt tttcaacttt aattttctta agtataaatt 5880
atttatgtaa attctttgtt ttgcatattt catagaacat gcatctttaa gctttatcat 5940
tgccaacaat gtacagaaag agaataaaag tataagttta tgaatgtaaa aaaaaaaaaa 6000
a 6001

<210> SEQ ID NO 50
<211> LENGTH: 1181
<212> TYPE: DNA
<213> ORGANISM: Mus musculus

<400> SEQUENCE: 50

```
caagtgggtg tagaggaggc tgagcgtgag cctcctcgtc tctctggggc agtcgcctgc     60
acgcagagac ctttcgctga cctcagcgtc ccgctgctgc gcaaggaagg gcggggccgc    120
tccggcctgg acagcgtcct aagccagtcc tctggaggcc gccgtagtcc gggggagtcg    180
gtggtcacat gacccaaagc tgtactatgg cttccaccaa accgctgtct cgtttctggg    240
agtggggcaa gaatatcgtc tgcgtgggga ggaactatgc agatcacgtc aaagagatgc    300
gcagcaccgt gctgagtgag cctgtgcttt tcctgaagcc gtccaccgcg tatgctcccg    360
agggctcacc ggtgttaatg cccgcttact gccgcaacct ccaccacgag gtggagttgg    420
gagtgcttct gggcaagcgt ggtgaagcga tcccggaggc tgcagccatg gactacgtgg    480
ccggctatgc cctgtgcctg gacatgactg ccagagatgt gcaggaggag tgcaagaaga    540
aggggctgcc gtggaccctg gctaagagct ttacgtcctc ctgcccggtc agtgccttcg    600
tgcccaagga gaagattcct gaccctcatg ccctaagact gtggctcaag gtcaacggag    660
agctcaggca ggagggcaaa acatcatcta tgatcttttc catcccctac atcatcagct    720
atgtttctaa gataataacc ttggaagaag gagatcttat cttgaccggg actccaaagg    780
gagttgggcc agttaaagaa aacgatgaga tcgaggccgg catagatggg gtggttagta    840
tgaggttcaa ggtgaaaaga tcagaatact gagagtagag tgccaaaggg gaagggagac    900
agaagcaagg gaaataaatg acactaataa tgaaaatcta aaaattatgc tagacatgtc    960
aaaaaagatg aatccttaaa aaataacgtg atctaaaaga gctgggacag aaatagaaac   1020
aggaacaacg aagctaaagg atatagaatg cttcccaaga gggcaatgtt aaactaaact   1080
ttgagaagtt gtagttttct tttctaaaac tgaactgaat agacttttca ataaatcatt   1140
ctgaagtcta aaaaaaaaaa aaaaaaaaaa aaaaaaaaaa a                       1181
```

```
<210> SEQ ID NO 51
<211> LENGTH: 1253
<212> TYPE: DNA
<213> ORGANISM: Mus musculus
<220> FEATURE:
<221> NAME/KEY: misc_feature
<222> LOCATION: (204)..(204)
<223> OTHER INFORMATION: n is a, c, g, or t

<400> SEQUENCE: 51
```

```
gctggagacc cggccctagt cgccggcccc accgccccgg ggcgccaatc gagacgacgc     60
ggccccgcgc ggcgcgagga ggagccatgg gcaagtgcag cggccgctgc acgctggtcg    120
ccttctgctg cctgcagctg gtggctgcac tccagcggca gatcttcgat ttcctgggct    180
accagtgggc tcctatcctg gccnacttcc tgcatatcat ggctgtcatc ctgggcatct    240
ttggtaccgt gcagtatcgg tcccggtatc tcatcctgta tgcagcctgg cttgtactct    300
gggttggctg gaacgccttc atcatctgct tctacctgga agttggacag ctatcccagg    360
accgggactt catcatgacc ttcaacacat ccctgcatcg ctcctggtgg atggagaatg    420
gtccaggctg cctggtgact cctgttctga actctcgcct ggccctggag gaccaccacg    480
tcatctcggt cactggctgc ctgcttgatt atccttacat tgaagccctc agtagtgccc    540
tgcagatctt cctagctctg ttcggcttcg tgtttgcctg ttatgtgagc aaagtattcc    600
tggaagagga ggacagcttt gacttcatcg gtggctttga ctcctatgga taccaggcgc    660
cgcagaagac gtcgcattta cagctgcagc ctctgtacac gtccggatag cttctgtccc    720
acccgcgtac agttttccct ggaccactgg agcctgaagc agtgctgtcc ggaggcgcgg    780
atcacgatag gcaggcgcgc ccctggtggc gcttaggcta actgcagctt gtgcagcctc    840
```

ctggatctgc agcccctgga gaaaatgcgg actctcaaga cttgaacttg gacctgaccc 900
tagctctagc aggacttcag ggttggggca ggacgggcag ggggggaggg ggaatcactg 960
ggtttgtatt ttttttaatc tcagccttgg tacgtgccgg ggtcttcctc tttcttcagc 1020
tctactcctt acctagtatc ttgccctcag tccaaacagc aagacagacc gaactcaccc 1080
catctcacct ctcattcacc tgccctgggg aaagatactg tgaactagaa gcaggagtcc 1140
tgggctccag ctacggcacc atcactgaca tccggtgtga catcgggccg agtctttgct 1200
tcctccgggc ctcagtttcc ccacatcaaa taattaaaat tatcccttag ttg 1253

<210> SEQ ID NO 52
<211> LENGTH: 4260
<212> TYPE: DNA
<213> ORGANISM: Mus musculus

<400> SEQUENCE: 52
acgatcgaac ggctcaactt tgcgaggtga ggtgtcaaaa agggaaaagt gaatgtggct 60
ttcgctccac ggggtgtgct gtcgtctggg gccgtcaggg agctcagccc ttgtgttgtg 120
ccagggtggg gtccagggtc tggcactgag gagggtagcc tgctggctga agtggcagag 180
cagtggcctt gatttgtctt gtggaagatt taaaaacaaa aaagcataaa tattctggtc 240
cttcagcaat gctttctctg aagaaatatt taacggaagg acttctccag ttcaccatcc 300
tgctgagtct gattggggtt cgggtggacg tggatactta cctgacctca cagctccccc 360
ctctccggga gatcatcctg gggcccagct ctgcctatac ccagacccag ttccacaacc 420
tgaggaatac cttggatggc tatgggatcc accccaagag catagacctg gacaattact 480
tcactgcccg gcggctcctt agtcaggtga gggccctgga taggttccag gtgcctacca 540
ctgaggtcaa tgcttggctg gtccaccgag acccggaggg gtctgtctct ggcagccagc 600
ccaactcagg cctcgccctc gagagttcca gtggcctcca agatgtgaca ggcccagaca 660
acggggtgag agaaagcgaa acggagcagg gattcggtga agatttggag gacctggggg 720
ctgtagcccc tcctgtcagt ggagacttaa ccaaagagga tatagatctg attgacatcc 780
tttggcgaca ggatattgat ctgggggctg ggcgtgaggt tttgactac agtcatcgcc 840 agaaggagca ggatgtggat aaggaactgc aagatggacg agaacgagag gacacctggt 900
caggcgaggg tgcggaagct ctggcccgag acctgctagt agatggagag actggggaga 960
gcttccctgc acagttccca gctgacgttt ccagcatccc agaagcagtg cctagtgaga 1020
gtgagtcccc cgcccttcag aacagccttc tatctcctct tctgacgggg acagaatcac 1080
catttgattt ggaacagcag tggcaagatc tcatgtccat catggaaatg caggctatgg 1140
aagtaaatac atcagcaagt gagattctgt acaatgcccc tcctggagac cctcttagca 1200
ccaactacag ccttgcaccc aacactccca tcaatcagaa tgtcagcctg catcaggcgt 1260
ccctgggggg ctgcagtcag gacttctccc tcttcagccc cgaggtggag agcctgcctg 1320
tggctagcag ctccacactg cttccactcg tccccagcaa ctccaccagt ctcaactcca 1380
cctttggctc taccaaccta gcagggcttt tctttccatc ccagctcaat ggcacagcca 1440
atgacacatc aggccctgag ctacctgacc cccttggggg cctgttagac gaagctatgc 1500
tggatgagat cagcctgatg gacctggcca ttgaggaggg cttcaacccg gtgcaggctt 1560
cccagctcga agaggagttt gactctgact caggcctctc cttggactcc agccatagcc 1620
cttcctctct gagcagctct gaagggagct cttcttcttc ctcctcctcc tcttcctctt 1680
ctgcttcctc ctctgcctct tcttccttct ctgaggaggg tgctgttggt tacagctctg 1740

-continued

```
actctgagac cctagaccta gaagaggctg agggtgcagt gggctaccag ccggaatact   1800
ccaagttctg ccgcatgagc tatcaggatc cttctcagct ctcttgcctt ccctacttag   1860
agcatgtggg ccacaatcat acatacaata tggcacccag tgcccttgac tctgctgatc   1920
taccaccacc cagcaccctc aagaaaggta gcaaggaaaa gcaggctgac ttcctggaca   1980
agcagatgag ccgagatgag cacagagccc gagccatgaa gatcccattc accaatgaca   2040
agatcatcaa cctgcctgta gaagaattca atgagctgct gtccaaatac cagctgagcg   2100
aggcccagct cagcctcatc cgggatatcc ggcgccgggg caaaaacaag atggctgcac   2160
agaactgccg caagcgcaag ttggacacca tcctaaacct agaacgtgat gtggaggact   2220
tgcagcgaga taaggcccga ttgcttcgag aaaaggtaga gttccttcgg tctctgcgac   2280
agatgaagca gaaggtccaa agcttatacc aggaggtgtt tgggcggctg cgggatgagc   2340
atgggaggcc ctactcaccc agtcagtatg cccttcagta tgctggggat ggcagtgtcc   2400
tcctcattcc tcgcacgatg gctgaccagc aggctcggcg acaggagaga aagccaaagg   2460
accggaggaa gtgagcctgg ggaggcaggg ggtggacgct cactaagacc gaaactggag   2520
aagggctggg cctggaccta acattgggga cttaaatgcc ttcttatcca atatatcttc   2580
tcagatggga tgactgcggg tcagtgcacc gaagaggcgg gcgcaggcgc tgtctggctc   2640
agctgccccc ttggggtggg cagggaggac cagactgctt gggtgattgg ggtccccagc   2700
ctattccctt tctcttgagg ggagggtagt gtcggcatgc tggaagtaga ggagctgtgt   2760
ggagtgaagg agagaaagtg tgggagatct cattgctgga aggagaaaag gaaggaatcc   2820
cccgaaaatc aaagcagtca gaaaaaccag agcgactgtt aagggctttg gccagctttc   2880
taggcagcga gtgcaggtga caacggtggt ctagggagag ttactggtat ggaacacaga   2940
catggcgggg ccccagaagg cctttgtaac tgtttcttca actcttgcat ccctgaaggg   3000
aagatgctct tggatgcacc tgtaatatct tagttactga atgggaagct gtaggggccg   3060
aggagggcag agggtatagg aagtgagaac gaggcctgtg tcgcagcagc ccagcatcaa   3120
gcatgtcaca cactgccctg ccacagccac ctccctccct ggccatccca gagccgaggc   3180
tcccactgtc ctcagagagc ctgcatggaa atgctgtcct cttccactct cctcctcttt   3240
ttgataccca ccctcactag ctgcctccag ctctggagtg gggtgctatt ctggcagtat   3300
ctggaacttg gcctacagct tcctctgcag ggtctaaaca gggaaggcac gtgtggagga   3360
gtggtcccag tgacatccag gcaccattca gcacaacact gggaagtgat tcttccctca   3420
ggcccctctg cctaccaaca cctgggctcc tcactggggg aaacaaaagc ctataaaccc   3480
cagcaacaaa acctagtcct cttagacgtt cttgcgcttt gattttttta gggcgtgtgc   3540
cctgttacac ttatagggcc taggatgctt gtgttgagta aaaaggagat gccccaatat   3600
tcaaagctgc taaatgttct ctttgccata aagactccgt gttaactgtg taaacacttg   3660
ggatttttct cctatgtccc gaggtctggt cttgatttct tttttgggtt tctttctagg   3720
aaaatgagaa gtgcatgcaa ggggcaggag atgaccctcc cctaggcttt cagcttcagg   3780
cagcttcttc acagcctgtt cagcctgggc tcctggagga cagccctggg ggaggcagtg   3840
aggggcagcg ccaagatagc caggtggttg gttccaggac cacagtgtct tttttttgtt   3900
gttggttttt tgttgttgtt gtttgtttgt ttgtttttta actgccactg ccgccccctg   3960
acccccaatc ttggtcagct ctggagtact gcctgcccca gacgagcagg ggttgggggg   4020
gagcactgat cctcctccct gggcagggca gagggctttc ctaaccgagc agtagggata   4080
gaaagcgtga gcctgggagt gctttttata aattattttc cttgtagatt ttatttttaa   4140
```

tttatctctg tgacctgcca gggagaggag agaaagaaat gctgtgagca catgacaaaa 4200
taaaatcaaa taaaatggaa aaaaaaaaaa aaaaaaaaaa aaaaaaaaaa aaaaaaaaaa 4260

<210> SEQ ID NO 53
<211> LENGTH: 1872
<212> TYPE: DNA
<213> ORGANISM: Mus musculus

<400> SEQUENCE: 53
cccacgcgtc cgcgcgtttt acccggagca tggcggatac cggcttgcgc cgcgtggttc 60
ccagcgacct ttatcccctt gtgctcagat ttctgcggga tagccaactc tcggaggtgg 120
ccagtaaatt tgcaaaagcg accggcgcta cacagcagga cgccaatgcc tcgtccctct 180
tggacatcta tagcttctgg ctcaagtcca ccaaagcccc aaaggtgaag ttacagtcaa 240
atggaccagt gaccaagaag gctaagaaag agacttcatc cagtgacagc agtgaggaca 300
gcagtgagga cgaggacaaa aaagcccagg gacttcccac acagaaggct gccgcacagg 360
tcaagcgagc cagtgtgcct cagcatgctg gaaaggcagc agccaaagct tcagagagca 420
gcagtagtga agaatccagt gaggaagagg aagaggacaa aaagaaaaag cctgtccaga 480
aggcagctaa gccccaagcc aaggcagtca gacctcctgc gaagaaggca gagagctctg 540
agtcggactc agactcggat tcggactcca gctcagagga agaaacacca cagacccaga 600
agccaaaggc agctgtggca gcaaaagctc agactaaagc cgaagccaaa ccaggtacac 660
cagcgaaagc acagcctaag gtagccaatg gcaaagcagc cgccagcagc agcagcagca 720
gcagcagcag cagcagcgat gactcagagg aagagaagaa ggcagctgca cctcccaaga 780
agactgtacc aaaaaagcaa gtcgtggcca aggccccagt gaaagtagct gccgccccca 840
cccagaagag ctccagcagt gaggattctt ccagtgaaga ggaggaggga cagagacaac 900
ccatgaagaa aaaagcaggt ccctacagtt cagttccacc accctctgtt cctttaccaa 960
agaagtcccc gggaacccag gctccaaaga aagctgctgc gcagacacag cctgcagaca 1020
gcagtgacga cagcagtgac gattctgatt caagttctga ggaagagaaa aaacctccag 1080
ctaagacggt cgtctccaag acacccgcca aagcagctcc agtgaagaag aaagcagaaa 1140
gctcttcaga cagctcgggt aacgctgccc agagctctgg gctgctgggg tactcactgc 1200
cttgggctgc tcttacaggg ctcccctgag gttgattttg gggagctgtt cattctgtct 1260
cctctctcta gattctgaca gttctgagga tgaagctcct gccaagccag tcagtacaac 1320
caagagtccc aagccagctg tcactccgaa gccatctgca gcaaaggcag tgacaactcc 1380
taagcaacct gcaggcagta accagaaacc tcagagcagg aaggctgaca gcagctccag 1440
cgaggaggaa agcagctcca gcgaggagga ggaggcctcc aagaaaagtg ccacaacccc 1500
caaggccaag gtgactgcta aagcagcacc cgccaaacag gcccctcagg ctgctgggga 1560
cagcagctct gactcagata gttccagcag tgaagaggag gagaagactc ctaagccccc 1620
agctaagaag aaggcagcag gtggagccgt ttctacacca gcccctggga agaaagcaga 1680
ggccgagagc agcagcagca gcagcagcag ctctgaagat tccagtgaag aggagaaaaa 1740
aaagaagccc aaagctacta cccctaaaat acaggcaagc aaggccaatg gcactccagc 1800
ttctctgaat ggaaaagcag ccaaggaaag tgaggaggaa gaggaggagg aagaaacaaa 1860
aaaaaaaaaa aa 1872

<210> SEQ ID NO 54
<211> LENGTH: 3435

<212> TYPE: DNA
<213> ORGANISM: Mus musculus

<400> SEQUENCE: 54
aagcagagcc tgaagtgcga gtgtgggagc cggggcccgg gagggaaagg tcgccacgat 60
gaacaccgtc ctgtcgcgcg cgaactccct gttcgccttc tcgctgagcg tgatggcggc 120
gctcaccttc ggctgcttca tcaccaccgc cttcaaagac aggagcgtcc cagtgcggct 180
gcacgtctcg cggatcatgc taaaaaatgt agaagacttc acgggcccta gagaaagaag 240
tgacctggga ttcatcacat ttgatataac agctgatcta gagaatatat ttgattggaa 300
tgttaagcag ttatttcttt atttatctgc agagtattca acaaaaaata atgctctgaa 360
ccaagttgtc ctttgggaca aaattgtttt gagaggtgat aatccgaagc tacttttgaa 420
agatatgaag acaaagtatt tcttctttga cgatggaaat ggcctcaagg gaaacaggaa 480
tgtcactctg acgctctcct ggaacgttgt accaaacgct ggaattctac ctcttgtgac 540
aggatcggga catgtgtctg tgccatttcc agatacatac gaaataacca agagttacta 600
aattattctg aatttgaagc atatttttat acatgttgaa ttgcatctca tctcttcccg 660
gtttcttcat tgattttttt ttttcttttt ttttttcctt ttttgtttgg atgtaagaaa 720
aactcacgtc agaagacgca gttgaagtga aaggttctga gctgcttaag cttagctttg 780
taaacagaca gaaaaagcct cccagaggag agtagttatg aagaacgagg caactgcata 840
ggaagaatct atcagcagtg tagggttgaa acacgtattt atattatctt acggaataca 900
aaatgatcat aaagggctgt tagacattca ggtgtcataa gaattctgaa ttgtatcctt 960
tgtgttcatg caaggcagtt gtgacttact catgggcatt ctcttatatc tctaagtgta 1020
tacacttaga gatcctaagt gtagatgact ggaaactaga tgaatgtggt tctttgaagt 1080
ctggtttaca aacgagcaga gtggtataat tgtatcccat ttcttttaca aagcccaatc 1140
atgcttgctt ttcttaggtg agtagcagct tctccaaatg aagaggaaga acctgtttgt 1200
atgctgaaaa atctagcagg ctcattttaa agtttcaacc cagccaaatg tgtatctttc 1260
agtcttttca gagtgtttct ttgtgtattt ctttaaaatt ttacctttgc catgcaaagt 1320
tgaaaatgtt tgcatggatt tcctcctgaa ctgaattggt cccactgagc ttgcctctgt 1380
ggttaagtac agtttgcata gctccatact tttacagttg gaacagtagg gacagctgtc 1440
agtgcttttc cacccacagg tttctctcct gtgttgagtg ttgtcttgag tgatcctaat 1500
gaggtagaga gtacaaatgt tagctctttg caggtgaaga aactgaaacc cagaaactta 1560
ctgacttgca cccaaattaa aaagcaagca gtggtcttgt tttatacctc agtttacaca 1620
ttggtcacat tcatataatt ttattgtagt tcattactct cattttcctt ctgggaatga 1680
gagtttgaaa ctaattttct agcagccaac aacttacaca gtgatatctt tgtgtatatt 1740
catttttacc catattaaaa taactatata gatttgtaaa ataatttaga gattaaatat 1800
gttgtatatg attgaatatg taattgtatt tgacatgaaa tttattttcc tcattgataa 1860
atactctcag aattagcatc tgcatcttgg ctactcttaa atgcaagagt agacactacg 1920
cacattctaa agtaacctaa aagggctgtt tactagcaat agcataaatt agcatttgtt 1980
ctgtttacct catgtgctta gtgacattca tcaaacagct cttgtatgtg gtggtacagt 2040
tcttacaaat gcatgtgttt gaggttttct taccagcaga aaggtcagag gcgcaccttg 2100
agattggcac cagcacgttc cttaaacatt tcggggtctc tgtttctttg tctataaaag 2160
gatcctttac taggatagaa agttgtgata tgttttctgt tcagcagatt tcgaacagga 2220
aaccacctta gtgatctgaa gtcagaaaag tgatggaaag attaacagag ttcataagga 2280
tctgagcttc tgctacattt tacacctaca aaagtgagct ttatacatcg atgagatagt 2340
agatgtgtaa agtctgcaag cgtcagagtt agagggtctg ggtgtgtcct agctaaggaa 2400
gccctcccaa gcctagggca ttaaagccac acctcagttc agttaacagt tcactgtacc 2460
tttgtgatga gtggctatgt tggttgagca cagactatct aacactgaca tttatgtatc 2520
tgaaaagccc agttcaggtg tttggtaagg aaagcccaat atggcaaatg gcctttgttt 2580
ttagcagctg agggagcagc tgctccggca tgccactagc cctgtctctc aggaactcca 2640
ttgcgtgcgt gcacggcttt atcagtctgt gatgatgctg taacttgcaa agttcgtatg 2700
tgtgataagc atctctggtc tcagtgtttt agagaagact cagtgcttca gtggctgagc 2760
ccagaggtga ttctatgaaa agaagatgat tgcaagagtg ttagtaaaga ggttgcagtt 2820
agaaatgaac ttgaacatgt agcacccagc gtatccctct cagtcttaac tagacaactg 2880
tgtgcttttg tgtctggccc tattgcattt actgtgctca tgctgaaagg aaagtaacag 2940
ctttagaaac tgttgaaaat aaaataggaa aacaggctgg gttgaattcc tttgctggga 3000
attgttttac agctcttcag tggtctttct agccagttat tcctgtgaag aattggactt 3060
tgaggagcta aagctttgaa tgggggctgg tgcaggggcc tgggagtgga gagtctgctt 3120
tcagatactt taacctcgga gctgtgacct ttgattgtag caaacatcga tttcaaaagc 3180
ttcttttgct ttcagtcaca agcctgcgta ccttactgcg agactgccaa tgcttcaaag 3240
atgtatgttt gaaaaagttc tttcatagtt tttatgaaat ttgggaagtt gtttacttaa 3300
acaaatgcac aagaaaataa ttcataaaaa tactgaatat atatgtgcaa aatttttctt 3360
agctacaata aatgttcaac atttttctaa taaagatttt ttttctgagt aaaaaaaaaa 3420
aaaaaaaaaa aaaaa 3435

<210> SEQ ID NO 55
<211> LENGTH: 2086
<212> TYPE: DNA
<213> ORGANISM: Mus musculus

<400> SEQUENCE: 55
caggttttga aatcacctgg ggatttcttg ggtgcggggt ggaccttagg gagaacagaa 60
agcagagctg gctgcagcca ttactggcct cgggcgggcg gccacagagg cagttgaagt 120
gaaagtgaaa gagaaacgat aagagaacgg agaccacagg tgctaagtga gggtgctcac 180 agaacccccct cttcagccag agatcactag caggggaact gtggagaagg cagccagcaa 240
ggaagagcct gagagtagcc tccatgggct tggagcccag ctggtatctg ctgctctgtt 300
tggctgtctc tggggcagca gggactgacc ctcccacagc gcccaccaca gcagaaagac 360
agcggcagcc cacggacatc atcttagact gcttcttggt gacagaagac aggcaccgcg 420
gggcttttgc cagcagtggg gacagggaga gggccttgct tgtgctgaag caggtaccag 480
tgctggatga tggctccctg gaaggcatca cagatttcca ggggagcact gagaccaaac 540
aggattcacc tgttatcttt gaggcctcat tggacttggt acagattccc caggcagagg 600
cgttgctcca tgctgactgc agcgggaagg cagtgacctg cgagatctcc aagtatttcc 660
tccaggccag acaagaggcc acttttgaga aagcacattg gttcatcagc aacatgcagg 720
tttctagagg tggccccagt gtctccatgg tgatgaagac tctaagagat gctgaagttg 780
gagctgtccg gcaccctaca ctgaacctac ctctgagtgc ccagggcaca gtgaagactc 840
aagtggagtt ccaggtgaca tcagagaccc aaaccctgaa ccacctgctg gggtcctctg 900
tctccctgca ctgcagtttc tccatggcac cagacctgga cctcactggc gtggagtggc 960

```
ggctgcagca taaaggcagc ggccagctgg tgtacagctg gaagacaggg caggggcagg   1020
ccaagcgcaa gggcgctaca ctggagcctg aggagctact cagggctgga aacgcctctc   1080
tcaccttacc caacctcact ctaaaggatg aggggaccta catctgccag atctccacct   1140
ctctgtatca agctcaacag atcatgccac ttaacatcct ggctcccccc aaagtacaac   1200
tgcacttggc aaacaaggat cctctgcctt ccctcgtctg cagcattgcc ggctactatc   1260
ctctggatgt gggagtgacg tggattcgag aggagctggg tggaattcca gcccaagtct   1320
ctggtgcctc cttctccagc ctcaggcaga gcacgatggg aacctacagc atttcttcca   1380
cggtgatggc tgacccaggc cccacaggtg ccacttatac ctgccaagtc gcccacgtct   1440
ccctggagga gcccccttaca accagcatga gggttttgcc aaatccagag cagagaggaa   1500
ccttgggagt catctttgcc agcatcatct tcctttctgc gctgttgttg tttctgggac   1560
ttcacagaca gcaagcttct tcgtcaaggt ccaccaggcc tatgaggcat tctgggtagc   1620
cgcctgcctg cctccgaata caaagtaaag tactccacat cctggctact taaaggaccc   1680
cgtgtgaggt gtggggctga gctgggcctg aaggtgccag cacattggga gtgcagtact   1740
ggccctggac tgtacaagtc tctgctttct gtgctattga gaagagagcc ctgggctgat   1800
gaaaagggac aggacaagag gatggcagaa ttatcaaagt ggaagctaac accatctatg   1860
tgaggtatta agaaattggg ggtgggggct ggtgagatgg ctcagtgggt aagagcaccc   1920
gactgctctt ccgaagatct ggagttcaaa tcccagcaac cacatggtgg ctcacaacca   1980
tctgtaacga gatctgactc cctcttctgg agtgtctgaa gacagctaca gtgtacttac   2040
atataataaa taaataaatc taataaaaaa gaaaaaaaaa aaaaaa                 2086
```

<210> SEQ ID NO 56
<211> LENGTH: 1825
<212> TYPE: DNA
<213> ORGANISM: Mus musculus

<400> SEQUENCE: 56

```
gtgctttgtg cttgtggagg aacctaagcg gaacttagac acagggagaa tgaggctctg     60
gaccttgggc accagtattt tcctgaggct ttgggggact tatgtgtttc cacgaagccc    120
tagctggctg gacttcatcc agcatttggg agtctgttgc tttgtggcct tcctttcggt    180
gagcctcttc tctgcagcct tttactggat cctgccaccc gttgccctgc tctcttctgt    240
ctggatgatc acctgtgttt tcctatgctg ttccaagcgc gcacgatgct tcattcttct    300
ggccgttctg tcgtgtggcc tccgtgaagg taggaacgct ttgattgcgg ctggcactgg    360
ggtagtgatc tttggacatg tggaaaatat tttttataac ttcagaggtc tcctagacag    420
catgacttgc aacctaaggg caaagagctt ttcagtacat ttcccacttt taaaacggta    480
tactgaagcc atccagtgga tttacggcct tgccactccg ctgaatctat ttgatgacct    540
tgtttcttgg aaccagactc tggtggtctc tctttttagt cccagccatg ccctggaggc    600
tcatatgaat gacactagag gagaagtcct gggagtcctg caccatatgg tggtcacgac    660
agagctgttg acttccgtgg gccagaagtt gcttgccctt gccgggcttc tgctcatcct    720
agtcagcact ggcctcttcc tgaagcgatt cctgggccct tgtggctgga agtatgagaa    780
tgtctacatc accaaacaat ttgttcggtt tgatgaaaag gagaggcacc aacagcggcc    840
ctgtgtcctc ccgctgaata agaaggaaag gaagaaatat gtcatcgtcc catctttgca    900
gctgactcct aaggagaaga aaacccttgg gctgttcttc cttcctgtcc tgacctatct    960
ctacatgtgg gtgctgtttg ccgctgtgga ctatctgctg tatcggctca tctcctccat   1020
```

gaacaaacag ttccaaagct tgccagggct ggaagttcac ttgaaactac gtggagagct 1080
taaaattctc gtgtcagtct ccttctaccc caaagtggag agggagagaa ttgaatacct 1140
gcatgcgaag ctccttgaga aacgatcaaa gcagccattg agagaggctg acgggaaacc 1200
gagcctgtac tttaaaaaga ttcatttctg gtttccagtc ctgaaaatga ttaggaagaa 1260
gcagacaatc cctgcaaatg aagatgatct atgagcaaca cagtccctct ttctgggcca 1320
actgctgctt ctgtctactc aacaagaggg ggctatctga gaaggtctac agatgtttga 1380
gtttgcaagg ctgcctttct ctttggtgat ccttcaagat acatgtcgat cataatgcca 1440
aatagcccct aggtaaatag tttcagagtc tgtcttccaa acaaaacaca gtatctaaac 1500
tgtgtcatag ttaaagctat ggtgatggct ggcatggaaa tgtcctccaa aggcttagat 1560
atttgaaaac ttggtcccca gttagtgcat cttgggggag gcttataagg tgtcatgttg 1620
ctggacaaag tgtgactcca gaggagtgtt ttgcagtttt aaaagtcatg tgctactcct 1680
gttcactcta ctcagcctgt ggctggagat gtgggctctc agctgtccct gcctccatgt 1740
ctgtctgtaa tagagttccc aactgtgata ttgatggagt cttacctctc tgaaacctta 1800
agcccaaata aatccttcct tctat 1825

<210> SEQ ID NO 57
<211> LENGTH: 1662
<212> TYPE: DNA
<213> ORGANISM: Mus musculus

<400> SEQUENCE: 57
gcgggaggga cactcggcgg ccgcgacggg gggcgctggc ggcagcggac gctgcagcgg 60
cggcggcggg gctggcgccg cggcggctcc cgggccggga cgggcctggg cagcgggcgg 120
cagcagcgcg gagtgggcac cgcgcctgca gcagggttct gggcccgggg ccgccgcctc 180
cgccagcggc ttctgcacgc ccctccaggc cggcctgcca ctcctcctgc tatgatgcct 240
gggcagatcc cagacccttc agtgaccgca ggctctctgc cagggctcgg ccccctcacc 300
ggacttccca gctctgctct gaccacagag gagctgaaat acgctgacat ccgcaacatt 360
ggggcgatga ttgcgccctt gcacttcctg gaggtgaaac tgggcaagag gccccaaccc 420
gtgaagagtg agctagacga ggaagaagag cgaaggaaaa ggcgccggga aaagaacaaa 480
gtcgctgcag ccagatgccg gaacaagaag aaggaacgca cagagtttct gcagagggag 540
tcagagcggc tggagctcat gaacgcagag ctgaagacgc agatagagga gctgaagctg 600
gagcggcaac agcttatcct gatgctcaac cgccaccgcc ccacctgcat cgtgcgcaca 660
gatagcgtca ggacgcccga gtccgaaggc aacccactgc tggagcagct ggacaagaag 720
tgactgaagg cctggaggag gcatcagagg aagaggagga aggggaggag cataaaagag 780
aaagaggacg agcaaggtga cagagggccc ctcccaggca cgtgacaaac tctatgatga 840
ggcttagcat aactagcctc cagctggctc ttttttgaaa ctcagccctg ccgcgcaaga 900
gcaagagcgg actgaagaaa ccagagggac caggtgctga gaccaaggtt gacccgcaga 960
taggggctgt cccactccag ggcccagctt gaagagcacc tgagccagag aggtgccaaa 1020
ccaggtagta gcctcaggca ctcctttggc ctctctgcca agacccccac ccaggggact 1080
actgagcagc caagaaaagc catgcattgc aaacacagtg tggcccgcgg atggaactca 1140
gcatagactg caatccacct ccccagccct gcccaagccc agtggaaggg ggtgcactgt 1200
ggggctgcaa tggcccagct ggagttggct gcggcacaga ggcgcgggcg cccttccaaa 1260
gcacatactt aatcaatgaa tgtttacaga ctggctgtcc tggcggggct tccaactgca 1320

```
cacggttttt atactttctt tctttttctt tcttttttttt tttaatattt tttacaaaaa   1380

aaaagatttt atacaagcaa tatatatata tatatatata tatatatata tggatttcta   1440

taatcactcg atgtgacaca gtacaaatat gctatggtct gttatggaca tccacccacc   1500

agttaaggcc attgtaattc ctaagtactg taggctctgg gtgttggggg gtggccaggc   1560

gggtgaggta catttccatc cttgtaaccc cttcctagta cccagtcctg tatcgttcag   1620

taaacattgc tcttaattac ccaaaaaaaa aaaaaaaaaa aa                       1662
```

<210> SEQ ID NO 58
<211> LENGTH: 2996
<212> TYPE: DNA
<213> ORGANISM: Artificial
<220> FEATURE:
<223> OTHER INFORMATION: Plasmid p14

<400> SEQUENCE: 58

```
ttttcccagt cacgacgttg taaaacgacg gccagtgaat tctaatacga ctcactatag     60

ggagacgaga gcacctggat aggttcgcgt ggcgcgccgc atgcgtcgac ggatcctgag    120

aacttcaggc tcctgggcaa cgtgctggtt attgtgctgt ctcatcattt tggcaaagaa    180

ttcactcctc aggtgcaggc tgcctatcag aaggtggtgg ctggtgtggc caatgccctg    240

gctcacaaat accactgaga tctttttccc tctgccaaaa attatgggga catcatgaag    300

ccccttgagc atctgacttc tggctaataa aggaaattta ttttcattgc aaaaaaaaaa    360

agcggccgct aactgttggt gcaggcgctc ggaccgctag cttggcgtaa tcatggtcat    420

agctgtttcc tgtgtgaaat tgttatccgc tcacaattcc acacaacata cgagccggaa    480

gcataaagtg taaagcctgg ggtgcctaat gagtgagcta actcacatta attgcgttgc    540

gctcactgcc cgctttccag tcgggaaacc tgtcgtgcca gctgcattaa tgaatcggcc    600

aacgcgcggg gagaggcggt ttgcgtattg ggcgctcttc cgcttcctcg ctcactgact    660

cgctgcgctc ggtcgttcgg ctgcggcgag cggtatcagc tcactcaaag gcggtaatac    720

ggttatccac agaatcaggg gataacgcag gaaagaacat gtgagcaaaa ggccagcaaa    780

aggccaggaa ccgtaaaaag gccgcgttgc tggcgttttt ccataggctc cgcccccctg    840

acgagcatca caaaaatcga cgctcaagtc agaggtggcg aaacccgaca ggactataaa    900

gataccaggc gtttccccct ggaagctccc tcgtgcgctc tcctgttccg accctgccgc    960

ttaccggata cctgtccgcc tttctccctt cgggaagcgt ggcgctttct caatgctcac   1020

gctgtaggta tctcagttcg gtgtaggtcg ttcgctccaa gctgggctgt gtgcacgaac   1080

cccccgttca gcccgaccgc tgcgccttat ccggtaacta tcgtcttgag tccaacccgg   1140

taagacacga cttatcgcca ctggcagcag ccactggtaa caggattagc agagcgaggt   1200

atgtaggcgg tgctacagag ttcttgaagt ggtggcctaa ctacggctac actagaagga   1260

cagtatttgg tatctgcgct ctgctgaagc cagttacctt cggaaaaaga gttggtagct   1320

cttgatccgg caaacaaacc accgctggta gcggtggttt ttttgtttgc aagcagcaga   1380

ttacgcgcag aaaaaaagga tctcaagaag atcctttgat cttttctacg gggtctgacg   1440

ctcagtggaa cgaaaactca cgttaaggga ttttggtcat gagattatca aaaaggatct   1500

tcacctagat ccttttaaat taaaaatgaa gttttaaatc aatctaaagt atatatgagt   1560

aaacttggtc tgacagttac caatgcttaa tcagtgaggc acctatctca gcgatctgtc   1620

tatttcgttc atccatagtt gcctgactcc ccgtcgtgta gataactacg atacgggagg   1680

gcttaccatc tggccccagt gctgcaatga taccgcgaga cccacgctca ccggctccag   1740
```

atttatcagc aataaaccag ccagccggaa gggccgagcg cagaagtggt cctgcaactt 1800
tatccgcctc catccagtct attaattgtt gccgggaagc tagagtaagt agttcgccag 1860
ttaatagttt gcgcaacgtt gttgccattg ctacaggcat cgtggtgtca cgctcgtcgt 1920
ttggtatggc ttcattcagc tccggttccc aacgatcaag gcgagttaca tgatccccca 1980
tgttgtgcaa aaaagcggtt agctccttcg gtcctccgat cgttgtcaga agtaagttgg 2040
ccgcagtgtt atcactcatg gttatggcag cactgcataa ttctcttact gtcatgccat 2100
ccgtaagatg cttttctgtg actggtgagt actcaaccaa gtcattctga gaatagtgta 2160
tgcggcgacc gagttgctct tgcccggcgt caatacggga taataccgcg ccacatagca 2220
gaactttaaa agtgctcatc attggaaaac gttcttcggg gcgaaaactc tcaaggatct 2280
taccgctgtt gagatccagt tcgatgtaac ccactcgtgc acccaactga tcttcagcat 2340
cttttacttt caccagcgtt tctgggtgag caaaaacagg aaggcaaaat gccgcaaaaa 2400
agggaataag ggcgacacgg aaatgttgaa tactcatact cttccttttt caatattatt 2460
gaagcattta tcagggttat tgtctcatga gcggatacat atttgaatgt atttagaaaa 2520
ataaacaaat aggggttccg cgcacatttc cccgaaaagt gccacctgac gtctaagaaa 2580
ccattattat catgacatta acctataaaa ataggcgtat cacgaggccc tttcgtctcg 2640
cgcgtttcgg tgatgacggt gaaaacctct gacacatgca gctcccggag acggtcacag 2700
cttgtctgta agcggatgcc gggagcagac aagcccgtca gggcgcgtca gcgggtgttg 2760
gcgggtgtcg gggctggctt aactatgcgg catcagagca gattgtactg agagtgcacc 2820
atatgcggtg tgaaataccg cacagatgcg taaggagaaa ataccgcatc aggcgccatt 2880
cgccattcag gctgcgcaac tgttgggaag ggcgatcggt gcgggcctct tcgctattac 2940
gccagctggc gaaaggggga tgtgctgcaa ggcgattaag ttgggtaacg ccaggg 2996

<210> SEQ ID NO 59
<211> LENGTH: 2992
<212> TYPE: DNA
<213> ORGANISM: Artificial
<220> FEATURE:
<223> OTHER INFORMATION: Plasmid p17+

<400> SEQUENCE: 59
ttttcccagt cacgacgttg taaaacgacg gccagtgaat tcgagctcac atacgattta 60
ggtgacacta taggcctgca ccaacagtta acacggcgcg ccgcatgcgt cgacggatcc 120
tgagaacttc aggctcctgg gcaacgtgct ggttattgtg ctgtctcatc attttggcaa 180
agaattcact cctcaggtgc aggctgccta tcagaaggtg gtggctggtg tggccaatgc 240
cctggctcac aaataccact gagatctttt tccctctgcc aaaaattatg gggacatcat 300
gaagcccctt gagcatctga cttctggcta ataaaggaaa tttattttca ttgcaaaaaa 360
aaaaagcggc cgctagagtc ggccgcagcg gccgagcttg gcgtaatcat ggtcatagct 420
gtttcctgtg tgaaattgtt atccgctcac aattccacac aacatacgag ccggaagcat 480
aaagtgtaaa gcctggggtg cctaatgagt gagctaactc acattaattg cgttgcgctc 540
actgcccgct ttccagtcgg gaaacctgtc gtgccagctg cattaatgaa tcggccaacg 600
cgcggggaga ggcggtttgc gtattgggcg ctcttccgct tcctcgctca ctgactcgct 660
gcgctcggtc gttcggctgc ggcgagcggt atcagctcac tcaaaggcgg taatacggtt 720
atccacagaa tcaggggata acgcaggaaa gaacatgtga gcaaaaggcc agcaaaaggc 780
caggaaccgt aaaaaggccg cgttgctggc gtttttccat aggctccgcc cccctgacga 840
gcatcacaaa aatcgacgct caagtcagag gtggcgaaac ccgacaggac tataaagata 900
ccaggcgttt ccccctggaa gctccctcgt gcgctctcct gttccgaccc tgccgcttac 960
cggatacctg tccgcctttc tcccttcggg aagcgtggcg ctttctcaaa gctcacgctg 1020
taggtatctc agttcggtgt aggtcgttcg ctccaagctg ggctgtgtgc acgaaccccc 1080
cgttcagccc gaccgctgcg ccttatccgg taactatcgt cttgagtcca acccggtaag 1140
acacgactta tcgccactgg cagcagccac tggtaacagg attagcagag cgaggtatgt 1200
aggcggtgct acagagttct tgaagtggtg gcctaactac ggctacacta gaagaacagt 1260
atttggtatc tgcgctctgc tgaagccagt taccttcgga aaaagagttg gtagctcttg 1320
atccggcaaa caaaccaccg ctggtagcgg tggttttttt gtttgcaagc agcagattac 1380
gcgcagaaaa aaaggatctc aagaagatcc tttgatcttt tctacggggt ctgacgctca 1440
gtggaacgaa aactcacgtt aagggatttt ggtcatgaga ttatcaaaaa ggatcttcac 1500
ctagatcctt ttaaattaaa aatgaagttt taaatcaatc taaagtatat atgagtaaac 1560
ttggtctgac agttaccaat gcttaatcag tgaggcacct atctcagcga tctgtctatt 1620
tcgttcatcc atagttgcct gactccccgt cgtgtagata actacgatac gggagggctt 1680
accatctggc cccagtgctg caatgatacc gcgagaccca cgctcaccgg ctccagattt 1740
atcagcaata aaccagccag ccggaagggc cgagcgcaga agtggtcctg caactttatc 1800
cgcctccatc cagtctatta attgttgccg ggaagctaga gtaagtagtt cgccagttaa 1860
tagtttgcgc aacgttgttg ccattgctac aggcatcgtg gtgtcacgct cgtcgtttgg 1920
tatggcttca ttcagctccg gttcccaacg atcaaggcga gttacatgat cccccatgtt 1980
gtgcaaaaaa gcggttagct ccttcggtcc tccgatcgtt gtcagaagta agttggccgc 2040
agtgttatca ctcatggtta tggcagcact gcataattct cttactgtca tgccatccgt 2100
aagatgcttt tctgtgactg gtgagtactc aaccaagtca ttctgagaat agtgtatgcg 2160
gcgaccgagt tgctcttgcc cggcgtcaat acgggataat accgcgccac atagcagaac 2220
tttaaaagtg ctcatcattg gaaaacgttc ttcggggcga aaactctcaa ggatcttacc 2280
gctgttgaga tccagttcga tgtaacccac tcgtgcaccc aactgatctt cagcatcttt 2340
tactttcacc agcgtttctg ggtgagcaaa aacaggaagg caaaatgccg caaaaaaggg 2400
aataagggcg acacggaaat gttgaatact catactcttc ctttttcaat attattgaag 2460
catttatcag ggttattgtc tcatgagcgg atacatattt gaatgtattt agaaaaataa 2520
acaaataggg gttccgcgca catttccccg aaaagtgcca cctgacgtct aagaaaccat 2580
tattatcatg acattaacct ataaaaatag gcgtatcacg aggccctttc gtctcgcgcg 2640
tttcggtgat gacggtgaaa acctctgaca catgcagctc ccggagacgg tcacagcttg 2700
tctgtaagcg gatgccggga gcagacaagc ccgtcagggc gcgtcagcgg gtgttggcgg 2760
gtgtcggggc tggcttaact atgcggcatc agagcagatt gtactgagag tgcaccatat 2820
gcggtgtgaa ataccgcaca gatgcgtaag gagaaaatac cgcatcaggc gccattcgcc 2880
attcaggctg cgcaactgtt gggaagggcg atcggtgcgg gcctcttcgc tattacgcca 2940
gctggcgaaa gggggatgtg ctgcaaggcg attaagttgg gtaacgccag gg 2992

<210> SEQ ID NO 60
<211> LENGTH: 2757
<212> TYPE: DNA
<213> ORGANISM: Artificial
<220> FEATURE:
<223> OTHER INFORMATION: Plasmid pCATRMAN

<400> SEQUENCE: 60

```
ttttcccagt cacgacgttg taaaacgacg gccagtgaat tctaatacga ctcactatag     60
ggagatggag aaaaaaatca ctggacgcgt ggcgcgccat taattaatgc ggccgctagc    120
tcgagtgata ataagcggat gaatggctgc aggcatgcaa gcttggcgta atcatggtca    180
tagctgtttc ctgtgtgaaa ttgttatccg ctcacaattc cacacaacat acgagccgga    240
agcataaagt gtaaagcctg gggtgcctaa tgagtgagct aactcacatt aattgcgttg    300
cgctcactgc ccgctttcca gtcgggaaac ctgtcgtgcc agctgcatta atgaatcggc    360
caacgcgcgg ggagaggcgg tttgcgtatt gggcgctctt ccgcttcctc gctcactgac    420
tcgctgcgct cggtcgttcg gctgcggcga gcggtatcag ctcactcaaa ggcggtaata    480
cggttatcca cagaatcagg ggataacgca ggaaagaaca tgtgagcaaa aggccagcaa    540
aaggccagga accgtaaaaa ggccgcgttg ctggcgtttt tccataggct ccgcccccct    600
gacgagcatc acaaaaatcg acgctcaagt cagaggtggc gaaacccgac aggactataa    660
agataccagg cgtttccccc tggaagctcc ctcgtgcgct ctcctgttcc gaccctgccg    720
cttaccggat acctgtccgc ctttctccct tcgggaagcg tggcgctttc tcaatgctca    780
cgctgtaggt atctcagttc ggtgtaggtc gttcgctcca agctgggctg tgtgcacgaa    840
ccccccgttc agcccgaccg ctgcgcctta tccggtaact atcgtcttga gtccaacccg    900
gtaagacacg acttatcgcc actggcagca gccactggta acaggattag cagagcgagg    960
tatgtaggcg gtgctacaga gttcttgaag tggtggccta actacggcta cactagaagg   1020
acagtatttg gtatctgcgc tctgctgaag ccagttacct tcggaaaaag agttggtagc   1080
tcttgatccg gcaaacaaac caccgctggt agcggtggtt tttttgtttg caagcagcag   1140
attacgcgca gaaaaaaagg atctcaagaa gatcctttga tcttttctac ggggtctgac   1200
gctcagtgga acgaaaactc acgttaaggg attttggtca tgagattatc aaaaaggatc   1260
ttcacctaga tccttttaaa ttaaaaatga agttttaaat caatctaaag tatatatgag   1320
taaacttggt ctgacagtta ccaatgctta atcagtgagg cacctatctc agcgatctgt   1380
ctatttcgtt catccatagt tgcctgactc cccgtcgtgt agataactac gatacgggag   1440
ggcttaccat ctggccccag tgctgcaatg ataccgcgag acccacgctc accggctcca   1500
gatttatcag caataaacca gccagccgga agggccgagc gcagaagtgg tcctgcaact   1560
ttatccgcct ccatccagtc tattaattgt tgccgggaag ctagagtaag tagttcgcca   1620
gttaatagtt tgcgcaacgt tgttgccatt gctacaggca tcgtggtgtc acgctcgtcg   1680
tttggtatgg cttcattcag ctccggttcc caacgatcaa ggcgagttac atgatccccc   1740
atgttgtgca aaaaagcggt tagctccttc ggtcctccga tcgttgtcag aagtaagttg   1800
gccgcagtgt tatcactcat ggttatggca gcactgcata attctcttac tgtcatgcca   1860
tccgtaagat gcttttctgt gactggtgag tactcaacca agtcattctg agaatagtgt   1920
atgcggcgac cgagttgctc ttgcccggcg tcaatacggg ataataccgc gccacatagc   1980
agaactttaa aagtgctcat cattggaaaa cgttcttcgg ggcgaaaact ctcaaggatc   2040
ttaccgctgt tgagatccag ttcgatgtaa cccactcgtg cacccaactg atcttcagca   2100
tcttttactt tcaccagcgt ttctgggtga gcaaaaacag gaaggcaaaa tgccgcaaaa   2160
aagggaataa gggcgacacg gaaatgttga atactcatac tcttcctttt tcaatattat   2220
tgaagcattt atcagggtta ttgtctcatg agcggataca tatttgaatg tatttagaaa   2280
aataaacaaa taggggttcc gcgcacattt ccccgaaaag tgccacctga cgtctaagaa   2340
```

accattatta tcatgacatt aacctataaa aataggcgta tcacgaggcc ctttcgtctc 2400
gcgcgtttcg gtgatgacgg tgaaaacctc tgacacatgc agctcccgga gacggtcaca 2460
gcttgtctgt aagcggatgc cgggagcaga caagcccgtc agggcgcgtc agcgggtgtt 2520
ggcgggtgtc ggggctggct taactatgcg gcatcagagc agattgtact gagagtgcac 2580
catatgcggt gtgaaatacc gcacagatgc gtaaggagaa aataccgcat caggcgccat 2640
tcgccattca ggctgcgcaa ctgttgggaa gggcgatcgg tgcgggcctc ttcgctatta 2700
cgccagctgg cgaaaggggg atgtgctgca aggcgattaa gttgggtaac gccaggg 2757

<210> SEQ ID NO 61
<211> LENGTH: 2995
<212> TYPE: DNA
<213> ORGANISM: Artificial
<220> FEATURE:
<223> OTHER INFORMATION: Plasmid p20

<400> SEQUENCE: 61
ttttcccagt cacgacgttg taaaacgacg gccagtgaat tcaattaacc ctcactaaag 60
ggagacttgt tccaaatgtg ttaggcgcgc cgcatgcgtc gacggatcct gagaacttca 120
ggctcctggg caacgtgctg gttattgtgc tgtctcatca ttttggcaaa gaattcactc 180
ctcaggtgca ggctgcctat cagaaggtgg tggctggtgt ggccaatgcc ctggctcaca 240
aataccactg agatcttttt ccctctgcca aaaattatgg ggacatcatg aagccccttg 300
agcatctgac ttctggctaa taaaggaaat ttattttcat tgcaaaaaaa aaaagcggcc 360
gctcttctat agtgtcacct aaatggccca gcggccgagc ttggcgtaat catggtcata 420
gctgtttcct gtgtgaaatt gttatccgct cacaattcca cacaacatac gagccggaag 480
cataaagtgt aaagcctggg gtgcctaatg agtgagctaa ctcacattaa ttgcgttgcg 540
ctcactgccc gctttccagt cgggaaacct gtcgtgccag ctgcattaat gaatcggcca 600
acgcgcgggg agaggcggtt tgcgtattgg gcgctcttcc gcttcctcgc tcactgactc 660
gctgcgctcg gtcgttcggc tgcggcgagc ggtatcagct cactcaaagg cggtaatacg 720
gttatccaca gaatcagggg ataacgcagg aaagaacatg tgagcaaaag gccagcaaaa 780
ggccaggaac cgtaaaaagg ccgcgttgct ggcgtttttc cataggctcc gcccccctga 840
cgagcatcac aaaaatcgac gctcaagtca gaggtggcga aacccgacag gactataaag 900
ataccaggcg tttccccctg gaagctccct cgtgcgctct cctgttccga ccctgccgct 960
taccggatac ctgtccgcct ttctcccttc gggaagcgtg gcgctttctc aaagctcacg 1020
ctgtaggtat ctcagttcgg tgtaggtcgt tcgctccaag ctgggctgtg tgcacgaacc 1080
ccccgttcag cccgaccgct gcgccttatc cggtaactat cgtcttgagt ccaacccggt 1140
aagacacgac ttatcgccac tggcagcagc cactggtaac aggattagca gagcgaggta 1200
tgtaggcggt gctacagagt tcttgaagtg gtggcctaac tacggctaca ctagaagaac 1260
agtatttggt atctgcgctc tgctgaagcc agttaccttc ggaaaaagag ttggtagctc 1320
ttgatccggc aaacaaacca ccgctggtag cggtggtttt tttgtttgca agcagcagat 1380
tacgcgcaga aaaaaaggat ctcaagaaga tcctttgatc ttttctacgg ggtctgacgc 1440
tcagtggaac gaaaactcac gttaagggat tttggtcatg agattatcaa aaaggatctt 1500
cacctagatc cttttaaatt aaaaatgaag ttttaaatca atctaaagta tatatgagta 1560
aacttggtct gacagttacc aatgcttaat cagtgaggca cctatctcag cgatctgtct 1620
atttcgttca tccatagttg cctgactccc cgtcgtgtag ataactacga tacgggaggg 1680
cttaccatct ggccccagtg ctgcaatgat accgcgagac ccacgctcac cggctccaga 1740
tttatcagca ataaaccagc cagccggaag ggccgagcgc agaagtggtc ctgcaacttt 1800
atccgcctcc atccagtcta ttaattgttg ccgggaagct agagtaagta gttcgccagt 1860
taatagtttg cgcaacgttg ttgccattgc tacaggcatc gtggtgtcac gctcgtcgtt 1920
tggtatggct tcattcagct ccggttccca acgatcaagg cgagttacat gatcccccat 1980
gttgtgcaaa aaagcggtta gctccttcgg tcctccgatc gttgtcagaa gtaagttggc 2040
cgcagtgtta tcactcatgg ttatggcagc actgcataat tctcttactg tcatgccatc 2100
cgtaagatgc ttttctgtga ctggtgagta ctcaaccaag tcattctgag aatagtgtat 2160
gcggcgaccg agttgctctt gcccggcgtc aatacgggat aataccgcgc cacatagcag 2220
aactttaaaa gtgctcatca ttggaaaacg ttcttcgggg cgaaaactct caaggatctt 2280
accgctgttg agatccagtt cgatgtaacc cactcgtgca cccaactgat cttcagcatc 2340
ttttactttc accagcgttt ctgggtgagc aaaaacagga aggcaaaatg ccgcaaaaaa 2400
gggaataagg gcgacacgga aatgttgaat actcatactc ttcctttttc aatattattg 2460
aagcatttat cagggttatt gtctcatgag cggatacata tttgaatgta tttagaaaaa 2520
taaacaaata ggggttccgc gcacatttcc ccgaaaagtg ccacctgacg tctaagaaac 2580
cattattatc atgacattaa cctataaaaa taggcgtatc acgaggccct ttcgtctcgc 2640
gcgtttcggt gatgacggtg aaaacctctg acacatgcag ctcccggaga cggtcacagc 2700
ttgtctgtaa gcggatgccg ggagcagaca agcccgtcag ggcgcgtcag cgggtgttgg 2760
cgggtgtcgg ggctggctta actatgcggc atcagagcag attgtactga gagtgcacca 2820
tatgcggtgt gaaataccgc acagatgcgt aaggagaaaa taccgcatca ggcgccattc 2880
gccattcagg ctgcgcaact gttgggaagg gcgatcggtg cgggcctctt cgctattacg 2940
ccagctggcg aaagggggat gtgctgcaag gcgattaagt tgggtaacgc caggg 2995

<210> SEQ ID NO 62
<211> LENGTH: 48
<212> TYPE: DNA
<213> ORGANISM: Mus musculus

<400> SEQUENCE: 62
aattctaata cgactcacta tagggagacg agagcacctg gataggtt 48

<210> SEQ ID NO 63
<211> LENGTH: 20
<212> TYPE: DNA
<213> ORGANISM: Mus musculus

<400> SEQUENCE: 63
gcctgcacca acagttaaca 20

<210> SEQ ID NO 64
<211> LENGTH: 19
<212> TYPE: DNA
<213> ORGANISM: Mus musculus

<400> SEQUENCE: 64
ctcacagacc atggctcca 19

<210> SEQ ID NO 65
<211> LENGTH: 19
<212> TYPE: DNA
<213> ORGANISM: Mus musculus

<400> SEQUENCE: 65
tctcctctct ggttcggat 19

<210> SEQ ID NO 66
<211> LENGTH: 19
<212> TYPE: DNA
<213> ORGANISM: Mus musculus

<400> SEQUENCE: 66
atacgtgtgg cccatctgc 19

<210> SEQ ID NO 67
<211> LENGTH: 19
<212> TYPE: DNA
<213> ORGANISM: Mus musculus

<400> SEQUENCE: 67
gttctagcca agtgtcacc 19

<210> SEQ ID NO 68
<211> LENGTH: 19
<212> TYPE: DNA
<213> ORGANISM: Mus musculus

<400> SEQUENCE: 68
tgtgctggca ttcaacagg 19

<210> SEQ ID NO 69
<211> LENGTH: 19
<212> TYPE: DNA
<213> ORGANISM: Mus musculus

<400> SEQUENCE: 69
ttctgcaagg atcacggtg 19

<210> SEQ ID NO 70
<211> LENGTH: 19
<212> TYPE: DNA
<213> ORGANISM: Mus musculus

<400> SEQUENCE: 70
gcatccagat gacgagatg 19

<210> SEQ ID NO 71
<211> LENGTH: 19
<212> TYPE: DNA
<213> ORGANISM: Mus musculus

<400> SEQUENCE: 71
ggaactgtac gacttcgct 19

<210> SEQ ID NO 72
<211> LENGTH: 19
<212> TYPE: DNA
<213> ORGANISM: Mus musculus

<400> SEQUENCE: 72
tggatgacga tgagggaga 19

<210> SEQ ID NO 73
<211> LENGTH: 19
<212> TYPE: DNA
<213> ORGANISM: Mus musculus

<400> SEQUENCE: 73
ttacttcgag gcagaaggc 19

<210> SEQ ID NO 74
<211> LENGTH: 19
<212> TYPE: DNA
<213> ORGANISM: Mus musculus

<400> SEQUENCE: 74
acatagtggg tgtaaggta 19

<210> SEQ ID NO 75
<211> LENGTH: 19
<212> TYPE: DNA
<213> ORGANISM: Mus musculus

<400> SEQUENCE: 75
ctcttccggc ctgacaact 19

<210> SEQ ID NO 76
<211> LENGTH: 19
<212> TYPE: DNA
<213> ORGANISM: Mus musculus

<400> SEQUENCE: 76
ggtagctgtg tgcgacatc 19

<210> SEQ ID NO 77
<211> LENGTH: 19
<212> TYPE: DNA
<213> ORGANISM: Mus musculus

<400> SEQUENCE: 77
cgtcttccag gacagcaac 19

<210> SEQ ID NO 78
<211> LENGTH: 19
<212> TYPE: DNA
<213> ORGANISM: Mus musculus

<400> SEQUENCE: 78
gatgccagag tggattgga 19

<210> SEQ ID NO 79
<211> LENGTH: 19
<212> TYPE: DNA
<213> ORGANISM: Mus musculus

<400> SEQUENCE: 79
tctacgagca gaggaaccg 19

<210> SEQ ID NO 80
<211> LENGTH: 19
<212> TYPE: DNA
<213> ORGANISM: Mus musculus

<400> SEQUENCE: 80
ggaagtaacc aggagcctg 19

<210> SEQ ID NO 81
<211> LENGTH: 19
<212> TYPE: DNA
<213> ORGANISM: Mus musculus

<400> SEQUENCE: 81
cccgtgaaga gtgagctag 19

<210> SEQ ID NO 82
<211> LENGTH: 19
<212> TYPE: DNA
<213> ORGANISM: Mus musculus

<400> SEQUENCE: 82
gaaggaacgc acggagttc 19

<210> SEQ ID NO 83
<211> LENGTH: 1294
<212> TYPE: DNA
<213> ORGANISM: Mus musculus

<400> SEQUENCE: 83
tggaggaacc tagcggcgca atggagccct ggtgcggggc agaggtccgt gggcagggcc 60
ctcagggtcc ccgtgtgcct ggggcttccc gctcccgctc ccgcgccctt ctcctgctgt 120
tgctgctgct gctgctgctc ctgcctcggc ggccggcagg tgagcgcatc cgcccccgac 180
gccctccccg gcacgcccac ccgcggccac ctctgactcg ctggagacct tccacaggct 240
acttggccgc aggagcatcc ccggggacgc tgtccaccac cgtcccgacc ggacccgggg 300
tctcctgtgg ctccagaggc acctgtccct caggcaggct tcgccttcct cggcaagccc 360
agactaacca gaccacgacg gctccaccga actcacagac catggctcca ctgaaaacgg 420
tggggactct cggcatgatg gacactactg ggtccgttct taagacggtt cattccagca 480
acctcccctt ctgtggctcc tcccacgagc cagaccctac tctcagggac ccagaagcca 540
tgactcggcg gtggccctgg atggtcagcg tgcaggctaa cggctcacac gtctgtgctg 600
gcatccttat cgcttcccag tgggtgctga ccgtggccca ttgcttgagc cagaaccatg 660
ttaactacat agtgagggcg gggagcccgt ggattaatca gacggcagga accagctcag 720
atgtgccggt ccatcgagtc atcataaacc atggctacca acccagacgg tactggtcat 780
gggttggccg ggcccatgac atcggccttc tcaagctcaa gtgggggctc aagtacagta 840
aatacgtgtg gcccatctgc ctgcctggcc tggattacat ggtggaggac agttctctct 900
gcactgtgac aggctgggga tatcccaggg ctaacggaga taactggcga gcccctggtc 960
tgctcttcag atggcacatg gtacctggtg ggaatgatga gctggggccc aggctgcaag 1020
aagagcgagg ccccacccat ctttctgcag gtctcctact acaggccctg gatctgggac 1080
cggctcagtg gggagcccct ggcccttcca gccccatcca ggaccttgct cctggctttc 1140
cttctgctcc tcatccttct gggcacactg tgacactgcc atgtctctcc ttccttccct 1200
tccttctaag tgctgctgtg gggtggcgc tcagcctgcc ggaggcgggg aggagctagc 1260
agagattaaa cacttctttt ccccaaaaaa aaaa 1294

<210> SEQ ID NO 84
<211> LENGTH: 1447
<212> TYPE: DNA
<213> ORGANISM: Homo sapiens

<400> SEQUENCE: 84
gagctgtttc accctacctt ggcttcaatc tcttccccca tgctcgaagg tgcggagctg 60
tacttcaacg tggaccatgg ctacctggag ggcctggttc gaggatgcaa ggccagcctc 120
ctgacccagc aagactatat caacctggtc cagtgtgaga ccctagaaga cctgaaaatt 180

```
catctccaga ctactgatta tggtaacttt ttggctaatc acacaaatcc tcttactgtt    240
tccaaaattg acactgagat gaggaaaaga ctatgtggag aatttgagta tttccggaat    300
cattccctgg agcccctcag cacatttctc acctatatga cgtgcagtta tatgatagac    360
aatgtgattc tgctgatgaa tggtgcattg cagaaaaaat ctgtgaaaga aattctgggg    420
aagtgccacc ccttgggccg tttcacagaa atggaagctg tcaacattgc agagacacct    480
tcagatctct ttaatgccat tctgatcgaa acgccattag ctccattctt ccaagactgc    540
atgtctgaaa atgctctaga tgaactgaat attgaattgc tacgcaataa actatacaag    600
tcttaccttg aggcattcta taaattctgt aagaatcatg gtgatgtcac agcagaagtt    660
atgtgtccca ttcttgagtt tgaggccgac agacgtgctt ttatcatcac tcttaactcc    720
tttggcactg aattgagcaa agaagaccga gagaccctct atccaacctt cggcaaactc    780
tatcctgagg ggttgcggct gttggctcaa gcagaagact ttgaccagat gaagaacgta    840
gcggatcatt acggagtata caaacottta tttgaagctg taggtggcag tgggggaaag    900
acattggagg acgtgtttta cgagcgtgag gtacaaatga atgtgctggc attcaacaga    960
cagttccact acggtgtgtt ttatgcatat gtaaagctga aggaacagga aattagaaat   1020
attgtgtgga tagcagaatg tatttcacag aggcatcgaa ctaaaatcaa cagttacatt   1080
ccaattttat aacccaagct agagtgcaat ggcgtgatct cggctcactg caacctccac   1140
ctcccagatt caagcaactc tctgcctcag cctcccgagt agctgggatt acaagcaccc   1200
accactacac tcagctaatt ttttgtattt ttagtagagc cggggtttca ccatcttggc   1260
caggctgatc ttgaactcct gagctcatga tccacccgcc tcagcctccc aaagtgctgg   1320
gattacaggc cccttgttca gccactgcac ctggcccctt attttgtttt tgttttctaa   1380
tatactttga tgtaatcagc ttgagaaagc aacacaattt caaatcctat cttctagatg   1440
caagcag                                                             1447
```

<210> SEQ ID NO 85
<211> LENGTH: 1323
<212> TYPE: DNA
<213> ORGANISM: Homo sapiens

<400> SEQUENCE: 85

```
gagctgtttc accctacctt ggcttcaatc tcttccccca tgctcgaagg tgcggagctg     60
tacttcaacg tggaccatgg ctacctggag ggcctggttc gaggatgcaa ggccagcctc    120
ctgacccagc aagactatat caacctggtc cagtgtgaga ccctagaaga cctgaaaatt    180
catctccaga ctactgatta tggtaacttt ttggctaatc acacaaatcc tcttactgtt    240
tccaaaattg acactgagat gaggaaaaga ctatgtggag aatttgagta tttccggaat    300
cattccctgg agcccctcag cacatttctc acctatatga cgtgcagtta tatgataggc    360
aatgtgattc tgctgatgaa tggtgcattg cagaaaaaat ctgtgaaaga aattctgggg    420
aagtgccacc ccttgggccg tttcacagaa atggaagctg tcaacattgc agagacacct    480
tcagatctct ttaatgccat tctgatcgaa acgccattag ctccattctt ccaagactgc    540
atgtctgaaa atgctctaga tgaactgaat attgaattgc tacgcaataa actatacaag    600
tcttaccttg aggcattcta taaattctgt aagaatcatg gtgatgtcac agcagaagtt    660
atgtgtccca ttcttgagtt tgaggccgac agacgtgctt ttatcatcac tcttaactcc    720
tttggcactg aattgagcaa agaagaccga gagaccctct atccaacctt cggcaaactc    780
tatcctgagg ggttgcggct gttggctcaa gcagaagact ttgaccagat gaagaacgta    840
```

-continued

```
gcggatcatt acggagtata caaacccttta tttgaagctg taggtggcag tgggggaaag    900

acattggagg acgtgtttta cgagcgtgag gtacaaatga atgtgctggc attcaacaga    960

cagttccact acggctagag tgcaatggcg tgatctcggc tcactgcaac ctccacctcc   1020

cagattcaag caactctctg cctcagcctc ccgagtagct gggattacaa gcacccacca   1080

ctacactcag ctaatttttt gtatttttag tagagccggg gtttcaccat cttggccagg   1140

ctgatcttga actcctgagc tcatgatcca cccgcctcag cctcccaaag tgctgggatt   1200

acaggcccct tgttcagcca ctgcacctgg ccccttattt tgtttttgtt ttctaatata   1260

ctttgatgta atcagcttga gaaagcaaca caatttcaaa tcctatcttc tagatgcaag   1320

cag                                                                 1323
```

<210> SEQ ID NO 86
<211> LENGTH: 1131
<212> TYPE: DNA
<213> ORGANISM: Mus musculus

<400> SEQUENCE: 86

```
attaagacag ttgtttatag aagcgtgcag ggtacacac gggatcttct aatccctagc     60

actagggcca ctcaggggta cccagccctt ggccagaagg agcaggggag ccaatgacct    120

cccgaaggcc atcgctgcgg ctcacaccta tctcctgaag catccagatg acgagatgat    180

gaagagaaac atggagtatt ataagagctt gcctggagcc gaggaccaca ttaaagactt    240

ggaaaccaag tcgtacgaga gcctgtttgt ccgtgcggtg cgggcctaca acggggagaa    300

ctggagaacg tccatttccg acatggagct cgcgcttccc gacttcctca aggccttcta    360

cgagtgcctg gctgcctgcg aggggtcgcg ggagatcaag gacttcaagg acttctacct    420

gtccatagca gatcactatg tggaagttct ggagtgtaag attcgttgtg aggagaccct    480

caccccagtc ataggaggct atcccgtgga gaaatttgtg gcgaccatgt accactattt    540

acagtttgcg tattacaagt tgaatgatct gaagaatgca gccccgtgtg ccgtcagcta    600

cctgctcttt gaccagagtg acagggtcat gcaacagaac ctggtgtact atcagtacca    660

ccgggacaag tggggcctct cggatgagca cttccagccc agacccgaag cagttcagtt    720

ctttaatgtg acgacgctcc agaaggaact gtacgacttc gctcaggaac acctaatgga    780

tgacgatgag ggagaggttg tggagtatgt ggacgacttg ttggagacgg aagagtctgc    840

ctagtccaca ggggctaagg aacctctctt ccgagttcct ctttcttcaa gtgcctgggt    900

tgttgatacc tcacagcctt ttcttcttaa agtaagaagg aagccaccat ctctccctac    960

caaggtcaag cctgacttcc ccttgttcac actcagtatt cacgcttgtc ttcatggtta   1020

cacgtcttca tgcctgtctt tcccttcaca catgtgttcc cgtcatctag tctgtcctcc   1080

tcaaagtcac gttcgtctcc cctctgatcc catgtgtctc cccccatgtt c            1131
```

<210> SEQ ID NO 87
<211> LENGTH: 1037
<212> TYPE: DNA
<213> ORGANISM: Mus musculus

<400> SEQUENCE: 87

```
atttggagtt gaactgaaga ggacatgtgg tcatttgggc tggggggtgt agctcagtgg     60

tagagggttt gcatacccgc acagcgccct gggttcattc cccagcactg tataaaactg    120

ggcatgatgg tgcatacccg agagtccagc acacagcagt tcaagagcct gtttgtccgt    180

gcggtgcggg cctacaacgg ggagaactgg agaacgtcca tttccgacat ggagctcgcg    240
```

cttcccgact tcctcaaggc cttctacgag tgcctggctg cctgcgaggg gtcgcgggag 300
atcaaggact tcaaggactt ctacctgtcc atagcagatc actatgtgga agttctggag 360
tgtaagattc gttgtgagga gaccctcacc ccagtcatag gaggctatcc cgtggagaaa 420
tttgtggcga ccatgtacca ctatttacag tttgcgtatt acaagttgaa tgatctgaag 480
aatgcagccc cgtgtgccgt cagctacctg ctctttgacc agagtgacag ggtcatgcaa 540
cagaacctgg tgtactatca gtaccaccgg gacaagtggg gcctctcgga tgagcacttc 600
cagcccagac ccgaagcagt tcagttcttt aatgtgacga cgctccagaa ggaactgtac 660
gacttcgctc aggaacacct aatggatgac gatgagggag aggttgtgga gtatgtggac 720
gacttgttgg agacggaaga gtctgcctag tccacagggg ctaaggaacc tctcttccga 780
gttcctcttt cttcaagtgc ctgggttgtt gatacctcac agccttttct tcttaaagta 840
agaaggaagc caccatctct ccctaccaag gtcaagcctg acttcccctt gttcacactc 900
agtattcacg cttgtcttca tggttacacg tcttcatgcc tgcctttccc ttcacacatg 960
tgttcccgtc atctagtctg tcctcctcaa agtcacgttc gtctcccctc tgatcccatg 1020
tgtctccccc atgttca 1037

<210> SEQ ID NO 88
<211> LENGTH: 1354
<212> TYPE: DNA
<213> ORGANISM: Homo sapiens

<400> SEQUENCE: 88
agcggactgg gagcgccttc cggagagacg cagtcggctg ccaccccggg atgggtcgct 60
ggtgccagac cgtcgcgcgc gggcagcgcc cccggacgtc tgccccctcc cgcgccggtg 120
ccctgctgct gctgcttctg ttgctgaggt ctgcaggttg ctggggcgca ggggaagccc 180
cgggggcgct gtccactgct gatcccgccg accagagcgt ccagtgtgtc cccaaggcca 240
cctgtccttc cagccggcct cgccttctct ggcagacccc gaccacccag acactgccct 300
cgaccaccat ggagacccaa ttcccagttt ctgaaggcaa agtcgaccca taccgctcct 360
gtggcttttc ctacgagcag gaccccaccc tcagggaccc agaagccgtg gctcggcggt 420
ggccctggat ggtcagcgtg cgggccaatg gcacacacat ctgtgccggc accatcattg 480
cctcccagtg ggtgctgact gtggcccact gcctgatctg gcgtgatgtt atctactcag 540
tgagggtggg gagtccgtgg attgaccaga tgacgcagac cgcctccgat gtcccggtgc 600
tccaggtcat catgcatagc aggtaccggg cccagcggtt ctggtcctgg gtgggccagg 660
ccaacgacat cggcctcctc aagctcaagc aggaactcaa gtacagcaat tacgtgcggc 720
ccatctgcct gcctggcacg gactatgtgt tgaaggacca ttcccgctgc actgtgacgg 780
gctggggact ttccaaggct gacggcatgt ggcctcagtt ccggaccatt caggagaagg 840
aagtcatcat cctgaacaac aaagagtgtg acaatttcta ccacaacttc accaaaatcc 900
ccactctggt tcagatcatc aagtcccaga tgatgtgtgc ggaggacacc cacagggaga 960
agttctgcta tgagctaact ggagagccct tggtctgctc catggagggc acgtggtacc 1020
tggtgggatt ggtgagctgg ggtgcaggct gccagaagag cgaggcccca cccatctacc 1080
tacaggtctc ctcctaccaa cactggatct gggactgcct caacgggcag gccctggccc 1140
tgccagcccc atccaggacc ctgctcctgg cactcccact gcccctcagc ctccttgctg 1200
ccctctgact ctgtgtgccc tccctcactt gtgggccccc cttgcctccg tgcccaggtt 1260
gctgtaggtg cagctgtcac agccctgaga gtcagggtgg agatgaggtg ctcaattaaa 1320
cattactgtt ttccatgcaa aaaaaaaaaa aaaa 1354

<210> SEQ ID NO 89
<211> LENGTH: 2370
<212> TYPE: DNA
<213> ORGANISM: Homo sapiens

<400> SEQUENCE: 89
gcaaatcttc aggggccgtc caggactaca gagctgtttc accctacctt ggcttcaatc 60
tcttccccca tgctcgaagg tgcggagctg tacttcaacg tggaccatgg ctacctggag 120
ggcctggttc gaggatgcaa ggccagcctc ctgacccagc aagactatat caacctggtc 180
cagtgtgaga ccctagaaga cctgaaaatt catctccaga ctactgatta tggtaacttt 240
ttggctaatc acacaaatcc tcttactgtt tccaaaattg acactgagat gaggaaaaga 300
ctatgtggag aatttgagta tttccggaat cattccctgg agcccctcag cacatttctc 360
acctatatga cgtgcagtta tatgatagac aatgtgattc tgctgatgaa tggtgcattg 420
cagaaaaaat ctgtgaaaga aattctgggg aagtgccacc ccttgggccg tttcacagaa 480
atggaagctg tcaacattgc agagacacct tcagatctct ttaatgccat tctgatcgaa 540
acgccattag ctccattctt ccaagactgc atgtctgaaa atgctctaga tgaactgaat 600
attgaattgc tacgcaataa actatacaag tcttaccttg aggcattcta taaattctgt 660
aagaatcatg gtgatgtcac agcagaagtt atgtgtccca ttcttgagtt tgaggccgac 720
agacgtgctt ttatcatcac tcttaactcc tttggcactg aattgagcaa agaagaccga 780
gagaccctct atccaacctt cggcaaactc tatcctgagg ggttgcggct gttggctcaa 840
gcagaagact ttgaccagat gaagaacgta gcggatcatt acggagtata caaaccttta 900
tttgaagctg taggtggcag tgggggaaag acattggagg acgtgtttta cgagcgtgag 960
gtacaaatga atgtgctggc attcaacaga cagttccact acggtgtgtt ttatgcatat 1020
gtaaagctga aggaacagga aattagaaat attgtgtgga tagcagaatg tatttcacag 1080
aggcatcgaa ctaaaatcaa cagttacatt ccaattttat aacccaagta aggttctcaa 1140
atgtagaaaa ttataaatgt taaaaggaag ttattgaaga aaataaaaga aattatgtta 1200
tattatctag actacacaaa agtaagccac actatatctt catgagttgc aaatccatgg 1260
aaacacagta aaccagccct gaaacaaagc atttccttgt tttcagtggt attagatctt 1320
gtttccacat gtctgtctca ttcttcactg ggccttacag gttagtttta attaactcta 1380
tggtattttt cttattcttg tttgatcatg ttaaaaattg gacctaataa aagtatttta 1440
ttcttgcttt tccatgcttc tctacaggtc caaatactga atgtctcctt tactttttct 1500
cttttaaatt tttttctaga cagggtctca ctctgtcacc taggctacag tgcagtggtg 1560
tgatcacagc tcactgcagc ctcgacttcc caggctcaag tgatcctccc agctctcagc 1620
ctccaaagta gctggcacta caagtgtaca cccccacaca aggctaagtt ttgtattttt 1680
tgtagagaca gggtttcaac atattatcca ggctggtgtc gaattcctgg gctccaggga 1740
tccacagtcc ccccttggcct cccaaagtgt tgggattaca tgcatgagcc actgtgctgg 1800
gcttcattta cattttaact gtctgttcct tgcctagatt cacagaaatc caaagctgta 1860
tgtagtcaac atggttcaca agtgttggaa aatgtgtttt ttgttttgtt ttgttttgtt 1920
tcgttttgtt ttgagacaga gtttccctct gtcgcccagg ctagagtgca atggcgtgat 1980
ctcggctcac tgcaacctcc acctcccaga ttcaagcaac tctctgcctc agcctcccga 2040
gtagctggga ttacaagcac ccaccactac actcagctaa tttttgtat ttttagtaga 2100 gccggggttt caccatcttg gccaggctga tcttgaactc ctgagctcat gatccacccg 2160
cctcagcctc ccaaagtgct gggattacag gccccttgtt cagccactgc acctggcccc 2220
ttattttgtt tttgttttct aatatacttt gatgtaatca gcttgagaaa gcaacacaat 2280
ttcaaatcct atcttctaga tgcaagcagt gttaaatttg ttaataaatt tgcttttcac 2340
acctttcttt aaataaaagg tatatctctc 2370

<210> SEQ ID NO 90
<211> LENGTH: 19
<212> TYPE: DNA
<213> ORGANISM: Homo sapiens

<400> SEQUENCE: 90
ctgcctgatc tggcgtgat 19

<210> SEQ ID NO 91
<211> LENGTH: 6034
<212> TYPE: DNA
<213> ORGANISM: Artificial
<220> FEATURE:
<223> OTHER INFORMATION: Ip200 expression vector

<400> SEQUENCE: 91
tagttattac gaacgccagc aagacgtagc ccagcgcgtc ggccccgaga tgcgccgcgt 60
gcggctgctg gagatggcgg acgcgatgga tatgttctgc caagggttgg tttgcgcatt 120
cacagttctc cgcaagaatt gattggctcc aattcttgga gtggtgaatc cgttagcgag 180
gtgccgccct gcttcatccc cgtggcccgt tgctcgcgtt tgctggcggt gtccccggaa 240
gaaatatatt tgcatgtctt tagttctatg atgacacaaa ccccgcccag cgtcttgtca 300
ttggcgaatt cgaacacgca gatgcagtcg gggcggcgcg gtccgaggtc cacttcgcat 360
attaaggtga cgcgtgtggc ctcgaacacc gagcgaccct gcagcgaccc gcttaacagc 420
gtcaacagcg tgccgcagat cccgggggc aatgagatat gaaaaagcct gaactcaccg 480
cgacgtctgt cgagaagttt ctgatcgaaa agttcgacag cgtctccgac ctgatgcagc 540
tctcggaggg cgaagaatct cgtgctttca gcttcgatgt aggagggcgt ggatatgtcc 600
tgcgggtaaa tagctgcgcc gatggtttct acaaagatcg ttatgtttat cggcactttg 660
catcggccgc gctcccgatt ccggaagtgc ttgacattgg ggaattcagc gagagcctga 720
cctattgcat ctcccgccgt gcacagggtg tcacgttgca agacctgcct gaaaccgaac 780
tgcccgctgt tctgcagccg gtcgcggagg ccatggatgc gatcgctgcg gccgatctta 840
gccagacgag cgggttcggc ccattcggac cgcaaggaat cggtcaatac actacatggc 900
gtgatttcat atgcgcgatt gctgatcccc atgtgtatca ctggcaaact gtgatggacg 960
acaccgtcag tgcgtccgtc gcgcaggctc tcgatgagct gatgctttgg gccgaggact 1020
gccccgaagt ccggcacctc gtgcacgcgg atttcggctc caacaatgtc ctgacggaca 1080
atggccgcat aacagcggtc attgactgga gcgaggcgat gttcggggat tcccaatacg 1140
aggtcgccaa catcttcttc tggaggccgt ggttggcttg tatggagcag cagacgcgct 1200
acttcgagcg gaggcatccg gagcttgcag gatcgccgcg gctccgggcg tatatgctcc 1260
gcattggtct tgaccaactc tatcagagct tggttgacgg caatttcgat gatgcagctt 1320
gggcgcaggg tcgatgcgac gcaatcgtcc gatccggagc cgggactgtc gggcgtacac 1380
aaatcgcccg cagaagcgcg gccgtctgga ccgatggctg tgtagaagta ctcgccgata 1440
gtggaaaccg acgccccagc actcgtccgg atcgggagat gggggaggct aactgaaaca 1500

-continued

```
cggaaggaga caataccgga aggaacccgc gctatgacgg caataaaaag acagaataaa   1560
acgcacgggt gttgggtcgt ttgttcataa acgcggggtt cggtcccagg gctggcactc   1620
tgtcgatacc ccaccgagac cccattgggg ccaatacgcc cgcgtttctt ccttttcccc   1680
accccacccc ccaagttcgg gtgaaggccc agggctcgca gccaacgtcg gggcggcagg   1740
ccctgccata gccactggcc ccgtgggtta gggacggggt cccccatggg gaatggttta   1800
tggttcgtgg gggttattat tttgggcgtt gcgtggggtc aggtccacga ctggactgag   1860
cagacagacc catggttttt ggatggcctg ggcatggacc gcatgtactg gcgcgacacg   1920
aacaccgggc gtctgtggct gccaaacacc cccgaccccc aaaaaccacc gcgcggattt   1980
ctggcgtgcc aagctagtcg accaattctc atgtttgaca gcttatcatc gcagatccgg   2040
gcaacgttgt tgccattgct gcaggcgcag aactggtagg tatggagatc aatagtaatc   2100
aattacgggg tcattagttc atagcccata tatggagttc cgcgttacat aacttacggt   2160
aaatggcccg cctggctgac cgcccaacga cccccgccca ttgacgtcaa taatgacgta   2220
tgttcccata gtaacgccaa tagggacttt ccattgacgt caatgggtgg agtatttacg   2280
gtaaactgcc cacttggcag tacatcaagt gtatcatatg ccaagtacgc cccctattga   2340
cgtcaatgac ggtaaatggc ccgcctggca ttatgcccag tacatgacct tatgggactt   2400
tcctacttgg cagtacatct acgtattagt catcgctatt accatggtga tgcggttttg   2460
gcagtacatc aatgggcgtg gatagcggtt tgactcacgg ggatttccaa gtctccaccc   2520
cattgacgtc aatgggagtt tgttttggca ccaaaatcaa cgggactttc caaaatgtcg   2580
taacaactcc gccccattga cgcaaatggg cggtaggcgt gtacggtggg aggtctatat   2640
aagcagagct ggtttagtga accgtcagat ccgctagcgc taccggactc agatcttaat   2700
acgactcact ataggaagct tcgaattctg cagtcgacga ctataaggat gacgatgaca   2760
agtaaggatc caccggggcc gcgactctag atcataatca gccataccac atttgtagag   2820
gttttacttg ctttaaaaaa cctcccacac ctccccctga acctgaaaca taaaatgaat   2880
gcaattgttg ttgttaactt gtttattgca gcttataatg gttacaaata aagcaatagc   2940
atcacaaatt tcacaaataa agcatttttt tcactgcatt ctagttgtgg tttgtccaaa   3000
ctcatcaatg tatcttaagg cgtaaattgt aagcgttaat attttgttaa aattcgcgtt   3060
aaatttttgt taaatcagct cattttttaa ccaataggcc gaaatcggca aaatccctta   3120
taaatcaaaa gaatagaccg agatagggtt gagtgttgtt ccagtttgga acaagagtcc   3180
actattaaag aacgtggact ccaacgtcaa agggcgaaaa accgtctatc agggcgatgg   3240
cccactacgt gaaccatcac cctaatcaag ttttttgggg tcgaggtgcc gtaaagcact   3300
aaatcggaac cctaaaggga gcccccgatt tagagcttga cggggaaagc cggcgaacgt   3360
ggcgagaaag gaagggaaga aagcgaaagg agcgggcgct agggcgctgg caagtgtagc   3420
ggtcacgctg cgcgtaacca ccacacccgc cgcgcttaat gcgccgctac agggcgcgtc   3480
aggtggcact tttcggggaa atgtgcgcgg aacccctatt tgtttatttt tctaaataca   3540
ttcaaatatg tatccgctca tgagacaata accctgataa atgcttcaat aatattgaaa   3600
aaggaagagt cctgaggcgg aaagaaccag ctgtggaatg tgtgtcagtt agggtgtgga   3660
aagtccccag gctccccagc aggcagaagt atgcaaagca tgcatctcaa ttagtcagca   3720
accaggtgtg gaaagtcccc aggctcccca gcaggcagaa gtatgcaaag catgcatctc   3780
aattagtcag caaccatagt cccgccccta actccgccca tcccgcccct aactccgccc   3840
agttccgccc attctccgcc ccatggctga ctaatttttt ttagttacca atgcttaatc   3900
```

agtgaggcac ctatctcagc gatctgtcta tttcgttcat ccatagttgc ctgactcccc 3960
gtcgtgtaga taactacgat acgggagggc ttaccatctg gccccagtgc tgcaatgata 4020
ccgcgagacc cacgctcacc ggctccagat ttatcagcaa taaaccagcc agccggaagg 4080
gccgagcgca gaagtggtcc tgcaacttta tccgcctcca tccagtctat taattgttgc 4140
cgggaagcta gagtaagtag ttcgccagtt aatagtttgc gcaacgttgt tgccattgct 4200
acaggcatcg tggtgtcacg ctcgtcgttt ggtatggctt cattcagctc cggttcccaa 4260
cgatcaaggc gagttacatg atcccccatg ttgtgcaaaa aagcggttag ctccttcggt 4320
cctccgatcg ttgtcagaag taagttggcc gcagtgttat cactcatggt tatggcagca 4380
ctgcataatt ctcttactgt catgccatcc gtaagatgct tttctgtgac tggtgagtac 4440
tcaaccaagt cattctgaga atagtgtatg cggcgaccga gttgctcttg cccggcgtca 4500
atacgggata ataccgcgcc acatagcaga actttaaaag tgctcatcat tggaaaacgtt 4560 cttcggggcg aaaactctca aggatcttac cgctgttgag atccagttcg atgtaaccca 4620
ctcgtgcacc caactgatct tcagcatctt ttactttcac cagcgtttct gggtgagcaa 4680
aaacaggaag gcaaaatgcc gcaaaaaagg gaataagggc gacacggaaa tgttgaatac 4740
tcatacgacc gaccaagcga cgcccaacct gccatcacga gatttcgatt ccaccgccgc 4800
cttctatgaa aggttgggct tcggaatcgt tttccgggac gccggctgga tgatcctcca 4860
gcgcggggat ctcatgctgg agttcttcgc ccaccctagg gggaggctaa ctgaaacacg 4920
gaaggagaca ataccggaag gaacccgcgc tatgacggca ataaaaagac agaataaaac 4980
gcacggtgtt gggtcgtttg ttcataaacg cggggttcgg tcccagggct ggcactctgt 5040 cgataccccca ccgagacccc attggggcca atacgcccgc gtttcttcct tttccccacc 5100 ccaccccccca agttcgggtg aaggcccagg gctcgcagcc aacgtcgggg cggcaggccc 5160
tgccatagcc tcaggttact catatatact ttagattgat ttaaaacttc atttttaatt 5220
taaaaggatc taggtgaaga tcctttttga taatctcatg accaaaatcc cttaacgtga 5280
gttttcgttc cactgagcgt cagaccccgt agaaaagatc aaaggatctt cttgagatcc 5340
tttttttctg cgcgtaatct gctgcttgca aacaaaaaaa ccaccgctac cagcggtggt 5400
ttgtttgccg gatcaagagc taccaactct ttttccgaag gtaactggct tcagcagagc 5460
gcagatacca aatactgtcc ttctagtgta gccgtagtta ggccaccact tcaagaactc 5520
tgtagcaccg cctacatacc tcgctctgct aatcctgtta ccagtggctg ctgccagtgg 5580
cgataagtcg tgtcttaccg ggttggactc aagacgatag ttaccggata aggcgcagcg 5640
gtcgggctga acggggggtt cgtgcacaca gcccagcttg gagcgaacga cctacaccga 5700
actgagatac ctacagcgtg agctatgaga aagcgccacg cttcccgaag ggagaaaggc 5760
ggacaggtat ccggtaagcg gcagggtcgg aacaggagag cgcacgaggg agcttccagg 5820
gggaaacgcc tggtatcttt atagtcctgt cgggtttcgc cacctctgac ttgagcgtcg 5880
atttttgtga tgctcgtcag gggggcggag cctatggaaa aacgccagca acgcggcctt 5940
tttacggttc ctggcctttt gctggccttt tgctcacatg ttctttcctg cgttatcccc 6000
tgattctgtg gataaccgta ttaccgccat gcat 6034

<210> SEQ ID NO 92
<211> LENGTH: 4395
<212> TYPE: DNA
<213> ORGANISM: Artificial
<220> FEATURE:
<223> OTHER INFORMATION: pCMX-HA expression vector

<400> SEQUENCE: 92

```
ttgacattga ttattgacta gttattaata gtaatcaatt acggggtcat tagttcatag     60
cccatatatg gagttcgcgt tacataactt acggtaaatg gcccgcctgc tgaccgccca    120
acgacccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgccaagt acgcccccta ttgacgtcaa tgacggtaaa tggcccgcct    300
ggcattatgc ccagtacatg accttatggg actttcctac ttggcagtac atctacgtat    360
tagtcatcgc tattaccatg gtgatgcggt tttggcagta catcaatggg cgtggatagc    420
ggtttgactc acggggattt ccaagtctcc accccattga cgtcaatggg agtttgtttt    480
tggcaccaaa atcaacggga ctttccaaaa tgtcgtaaca actccgcccc attgacgcaa    540
atgggcggta ggcgtgtacg gtgggaggtc tatataagca gagctctctg gctaactaga    600
gaacccactg cttactggct tatcgaaatt aatacgactc actataggga gacccaagct    660
tctaggtacc gggccccccc tcgaggtcga cggtatcgat aagcttgata tcgaattcct    720
gcagcccggg ggatcctggc cagctagcta ggtagctaga ggatctttgt gaaggaacct    780
tacttctgtg gtgtgacata attggacaaa ctacctacag agatttaaag ctctaaggta    840
aatataaaat ttttaagtgt ataatgtgtt aaactactga ttctaattgt ttgtgtattt    900
tagattccaa cctatggaac tgatgaatgg gagcagtggt ggaatgcctt taatgaggaa    960
aacctgtttt gctcagaaga aatgccatct agtgatgatg aggctactgc tgactctcaa   1020
cattctactc ctccaaaaaa gaagagaaag gtagaagacc ccaaggactt tccttcagaa   1080
ttgctaagtt ttttgagtca tgctgtgttt agtaatagaa ctcttgcttg ctttgctatt   1140
tacaccacaa aggaaaaagc tgcactgcta tacaagaaaa ttatggaaaa atatttgatg   1200
tatagtgcct tgactagaga tcataatcag ccataccaca tttgtagagg ttttacttgc   1260
tttaaaaaac ctcccacacc tccccctgaa cctgaaacat aaaatgaatg caattgttgt   1320
tgttaacttg tttattgcag cttataatgg ttacaaataa agcaatagca tcacaaattt   1380
cacaaataaa gcattttttt cactgcattc tagttgtggt ttgtccaaac tcatcaatgt   1440
atcttatcat gtctgggtca gcttcagaag atgggcgagg gcctccaaca cagtaatttt   1500
cctcccgact cttaaaatag aaaatgtcaa gtcagttaag caggaagtgg actaactgac   1560
gcagctggcc gtgcgacatc ctcttttaat tagttgctag gcaactgccc tccagagggc   1620
atgtggtttt gcaagaggaa gcaaaaagcc tctccaccca ggcctcagaa tgtttccacc   1680
caatcattac tatgacaaca gctgtttttt ttagtattaa gcagaggccg gggccctgc    1740
gtccgcttac tctggagaaa aagaagagag gcattgtaga ggcttccaga ggcaacttgt   1800
caaaacagga ctgcttctat ttctgtcaca ctgtctggcc ctgtcacaag gtcagcacct   1860
ccataccccc tttaataagc agtttgggaa cgggtgcggg tcttactccg cccatcccgc   1920
ccctaactcc gcccagttcc gcccattctc cgggccatgg ctgactaatt ttttttattt   1980
atgcagagcc gacgcgcctc ggcctctgag ctattccaga agtagtgagg aggctttttt   2040
ggaggagctg cattaatgaa tcggccaacg cgcggggaga ggcggtttgc gtattgggcg   2100
ctcttccgct tcctcgctca ctgactcgct gcgctcggtc gttcggctgc ggcgagcggt   2160
atcagctcac tcaaaggcgg taatacggtt atccacagaa tcaggggata acgcaggaaa   2220
gaacatgtga gcaaaaggcc agcaaaaggc caggaaccgt aaaaaggccg cgttgctggc   2280
gtttttccat aggctccgcc cccctgacga gcatcacaaa aatcgacgct caagtcagag   2340
```

-continued gtggcgaaac ccgacaggac tataaagata ccaggcgttt ccccctggaa gctccctcgt 2400
gcgctctcct gttccgaccc tgccgcttac cggatacctg tccgcctttc tcccttggaa 2460
gcgtggcgct ttctcatagc tcacgctgta ggtatctcag ttcggtgtag gtcgttcgct 2520
ccaagctggg ctgtgtgcac gaaccccccg ttcagcccga ccgtgcgcct tatccggtaa 2580
ctatcgtctt gagtccaacc cggtaagaca cgacttatgc ccactggcag cagccactgg 2640
taacaggatt agcagagcga ggtatgtagg cggtgctaca gagttcttga agtggtggcc 2700
taactacggc tacactagaa gaacagtatt tggtatctgc gctctgctga agccagttac 2760
ttcggaaaaa gagttggtag ctcttgatcc ggcaaacaac ctggtagcgg tggttttttt 2820
gtttgcaagc agcagattac gcgcagaaaa aaaggatctc aagaagatcc tttgatcttt 2880
tctacggggt ctgacgctca gtggaacgaa aactcacgtt aagggatttt ggtcatgaga 2940
ttatcaaaaa ggatcttcac ctagatcctt ttaaattaaa aatgaagttt taaatcaatc 3000
taaagtatat atgagtaaac ttggtctgac agttaccaat gcttaatcag tgaggcacct 3060
atctcagcga tctgtctatt tcgttcatcc atagttgcct gactccccgt cgtgtagata 3120
actacgatac gggagggctt accatctggc cccagtgctg caatgatacc gcgagaccca 3180
cgctcaccgg ctccagattt atcagcaata aaccagccag ccggaagggc cgagcgcaga 3240
agtggtcctg caactttatc cgcctccatc cagtctatta attgttgccg ggaagctaga 3300
gtaagtagtt cgccagttaa tagtttgcgc aacgttgttg ccattgctac aggcatcgtg 3360
gtgtcacgct cgtcgtttgg tatggcttca ttcagctccg gttcccaacg atcaaggcga 3420
gttacatgat cccccatgtt gtgcaaaaaa gcggttagct ccttcggtcc tccgatcgtt 3480
gtcagaagta agttggccgc agtgttatca ctcatggtta tggcagcact gcataattct 3540
cttactgtca tgccatccgt aagatgcttt tctgtgactg gtgagtactc aaccaagtca 3600
ttctgagaat agtgtatgcg gcgaccgagt tgctcttgcc cggcgtcaat acgggataat 3660
accgcgccac atagcagaac tttaaaagtg ctcatcattg gaaaacgttc ttcggggcga 3720
aaactctcaa ggatcttacc gctgttgaga tccagttcga tgtaacccac tcgtgcaccc 3780
aactgatctt cagcatcttt tactttcacc agcgtttctg ggtgagcaaa aacaggaagg 3840
caaaatgccg caaaaaaggg aataagggcg acacggaaat gttgaatact catactcttc 3900
ctttttcaat attattgaag catttatcag ggttattgtc tcatgagcgg atacatattt 3960
gaatgtattt agaaaaataa acaaataggg gttccgcgca catttccccg aaaagtgcca 4020
cctgacgtct aagaaaccat tattatcatg acattaacct ataaaaatag gcgtatcacg 4080
aggccctttc gtctcgcgcg tttcggtgat gacggtgaaa acctctgaca catgcagctc 4140
ccggagacgg tcacagcttg tctgtaagcg gatccgggag cagacaagcc cgtcactcag 4200
cgggtgttgg cgggtgtcgg ggctggctta actatgcggc atcagagcag attgtactga 4260
gagtgcacca tatgcggtgt gaaataccgc acagatgcgt aaggagaaaa taccgcatca 4320
ggcgccattc gccattcagg ctgcgcaact gttgggaagg gcgatcggtg cgggcctctt 4380
cgctattacg ccagc 4395

<210> SEQ ID NO 93
<211> LENGTH: 439
<212> TYPE: PRT
<213> ORGANISM: Mus musculus

<400> SEQUENCE: 93

Met Glu Pro Trp Cys Gly Ala Glu Val Arg Gly Gln Gly Pro Gln Gly

-continued

```
1               5                   10                  15

Pro Arg Val Pro Gly Ala Ser Arg Ser Arg Ser Arg Ala Leu Leu Leu
            20                  25                  30

Leu Leu Leu Leu Leu Leu Leu Leu Leu Pro Arg Arg Pro Ala Gly Glu
        35                  40                  45

Arg Ile Arg Pro Arg Arg Pro Pro Arg His Ala His Pro Arg Pro Pro
    50                  55                  60

Leu Thr Arg Trp Arg Pro Ser Thr Gly Tyr Leu Ala Ala Gly Ala Ser
65                  70                  75                  80

Pro Gly Thr Leu Ser Thr Thr Val Pro Thr Gly Pro Gly Val Ser Cys
                85                  90                  95

Gly Ser Arg Gly Ile Cys Pro Ser Gly Arg Leu Arg Leu Pro Arg Gln
            100                 105                 110

Ala Gln Thr Asn Gln Thr Thr Thr Ala Pro Pro Asn Ser Gln Thr Met
        115                 120                 125

Ala Pro Leu Lys Thr Val Gly Thr Leu Gly Met Met Asp Thr Thr Gly
    130                 135                 140

Ser Val Leu Lys Thr Val His Ser Ser Asn Leu Pro Phe Cys Gly Ser
145                 150                 155                 160

Ser His Glu Pro Asp Pro Thr Leu Arg Asp Pro Glu Ala Met Thr Arg
                165                 170                 175

Arg Trp Pro Trp Met Val Ser Val Gln Ala Asn Gly Ser His Ile Cys
            180                 185                 190

Ala Gly Ile Leu Ile Ala Ser Gln Trp Val Leu Thr Val Ala His Cys
        195                 200                 205

Leu Ser Gln Asn His Val Asn Tyr Ile Val Arg Ala Gly Ser Pro Trp
    210                 215                 220

Ile Asn Gln Thr Ala Gly Thr Ser Ser Asp Val Pro Val His Arg Val
225                 230                 235                 240

Ile Ile Asn His Gly Tyr Gln Pro Arg Arg Tyr Trp Ser Trp Val Gly
                245                 250                 255

Arg Ala His Asp Ile Gly Leu Leu Lys Leu Lys Trp Gly Leu Lys Tyr
            260                 265                 270

Ser Lys Tyr Val Trp Pro Ile Cys Leu Pro Gly Leu Asp Tyr Val Val
        275                 280                 285

Glu Asp Ser Ser Leu Cys Thr Val Thr Gly Trp Gly Tyr Pro Arg Ala
    290                 295                 300

Asn Gly Ile Trp Pro Gln Phe Gln Ser Leu Gln Glu Lys Glu Val Ser
305                 310                 315                 320

Ile Leu Asn Ser Lys Lys Cys Asp His Phe Tyr His Lys Phe Ser Arg
                325                 330                 335

Ile Ser Ser Leu Val Arg Ile Ile Asn Pro Gln Met Ile Cys Ala Ser
            340                 345                 350

Asp Asn Asn Arg Glu Glu Phe Cys Tyr Glu Ile Thr Gly Glu Pro Leu
        355                 360                 365

Val Cys Ser Ser Asp Gly Thr Trp Tyr Leu Val Gly Met Met Ser Trp
    370                 375                 380

Gly Pro Gly Cys Lys Lys Ser Glu Ala Pro Pro Ile Phe Leu Gln Val
385                 390                 395                 400

Ser Tyr Tyr Arg Pro Trp Ile Trp Asp Arg Leu Ser Gly Glu Pro Leu
                405                 410                 415

Ala Leu Pro Ala Pro Ser Arg Thr Leu Leu Leu Ala Phe Leu Leu Leu
            420                 425                 430
```

```
Leu Ile Leu Leu Gly Thr Leu
        435


<210> SEQ ID NO 94
<211> LENGTH: 350
<212> TYPE: PRT
<213> ORGANISM: Mus musculus

<400> SEQUENCE: 94

Met Leu Glu Thr Ala Glu Leu Tyr Phe Asn Val Asp His Gly Tyr Leu
1               5                   10                  15

Glu Gly Leu Val Arg Gly Cys Lys Ala Ser Leu Leu Thr Gln Gln Asp
            20                  25                  30

Tyr Val Asn Leu Val Gln Cys Glu Thr Leu Glu Asp Leu Lys Ile His
        35                  40                  45

Leu Gln Thr Thr Asp Tyr Gly Asn Phe Leu Ala Asn Glu Thr Asn Pro
    50                  55                  60

Leu Thr Val Ser Lys Ile Asp Thr Glu Met Arg Lys Lys Leu Cys Arg
65                  70                  75                  80

Glu Phe Asp Tyr Phe Arg Asn His Ser Leu Glu Pro Leu Ser Thr Phe
                85                  90                  95

Leu Thr Tyr Met Thr Cys Ser Tyr Met Ile Asp Asn Ile Ile Leu Leu
            100                 105                 110

Met Asn Gly Ala Leu Gln Lys Lys Ser Val Lys Glu Val Leu Ala Lys
        115                 120                 125

Cys His Pro Leu Gly Arg Phe Thr Glu Met Glu Ala Val Asn Ile Ala
    130                 135                 140

Glu Thr Pro Ser Asp Leu Phe Lys Ala Val Leu Val Glu Thr Pro Leu
145                 150                 155                 160

Ala Pro Phe Phe Gln Asp Cys Met Ser Glu Asn Thr Leu Asp Glu Leu
                165                 170                 175

Asn Ile Glu Leu Leu Arg Asn Lys Leu Tyr Lys Ser Tyr Leu Glu Ala
            180                 185                 190

Phe Tyr Lys Phe Cys Lys Asp His Gly Asp Val Thr Ala Asp Val Met
        195                 200                 205

Cys Pro Ile Leu Glu Phe Glu Ala Asp Arg Arg Ala Leu Ile Ile Thr
    210                 215                 220

Leu Asn Ser Phe Gly Thr Glu Leu Ser Lys Glu Asp Arg Glu Thr Leu
225                 230                 235                 240

Phe Pro Thr Cys Gly Arg Leu Tyr Pro Glu Gly Leu Arg Leu Leu Ala
                245                 250                 255

Gln Ala Glu Asp Phe Glu Gln Met Lys Arg Val Ala Asp Asn Tyr Gly
            260                 265                 270

Val Tyr Lys Pro Leu Phe Asp Ala Val Gly Gly Ser Gly Gly Lys Thr
        275                 280                 285

Leu Glu Asp Val Phe Tyr Glu Arg Glu Val Gln Met Asn Val Leu Ala
    290                 295                 300

Phe Asn Arg Gln Leu His Tyr Gly Val Phe Tyr Ala Tyr Val Lys Leu
305                 310                 315                 320

Lys Glu Gln Glu Met Arg Asn Ile Val Trp Ile Ala Glu Cys Ile Ser
                325                 330                 335

Gln Arg His Arg Thr Lys Ile Asn Ser Tyr Ile Pro Ile Leu
            340                 345                 350


<210> SEQ ID NO 95
<211> LENGTH: 400
```

<212> TYPE: PRT
<213> ORGANISM: Mus musculus

<400> SEQUENCE: 95

```
Met Gly Pro Arg Ser Pro Ala Ala Ala Leu Leu Val Leu Leu Cys Val
1               5                   10                  15

Gly Cys Ala Pro Thr Pro Gly Arg Gly Gln Tyr Glu Arg Tyr Ser Phe
            20                  25                  30

Arg Asn Phe Pro Arg Asp Glu Leu Met Pro Leu Glu Ser Ala Tyr Arg
        35                  40                  45

His Ala Leu Asp Gln Tyr Ser Gly Glu His Trp Ala Glu Ser Val Gly
    50                  55                  60

Tyr Leu Glu Val Ser Leu Arg Leu His Arg Leu Leu Arg Asp Ser Glu
65                  70                  75                  80

Ala Phe Cys His Arg Asn Cys Ser Ala Ala Thr Pro Ala Pro Ala Pro
                85                  90                  95

Ala Gly Pro Ala Ser His Ala Glu Leu Arg Leu Phe Gly Ser Val Leu
            100                 105                 110

Arg Arg Ala Gln Cys Leu Lys Arg Cys Lys Gln Gly Leu Pro Ala Phe
        115                 120                 125

Arg Gln Ser Gln Pro Ser Arg Ser Val Leu Ala Asp Phe Gln Gln Arg
    130                 135                 140

Glu Pro Tyr Lys Phe Leu Gln Phe Ala Tyr Phe Lys Ala Asn Asp Leu
145                 150                 155                 160

Pro Lys Ala Ile Ala Ala Ala His Thr Tyr Leu Leu Lys His Pro Asp
                165                 170                 175

Asp Glu Met Met Lys Arg Asn Met Glu Tyr Tyr Lys Ser Leu Pro Gly
            180                 185                 190

Ala Glu Asp His Ile Lys Asp Leu Glu Thr Lys Ser Tyr Glu Ser Leu
        195                 200                 205

Phe Val Arg Ala Val Arg Ala Tyr Asn Gly Glu Asn Trp Arg Thr Ser
    210                 215                 220

Ile Ser Asp Met Glu Leu Ala Leu Pro Asp Phe Leu Lys Ala Phe Tyr
225                 230                 235                 240

Glu Cys Leu Ala Ala Cys Glu Gly Ser Arg Glu Ile Lys Asp Phe Lys
                245                 250                 255

Asp Phe Tyr Leu Ser Ile Ala Asp His Tyr Val Glu Val Leu Glu Cys
            260                 265                 270

Lys Ile Arg Cys Glu Glu Thr Leu Thr Pro Val Ile Gly Gly Tyr Pro
        275                 280                 285

Val Glu Lys Phe Val Ala Thr Met Tyr His Tyr Leu Gln Phe Ala Tyr
    290                 295                 300

Tyr Lys Leu Asn Asp Leu Lys Asn Ala Ala Pro Cys Ala Val Ser Tyr
305                 310                 315                 320

Leu Leu Phe Asp Gln Ser Asp Arg Val Met Gln Gln Asn Leu Val Tyr
                325                 330                 335

Tyr Gln Tyr His Arg Asp Lys Trp Gly Leu Ser Asp Glu His Phe Gln
            340                 345                 350

Pro Arg Pro Glu Ala Val Gln Phe Phe Asn Val Thr Thr Leu Gln Lys
        355                 360                 365

Glu Leu Tyr Asp Phe Ala Gln Glu His Leu Met Asp Asp Asp Glu Gly
    370                 375                 380

Glu Val Val Glu Tyr Val Asp Asp Leu Leu Glu Thr Glu Glu Ser Ala
385                 390                 395                 400
```

<210> SEQ ID NO 96
<211> LENGTH: 266
<212> TYPE: PRT
<213> ORGANISM: Mus musculus

<400> SEQUENCE: 96

```
Met Lys Leu Asn Glu Arg Ser Leu Ala Phe Tyr Ala Thr Cys Asp Ala
1               5                   10                  15

Pro Val Asp Asn Ala Gly Phe Leu Tyr Lys Arg Gly Gly Arg Gly Thr
            20                  25                  30

Gly Ser His Arg Arg Trp Phe Val Leu Arg Gly Asn Ile Leu Phe Tyr
        35                  40                  45

Phe Glu Ala Glu Gly Ser Arg Glu Pro Leu Gly Val Ile Leu Leu Glu
    50                  55                  60

Gly Cys Thr Val Glu Leu Val Asp Ala Arg Glu Glu Phe Ala Phe Ala
65                  70                  75                  80

Val Arg Phe Ala Gly Gly Arg Ser Arg Pro Tyr Val Leu Ala Ala Asp
                85                  90                  95

Ser Gln Ala Ala Leu Glu Gly Trp Val Lys Ala Leu Ser Arg Ala Ser
            100                 105                 110

Phe His Tyr Leu Arg Leu Val Val Arg Glu Leu Glu Gln Gln Leu Ala
        115                 120                 125

Ala Met Arg Glu Gly Ser Pro Ala Asn Ala Leu Pro Ala Asn Pro Ser
    130                 135                 140

Pro Val Leu Thr Gln Arg Pro Lys Glu Asn Gly Trp Val Val Trp Ser
145                 150                 155                 160

Thr Leu Pro Glu Gln Pro Ser Val Ala Pro Gln Arg Pro Pro Pro Leu
                165                 170                 175

Pro Pro Arg Arg Arg Ala Ser Ala Ala Asn Gly Pro Leu Ala Ser Phe
            180                 185                 190

Ala Gln Leu His Ala Arg Tyr Gly Leu Glu Val Gln Ala Leu Arg Asp
        195                 200                 205

Gln Trp Arg Gly Gly Gln Ala Gly Leu Ala Ser Leu Glu Val Pro Trp
    210                 215                 220

His Pro Gly Ser Ala Glu Thr Gln Thr Gln Asp Gln Pro Ala Leu Arg
225                 230                 235                 240

Gly His Ser Gly Cys Lys Val Leu His Val Phe Arg Ser Val Glu Trp
                245                 250                 255

Pro Val Cys Asn Pro Gly Ser Gln Gly Thr
            260                 265
```

<210> SEQ ID NO 97
<211> LENGTH: 447
<212> TYPE: PRT
<213> ORGANISM: Mus musculus

<400> SEQUENCE: 97

```
Met Arg Glu Ile Val His Ile Gln Ala Gly Gln Cys Gly Asn Gln Ile
1               5                   10                  15

Gly Thr Lys Phe Trp Glu Val Ile Ser Asp Glu His Gly Ile Asp Gln
            20                  25                  30

Ala Gly Gly Tyr Val Gly Asp Ser Ala Leu Gln Leu Glu Arg Ile Ser
        35                  40                  45

Val Tyr Tyr Asn Glu Ser Ser Ser Lys Lys Tyr Val Pro Arg Ala Ala
    50                  55                  60

Leu Val Asp Leu Glu Pro Gly Thr Met Asp Ser Val Arg Ser Gly Pro
```

```
65                  70                  75                  80

Phe Gly Gln Leu Phe Arg Pro Asp Asn Phe Ile Phe Gly Gln Thr Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Cys Glu His Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Met Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Ser Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ala Arg Gly Ser Gln Gln Tyr Arg Ala Leu Thr Val Pro Glu
        275                 280                 285

Leu Thr Gln Gln Met Phe Asp Ala Lys Asn Met Met Ala Ala Cys Asp
    290                 295                 300

Pro Arg His Gly Arg Tyr Leu Thr Val Ala Thr Val Phe Arg Gly Pro
305                 310                 315                 320

Met Ser Met Lys Glu Val Asp Glu Gln Met Leu Ala Ile Gln Asn Lys
                325                 330                 335

Asn Ser Ser Tyr Phe Val Glu Trp Ile Pro Asn Asn Val Lys Val Ala
            340                 345                 350

Val Cys Asp Ile Pro Pro Arg Gly Leu Lys Met Ala Ser Thr Phe Ile
        355                 360                 365

Gly Asn Ser Thr Ala Ile Gln Glu Leu Phe Lys Arg Ile Ser Glu Gln
    370                 375                 380

Phe Ser Ala Met Phe Arg Arg Lys Ala Phe Leu His Trp Phe Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Val Asn Asp
            420                 425                 430

Gly Glu Glu Ala Phe Glu Asp Glu Asp Glu Glu Glu Ile Asn Glu
        435                 440                 445


<210> SEQ ID NO 98
<211> LENGTH: 202
<212> TYPE: PRT
<213> ORGANISM: Mus musculus

<400> SEQUENCE: 98

Met Ser Cys Val Pro Trp Lys Gly Asp Lys Ala Lys Ala Glu Ser Ser
```

-continued

```
1               5                   10                  15

Asp Leu Pro Gln Ala Ala Pro Pro Gln Ile Tyr His Glu Lys Gln Arg
            20                  25                  30

Arg Glu Leu Cys Ala Leu His Ala Leu Asn Asn Val Phe Gln Asp Ser
        35                  40                  45

Asn Ala Phe Thr Arg Glu Thr Leu Gln Glu Ile Phe Gln Arg Leu Ser
    50                  55                  60

Pro Asn Thr Met Val Thr Pro His Lys Lys Ser Met Leu Gly Asn Gly
65                  70                  75                  80

Asn Tyr Asp Val Asn Val Ile Met Ala Ala Leu Gln Thr Lys Gly Tyr
                85                  90                  95

Glu Ala Val Trp Trp Asp Lys Arg Arg Asp Val Gly Val Ile Ala Leu
            100                 105                 110

Thr Asn Val Met Gly Phe Ile Met Asn Leu Pro Ser Ser Leu Cys Trp
        115                 120                 125

Gly Pro Leu Lys Leu Pro Leu Lys Arg Gln His Trp Ile Cys Val Arg
    130                 135                 140

Glu Val Gly Gly Ala Tyr Tyr Asn Leu Asp Ser Lys Leu Lys Met Pro
145                 150                 155                 160

Glu Trp Ile Gly Gly Glu Ser Glu Leu Arg Lys Phe Leu Lys Tyr His
                165                 170                 175

Leu Arg Gly Lys Asn Cys Glu Leu Leu Leu Val Val Pro Glu Glu Val
            180                 185                 190

Glu Ala His Gln Ser Trp Arg Ala Asp Val
        195                 200


<210> SEQ ID NO 99
<211> LENGTH: 191
<212> TYPE: PRT
<213> ORGANISM: Mus musculus

<400> SEQUENCE: 99

Met Ser Ala Glu Leu Glu Leu Leu Trp Pro Val Ser Gly Leu Leu Leu
1               5                   10                  15

Leu Leu Leu Gly Ala Thr Ala Trp Leu Cys Val His Cys Ser Arg Pro
            20                  25                  30

Gly Val Lys Arg Asn Glu Lys Ile Tyr Glu Gln Arg Asn Arg Gln Glu
        35                  40                  45

Asn Ala Gln Ser Ser Ala Ala Ala Gln Thr Tyr Ser Leu Ala Arg Gln
    50                  55                  60

Val Trp Pro Gly Pro Gln Met Asp Thr Ala Pro Asn Lys Ser Phe Glu
65                  70                  75                  80

Arg Lys Asn Lys Met Leu Phe Ser His Leu Glu Gly Ser Asn Gln Glu
                85                  90                  95

Pro Asp Ala Ala Tyr Val Asp Pro Ile Pro Thr Asn Tyr Tyr Asn Trp
            100                 105                 110

Gly Cys Phe Gln Lys Pro Ser Glu Asp Asp Asp Ser Asn Ser Tyr Glu
        115                 120                 125

Asn Val Leu Val Cys Lys Pro Ser Thr Pro Glu Ser Gly Val Glu Asp
    130                 135                 140

Phe Glu Asp Tyr Gln Asn Ser Val Ser Ile His Gln Trp Arg Glu Ser
145                 150                 155                 160

Lys Arg Thr Met Gly Ala Pro Met Ser Leu Ser Gly Ser Pro Asp Glu
                165                 170                 175

Glu Pro Asp Tyr Val Asn Gly Asp Val Ala Ala Ala Glu Asn Ile
```

180 185 190

<210> SEQ ID NO 100
<211> LENGTH: 163
<212> TYPE: PRT
<213> ORGANISM: Mus musculus

<400> SEQUENCE: 100

Met Met Pro Gly Gln Ile Pro Asp Pro Ser Val Thr Ala Gly Ser Leu
1 5 10 15

Pro Gly Leu Gly Pro Leu Thr Gly Leu Pro Ser Ser Ala Leu Thr Thr
20 25 30

Glu Glu Leu Lys Tyr Ala Asp Ile Arg Asn Ile Gly Ala Met Ile Ala
35 40 45

Pro Leu His Phe Leu Glu Val Lys Leu Gly Lys Arg Pro Gln Pro Val
50 55 60

Lys Ser Glu Leu Asp Glu Glu Glu Glu Arg Arg Lys Arg Arg Arg Glu
65 70 75 80

Lys Asn Lys Val Ala Ala Ala Arg Cys Arg Asn Lys Lys Lys Glu Arg
85 90 95

Thr Glu Phe Leu Gln Arg Glu Ser Glu Arg Leu Glu Leu Met Asn Ala
100 105 110

Glu Leu Lys Thr Gln Ile Glu Glu Leu Lys Leu Glu Arg Gln Gln Leu
115 120 125

Ile Leu Met Leu Asn Arg His Arg Pro Thr Cys Ile Val Arg Thr Asp
130 135 140

Ser Val Arg Thr Pro Glu Ser Glu Gly Asn Pro Leu Leu Glu Gln Leu
145 150 155 160

Asp Lys Lys

<210> SEQ ID NO 101
<211> LENGTH: 627
<212> TYPE: PRT
<213> ORGANISM: Mus musculus

<400> SEQUENCE: 101

Met Ala Gly Glu Arg Pro Pro Leu Arg Gly Pro Gly Pro Gly Glu Ala
1 5 10 15

Pro Gly Glu Gly Pro Gly Gly Ala Gly Gly Gly Pro Gly Arg Gly Arg
20 25 30

Pro Ser Ser Tyr Arg Ala Leu Arg Ser Ala Val Ser Ser Leu Ala Arg
35 40 45

Val Asp Asp Phe Asp Cys Ala Glu Lys Ile Gly Ala Gly Phe Phe Ser
50 55 60

Glu Val Tyr Lys Val Arg His Arg Gln Ser Gly Gln Val Met Val Leu
65 70 75 80

Lys Met Asn Lys Leu Pro Ser Asn Arg Ser Asn Thr Leu Arg Glu Val
85 90 95

Gln Leu Met Asn Arg Leu Arg His Pro Asn Ile Leu Arg Phe Met Gly
100 105 110

Val Cys Val His Gln Gly Gln Leu His Ala Leu Thr Glu Tyr Met Asn
115 120 125

Gly Gly Thr Leu Glu Gln Leu Leu Ser Ser Pro Glu Pro Leu Ser Trp
130 135 140

Pro Val Arg Leu His Leu Ala Leu Asp Ile Ala Gln Gly Leu Arg Tyr
145 150 155 160

-continued

```
Leu His Ala Lys Gly Val Phe His Arg Asp Leu Thr Ser Lys Asn Cys
                165                 170                 175

Leu Val Arg Arg Glu Asp Arg Gly Phe Thr Ala Val Val Gly Asp Phe
            180                 185                 190

Gly Leu Ala Glu Lys Ile Pro Val Tyr Arg Glu Gly Thr Arg Lys Glu
        195                 200                 205

Pro Leu Ala Val Val Gly Ser Pro Tyr Trp Met Ala Pro Glu Val Leu
    210                 215                 220

Arg Gly Glu Leu Tyr Asp Glu Lys Ala Asp Val Phe Ala Phe Gly Ile
225                 230                 235                 240

Val Leu Cys Glu Leu Ile Ala Arg Val Pro Ala Asp Pro Asp Tyr Leu
                245                 250                 255

Pro Arg Thr Glu Asp Phe Gly Leu Asp Val Pro Ala Phe Arg Thr Leu
            260                 265                 270

Val Gly Asn Asp Cys Pro Leu Pro Phe Leu Leu Leu Ala Ile His Cys
        275                 280                 285

Cys Ser Met Glu Pro Ser Thr Arg Ala Pro Phe Thr Glu Ile Thr Gln
    290                 295                 300

His Leu Glu Gln Ile Leu Glu Gln Gln Pro Glu Ala Thr Pro Leu Ala
305                 310                 315                 320

Lys Pro Pro Leu Thr Lys Ala Pro Leu Thr Tyr Asn Gln Gly Ser Val
                325                 330                 335

Pro Arg Gly Gly Pro Ser Ala Thr Leu Pro Arg Pro Asp Pro Arg Leu
            340                 345                 350

Ser Arg Ser Arg Ser Asp Leu Phe Leu Pro Pro Ser Pro Glu Ser Pro
        355                 360                 365

Pro Ser Trp Gly Asp Asn Leu Thr Arg Val Asn Pro Phe Ser Leu Arg
    370                 375                 380

Glu Asp Leu Arg Gly Gly Lys Ile Lys Leu Leu Asp Thr Pro Cys Lys
385                 390                 395                 400

Pro Ala Thr Pro Leu Pro Leu Val Pro Pro Ser Pro Leu Thr Ser Thr
                405                 410                 415

Gln Leu Pro Leu Val Thr Thr Pro Asp Ile Leu Val Gln Pro Glu Thr
            420                 425                 430

Pro Val Arg Arg Cys Arg Ser Leu Pro Ser Ser Pro Glu Leu Pro Arg
        435                 440                 445

Arg Met Glu Thr Ala Leu Pro Gly Pro Gly Pro Ser Pro Met Gly Pro
    450                 455                 460

Thr Glu Glu Arg Met Asp Cys Glu Gly Ser Ser Pro Glu Pro Glu Pro
465                 470                 475                 480

Pro Gly Leu Ala Pro Gln Leu Pro Leu Ala Val Ala Thr Asp Asn Phe
                485                 490                 495

Ile Ser Thr Cys Ser Ser Ala Ser Gln Pro Trp Ser Pro Arg Ser Gly
            500                 505                 510

Pro Pro Leu Asn Asn Asn Pro Pro Ala Val Val Val Asn Ser Pro Gln
        515                 520                 525

Gly Trp Ala Arg Glu Pro Trp Asn Arg Ala Gln His Ser Leu Pro Arg
    530                 535                 540

Ala Ala Ala Leu Glu Gln Thr Glu Pro Ser Pro Pro Pro Ser Ala Pro
545                 550                 555                 560

Arg Glu Pro Glu Glu Gly Leu Pro Cys Pro Gly Cys Cys Leu Gly Pro
                565                 570                 575

Phe Ser Phe Gly Phe Leu Ser Met Cys Pro Arg Pro Thr Pro Ala Val
            580                 585                 590
```

Ala Arg Tyr Arg Asn Leu Asn Cys Glu Ala Gly Ser Leu Leu Cys His
        595                 600                 605

Arg Gly His His Ala Lys Pro Pro Thr Pro Ser Leu Gln Leu Pro Gly
    610                 615                 620

Ala Arg Ser
625

<210> SEQ ID NO 102
<211> LENGTH: 566
<212> TYPE: PRT
<213> ORGANISM: Mus musculus

<400> SEQUENCE: 102

Met Thr Ile Leu Pro Lys Lys Lys Pro Pro Pro Pro Asp Ala Asp Pro
1               5                   10                  15

Ala Asn Glu Pro Pro Pro Pro Gly Pro Leu Pro Pro Ala Pro Arg Arg
            20                  25                  30

Gly Ala Gly Val Gly Val Gly Gly Gly Gly Thr Gly Val Gly Gly Gly
        35                  40                  45

Glu Arg Asp Arg Asp Ser Gly Val Val Gly Ala Arg Pro Arg Ala Ser
    50                  55                  60

Pro Pro Pro Gln Gly Pro Leu Pro Gly Pro Pro Gly Ala Leu His Arg
65                  70                  75                  80

Trp Ala Leu Ala Val Pro Pro Gly Ala Val Ala Gly Pro Arg Pro Gln
                85                  90                  95

Gln Ala Ser Pro Pro Pro Cys Gly Gly Pro Gly Gly Pro Gly Gly Gly
            100                 105                 110

Pro Gly Asp Ala Leu Gly Ala Thr Thr Ala Gly Val Gly Ala Ala Gly
        115                 120                 125

Val Val Val Gly Val Gly Gly Thr Val Gly Val Gly Gly Cys Cys Ser
    130                 135                 140

Gly Pro Gly His Ser Lys Arg Arg Arg Gln Ala Pro Gly Val Gly Ala
145                 150                 155                 160

Val Gly Gly Ala Ser Pro Glu Arg Glu Glu Val Gly Ala Gly Tyr Asn
                165                 170                 175

Ser Glu Asp Glu Tyr Glu Ala Ala Ala Ala Arg Ile Glu Ala Met Asp
            180                 185                 190

Pro Ala Thr Val Glu Gln Gln Glu His Trp Phe Glu Lys Ala Leu Arg
        195                 200                 205

Asp Lys Lys Gly Phe Ile Ile Lys Gln Met Lys Glu Asp Gly Ala Cys
    210                 215                 220

Leu Phe Arg Ala Val Ala Asp Gln Val Tyr Gly Asp Gln Asp Met His
225                 230                 235                 240

Glu Val Val Arg Lys His Cys Met Asp Tyr Leu Met Lys Asn Ala Asp
                245                 250                 255

Tyr Phe Ser Asn Tyr Val Thr Glu Asp Phe Thr Thr Tyr Ile Asn Arg
            260                 265                 270

Lys Arg Lys Asn Asn Cys His Gly Asn His Ile Glu Met Gln Ala Met
        275                 280                 285

Ala Glu Met Tyr Asn Arg Pro Val Glu Val Tyr Gln Tyr Ser Thr Glu
    290                 295                 300

Pro Ile Asn Thr Phe His Gly Ile His Gln Asn Glu Asp Glu Pro Ile
305                 310                 315                 320

Arg Val Ser Tyr His Arg Asn Ile His Tyr Asn Ser Val Val Asn Pro
                325                 330                 335

Asn Lys Ala Thr Ile Gly Val Gly Leu Gly Leu Pro Ser Phe Lys Pro
340 345 350

Gly Phe Ala Glu Gln Ser Leu Met Lys Asn Ala Ile Lys Thr Ser Glu
355 360 365

Glu Ser Trp Ile Glu Gln Gln Met Leu Glu Asp Lys Lys Arg Ala Thr
370 375 380

Asp Trp Glu Ala Thr Asn Glu Ala Ile Glu Glu Gln Val Ala Arg Glu
385 390 395 400

Ser Tyr Leu Gln Trp Leu Arg Asp Gln Glu Lys Gln Ala Arg Gln Val
405 410 415

Arg Gly Pro Ser Gln Pro Arg Lys Ala Ser Ala Thr Cys Ser Ser Ala
420 425 430

Thr Ala Ala Ala Ser Ser Gly Leu Glu Glu Trp Thr Ser Arg Ser Pro
435 440 445

Arg Gln Arg Ser Ser Ala Ser Ser Pro Glu His Pro Glu Leu His Ala
450 455 460

Glu Leu Gly Ile Lys Pro Pro Ser Pro Gly Thr Val Leu Ala Leu Ala
465 470 475 480

Lys Pro Pro Ser Pro Cys Ala Pro Gly Thr Ser Ser Gln Phe Ser Ala
485 490 495

Gly Gly Asp Arg Ala Thr Ser Pro Leu Val Ser Leu Tyr Pro Ala Leu
500 505 510

Glu Cys Arg Ala Leu Ile Gln Gln Met Ser Pro Ser Ala Phe Gly Leu
515 520 525

Asn Asp Trp Asp Asp Asp Glu Ile Leu Ala Ser Val Leu Ala Val Ser
530 535 540

Gln Gln Glu Tyr Leu Asp Ser Met Lys Lys Asn Lys Val His Arg Glu
545 550 555 560

Pro Pro Pro Asp Lys Ser
565

<210> SEQ ID NO 103
<211> LENGTH: 102
<212> TYPE: PRT
<213> ORGANISM: Mus musculus

<400> SEQUENCE: 103

Phe Ile Cys Glu Ala Ser Val Gly Val Asp Arg Ser Cys Pro Leu Thr
1 5 10 15

Val Gln Ile Asp Ile Thr Ile Arg Gly Gln Leu Gly Ile Ala Pro Pro
20 25 30

Ser Arg Ala Cys Thr Val Lys Met Gln Leu Met Val Leu Ala Val Glu
35 40 45

Cys Gly Ser Thr Asp Arg Gln Ile Ser Thr Pro Pro Gln Leu Arg Gln
50 55 60

Pro Ser Pro Ala Ala Thr Gln Leu Leu Val Ser Ala Lys Arg Ser Ala
65 70 75 80

Glu Thr Arg Ser Leu His Leu Glu Gln His Leu Gly Thr Ser Leu Gln
85 90 95

Val Arg Thr Leu Ile Asp
100

<210> SEQ ID NO 104
<211> LENGTH: 331
<212> TYPE: PRT
<213> ORGANISM: Mus musculus

<400> SEQUENCE: 104

Met Lys Ser Thr Ser Arg Asp Ala Val Leu Phe Phe Ser Glu Ser Leu
1               5                   10                  15

Val Pro Thr Ala Arg Lys Ala Leu Cys Asp Pro Leu Glu Glu Val Arg
            20                  25                  30

Glu Ala Ala Ala Lys Thr Phe Glu Gln Leu His Ser Thr Ile Gly His
        35                  40                  45

Gln Ala Leu Glu Asp Ile Leu Pro Phe Leu Leu Lys Gln Leu Asp Asp
    50                  55                  60

Glu Glu Val Ser Glu Phe Ala Leu Asp Gly Leu Lys Gln Val Met Ala
65                  70                  75                  80

Val Lys Ser Arg Val Val Leu Pro Tyr Leu Val Pro Lys Leu Thr Thr
                85                  90                  95

Pro Pro Val Asn Thr Arg Val Leu Ala Phe Leu Ser Ser Val Ala Gly
            100                 105                 110

Asp Ala Leu Thr Arg His Leu Gly Val Ile Leu Pro Ala Val Met Leu
        115                 120                 125

Ala Leu Lys Glu Lys Leu Gly Thr Pro Asp Glu Gln Leu Glu Met Ala
    130                 135                 140

Asn Cys Gln Ala Val Ile Leu Ser Val Glu Asp Asp Thr Gly His Arg
145                 150                 155                 160

Ile Ile Ile Glu Asp Leu Leu Glu Ala Thr Arg Ser Pro Glu Val Gly
                165                 170                 175

Met Arg Gln Ala Ala Ala Ile Ile Leu Asn Met Tyr Cys Ser Arg Ser
            180                 185                 190

Lys Ala Asp Tyr Ser Ser His Leu Arg Ser Leu Val Ser Gly Leu Ile
        195                 200                 205

Arg Leu Phe Asn Asp Ser Ser Pro Val Val Leu Glu Glu Ser Trp Asp
    210                 215                 220

Ala Leu Asn Ala Ile Thr Lys Lys Leu Asp Ala Gly Asn Gln Leu Ala
225                 230                 235                 240

Leu Ile Glu Glu Leu His Lys Glu Ile Arg Phe Ile Gly Asn Glu Cys
                245                 250                 255

Lys Gly Glu His Val Pro Gly Phe Cys Leu Pro Lys Arg Gly Val Thr
            260                 265                 270

Ser Ile Leu Pro Val Leu Arg Glu Gly Val Leu Thr Gly Ser Pro Glu
        275                 280                 285

Gln Lys Glu Glu Ala Ala Lys Gly Leu Gly Leu Val Ile Arg Leu Thr
    290                 295                 300

Ser Ala Asp Ala Leu Arg Pro Ser Val Val Ser Ile Thr Gly Pro Leu
305                 310                 315                 320

Ile Arg Ile Leu Gly Thr Gly Ser Thr Gly Leu
                325                 330

<210> SEQ ID NO 105
<211> LENGTH: 531
<212> TYPE: PRT
<213> ORGANISM: Mus musculus

<400> SEQUENCE: 105

Met Ala Ala Val Lys Thr Leu Asn Pro Lys Ala Glu Val Ala Arg Ala
1               5                   10                  15

Gln Ala Ala Leu Ala Val Asn Ile Ser Ala Ala Arg Gly Leu Gln Asp
            20                  25                  30

```
Val Leu Arg Thr Asn Leu Gly Pro Lys Gly Thr Met Lys Met Leu Val
        35                  40                  45

Ser Gly Ala Gly Asp Ile Lys Leu Thr Lys Asp Gly Asn Val Leu Leu
    50                  55                  60

His Glu Met Gln Ile Gln His Pro Thr Ala Ser Leu Ile Ala Lys Val
65                  70                  75                  80

Ala Thr Ala Gln Asp Asp Ile Thr Gly Asp Gly Thr Thr Ser Asn Val
                85                  90                  95

Leu Ile Ile Gly Glu Leu Leu Lys Gln Ala Asp Leu Tyr Ile Ser Glu
            100                 105                 110

Gly Leu His Pro Arg Ile Ile Thr Glu Gly Phe Glu Ala Ala Lys Glu
        115                 120                 125

Lys Ala Leu Gln Phe Leu Glu Gln Val Lys Val Ser Lys Glu Met Asp
    130                 135                 140

Arg Glu Thr Leu Ile Asp Val Ala Arg Thr Ser Leu Arg Thr Lys Val
145                 150                 155                 160

His Ala Glu Leu Ala Asp Val Leu Thr Glu Ala Val Val Asp Ser Ile
                165                 170                 175

Leu Ala Ile Arg Lys Lys Asp Glu Pro Ile Asp Leu Phe Met Val Glu
            180                 185                 190

Ile Met Glu Met Lys His Lys Ser Glu Thr Asp Thr Ser Leu Ile Arg
        195                 200                 205

Gly Leu Val Leu Asp His Gly Ala Arg His Pro Asp Met Lys Lys Arg
    210                 215                 220

Val Glu Asn Ala Tyr Ile Leu Thr Cys Asn Val Ser Leu Glu Tyr Glu
225                 230                 235                 240

Lys Thr Glu Val Asn Ser Gly Phe Phe Tyr Lys Ser Ala Glu Glu Arg
                245                 250                 255

Glu Lys Leu Val Lys Ala Glu Arg Lys Phe Ile Glu Asp Arg Val Lys
            260                 265                 270

Lys Ile Ile Glu Leu Lys Lys Lys Val Cys Gly Asp Ser Asp Lys Gly
        275                 280                 285

Phe Val Val Ile Asn Gln Lys Gly Ile Asp Pro Phe Ser Leu Asp Ala
    290                 295                 300

Leu Ala Lys Glu Gly Ile Val Ala Leu Arg Arg Ala Lys Arg Arg Asn
305                 310                 315                 320

Met Glu Arg Leu Thr Leu Ala Cys Gly Gly Ile Ala Leu Asn Ser Phe
                325                 330                 335

Asp Asp Leu Asn Pro Asp Cys Leu Gly His Ala Gly Leu Val Tyr Glu
            340                 345                 350

Tyr Thr Leu Gly Glu Glu Lys Phe Thr Phe Ile Glu Lys Cys Asn Asn
        355                 360                 365

Pro Arg Ser Val Thr Leu Leu Val Lys Gly Pro Asn Lys His Thr Leu
    370                 375                 380

Thr Gln Ile Lys Asp Ala Ile Arg Asp Gly Leu Arg Ala Val Lys Asn
385                 390                 395                 400

Ala Ile Asp Asp Gly Cys Val Val Pro Gly Ala Gly Ala Val Glu Val
                405                 410                 415

Ala Leu Ala Glu Ala Leu Ile Lys Tyr Lys Pro Ser Val Lys Gly Arg
            420                 425                 430

Ala Gln Leu Gly Val Gln Ala Phe Ala Asp Ala Leu Leu Ile Ile Pro
        435                 440                 445

Lys Val Leu Ala Gln Asn Ser Gly Phe Asp Leu Gln Glu Thr Leu Val
    450                 455                 460
```

```
Lys Val Gln Ala Glu His Ser Glu Ser Gly Gln Leu Val Gly Val Asp
465                 470                 475                 480

Leu Ser Thr Gly Glu Pro Met Val Ala Ala Glu Met Gly Val Trp Asp
                485                 490                 495

Asn Tyr Cys Val Lys Lys Gln Leu Leu His Ser Cys Thr Val Ile Ala
            500                 505                 510

Thr Asn Ile Leu Leu Val Asp Glu Ile Met Arg Ala Gly Met Ser Ser
        515                 520                 525

Leu Lys Gly
    530


<210> SEQ ID NO 106
<211> LENGTH: 144
<212> TYPE: PRT
<213> ORGANISM: Mus musculus

<400> SEQUENCE: 106

Met Ala Asp Ser Ala Gln Val Pro Thr Leu Val Tyr Leu Val Thr Gly
1               5                   10                  15

Gly Cys Gly Phe Leu Gly Glu His Ile Val Arg Met Leu Leu Glu Arg
            20                  25                  30

Glu Pro Arg Leu Arg Glu Leu Arg Val Phe Asp Leu His Leu Ser Ser
        35                  40                  45

Trp Leu Glu Glu Leu Lys Ala Gly Pro Val Gln Val Thr Ala Ile Gln
    50                  55                  60

Gly Asp Val Thr Gln Ala His Glu Val Ala Ala Ala Met Ser Gly Ser
65                  70                  75                  80

His Val Val Ile His Thr Ala Gly Leu Val Asp Val Phe Gly Lys Ala
                85                  90                  95

Ser Pro Lys Thr Ile His Lys Val Asn Val Gln Gly Thr Gln Asn Val
            100                 105                 110

Ile Asp Ala Cys Val Gln Thr Gly Thr Gln Tyr Leu Val Tyr Thr Ser
        115                 120                 125

Ser Met Glu Val Val Gly Pro Asn Ile Lys Gly His Pro Phe Tyr Arg
    130                 135                 140


<210> SEQ ID NO 107
<211> LENGTH: 313
<212> TYPE: PRT
<213> ORGANISM: Mus musculus

<400> SEQUENCE: 107

Met Ala Ala Thr Ala Ala Val Ser Gly Val Leu Gly Arg Leu Gly Trp
1               5                   10                  15

Arg Leu Leu Gln Leu Arg Cys Leu Pro Val Ala Arg Cys Arg Pro Ala
            20                  25                  30

Leu Val Pro Arg Ala Phe His Thr Ala Val Gly Phe Arg Ser Ser Glu
        35                  40                  45

Glu Gln Lys Gln Gln Pro Pro His Ser Ser Ser Gln Gln His Ser Glu
    50                  55                  60

Thr Gln Gly Pro Glu Phe Ser Arg Pro Pro Pro Arg Tyr Thr Asp Gln
65                  70                  75                  80

Ser Gly Glu Glu Glu Glu Asp Tyr Glu Ser Glu Glu Gln Leu Gln His
                85                  90                  95

Arg Ile Leu Thr Ala Ala Leu Glu Phe Val Pro Ala His Gly Trp Thr
            100                 105                 110
```

-continued

```
Ala Glu Ala Ile Ala Glu Gly Ala Gln Ser Leu Gly Leu Ser Ser Ala
        115                 120                 125

Ala Ala Ser Met Phe Gly Ser Asp Gly Ser Glu Leu Ile Leu His Phe
    130                 135                 140

Val Thr Gln Cys Asn Ala Arg Leu Asn Gln Val Leu Glu Glu Glu Gln
145                 150                 155                 160

Lys Leu Val Gln Leu Gly Gln Ala Glu Lys Arg Lys Thr Asp Gln Phe
                165                 170                 175

Leu Arg Asp Ala Val Glu Thr Arg Leu Arg Met Leu Ile Pro Tyr Ile
            180                 185                 190

Glu His Trp Pro Arg Ala Leu Ser Ile Leu Leu Leu Pro His Asn Ile
        195                 200                 205

Pro Pro Ser Leu Asn Leu Leu Thr Ser Met Val Asp Asp Met Trp His
    210                 215                 220

Tyr Ala Gly Asp Gln Ser Thr Asp Phe Asn Trp Tyr Thr Arg Arg Ala
225                 230                 235                 240

Val Leu Ala Gly Ile Tyr Asn Thr Thr Glu Leu Val Met Met Gln Asp
                245                 250                 255

Ser Ser Pro Asp Phe Glu Asp Thr Trp Arg Phe Leu Glu Asn Arg Ile
            260                 265                 270

Asn Asp Ala Met Asn Met Gly His Thr Ala Lys Gln Val Lys Ser Thr
        275                 280                 285

Gly Glu Ala Leu Val Gln Gly Leu Met Gly Ala Ala Val Thr Leu Lys
    290                 295                 300

Asn Leu Thr Gly Leu Asn Gln Arg Arg
305                 310
```

```
<210> SEQ ID NO 108
<211> LENGTH: 914
<212> TYPE: PRT
<213> ORGANISM: Mus musculus

<400> SEQUENCE: 108

Met Asp Met Phe Pro Leu Thr Trp Val Phe Leu Ala Leu Tyr Phe Ser
1               5                   10                  15

Gly His Glu Val Arg Ser Gln Gln Asp Pro Pro Cys Gly Gly Arg Pro
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175
```

-continued

```
Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Ile His Gln Glu Pro Pro
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Phe Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Ile Phe
    370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
        435                 440                 445

Gln Ile Ser Ala Ser Ser Thr Arg Glu Tyr Leu Trp Ser Pro Ser Ala
    450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
        515                 520                 525

Ser Leu Asn Gly Lys Asp Trp Glu Tyr Ile Gln Asp Pro Arg Thr Gln
    530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
        595                 600                 605
```

Lys Ser Glu Glu Thr Thr Thr Pro Tyr Pro Met Asp Glu Asp Ala Thr
610 615 620

Glu Cys Gly Glu Asn Cys Ser Phe Glu Asp Asp Lys Asp Leu Gln Leu
625 630 635 640

Pro Ser Gly Phe Asn Cys Asn Phe Asp Phe Pro Glu Glu Thr Cys Gly
645 650 655

Trp Val Tyr Asp His Ala Lys Trp Leu Arg Ser Thr Trp Ile Ser Ser
660 665 670

Ala Asn Pro Asn Asp Arg Thr Phe Pro Asp Asp Lys Asn Phe Leu Lys
675 680 685

Leu Gln Ser Asp Gly Arg Arg Glu Gly Gln Tyr Gly Arg Leu Ile Ser
690 695 700

Pro Pro Val His Leu Pro Arg Ser Pro Val Cys Met Glu Phe Gln Tyr
705 710 715 720

Gln Ala Met Gly Gly His Gly Val Ala Leu Gln Val Val Arg Glu Ala
725 730 735

Ser Gln Glu Ser Lys Leu Leu Trp Val Ile Arg Glu Asp Gln Gly Ser
740 745 750

Glu Trp Lys His Gly Arg Ile Ile Leu Pro Ser Tyr Asp Met Glu Tyr
755 760 765

Gln Ile Val Phe Glu Gly Val Ile Gly Lys Gly Arg Ser Gly Glu Ile
770 775 780

Ser Gly Asp Asp Ile Arg Ile Ser Thr Asp Val Pro Leu Glu Asn Cys
785 790 795 800

Met Glu Pro Ile Ser Ala Phe Ala Gly Glu Asp Phe Lys Asp Glu Tyr
805 810 815

Glu Gly Asp Trp Ser Asn Ser Ser Ser Ser Thr Ser Gly Ala Gly Asp
820 825 830

Pro Ser Ser Gly Lys Glu Lys Ser Trp Leu Tyr Thr Leu Asp Pro Ile
835 840 845

Leu Ile Thr Ile Ile Ala Met Ser Ser Leu Gly Val Leu Leu Gly Ala
850 855 860

Thr Cys Ala Gly Leu Leu Leu Tyr Cys Thr Cys Ser Tyr Ser Gly Leu
865 870 875 880

Ser Ser Arg Ser Cys Thr Thr Leu Glu Asn Tyr Asn Phe Glu Leu Tyr
885 890 895

Asp Gly Leu Lys His Lys Val Lys Ile Asn His Gln Lys Cys Cys Ser
900 905 910

Glu Ala

<210> SEQ ID NO 109
<211> LENGTH: 240
<212> TYPE: PRT
<213> ORGANISM: Mus musculus

<400> SEQUENCE: 109

Met Ala Thr Asp Glu Leu Ala Ser Lys Leu Ser Arg Arg Leu Gln Met
1 5 10 15

Glu Gly Glu Gly Gly Glu Ala Thr Glu Gln Pro Gly Leu Asn Gly Ala
20 25 30

Ala Ala Ala Ala Ala Ala Glu Ala Pro Asp Glu Thr Ala Gln Ala Leu
35 40 45

Gly Ser Ala Asp Asp Glu Leu Ser Ala Lys Leu Leu Arg Arg Ala Asp
50 55 60

```
Leu Asn Gln Gly Ile Gly Glu Pro Gln Ser Pro Ser Arg Arg Val Phe
65                  70                  75                  80

Asn Pro Tyr Thr Glu Phe Lys Glu Phe Ser Arg Lys Gln Ile Lys Asp
                85                  90                  95

Met Glu Lys Met Phe Lys Gln Tyr Asp Ala Gly Arg Asp Gly Phe Ile
            100                 105                 110

Asp Leu Met Glu Leu Lys Leu Met Met Glu Lys Leu Gly Ala Pro Gln
        115                 120                 125

Thr His Leu Gly Leu Lys Ser Met Ile Gln Glu Val Asp Glu Asp Phe
    130                 135                 140

Asp Ser Lys Leu Ser Phe Arg Glu Phe Leu Leu Ile Phe Arg Lys Ala
145                 150                 155                 160

Ala Ala Gly Glu Leu Gln Glu Asp Ser Gly Leu His Val Leu Ala Arg
                165                 170                 175

Leu Ser Glu Ile Asp Val Ser Thr Glu Gly Val Lys Gly Ala Lys Asn
            180                 185                 190

Phe Phe Glu Ala Lys Val Gln Ala Ile Asn Val Ser Ser Arg Phe Glu
        195                 200                 205

Glu Glu Ile Lys Ala Glu Gln Glu Glu Arg Lys Lys Gln Ala Glu Glu
    210                 215                 220

Val Lys Gln Arg Lys Ala Ala Phe Lys Glu Leu Gln Ser Thr Phe Lys
225                 230                 235                 240


<210> SEQ ID NO 110
<211> LENGTH: 280
<212> TYPE: PRT
<213> ORGANISM: Mus musculus

<400> SEQUENCE: 110

Met Pro Met Tyr Gln Glu Thr Ser Glu Pro Ser Leu Gln Ala Leu Glu
1               5                   10                  15

Ser Arg Gln Asp Asp Ile Leu Lys Arg Leu Tyr Glu Leu Lys Ala Ala
            20                  25                  30

Val Asp Gly Leu Ser Lys Met Ile His Thr Pro Asp Ala Asp Leu Asp
        35                  40                  45

Val Thr Asn Ile Leu Gln Ala Asp Glu Pro Thr Thr Leu Ala Thr Asn
    50                  55                  60

Thr Leu Asp Leu Asn Ser Val Leu Gly Lys Asp Tyr Gly Ala Leu Lys
65                  70                  75                  80

Asp Ile Val Ile Asn Ala Asn Pro Ala Ser Pro Pro Leu Ser Leu Leu
                85                  90                  95

Val Leu His Arg Leu Leu Cys Glu Arg Tyr Arg Val Leu Ser Thr Val
            100                 105                 110

His Thr His Ser Ser Val Lys Asn Val Pro Glu Asn Leu Val Lys Cys
        115                 120                 125

Phe Gly Glu Gln Ala Arg Lys Gln Ser Arg His Glu Tyr Gln Leu Gly
    130                 135                 140

Phe Thr Leu Ile Trp Lys Asn Val Pro Lys Thr Gln Met Lys Phe Ser
145                 150                 155                 160

Val Gln Thr Met Cys Pro Ile Glu Gly Glu Gly Asn Ile Ala Arg Phe
                165                 170                 175

Leu Phe Ser Leu Phe Gly Gln Lys His Asn Ala Val Thr Leu Thr Leu
            180                 185                 190

Ile Asp Ser Trp Val Asp Ile Ala Met Phe Gln Leu Arg Glu Gly Ser
        195                 200                 205
```

```
Ser Lys Glu Lys Ala Ala Val Phe Arg Ser Met Asn Ser Ala Leu Gly
    210                 215                 220

Arg Ser Pro Trp Leu Val Gly Asn Glu Leu Thr Val Ala Asp Val Val
225                 230                 235                 240

Leu Trp Ser Val Leu Gln Gln Thr Gly Gly Ser Ser Gly Ala Ala Pro
                245                 250                 255

Thr Asn Val Gln Arg Trp Leu Lys Ser Cys Glu Asn Leu Ala Pro Phe
            260                 265                 270

Ser Thr Ala Leu Gln Leu Leu Lys
        275                 280


<210> SEQ ID NO 111
<211> LENGTH: 1436
<212> TYPE: PRT
<213> ORGANISM: Mus musculus

<400> SEQUENCE: 111

Met Lys Asp Ile Asp Met Gly Lys Glu Tyr Ile Ile Pro Ser Pro Gly
1               5                   10                  15

Tyr Arg Ser Asp Arg Asp Arg Ser Ala Val Pro Gly Gln His Arg Asp
            20                  25                  30

Pro Glu Glu Pro Arg Phe Arg Arg Thr Arg Ser Leu Glu Cys Gln Asp
        35                  40                  45

Ala Leu Glu Thr Ala Ala Arg Val Glu Gly Leu Ser Leu Asp Ile Ser
    50                  55                  60

Val His Ser His Leu Gln Ile Leu Asp Glu Glu His Ser Lys Gly Lys
65                  70                  75                  80

Tyr His His Gly Leu Ser Val Leu Lys Pro Phe Arg Thr Thr Thr Lys
                85                  90                  95

His Gln His Pro Val Asp Asn Ala Gly Leu Phe Ser Tyr Met Thr Phe
            100                 105                 110

Ser Trp Leu Ser Pro Leu Ala Arg Val Val His Lys Lys Gly Glu Leu
        115                 120                 125

Leu Met Glu Asp Val Trp Pro Leu Ser Lys Tyr Glu Ser Ser Asp Val
    130                 135                 140

Asn Ser Arg Arg Leu Glu Arg Leu Trp Gln Glu Glu Leu Asn Glu Val
145                 150                 155                 160

Gly Pro Asp Ala Ala Ser Leu Arg Arg Val Val Trp Ile Phe Cys Arg
                165                 170                 175

Thr Arg Leu Ile Leu Ser Ile Val Cys Leu Met Ile Thr Gln Leu Ala
            180                 185                 190

Gly Phe Ser Gly Pro Ala Phe Val Val Lys His Leu Leu Glu Tyr Thr
        195                 200                 205

Gln Ala Thr Glu Ser Asn Leu Gln Tyr Ser Leu Leu Leu Val Leu Gly
    210                 215                 220

Leu Leu Leu Thr Glu Val Val Arg Ser Trp Ser Leu Ala Leu Thr Trp
225                 230                 235                 240

Ala Leu Asn Tyr Arg Thr Gly Val Arg Leu Arg Gly Ala Ile Leu Thr
                245                 250                 255

Met Ala Phe Lys Lys Ile Leu Lys Leu Lys Asn Ile Lys Glu Lys Ser
            260                 265                 270

Leu Gly Glu Leu Ile Asn Ile Cys Ser Asn Asp Gly Gln Arg Met Phe
        275                 280                 285

Glu Ala Ala Ala Val Gly Ser Leu Leu Ala Gly Gly Pro Val Val Ala
    290                 295                 300
```

```
Ile Leu Gly Met Ile Tyr Asn Val Ile Ile Leu Gly Pro Thr Gly Phe
305                 310                 315                 320

Leu Gly Ser Ala Val Phe Ile Leu Phe Tyr Pro Ala Met Met Phe Val
                325                 330                 335

Ser Arg Leu Thr Ala Tyr Phe Arg Arg Lys Cys Val Ala Ala Thr Asp
            340                 345                 350

Asp Arg Val Gln Lys Met Asn Glu Val Leu Thr Tyr Ile Lys Phe Ile
        355                 360                 365

Lys Met Tyr Ala Trp Val Lys Ala Phe Ser Gln Cys Val Gln Lys Ile
    370                 375                 380

Arg Glu Glu Glu Arg Arg Ile Leu Glu Lys Ala Gly Tyr Phe Gln Ser
385                 390                 395                 400

Ile Thr Val Gly Val Ala Pro Ile Val Val Val Ile Ala Ser Val Val
                405                 410                 415

Thr Phe Ser Val His Met Thr Leu Gly Phe His Leu Thr Ala Ala Gln
            420                 425                 430

Ala Phe Thr Val Val Thr Val Phe Asn Ser Met Thr Phe Ala Leu Lys
        435                 440                 445

Val Thr Pro Phe Ser Val Lys Ser Leu Ser Glu Ala Ser Val Ala Val
    450                 455                 460

Asp Arg Phe Lys Ser Leu Phe Leu Met Glu Glu Val His Met Ile Lys
465                 470                 475                 480

Asn Lys Pro Ala Ser Pro His Ile Lys Ile Glu Met Lys Asn Ala Thr
                485                 490                 495

Leu Ala Trp Asp Ser Ser His Ser Ser Ile Gln Asn Ser Pro Lys Leu
            500                 505                 510

Thr Pro Lys Met Lys Lys Asp Lys Arg Ala Thr Arg Gly Lys Lys Glu
        515                 520                 525

Lys Ser Arg Gln Leu Gln His Thr Glu His Gln Ala Val Leu Ala Glu
    530                 535                 540

Gln Lys Gly His Leu Leu Leu Asp Ser Asp Glu Arg Pro Ser Pro Glu
545                 550                 555                 560

Glu Glu Glu Gly Lys Gln Ile His Thr Gly Ser Leu Arg Leu Gln Arg
                565                 570                 575

Thr Leu Tyr Asn Ile Asp Leu Glu Ile Glu Glu Gly Lys Leu Val Gly
            580                 585                 590

Ile Cys Gly Ser Val Gly Ser Gly Lys Thr Ser Leu Val Ser Ala Ile
        595                 600                 605

Leu Gly Gln Met Thr Leu Leu Glu Gly Ser Ile Ala Val Ser Gly Thr
    610                 615                 620

Phe Ala Tyr Val Ala Gln Gln Ala Trp Ile Leu Asn Ala Thr Leu Arg
625                 630                 635                 640

Asp Asn Ile Leu Phe Gly Lys Glu Phe Asp Glu Glu Arg Tyr Asn Ser
                645                 650                 655

Val Leu Asn Ser Cys Cys Leu Arg Pro Asp Leu Ala Ile Leu Pro Asn
            660                 665                 670

Ser Asp Leu Thr Glu Ile Gly Glu Arg Gly Ala Asn Leu Ser Gly Gly
        675                 680                 685

Gln Arg Gln Arg Ile Ser Leu Ala Arg Ala Leu Tyr Ser Asp Arg Ser
    690                 695                 700

Ile Tyr Ile Leu Asp Asp Pro Leu Ser Ala Leu Asp Ala His Val Gly
705                 710                 715                 720

Asn His Ile Phe Asn Ser Ala Ile Arg Lys Arg Leu Lys Ser Lys Thr
                725                 730                 735
```

```
Val Leu Phe Val Thr His Gln Leu Gln Tyr Leu Val Asp Cys Asp Glu
            740                 745                 750

Val Ile Phe Met Lys Glu Gly Cys Ile Thr Glu Arg Gly Thr His Glu
        755                 760                 765

Glu Leu Met Asn Leu Asn Gly Asp Tyr Ala Thr Ile Phe Asn Asn Leu
    770                 775                 780

Leu Leu Gly Glu Thr Pro Pro Val Glu Ile Asn Ser Lys Lys Glu Ala
785                 790                 795                 800

Thr Gly Ser Gln Lys Ser Gln Asp Lys Gly Pro Lys Pro Gly Ser Val
                805                 810                 815

Lys Lys Glu Lys Ala Val Lys Ser Glu Glu Gly Gln Leu Val Gln Val
            820                 825                 830

Glu Glu Lys Gly Gln Gly Ser Val Pro Trp Ser Val Tyr Trp Val Tyr
        835                 840                 845

Ile Gln Ala Ala Gly Gly Pro Leu Ala Phe Leu Val Ile Met Val Leu
    850                 855                 860

Phe Met Leu Asn Val Gly Ser Thr Ala Phe Ser Thr Trp Trp Leu Ser
865                 870                 875                 880

Tyr Trp Ile Lys Gln Gly Ser Gly Asn Ser Thr Val Tyr Gln Gly Asn
                885                 890                 895

Arg Ser Phe Val Ser Asp Ser Met Lys Asp Asn Pro Phe Met Gln Tyr
            900                 905                 910

Tyr Ala Ser Ile Tyr Ala Leu Ser Met Ala Val Met Leu Ile Leu Lys
        915                 920                 925

Ala Ile Arg Gly Val Val Phe Val Lys Gly Thr Leu Arg Ala Ser Ser
    930                 935                 940

Arg Leu His Asp Glu Leu Phe Arg Arg Ile Leu Arg Ser Pro Met Lys
945                 950                 955                 960

Phe Phe Asp Thr Thr Pro Thr Gly Arg Ile Leu Asn Arg Phe Ser Lys
                965                 970                 975

Asp Met Asp Glu Val Asp Val Arg Leu Pro Phe Gln Ala Glu Met Phe
            980                 985                 990

Ile Gln Asn Val Ile Leu Val Phe  Phe Cys Val Gly Met  Ile Ala Gly
        995                 1000                1005

Val Phe  Pro Trp Phe Leu Val  Ala Val Gly Pro Leu  Leu Ile Leu
    1010                1015                1020

Phe Ser  Leu Leu His Ile Val  Ser Arg Val Leu Ile  Arg Glu Leu
    1025                1030                1035

Lys Arg  Leu Asp Asn Ile Thr  Gln Ser Pro Phe Leu  Ser His Ile
    1040                1045                1050

Thr Ser  Ser Ile Gln Gly Leu  Ala Thr Ile His Ala  Tyr Asn Lys
    1055                1060                1065

Arg Gln  Glu Phe Leu His Arg  Tyr Gln Glu Leu Leu  Asp Asp Asn
    1070                1075                1080

Gln Ala  Pro Phe Phe Leu Phe  Thr Cys Ala Met Arg  Trp Leu Ala
    1085                1090                1095

Val Arg  Leu Asp Leu Ile Ser  Ile Ala Leu Ile Thr  Thr Thr Gly
    1100                1105                1110

Leu Met  Ile Val Leu Met His  Gly Gln Ile Pro Ser  Ala Tyr Ala
    1115                1120                1125

Gly Leu  Ala Ile Ser Tyr Ala  Val Gln Leu Thr Gly  Leu Phe Gln
    1130                1135                1140

Phe Thr  Val Arg Leu Ala Ser  Glu Thr Glu Ala Arg  Phe Thr Ser
```

```
    1145                1150                1155

Val Glu  Arg Ile Asn His Tyr  Ile Lys Thr Leu Ser  Leu Glu Ala
    1160                1165                1170

Pro Ala  Arg Ile Lys Asn Lys  Ala Pro Pro His Asp  Trp Pro Gln
    1175                1180                1185

Glu Gly  Glu Val Thr Phe Glu  Asn Ala Glu Met Arg  Tyr Arg Glu
    1190                1195                1200

Asn Leu  Pro Leu Val Leu Lys  Lys Val Ser Phe Thr  Ile Lys Pro
    1205                1210                1215

Lys Glu  Lys Ile Gly Ile Val  Gly Arg Thr Gly Ser  Gly Lys Ser
    1220                1225                1230

Ser Leu  Gly Met Ala Leu Phe  Arg Leu Val Glu Leu  Ser Gly Gly
    1235                1240                1245

Cys Ile  Lys Ile Asp Gly Ile  Arg Ile Ser Asp Ile  Gly Leu Ala
    1250                1255                1260

Asp Leu  Arg Ser Lys Leu Ala  Ile Ile Pro Gln Glu  Pro Val Leu
    1265                1270                1275

Phe Ser  Gly Thr Val Arg Ser  Asn Leu Asp Pro Phe  Asn Gln Tyr
    1280                1285                1290

Thr Glu  Asp Gln Ile Trp Asp  Ala Leu Glu Arg Thr  His Met Lys
    1295                1300                1305

Glu Cys  Ile Ala Gln Leu Pro  Leu Lys Leu Glu Ser  Glu Val Met
    1310                1315                1320

Glu Asn  Gly Asp Asn Phe Ser  Val Gly Glu Arg Gln  Leu Leu Cys
    1325                1330                1335

Ile Ala  Arg Ala Leu Leu Arg  His Cys Lys Ile Leu  Ile Leu Asp
    1340                1345                1350

Glu Ala  Thr Ala Ala Met Asp  Thr Glu Thr Asp Leu  Leu Ile Gln
    1355                1360                1365

Glu Thr  Ile Arg Glu Ala Phe  Ala Asp Cys Thr Met  Leu Thr Ile
    1370                1375                1380

Ala His  Arg Leu His Thr Val  Leu Gly Ser Asp Arg  Ile Met Val
    1385                1390                1395

Leu Ala  Gln Gly Gln Val Val  Glu Phe Asp Thr Pro  Ser Val Leu
    1400                1405                1410

Leu Ser  Asn Asp Ser Ser Arg  Phe Tyr Ala Met Phe  Ala Ala Ala
    1415                1420                1425

Glu Asn  Lys Val Ala Val Lys  Gly
    1430                1435


<210> SEQ ID NO 112
<211> LENGTH: 458
<212> TYPE: PRT
<213> ORGANISM: Mus musculus

<400> SEQUENCE: 112

Met Ala Ala Leu Lys Ala Gly Arg Gly Ala Asn Trp Ser Leu Arg Ala
1               5                   10                  15

Trp Arg Ala Leu Gly Gly Ile Phe Trp Arg Lys Pro Pro Leu Leu Ala
            20                  25                  30

Pro Asp Leu Arg Ala Leu Leu Thr Ser Gly Thr Pro Asp Ser Gln Ile
        35                  40                  45

Trp Met Thr Tyr Gly Thr Pro Ser Leu Pro Ala Gln Val Pro Glu Gly
    50                  55                  60

Phe Leu Ala Ser Arg Ala Asp Leu Thr Ser Arg Thr Pro Asp Leu Trp
```

-continued

```
65                  70                  75                  80

Ala Arg Leu Asn Val Gly Thr Ser Gly Ser Ser Asp Gln Glu Ala Arg
                85                  90                  95

Arg Ser Pro Gly Ser Arg Arg Arg Glu Trp Leu Ala Val Ala Val Gly
            100                 105                 110

Ala Gly Gly Ala Val Val Leu Leu Leu Trp Gly Trp Gly Arg Gly Leu
        115                 120                 125

Ser Thr Val Leu Ala Ala Val Pro Ala Pro Pro Pro Thr Ser Pro Arg
    130                 135                 140

Ser Gln Tyr Asn Phe Ile Ala Asp Val Val Glu Lys Thr Ala Pro Ala
145                 150                 155                 160

Val Val Tyr Ile Glu Ile Leu Asp Arg His Pro Phe Ser Gly Arg Glu
                165                 170                 175

Val Pro Ile Ser Asn Gly Ser Gly Phe Val Val Ala Ser Asp Gly Leu
            180                 185                 190

Ile Val Thr Asn Ala His Val Val Ala Asp Arg Arg Arg Val Arg Val
        195                 200                 205

Arg Leu Pro Ser Gly Asp Thr Tyr Glu Ala Met Val Thr Ala Val Asp
    210                 215                 220

Pro Val Ala Asp Ile Ala Thr Leu Arg Ile Gln Thr Lys Glu Pro Pro
225                 230                 235                 240

Pro Thr Leu Pro Leu Gly Arg Ser Ala Asp Val Arg Gln Gly Glu Phe
                245                 250                 255

Val Val Ala Met Gly Ser Pro Phe Ala Leu Gln Asn Thr Ile Thr Ser
            260                 265                 270

Gly Ile Val Ser Ser Ala Gln Arg Pro Ala Arg Asp Leu Gly Leu Pro
        275                 280                 285

Gln Asn Asn Val Glu Tyr Ile Gln Thr Asp Ala Ala Ile Asp Phe Gly
    290                 295                 300

Asn Ser Gly Gly Pro Leu Val Asn Leu Asp Gly Glu Val Ile Gly Val
305                 310                 315                 320

Asn Thr Met Lys Val Thr Ala Gly Ile Ser Phe Ala Ile Pro Ser Asp
                325                 330                 335

Arg Leu Arg Glu Phe Leu His Arg Gly Glu Lys Lys Asn Ser Trp Phe
            340                 345                 350

Gly Thr Ser Gly Ser Gln Arg Arg Tyr Ile Gly Val Met Met Leu Thr
        355                 360                 365

Leu Thr Pro Ser Ile Leu Ile Glu Leu Gln Leu Arg Glu Pro Ser Phe
    370                 375                 380

Pro Asp Val Gln His Gly Val Leu Ile His Lys Val Ile Leu Gly Ser
385                 390                 395                 400

Pro Ala His Arg Ala Gly Leu Arg Pro Gly Asp Val Ile Leu Ala Ile
                405                 410                 415

Gly Glu Lys Leu Ala Gln Asn Ala Glu Asp Val Tyr Glu Ala Val Arg
            420                 425                 430

Thr Gln Ser Gln Leu Ala Val Arg Ile Arg Arg Gly Ser Glu Thr Leu
        435                 440                 445

Ile Leu Tyr Val Thr Pro Glu Val Thr Glu
    450                 455
```

<210> SEQ ID NO 113
<211> LENGTH: 122
<212> TYPE: PRT
<213> ORGANISM: Mus musculus

<400> SEQUENCE: 113

```
Met Lys Pro Phe His Thr Ala Leu Ser Phe Leu Ile Leu Thr Thr Ala
1               5                   10                  15

Leu Gly Ile Trp Ala Gln Ile Thr His Ala Thr Glu Thr Lys Glu Val
            20                  25                  30

Gln Ser Ser Leu Lys Ala Gln Gln Gly Leu Glu Ile Glu Met Phe His
        35                  40                  45

Met Gly Phe Gln Asp Ser Ser Asp Cys Cys Leu Ser Tyr Asn Ser Arg
    50                  55                  60

Ile Gln Cys Ser Arg Phe Ile Gly Tyr Phe Pro Thr Ser Gly Gly Cys
65                  70                  75                  80

Thr Arg Pro Gly Ile Ile Phe Ile Ser Lys Arg Gly Phe Gln Val Cys
                85                  90                  95

Ala Asn Pro Ser Asp Arg Arg Val Gln Arg Cys Ile Glu Arg Leu Glu
            100                 105                 110

Gln Asn Ser Gln Pro Arg Thr Tyr Lys Gln
        115                 120
```

<210> SEQ ID NO 114
<211> LENGTH: 326
<212> TYPE: PRT
<213> ORGANISM: Mus musculus

<400> SEQUENCE: 114

```
Met Tyr Gln Asp Tyr Pro Gly Asn Phe Asp Thr Ser Ser Arg Gly Ser
1               5                   10                  15

Ser Gly Ser Pro Ala His Ala Glu Ser Tyr Ser Ser Gly Gly Gly Gly
            20                  25                  30

Gln Gln Lys Phe Arg Val Asp Met Pro Gly Ser Gly Ser Ala Phe Ile
        35                  40                  45

Pro Thr Ile Asn Ala Ile Thr Thr Ser Gln Asp Leu Gln Trp Met Val
    50                  55                  60

Gln Pro Thr Val Ile Thr Ser Met Ser Asn Pro Tyr Pro Arg Ser His
65                  70                  75                  80

Pro Tyr Ser Pro Leu Pro Gly Leu Ala Ser Val Pro Gly His Met Ala
                85                  90                  95

Leu Pro Arg Pro Gly Val Ile Lys Thr Ile Gly Thr Thr Val Gly Arg
            100                 105                 110

Arg Arg Arg Asp Glu Gln Leu Ser Pro Glu Glu Glu Glu Lys Arg Arg
        115                 120                 125

Ile Arg Arg Glu Arg Asn Lys Leu Ala Ala Ala Lys Cys Arg Asn Arg
    130                 135                 140

Arg Arg Glu Leu Thr Glu Lys Leu Gln Ala Glu Thr Glu Glu Leu Glu
145                 150                 155                 160

Glu Glu Lys Ser Gly Leu Gln Lys Glu Ile Ala Glu Leu Gln Lys Glu
                165                 170                 175

Lys Glu Lys Leu Glu Phe Met Leu Val Ala His Gly Pro Val Cys Lys
            180                 185                 190

Ile Ser Pro Glu Glu Arg Arg Ser Pro Pro Thr Ser Gly Leu Gln Ser
        195                 200                 205

Leu Arg Gly Thr Gly Ser Ala Val Gly Pro Val Val Val Lys Gln Glu
    210                 215                 220

Pro Pro Glu Glu Asp Ser Pro Ser Ser Ser Ala Gly Met Asp Lys Thr
225                 230                 235                 240

Gln Arg Ser Val Ile Lys Pro Ile Ser Ile Ala Gly Gly Gly Phe Tyr
```

```
                245                 250                 255

Gly Glu Glu Pro Leu His Thr Pro Ile Val Val Thr Ser Thr Pro Ala
            260                 265                 270

Ile Thr Pro Gly Thr Ser Asn Leu Val Phe Thr Tyr Pro Asn Val Leu
        275                 280                 285

Glu Gln Glu Ser Pro Ser Ser Pro Ser Glu Ser Cys Ser Lys Ala His
    290                 295                 300

Arg Arg Ser Ser Ser Ser Gly Asp Gln Ser Ser Asp Ser Leu Asn Ser
305                 310                 315                 320

Pro Thr Leu Leu Ala Leu
                325
```

<210> SEQ ID NO 115
<211> LENGTH: 296
<212> TYPE: PRT
<213> ORGANISM: Mus musculus

<400> SEQUENCE: 115

```
Met Gly Gly Glu Ala Gly Ala Asn Gly Pro Arg Gly Arg Val Lys Ser
1               5                   10                  15

Leu Gly Leu Val Phe Glu Asp Glu Ser Lys Gly Cys Tyr Ser Ser Gly
            20                  25                  30

Glu Thr Val Ala Gly His Val Leu Leu Glu Ala Ala Glu Pro Val Ala
        35                  40                  45

Leu Arg Gly Leu Arg Leu Glu Ala Gln Gly Arg Ala Thr Ser Ala Trp
    50                  55                  60

Gly Pro Ser Ala Gly Ala Arg Val Cys Ile Gly Gly Gly Ser Pro Ala
65                  70                  75                  80

Ala Ser Ser Glu Val Glu Tyr Leu Asn Leu Arg Leu Ser Leu Leu Glu
                85                  90                  95

Ala Pro Ala Gly Glu Gly Val Thr Leu Leu Gln Pro Gly Lys His Glu
            100                 105                 110

Phe Pro Phe Arg Phe Gln Leu Arg Ser Glu Pro Leu Ala Thr Ser Phe
        115                 120                 125

Thr Gly Lys Tyr Gly Ser Ile Gln Tyr Cys Val Arg Ala Val Leu Glu
    130                 135                 140

Arg Pro Gln Val Pro Asp Gln Ser Val Arg Arg Glu Leu Gln Val Val
145                 150                 155                 160

Ser His Val Asp Val Asn Thr Pro Pro Leu Leu Thr Pro Met Leu Lys
                165                 170                 175

Thr Gln Glu Lys Met Val Gly Cys Trp Leu Phe Thr Ser Gly Pro Val
            180                 185                 190

Ser Leu Ser Val Lys Ile Glu Arg Lys Gly Tyr Cys Asn Gly Glu Ala
        195                 200                 205

Ile Pro Ile Tyr Ala Glu Ile Glu Asn Cys Ser Ser Arg Leu Val Val
    210                 215                 220

Pro Lys Ala Ala Ile Phe Gln Thr Gln Thr Tyr Leu Ala Ser Gly Lys
225                 230                 235                 240

Thr Lys Thr Val Arg His Met Val Ala Asn Val Arg Gly Asn His Ile
                245                 250                 255

Gly Ser Gly Ser Thr Asp Thr Trp Asn Gly Lys Met Leu Lys Ile Pro
            260                 265                 270

Pro Val Thr Pro Ser Ile Leu Asp Cys Cys Ile Ile Arg Val Asp Tyr
        275                 280                 285

Ser Leu Ala Val Ile Gln Ala Ser
```

290 295

<210> SEQ ID NO 116
<211> LENGTH: 415
<212> TYPE: PRT
<213> ORGANISM: Mus musculus

<400> SEQUENCE: 116

Met Met Ala Gln Leu Gln Phe Arg Asp Ala Phe Trp Cys Arg Asp Phe
1 5 10 15

Thr Ala His Thr Gly Tyr Glu Val Leu Leu Gln Arg Leu Leu Asp Gly
20 25 30

Arg Lys Met Cys Lys Asp Val Glu Glu Leu Leu Arg Gln Arg Ala Gln
35 40 45

Ala Glu Glu Arg Tyr Gly Lys Glu Leu Val Gln Ile Ala Arg Lys Ala
50 55 60

Gly Gly Gln Thr Glu Met Asn Ser Leu Arg Thr Ser Phe Asp Ser Leu
65 70 75 80

Lys Gln Gln Thr Glu Asn Val Gly Ser Ala His Ile Gln Leu Ala Leu
85 90 95

Ala Leu Arg Glu Glu Leu Arg Ser Leu Glu Glu Phe Arg Glu Arg Gln
100 105 110

Lys Glu Gln Arg Lys Lys Tyr Glu Ala Ile Met Asp Arg Val Gln Lys
115 120 125

Ser Lys Leu Ser Leu Tyr Lys Lys Thr Met Glu Ser Lys Lys Ala Tyr
130 135 140

Asp Gln Lys Cys Arg Asp Ala Asp Asp Ala Glu Gln Ala Phe Glu Arg
145 150 155 160

Val Ser Ala Asn Gly His Gln Lys Gln Val Glu Lys Ser Gln Asn Lys
165 170 175

Ala Lys Gln Cys Lys Glu Ser Ala Thr Glu Ala Glu Arg Val Tyr Arg
180 185 190

Gln Asn Ile Glu Gln Leu Glu Arg Ala Arg Thr Glu Trp Glu Gln Glu
195 200 205

His Arg Thr Thr Cys Glu Ala Phe Gln Leu Gln Glu Phe Asp Arg Leu
210 215 220

Thr Ile Leu Arg Asn Ala Leu Trp Val His Cys Asn Gln Leu Ser Met
225 230 235 240

Gln Cys Val Lys Asp Asp Glu Leu Tyr Glu Glu Val Arg Leu Thr Leu
245 250 255

Glu Gly Cys Asp Val Glu Gly Asp Ile Asn Gly Phe Ile Gln Ser Lys
260 265 270

Ser Thr Gly Arg Glu Pro Pro Ala Pro Val Pro Tyr Gln Asn Tyr Tyr
275 280 285

Asp Arg Glu Val Thr Pro Leu Ile Gly Ser Pro Ser Ile Gln Pro Ser
290 295 300

Cys Gly Val Ile Lys Arg Phe Ser Gly Leu Leu His Gly Ser Pro Lys
305 310 315 320

Thr Thr Pro Ser Ala Pro Ala Ala Ser Thr Glu Thr Leu Thr Pro Thr
325 330 335

Pro Glu Arg Asn Glu Leu Val Tyr Ala Ser Ile Glu Val Gln Ala Thr
340 345 350

Gln Gly Asn Leu Asn Ser Ser Ala Gln Asp Tyr Arg Ala Leu Tyr Asp
355 360 365

Tyr Thr Ala Gln Asn Ser Asp Glu Leu Asp Ile Ser Ala Gly Asp Ile

```
    370                 375                 380

Leu Ala Val Ile Leu Glu Gly Glu Asp Gly Trp Trp Thr Val Glu Arg
385                 390                 395                 400

Asn Gly Gln Arg Gly Phe Val Pro Gly Ser Tyr Leu Glu Lys Leu
                405                 410                 415


<210> SEQ ID NO 117
<211> LENGTH: 328
<212> TYPE: PRT
<213> ORGANISM: Mus musculus

<400> SEQUENCE: 117

Met Val Arg Gly Gly Gly Pro Val Met Ser Ala Ala Ser Asn Arg Ser
1               5                   10                  15

Lys Arg Thr Lys Val Leu Arg His Leu Pro Ala Glu Asp Ala Ala Ser
            20                  25                  30

Ala Arg Gly Ala Ala Val Ala Ser Leu Leu Leu Gln Ser Arg Gln Ser
        35                  40                  45

Phe Arg Ser Lys Ser Ile Gly Leu Ala Leu Leu Phe Pro Ser Pro Arg
    50                  55                  60

Ser Pro Ala Phe Asp Leu Leu Trp Arg Pro Gly Gly Arg Lys Gln Gly
65                  70                  75                  80

Thr Leu Pro Leu Leu Arg Lys Gly Arg Arg Gly Gly Asp Arg Asp Ser
                85                  90                  95

His Arg Arg Ser Pro Lys Pro Cys Ile Leu Leu Pro Thr Pro Arg Pro
            100                 105                 110

His Thr Arg Ala Gly Pro Met Leu Ala Ser Gly Pro Leu Ala Lys Val
        115                 120                 125

Ser Val Leu Thr Pro Gly Ala Gly Ile Gln Ala Gly Leu Pro Ser Leu
    130                 135                 140

Arg Val Arg Ser Pro Pro Ala Pro Leu Pro Ala Trp Thr Ser Ala Glu
145                 150                 155                 160

Lys Glu Asp Lys Arg Val Pro Gly Ala Asn Thr Met Thr Ser Phe Ser
                165                 170                 175

Arg Tyr Thr Leu Gly Phe Leu Glu Val Asp Arg Gln Arg Ala Gly Ala
            180                 185                 190

Asp Gly Gly Pro Gly Asn Arg Gly Ala Gly Ser Arg Arg Ala Arg Arg
        195                 200                 205

Val Arg Ala Gly Arg Ser Ala Pro Arg Thr Ala Pro Cys Ala Arg Ser
    210                 215                 220

Arg Ala Ala Ala Gln Arg Trp Ala Arg Ala Ala Ser Thr Met His Arg
225                 230                 235                 240

Ser Ala Gly Gly Arg Arg Arg Gly Asn Pro Ala Gln Leu Leu Leu Gly
                245                 250                 255

Pro Arg Ala Ser Leu Ala Ile His Arg Arg Arg Ser Arg Ala Leu Leu
            260                 265                 270

Pro Leu Pro Pro Lys Gln Glu Gly Arg Lys Gly Lys Pro Asp Arg Lys
        275                 280                 285

Gly Ala Gly Cys Gln Tyr Lys Val Cys Leu Pro Leu Cys Pro Pro Ile
    290                 295                 300

Arg Asn Ala Pro Arg Asp Asn Val Arg Arg Pro Ala Ile Phe Cys Ala
305                 310                 315                 320

Ser Gly Asn Gly Arg Lys Glu Lys
                325
```

<210> SEQ ID NO 118
<211> LENGTH: 481
<212> TYPE: PRT
<213> ORGANISM: Mus musculus

<400> SEQUENCE: 118

```
Met Ala Gln Ser Pro Val Ser Ala Glu Val Ile His Gln Val Glu Glu
1               5                   10                  15

Cys Leu Asp Glu Asp Glu Lys Glu Met Met Leu Phe Leu Cys Arg Asp
            20                  25                  30

Val Thr Glu Asn Leu Ala Ala Pro Asn Val Arg Asp Leu Leu Asp Ser
        35                  40                  45

Leu Ser Glu Arg Gly Gln Leu Ser Phe Ala Thr Leu Ala Glu Leu Leu
    50                  55                  60

Tyr Arg Val Arg Arg Phe Asp Leu Leu Lys Arg Ile Leu Lys Thr Asp
65                  70                  75                  80

Lys Ala Thr Val Glu Asp His Leu Arg Arg Asn Pro His Leu Val Ser
                85                  90                  95

Asp Tyr Arg Val Leu Leu Met Glu Ile Gly Glu Ser Leu Asp Gln Asn
            100                 105                 110

Asp Val Ser Ser Leu Val Phe Leu Thr Arg Asp Tyr Thr Gly Arg Gly
        115                 120                 125

Lys Ile Ala Lys Asp Lys Ser Phe Leu Asp Leu Val Ile Glu Leu Glu
    130                 135                 140

Lys Leu Asn Leu Ile Ala Ser Asp Gln Leu Asn Leu Leu Glu Lys Cys
145                 150                 155                 160

Leu Lys Asn Ile His Arg Ile Asp Leu Asn Thr Lys Ile Gln Lys Tyr
                165                 170                 175

Thr Gln Ser Ser Gln Gly Ala Arg Ser Asn Met Asn Thr Leu Gln Ala
            180                 185                 190

Ser Leu Pro Lys Leu Ser Ile Lys Tyr Asn Ser Arg Leu Gln Asn Gly
        195                 200                 205

Arg Ser Lys Glu Pro Arg Phe Val Glu Tyr Arg Asp Ser Gln Arg Thr
    210                 215                 220

Leu Val Lys Thr Ser Ile Gln Glu Ser Gly Ala Phe Leu Pro Pro His
225                 230                 235                 240

Ile Arg Glu Glu Thr Tyr Arg Met Gln Ser Lys Pro Leu Gly Ile Cys
                245                 250                 255

Leu Ile Ile Asp Cys Ile Gly Asn Asp Thr Lys Tyr Leu Gln Glu Thr
            260                 265                 270

Phe Thr Ser Leu Gly Tyr His Ile Gln Leu Phe Leu Phe Pro Lys Ser
        275                 280                 285

His Asp Ile Thr Gln Ile Val Arg Arg Tyr Ala Ser Met Ala Gln His
    290                 295                 300

Gln Asp Tyr Asp Ser Phe Ala Cys Val Leu Val Ser Leu Gly Gly Ser
305                 310                 315                 320

Gln Ser Met Met Gly Arg Asp Gln Val His Ser Gly Phe Ser Leu Asp
                325                 330                 335

His Val Lys Asn Met Phe Thr Gly Asp Thr Cys Pro Ser Leu Arg Gly
            340                 345                 350

Lys Pro Lys Leu Phe Phe Ile Gln Asn Tyr Glu Ser Leu Gly Ser Gln
        355                 360                 365

Leu Glu Asp Ser Ser Leu Glu Val Asp Gly Pro Ser Ile Lys Asn Val
    370                 375                 380

Asp Ser Lys Pro Leu Gln Pro Arg His Cys Thr Thr His Pro Glu Ala
```

385 390 395 400

Asp Ile Phe Trp Ser Leu Cys Thr Ala Asp Val Ser His Leu Glu Lys
405 410 415

Pro Ser Ser Ser Ser Ser Val Tyr Leu Gln Lys Leu Ser Gln Gln Leu
420 425 430

Lys Gln Gly Arg Arg Arg Pro Leu Val Asp Leu His Val Glu Leu Met
435 440 445

Asp Lys Val Tyr Ala Trp Asn Ser Gly Val Ser Ser Lys Glu Lys Tyr
450 455 460

Ser Leu Ser Leu Gln His Thr Leu Arg Lys Lys Leu Ile Leu Ala Pro
465 470 475 480

Thr

<210> SEQ ID NO 119
<211> LENGTH: 346
<212> TYPE: PRT
<213> ORGANISM: Mus musculus

<400> SEQUENCE: 119

Met Pro Pro Pro Gln Ser Arg Leu Leu Gln Tyr Arg Gln Val Gln Pro
1 5 10 15

Arg Ser Pro Pro Ala Val Pro Ser Pro Pro Ser Ser Thr Asp His Ser
20 25 30

Ser Gln Phe Ala Asn Phe Asn Asp Ser Ser Arg Asp Ile Glu Val Ala
35 40 45

Asn Ser Pro Ala Phe Pro Gln Arg Leu Pro Pro Gln Leu Phe Gly Ser
50 55 60

Pro Phe Ser Leu Pro Ser Glu His Leu Ala Pro Pro Pro Leu Lys Tyr
65 70 75 80

Leu Ala Pro Glu Gly Ala Trp Asn Phe Ala Asn Leu Gln Gln Asn His
85 90 95

Leu Ile Gly Pro Gly Phe Pro Tyr Gly Leu Pro Pro Leu Pro Pro Arg
100 105 110

Pro Pro Gln Asn Pro Phe Ile His Ile Gln Asn His Gln His Ala Ala
115 120 125

Gly Gln Glu Pro Phe His Pro Leu Ser Ser Arg Thr Val Ser Ala Ser
130 135 140

Ser Leu Pro Ser Leu Glu Glu Tyr Glu Pro Arg Gly Pro Gly Arg Pro
145 150 155 160

Leu Tyr Gln Arg Arg Ile Ser Ser Ser Ser Ala Gln Pro Cys Val Glu
165 170 175

Glu Ala Ser Ala Pro Gln Asp Ser Leu Ala Gln Gly Lys Glu Ser Gln
180 185 190

Gly His Ser Asn Pro Pro Ala Phe Asn Phe Pro Ala Pro Glu Ser Trp
195 200 205

Ala Asn Thr Thr Ser Ser Ala Pro Tyr Gln Asn Ile Pro Cys Asn Gly
210 215 220

Ser Ser Arg Thr Ser Gln Pro Arg Glu Leu Ile Ala Pro Pro Lys Thr
225 230 235 240

Val Lys Pro Pro Glu Asp Gln Leu Lys Pro Glu Ser Gly Glu Val Ser
245 250 255

Ser Ser Phe Asn Tyr Ser Met Leu Gln His Leu Gly Gln Phe Pro Pro
260 265 270

Leu Met Pro Asn Lys Gln Ile Ala Glu Ser Ala Asn Cys Ser Ser Gln
275 280 285

```
Gln Ser Pro Ala Gly Ser Lys Pro Ala Met Ser Tyr Ala Ser Ala Leu
    290                 295                 300

Arg Ala Pro Pro Lys Pro Arg Pro Pro Pro Glu Gln Ala Lys Lys Gly
305                 310                 315                 320

Ser Asp Pro Leu Ser Leu Leu Gln Glu Leu Ser Leu Gly Ser Ser Pro
                325                 330                 335

Gly Ser Asn Gly Phe Tyr Ser Tyr Phe Lys
            340                 345


<210> SEQ ID NO 120
<211> LENGTH: 168
<212> TYPE: PRT
<213> ORGANISM: Mus musculus

<400> SEQUENCE: 120

Met Lys Gly Arg Ile Glu Leu Gly Asp Val Thr Pro His Asn Ile Lys
1               5                   10                  15

Gln Leu Lys Arg Leu Asn Gln Val Ile Phe Pro Val Ser Tyr Asn Asp
            20                  25                  30

Lys Phe Tyr Lys Asp Val Leu Glu Val Gly Glu Leu Ala Lys Leu Ala
        35                  40                  45

Tyr Phe Asn Asp Ile Ala Val Gly Ala Val Cys Cys Arg Val Asp His
    50                  55                  60

Ser Gln Asn Gln Lys Arg Leu Tyr Ile Met Thr Leu Gly Cys Leu Ala
65                  70                  75                  80

Pro Tyr Arg Arg Leu Gly Ile Gly Thr Lys Met Leu Asn His Val Leu
                85                  90                  95

Asn Ile Cys Glu Lys Asp Gly Thr Phe Asp Asn Ile Tyr Leu His Val
            100                 105                 110

Gln Ile Ser Asn Glu Ser Ala Ile Asp Phe Tyr Arg Lys Phe Gly Phe
        115                 120                 125

Glu Ile Ile Glu Thr Lys Lys Asn Tyr Tyr Lys Arg Ile Glu Pro Ala
    130                 135                 140

Asp Ala His Val Leu Gln Lys Asn Leu Lys Val Pro Ser Gly Gln Asn
145                 150                 155                 160

Ala Glu Thr Gln Lys Thr Asp Asn
                165


<210> SEQ ID NO 121
<211> LENGTH: 127
<212> TYPE: PRT
<213> ORGANISM: Mus musculus

<400> SEQUENCE: 121

Met Ser Asp Asn Glu Asp Asn Phe Asp Gly Asp Asp Phe Asp Asp Val
1               5                   10                  15

Glu Glu Asp Glu Gly Leu Asp Asp Leu Glu Asn Ala Glu Glu Glu Gly
            20                  25                  30

Gln Glu Asn Val Glu Ile Leu Pro Ser Gly Glu Arg Pro Gln Ala Asn
        35                  40                  45

Gln Lys Arg Ile Thr Thr Pro Tyr Met Thr Lys Tyr Glu Arg Ala Arg
    50                  55                  60

Val Leu Gly Thr Arg Ala Leu Gln Ile Ala Met Cys Ala Pro Val Met
65                  70                  75                  80

Val Glu Leu Glu Gly Glu Thr Asp Pro Leu Leu Ile Ala Met Lys Glu
                85                  90                  95
```

-continued

```
Leu Lys Ala Arg Lys Ile Pro Ile Ile Ile Arg Arg Tyr Leu Pro Asp
            100                 105                 110

Gly Ser Tyr Glu Asp Trp Gly Val Asp Glu Leu Ile Ile Ser Asp
        115                 120                 125


<210> SEQ ID NO 122
<211> LENGTH: 261
<212> TYPE: PRT
<213> ORGANISM: Mus musculus

<400> SEQUENCE: 122

Met Ala Gly Asp Ser Glu Gln Thr Leu Gln Asn His Gln Gln Pro Asn
1               5                   10                  15

Gly Gly Glu Pro Phe Leu Ile Gly Val Ser Gly Gly Thr Ala Ser Gly
            20                  25                  30

Lys Ser Ser Val Cys Ala Lys Ile Val Gln Leu Leu Gly Gln Asn Glu
        35                  40                  45

Val Asp Tyr His Gln Lys Gln Val Val Ile Leu Ser Gln Asp Ser Phe
    50                  55                  60

Tyr Arg Val Leu Thr Ser Glu Gln Lys Ala Lys Ala Leu Lys Gly Gln
65                  70                  75                  80

Phe Asn Phe Asp His Pro Asp Ala Phe Asp Asn Glu Leu Ile Phe Lys
                85                  90                  95

Thr Leu Lys Glu Ile Thr Glu Gly Lys Thr Val Gln Ile Pro Val Tyr
            100                 105                 110

Asp Phe Val Ser His Ser Arg Lys Glu Glu Thr Val Thr Ile Tyr Pro
        115                 120                 125

Ala Asp Val Val Leu Phe Glu Gly Ile Leu Ala Phe Tyr Ser Gln Glu
    130                 135                 140

Val Arg Asp Leu Phe Gln Met Lys Leu Phe Val Asp Thr Asp Ala Asp
145                 150                 155                 160

Thr Arg Leu Ser Arg Arg Val Leu Arg Asp Ile Ser Glu Arg Gly Arg
                165                 170                 175

Asp Leu Glu Gln Ile Leu Ser Gln Tyr Ile Thr Phe Val Lys Pro Ala
            180                 185                 190

Phe Glu Glu Phe Cys Leu Pro Thr Lys Lys Tyr Ala Asp Val Ile Ile
        195                 200                 205

Pro Arg Gly Ala Asp Asn Leu Val Ala Ile Asn Leu Ile Val Gln His
    210                 215                 220

Ile Gln Asp Ile Leu Asn Gly Gly Leu Ser Lys Arg Gln Thr Asn Gly
225                 230                 235                 240

Tyr Leu Asn Gly Tyr Thr Pro Ser Arg Lys Arg Gln Ala Ser Glu Ser
                245                 250                 255

Ser Ser Arg Pro His
            260


<210> SEQ ID NO 123
<211> LENGTH: 1115
<212> TYPE: PRT
<213> ORGANISM: Mus musculus

<400> SEQUENCE: 123

Met Ser Lys Val Ile Gln Lys Lys Asn His Trp Thr Gly Arg Val His
1               5                   10                  15

Glu Cys Thr Val Lys Arg Gly Pro Gln Gly Glu Leu Gly Val Thr Val
            20                  25                  30

Leu Gly Gly Ala Glu His Gly Glu Phe Pro Tyr Val Gly Ala Val Ala
```

```
        35                  40                  45

Ala Ala Glu Ala Ala Gly Leu Pro Gly Gly Gly Glu Gly Pro Lys Leu
    50                  55                  60

Ala Glu Gly Glu Leu Leu Leu Glu Val Gln Gly Val Arg Val Ser Gly
65                  70                  75                  80

Leu Pro Arg Tyr Asp Val Leu Gly Val Ile Asp Ser Cys Lys Glu Ala
                85                  90                  95

Val Thr Phe Lys Ala Val Arg Gln Gly Gly Arg Leu Asn Lys Asp Leu
            100                 105                 110

Arg His Phe Leu Asn Gln Arg Phe Gln Lys Gly Ser Pro Asp His Glu
        115                 120                 125

Leu Gln Gln Thr Ile Arg Asp Asn Leu Tyr Arg His Ala Val Pro Cys
    130                 135                 140

Thr Thr Arg Ser Pro Arg Glu Gly Glu Val Pro Gly Val Asp Tyr Ser
145                 150                 155                 160

Phe Leu Thr Val Lys Glu Phe Leu Asp Leu Glu Gln Ser Gly Thr Leu
                165                 170                 175

Leu Glu Val Gly Thr Tyr Glu Gly Asn Tyr Tyr Gly Thr Pro Lys Pro
            180                 185                 190

Pro Ser Gln Pro Val Ser Gly Lys Val Ile Thr Thr Asp Ala Leu His
        195                 200                 205

Ser Leu Gln Ser Gly Ser Lys Gln Ser Thr Pro Lys Arg Thr Lys Ser
    210                 215                 220

Tyr Asn Asp Met Gln Asn Ala Gly Ile Val His Pro Glu Asn Glu Glu
225                 230                 235                 240

Glu Glu Asp Val Pro Glu Met Asn Ser Ser Phe Thr Ala Asp Ser Gly
                245                 250                 255

Asp Gln Asp Glu His Thr Leu Gln Glu Ala Thr Leu Pro Pro Val Asn
            260                 265                 270

Ser Ser Ile Leu Ala Ala Pro Ile Thr Asp Pro Ser Gln Lys Phe Pro
        275                 280                 285

Gln Tyr Leu Pro Leu Ser Ala Glu Asp Asn Leu Gly Pro Leu Pro Glu
    290                 295                 300

Asn Trp Glu Met Ala Tyr Thr Glu Asn Gly Glu Val Tyr Phe Ile Asp
305                 310                 315                 320

His Asn Thr Lys Thr Thr Ser Trp Leu Asp Pro Arg Cys Leu Asn Lys
                325                 330                 335

Gln Gln Lys Pro Leu Glu Glu Cys Glu Asp Asp Glu Gly Val His Thr
            340                 345                 350

Glu Glu Leu Asp Ser Glu Leu Glu Leu Pro Ala Gly Trp Glu Lys Ile
        355                 360                 365

Glu Asp Pro Val Tyr Gly Val Tyr Tyr Val Asp His Ile Asn Arg Lys
    370                 375                 380

Thr Gln Tyr Glu Asn Pro Val Leu Glu Ala Lys Arg Lys Lys Gln Leu
385                 390                 395                 400

Glu Gln Gln Gln Gln Gln Gln Gln Pro Gln Pro Pro Gln Pro Glu Glu
                405                 410                 415

Trp Thr Glu Asp His Ala Ser Val Val Pro Pro Val Ala Pro Ser His
            420                 425                 430

Pro Pro Ser Asn Pro Glu Pro Ala Arg Glu Thr Pro Leu Gln Gly Lys
        435                 440                 445

Pro Phe Phe Thr Arg Asn Pro Ser Glu Leu Lys Gly Lys Phe Ile His
    450                 455                 460
```

```
Thr Lys Leu Arg Lys Ser Ser Arg Gly Phe Gly Phe Thr Val Val Gly
465                 470                 475                 480

Gly Asp Glu Pro Asp Glu Phe Leu Gln Ile Lys Ser Leu Val Leu Asp
                485                 490                 495

Gly Pro Ala Ala Leu Asp Gly Lys Met Glu Thr Gly Asp Val Ile Val
            500                 505                 510

Ser Val Asn Asp Thr Cys Val Leu Gly His Thr His Ala Gln Val Val
        515                 520                 525

Lys Ile Phe Gln Ser Ile Pro Ile Gly Ala Ser Val Asp Leu Glu Leu
    530                 535                 540

Cys Arg Gly Tyr Pro Leu Pro Phe Asp Pro Asp Asp Pro Asn Thr Ser
545                 550                 555                 560

Leu Val Thr Ser Val Ala Ile Leu Asp Lys Glu Pro Ile Ile Val Asn
                565                 570                 575

Gly Gln Glu Thr Tyr Asp Ser Pro Ala Ser His Ser Ser Lys Thr Gly
            580                 585                 590

Lys Val Ser Ser Met Lys Asp Ala Arg Pro Ser Ser Pro Ala Asp Val
        595                 600                 605

Ala Ser Asn Ser Ser His Gly Tyr Pro Asn Asp Thr Val Ser Leu Ala
    610                 615                 620

Ser Ser Ile Ala Thr Gln Pro Glu Leu Ile Thr Val His Ile Val Lys
625                 630                 635                 640

Gly Pro Met Gly Phe Gly Phe Thr Ile Ala Asp Ser Pro Gly Gly Gly
                645                 650                 655

Gly Gln Arg Val Lys Gln Ile Val Asp Ser Pro Arg Cys Arg Gly Leu
            660                 665                 670

Lys Glu Gly Asp Leu Ile Val Glu Val Asn Lys Lys Asn Val Gln Ala
        675                 680                 685

Leu Thr His Asn Gln Val Val Asp Met Leu Ile Glu Cys Pro Lys Gly
    690                 695                 700

Ser Glu Val Thr Leu Leu Val Gln Arg Gly Gly Leu Pro Val Pro Lys
705                 710                 715                 720

Lys Ser Pro Lys Ser Pro Leu Glu Arg Lys Asp Ser Gln Asn Ser Ser
                725                 730                 735

Gln His Ser Val Ser Ser His Arg Ser Leu His Thr Ala Ser Pro Ser
            740                 745                 750

His Gly Ile Gln Val Leu Pro Glu Tyr Leu Pro Ala Asp Ala Pro Ala
        755                 760                 765

Pro Asp Gln Thr Asp Ser Ser Gly Gln Lys Lys Pro Asp Pro Phe Lys
    770                 775                 780

Ile Trp Ala Gln Ser Arg Ser Met Tyr Glu Asn Arg Leu Pro Asp Tyr
785                 790                 795                 800

Gln Glu Gln Asp Ile Phe Leu Trp Arg Lys Glu Thr Gly Phe Gly Phe
                805                 810                 815

Arg Ile Leu Gly Gly Asn Glu Pro Gly Glu Pro Ile Tyr Ile Gly His
            820                 825                 830

Ile Val Pro Leu Gly Ala Ala Asp Thr Asp Gly Arg Leu Arg Ser Gly
        835                 840                 845

Asp Glu Leu Ile Cys Val Asp Gly Thr Pro Val Ile Gly Lys Ser His
    850                 855                 860

Gln Leu Val Val Gln Leu Met Gln Gln Ala Ala Lys Gln Gly His Val
865                 870                 875                 880

Asn Leu Thr Val Arg Arg Lys Val Val Phe Ala Val Pro Lys Ala Glu
                885                 890                 895
```

```
Asn Glu Val Pro Ser Pro Ala Ser Ser His His Ser Ser Asn Gln Pro
            900                 905                 910

Ala Ser Leu Thr Glu Glu Lys Arg Thr Pro Gln Gly Ser Gln Asn Ser
        915                 920                 925

Leu Asn Thr Val Ser Ser Gly Ser Gly Ser Thr Ser Gly Ile Gly Ser
    930                 935                 940

Gly Gly Gly Gly Gly Ser Gly Val Val Ser Ala Val Leu Gln Pro Tyr
945                 950                 955                 960

Asp Val Glu Ile Arg Arg Gly Glu Asn Glu Gly Phe Gly Phe Val Ile
                965                 970                 975

Val Ser Ser Val Ser Arg Pro Glu Ala Gly Thr Thr Phe Glu Ser Ser
            980                 985                 990

Asn Ala Thr Leu Leu Thr Asn Ala  Glu Lys Ile Ala Thr  Ile Thr Thr
        995                 1000                1005

Thr His  Ala Pro Ser Gln Gln  Gly Thr Gln Glu Thr  Arg Thr Thr
    1010                1015                1020

Thr Lys  Pro Lys Gln Asp Ser  Gln Phe Glu Phe Lys  Gly Pro Gln
    1025                1030                1035

Ala Ala  Gln Glu Gln Asp Phe  Tyr Thr Val Glu Leu  Glu Arg Gly
    1040                1045                1050

Ala Lys  Gly Phe Gly Phe Ser  Leu Arg Gly Gly Arg  Glu Tyr Asn
    1055                1060                1065

Met Asp  Leu Tyr Val Leu Arg  Leu Ala Glu Asp Gly  Pro Ala Glu
    1070                1075                1080

Arg Cys  Gly Lys Met Arg Ile  Gly Asp Glu Ile Leu  Glu Ile Asn
    1085                1090                1095

Gly Glu  Thr Thr Lys Asn Met  Lys His Ser Arg Ala  Ile Glu Leu
    1100                1105                1110

Ile Lys
    1115


<210> SEQ ID NO 124
<211> LENGTH: 375
<212> TYPE: PRT
<213> ORGANISM: Mus musculus

<400> SEQUENCE: 124

Met Ala Ser Lys Pro Glu Lys Arg Val Ala Ser Ser Val Phe Ile Thr
1               5                   10                  15

Leu Ala Pro Pro Arg Arg Asp Val Ala Val Ser Glu Glu Val Gly Gln
            20                  25                  30

Ala Ala Cys Glu Ala Arg Arg Ala Arg Pro Trp Glu Met Leu Pro Thr
        35                  40                  45

Lys Thr Pro Gly Ala Ala Val Gly Arg Ser Pro Lys Thr Trp Thr Pro
    50                  55                  60

Ser Gly Lys Thr Asn Ala Ser Leu Ser Gly Val Thr Pro Gln Leu Ser
65                  70                  75                  80

Asn Gly Gly Cys Ser Leu Pro Pro Pro Ser Leu Asn Glu Glu Asp Leu
                85                  90                  95

Asp Leu Pro Pro Pro Pro Pro Pro Pro Ser Ala Tyr Leu Pro Leu Pro
            100                 105                 110

Glu Glu Glu Pro Pro Val Leu Pro Gly Lys Ser Leu Ile Ser Asp Leu
        115                 120                 125

Glu Gln Leu His Leu Pro Pro Pro Pro Pro Pro Pro Pro Pro Gln Ala
    130                 135                 140
```

```
Pro Ser Lys Gly Ser Ser Val His Pro Pro Pro Gly His Ala Arg Pro
145                 150                 155                 160

Ser Glu Glu Glu Leu Pro Pro Pro Pro Glu Glu Pro Val Thr Leu Pro
                165                 170                 175

Glu Arg Glu Val Ser Thr Asp Val Cys Gly Phe Cys His Lys Pro Val
            180                 185                 190

Ser Pro Arg Glu Leu Ala Val Glu Ala Met Lys Arg Gln Tyr His Ala
        195                 200                 205

Gln Cys Phe Thr Cys Arg Thr Cys Arg Arg Gln Leu Ala Gly Gln Arg
    210                 215                 220

Phe Tyr Gln Lys Asp Gly Arg Pro Leu Cys Glu Pro Cys Tyr Gln Asp
225                 230                 235                 240

Thr Leu Glu Lys Cys Gly Lys Cys Gly Glu Val Val Gln Glu His Val
                245                 250                 255

Ile Arg Ala Leu Gly Lys Ala Phe His Pro Pro Cys Phe Thr Cys Val
            260                 265                 270

Thr Cys Ala Arg Cys Ile Ser Asp Glu Ser Phe Ala Leu Asp Ser Gln
        275                 280                 285

Asn Gln Val Tyr Cys Val Ala Asp Phe Tyr Arg Lys Phe Ala Pro Val
    290                 295                 300

Cys Ser Ile Cys Glu Asn Pro Ile Ile Pro Arg Asp Gly Lys Asp Ala
305                 310                 315                 320

Phe Lys Ile Glu Cys Met Gly Arg Asn Phe His Glu Asn Cys Tyr Arg
                325                 330                 335

Cys Glu Asp Cys Ser Val Leu Leu Ser Val Glu Pro Thr Asp Gln Gly
            340                 345                 350

Cys Tyr Pro Leu Asn Asp His Leu Phe Cys Lys Pro Cys His Leu Lys
        355                 360                 365

Arg Ser Ala Ala Gly Cys Cys
    370                 375


<210> SEQ ID NO 125
<211> LENGTH: 610
<212> TYPE: PRT
<213> ORGANISM: Mus musculus

<400> SEQUENCE: 125

Met Glu Arg Pro His Gln Asp Ala Ser Leu Ser Lys Lys Asp Ala Cys
1               5                   10                  15

Thr Gln Thr Tyr Pro Pro Arg Arg Arg Ile Arg His Ala Gln Val Gln
            20                  25                  30

Asp Ala Gly Gln Leu Lys Leu Ser Ile Asp Ala Gln Asp Arg Val Leu
        35                  40                  45

Leu Pro His Ile Ile Glu Gly Lys Gly Leu Met Ser Arg Glu Pro Gly
    50                  55                  60

Ile Cys Asp Pro Tyr Val Lys Val Ser Leu Ile Pro Glu Asp Ser Gln
65                  70                  75                  80

Leu Pro Cys Gln Thr Thr Gln Ile Ile Pro Asp Cys Arg Asp Pro Ala
                85                  90                  95

Phe His Glu His Phe Phe Phe Pro Val Pro Glu Glu Gly Asp Gln Lys
            100                 105                 110

Arg Leu Leu Val Thr Val Trp Asn Arg Ala Ser Glu Thr Arg Gln His
        115                 120                 125

Thr Leu Ile Gly Cys Met Ser Phe Gly Val Arg Ser Leu Leu Thr Pro
    130                 135                 140
```

```
Asp Lys Glu Ile Ser Gly Trp Tyr Tyr Leu Leu Gly Glu Asp Leu Gly
145                 150                 155                 160

Arg Thr Lys His Leu Lys Val Ala Arg Arg Arg Leu Gln Pro Leu Arg
                165                 170                 175

Asp Met Leu Leu Arg Met Pro Gly Glu Gly Asp Pro Glu Asn Gly Glu
            180                 185                 190

Lys Leu Gln Ile Thr Ile Arg Arg Gly Lys Asp Gly Phe Gly Phe Thr
        195                 200                 205

Ile Cys Cys Asp Ser Pro Val Arg Val Gln Ala Val Asp Ser Gly Gly
    210                 215                 220

Pro Ala Glu Arg Ala Gly Leu Gln Gln Leu Asp Thr Val Leu Gln Leu
225                 230                 235                 240

Asn Glu Arg Pro Val Glu His Trp Lys Cys Val Glu Leu Ala His Glu
                245                 250                 255

Ile Arg Ser Cys Pro Ser Glu Ile Ile Leu Leu Val Trp Arg Val Val
            260                 265                 270

Pro Gln Ile Lys Pro Gly Pro Asp Gly Gly Val Leu Arg Arg Ala Ser
        275                 280                 285

Cys Lys Ser Thr His Asp Leu Leu Ser Pro Pro Asn Lys Arg Glu Lys
    290                 295                 300

Asn Cys Thr His Gly Ala Pro Val Arg Pro Glu Gln Arg His Ser Cys
305                 310                 315                 320

His Leu Val Cys Asp Ser Ser Asp Gly Leu Leu Leu Gly Gly Trp Glu
                325                 330                 335

Arg Tyr Thr Glu Val Gly Lys Arg Ser Gly Gln His Thr Leu Pro Ala
            340                 345                 350

Leu Ser Arg Thr Thr Thr Pro Thr Asp Pro Asn Tyr Ile Ile Leu Ala
        355                 360                 365

Pro Leu Asn Pro Gly Ser Gln Leu Leu Arg Pro Val Tyr Gln Glu Asp
    370                 375                 380

Thr Ile Pro Glu Glu Pro Gly Thr Thr Thr Lys Gly Lys Ser Tyr Thr
385                 390                 395                 400

Gly Leu Gly Lys Lys Ser Arg Leu Met Lys Thr Val Gln Thr Met Lys
                405                 410                 415

Gly His Ser Asn Tyr Gln Asp Cys Ser Ala Leu Arg Pro His Ile Pro
            420                 425                 430

His Ser Ser Tyr Gly Thr Tyr Val Thr Leu Ala Pro Lys Val Leu Val
        435                 440                 445

Phe Pro Val Phe Val Gln Pro Leu Asp Leu Cys Asn Pro Ala Arg Thr
    450                 455                 460

Leu Leu Leu Ser Glu Glu Leu Leu Leu Tyr Glu Gly Arg Asn Lys Thr
465                 470                 475                 480

Ser Gln Val Thr Leu Phe Ala Tyr Ser Asp Leu Leu Leu Phe Thr Lys
                485                 490                 495

Glu Glu Glu Pro Gly Arg Cys Asp Val Leu Arg Asn Pro Leu Tyr Leu
            500                 505                 510

Gln Ser Val Lys Leu Gln Glu Gly Ser Ser Glu Asp Leu Lys Phe Cys
        515                 520                 525

Val Leu Tyr Leu Ala Glu Lys Ala Glu Cys Leu Phe Thr Leu Glu Ala
    530                 535                 540

His Ser Gln Glu Gln Lys Lys Arg Val Cys Trp Cys Leu Ser Glu Asn
545                 550                 555                 560

Ile Ala Lys Gln Gln Gln Leu Ala Ala Pro Pro Thr Glu Arg Lys Lys
```

```
                565                 570                 575

Leu His Pro Tyr Gly Ser Leu Gln Gln Glu Met Gly Pro Val Thr Ser
            580                 585                 590

Ile Ser Ala Thr Gln Asp Arg Ser Phe Thr Ser Ser Gly Gln Thr Leu
        595                 600                 605

Ile Gly
    610


<210> SEQ ID NO 126
<211> LENGTH: 1354
<212> TYPE: PRT
<213> ORGANISM: Mus musculus

<400> SEQUENCE: 126

Met Ser Val Arg Phe Ser Ala Thr Ser Met Lys Glu Val Leu Ala Pro
1               5                   10                  15

Glu Ala Ser Glu Phe Asp Glu Trp Glu Pro Glu Gly Thr Ala Thr Leu
            20                  25                  30

Gly Gly Pro Val Thr Ala Ile Ile Pro Thr Trp Gln Ala Leu Thr Thr
        35                  40                  45

Leu Asp Leu Ser His Asn Ser Ile Cys Glu Ile Asp Glu Ser Val Lys
    50                  55                  60

Leu Ile Pro Lys Ile Glu Tyr Leu Asp Leu Ser His Asn Gly Leu Arg
65                  70                  75                  80

Val Val Asp Asn Leu Gln His Leu Tyr Asn Leu Val His Leu Asp Leu
                85                  90                  95

Ser Tyr Asn Lys Leu Ser Ser Leu Glu Gly Val His Thr Lys Leu Gly
            100                 105                 110

Asn Val Lys Thr Leu Asn Leu Ala Gly Asn Phe Leu Glu Ser Leu Ser
        115                 120                 125

Gly Leu His Lys Leu Tyr Ser Leu Val Asn Val Asp Leu Arg Asp Asn
    130                 135                 140

Arg Ile Glu Gln Leu Asp Glu Val Lys Ser Ile Gly Ser Leu Pro Cys
145                 150                 155                 160

Leu Glu Arg Leu Thr Leu Leu Asn Asn Pro Leu Ser Ile Ile Pro Asp
                165                 170                 175

Tyr Arg Thr Lys Val Leu Ser Gln Phe Gly Glu Arg Ala Ser Glu Ile
            180                 185                 190

Cys Leu Asp Asp Val Ala Thr Thr Glu Lys Glu Leu Asp Thr Val Glu
        195                 200                 205

Val Leu Lys Ala Ile Gln Lys Ala Lys Asp Val Lys Ser Lys Leu Ser
    210                 215                 220

Asn Thr Glu Lys Lys Ala Gly Glu Asp Phe Arg Leu Pro Pro Ala Pro
225                 230                 235                 240

Cys Ile Arg Pro Gly Gly Ser Pro Pro Ala Ala Pro Ala Ser Ala Ser
                245                 250                 255

Leu Pro Gln Pro Ile Leu Ser Asn Gln Gly Ile Met Phe Val Gln Glu
            260                 265                 270

Glu Ala Leu Ala Ser Ser Leu Ser Ser Thr Asp Ser Leu Pro Pro Glu
        275                 280                 285

Asp His Arg Pro Ile Ala Arg Ala Cys Ser Asp Ser Leu Glu Ser Ile
    290                 295                 300

Pro Ala Gly Gln Val Ala Ser Asp Asp Leu Arg Asp Val Pro Gly Ala
305                 310                 315                 320

Val Gly Gly Val Ser Pro Asp His Ala Glu Pro Glu Val Gln Val Val
```

```
                325                 330                 335

Pro Gly Ser Gly Gln Ile Ile Phe Leu Pro Phe Thr Cys Ile Gly Tyr
            340                 345                 350

Thr Ala Thr Asn Gln Asp Phe Ile Gln Arg Leu Ser Thr Leu Ile Arg
        355                 360                 365

Gln Ala Ile Glu Arg Gln Leu Pro Ala Trp Ile Glu Ala Ala Asn Gln
    370                 375                 380

Arg Glu Glu Ala His Gly Glu Gln Gly Glu Glu Glu Glu Glu Glu Glu
385                 390                 395                 400

Glu Glu Glu Asp Val Ala Glu Asn Arg Tyr Phe Glu Met Gly Pro Pro
                405                 410                 415

Asp Ala Glu Glu Glu Glu Gly Ser Gly Gln Gly Glu Glu Asp Glu Glu
            420                 425                 430

Asp Glu Asp Glu Glu Ala Glu Glu Glu Arg Leu Ala Leu Glu Trp Ala
        435                 440                 445

Leu Gly Ala Asp Glu Asp Phe Leu Leu Glu His Ile Arg Ile Leu Lys
    450                 455                 460

Val Leu Trp Cys Phe Leu Ile His Val Gln Gly Ser Ile Arg Gln Phe
465                 470                 475                 480

Ala Ala Cys Leu Val Leu Thr Asp Phe Gly Ile Ala Val Phe Glu Ile
                485                 490                 495

Pro His Gln Glu Ser Arg Gly Ser Ser Gln His Ile Leu Ser Ser Leu
            500                 505                 510

Arg Phe Val Phe Cys Phe Pro His Gly Asp Leu Thr Glu Phe Gly Phe
        515                 520                 525

Leu Met Pro Glu Leu Cys Leu Val Leu Lys Val Arg His Ser Glu Asn
    530                 535                 540

Thr Leu Phe Ile Ile Ser Asp Ala Ala Asn Leu His Glu Phe His Ala
545                 550                 555                 560

Asp Leu Arg Ser Cys Phe Ala Pro Gln His Met Ala Met Leu Cys Ser
                565                 570                 575

Pro Ile Leu Tyr Gly Ser His Thr Thr Leu Gln Glu Phe Leu Arg Gln
            580                 585                 590

Leu Leu Thr Phe Tyr Lys Val Ala Gly Gly Ser Gln Glu Arg Ser Gln
        595                 600                 605

Gly Cys Phe Pro Val Tyr Leu Val Tyr Ser Asp Lys Arg Met Val Gln
    610                 615                 620

Thr Pro Ala Gly Asp Tyr Ser Gly Asn Ile Glu Trp Ala Ser Cys Thr
625                 630                 635                 640

Leu Cys Ser Ala Val Arg Arg Ser Cys Cys Ala Pro Ser Glu Ala Val
                645                 650                 655

Lys Ser Ala Ala Ile Pro Tyr Trp Leu Leu Leu Thr Ser Gln His Leu
            660                 665                 670

Asn Val Ile Lys Ala Asp Phe Asn Pro Met Pro Asn Arg Gly Thr His
        675                 680                 685

Asn Cys Arg Asn Arg Asn Ser Phe Lys Leu Ser Arg Val Pro Leu Ser
    690                 695                 700

Thr Val Leu Leu Asp Pro Thr Arg Ser Cys Thr Gln Pro Arg Gly Ala
705                 710                 715                 720

Phe Ala Asp Gly His Val Leu Glu Leu Leu Val Gly Tyr Arg Phe Val
                725                 730                 735

Thr Ala Ile Phe Val Leu Pro His Glu Lys Phe His Phe Leu Arg Val
            740                 745                 750
```

```
Tyr Asn Gln Leu Arg Ala Ser Leu Gln Asp Leu Lys Thr Val Val Ile
        755                 760                 765

Ser Lys Asn Pro Ser Ala Lys Pro Arg Asn Gln Pro Ala Lys Ser Arg
    770                 775                 780

Ala Ser Ala Glu Gln Arg Leu Gln Glu Thr Pro Ala Asp Ala Pro Ala
785                 790                 795                 800

Pro Ala Ala Val Pro Pro Thr Ala Ser Ala Pro Ala Pro Ala Glu Ala
                805                 810                 815

Leu Ala Pro Asp Leu Ala Pro Val Gln Ala Pro Gly Glu Asp Arg Gly
            820                 825                 830

Leu Thr Ser Ala Glu Ala Pro Ala Ala Ala Glu Ala Pro Ala Ala Ala
        835                 840                 845

Glu Ala Pro Ala Ala Ala Glu Ala Pro Ala Ala Ala Glu Ala Pro Ala
    850                 855                 860

Ala Ala Glu Ala Pro Ala Ala Ala Glu Ala Pro Ala Pro Ala Glu Ala
865                 870                 875                 880

Pro Ala Ala Ala Glu Ala Pro Ala Ala Ala Glu Ala Pro Ala Ala Ala
                885                 890                 895

Glu Ala Pro Ala Ala Ala Glu Ala Pro Ala Ser Ala Glu Ala Pro Ala
            900                 905                 910

Pro Asn Gln Ala Pro Ala Pro Ala Arg Gly Pro Ala Pro Ala Arg Gly
        915                 920                 925

Pro Ala Pro Ala Gly Gly Pro Ala Pro Ala Gly Gly Pro Ala Pro Ala
    930                 935                 940

Glu Ala Leu Ala Gln Ala Glu Val Pro Ala Gln Tyr Pro Ser Glu Arg
945                 950                 955                 960

Leu Ile Gln Ser Thr Ser Glu Glu Asn Gln Ile Pro Ser His Leu Pro
                965                 970                 975

Val Cys Pro Ser Leu Gln His Ile Ala Arg Leu Arg Gly Arg Ala Ile
            980                 985                 990

Ile Asp Leu Phe His Asn Ser Ile  Ala Glu Val Glu Asn  Glu Glu Leu
        995                 1000                1005

Arg His  Leu Leu Trp Ser Ser  Val Val Phe Tyr Gln  Thr Pro Gly
    1010                 1015                 1020

Leu Glu  Val Thr Ala Cys Val  Leu Leu Ser Ser Lys  Ala Val Tyr
    1025                 1030                 1035

Phe Ile  Leu His Asp Gly Leu  Arg Arg Tyr Phe Ser  Glu Pro Leu
    1040                 1045                 1050

Gln Asp  Phe Trp His Gln Lys  Asn Thr Asp Tyr Asn  Asn Ser Pro
    1055                 1060                 1065

Phe His  Val Ser Gln Cys Phe  Val Leu Lys Leu Ser  Asp Leu Gln
    1070                 1075                 1080

Ser Val  Asn Val Gly Leu Phe  Asp Gln Tyr Phe Arg  Leu Thr Gly
    1085                 1090                 1095

Ser Ser  Pro Thr Gln Val Val  Thr Cys Leu Thr Arg  Asp Ser Tyr
    1100                 1105                 1110

Leu Thr  His Cys Phe Leu Gln  His Leu Met Leu Val  Leu Ser Ser
    1115                 1120                 1125

Leu Glu  Arg Thr Pro Ser Pro  Glu Pro Val Asp Lys  Asp Phe Tyr
    1130                 1135                 1140

Ser Glu  Phe Gly Asp Lys Asn  Thr Gly Lys Met Glu  Asn Tyr Glu
    1145                 1150                 1155

Leu Ile  His Ser Ser Arg Val  Lys Phe Thr Tyr Pro  Ser Glu Glu
    1160                 1165                 1170
```

```
Glu Val  Gly Asp Leu Thr Tyr  Ile Val Ala Gln Lys  Met Ala Asp
    1175                 1180                 1185

Pro Ala  Lys Asn Pro Ala Leu  Ser Ile Leu Leu Tyr  Ile Gln Ala
    1190                 1195                 1200

Phe Gln  Val Val Thr Pro His  Leu Gly Arg Gly Arg  Gly Pro Leu
    1205                 1210                 1215

Arg Pro  Lys Thr Leu Leu Leu  Thr Ser Ala Glu Ile  Phe Leu Leu
    1220                 1225                 1230

Asp Glu  Asp Tyr Ile His Tyr  Pro Leu Pro Glu Phe  Ala Lys Glu
    1235                 1240                 1245

Pro Pro  Gln Arg Asp Arg Tyr  Arg Leu Asp Asp Gly  Arg Arg Val
    1250                 1255                 1260

Arg Asp  Leu Asp Arg Val Leu  Met Gly Tyr Tyr Pro  Tyr Pro Gln
    1265                 1270                 1275

Ala Leu  Thr Leu Val Phe Asp  Asp Thr Gln Gly His  Asp Leu Met
    1280                 1285                 1290

Gly Ser  Val Thr Leu Asp His  Phe Gly Glu Met Pro  Gly Gly Pro
    1295                 1300                 1305

Gly Arg  Val Gly Gln Gly Arg  Glu Val Gln Trp Gln  Val Phe Val
    1310                 1315                 1320

Pro Ser  Ala Glu Ser Arg Glu  Lys Leu Ile Ser Leu  Leu Ala Arg
    1325                 1330                 1335

Gln Trp  Glu Ala Leu Cys Gly  Arg Glu Leu Pro Val  Glu Leu Thr
    1340                 1345                 1350

Gly

<210> SEQ ID NO 127
<211> LENGTH: 1118
<212> TYPE: PRT
<213> ORGANISM: Mus musculus

<400> SEQUENCE: 127

Met Lys Glu Ile Cys Arg Ile Cys Ala Arg Glu Leu Cys Gly Asn Gln
1               5                   10                  15

Arg Arg Trp Ile Phe His Thr Ala Ser Lys Leu Asn Leu Gln Val Leu
            20                  25                  30

Leu Ser His Val Leu Gly Lys Asp Val Ser Arg Asp Gly Lys Ala Glu
        35                  40                  45

Phe Ala Cys Ser Lys Cys Ala Phe Met Leu Asp Arg Ile Tyr Arg Phe
    50                  55                  60

Asp Thr Val Ile Ala Arg Ile Glu Ala Leu Ser Leu Glu Arg Leu Gln
65                  70                  75                  80

Lys Leu Leu Leu Glu Lys Asp Arg Leu Lys Phe Cys Ile Ala Ser Met
                85                  90                  95

Tyr Arg Lys Asn Asn Asp Asp Ser Gly Glu Glu Asn Lys Ala Gly Ser
            100                 105                 110

Gly Thr Val Asp Ile Ser Gly Leu Pro Asp Met Arg Tyr Ala Ala Leu
        115                 120                 125

Leu Gln Glu Asp Phe Ala Tyr Ser Gly Phe Glu Cys Trp Val Glu Asn
    130                 135                 140

Glu Asp Gln Ile Asn Asp Ser His Ser Cys His Ala Ser Glu Gly Pro
145                 150                 155                 160

Gly Asn Arg Pro Arg Arg Cys Arg Gly Cys Ala Ala Leu Arg Val Ala
                165                 170                 175
```

-continued

```
Asp Ser Asp Tyr Glu Ala Ile Cys Lys Val Pro Arg Lys Val Ala Arg
            180                 185                 190

Ser Ile Ser Tyr Ala Pro Ser Ser Arg Trp Ser Thr Ser Ile Cys Thr
        195                 200                 205

Glu Glu Pro Ala Leu Ser Glu Val Gly Pro Pro Asp Leu Ala Ser Thr
    210                 215                 220

Lys Val Pro Pro Asp Gly Glu Ser Met Glu Glu Gly Thr Pro Gly Ser
225                 230                 235                 240

Ser Val Glu Ser Leu Asp Ala Ser Val Gln Ala Ser Pro Pro Gln Gln
                245                 250                 255

Lys Asp Glu Glu Thr Glu Arg Ser Ala Lys Glu Leu Val Lys Cys Asp
            260                 265                 270

Tyr Cys Ser Asp Glu Gln Ala Pro Gln His Leu Cys Asn His Lys Leu
        275                 280                 285

Glu Leu Ala Leu Ser Met Ile Lys Gly Leu Asp Tyr Lys Pro Ile Gln
    290                 295                 300

Ser Pro Arg Gly Ser Lys Leu Pro Ile Pro Val Lys Ser Ile Leu Pro
305                 310                 315                 320

Gly Ala Lys Pro Gly His Ile Leu Thr Asn Gly Val Ser Ser Ser Phe
                325                 330                 335

Leu Asn Arg Pro Leu Lys Pro Leu Tyr Arg Thr Pro Val Ser Tyr Pro
            340                 345                 350

Trp Glu Ile Ser Asp Gly Gln Glu Leu Trp Asp Asp Leu Cys Asp Glu
        355                 360                 365

Tyr Leu Pro Ile Gly Phe Gln Pro Val Pro Lys Gly Leu Pro Thr Gln
    370                 375                 380

Gln Lys Pro Asp Leu His Glu Thr Pro Thr Thr Gln Pro Pro Val Ser
385                 390                 395                 400

Glu Ser His Leu Ala Glu Leu Gln Asp Lys Ile Gln Gln Thr Glu Ala
                405                 410                 415

Thr Asn Lys Ile Leu Gln Glu Lys Leu Asn Asp Leu Ser Cys Glu Leu
            420                 425                 430

Lys Ser Ala Gln Glu Ser Ser Gln Lys Gln Asp Thr Thr Ile Gln Ser
        435                 440                 445

Leu Lys Glu Met Leu Lys Ser Arg Glu Ser Glu Thr Glu Glu Leu Tyr
    450                 455                 460

Gln Val Ile Glu Gly Gln Asn Asp Thr Met Ala Lys Leu Arg Glu Met
465                 470                 475                 480

Leu His Gln Ser Gln Leu Gly Gln Leu His Ser Ser Glu Gly Ile Ala
                485                 490                 495

Pro Ala Gln Gln Gln Val Ala Leu Leu Asp Leu Gln Ser Ala Leu Phe
            500                 505                 510

Cys Ser Gln Leu Glu Ile Gln Arg Leu Gln Arg Leu Val Arg Gln Lys
        515                 520                 525

Glu Arg Gln Leu Ala Asp Gly Lys Arg Cys Val Gln Leu Val Glu Ala
    530                 535                 540

Ala Ala Gln Glu Arg Glu His Gln Lys Glu Ala Ala Trp Lys His Asn
545                 550                 555                 560

Gln Glu Leu Arg Lys Ala Leu Gln His Leu Gln Gly Glu Leu His Ser
                565                 570                 575

Lys Ser Gln Gln Leu His Val Leu Glu Ala Glu Lys Tyr Asn Glu Ile
            580                 585                 590

Arg Thr Gln Gly Gln Asn Ile Gln His Leu Ser His Ser Leu Ser His
        595                 600                 605
```

```
Lys Glu Gln Leu Ile Gln Glu Leu Gln Glu Leu Leu Gln Tyr Arg Asp
    610                 615                 620

Asn Ala Asp Lys Thr Leu Asp Thr Asn Glu Val Phe Leu Glu Lys Leu
625                 630                 635                 640

Arg Gln Arg Ile Gln Asp Arg Ala Val Ala Leu Glu Arg Val Ile Asp
                645                 650                 655

Glu Lys Phe Ser Ala Leu Glu Glu Lys Asp Lys Glu Leu Arg Gln Leu
            660                 665                 670

Arg Leu Ala Val Arg Asp Arg Asp His Asp Leu Glu Arg Leu Arg Cys
        675                 680                 685

Val Leu Ser Ala Asn Glu Ala Thr Met Gln Ser Met Glu Ser Leu Leu
    690                 695                 700

Arg Ala Arg Gly Leu Glu Val Glu Gln Leu Thr Ala Thr Cys Gln Asn
705                 710                 715                 720

Leu Gln Trp Leu Lys Glu Glu Leu Glu Thr Lys Phe Gly His Trp Gln
                725                 730                 735

Lys Glu Gln Glu Ser Ile Ile Gln Gln Leu Gln Thr Ser Leu His Asp
            740                 745                 750

Arg Asn Lys Glu Val Glu Asp Leu Ser Ala Thr Leu Leu Cys Lys Leu
        755                 760                 765

Gly Pro Gly Gln Ser Glu Val Ala Glu Glu Leu Cys Gln Arg Leu Gln
    770                 775                 780

Arg Lys Glu Arg Met Leu Gln Asp Leu Leu Ser Asp Arg Asn Lys Gln
785                 790                 795                 800

Ala Val Glu His Glu Met Glu Ile Gln Gly Leu Leu Gln Ser Met Gly
                805                 810                 815

Thr Arg Glu Gln Glu Arg Gln Ala Ala Ala Glu Lys Met Val Gln Ala
            820                 825                 830

Phe Met Glu Arg Asn Ser Glu Leu Gln Ala Leu Arg Gln Tyr Leu Gly
        835                 840                 845

Gly Lys Glu Leu Met Thr Ser Ser Gln Thr Phe Ile Ser Asn Gln Pro
    850                 855                 860

Ala Gly Val Thr Ser Ile Gly Pro His His Gly Glu Gln Thr Asp Gln
865                 870                 875                 880

Gly Ser Met Gln Met Pro Ser Arg Asp Asp Ser Thr Ser Leu Thr Ala
                885                 890                 895

Arg Glu Glu Ala Ser Ile Pro Arg Ser Thr Leu Gly Asp Ser Asp Thr
            900                 905                 910

Val Ala Gly Leu Glu Lys Glu Leu Ser Asn Ala Lys Glu Glu Leu Glu
        915                 920                 925

Leu Met Ala Lys Lys Glu Arg Glu Ser Gln Met Glu Leu Ser Ala Leu
    930                 935                 940

Gln Ser Met Met Ala Met Gln Glu Glu Glu Leu Gln Val Gln Ala Ala
945                 950                 955                 960

Asp Leu Glu Ser Leu Thr Arg Asn Val Gln Ile Lys Glu Asp Leu Ile
                965                 970                 975

Lys Asp Leu Gln Met Gln Leu Val Asp Pro Glu Asp Ile Pro Ala Met
            980                 985                 990

Glu Arg Leu Thr Gln Glu Val Leu  Leu Leu Arg Glu Lys  Val Ala Ser
        995                 1000                1005

Val Glu  Pro Gln Gly Gln Glu  Val Ser Gly Asn Lys  Arg Gln Gln
    1010                1015                1020

Leu Leu  Leu Met Leu Glu Gly  Leu Val Asp Glu Arg  Ser Arg Leu
```

```
    1025                1030                1035

Asn Glu  Ala Leu Gln Ala Glu  Arg Gln Leu Tyr Ser  Ser Leu Val
    1040                1045                1050

Lys Phe  His Ala Gln Pro Glu  Asn Ser Glu Arg Asp  Gly Thr Leu
    1055                1060                1065

Gln Val  Glu Leu Glu Gly Ala  Gln Val Leu Arg Thr  Arg Leu Glu
    1070                1075                1080

Glu Val  Leu Gly Arg Ser Leu  Glu Arg Leu Ser Arg  Leu Glu Ser
    1085                1090                1095

Leu Ala  Ala Ile Gly Gly Gly  Glu Leu Glu Ser Val  Gln Ala Arg
    1100                1105                1110

His Lys  His Ala Phe
    1115


<210> SEQ ID NO 128
<211> LENGTH: 326
<212> TYPE: PRT
<213> ORGANISM: Mus musculus

<400> SEQUENCE: 128

Met Glu Lys Asp Ser Leu Ser Arg Ala Asp Gln Gln Tyr Glu Cys Val
1               5                   10                  15

Ala Glu Ile Gly Glu Gly Ala Tyr Gly Lys Val Phe Lys Ala Arg Asp
            20                  25                  30

Leu Lys Asn Gly Gly Arg Phe Val Ala Leu Lys Arg Val Arg Val Gln
        35                  40                  45

Thr Ser Glu Glu Gly Met Pro Leu Ser Thr Ile Arg Glu Val Ala Val
    50                  55                  60

Leu Arg His Leu Glu Thr Phe Glu His Pro Asn Val Val Arg Leu Phe
65                  70                  75                  80

Asp Val Cys Thr Val Ser Arg Thr Asp Arg Glu Thr Lys Leu Thr Leu
                85                  90                  95

Val Phe Glu His Val Asp Gln Asp Leu Thr Thr Tyr Leu Asp Lys Val
            100                 105                 110

Pro Glu Pro Gly Val Pro Thr Glu Thr Ile Lys Asp Met Met Phe Gln
        115                 120                 125

Leu Leu Arg Gly Leu Asp Phe Leu His Ser His Arg Val Val His Arg
    130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Thr Ser Val Val Val Thr Leu Trp Tyr Arg Ala Pro Glu Val Leu Leu
            180                 185                 190

Gln Ser Ser Tyr Ala Thr Pro Val Asp Leu Trp Ser Val Gly Cys Ile
        195                 200                 205

Phe Ala Glu Met Phe Arg Arg Lys Pro Leu Phe Arg Gly Ser Ser Asp
    210                 215                 220

Val Asp Gln Leu Gly Lys Ile Leu Asp Ile Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
            260                 265                 270

Gly Lys Asp Leu Leu Leu Lys Cys Leu Thr Phe Asn Pro Ala Lys Arg
```

```
        275                 280                 285

Ile Ser Ala Tyr Gly Ala Leu Asn His Pro Tyr Phe Gln Asp Leu Glu
    290                 295                 300

Arg Tyr Lys Asp Asn Leu Asn Ser His Leu Pro Ser Asn Gln Ser Thr
305                 310                 315                 320

Ser Glu Leu Asn Thr Ala
                325


<210> SEQ ID NO 129
<211> LENGTH: 560
<212> TYPE: PRT
<213> ORGANISM: Mus musculus

<400> SEQUENCE: 129

Met Ser Thr Glu Arg Thr Ser Trp Thr Asn Leu Ser Thr Ile Gln Lys
1               5                   10                  15

Ile Ala Leu Gly Leu Gly Ile Pro Ala Ser Ala Thr Val Ala Tyr Ile
            20                  25                  30

Leu Tyr Arg Arg Tyr Arg Glu Ser Arg Glu Glu Arg Leu Thr Phe Val
        35                  40                  45

Gly Glu Asp Asp Ile Glu Ile Glu Met Arg Val Pro Gln Glu Ala Val
    50                  55                  60

Lys Leu Ile Ile Gly Arg Gln Gly Ala Asn Ile Lys Gln Leu Arg Lys
65                  70                  75                  80

Gln Thr Gly Ala Arg Ile Asp Val Asp Thr Glu Asp Val Gly Asp Glu
                85                  90                  95

Arg Val Leu Leu Ile Ser Gly Phe Pro Val Gln Val Cys Lys Ala Lys
            100                 105                 110

Ala Ala Ile His Gln Ile Leu Thr Glu Asn Thr Pro Val Phe Glu Gln
        115                 120                 125

Leu Ser Val Pro Gln Arg Ser Val Gly Arg Ile Ile Gly Arg Gly Gly
    130                 135                 140

Glu Thr Ile Arg Ser Ile Cys Lys Ala Ser Gly Ala Lys Ile Thr Cys
145                 150                 155                 160

Asp Lys Glu Ser Glu Gly Thr Leu Leu Leu Ser Arg Leu Ile Lys Ile
                165                 170                 175

Ser Gly Thr Gln Lys Glu Val Ala Ala Ala Lys His Leu Ile Leu Glu
            180                 185                 190

Lys Val Ser Glu Asp Glu Glu Leu Arg Lys Arg Ile Ala His Ser Ala
        195                 200                 205

Glu Thr Arg Val Pro Arg Lys Gln Pro Ile Ser Val Arg Arg Glu Glu
    210                 215                 220

Val Thr Glu Pro Gly Gly Ala Gly Glu Ala Ala Leu Trp Lys Asn Thr
225                 230                 235                 240

Asn Ser Ser Met Gly Pro Ala Thr Pro Leu Glu Val Pro Leu Arg Lys
                245                 250                 255

Gly Gly Gly Asp Met Val Val Val Gly Pro Lys Glu Gly Ser Trp Glu
            260                 265                 270

Lys Pro Asn Asp Asp Ser Phe Gln Asn Ser Gly Ala Gln Ser Ser Pro
        275                 280                 285

Glu Thr Ser Met Phe Glu Ile Pro Ser Pro Asp Phe Ser Phe His Ala
    290                 295                 300

Asp Glu Tyr Leu Glu Val Tyr Val Ser Ser Ser Glu His Pro Asn His
305                 310                 315                 320

Phe Trp Ile Gln Ile Ile Gly Ser Arg Ser Leu Gln Leu Asp Lys Leu
```

```
                325                 330                 335

Val Ser Glu Met Thr Gln His Tyr Glu Asn Ser Leu Pro Glu Asp Leu
            340                 345                 350

Thr Val His Val Gly Asp Ile Val Ala Ala Pro Leu Ser Thr Asn Gly
        355                 360                 365

Ser Trp Tyr Arg Ala Arg Val Leu Gly Thr Leu Glu Asn Gly Asn Leu
    370                 375                 380

Asp Leu Tyr Phe Val Asp Phe Gly Asp Asn Gly Asp Cys Ala Leu Lys
385                 390                 395                 400

Asp Leu Arg Ala Leu Arg Ser Asp Phe Leu Ser Leu Pro Phe Gln Ala
                405                 410                 415

Ile Glu Cys Ser Leu Ala Arg Ile Ala Pro Thr Gly Glu Glu Trp Glu
            420                 425                 430

Glu Glu Ala Leu Asp Glu Phe Asp Arg Leu Thr His Cys Ala Asp Trp
        435                 440                 445

Lys Pro Leu Val Ala Lys Ile Ser Ser Tyr Val Gln Thr Gly Ile Ser
    450                 455                 460

Thr Trp Pro Lys Ile Tyr Leu Tyr Asp Thr Ser Asp Glu Lys Lys Leu
465                 470                 475                 480

Asp Ile Gly Leu Glu Leu Val Arg Lys Gly Tyr Ala Val Glu Leu Pro
                485                 490                 495

Glu Asp Met Glu Glu Asn Arg Thr Val Pro Asn Met Leu Lys Asp Met
            500                 505                 510

Ala Thr Glu Thr Asp Asp Ser Leu Ala Ser Ile Leu Thr Glu Thr Lys
        515                 520                 525

Lys Ser Pro Glu Glu Met Pro His Thr Leu Ser Cys Leu Ser Leu Ser
    530                 535                 540

Glu Ala Ala Ser Met Ser Gly Asp Asp Asn Leu Glu Asp Asp Leu Phe
545                 550                 555                 560


<210> SEQ ID NO 130
<211> LENGTH: 429
<212> TYPE: PRT
<213> ORGANISM: Mus musculus

<400> SEQUENCE: 130

Met Arg Gly Pro Glu Leu Gly Pro Glu Thr Ser Met Glu Gly Asp Val
1               5                   10                  15

Leu Asp Thr Leu Glu Ala Leu Gly Tyr Lys Gly Pro Leu Leu Glu Glu
            20                  25                  30

Gln Ala Leu Ser Lys Ala Ala Glu Gly Gly Leu Ser Ser Pro Glu Phe
        35                  40                  45

Ser Glu Leu Cys Ile Trp Leu Gly Ser Gln Ile Lys Ser Leu Cys Asn
    50                  55                  60

Leu Glu Glu Ser Ile Thr Ser Ala Gly Arg Asp Asp Leu Glu Ser Phe
65                  70                  75                  80

Gln Leu Glu Ile Ser Gly Phe Leu Lys Glu Met Ala Cys Pro Tyr Ser
                85                  90                  95

Val Leu Val Ser Gly Asp Ile Lys Glu Arg Leu Thr Lys Lys Asp Asp
            100                 105                 110

Cys Leu Lys Leu Leu Leu Phe Leu Ser Thr Glu Leu Gln Ala Leu Gln
        115                 120                 125

Ile Leu Gln Lys Lys Lys His Lys Asn Ser Gln Leu Asp Lys Asn Ser
    130                 135                 140

Glu Ile Cys Gln Glu Val Gln Ala Val Cys Asp Ala Leu Gly Val Pro
```

145 150 155 160

Lys Ser Asp Thr Ser Asp Ile Pro Leu Leu Leu Ser Gln Val Glu Ser
165 170 175

Lys Val Lys Asp Ile Leu Cys Arg Val Gln Lys Asn His Val Gly Lys
180 185 190

Pro Leu Leu Lys Val Asp Leu Ser Ser Glu Gln Ala Glu Lys Leu Glu
195 200 205

Arg Ile Asn Asp Ala Leu Ser Cys Glu Tyr Glu Cys Arg Arg Arg Met
210 215 220

Leu Met Lys Arg Leu Asp Val Thr Val Gln Ser Phe Gly Trp Ser Asp
225 230 235 240

Arg Ala Lys Ala Lys Thr Asp Asn Ile Ala Arg Ile Tyr Gln Pro Lys
245 250 255

Arg Tyr Ala Leu Ser Pro Lys Thr Thr Val Thr Leu Ala His Leu Leu
260 265 270

Ala Ala Arg Glu Asp Leu Ser Lys Ile Ile Arg Thr Ser Ser Gly Ile
275 280 285

Ser Arg Glu Lys Thr Ala Cys Ala Ile Asn Lys Val Leu Met Gly Arg
290 295 300

Val Pro Asp Arg Gly Gly Arg Pro Asn Glu Ile Glu Pro Pro Pro Pro
305 310 315 320

Glu Met Pro Pro Trp Gln Lys Arg Gln Glu Gly Gly Gly Arg Gly Gly
325 330 335

Trp Gly Gly Gly Gly Gly Gly Arg Gly Gly Gly Gly Gly Gly Arg Gly
340 345 350

Gly Trp Gly Gly Gly Gly Gly Trp Gly Gly Gly Gly Gly Ser Gly Gly
355 360 365

Gly Trp Gly Gly Ser Gly Gly Gly Gly Gly Gly Arg Gly Gly Phe Gln
370 375 380

Gly Arg Gly Asp Tyr Gly Gly Arg Gly Asp Tyr Gly Gly Arg Gly Gly
385 390 395 400

Tyr Gly Gly Arg Gly Gly Tyr Gly Gly Arg Gly Tyr Gly Asp Pro Tyr
405 410 415

Gly Gly Gly Gly Gly Gly Gly Gly Gly Tyr Arg Arg Tyr
420 425

<210> SEQ ID NO 131
<211> LENGTH: 93
<212> TYPE: PRT
<213> ORGANISM: Mus musculus

<400> SEQUENCE: 131

Met Cys Gly Pro Asn Ala Asn Ala Pro Gln Thr Thr Val Lys Ala His
1 5 10 15

Thr Ile Glu Trp His Cys Pro Ala Gly His Cys Trp His Pro Thr Asn
20 25 30

Ser Pro His Arg Pro Thr Leu Glu Pro Gly Gln Ser Tyr Gly Pro Ser
35 40 45

Leu Val Val Cys Trp Ser Leu Pro Pro His Gln Arg Ser Leu Ser Leu
50 55 60

His Ser Glu Arg Asn Val Val Thr Ser Arg Cys Pro Ala Leu Ser Leu
65 70 75 80

Ala Pro Phe Leu His Asp Leu Lys Leu Asn Arg Leu Pro
85 90

<210> SEQ ID NO 132
<211> LENGTH: 123
<212> TYPE: PRT
<213> ORGANISM: Mus musculus

<400> SEQUENCE: 132

```
Met Val Ala Trp Leu Trp Lys Val Leu Met Gly Val Gly Leu Phe Ala
1               5                   10                  15

Leu Thr His Ala Ala Phe Ser Ala Ala Gln His Arg Ser His Ala Arg
            20                  25                  30

Leu Thr Glu Lys Lys Tyr Glu Pro Leu Pro Ala Asp Ile Val Leu Gln
        35                  40                  45

Thr Leu Leu Ala Phe Ala Leu Thr Cys Tyr Gly Val Val His Thr Ala
    50                  55                  60

Gly Asp Phe Arg Asp Arg Asp Ala Thr Ser Glu Leu Lys Asp Met Thr
65                  70                  75                  80

Phe Asp Thr Leu Arg Asn Arg Pro Ser Phe Tyr Val Phe His Arg Ser
                85                  90                  95

Gly Tyr Arg Leu Phe Gln Arg Pro Asp Ser Thr His Ser Ser Asn Leu
            100                 105                 110

Ser Ala Ser Ser Ser Asp Leu Pro Leu Lys Phe
        115                 120
```

<210> SEQ ID NO 133
<211> LENGTH: 820
<212> TYPE: PRT
<213> ORGANISM: Mus musculus

<400> SEQUENCE: 133

```
Met Ala Ala Gly Lys Phe Ala Ser Leu Pro Arg Asn Met Pro Val Asn
1               5                   10                  15

His Gln Phe Pro Leu Ala Ser Ser Met Asp Leu Leu Ser Ser Lys Ser
            20                  25                  30

Pro Leu Ala Glu Arg Arg Thr Asp Ala Tyr Gln Asp Val Ser Ile His
        35                  40                  45

Gly Thr Leu Pro Arg Lys Lys Lys Gly Pro Pro Ser Ile Arg Ser Cys
    50                  55                  60

Asp Asn Ala Gly His Ser Lys Ser Pro Arg Gln Ser Ser Pro Leu Thr
65                  70                  75                  80

Gln Asp Ile Ile Gln Glu Asn Pro Leu Gln Asp Arg Lys Gly Glu Asn
                85                  90                  95

Phe Ile Phe Arg Asp Pro Tyr Leu Leu Asp Pro Thr Leu Glu Tyr Val
            100                 105                 110

Lys Phe Ser Lys Glu Arg His Ile Met Asp Arg Thr Pro Glu Arg Leu
        115                 120                 125

Lys Lys Glu Leu Glu Glu Glu Leu Leu Leu Ser Ser Glu Asp Leu Arg
    130                 135                 140

Ser His Ala Trp Tyr His Gly Arg Ile Pro Arg Gln Val Ser Glu Asn
145                 150                 155                 160

Leu Val Gln Arg Asp Gly Asp Phe Leu Val Arg Asp Ser Leu Ser Ser
                165                 170                 175

Pro Gly Asn Phe Val Leu Thr Cys Gln Trp Lys Asn Leu Ala Gln His
            180                 185                 190

Phe Lys Ile Asn Arg Thr Val Leu Arg Leu Ser Glu Ala Tyr Ser Arg
        195                 200                 205

Val Gln Tyr Gln Phe Glu Met Glu Ser Phe Asp Ser Ile Pro Gly Leu
    210                 215                 220
```

```
Val Arg Cys Tyr Val Gly Asn Arg Arg Pro Ile Ser Gln Gln Ser Gly
225                 230                 235                 240

Ala Ile Ile Phe Gln Pro Ile Asn Arg Thr Val Pro Leu Trp Cys Leu
                245                 250                 255

Glu Glu Arg Tyr Gly Thr Ser Pro Gly Arg Gly Arg Glu Gly Ser Leu
            260                 265                 270

Ala Glu Gly Arg Pro Asp Val Val Lys Arg Leu Ser Leu Thr Thr Gly
        275                 280                 285

Ser Ser Ile Gln Ala Arg Glu His Ser Leu Pro Arg Gly Asn Leu Leu
    290                 295                 300

Arg Asn Lys Glu Lys Ser Gly Ser Gln Pro Ala Cys Leu Asp His Val
305                 310                 315                 320

Gln Asp Arg Lys Ala Leu Thr Leu Lys Ala His Gln Ser Glu Ser His
                325                 330                 335

Leu Pro Ile Gly Cys Lys Leu Pro Pro Gln Ser Pro Ser Met Asp Thr
            340                 345                 350

Ser Pro Cys Pro Ser Ser Pro Val Phe Arg Thr Gly Ser Glu Pro Thr
        355                 360                 365

Leu Ser Pro Ala Leu Val Arg Arg Phe Ser Ser Asp Ala Arg Thr Gly
    370                 375                 380

Glu Ala Leu Arg Gly Ser Asp Ser Gln Leu Cys Pro Lys Pro Pro Pro
385                 390                 395                 400

Lys Pro Cys Lys Val Pro Phe Leu Lys Thr Pro Pro Ser Pro Ser Pro
                405                 410                 415

Trp Leu Thr Ser Glu Ala Asn Tyr Cys Glu Leu Asn Pro Ala Phe Ala
            420                 425                 430

Val Gly Cys Asp Arg Gly Ala Lys Leu Pro Met Gln Ala His Asp Ser
        435                 440                 445

His Glu Met Leu Leu Thr Ala Lys Gln Asn Gly Pro Ser Gly Pro Arg
    450                 455                 460

Asn Ser Gly Ile Asn Tyr Met Ile Leu Asp Gly Asp Asp Gln Ala Arg
465                 470                 475                 480

His Trp Asp Pro Leu Ala Val Gln Thr Asp Glu Gly Gln Glu Asp Lys
                485                 490                 495

Thr Lys Phe Val Pro Pro Leu Met Glu Thr Val Ser Ser Phe Arg Pro
            500                 505                 510

Asn Asp Phe Glu Ser Lys Leu Leu Pro Pro Glu Asn Lys Pro Leu Glu
        515                 520                 525

Thr Ala Met Leu Lys His Ala Lys Glu Leu Phe Thr Asn His Asp Ala
    530                 535                 540

Arg Val Ile Ala Gln His Met Leu Ser Val Asp Cys Lys Val Ala Arg
545                 550                 555                 560

Ile Leu Glu Val Ser Glu Asp Arg Lys Arg Ser Met Gly Val Ser Ser
                565                 570                 575

Gly Leu Glu Leu Ile Thr Leu Pro His Gly Arg Gln Leu Arg Leu Asp
            580                 585                 590

Ile Ile Glu Arg His Asn Thr Met Ala Ile Gly Ile Ala Val Asp Ile
        595                 600                 605

Leu Gly Cys Thr Gly Thr Leu Glu Asn Arg Ala Gly Thr Leu Asn Lys
    610                 615                 620

Ile Ile Gln Val Ala Val Glu Leu Lys Asp Ala Met Gly Asp Leu Tyr
625                 630                 635                 640

Ala Phe Ser Ala Ile Met Lys Ala Leu Glu Met Pro Gln Ile Thr Arg
```

-continued

```
                645                 650                 655

Leu Glu Lys Thr Trp Thr Ala Leu Arg His His Tyr Thr Gln Thr Ala
            660                 665                 670

Ile Leu Tyr Glu Lys Gln Leu Lys Pro Phe Ser Lys Ile Leu His Glu
        675                 680                 685

Gly Arg Glu Ser Thr Tyr Val Pro Ala Ser Asn Val Ser Val Pro Leu
    690                 695                 700

Leu Met Pro Leu Val Thr Leu Met Glu Arg Gln Ala Val Thr Phe Glu
705                 710                 715                 720

Gly Thr Asp Met Trp Glu Asn Asn Asp Glu Ser Cys Glu Ile Leu Leu
                725                 730                 735

Asn His Leu Ala Thr Ala Arg Phe Met Ala Glu Ala Ser Glu Ser Tyr
            740                 745                 750

Arg Met Asn Ala Glu Arg Ile Leu Ala Asp Phe Gln Pro Asp Glu Glu
        755                 760                 765

Met Thr Glu Ile Leu Arg Thr Glu Phe Gln Met Arg Leu Leu Trp Gly
    770                 775                 780

Ser Lys Gly Ala Glu Val Asn Gln Asn Glu Arg Tyr Asp Lys Phe Asn
785                 790                 795                 800

Gln Ile Leu Thr Ala Leu Ser Arg Lys Leu Glu Pro Pro Ser Gly Lys
                805                 810                 815

Gln Ala Glu Leu
            820


<210> SEQ ID NO 134
<211> LENGTH: 849
<212> TYPE: PRT
<213> ORGANISM: Mus musculus

<400> SEQUENCE: 134

Met His Lys His Gln His Cys Cys Lys Cys Pro Glu Cys Tyr Glu Val
1               5                   10                  15

Thr Arg Leu Ala Ala Leu Arg Arg Leu Glu Pro Pro Gly Tyr Gly Asp
            20                  25                  30

Trp Gln Val Pro Asp Pro Tyr Gly Pro Ser Gly Gly Asn Gly Ala Ser
        35                  40                  45

Ser Gly Tyr Gly Gly Tyr Ser Ser Gln Thr Leu Pro Ser Gln Ala Gly
    50                  55                  60

Ala Thr Pro Thr Pro Arg Thr Lys Ala Lys Leu Ile Pro Thr Gly Arg
65                  70                  75                  80

Asp Val Gly Pro Val Pro Pro Lys Pro Val Pro Gly Lys Ser Thr Pro
                85                  90                  95

Lys Leu Asn Gly Ser Gly Pro Gly Trp Trp Pro Glu Cys Thr Cys Thr
            100                 105                 110

Asn Arg Asp Trp Tyr Glu Gln Ala Ser Pro Ala Pro Leu Leu Val Asn
        115                 120                 125

Pro Glu Ala Leu Glu Pro Ser Leu Ser Val Asn Gly Ser Asp Gly Met
    130                 135                 140

Phe Lys Tyr Glu Glu Ile Val Leu Glu Arg Gly Asn Ser Gly Leu Gly
145                 150                 155                 160

Phe Ser Ile Ala Gly Gly Ile Asp Asn Pro His Val Pro Asp Asp Pro
                165                 170                 175

Gly Ile Phe Ile Thr Lys Ile Ile Pro Gly Gly Ala Ala Ala Met Asp
            180                 185                 190

Gly Arg Leu Gly Val Asn Asp Cys Val Leu Arg Val Asn Glu Val Asp
```

-continued

```
        195                 200                 205

Val Ser Glu Val Val His Ser Arg Ala Val Glu Ala Leu Lys Glu Ala
    210                 215                 220

Gly Pro Val Val Arg Leu Val Val Arg Arg Arg Gln Pro Pro Pro Glu
225                 230                 235                 240

Thr Ile Met Glu Val Asn Leu Leu Lys Gly Pro Lys Gly Leu Gly Phe
                245                 250                 255

Ser Ile Ala Gly Gly Ile Gly Asn Gln His Ile Pro Gly Asp Asn Ser
            260                 265                 270

Ile Tyr Ile Thr Lys Ile Ile Glu Gly Gly Ala Ala Gln Lys Asp Gly
        275                 280                 285

Arg Leu Gln Ile Gly Asp Arg Leu Leu Ala Val Asn Asn Thr Asn Leu
    290                 295                 300

Gln Asp Val Arg His Glu Glu Ala Val Ala Ser Leu Lys Asn Thr Ser
305                 310                 315                 320

Asp Met Val Tyr Leu Lys Val Ala Lys Pro Gly Ser Ile His Leu Asn
                325                 330                 335

Asp Met Tyr Ala Pro Pro Asp Tyr Ala Ser Thr Phe Thr Ala Leu Ala
            340                 345                 350

Asp Asn His Ile Ser His Asn Ser Ser Leu Gly Tyr Leu Gly Ala Val
        355                 360                 365

Glu Ser Lys Val Thr Tyr Pro Ala Pro Pro Gln Val Pro Pro Thr Arg
    370                 375                 380

Tyr Ser Pro Ile Pro Arg His Met Leu Ala Glu Glu Asp Phe Thr Arg
385                 390                 395                 400

Glu Pro Arg Lys Ile Ile Leu His Lys Gly Ser Thr Gly Leu Gly Phe
                405                 410                 415

Asn Ile Val Gly Gly Glu Asp Gly Glu Gly Ile Phe Val Ser Phe Ile
            420                 425                 430

Leu Ala Gly Gly Pro Ala Asp Leu Ser Gly Glu Leu Arg Arg Gly Asp
        435                 440                 445

Arg Ile Leu Ser Val Asn Gly Val Asn Leu Arg Asn Ala Thr His Glu
    450                 455                 460

Gln Ala Ala Ala Ala Leu Lys Arg Ala Gly Gln Ser Val Thr Ile Val
465                 470                 475                 480

Ala Gln Tyr Arg Pro Glu Glu Tyr Ser Arg Phe Glu Ser Lys Ile His
                485                 490                 495

Asp Leu Arg Glu Gln Met Met Asn Ser Ser Met Ser Ser Gly Ser Gly
            500                 505                 510

Ser Leu Arg Thr Ser Glu Lys Arg Ser Leu Tyr Val Arg Ala Leu Phe
        515                 520                 525

Asp Tyr Asp Arg Thr Arg Asp Ser Cys Leu Pro Ser Gln Gly Leu Ser
    530                 535                 540

Phe Ser Tyr Gly Asp Ile Leu His Val Ile Asn Ala Ser Asp Asp Glu
545                 550                 555                 560

Trp Trp Gln Ala Arg Leu Val Thr Pro His Gly Glu Ser Glu Gln Ile
                565                 570                 575

Gly Val Ile Pro Ser Lys Lys Arg Val Glu Lys Lys Glu Arg Ala Arg
            580                 585                 590

Leu Lys Thr Val Lys Phe His Ala Arg Thr Gly Met Ile Glu Ser Asn
        595                 600                 605

Arg Asp Phe Pro Gly Leu Ser Asp Asp Tyr Tyr Gly Ala Lys Asn Leu
    610                 615                 620
```

```
Lys Gly Val Thr Ser Asn Thr Ser Asp Ser Glu Ser Ser Ser Lys Gly
625                 630                 635                 640

Gln Glu Asp Ala Ile Leu Ser Tyr Glu Pro Val Thr Arg Gln Glu Ile
                645                 650                 655

His Tyr Ala Arg Pro Val Ile Ile Leu Gly Pro Met Lys Asp Arg Val
            660                 665                 670

Asn Asp Asp Leu Ile Ser Glu Phe Pro His Lys Phe Gly Ser Cys Val
        675                 680                 685

Pro His Thr Thr Arg Pro Arg Arg Asp Asn Glu Val Asp Gly Gln Asp
    690                 695                 700

Tyr His Phe Val Val Ser Arg Glu Gln Met Glu Lys Asp Ile Gln Asp
705                 710                 715                 720

Asn Lys Phe Ile Glu Ala Gly Gln Phe Asn Asp Asn Leu Tyr Gly Thr
                725                 730                 735

Ser Ile Gln Ser Val Arg Ala Val Ala Glu Arg Gly Lys His Cys Ile
            740                 745                 750

Leu Asp Val Ser Gly Asn Ala Ile Lys Arg Leu Gln Gln Ala Gln Leu
        755                 760                 765

Tyr Pro Ile Ala Ile Phe Ile Lys Pro Lys Ser Ile Glu Ala Leu Met
    770                 775                 780

Glu Met Asn Arg Arg Gln Thr Tyr Glu Gln Ala Asn Lys Ile Phe Asp
785                 790                 795                 800

Lys Ala Met Lys Leu Glu Gln Glu Phe Gly Glu Tyr Phe Thr Ala Ile
                805                 810                 815

Val Gln Gly Asp Ser Leu Glu Glu Ile Tyr Asn Lys Ile Lys Gln Ile
            820                 825                 830

Ile Glu Asp Gln Ser Gly His Tyr Ile Trp Val Pro Ser Pro Glu Lys
        835                 840                 845

Leu


<210> SEQ ID NO 135
<211> LENGTH: 59
<212> TYPE: PRT
<213> ORGANISM: Mus musculus

<400> SEQUENCE: 135

Met Arg Gln Leu Lys Gly Lys Pro Lys Lys Glu Thr Ser Lys Asp Lys
1               5                   10                  15

Lys Glu Arg Lys Gln Ala Met Gln Glu Ala Arg Gln Gln Ile Thr Thr
            20                  25                  30

Val Val Leu Pro Thr Leu Ala Val Val Val Leu Leu Ile Val Val Phe
        35                  40                  45

Val Tyr Val Ala Thr Arg Pro Ala Val Thr Glu
    50                  55


<210> SEQ ID NO 136
<211> LENGTH: 683
<212> TYPE: PRT
<213> ORGANISM: Mus musculus

<400> SEQUENCE: 136

Met Thr Met Gln Pro Ala Ile Gln Val Trp Phe Gly Glu Asp Leu Pro
1               5                   10                  15

Leu Ser Pro Arg Cys Pro Leu Thr Pro Arg His Gly Pro Gly Leu Ala
            20                  25                  30

Asp Val Cys Gln Tyr Asp Glu Trp Ile Ala Val Arg His Glu Ala Thr
        35                  40                  45
```

```
Leu Leu Pro Met Gln Glu Asp Leu Ser Ile Trp Leu Ser Gly Leu Leu
    50                  55                  60

Gly Val Asp Ile Lys Ala Glu Arg Leu Leu Glu Glu Leu Asp Asn Gly
65                  70                  75                  80

Val Leu Leu Cys Gln Leu Ile Asn Val Leu Gln Asn Met Val Lys Gly
                85                  90                  95

Cys His Ser Asp Glu Pro Gly Asn Phe Pro Met Arg Lys Val Pro Cys
            100                 105                 110

Lys Lys Asp Ala Ala Ser Gly Ser Phe Phe Ala Arg Asp Asn Thr Ala
        115                 120                 125

Asn Phe Leu His Trp Cys Arg His Ile Gly Val Asp Glu Thr Tyr Leu
    130                 135                 140

Phe Glu Ser Glu Gly Leu Val Leu His Lys Asp Pro Arg Gln Val Tyr
145                 150                 155                 160

Leu Cys Leu Leu Glu Ile Gly Arg Ile Val Ser Arg Tyr Gly Val Glu
                165                 170                 175

Pro Pro Val Leu Val Lys Leu Glu Lys Glu Ile Glu Leu Glu Glu Thr
            180                 185                 190

Leu Leu Asn Ala Ser Gly Leu Glu Glu Ser Ile Ser Ile Pro Lys Ser
        195                 200                 205

Cys Cys Gln Gln Glu Glu Leu His Glu Ala Val Lys His Ile Ala Glu
    210                 215                 220

Asp Pro Pro Cys Ser Cys Ser His Arg Phe Ser Ile Glu Tyr Leu Ser
225                 230                 235                 240

Glu Gly Arg Tyr Arg Leu Gly Glu Lys Ile Leu Phe Ile Arg Met Leu
                245                 250                 255

His Gly Lys His Val Met Val Arg Val Gly Gly Gly Trp Asp Thr Leu
            260                 265                 270

Gln Gly Phe Leu Leu Lys Tyr Asp Pro Cys Arg Ile Leu Gln Phe Ala
        275                 280                 285

Thr Leu Glu Gln Lys Ile Leu Ala Phe Gln Lys Gly Val Ser Asn Glu
    290                 295                 300

Ser Val Pro Asp Ser Pro Ala Arg Thr Pro Gln Pro Pro Glu Met Asn
305                 310                 315                 320

Pro Leu Ser Ala Val Asn Met Phe Gln Lys Gln Asn Leu Arg Pro Gly
                325                 330                 335

Thr Pro Val Ser Val Pro Lys Asn Lys Glu Lys Gln Val Arg Leu Pro
            340                 345                 350

Gly Ala Arg Leu Pro Ala Ser Ser Val Lys Gly Asn Leu Ala Ser Pro
        355                 360                 365

Ser Thr Arg Ala Lys Arg Pro Asp Ser Pro Ala Ser Phe Pro His Pro
    370                 375                 380

Lys Val Thr Ser Leu Lys Asp Ala Ala Lys Lys Thr Thr Ala Pro Ser
385                 390                 395                 400

Asn Ser Val Ser Gln Ser Leu Ala Ser Pro Asn Pro Gly Ser Lys Pro
                405                 410                 415

Ser Thr Ala Gln Cys Ala Ser Glu Ser Ser Arg Lys Cys Val Thr Phe
            420                 425                 430

Pro Lys Thr Ala Gln Thr Lys Ala Ile Pro Ala Gln Asn Ser Arg Asp
        435                 440                 445

Leu Ser Lys Ser Arg Leu Leu Pro Ser Lys Ser Pro Gly Lys Met Glu
    450                 455                 460

Pro Lys His Leu Lys His Asn His Leu Ser Ser Arg Asp Glu Ser Arg
```

```
465                 470                 475                 480

Ile Asn Leu Ser Ser Lys Ser Pro Lys Leu Pro Lys Gly Ala Met His
                485                 490                 495

Gly Arg Pro Asn Pro Ser Pro Phe Gln Pro Pro Ala Lys Val Thr Lys
            500                 505                 510

Pro Ser Ser Lys Thr Gly Ala Ile Gly Leu Gly Thr Gln Ser Gln Pro
        515                 520                 525

Pro Thr Arg Thr Pro Arg Ser Gly Ala Val Ser Ala Gln Arg Leu Gln
    530                 535                 540

Ser Thr Leu Asn Leu Asn Ser Pro Ala Ser Val Cys Ser Gly Ser Ser
545                 550                 555                 560

Ala Lys Ala Thr Gln Gly Ser Lys Gly Lys Asn Thr Val Ser Val Ala
                565                 570                 575

Lys Lys Gln Pro Gln Ser Lys Gly Val Cys Arg Asn Pro Gly Pro Gly
            580                 585                 590

Ser Ser Lys Ser Pro Gly Arg Thr Pro Leu Ser Ile Val Thr Val Pro
        595                 600                 605

Gln Ser Ala Thr Lys Thr Glu Thr Val Ser Lys Ser Ala Lys Thr Ala
    610                 615                 620

Met Lys Gly Gln Tyr Ser Ala Lys Gly Pro Pro Lys Ser Ser Lys Pro
625                 630                 635                 640

Pro Thr Ser Phe Arg Asp Pro Pro Ser Ser Gly Lys Gly Ala Asp Ser
                645                 650                 655

Gly Asp Lys Met Pro Thr Ala Arg Lys Lys Glu Glu Asp Asp His Tyr
            660                 665                 670

Phe Val Met Thr Gly Asn Lys Lys Leu Arg Lys
        675                 680


<210> SEQ ID NO 137
<211> LENGTH: 115
<212> TYPE: PRT
<213> ORGANISM: Mus musculus

<400> SEQUENCE: 137

Met Gly Lys Arg Asp Asn Arg Val Ala Tyr Met Asn Pro Ile Ala Met
1               5                   10                  15

Ala Arg Ser Arg Gly Pro Ile Gln Ser Ser Gly Pro Thr Ile Gln Asp
            20                  25                  30

Tyr Leu Asn Arg Pro Arg Pro Thr Trp Glu Glu Val Lys Glu Gln Leu
        35                  40                  45

Glu Lys Lys Lys Lys Gly Ser Lys Ala Leu Ala Glu Phe Glu Glu Lys
    50                  55                  60

Met Asn Glu Asn Trp Lys Lys Glu Leu Glu Lys His Arg Glu Lys Leu
65                  70                  75                  80

Leu Ser Gly Asn Glu Ser Ser Ser Lys Lys Arg Gln Lys Lys Lys Lys
                85                  90                  95

Glu Lys Lys Lys Ser Gly Arg Val Ser Lys Ser Phe Leu Phe Ser Lys
            100                 105                 110

Cys Tyr Ser
        115


<210> SEQ ID NO 138
<211> LENGTH: 343
<212> TYPE: PRT
<213> ORGANISM: Mus musculus

<400> SEQUENCE: 138
```

```
Met Glu Val Ser Cys Gly Gln Ala Glu Ser Ser Glu Lys Pro Asn Ala
1               5                   10                  15

Glu Asp Met Thr Ser Lys Asp Tyr Tyr Phe Asp Ser Tyr Ala His Phe
            20                  25                  30

Gly Ile His Glu Glu Met Leu Lys Asp Glu Val Arg Thr Leu Thr Tyr
        35                  40                  45

Arg Asn Ser Met Phe His Asn Arg His Leu Phe Lys Asp Lys Val Val
    50                  55                  60

Leu Asp Val Gly Ser Gly Thr Gly Ile Leu Cys Met Phe Ala Ala Lys
65                  70                  75                  80

Ala Gly Ala Arg Lys Val Ile Gly Ile Glu Cys Ser Ser Ile Ser Asp
                85                  90                  95

Tyr Ala Val Lys Ile Val Lys Ala Asn Lys Leu Asp His Val Val Thr
            100                 105                 110

Ile Ile Lys Gly Lys Val Glu Glu Val Glu Leu Pro Val Glu Lys Val
        115                 120                 125

Asp Ile Ile Ile Ser Glu Trp Met Gly Tyr Cys Leu Phe Tyr Glu Ser
    130                 135                 140

Met Leu Asn Thr Val Leu His Ala Arg Asp Lys Trp Leu Ala Pro Asp
145                 150                 155                 160

Gly Leu Ile Phe Pro Asp Arg Ala Thr Leu Tyr Val Thr Ala Ile Glu
                165                 170                 175

Asp Arg Gln Tyr Lys Asp Tyr Lys Ile His Trp Trp Glu Asn Val Tyr
            180                 185                 190

Gly Phe Asp Met Ser Cys Ile Lys Asp Val Ala Ile Lys Glu Pro Leu
        195                 200                 205

Val Asp Val Val Asp Pro Lys Gln Leu Val Thr Asn Ala Cys Leu Ile
    210                 215                 220

Lys Glu Val Asp Ile Tyr Thr Val Lys Val Glu Asp Leu Thr Phe Thr
225                 230                 235                 240

Ser Pro Phe Cys Leu Gln Val Lys Arg Asn Asp Tyr Val His Ala Leu
                245                 250                 255

Val Ala Tyr Phe Asn Ile Glu Phe Thr Arg Cys His Lys Arg Thr Gly
            260                 265                 270

Phe Ser Thr Ser Pro Glu Ser Pro Tyr Thr His Trp Lys Gln Thr Val
        275                 280                 285

Phe Tyr Met Glu Asp Tyr Leu Thr Val Lys Thr Gly Glu Glu Ile Phe
    290                 295                 300

Gly Thr Ile Gly Met Arg Pro Asn Ala Lys Asn Asn Arg Asp Leu Asp
305                 310                 315                 320

Phe Thr Ile Asp Leu Asp Phe Lys Gly Gln Leu Cys Glu Leu Ser Cys
                325                 330                 335

Ser Thr Asp Tyr Arg Met Arg
            340
```

```
<210> SEQ ID NO 139
<211> LENGTH: 97
<212> TYPE: PRT
<213> ORGANISM: Mus musculus

<400> SEQUENCE: 139

Met Ser Ser Ala Pro Asp Pro Pro Thr Val Lys Lys Glu Pro Leu Lys
1               5                   10                  15

Glu Lys Asn Phe Glu Asn Pro Gly Leu Arg Gly Ala His Thr Thr Thr
            20                  25                  30
```

Leu Phe Arg Ala Val Asn Pro Glu Leu Phe Ile Lys Pro Asn Lys Pro
35 40 45

Val Met Ala Phe Gly Leu Val Thr Leu Ser Leu Cys Val Ala Tyr Ile
50 55 60

Gly Tyr Leu His Ala Thr Gln Glu Asn Arg Lys Asp Leu Tyr Glu Ala
65 70 75 80

Ile Asp Ser Glu Gly His Arg Tyr Met Arg Arg Lys Thr Ser Lys Trp
85 90 95

Asp

<210> SEQ ID NO 140
<211> LENGTH: 393
<212> TYPE: PRT
<213> ORGANISM: Mus musculus

<400> SEQUENCE: 140

Met Gly Ala Ala Ala Trp Ala Pro Pro His Leu Leu Leu Arg Ala Ser
1 5 10 15

Phe Leu Leu Leu Leu Leu Leu Leu Pro Leu Arg Gly Arg Ser Ala Gly
20 25 30

Ser Trp Asp Leu Ala Gly Tyr Leu Leu Tyr Cys Pro Cys Met Gly Arg
35 40 45

Phe Gly Asn Gln Ala Asp His Phe Leu Gly Ser Leu Ala Phe Ala Lys
50 55 60

Leu Leu Asn Arg Thr Leu Ala Val Pro Pro Trp Ile Glu Tyr Gln His
65 70 75 80

His Lys Pro Pro Phe Thr Asn Leu His Val Ser Tyr Gln Lys Tyr Phe
85 90 95

Lys Leu Glu Pro Leu Gln Ala Tyr His Arg Val Val Ser Leu Glu Asp
100 105 110

Phe Met Glu Asn Leu Ala Pro Ser His Trp Pro Pro Glu Lys Arg Val
115 120 125

Ala Tyr Cys Phe Glu Val Ala Ala Gln Arg Ser Pro Asp Lys Lys Thr
130 135 140

Cys Pro Met Lys Glu Gly Asn Pro Phe Gly Pro Phe Trp Asp Gln Phe
145 150 155 160

His Val Ser Phe Asn Lys Ser Glu Leu Phe Thr Gly Ile Ser Phe Ser
165 170 175

Ala Ser Tyr Lys Glu Gln Trp Thr Gln Arg Phe Pro Ala Lys Glu His
180 185 190

Pro Val Leu Ala Leu Pro Gly Ala Pro Ala Gln Phe Pro Val Leu Glu
195 200 205

Glu His Arg Glu Leu Gln Lys Tyr Met Val Trp Ser Asp Glu Met Val
210 215 220

Arg Thr Gly Glu Ala Leu Ile Ser Ala His Leu Val Arg Pro Tyr Val
225 230 235 240

Gly Ile His Leu Arg Ile Gly Ser Asp Trp Lys Asn Ala Cys Ala Met
245 250 255

Leu Lys Asp Gly Thr Ala Gly Ser His Phe Met Ala Ser Pro Gln Cys
260 265 270

Val Gly Tyr Ser Arg Ser Thr Ala Thr Pro Leu Thr Met Thr Met Cys
275 280 285

Leu Pro Asp Leu Lys Glu Ile Gln Arg Ala Val Thr Leu Trp Val Arg
290 295 300

Ala Leu Asn Ala Arg Ser Val Tyr Ile Ala Thr Asp Ser Glu Ser Tyr
305 310 315 320

Val Ser Glu Ile Gln Gln Leu Phe Lys Asp Lys Val Arg Val Val Ser
325 330 335

Leu Lys Pro Glu Val Ala Gln Ile Asp Leu Tyr Ile Leu Gly Gln Ala
340 345 350

Asp His Phe Ile Gly Asn Cys Val Ser Ser Phe Thr Ala Phe Val Lys
355 360 365

Arg Glu Arg Asp Leu His Gly Arg Gln Ser Ser Phe Phe Gly Met Asp
370 375 380

Arg Pro Ser Gln Leu Arg Asp Glu Phe
385 390

<210> SEQ ID NO 141
<211> LENGTH: 1658
<212> TYPE: PRT
<213> ORGANISM: Mus musculus

<400> SEQUENCE: 141

Met Met Ala Gln Phe Pro Thr Ala Met Asn Gly Gly Pro Asn Met Trp
1 5 10 15

Ala Ile Thr Ser Glu Glu Arg Thr Lys His Asp Lys Gln Phe Asp Asn
20 25 30

Leu Lys Pro Ser Gly Gly Tyr Ile Thr Gly Asp Gln Ala Arg Thr Phe
35 40 45

Phe Leu Gln Ser Gly Leu Pro Ala Pro Val Leu Ala Glu Ile Trp Ala
50 55 60

Leu Ser Asp Leu Asn Lys Asp Gly Lys Met Asp Gln Gln Glu Phe Ser
65 70 75 80

Ile Ala Met Lys Leu Ile Lys Leu Lys Leu Gln Gly Gln Gln Leu Pro
85 90 95

Val Val Leu Pro Pro Ile Met Lys Gln Pro Pro Met Phe Ser Pro Leu
100 105 110

Ile Ser Ala Arg Phe Gly Met Gly Ser Met Pro Asn Leu Ser Ile His
115 120 125

Gln Pro Leu Pro Pro Val Ala Pro Ile Ala Thr Pro Leu Ser Ser Ala
130 135 140

Thr Ser Gly Thr Ser Ile Pro Pro Leu Met Met Pro Ala Pro Leu Val
145 150 155 160

Pro Ser Val Ser Thr Ser Ser Leu Pro Asn Gly Thr Ala Ser Leu Ile
165 170 175

Gln Pro Leu Ser Ile Pro Tyr Ser Ser Ser Thr Leu Pro His Ala Ser
180 185 190

Ser Tyr Ser Leu Met Met Gly Gly Phe Gly Gly Ala Ser Ile Gln Lys
195 200 205

Ala Gln Ser Leu Ile Asp Leu Gly Ser Ser Ser Ser Thr Ser Ser Thr
210 215 220

Ala Ser Leu Ser Gly Asn Ser Pro Lys Thr Gly Thr Ser Glu Trp Ala
225 230 235 240

Val Pro Gln Pro Ser Arg Leu Lys Tyr Arg Gln Lys Phe Asn Ser Leu
245 250 255

Asp Lys Gly Met Ser Gly Tyr Leu Ser Gly Phe Gln Ala Arg Asn Ala
260 265 270

Leu Leu Gln Ser Asn Leu Ser Gln Thr Gln Leu Ala Thr Ile Trp Thr
275 280 285

```
Leu Ala Asp Ile Asp Gly Asp Gly Gln Leu Lys Ala Glu Glu Phe Ile
    290                 295                 300

Leu Ala Met His Leu Thr Asp Met Ala Lys Ala Gly Gln Pro Leu Pro
305                 310                 315                 320

Leu Thr Leu Pro Pro Glu Leu Val Pro Pro Ser Phe Arg Gly Gly Lys
                325                 330                 335

Gln Val Asp Ser Val Asn Gly Thr Leu Pro Ser Tyr Gln Lys Thr Gln
            340                 345                 350

Glu Glu Glu Pro Gln Lys Lys Leu Pro Val Thr Phe Glu Asp Lys Arg
        355                 360                 365

Lys Ala Asn Tyr Glu Arg Gly Asn Met Glu Leu Glu Lys Arg Arg Gln
    370                 375                 380

Val Leu Met Glu Gln Gln Gln Arg Glu Ala Glu Arg Lys Ala Gln Lys
385                 390                 395                 400

Glu Lys Glu Glu Trp Glu Arg Lys Gln Arg Glu Leu Gln Glu Gln Glu
                405                 410                 415

Trp Lys Lys Gln Leu Glu Leu Glu Lys Arg Leu Glu Lys Gln Arg Glu
            420                 425                 430

Leu Glu Arg Gln Arg Glu Glu Glu Arg Arg Lys Glu Ile Glu Arg Arg
        435                 440                 445

Glu Ala Ala Lys Gln Glu Leu Glu Arg Gln Arg Arg Leu Glu Trp Glu
    450                 455                 460

Arg Leu Arg Arg Gln Glu Leu Leu Ser Gln Lys Thr Arg Glu Gln Glu
465                 470                 475                 480

Asp Ile Val Arg Leu Ser Ser Arg Lys Lys Ser Leu His Leu Glu Leu
                485                 490                 495

Glu Ala Val Asn Gly Lys His Gln Gln Ile Ser Gly Arg Leu Gln Asp
            500                 505                 510

Val Gln Ile Arg Lys Gln Thr Gln Lys Thr Glu Leu Glu Val Leu Asp
        515                 520                 525

Lys Gln Cys Asp Leu Glu Ile Met Glu Ile Lys Gln Leu Gln Gln Glu
    530                 535                 540

Leu Lys Glu Tyr Gln Asn Lys Leu Ile Tyr Leu Val Pro Glu Lys Gln
545                 550                 555                 560

Leu Leu Asn Glu Arg Ile Lys Asn Met Gln Leu Ser Asn Thr Pro Asp
                565                 570                 575

Ser Gly Ile Ser Leu Leu His Lys Lys Ser Ser Glu Lys Glu Glu Leu
            580                 585                 590

Cys Gln Arg Leu Lys Glu Gln Leu Asp Ala Leu Glu Lys Glu Thr Ala
        595                 600                 605

Ser Lys Leu Ser Glu Met Asp Ser Phe Asn Asn Gln Leu Lys Glu Leu
    610                 615                 620

Arg Glu Ser Tyr Asn Thr Gln Gln Leu Ala Leu Glu Gln Leu His Lys
625                 630                 635                 640

Ile Lys Arg Asp Lys Leu Lys Glu Ile Glu Arg Lys Arg Leu Glu Gln
                645                 650                 655

Ile Gln Lys Lys Lys Leu Glu Asp Glu Ala Ala Arg Lys Ala Lys Gln
            660                 665                 670

Gly Lys Glu Asn Leu Trp Arg Glu Ser Ile Arg Lys Glu Glu Glu Glu
        675                 680                 685

Lys Gln Lys Arg Leu Gln Glu Glu Lys Ser Gln Asp Lys Thr Gln Glu
    690                 695                 700

Glu Glu Arg Lys Ala Glu Ala Lys Gln Ser Glu Thr Ala Ser Ala Leu
705                 710                 715                 720
```

```
Val Asn Tyr Arg Ala Leu Tyr Pro Phe Glu Ala Arg Asn His Asp Glu
                725                 730                 735

Met Ser Phe Ser Ser Gly Asp Ile Ile Gln Val Asp Glu Lys Thr Val
            740                 745                 750

Gly Glu Pro Gly Trp Leu Tyr Gly Ser Phe Gln Gly Lys Phe Gly Trp
        755                 760                 765

Phe Pro Cys Asn Tyr Val Glu Lys Val Leu Ser Ser Glu Lys Ala Leu
    770                 775                 780

Ser Pro Lys Lys Ala Leu Leu Pro Pro Thr Val Ser Leu Ser Ala Thr
785                 790                 795                 800

Ser Thr Ser Ser Gln Pro Pro Ala Ser Val Thr Asp Tyr His Asn Val
                805                 810                 815

Ser Phe Ser Asn Leu Thr Val Asn Thr Thr Trp Gln Gln Lys Ser Ala
            820                 825                 830

Phe Thr Arg Thr Val Ser Pro Gly Ser Val Ser Pro Ile His Gly Gln
        835                 840                 845

Gly Gln Ala Val Glu Asn Leu Lys Ala Gln Ala Leu Cys Ser Trp Thr
    850                 855                 860

Ala Lys Lys Glu Asn His Leu Asn Phe Ser Lys His Asp Val Ile Thr
865                 870                 875                 880

Val Leu Glu Gln Gln Glu Asn Trp Trp Phe Gly Glu Val His Gly Gly
                885                 890                 895

Arg Gly Trp Phe Pro Lys Ser Tyr Val Lys Leu Ile Pro Gly Asn Glu
            900                 905                 910

Val Gln Arg Gly Glu Pro Glu Ala Leu Tyr Ala Ala Val Thr Lys Lys
        915                 920                 925

Pro Thr Ser Thr Ala Tyr Pro Val Thr Ser Thr Ala Tyr Pro Val Gly
    930                 935                 940

Glu Asp Tyr Ile Ala Leu Tyr Ser Tyr Ser Ser Val Glu Pro Gly Asp
945                 950                 955                 960

Leu Thr Phe Thr Glu Gly Glu Glu Ile Leu Val Thr Gln Lys Asp Gly
                965                 970                 975

Glu Trp Trp Thr Gly Ser Ile Gly Glu Arg Thr Gly Ile Phe Pro Ser
            980                 985                 990

Asn Tyr Val Arg Pro Lys Asp Gln  Glu Asn Phe Gly Asn  Ala Ser Lys
        995                 1000                 1005

Ser Gly  Ala Ser Asn Lys Lys  Pro Glu Ile Ala Gln  Val Thr Ser
    1010                 1015                 1020

Ala Tyr  Ala Ala Ser Gly Thr  Glu Gln Leu Ser Leu  Ala Pro Gly
    1025                 1030                 1035

Gln Leu  Ile Leu Ile Leu Lys  Lys Asn Thr Ser Gly  Trp Trp Gln
    1040                 1045                 1050

Gly Glu  Leu Gln Ala Arg Gly  Lys Lys Arg Gln Lys  Gly Trp Phe
    1055                 1060                 1065

Pro Ala  Ser His Val Lys Leu  Leu Gly Pro Ser Ser  Glu Arg Thr
    1070                 1075                 1080

Met Pro  Thr Phe His Ala Val  Cys Gln Val Ile Ala  Met Tyr Asp
    1085                 1090                 1095

Tyr Met  Ala Asn Asn Glu Asp  Glu Leu Asn Phe Ser  Lys Gly Gln
    1100                 1105                 1110

Leu Ile  Asn Val Met Asn Lys  Asp Asp Pro Asp Trp  Trp Gln Gly
    1115                 1120                 1125

Glu Thr  Asn Gly Leu Thr Gly  Leu Phe Pro Ser Asn  Tyr Val Lys
```

```
    1130                1135                1140

Met Thr  Thr Asp Ser Asp Pro  Ser Gln Gln Trp Cys  Ala Asp Leu
    1145                1150                1155

Gln Ala  Leu Asp Thr Met Gln  Pro Thr Glu Arg Lys  Arg Gln Gly
    1160                1165                1170

Tyr Ile  His Glu Leu Ile Gln  Thr Glu Glu Arg Tyr  Met Asp Asp
    1175                1180                1185

Leu Gln  Leu Val Ile Glu Val  Phe Gln Lys Arg Met  Ala Glu Ser
    1190                1195                1200

Gly Phe  Leu Thr Glu Ala Asp  Met Ala Leu Ile Phe  Val Asn Trp
    1205                1210                1215

Lys Glu  Leu Ile Met Ser Asn  Thr Lys Leu Leu Arg  Ala Leu Arg
    1220                1225                1230

Val Arg  Lys Lys Thr Gly Gly  Glu Lys Met Pro Val  Gln Met Ile
    1235                1240                1245

Gly Asp  Ile Leu Ala Ala Glu  Leu Ser His Met Gln  Ala Tyr Ile
    1250                1255                1260

Arg Phe  Cys Ser Cys Gln Leu  Asn Gly Ala Thr Leu  Leu Gln Gln
    1265                1270                1275

Lys Thr  Asp Glu Asp Thr Asp  Phe Lys Glu Phe Leu  Lys Lys Leu
    1280                1285                1290

Ala Ser  Asp Pro Arg Cys Lys  Gly Met Pro Leu Ser  Ser Phe Leu
    1295                1300                1305

Leu Lys  Pro Met Gln Arg Ile  Thr Arg Tyr Pro Leu  Leu Ile Arg
    1310                1315                1320

Ser Ile  Leu Glu Asn Thr Pro  Gln Ser His Val Asp  His Ser Ser
    1325                1330                1335

Leu Lys  Leu Ala Leu Glu Arg  Ala Glu Glu Leu Cys  Ser Gln Val
    1340                1345                1350

Asn Glu  Gly Val Arg Glu Lys  Glu Asn Ser Asp Arg  Leu Glu Trp
    1355                1360                1365

Ile Gln  Ala His Val Gln Cys  Glu Gly Leu Ala Glu  Gln Leu Ile
    1370                1375                1380

Phe Asn  Ser Leu Thr Asn Cys  Leu Gly Pro Arg Lys  Leu Leu His
    1385                1390                1395

Ser Gly  Lys Leu Tyr Lys Thr  Lys Ser Asn Lys Glu  Leu His Ala
    1400                1405                1410

Phe Leu  Phe Asn Asp Phe Leu  Leu Leu Thr Tyr Leu  Val Arg Gln
    1415                1420                1425

Phe Ala  Ala Ala Ser Gly His  Glu Lys Leu Phe Asn  Ser Lys Ser
    1430                1435                1440

Ser Ala  Gln Phe Arg Met Tyr  Lys Thr Pro Ile Phe  Leu Asn Glu
    1445                1450                1455

Val Leu  Val Lys Leu Pro Thr  Asp Pro Ser Ser Asp  Glu Pro Val
    1460                1465                1470

Phe His  Ile Ser His Ile Asp  Arg Val Tyr Thr Leu  Arg Thr Asp
    1475                1480                1485

Asn Ile  Asn Glu Arg Thr Ala  Trp Val Gln Lys Ile  Lys Gly Ala
    1490                1495                1500

Ser Glu  Gln Tyr Ile Asp Thr  Glu Lys Lys Lys Arg  Glu Lys Ala
    1505                1510                1515

Tyr Gln  Ala Arg Ser Gln Lys  Thr Ser Gly Ile Gly  Arg Leu Met
    1520                1525                1530
```

Val His Val Ile Glu Ala Thr Glu Leu Lys Ala Cys Lys Pro Asn
1535 1540 1545

Gly Lys Ser Asn Pro Tyr Cys Glu Val Ser Met Gly Ser Gln Ser
1550 1555 1560

Tyr Thr Thr Arg Thr Leu Gln Asp Thr Leu Asn Pro Lys Trp Asn
1565 1570 1575

Phe Asn Cys Gln Phe Phe Ile Lys Asp Leu Tyr Gln Asp Val Leu
1580 1585 1590

Cys Leu Thr Met Phe Asp Arg Asp Gln Phe Ser Pro Asp Asp Phe
1595 1600 1605

Leu Gly Arg Thr Glu Val Pro Val Ala Lys Ile Arg Thr Glu Gln
1610 1615 1620

Glu Ser Lys Gly Pro Thr Thr Arg Arg Leu Leu Leu His Glu Val
1625 1630 1635

Pro Thr Gly Glu Val Trp Val Arg Phe Asp Leu Gln Leu Phe Glu
1640 1645 1650

Gln Lys Thr Leu Leu
1655

<210> SEQ ID NO 142
<211> LENGTH: 227
<212> TYPE: PRT
<213> ORGANISM: Mus musculus

<400> SEQUENCE: 142

Met Thr Gln Ser Cys Thr Met Ala Ser Thr Lys Pro Leu Ser Arg Phe
1 5 10 15

Trp Glu Trp Gly Lys Asn Ile Val Cys Val Gly Arg Asn Tyr Ala Asp
20 25 30

His Val Lys Glu Met Arg Ser Thr Val Leu Ser Glu Pro Val Leu Phe
35 40 45

Leu Lys Pro Ser Thr Ala Tyr Ala Pro Glu Gly Ser Pro Val Leu Met
50 55 60

Pro Ala Tyr Cys Arg Asn Leu His His Glu Val Glu Leu Gly Val Leu
65 70 75 80

Leu Gly Lys Arg Gly Glu Ala Ile Pro Glu Ala Ala Ala Met Asp Tyr
85 90 95

Val Ala Gly Tyr Ala Leu Cys Leu Asp Met Thr Ala Arg Asp Val Gln
100 105 110

Glu Glu Cys Lys Lys Lys Gly Leu Pro Trp Thr Leu Ala Lys Ser Phe
115 120 125

Thr Ser Ser Cys Pro Val Ser Ala Phe Val Pro Lys Glu Lys Ile Pro
130 135 140

Asp Pro His Ala Leu Arg Leu Trp Leu Lys Val Asn Gly Glu Leu Arg
145 150 155 160

Gln Glu Gly Lys Thr Ser Ser Met Ile Phe Ser Ile Pro Tyr Ile Ile
165 170 175

Ser Tyr Val Ser Lys Ile Ile Thr Leu Glu Glu Gly Asp Leu Ile Leu
180 185 190

Thr Gly Thr Pro Lys Gly Val Gly Pro Val Lys Glu Asn Asp Glu Ile
195 200 205

Glu Ala Gly Ile Asp Gly Val Val Ser Met Arg Phe Lys Val Lys Arg
210 215 220

Ser Glu Tyr
225

<210> SEQ ID NO 143
<211> LENGTH: 207
<212> TYPE: PRT
<213> ORGANISM: Mus musculus
<220> FEATURE:
<221> NAME/KEY: misc_feature
<222> LOCATION: (40)..(40)
<223> OTHER INFORMATION: Xaa can be any naturally occurring amino acid

<400> SEQUENCE: 143

```
Met Gly Lys Cys Ser Gly Arg Cys Thr Leu Val Ala Phe Cys Cys Leu
1               5                   10                  15

Gln Leu Val Ala Ala Leu Gln Arg Gln Ile Phe Asp Phe Leu Gly Tyr
            20                  25                  30

Gln Trp Ala Pro Ile Leu Ala Xaa Phe Leu His Ile Met Ala Val Ile
        35                  40                  45

Leu Gly Ile Phe Gly Thr Val Gln Tyr Arg Ser Arg Tyr Leu Ile Leu
    50                  55                  60

Tyr Ala Ala Trp Leu Val Leu Trp Val Gly Trp Asn Ala Phe Ile Ile
65                  70                  75                  80

Cys Phe Tyr Leu Glu Val Gly Gln Leu Ser Gln Asp Arg Asp Phe Ile
                85                  90                  95

Met Thr Phe Asn Thr Ser Leu His Arg Ser Trp Trp Met Glu Asn Gly
            100                 105                 110

Pro Gly Cys Leu Val Thr Pro Val Leu Asn Ser Arg Leu Ala Leu Glu
        115                 120                 125

Asp His His Val Ile Ser Val Thr Gly Cys Leu Leu Asp Tyr Pro Tyr
    130                 135                 140

Ile Glu Ala Leu Ser Ser Ala Leu Gln Ile Phe Leu Ala Leu Phe Gly
145                 150                 155                 160

Phe Val Phe Ala Cys Tyr Val Ser Lys Val Phe Leu Glu Glu Glu Asp
                165                 170                 175

Ser Phe Asp Phe Ile Gly Gly Phe Asp Ser Tyr Gly Tyr Gln Ala Pro
            180                 185                 190

Gln Lys Thr Ser His Leu Gln Leu Gln Pro Leu Tyr Thr Ser Gly
        195                 200                 205
```

<210> SEQ ID NO 144
<211> LENGTH: 741
<212> TYPE: PRT
<213> ORGANISM: Mus musculus

<400> SEQUENCE: 144

```
Met Leu Ser Leu Lys Lys Tyr Leu Thr Glu Gly Leu Leu Gln Phe Thr
1               5                   10                  15

Ile Leu Leu Ser Leu Ile Gly Val Arg Val Asp Val Asp Thr Tyr Leu
            20                  25                  30

Thr Ser Gln Leu Pro Pro Leu Arg Glu Ile Ile Leu Gly Pro Ser Ser
        35                  40                  45

Ala Tyr Thr Gln Thr Gln Phe His Asn Leu Arg Asn Thr Leu Asp Gly
    50                  55                  60

Tyr Gly Ile His Pro Lys Ser Ile Asp Leu Asp Asn Tyr Phe Thr Ala
65                  70                  75                  80

Arg Arg Leu Leu Ser Gln Val Arg Ala Leu Asp Arg Phe Gln Val Pro
                85                  90                  95

Thr Thr Glu Val Asn Ala Trp Leu Val His Arg Asp Pro Glu Gly Ser
            100                 105                 110
```

-continued

```
Val Ser Gly Ser Gln Pro Asn Ser Gly Leu Ala Leu Glu Ser Ser Ser
        115                 120                 125

Gly Leu Gln Asp Val Thr Gly Pro Asp Asn Gly Val Arg Glu Ser Glu
    130                 135                 140

Thr Glu Gln Gly Phe Gly Glu Asp Leu Glu Asp Leu Gly Ala Val Ala
145                 150                 155                 160

Pro Pro Val Ser Gly Asp Leu Thr Lys Glu Asp Ile Asp Leu Ile Asp
                165                 170                 175

Ile Leu Trp Arg Gln Asp Ile Asp Leu Gly Ala Gly Arg Glu Val Phe
            180                 185                 190

Asp Tyr Ser His Arg Gln Lys Glu Gln Asp Val Asp Lys Glu Leu Gln
        195                 200                 205

Asp Gly Arg Glu Arg Glu Asp Thr Trp Ser Gly Glu Gly Ala Glu Ala
    210                 215                 220

Leu Ala Arg Asp Leu Leu Val Asp Gly Glu Thr Gly Glu Ser Phe Pro
225                 230                 235                 240

Ala Gln Phe Pro Ala Asp Val Ser Ser Ile Pro Glu Ala Val Pro Ser
                245                 250                 255

Glu Ser Glu Ser Pro Ala Leu Gln Asn Ser Leu Leu Ser Pro Leu Leu
            260                 265                 270

Thr Gly Thr Glu Ser Pro Phe Asp Leu Glu Gln Gln Trp Gln Asp Leu
        275                 280                 285

Met Ser Ile Met Glu Met Gln Ala Met Glu Val Asn Thr Ser Ala Ser
    290                 295                 300

Glu Ile Leu Tyr Asn Ala Pro Pro Gly Asp Pro Leu Ser Thr Asn Tyr
305                 310                 315                 320

Ser Leu Ala Pro Asn Thr Pro Ile Asn Gln Asn Val Ser Leu His Gln
                325                 330                 335

Ala Ser Leu Gly Gly Cys Ser Gln Asp Phe Ser Leu Phe Ser Pro Glu
            340                 345                 350

Val Glu Ser Leu Pro Val Ala Ser Ser Ser Thr Leu Leu Pro Leu Val
        355                 360                 365

Pro Ser Asn Ser Thr Ser Leu Asn Ser Thr Phe Gly Ser Thr Asn Leu
    370                 375                 380

Ala Gly Leu Phe Phe Pro Ser Gln Leu Asn Gly Thr Ala Asn Asp Thr
385                 390                 395                 400

Ser Gly Pro Glu Leu Pro Asp Pro Leu Gly Gly Leu Leu Asp Glu Ala
                405                 410                 415

Met Leu Asp Glu Ile Ser Leu Met Asp Leu Ala Ile Glu Glu Gly Phe
            420                 425                 430

Asn Pro Val Gln Ala Ser Gln Leu Glu Glu Glu Phe Asp Ser Asp Ser
        435                 440                 445

Gly Leu Ser Leu Asp Ser Ser His Ser Pro Ser Ser Leu Ser Ser Ser
    450                 455                 460

Glu Gly Ser Ser Ser Ser Ser Ser Ser Ser Ser Ser Ser Ser Ala Ser
465                 470                 475                 480

Ser Ser Ala Ser Ser Ser Phe Ser Glu Glu Gly Ala Val Gly Tyr Ser
                485                 490                 495

Ser Asp Ser Glu Thr Leu Asp Leu Glu Glu Ala Glu Gly Ala Val Gly
            500                 505                 510

Tyr Gln Pro Glu Tyr Ser Lys Phe Cys Arg Met Ser Tyr Gln Asp Pro
        515                 520                 525

Ser Gln Leu Ser Cys Leu Pro Tyr Leu Glu His Val Gly His Asn His
    530                 535                 540
```

```
Thr Tyr Asn Met Ala Pro Ser Ala Leu Asp Ser Ala Asp Leu Pro Pro
545                 550                 555                 560

Pro Ser Thr Leu Lys Lys Gly Ser Lys Glu Lys Gln Ala Asp Phe Leu
                565                 570                 575

Asp Lys Gln Met Ser Arg Asp Glu His Arg Ala Arg Ala Met Lys Ile
            580                 585                 590

Pro Phe Thr Asn Asp Lys Ile Ile Asn Leu Pro Val Glu Glu Phe Asn
        595                 600                 605

Glu Leu Leu Ser Lys Tyr Gln Leu Ser Glu Ala Gln Leu Ser Leu Ile
    610                 615                 620

Arg Asp Ile Arg Arg Arg Gly Lys Asn Lys Met Ala Ala Gln Asn Cys
625                 630                 635                 640

Arg Lys Arg Lys Leu Asp Thr Ile Leu Asn Leu Glu Arg Asp Val Glu
                645                 650                 655

Asp Leu Gln Arg Asp Lys Ala Arg Leu Leu Arg Glu Lys Val Glu Phe
            660                 665                 670

Leu Arg Ser Leu Arg Gln Met Lys Gln Lys Val Gln Ser Leu Tyr Gln
        675                 680                 685

Glu Val Phe Gly Arg Leu Arg Asp Glu His Gly Arg Pro Tyr Ser Pro
    690                 695                 700

Ser Gln Tyr Ala Leu Gln Tyr Ala Gly Asp Gly Ser Val Leu Leu Ile
705                 710                 715                 720

Pro Arg Thr Met Ala Asp Gln Gln Ala Arg Arg Gln Glu Arg Lys Pro
                725                 730                 735

Lys Asp Arg Arg Lys
            740


<210> SEQ ID NO 145
<211> LENGTH: 399
<212> TYPE: PRT
<213> ORGANISM: Mus musculus

<400> SEQUENCE: 145

Met Ala Asp Thr Gly Leu Arg Arg Val Val Pro Ser Asp Leu Tyr Pro
1               5                   10                  15

Leu Val Leu Arg Phe Leu Arg Asp Ser Gln Leu Ser Glu Val Ala Ser
            20                  25                  30

Lys Phe Ala Lys Ala Thr Gly Ala Thr Gln Gln Asp Ala Asn Ala Ser
        35                  40                  45

Ser Leu Leu Asp Ile Tyr Ser Phe Trp Leu Lys Ser Thr Lys Ala Pro
    50                  55                  60

Lys Val Lys Leu Gln Ser Asn Gly Pro Val Thr Lys Lys Ala Lys Lys
65                  70                  75                  80

Glu Thr Ser Ser Ser Asp Ser Ser Glu Asp Ser Ser Glu Asp Glu Asp
                85                  90                  95

Lys Lys Ala Gln Gly Leu Pro Thr Gln Lys Ala Ala Ala Gln Val Lys
            100                 105                 110

Arg Ala Ser Val Pro Gln His Ala Gly Lys Ala Ala Ala Lys Ala Ser
        115                 120                 125

Glu Ser Ser Ser Ser Glu Glu Ser Ser Glu Glu Glu Glu Asp Lys
    130                 135                 140

Lys Lys Lys Pro Val Gln Lys Ala Ala Lys Pro Gln Ala Lys Ala Val
145                 150                 155                 160

Arg Pro Pro Ala Lys Lys Ala Glu Ser Ser Glu Ser Asp Ser Asp Ser
                165                 170                 175
```

```
Asp Ser Asp Ser Ser Ser Glu Glu Glu Thr Pro Gln Thr Gln Lys Pro
            180                 185                 190

Lys Ala Ala Val Ala Ala Lys Ala Gln Thr Lys Ala Glu Ala Lys Pro
        195                 200                 205

Gly Thr Pro Ala Lys Ala Gln Pro Lys Val Ala Asn Gly Lys Ala Ala
    210                 215                 220

Ala Ser Ser Ser Ser Ser Ser Ser Ser Ser Ser Ser Asp Asp Ser Glu
225                 230                 235                 240

Glu Glu Lys Lys Ala Ala Ala Pro Pro Lys Lys Thr Val Pro Lys Lys
                245                 250                 255

Gln Val Val Ala Lys Ala Pro Val Lys Val Ala Ala Ala Pro Thr Gln
            260                 265                 270

Lys Ser Ser Ser Ser Glu Asp Ser Ser Ser Glu Glu Glu Glu Gly Gln
        275                 280                 285

Arg Gln Pro Met Lys Lys Lys Ala Gly Pro Tyr Ser Ser Val Pro Pro
    290                 295                 300

Pro Ser Val Pro Leu Pro Lys Lys Ser Pro Gly Thr Gln Ala Pro Lys
305                 310                 315                 320

Lys Ala Ala Ala Gln Thr Gln Pro Ala Asp Ser Ser Asp Asp Ser Ser
                325                 330                 335

Asp Asp Ser Asp Ser Ser Ser Glu Glu Glu Lys Lys Pro Pro Ala Lys
            340                 345                 350

Thr Val Val Ser Lys Thr Pro Ala Lys Ala Ala Pro Val Lys Lys Lys
        355                 360                 365

Ala Glu Ser Ser Ser Asp Ser Ser Gly Asn Ala Ala Gln Ser Ser Gly
    370                 375                 380

Leu Leu Gly Tyr Ser Leu Pro Trp Ala Ala Leu Thr Gly Leu Pro
385                 390                 395


<210> SEQ ID NO 146
<211> LENGTH: 180
<212> TYPE: PRT
<213> ORGANISM: Mus musculus

<400> SEQUENCE: 146

Met Asn Thr Val Leu Ser Arg Ala Asn Ser Leu Phe Ala Phe Ser Leu
1               5                   10                  15

Ser Val Met Ala Ala Leu Thr Phe Gly Cys Phe Ile Thr Thr Ala Phe
            20                  25                  30

Lys Asp Arg Ser Val Pro Val Arg Leu His Val Ser Arg Ile Met Leu
        35                  40                  45

Lys Asn Val Glu Asp Phe Thr Gly Pro Arg Glu Arg Ser Asp Leu Gly
    50                  55                  60

Phe Ile Thr Phe Asp Ile Thr Ala Asp Leu Glu Asn Ile Phe Asp Trp
65                  70                  75                  80

Asn Val Lys Gln Leu Phe Leu Tyr Leu Ser Ala Glu Tyr Ser Thr Lys
                85                  90                  95

Asn Asn Ala Leu Asn Gln Val Val Leu Trp Asp Lys Ile Val Leu Arg
            100                 105                 110

Gly Asp Asn Pro Lys Leu Leu Leu Lys Asp Met Lys Thr Lys Tyr Phe
        115                 120                 125

Phe Phe Asp Asp Gly Asn Gly Leu Lys Gly Asn Arg Asn Val Thr Leu
    130                 135                 140

Thr Leu Ser Trp Asn Val Val Pro Asn Ala Gly Ile Leu Pro Leu Val
145                 150                 155                 160
```

```
Thr Gly Ser Gly His Val Ser Val Pro Phe Pro Asp Thr Tyr Glu Ile
                165                 170                 175

Thr Lys Ser Tyr
            180


<210> SEQ ID NO 147
<211> LENGTH: 451
<212> TYPE: PRT
<213> ORGANISM: Mus musculus

<400> SEQUENCE: 147

Met Gly Leu Glu Pro Ser Trp Tyr Leu Leu Leu Cys Leu Ala Val Ser
1               5                   10                  15

Gly Ala Ala Gly Thr Asp Pro Pro Thr Ala Pro Thr Thr Ala Glu Arg
            20                  25                  30

Gln Arg Gln Pro Thr Asp Ile Ile Leu Asp Cys Phe Leu Val Thr Glu
        35                  40                  45

Asp Arg His Arg Gly Ala Phe Ala Ser Ser Gly Asp Arg Glu Arg Ala
    50                  55                  60

Leu Leu Val Leu Lys Gln Val Pro Val Leu Asp Asp Gly Ser Leu Glu
65                  70                  75                  80

Gly Ile Thr Asp Phe Gln Gly Ser Thr Glu Thr Lys Gln Asp Ser Pro
                85                  90                  95

Val Ile Phe Glu Ala Ser Leu Asp Leu Val Gln Ile Pro Gln Ala Glu
            100                 105                 110

Ala Leu Leu His Ala Asp Cys Ser Gly Lys Ala Val Thr Cys Glu Ile
        115                 120                 125

Ser Lys Tyr Phe Leu Gln Ala Arg Gln Glu Ala Thr Phe Glu Lys Ala
    130                 135                 140

His Trp Phe Ile Ser Asn Met Gln Val Ser Arg Gly Gly Pro Ser Val
145                 150                 155                 160

Ser Met Val Met Lys Thr Leu Arg Asp Ala Glu Val Gly Ala Val Arg
                165                 170                 175

His Pro Thr Leu Asn Leu Pro Leu Ser Ala Gln Gly Thr Val Lys Thr
            180                 185                 190

Gln Val Glu Phe Gln Val Thr Ser Glu Thr Gln Thr Leu Asn His Leu
        195                 200                 205

Leu Gly Ser Ser Val Ser Leu His Cys Ser Phe Ser Met Ala Pro Asp
    210                 215                 220

Leu Asp Leu Thr Gly Val Glu Trp Arg Leu Gln His Lys Gly Ser Gly
225                 230                 235                 240

Gln Leu Val Tyr Ser Trp Lys Thr Gly Gln Gly Gln Ala Lys Arg Lys
                245                 250                 255

Gly Ala Thr Leu Glu Pro Glu Glu Leu Leu Arg Ala Gly Asn Ala Ser
            260                 265                 270

Leu Thr Leu Pro Asn Leu Thr Leu Lys Asp Glu Gly Thr Tyr Ile Cys
        275                 280                 285

Gln Ile Ser Thr Ser Leu Tyr Gln Ala Gln Gln Ile Met Pro Leu Asn
    290                 295                 300

Ile Leu Ala Pro Pro Lys Val Gln Leu His Leu Ala Asn Lys Asp Pro
305                 310                 315                 320

Leu Pro Ser Leu Val Cys Ser Ile Ala Gly Tyr Tyr Pro Leu Asp Val
                325                 330                 335

Gly Val Thr Trp Ile Arg Glu Glu Leu Gly Gly Ile Pro Ala Gln Val
            340                 345                 350
```

```
Ser Gly Ala Ser Phe Ser Ser Leu Arg Gln Ser Thr Met Gly Thr Tyr
        355                 360                 365

Ser Ile Ser Ser Thr Val Met Ala Asp Pro Gly Pro Thr Gly Ala Thr
    370                 375                 380

Tyr Thr Cys Gln Val Ala His Val Ser Leu Glu Glu Pro Leu Thr Thr
385                 390                 395                 400

Ser Met Arg Val Leu Pro Asn Pro Glu Gln Arg Gly Thr Leu Gly Val
                405                 410                 415

Ile Phe Ala Ser Ile Ile Phe Leu Ser Ala Leu Leu Leu Phe Leu Gly
            420                 425                 430

Leu His Arg Gln Gln Ala Ser Ser Ser Arg Ser Thr Arg Pro Met Arg
        435                 440                 445

His Ser Gly
    450


<210> SEQ ID NO 148
<211> LENGTH: 414
<212> TYPE: PRT
<213> ORGANISM: Mus musculus

<400> SEQUENCE: 148

Met Arg Leu Trp Thr Leu Gly Thr Ser Ile Phe Leu Arg Leu Trp Gly
1               5                   10                  15

Thr Tyr Val Phe Pro Arg Ser Pro Ser Trp Leu Asp Phe Ile Gln His
            20                  25                  30

Leu Gly Val Cys Cys Phe Val Ala Phe Leu Ser Val Ser Leu Phe Ser
        35                  40                  45

Ala Ala Phe Tyr Trp Ile Leu Pro Pro Val Ala Leu Leu Ser Ser Val
    50                  55                  60

Trp Met Ile Thr Cys Val Phe Leu Cys Cys Ser Lys Arg Ala Arg Cys
65                  70                  75                  80

Phe Ile Leu Leu Ala Val Leu Ser Cys Gly Leu Arg Glu Gly Arg Asn
                85                  90                  95

Ala Leu Ile Ala Ala Gly Thr Gly Val Val Ile Phe Gly His Val Glu
            100                 105                 110

Asn Ile Phe Tyr Asn Phe Arg Gly Leu Leu Asp Ser Met Thr Cys Asn
        115                 120                 125

Leu Arg Ala Lys Ser Phe Ser Val His Phe Pro Leu Leu Lys Arg Tyr
    130                 135                 140

Thr Glu Ala Ile Gln Trp Ile Tyr Gly Leu Ala Thr Pro Leu Asn Leu
145                 150                 155                 160

Phe Asp Asp Leu Val Ser Trp Asn Gln Thr Leu Val Val Ser Leu Phe
                165                 170                 175

Ser Pro Ser His Ala Leu Glu Ala His Met Asn Asp Thr Arg Gly Glu
            180                 185                 190

Val Leu Gly Val Leu His His Met Val Val Thr Thr Glu Leu Leu Thr
        195                 200                 205

Ser Val Gly Gln Lys Leu Leu Ala Leu Ala Gly Leu Leu Leu Ile Leu
    210                 215                 220

Val Ser Thr Gly Leu Phe Leu Lys Arg Phe Leu Gly Pro Cys Gly Trp
225                 230                 235                 240

Lys Tyr Glu Asn Val Tyr Ile Thr Lys Gln Phe Val Arg Phe Asp Glu
                245                 250                 255

Lys Glu Arg His Gln Gln Arg Pro Cys Val Leu Pro Leu Asn Lys Lys
            260                 265                 270
```

```
Glu Arg Lys Lys Tyr Val Ile Val Pro Ser Leu Gln Leu Thr Pro Lys
        275                 280                 285

Glu Lys Lys Thr Leu Gly Leu Phe Phe Leu Pro Val Leu Thr Tyr Leu
    290                 295                 300

Tyr Met Trp Val Leu Phe Ala Ala Val Asp Tyr Leu Leu Tyr Arg Leu
305                 310                 315                 320

Ile Ser Ser Met Asn Lys Gln Phe Gln Ser Leu Pro Gly Leu Glu Val
                325                 330                 335

His Leu Lys Leu Arg Gly Glu Leu Lys Ile Leu Val Ser Val Ser Phe
            340                 345                 350

Tyr Pro Lys Val Glu Arg Glu Arg Ile Glu Tyr Leu His Ala Lys Leu
        355                 360                 365

Leu Glu Lys Arg Ser Lys Gln Pro Leu Arg Glu Ala Asp Gly Lys Pro
    370                 375                 380

Ser Leu Tyr Phe Lys Lys Ile His Phe Trp Phe Pro Val Leu Lys Met
385                 390                 395                 400

Ile Arg Lys Lys Gln Thr Ile Pro Ala Asn Glu Asp Asp Leu
                405                 410


<210> SEQ ID NO 149
<211> LENGTH: 412
<212> TYPE: PRT
<213> ORGANISM: Mus musculus

<400> SEQUENCE: 149

Met Glu Pro Trp Cys Gly Ala Glu Val Arg Gly Gln Gly Pro Gln Gly
1               5                   10                  15

Pro Arg Val Pro Gly Ala Ser Arg Ser Arg Ser Arg Ala Leu Leu Leu
            20                  25                  30

Leu Leu Leu Leu Leu Leu Leu Leu Leu Pro Arg Arg Pro Ala Gly Glu
        35                  40                  45

Arg Ile Arg Pro Arg Arg Pro Pro Arg His Ala His Pro Arg Pro Pro
    50                  55                  60

Leu Thr Arg Trp Arg Pro Ser Thr Gly Tyr Leu Ala Ala Gly Ala Ser
65                  70                  75                  80

Pro Gly Thr Leu Ser Thr Thr Val Pro Thr Gly Pro Gly Val Ser Cys
                85                  90                  95

Gly Ser Arg Gly Thr Cys Pro Ser Gly Arg Leu Arg Leu Pro Arg Gln
            100                 105                 110

Ala Gln Thr Asn Gln Thr Thr Thr Ala Pro Pro Asn Ser Gln Thr Met
        115                 120                 125

Ala Pro Leu Lys Thr Val Gly Thr Leu Gly Met Met Asp Thr Thr Gly
    130                 135                 140

Ser Val Leu Lys Thr Val His Ser Ser Asn Leu Pro Phe Cys Gly Ser
145                 150                 155                 160

Ser His Glu Pro Asp Pro Thr Leu Arg Asp Pro Glu Ala Met Thr Arg
                165                 170                 175

Arg Trp Pro Trp Met Val Ser Val Gln Ala Asn Gly Ser His Val Cys
            180                 185                 190

Ala Gly Ile Leu Ile Ala Ser Gln Trp Val Leu Thr Val Ala His Cys
        195                 200                 205

Leu Ser Gln Asn His Val Asn Tyr Ile Val Arg Ala Gly Ser Pro Trp
    210                 215                 220

Ile Asn Gln Thr Ala Gly Thr Ser Ser Asp Val Pro Val His Arg Val
225                 230                 235                 240
```

```
Ile Ile Asn His Gly Tyr Gln Pro Arg Arg Tyr Trp Ser Trp Val Gly
                245                 250                 255

Arg Ala His Asp Ile Gly Leu Leu Lys Leu Lys Trp Gly Leu Lys Tyr
            260                 265                 270

Ser Lys Tyr Val Trp Pro Ile Cys Leu Pro Gly Leu Asp Tyr Met Val
        275                 280                 285

Glu Asp Ser Ser Leu Cys Thr Val Thr Gly Trp Gly Tyr Pro Arg Ala
    290                 295                 300

Asn Gly Asp Asn Trp Arg Ala Pro Gly Leu Leu Phe Arg Trp His Met
305                 310                 315                 320

Val Pro Gly Gly Asn Asp Glu Leu Gly Pro Arg Leu Gln Glu Glu Arg
                325                 330                 335

Gly Pro Thr His Leu Ser Ala Gly Leu Leu Leu Gln Ala Leu Asp Leu
            340                 345                 350

Gly Pro Ala Gln Trp Gly Ala Pro Gly Pro Ser Ser Pro Ile Gln Asp
        355                 360                 365

Leu Ala Pro Gly Phe Pro Ser Ala Pro His Pro Ser Gly His Thr Val
    370                 375                 380

Thr Leu Pro Cys Leu Ser Phe Leu Pro Phe Leu Leu Ser Ala Ala Val
385                 390                 395                 400

Gly Val Ala Leu Ser Leu Pro Glu Ala Gly Arg Ser
                405                 410


<210> SEQ ID NO 150
<211> LENGTH: 350
<212> TYPE: PRT
<213> ORGANISM: Homo sapiens

<400> SEQUENCE: 150

Met Leu Glu Gly Ala Glu Leu Tyr Phe Asn Val Asp His Gly Tyr Leu
1               5                   10                  15

Glu Gly Leu Val Arg Gly Cys Lys Ala Ser Leu Leu Thr Gln Gln Asp
            20                  25                  30

Tyr Ile Asn Leu Val Gln Cys Glu Thr Leu Glu Asp Leu Lys Ile His
        35                  40                  45

Leu Gln Thr Thr Asp Tyr Gly Asn Phe Leu Ala Asn His Thr Asn Pro
    50                  55                  60

Leu Thr Val Ser Lys Ile Asp Thr Glu Met Arg Lys Arg Leu Cys Gly
65                  70                  75                  80

Glu Phe Glu Tyr Phe Arg Asn His Ser Leu Glu Pro Leu Ser Thr Phe
                85                  90                  95

Leu Thr Tyr Met Thr Cys Ser Tyr Met Ile Asp Asn Val Ile Leu Leu
            100                 105                 110

Met Asn Gly Ala Leu Gln Lys Lys Ser Val Lys Glu Ile Leu Gly Lys
        115                 120                 125

Cys His Pro Leu Gly Arg Phe Thr Glu Met Glu Ala Val Asn Ile Ala
    130                 135                 140

Glu Thr Pro Ser Asp Leu Phe Asn Ala Ile Leu Ile Glu Thr Pro Leu
145                 150                 155                 160

Ala Pro Phe Phe Gln Asp Cys Met Ser Glu Asn Ala Leu Asp Glu Leu
                165                 170                 175

Asn Ile Glu Leu Leu Arg Asn Lys Leu Tyr Lys Ser Tyr Leu Glu Ala
            180                 185                 190

Phe Tyr Lys Phe Cys Lys Asn His Gly Asp Val Thr Ala Glu Val Met
        195                 200                 205
```

Cys Pro Ile Leu Glu Phe Glu Ala Asp Arg Arg Ala Phe Ile Ile Thr
    210                 215                 220

Leu Asn Ser Phe Gly Thr Glu Leu Ser Lys Glu Asp Arg Glu Thr Leu
225                 230                 235                 240

Tyr Pro Thr Phe Gly Lys Leu Tyr Pro Glu Gly Leu Arg Leu Leu Ala
                245                 250                 255

Gln Ala Glu Asp Phe Asp Gln Met Lys Asn Val Ala Asp His Tyr Gly
            260                 265                 270

Val Tyr Lys Pro Leu Phe Glu Ala Val Gly Gly Ser Gly Gly Lys Thr
        275                 280                 285

Leu Glu Asp Val Phe Tyr Glu Arg Glu Val Gln Met Asn Val Leu Ala
    290                 295                 300

Phe Asn Arg Gln Phe His Tyr Gly Val Phe Tyr Ala Tyr Val Lys Leu
305                 310                 315                 320

Lys Glu Gln Glu Ile Arg Asn Ile Val Trp Ile Ala Glu Cys Ile Ser
                325                 330                 335

Gln Arg His Arg Thr Lys Ile Asn Ser Tyr Ile Pro Ile Leu
            340                 345                 350

<210> SEQ ID NO 151
<211> LENGTH: 312
<212> TYPE: PRT
<213> ORGANISM: Mus musculus

<400> SEQUENCE: 151

Met Leu Glu Gly Ala Glu Leu Tyr Phe Asn Val Asp His Gly Tyr Leu
1               5                   10                  15

Glu Gly Leu Val Arg Gly Cys Lys Ala Ser Leu Leu Thr Gln Gln Asp
            20                  25                  30

Tyr Ile Asn Leu Val Gln Cys Glu Thr Leu Glu Asp Leu Lys Ile His
        35                  40                  45

Leu Gln Thr Thr Asp Tyr Gly Asn Phe Leu Ala Asn His Thr Asn Pro
    50                  55                  60

Leu Thr Val Ser Lys Ile Asp Thr Glu Met Arg Lys Arg Leu Cys Gly
65                  70                  75                  80

Glu Phe Glu Tyr Phe Arg Asn His Ser Leu Glu Pro Leu Ser Thr Phe
                85                  90                  95

Leu Thr Tyr Met Thr Cys Ser Tyr Met Ile Gly Asn Val Ile Leu Leu
            100                 105                 110

Met Asn Gly Ala Leu Gln Lys Lys Ser Val Lys Glu Ile Leu Gly Lys
        115                 120                 125

Cys His Pro Leu Gly Arg Phe Thr Glu Met Glu Ala Val Asn Ile Ala
    130                 135                 140

Glu Thr Pro Ser Asp Leu Phe Asn Ala Ile Leu Ile Glu Thr Pro Leu
145                 150                 155                 160

Ala Pro Phe Phe Gln Asp Cys Met Ser Glu Asn Ala Leu Asp Glu Leu
                165                 170                 175

Asn Ile Glu Leu Leu Arg Asn Lys Leu Tyr Lys Ser Tyr Leu Glu Ala
            180                 185                 190

Phe Tyr Lys Phe Cys Lys Asn His Gly Asp Val Thr Ala Glu Val Met
        195                 200                 205

Cys Pro Ile Leu Glu Phe Glu Ala Asp Arg Arg Ala Phe Ile Ile Thr
    210                 215                 220

Leu Asn Ser Phe Gly Thr Glu Leu Ser Lys Glu Asp Arg Glu Thr Leu
225                 230                 235                 240

```
Tyr Pro Thr Phe Gly Lys Leu Tyr Pro Glu Gly Leu Arg Leu Leu Ala
                245                 250                 255

Gln Ala Glu Asp Phe Asp Gln Met Lys Asn Val Ala Asp His Tyr Gly
            260                 265                 270

Val Tyr Lys Pro Leu Phe Glu Ala Val Gly Gly Ser Gly Gly Lys Thr
        275                 280                 285

Leu Glu Asp Val Phe Tyr Glu Arg Glu Val Gln Met Asn Val Leu Ala
    290                 295                 300

Phe Asn Arg Gln Phe His Tyr Gly
305                 310


<210> SEQ ID NO 152
<211> LENGTH: 208
<212> TYPE: PRT
<213> ORGANISM: Mus musculus

<400> SEQUENCE: 152

Met Met Val His Thr Arg Glu Ser Ser Thr Gln Gln Phe Lys Ser Leu
1               5                   10                  15

Phe Val Arg Ala Val Arg Ala Tyr Asn Gly Glu Asn Trp Arg Thr Ser
            20                  25                  30

Ile Ser Asp Met Glu Leu Ala Leu Pro Asp Phe Leu Lys Ala Phe Tyr
        35                  40                  45

Glu Cys Leu Ala Ala Cys Glu Gly Ser Arg Glu Ile Lys Asp Phe Lys
    50                  55                  60

Asp Phe Tyr Leu Ser Ile Ala Asp His Tyr Val Glu Val Leu Glu Cys
65                  70                  75                  80

Lys Ile Arg Cys Glu Glu Thr Leu Thr Pro Val Ile Gly Gly Tyr Pro
                85                  90                  95

Val Glu Lys Phe Val Ala Thr Met Tyr His Tyr Leu Gln Phe Ala Tyr
            100                 105                 110

Tyr Lys Leu Asn Asp Leu Lys Asn Ala Ala Pro Cys Ala Val Ser Tyr
        115                 120                 125

Leu Leu Phe Asp Gln Ser Asp Arg Val Met Gln Gln Asn Leu Val Tyr
    130                 135                 140

Tyr Gln Tyr His Arg Asp Lys Trp Gly Leu Ser Asp Glu His Phe Gln
145                 150                 155                 160

Pro Arg Pro Glu Ala Val Gln Phe Phe Asn Val Thr Thr Leu Gln Lys
                165                 170                 175

Glu Leu Tyr Asp Phe Ala Gln Glu His Leu Met Asp Asp Asp Glu Gly
            180                 185                 190

Glu Val Val Glu Tyr Val Asp Asp Leu Leu Glu Thr Glu Glu Ser Ala
        195                 200                 205


<210> SEQ ID NO 153
<211> LENGTH: 385
<212> TYPE: PRT
<213> ORGANISM: Homo sapiens

<400> SEQUENCE: 153

Met Gly Arg Trp Cys Gln Thr Val Ala Arg Gly Gln Arg Pro Arg Thr
1               5                   10                  15

Ser Ala Pro Ser Arg Ala Gly Ala Leu Leu Leu Leu Leu Leu Leu Leu
            20                  25                  30

Arg Ser Ala Gly Cys Trp Gly Ala Gly Glu Ala Pro Gly Ala Leu Ser
        35                  40                  45
```

Thr Ala Asp Pro Ala Asp Gln Ser Val Gln Cys Val Pro Lys Ala Thr
50 55 60

Cys Pro Ser Ser Arg Pro Arg Leu Leu Trp Gln Thr Pro Thr Thr Gln
65 70 75 80

Thr Leu Pro Ser Thr Thr Met Glu Thr Gln Phe Pro Val Ser Glu Gly
85 90 95

Lys Val Asp Pro Tyr Arg Ser Cys Gly Phe Ser Tyr Glu Gln Asp Pro
100 105 110

Thr Leu Arg Asp Pro Glu Ala Val Ala Arg Arg Trp Pro Trp Met Val
115 120 125

Ser Val Arg Ala Asn Gly Thr His Ile Cys Ala Gly Thr Ile Ile Ala
130 135 140

Ser Gln Trp Val Leu Thr Val Ala His Cys Leu Ile Trp Arg Asp Val
145 150 155 160

Ile Tyr Ser Val Arg Val Gly Ser Pro Trp Ile Asp Gln Met Thr Gln
165 170 175

Thr Ala Ser Asp Val Pro Val Leu Gln Val Ile Met His Ser Arg Tyr
180 185 190

Arg Ala Gln Arg Phe Trp Ser Trp Val Gly Gln Ala Asn Asp Ile Gly
195 200 205

Leu Leu Lys Leu Lys Gln Glu Leu Lys Tyr Ser Asn Tyr Val Arg Pro
210 215 220

Ile Cys Leu Pro Gly Thr Asp Tyr Val Leu Lys Asp His Ser Arg Cys
225 230 235 240

Thr Val Thr Gly Trp Gly Leu Ser Lys Ala Asp Gly Met Trp Pro Gln
245 250 255

Phe Arg Thr Ile Gln Glu Lys Glu Val Ile Ile Leu Asn Asn Lys Glu
260 265 270

Cys Asp Asn Phe Tyr His Asn Phe Thr Lys Ile Pro Thr Leu Val Gln
275 280 285

Ile Ile Lys Ser Gln Met Met Cys Ala Glu Asp Thr His Arg Glu Lys
290 295 300

Phe Cys Tyr Glu Leu Thr Gly Glu Pro Leu Val Cys Ser Met Glu Gly
305 310 315 320

Thr Trp Tyr Leu Val Gly Leu Val Ser Trp Gly Ala Gly Cys Gln Lys
325 330 335

Ser Glu Ala Pro Pro Ile Tyr Leu Gln Val Ser Ser Tyr Gln His Trp
340 345 350

Ile Trp Asp Cys Leu Asn Gly Gln Ala Leu Ala Leu Pro Ala Pro Ser
355 360 365

Arg Thr Leu Leu Leu Ala Leu Pro Leu Pro Leu Ser Leu Leu Ala Ala
370 375 380

Leu
385

<210> SEQ ID NO 154
<211> LENGTH: 350
<212> TYPE: PRT
<213> ORGANISM: Homo sapiens

<400> SEQUENCE: 154

Met Leu Glu Gly Ala Glu Leu Tyr Phe Asn Val Asp His Gly Tyr Leu
1 5 10 15

Glu Gly Leu Val Arg Gly Cys Lys Ala Ser Leu Leu Thr Gln Gln Asp
20 25 30

```
Tyr Ile Asn Leu Val Gln Cys Glu Thr Leu Glu Asp Leu Lys Ile His
        35                  40                  45

Leu Gln Thr Thr Asp Tyr Gly Asn Phe Leu Ala Asn His Thr Asn Pro
    50                  55                  60

Leu Thr Val Ser Lys Ile Asp Thr Glu Met Arg Lys Arg Leu Cys Gly
65                  70                  75                  80

Glu Phe Glu Tyr Phe Arg Asn His Ser Leu Glu Pro Leu Ser Thr Phe
                85                  90                  95

Leu Thr Tyr Met Thr Cys Ser Tyr Met Ile Asp Asn Val Ile Leu Leu
            100                 105                 110

Met Asn Gly Ala Leu Gln Lys Lys Ser Val Lys Glu Ile Leu Gly Lys
        115                 120                 125

Cys His Pro Leu Gly Arg Phe Thr Glu Met Glu Ala Val Asn Ile Ala
    130                 135                 140

Glu Thr Pro Ser Asp Leu Phe Asn Ala Ile Leu Ile Glu Thr Pro Leu
145                 150                 155                 160

Ala Pro Phe Phe Gln Asp Cys Met Ser Glu Asn Ala Leu Asp Glu Leu
                165                 170                 175

Asn Ile Glu Leu Leu Arg Asn Lys Leu Tyr Lys Ser Tyr Leu Glu Ala
            180                 185                 190

Phe Tyr Lys Phe Cys Lys Asn His Gly Asp Val Thr Ala Glu Val Met
        195                 200                 205

Cys Pro Ile Leu Glu Phe Glu Ala Asp Arg Arg Ala Phe Ile Ile Thr
    210                 215                 220

Leu Asn Ser Phe Gly Thr Glu Leu Ser Lys Glu Asp Arg Glu Thr Leu
225                 230                 235                 240

Tyr Pro Thr Phe Gly Lys Leu Tyr Pro Glu Gly Leu Arg Leu Leu Ala
                245                 250                 255

Gln Ala Glu Asp Phe Asp Gln Met Lys Asn Val Ala Asp His Tyr Gly
            260                 265                 270

Val Tyr Lys Pro Leu Phe Glu Ala Val Gly Gly Ser Gly Gly Lys Thr
        275                 280                 285

Leu Glu Asp Val Phe Tyr Glu Arg Glu Val Gln Met Asn Val Leu Ala
    290                 295                 300

Phe Asn Arg Gln Phe His Tyr Gly Val Phe Tyr Ala Tyr Val Lys Leu
305                 310                 315                 320

Lys Glu Gln Glu Ile Arg Asn Ile Val Trp Ile Ala Glu Cys Ile Ser
                325                 330                 335

Gln Arg His Arg Thr Lys Ile Asn Ser Tyr Ile Pro Ile Leu
            340                 345                 350


<210> SEQ ID NO 155
<211> LENGTH: 312
<212> TYPE: PRT
<213> ORGANISM: Homo sapiens

<400> SEQUENCE: 155

Met Leu Glu Gly Ala Glu Leu Tyr Phe Asn Val Asp His Gly Tyr Leu
1               5                   10                  15

Glu Gly Leu Val Arg Gly Cys Lys Ala Ser Leu Leu Thr Gln Gln Asp
            20                  25                  30

Tyr Ile Asn Leu Val Gln Cys Glu Thr Leu Glu Asp Leu Lys Ile His
        35                  40                  45

Leu Gln Thr Thr Asp Tyr Gly Asn Phe Leu Ala Asn His Thr Asn Pro
    50                  55                  60
```

-continued

```
Leu Thr Val Ser Lys Ile Asp Thr Glu Met Arg Lys Arg Leu Cys Gly
65                  70                  75                  80

Glu Phe Glu Tyr Phe Arg Asn His Ser Leu Glu Pro Leu Ser Thr Phe
                85                  90                  95

Leu Thr Tyr Met Thr Cys Ser Tyr Met Ile Gly Asn Val Ile Leu Leu
            100                 105                 110

Met Asn Gly Ala Leu Gln Lys Lys Ser Val Lys Glu Ile Leu Gly Lys
        115                 120                 125

Cys His Pro Leu Gly Arg Phe Thr Glu Met Glu Ala Val Asn Ile Ala
    130                 135                 140

Glu Thr Pro Ser Asp Leu Phe Asn Ala Ile Leu Ile Glu Thr Pro Leu
145                 150                 155                 160

Ala Pro Phe Phe Gln Asp Cys Met Ser Glu Asn Ala Leu Asp Glu Leu
                165                 170                 175

Asn Ile Glu Leu Leu Arg Asn Lys Leu Tyr Lys Ser Tyr Leu Glu Ala
            180                 185                 190

Phe Tyr Lys Phe Cys Lys Asn His Gly Asp Val Thr Ala Glu Val Met
        195                 200                 205

Cys Pro Ile Leu Glu Phe Glu Ala Asp Arg Arg Ala Phe Ile Ile Thr
    210                 215                 220

Leu Asn Ser Phe Gly Thr Glu Leu Ser Lys Glu Asp Arg Glu Thr Leu
225                 230                 235                 240

Tyr Pro Thr Phe Gly Lys Leu Tyr Pro Glu Gly Leu Arg Leu Leu Ala
                245                 250                 255

Gln Ala Glu Asp Phe Asp Gln Met Lys Asn Val Ala Asp His Tyr Gly
            260                 265                 270

Val Tyr Lys Pro Leu Phe Glu Ala Val Gly Gly Ser Gly Gly Lys Thr
        275                 280                 285

Leu Glu Asp Val Phe Tyr Glu Arg Glu Val Gln Met Asn Val Leu Ala
    290                 295                 300

Phe Asn Arg Gln Phe His Tyr Gly
305                 310
```

METHOD FOR INHIBITING BONE RESORPTION

This patent application is a divisional of U.S. Ser. No. 13/082,107 filed Apr. 7, 2011 which is a divisional of U.S. Ser. No. 11/792,932 with a 371(c) date of Feb. 25, 2008, now U.S. Pat. No. 7,947,436, which is a national stage filing under 35 U.S.C. §371 of International Application No. PCT/CA2005/001917 filed on Dec. 13, 2005 which claimed priority to U.S. provisional application No. 60/634,981 filed on Dec. 13, 2004. The entire contents of each of these priority applications are incorporated herein by reference.

In accordance with 37 CFR 1.52(e)(5), a Sequence Listing in the form of a text file (entitled "SequenceListing.txt", created on May 23, 2012, and 479 kilobytes in size) is incorporated herein by reference in its entirety.

FIELD OF THE INVENTION

This invention relates, in part, to unique and newly identified genetic polynucleotides involved in the process of bone remodeling; variants and derivatives of the polynucleotides and corresponding polypeptides; uses of the polynucleotides, polypeptides, variants and derivatives; methods and compositions for the amelioration of symptoms caused by bone remodeling disorders, including but not limited to osteoporosis, osteopenia, osteomalacia, hyperparathyroidism, hypothyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes.

In particular, this invention relates to polynucleotide expression profiles of active osteoclasts, the isolation and identification of polynucleotides, polypeptides, variants and derivatives involved in osteoclast activity, validation of the identified polynucleotides for their potential as therapeutic targets and use of the polynucleotides, polypeptides, variants and derivatives for the amelioration of disease states and research purposes, as well as in diagnosis of disease states or in the predisposition to develop same.

BACKGROUND OF THE INVENTION

Bone is a dynamic connective tissue comprised of functionally distinct cell populations required to support the structural, mechanical and biochemical integrity of bone and the human body's mineral homeostasis. The principal cell types involved include, osteoblasts responsible for bone formation and maintaining bone mass, and osteoclasts responsible for bone resorption. Osteoblasts and osteoclasts function in a dynamic process termed bone remodeling. The development and proliferation of these cells from their progenitors is governed by networks of growth factors and cytokines produced in the bone microenvironment as well as by systemic hormones. Bone remodeling is ongoing throughout the lifetime of the individual and is necessary for the maintenance of healthy bone tissue and mineral homeostasis. The process remains largely in equilibrium and is governed by a complex interplay of systemic hormones, peptides and downstream signalling pathway proteins, local transcription factors, cytokines, growth factors and matrix remodeling genes.

Any interference or imbalance arising in the bone remodeling process can produce skeletal disease, with the most common skeletal disorders characterized by a net decrease in bone mass. A primary cause of this reduction in bone mass is an increase in osteoclast number and/or activity. The most common such disease, and perhaps the most well known, is osteoporosis occurring particularly in women after the onset of menopause. In fact osteoporosis is the most significant underlying cause of skeletal fractures in late middle-aged and elderly women. While estrogen deficiency has been strongly implicated as a factor in postmenopausal osteoporosis, there is longstanding evidence that remodeling is a locally controlled process being that it takes place in discrete packets throughout the skeleton as first described by Frost over forty years ago (Frost H. M. 1964).

Since bone remodeling takes place in discrete packets, locally produced hormones and enzymes may be more important than systemic hormones for the initiation of bone resorption and the normal remodeling process. Such local control is mediated by osteoblasts and osteoclasts in the microenvironment in which they operate. For example, osteoclasts attach to the bone matrix and form a separate compartment between themselves and the bone surface delimited by a sealing zone formed by a ring of actin surrounding the ruffled border. Multiple small vesicles transport enzymes toward the bone matrix and internalize partially digested bone matrix. The microenvironment within the sealing zone is rich with the presence of lysosomal enzymes and is highly acidic compared to the normal physiological pH of the body. The ruffled border membrane also expresses RANK, the receptor for RANKL, and macrophage-colony stimulating factor (M-CSF) receptor, both of which are responsible for osteoclast differentiation, as well as the calcitonin receptor capable of rapidly inactivating the osteoclast (Baron, R. 2003).

In a complex pattern of inhibition and stimulation not yet fully understood, growth hormone, insulin-like growth factor-1, the sex steroids, thyroid hormone, calciotrophic hormones such as PTH and prostaglandin E2, various cytokines, such as interleukin-1 beta, interleukin-6, and tumour necrosis factor-alpha, and 1,25-dihydroxyvitamin D (calcitriol) act co-ordinately in the bone remodeling process (Jilka et al. 1992; Poli et al. 1994; Srivastava et al. 1998; de Vemejoul 1996).

Thus, it stands to reason that the unique local environments created by these specialized cells is due to the expression of either unique genetic sequences not expressed in other tissues and/or splice variants of polynucleotides and polypeptides expressed in other tissues. The isolation and identification of polynucleotides, polypeptides and their variants and derivatives specific to osteoclast activity will permit a clearer understanding of the remodeling process and offer tissue specific therapeutic targets for the treatment of disease states related to bone remodeling.

Many diseases linked to bone remodeling are poorly understood, generally untreatable or treatable only to a limited extent. For example, osteoarthritis is difficult to treat as there is no cure and treatment focuses on relieving pain and preventing the affected joint from becoming deformed. Non-steroidal anti-inflammatory drugs (NSAIDs) are generally used to relieve pain.

Another example is osteoporosis where the only current medications approved by the FDA for use in the United States are the anti-resorptive agents that prevent bone breakdown. Estrogen replacement therapy is one example of an anti-resorptive agent. Others include alendronate (Fosamax—a biphosphonate anti-resorptive), risedronate (Actonel—a bisphosphonate anti-resorptive), raloxifene (Evista—selective estrogen receptor modulator (SERM)), calcitonin (Calcimar—a hormone), and parathyroid hormone/teriparatide (Forteo—a synthetic version of the human hormone, parathyroid hormone, which helps to regulate calcium metabolism).

Bisphosphonates such as alendronate and risedronate bind permanently to the surface of bone and interfere with osteoclast activity. This allows the osteoblasts to outpace the rate of resorption. The most common side effects are nausea, abdominal pain and loose bowel movements. However, alendronate is reported to also cause irritation and inflammation of the esophagus, and in some cases, ulcers of the esophagus. Risedronate is chemically different from alendronate and has less likelihood of causing esophagus irritation. However, certain foods, calcium, iron supplements, vitamins and minerals, or antacids containing calcium, magnesium, or aluminium can reduce the absorption of risedronate, thereby resulting in loss of effectiveness.

The most common side effect of Raloxifen and other SERMS (such as Tamoxifen) are hot flashes. However, Raloxifene and other hormone replacement therapies have been shown to increase the risk of blood clots, including deep vein thrombosis and pulmonary embolism, cardiovascular disease and cancer.

Calcitonin is not as effective in increasing bone density and strengthening bone as estrogen and the other anti-resorptive agents. Common side effects of either injected or nasal spray calcitonin are nausea and flushing. Patients can develop nasal irritations, a runny nose, or nosebleeds. Injectable calcitonin can cause local skin redness at the site of injection, skin rash, and flushing.

A situation demonstrative of the link between several disorders or disease states involving bone remodeling is that of the use of etidronate (Didronel) first approved by the FDA to treat Paget's disease. Paget's disease is a bone disease characterized by a disorderly and accelerated remodeling of the bone, leading to bone weakness and pain. Didronel has been used 'off-label' and in some studies shown to increase bone density in postmenopausal women with established osteoporosis. It has also been found effective in preventing bone loss in patients requiring long-term steroid medications (such as Prednisone or Cortisone). However, high dose or continuous use of Didronel can cause another bone disease called osteomalacia. Like osteoporosis, osteomalacia can lead to weak bones with increased risk of fractures. Because of osteomalacia concerns and lack of enough studies yet regarding reduction in the rate of bone fractures, the United States FDA has not approved Didronel for the treatment of osteoporosis.

Osteoporosis therapy has been largely focused on antiresorptive drugs that reduce the rate of bone loss but emerging therapies show promise in increasing bone mineral density instead of merely maintaining it or slowing its deterioration. The osteoporosis early stage pipeline consists largely of drug candidates in new therapeutic classes, in particular cathepsin K inhibitors, osteoprotegerin and calcilytics as well as novel bisphosphonates. Some of these are examples where novel drugs exploiting genomics programs are being developed based on a deeper understanding of bone biology and have the potential to change the face of treatment of bone disorders in the long term.

The present invention satisfies a need in the art. There thus remains a need to better understand the bone remodeling process and to provide new compositions that are useful for the diagnosis, prognosis, treatment, prevention and evaluation of therapies for bone remodeling and associated disorders. A method for analysing polynucleotide expression patterns has been developed and applied to identify polynucleotides, polypeptides, variants and derivatives specifically involved in bone remodeling.

The present invention seeks to meet these and other needs.

The present description refers to a number of documents, the content of which is herein incorporated by reference in their entirety.

SUMMARY OF THE INVENTION

The present invention relates to polynucleotides comprising sequences involved in the process of bone remodeling including their open reading frame, substantially identical sequences, substantially complementary sequences and fragments thereof.

The present invention relates to polypeptide comprising sequences involved in the process of bone remodeling including biologically active analogs and biologically active fragments thereof.

The present invention also relates to compositions that are useful for the diagnosis, prognosis, treatment, prevention and/or evaluation of therapies for bone remodeling and associated disorders.

In addition, the present invention relates to a method for analyzing polynucleotide expression patterns, and applied to identify polynucleotides, polypeptides, variants and derivatives specifically involved in bone remodeling.

Furthermore, the present invention relates to polynucleotide and polypeptide sequences, variants and derivatives thereof which have been validated as potential therapeutic targets.

The identification of gene products involved in regulating osteoclast differentiation and function has led to the discovery of novel targets for the development of new and specific therapies of disease states characterized by abnormal bone remodeling.

The present invention relates to polynucleotide expression profiles of osteoclasts, the isolation and identification of polynucleotides, their corresponding polypeptides, variants and derivatives involved in osteoclast activity, validation of these identified elements for their potential as therapeutic targets and use of said polynucleotides, polypeptides, variants and derivatives for the amelioration of disease states.

It is an object of the present invention to provide polynucleotides and related polypeptides that have been isolated and identified. More specifically, the invention provides polynucleotides comprising any one of SEQ. ID. NOs:1 to 57 or 83 to 89, their coding sequence (open reading frame) and related polypeptides comprising any one of SEQ ID NO.: 93 to 155 which have been shown to be upregulated in a highly specific fashion in osteoclasts.

The present invention more particularly relates to polynucleotides, their coding sequence (open reading frame), and related polypeptides, which have been demonstrably shown to be necessary or crucial for osteoclast differentiation (e.g. SEQ. ID. NOs:1 to 7, 88 and 89).

Of the polynucleotides (e.g. SEQ. ID. NOs:8 to 56) whose gene expression is upregulated, 37 were tested in the model using siRNA for biological validation leaving 12 still to be tested, 28 does not appear to phenotypically perturb osteoclast differentiation in the model used whereas 9 did (SEQ ID NO.:16, SEQ ID NO.:19, SEQ ID NO.:21, SEQ ID NO.:24, SEQ ID NO.:29, SEQ ID NO.:31, SEQ ID NO.:37 and SEQ ID NO.:42). However, a more discrete effect not phenotypically measurable cannot be ruled out for those 28. Without being limited to a particular model, this may be due in part to non-functional siRNA and/or to their roles in the downstream bone remodeling activities of osteoclasts. For example, polynucleotides for cathepsin K (CTSK) and matrix metalloproteinase 9 (MMP-9) are well known markers which are essential for osteoclast activities in bone remodelling but are not required for osteoclast differentiation. NSEQ refers generally to polynucleotide sequences of the present invention and includes for example, SEQ. ID. NOs:1 to 56 and 83 to 89, whereas PSEQ refers generally to polypeptide sequences of the present invention and includes, for example, SEQ ID NO.:93 to 99 and 101 to 155. Of course it will be understood that NSEQ also encompasses polynucleotide sequences which are designed or derived from SEQ. ID. NOs:1 to 57 and 83 to 89 and more particularly from their coding sequence. Non-limiting examples of such sequences are disclosed herein (e.g. SEQ ID Nos 64-82 and 90).

The present invention also provides a method of using a polynucleotide selected from SEQ ID NO's 1 to 57 and 83 to 89 and more particularly their coding sequence and encoded polypeptides thereof to screen a library of molecules or compounds (e.g. DNA molecules, RNA molecules, PNAs, mimetics and proteins) to identify or purify a ligand which specifically binds the polynucleotide by combining a polynucleotide with a library of molecules or compounds under conditions to allow specific binding, and detecting specific binding, thereby identifying or purifying a ligand which specifically binds the polynucleotide.

The present invention relates in one aspect thereof to an isolated polynucleotide sequence having at least from about 80% to about 100% (e.g., 80%, 90%, 95%, etc.) nucleic acid sequence identity to a polynucleotide sequence selected from the group consisting of polynucleotides comprising (a) any one of a SEQ. ID. NOs:1 to 57 and 83 to 89; (b) an open reading frame of (a); (c) a full complement of (a) or (b), and; (d) a fragment of any one of (a) to (c).

Complements of the isolated polynucleotide sequence encompassed by the present invention may be those, for example, which hybridize under high stringency conditions to any of the nucleotide sequences in (a), or (b). The high stringency conditions may comprise, for example, a hybridization reaction at 65° C. in 5×SSC, 5× Denhardt's solution, 1% SDS, and 100 μg/ml denatured salmon sperm DNA.

In accordance with the present invention, the polynucleotide sequence may be used, for example, in the treatment of diseases or disorders involving bone remodelling.

Fragments of polynucleotides may be used, for example, as probes for determining the presence of the isolated polynucleotide (or its complement or fragments thereof) in a sample, cell, tissue, etc. for experimental purposes or for the purpose of diagnostic of a diseases or disorders involving bone remodelling.

The present invention also relates to a combination comprising a plurality of polynucleotides (substantially purified and/or isolated) that may be co-expressed with one or more genes known to be involved in bone remodelling, the plurality of polynucleotides may be selected, for example, from the group consisting of a polynucleotide comprising (a) any one of SEQ. ID. NOs:1 to 57, 83 to 89; (b) an open reading frame (a); (c) a full complement of (a) or (b); (d) a sequence that hybridizes under high stringency conditions to any one of the nucleotide sequences in (a), or (b) and; (e) fragments of (a), (b), (c) or (d).

The present invention further relates to a polynucleotide encoding any one of the polypeptides described herein. In accordance with the present invention, the polynucleotide (RNA, DNA, etc.) may encode a polypeptide which may be selected from the group consisting of any one of SEQ ID NO.:93 to 155, analogs or fragments thereof (e.g., biologically active fragments, immunologically active fragments, etc.).

The present invention also relates to an isolated nucleic acid molecule comprising the polynucleotides of the present invention, operatively linked to a nucleotide sequence encoding a heterologous polypeptide thereby encoding a fusion polypeptide.

The invention further relates to a polypeptide encoded by a polynucleotide of SEQ. ID. NOs:1 to 56 or 83 to 89 and more particularly from the open reading frame of any one of SEQ. ID. NOs:1 to 56 or 83 to 89, or a portion thereof, comprising the product of a gene that is co-expressed with one or more genes known to be involved in bone remodeling.

The invention additionally relates to the use of the polypeptide or a portion thereof to screen a library of molecules or compounds (DNA molecules, RNA molecules, PNAs, mimetics, proteins, agonists, antagonists, and antibodies) to identify or purify at least one ligand which specifically binds the polypeptide by combining the polypeptide or a portion thereof with the library of molecules or compounds under conditions to allow specific binding, and detecting specific binding between the polypeptide and ligand, thereby identifying or purifying a ligand which specifically binds the polypeptide.

Isolated naturally occurring allelic variant are also encompassed by the present invention as well as synthetic variants (e.g., made by recombinant DNA technology or by chemical synthesis, etc.) such as biologically active variant which may comprise one or more conservative amino acid substitutions (compared to a naturally occurring polypeptide).

The present invention, further provides a vector (mammalian, bacterial, viral, etc.) comprising the polynucleotides described herein or fragments thereof, such as an expression vector. The vector may further comprise a nucleic acid sequence which may help in the regulation of expression of the polynucleotide and/or a nucleotide sequence encoding a tag (e.g., affinity tag; HA, GST, His etc.).

In accordance with the present invention, an expression vector may comprise, for example, the following operatively linked elements:

a) a transcription promoter;

b) a polynucleotide segment (which may comprise an open reading frame); and c) a transcription terminator.

The invention also relates to an expression vector comprising a polynucleotide described herein, a host cell transformed with the expression vector and a method for producing a polypeptide of the present invention.

More particularly, the present invention therefore provides a cell which may be genetically engineered to contain and/or to express the polynucleotide (including complements and fragments) and/or polypeptides of the present invention. The cell may be, for example, a mammalian cell, an insect cell, a bacteria cell, etc.

The present invention, therefore provides a host cell which may comprise a vector as described herein. The cell may be, for example, mammalian cell, an insect cell, a bacteria, etc. The cell may be able to express or expresses a polypeptide encoded by the polynucleotide described herein.

Methods of producing the polypeptides of the present invention encompassed herewith includes for example, culturing the cell in conditions allowing the expression of the polypeptide. The polypeptide may be recovered, for example, from cell lysate or from the cell supernatant.

The present invention also relates to a method of using a polynucleotide sequence described herein to screen a library of molecules or compounds including but not limited to, DNA molecules, RNA molecules, PNAs (peptide nucleic acids), peptides, ribozymes, antibodies, agonists, antagonists, immunoglobulins, inhibitors, proteins including transcription factors, enhancers, repressors, and drugs and the like which regulate the activity of the selected polynucleotide sequence in a biological system, to identify or purify a ligand which may specifically bind the polynucleotide by combining a polynucleotide with a library of molecules or compounds under conditions which may allow specific binding, and detecting specific binding, thereby identifying or purifying a ligand which may specifically bind the polynucleotide.

The antagonist, agonist, ligand thus identified may be used in the treatment of bone remodelling diseases or disorders.

The invention relates to the use of at least one polynucleotide comprising any one of SEQ. ID. NOs:1 to 57 and/or 83 to 89, their coding sequence, substantially identical sequences, substantially complementary sequences and fragments thereof on an array and for the use of that array in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample indicates the presence of a bone remodeling disease or disorder. Of course, the use of a polynucleotide of the present invention in a diagnosis method is not dependent exclusively by way of an assay. The sequence or sequences may be used in conventionally used diagnosis methods known in the art.

The present invention also relates to a method of ameliorating bone remodelling disease or disorder symptoms, or for inhibiting or delaying bone disease or disorder, the method may comprise: contacting a compound capable of specifically inhibiting activity or expression of a polynucleotide sequence described herein or a polypeptide described herein, in osteoclasts so that symptoms of the bone remodelling disease or disorder may be ameliorated, or the disease or disorder may be prevented, delayed or lowered.

The present invention further relates to a method for ameliorating bone remodelling disease or disorder symptoms, or for inhibiting or delaying bone disease or disorder, the method may comprise: contacting a compound capable of specifically promoting activity or expression of a polynucleotide sequence described herein or a polypeptide described herein, in osteoclasts so that symptoms of the bone remodelling disease or disorder may be ameliorated, or the disease or disorder may be prevented, delayed or lowered.

The present invention also relates to a method of treating a condition in a mammal characterized by a deficiency in, or need for, bone growth or replacement and/or an undesirable level of bone resorption, which method may comprise administering to a mammalian subject in need of such treatment an effective amount of a suitable compound described herein.

The present invention further relates to a method of using a polynucleotide sequence described herein, a polypeptide described herein on an array and for the use of the array in a method for diagnosing a bone remodelling disease or disorder by hybridizing the array with a patient sample under conditions to allow complex formation, detecting complex formation, and comparing the amount of complex formation in the patient sample to that of standards for normal and diseased tissues wherein the complex formation in the patient sample may indicate the presence of a bone remodelling disease or disorder.

In accordance with the present invention the isolated polynucleotide sequence described herein, the antagonist described herein, the ligand described herein, or the method described herein, may be used for diseases or disorders which may be selected from the group consisting of, but not limited to, osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes.

In accordance with the present invention, the method of administration may be selected from, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In accordance with the present invention, the polynucleotide sequence described herein may be used for somatic cell gene therapy or for stem cell gene therapy.

The invention also relates to a pharmaceutical composition comprising a polynucleotide described herein, a polypeptide encoded by the selected polynucleotide, a portion thereof, a ligand (agonist or antagonist) identified or purified using a selected polynucleotide or a polypeptide encoded by the selected polynucleotide, or a portion thereof, which modulates the activity (activation, enhancement or inhibition) of the selected polynucleotide or a polypeptide encoded thereby, a portion thereof, and a suitable pharmaceutical carrier.

Additionally, the invention relates to products, compositions, processes and methods that comprises a polynucleotide described herein, a polypeptide encoded by the polynucleotides, a portion thereof, their variants or derivatives, for research, biological, clinical and therapeutic purposes.

The NSEQs and PSEQs may be used in diagnosis, prognosis, treatment, prevention, and selection and evaluation of therapies for diseases and disorders involving bone remodeling including, but not limited to, osteoporosis, osteopenia, osteomalacia, hyperparathyroidism, hyperthyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes.

Use of NSEQ as a Screening Tool

The polynucleotides obtained by the present invention may be used to detect and isolate expression products, for example, mRNA, complementary DNAs (cDNAs) and proteins derived from or homologous to the NSEQs. In one embodiment, the expression of mRNAs homologous to the NSEQs of the present invention may be detected, for example, by hybridization analysis, reverse transcription and in vitro nucleic acid amplification methods. Such procedures permit detection of mRNAs in a variety of tissue types or at different stages of development. The subject nucleic acids which are expressed in a tissue-specific or a developmentalstage-specific manner are useful as tissue-specific markers or for defining the developmental stage of a sample of cells or tissues that may define a particular disease state. One of skill in the art may readily adapt the NSEQs for these purposes.

Those skilled in the art will also recognize that the NSEQs, and its expression products such as cDNA nucleic acids and genomic DNA may be used to prepare short oligonucleotides sequences. For example, oligonucleotides having ten to twelve nucleotides or more may be prepared which hybridize specifically to the present NSEQs and cDNAs and allow detection, identification and isolation of unique nucleic sequences by hybridization. Sequences of for example, at least 15-20 nucleotides may be used and selected from regions that lack homology to other known sequences. Sequences of 20 or more nucleotides that lack such homology show an increased specificity toward the target sequence. Useful hybridization conditions for probes and primers are readily determinable by those of skill in the art. Stringent hybridization conditions encompassed herewith are those that may allow hybridization of nucleic acids that are greater than 90% homologous but which may prevent hybridization of nucleic acids that are less than 70% homologous. The specificity of a probe may be determined by whether it is made from a unique region, a regulatory region, or from a conserved motif. Both probe specificity and the stringency of diagnostic hybridization or amplification (maximal, high, intermediate, or low) reactions may be determined whether the probe identifies exactly complementary sequences, allelic variants, or related sequences. Probes designed to detect related sequences may have at least 50% sequence identity to any of the selected polynucleotides.

It is to be understood herein that the NSEQs (substantially identical sequences and fragments thereof) may hybridize to a substantially complementary sequence found in a test sample. Additionally, a sequence substantially complementary to NSEQ may bind a NSEQ found in a test sample.

Skilled practitioners will also recognize that the NSEQs and PSEQs may be used to screen a library of molecules for specific binding affinity. Typical assays may be used to screen a library of DNA molecules, RNA molecules, PNAs (peptide nucleic acids), peptides, ribozymes, antibodies, agonists, antagonists, immunoglobulins, inhibitors, proteins including transcription factors, enhancers, repressors, and drugs and the like which regulate the activity of the selected polynucleotide sequence in a biological system. Typical assays may involve providing a library of molecules, combining the polynucleotide sequence or a fragment thereof with the library of molecules under conditions suitable to allow specific binding, and detecting specific binding to identify or purify, at least one molecule (ligand) which may specifically bind the polynucleotide sequence. One of skill in the art may readily adapt the NSEQs for these purposes.

Those of skill in the art may readily label the NSEQs and PSEQs by standard methods to add them to a sample from a subject under conditions for the formation and detection of hybridization complexes. After incubation the sample may be washed, and the signal associated with hybrid complex formation may be quantified and compared with a standard or normal value. Standard or normal values may be derived from any control sample, typically one that may be free of a suspect disease. If the amount of signal in the subject sample is altered in comparison to the standard value, then the presence of altered levels of expression in the sample may indicate the presence of the disease. Qualitative and quantitative methods for comparing the hybridization complexes formed in subject samples with previously established standards are well known in the art.

Furthermore, a probe may be labelled by any procedure known in the art, for example by incorporation of nucleotides linked to a "reporter molecule". A "reporter molecule", as used herein, may be a molecule that provides an analytically identifiable signal allowing detection of a hybridized probe. Detection may be either qualitative or quantitative. Commonly used reporter molecules include fluorophores, enzymes, biotin, chemiluminescent molecules, bioluminescent molecules, digoxigenin, avidin, streptavidin or radioisotopes. Commonly used enzymes include horseradish peroxidase, alkaline phosphatase, glucose oxidase and β-galactosidase, among others. Enzymes may be conjugated to avidin or streptavidin for use with a biotinylated probe. Similarly, probes may be conjugated to avidin or streptavidin for use with a biotinylated enzyme. Incorporation of a reporter molecule into a DNA probe may be by any method known to the skilled artisan, for example by nick translation, primer extension, random oligo priming, by 3' or 5' end labeling or by other means. In addition, hybridization probes include the cloning of nucleic acid sequences into vectors for the production of mRNA probes. Such vectors are known in the art, are commercially available, and may be used to synthesize RNA probes in vitro. The labelled polynucleotide sequences may be used in Southern or northern analysis, dot blot, or other membrane-based technologies; in PCR technologies; and in micro arrays utilizing samples from subjects to detect altered expression. Oligonucleotides useful as probes for screening of samples by hybridization assays or as primers for amplification may be packaged into kits. Such kits may contain the probes or primers in a pre-measured or predetermined amount, as well as other suitably packaged reagents and materials needed for the particular hybridization or amplification protocol.

In another embodiment, the invention entails a substantially purified polypeptide encoded by the polynucleotides of NSEQs, polypeptide analogs or polypeptide fragments thereof. The polypeptides whether in a premature, mature or fused form, may be isolated from lysed cells, or from the culture medium, and purified to the extent needed for the intended use. One of skill in the art may readily purify these proteins, polypeptides and peptides by any available procedure. For example, purification may be accomplished by salt fractionation, size exclusion chromatography, ion exchange chromatography, reverse phase chromatography, affinity chromatography and the like.

The invention further provides for a polypeptide encoded by the polynucleotides of NSEQs, or a portion thereof, comprising the product of a gene that is co-expressed with one or more genes known to be involved in bone remodeling. The invention additionally provides for the use of the polypeptide or a portion thereof to screen a library of molecules or compounds (DNA molecules, RNA molecules, PNAs, mimetics, proteins, agonists, antagonists, and antibodies) to identify or purify at least one ligand which specifically binds the polypeptide by combining the polypeptide or a portion thereof with the library of molecules or compounds under conditions to allow specific binding, and detecting specific binding between the polypeptide and ligand, thereby identifying or purifying a ligand which specifically binds the polypeptide. One of skill in the art may readily adapt the NSEQs for these purposes.

The portion of a polypeptide employed in such screening may be free in solution, affixed to an abiotic or biotic substrate or located intra-cellularly. Specific binding between the polypeptide and the molecule may be measured. The assay may be used to screen a library of DNA molecules, RNA molecules, PNAs, peptides, mimetics, ribozymes, antibodies, agonists, antagonists, immunoglobulins, inhibitors, peptides, polypeptides, drugs and the like, which may specifically bind the polypeptide. Many such assay methodologies are well known in the art and may be readily adapted by a skilled practitioner.

Use of NSEQ for Development of an Expression System

In order to express a biologically active polypeptide, NSEQ, or derivatives thereof, may be inserted into an expression vector, i.e., a vector that contains the elements for transcriptional and translational control of the inserted coding sequence in a particular host. These elements include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express NSEQ. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, NSEQ may be transformed into cell lines using expression vectors that may contain viral origins of replication and/or endogenous expression elements and a selectable or visible marker gene on the same or on a separate vector. The invention is not to be limited by the vector or host cell employed.

In general, host cells that contain NSEQ and that express a polypeptide encoded by the NSEQ, or a portion thereof, may be identified by a variety of procedures known to those of skill in the art. These procedures include, but are not limited to, DNA-DNA or DNA-RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

The present invention additionally relates to a bioassay for evaluating compounds as potential antagonists of the polypeptide described herein, the bioassay may comprise:

a) culturing test cells in culture medium containing increasing concentrations of at least one compound whose ability to inhibit the action of a polypeptide described herein is sought to be determined, wherein the test cells may contain a polynucleotide sequence described herein in a form having improved trans-activation transcription activity, relative to wild-type polynucleotide, and comprising a response element operatively linked to a reporter gene; and thereafter b) monitoring in the cells the level of expression of the product of the reporter gene as a function of the concentration of the potential antagonist compound in the culture medium, thereby indicating the ability of the potential antagonist compound to inhibit activation of the polypeptide encoded by, the polynucleotide sequence described herein.

The present invention further relates to a bioassay for evaluating compounds as potential agonists for a polypeptide encoded by the polynucleotide sequence described herein, the bioassay may comprise:

a) culturing test cells in culture medium containing increasing concentrations of at least one compound whose ability to promote the action of the polypeptide encoded by the polynucleotide sequence described herein is sought to be determined, wherein the test cells may contain a polynucleotide sequence described herein in a form having improved trans-activation transcription activity, relative to wild-type polynucleotide, and comprising a response element operatively linked to a reporter gene; and thereafter b) monitoring in the cells the level of expression of the product of the reporter gene as a function of the concentration of the potential agonist compound in the culture medium, thereby indicating the ability of the potential agonist compound to promote activation of a polypeptide encoded by the polynucleotide sequence described herein.

Host cells transformed with NSEQ may be cultured under conditions for the expression and recovery of the polypeptide from cell culture. The polypeptide produced by a transgenic cell may be secreted or retained intracellularly depending on the sequence and/or the vector used. As will be understood by those of skill in the art, expression vectors containing NSEQ may be designed to contain signal sequences that direct secretion of the polypeptide through a prokaryotic or eukaryotic cell membrane. Due to the inherent degeneracy of the genetic code, other DNA sequences that encode substantially the same or a functionally equivalent amino acid sequence may be produced and used to express the polypeptide encoded by NSEQ. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His), FLAG, c-myc, hemaglutinin (HA), and monoclonal antibody epitopes.

In yet a further aspect, the present invention relates to an isolated polynucleotide which may comprise a nucleotide sequence encoding a fusion protein, the fusion protein may comprise a fusion partner fused to a peptide fragment of a protein encoded by, or a naturally occurring allelic variant polypeptide encoded by, the polynucleotide sequence described herein, which peptide fragment, when administered to a member of a mammalian species, may be capable of inducing the production of antibodies that bind specifically to the protein encoded by, or a naturally occurring allelic variant polypeptide encoded by, the polynucleotide sequence described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

Use of NSEQ as a Diagnostic Screening Tool

The skilled artisan will readily recognize that NSEQ may be used for diagnostic purposes to determine the absence, presence, or altered expression (i.e. increased or decreased compared to normal) of the gene. The polynucleotides may be at least 10 nucleotides long or at least 12 nucleotides long, or at least 15 nucleotides long up to any desired length and may comprise complementary RNA and DNA molecules, branched nucleic acids, and/or peptide nucleic acids (PNAs). In one alternative, the polynucleotides may be used to detect and quantify gene expression in samples in which expression of NSEQ is correlated with disease. In another alternative, NSEQ may be used to detect genetic polymorphisms associated with a disease. These polymorphisms may be detected in the transcript cDNA.

The invention provides for the use of at least one polynucleotide comprising NSEQ (e.g., an open reading frame of NSEQ, a substantially complementary sequence, a substantially identical sequence, and fragments thereof) on an array and for the use of that array in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample indicates the presence of a bone remodeling disease or disorder.

In another embodiment, the present invention provides one or more compartmentalized kits for detection of bone resorption disease states. A first kit has a receptacle containing at least one isolated probe. Such a probe may be a nucleic acid fragment which is present/absent in the genomic DNA of normal cells but which is absent/present in the genomic DNA of affected cells. Such a probe may be specific for a DNA site that is normally active/inactive but which may be inactive/active in certain cell types. Similarly, such a probe may be specific for a DNA site that may be abnormally expressed in certain cell types. Finally, such a probe may identify a specific DNA mutation. By specific for a DNA site is meant that the probe may be capable of hybridizing to the DNA sequence which is mutated, or may be capable of hybridizing to DNA sequences adjacent to the mutated DNA sequences. The probes provided in the present kits may have a covalently attached reporter molecule. Probes and reporter molecules may be readily prepared as described above by those of skill in the art.

Use of NSEQ as a Therapeutic

One of skill in the art will readily appreciate that the expression systems and assays discussed above may also be used to evaluate the efficacy of a particular therapeutic treatment regimen, in animal studies, in clinical trials, or to monitor the treatment of an individual subject. Once the presence of disease is established and a treatment protocol is initiated, hybridization or amplification assays may be repeated on a regular basis to determine if the level of expression in the patient begins to approximate the level observed in a healthy subject. The results obtained from successive assays may be used to show the efficacy of treatment over a period ranging from several days to many years.

Therefore, in a further aspect, the present invention relates to an antibody (e.g., isolated antibody), or antigen-binding fragment thereof, that may specifically bind to a protein or polypeptide described herein. The antibody may be, for example, a monoclonal antibody or a polyclonal antibody. The antibody may originate for example, from a mouse, rat or any other mammal.

The antibody may also be a human antibody which may be obtained, for example, from a transgenic non-human mammal capable of expressing human Ig genes. The antibody may also be a humanised antibody which may comprise, for example, one or more complementarity determining regions of non-human origin. It may also comprise a surface residue of a human antibody and/or framework regions of a human antibody. The antibody may also be a chimeric antibody which may comprise, for example, variable domains of a non-human antibody and constant domains of a human antibody.

Suitable antibodies may also include, for example, an antigen-binding fragment, an Fab fragment; an $F(ab')_2$ fragment, and Fv fragment; or a single-chain antibody comprising an antigen-binding fragment (e.g., a single chain Fv).

The antibody of the present invention may be mutated and selected based on an increased affinity and/or specificity for one of a polypeptide described herein and/or based on a reduced immunogenicity in a desired host.

The antibody may further comprise a detectable label attached thereto.

The present invention further relates to a method of producing antibodies able to bind to one of a polypeptide, polypeptide fragments, or polypeptide analogs described herein, the method may comprise:

a) immunizing a mammal (e.g., mouse, a transgenic mammal capable of producing human Ig, etc.) with a suitable amount of a desired polypeptide or a polypeptide fragment thereof;
b) collecting the serum from the mammal; and
c) isolating the polypeptide-specific antibodies from the serum of the mammal.

The present invention also relates to a method of producing a hybridoma which secretes an antibody that binds to a polypeptide described herein, the method may comprise:

a) immunizing a mammal (e.g., mouse, a transgenic mammal capable of producing human Ig, etc.) with a suitable amount of a desired polypeptide, a polypeptide fragment or analog thereof;

b) obtaining lymphoid cells from the immunized animal obtained from (a);

c) fusing the lymphoid cells with an immortalizing cell to produce hybrid cells; and d) selecting hybrid cells which produce antibody that specifically binds to the polypeptide, a polypeptide fragment or analog thereof.

The present invention further relates to a method of producing an antibody that binds to one of the polypeptide described herein, the method may comprise:

a) synthesizing a library of antibodies on phage or ribosomes;

b) panning the library against a sample by bringing the phage or ribosomes into contact with a composition comprising a polypeptide or polypeptide fragment described herein;

c) isolating phage which binds to the polypeptide or polypeptide fragment, and;

d) obtaining an antibody from the phage or ribosomes.

The antibody of the present invention may thus be obtained, for example, from a library (e.g., bacteriophage library) which may be prepared, for example, by a) extracting cells which are responsible for production of antibodies from a host mammal;

b) isolating RNA from the cells of (a);

c) reverse transcribing mRNA to produce cDNA;

d) amplifying the cDNA using a (antibody-specific) primer; and e) inserting the cDNA of (d) into a phage display vector or ribosome display cassette such that antibodies are expressed on the phage or ribosomes.

The host animal may be immunized with polypeptide and/or a polypeptide fragment and/or analog described herein to induce an immune response prior to extracting the cells which are responsible for production of antibodies.

The present invention also relates to a kit for specifically assaying a polypeptide described herein, the kit may comprise, for example, an antibody or antibody fragment capable of binding specifically to the polypeptide described herein.

Further, an antagonist, agonist, or an antibody that may bind specifically to a polypeptide encoded by the polynucleotides of NSEQ, or a portion thereof, may be administered to a subject to treat or prevent diseases or disorders associated with bone remodeling. The antagonist, antibody, or fragment may be used directly to inhibit the activity of the polypeptide or indirectly to deliver a therapeutic agent to cells or tissues that express the NSEQ. An immunoconjugate comprising a polypeptide-binding site of the antibody or the antagonist and a therapeutic agent may be administered to a subject in need to treat or prevent disease. The therapeutic agent may be a cytotoxic agent selected from a group including, but not limited to, abrin, ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, *Pseudomonas* exotoxin A and 40, radioisotopes, and glucocorticoid. Yet further, an agonist of the polypeptide may be administered to a subject to treat or prevent a disease associated with decreased expression, longevity or activity of NSEQ.

The present invention further contemplates antibodies that may bind to the polypeptide encoded by the polynucleotides of NSEQ, polypeptide analogs or portions thereof. Suitable antibodies may bind to unique antigenic regions or epitopes in the polypeptides, or a portion thereof. Epitopes and antigenic regions useful for generating antibodies may be found within the proteins, polypeptides or peptides by procedures available to one of skill in the art. For example, short, unique peptide sequences may be identified in the proteins and polypeptides that have little or no homology to known amino acid sequences. Preferably the region of a protein selected to act as a peptide epitope or antigen is not entirely hydrophobic; hydrophilic regions are preferred because those regions likely constitute surface epitopes rather than internal regions of the proteins and polypeptides. These surface epitopes are more readily detected in samples tested for the presence of the proteins and polypeptides. Such antibodies may include, but are not limited to, polyclonal, monoclonal, chimeric, and single chain antibodies, Fab fragments, and fragments produced by a Fab expression library. The production of antibodies is well known to one of skill in the art.

Peptides may be made by any procedure known to one of skill in the art, for example, by using in vitro translation or chemical synthesis procedures. Short peptides which provide an antigenic epitope but which by themselves are too small to induce an immune response may be conjugated to a suitable carrier. Suitable carriers and methods of linkage are well known in the art. Suitable carriers are typically large macromolecules such as proteins, polysaccharides and polymeric amino acids. Examples include serum albumins, keyhole limpet hemocyanin, ovalbumin, polylysine and the like. One of skill in the art may use available procedures and coupling reagents to link the desired peptide epitope to such a carrier. For example, coupling reagents may be used to form disulfide linkages or thioether linkages from the carrier to the peptide of interest. If the peptide lacks a disulfide group, one may be provided by the addition of a cysteine residue. Alternatively, coupling may be accomplished by activation of carboxyl groups.

The minimum size of peptides useful for obtaining antigen specific antibodies may vary widely. The minimum size must be sufficient to provide an antigenic epitope that is specific to the protein or polypeptide. The maximum size is not critical unless it is desired to obtain antibodies to one particular epitope. For example, a large polypeptide may comprise multiple epitopes, one epitope being particularly useful and a second epitope being immunodominant. Typically, antigenic peptides selected from the present proteins and polypeptides will range from 5 to about 100 amino acids in length. More typically, however, such an antigenic peptide will be a maximum of about 50 amino acids in length, and preferably a maximum of about 30 amino acids. It is usually desirable to select a sequence of about 10, 12 or 15 amino acids, up to about 20 or 25 amino acids.

Amino acid sequences comprising useful epitopes may be identified in a number of ways. For example, preparing a series of short peptides that taken together span the entire protein sequence may be used to screen the entire protein sequence. One of skill in the art may routinely test a few large polypeptides for the presence of an epitope showing a desired reactivity and also test progressively smaller and overlapping fragments to identify a preferred epitope with the desired specificity and reactivity.

Antigenic polypeptides and peptides are useful for the production of monoclonal and polyclonal antibodies. Antibodies to a polypeptide encoded by the polynucleotides of NSEQ, polypeptide analogs or portions thereof, may be generated using methods that are well known in the art. Such antibodies may include, but are not limited to, polyclonal, monoclonal, chimeric, and single chain antibodies, Fab fragments, and fragments produced by a Fab expression library. Neutralizing antibodies, such as those that inhibit dimer formation, are especially preferred for therapeutic use. Monoclonal antibodies may be prepared using any technique that provides for the production of antibody molecules by continuous cell lines in culture. These include, but are not limited to, the hybridoma, the human B-cell hybridoma, and the EBV-hybridoma techniques. In addition, techniques developed for the production of chimeric antibodies may be used. Alternatively, techniques described for the production of single chain antibodies may be employed. Fabs that may contain specific binding sites for a polypeptide encoded by the polynucleotides of NSEQ, or a portion thereof, may also be generated. Various immunoassays may be used to identify antibodies having the desired specificity. Numerous protocols for competitive binding or immunoradiometric assays using either polyclonal or monoclonal antibodies with established specificities are well known in the art.

To obtain polyclonal antibodies, a selected animal may be immunized with a protein or polypeptide. Serum from the animal may be collected and treated according to known procedures. Polyclonal antibodies to the protein or polypeptide of interest may then be purified by affinity chromatography. Techniques for producing polyclonal antisera are well known in the art.

Monoclonal antibodies (Mabs) may be made by one of several procedures available to one of skill in the art, for example, by fusing antibody producing cells with immortalized cells and thereby making a hybridoma. The general methodology for fusion of antibody producing B cells to an immortal cell line is well within the province of one skilled in the art. Another example is the generation of Mabs from mRNA extracted from bone marrow and spleen cells of immunized animals using combinatorial antibody library technology.

The major drawback of Mabs derived from animals or from derived cell lines is that although they may be administered to a patient for diagnostic or therapeutic purposes, they are often recognized as foreign antigens by the immune system and are unsuitable for continued use. Antibodies that are not recognized as foreign antigens by the human immune system have greater potential for both diagnosis and treatment. Methods for generating human and humanized antibodies are now well known in the art.

Chimeric antibodies may be constructed in which regions of a non-human Mab are replaced by their human counterparts. A preferred chimeric antibody is one that has amino acid sequences that comprise one or more complementarity determining regions (CDRs) of a non-human Mab that binds to a polypeptide encoded by the polynucleotides of NSEQ, or a portion thereof, grafted to human framework (FW) regions. Methods for producing such antibodies are well known in the art. Amino acid residues corresponding to CDRs and FWs are known to one of average skill in the art.

A variety of methods have been developed to preserve or to enhance affinity for antigen of antibodies comprising grafted CDRs. One way is to include in the chimeric antibody the foreign framework residues that influence the conformation of the CDR regions. A second way is to graft the foreign CDRs onto human variable domains with the closest homology to the foreign variable region. Thus, grafting of one or more non-human CDRs onto a human antibody may also involve the substitution of amino acid residues which are adjacent to a particular CDR sequence or which are not contiguous with the CDR sequence but which are packed against the CDR in the overall antibody variable domain structure and which affect the conformation of the CDR. Humanized antibodies of the invention therefore include human antibodies which comprise one or more non-human CDRs as well as such antibodies in which additional substitutions or replacements have been made to preserve or enhance binding characteristics.

Chimeric antibodies of the invention also include antibodies that have been humanized by replacing surface-exposed residues to make the Mab appear human. Because the internal packing of amino acid residues in the vicinity of the antigen-binding site remains unchanged, affinity is preserved. Substitution of surface-exposed residues of a polypeptide encoded by the polynucleotides of NSEQ (or a portion thereof)-antibody according to the invention for the purpose of humanization does not mean substitution of CDR residues or adjacent residues that influence affinity for a polypeptide encoded by the polynucleotides of NSEQ, or a portion thereof.

Chimeric antibodies may also include antibodies where some or all non-human constant domains have been replaced with human counterparts. This approach has the advantage that the antigen-binding site remains unaffected. However, significant amounts of non-human sequences may be present where variable domains are derived entirely from non-human antibodies.

Antibodies of the invention include human antibodies that are antibodies consisting essentially of human sequences. Human antibodies may be obtained from phage display libraries wherein combinations of human heavy and light chain variable domains are displayed on the surface of filamentous phage. Combinations of variable domains are typically displayed on filamentous phage in the form of Fab's or scFvs. The library may be screened for phage bearing combinations of variable domains having desired antigen-binding characteristics. Preferred variable domain combinations are characterized by high affinity for a polypeptide encoded by the polynucleotides of NSEQ, or a portion thereof. Preferred variable domain combinations may also be characterized by high specificity for a polypeptide encoded by the polynucleotides of NSEQ, or a portion thereof, and little cross-reactivity to other related antigens. By screening from very large repertoires of antibody fragments, ($2-10\times10^{10}$) a good diversity of high affinity Mabs may be isolated, with many expected to have sub-nanomolar affinities for a polypeptide encoded by the polynucleotides of NSEQ, or a portion thereof.

Alternatively, human antibodies may be obtained from transgenic animals into which un-rearranged human Ig gene segments have been introduced and in which the endogenous mouse Ig genes have been inactivated. Preferred transgenic animals contain very large contiguous Ig gene fragments that are over 1 Mb in size but human polypeptide-specific Mabs of moderate affinity may be raised from transgenic animals containing smaller gene loci. Transgenic animals capable of expressing only human Ig genes may also be used to raise polyclonal antiserum comprising antibodies solely of human origin.

Antibodies of the invention may include those for which binding characteristics have been improved by direct mutation or by methods of affinity maturation. Affinity and specificity may be modified or improved by mutating CDRs and screening for antigen binding sites having the desired characteristics. CDRs may be mutated in a variety of ways. One way is to randomize individual residues or combinations of residues so that in a population of otherwise identical antigen binding sites, all twenty amino acids may be found at particular positions. Alternatively, mutations may be induced over a range of CDR residues by error prone PCR methods. Phage display vectors containing heavy and light chain variable region gene may be propagated in mutator strains of *E. coli*. These methods of mutagenesis are illustrative of the many methods known to one of skill in the art.

Antibodies of the invention may include complete anti-polypeptide antibodies as well as antibody fragments and derivatives that comprise a binding site for a polypeptide encoded by the polynucleotides of NSEQ, or a portion thereof. Derivatives are macromolecules that comprise a binding site linked to a functional domain. Functional domains may include, but are not limited to signalling domains, toxins, enzymes and cytokines.

The antibodies obtained by the means described herein may be useful for detecting proteins, variant and derivative polypeptides in specific tissues or in body fluids. Moreover, detection of aberrantly expressed proteins or protein fragments is probative of a disease state. For example, expression of the present polypeptides encoded by the polynucleotides of NSEQ, or a portion thereof, may indicate that the protein is being expressed at an inappropriate rate or at an inappropriate developmental stage. Hence, the present antibodies may be useful for detecting diseases associated with protein expression from NSEQs disclosed herein.

A variety of protocols for measuring polypeptides, including ELISAs, RIAs, and FACS, are well known in the art and provide a basis for diagnosing altered or abnormal levels of expression. Standard values for polypeptide expression are established by combining samples taken from healthy subjects, preferably human, with antibody to the polypeptide under conditions for complex formation. The amount of complex formation may be quantified by various methods, such as photometric means. Quantities of polypeptide expressed in disease samples may be compared with standard values. Deviation between standard and subject values may establish the parameters for diagnosing or monitoring disease.

Design of immunoassays is subject to a great deal of variation and a variety of these are known in the art. Immunoassays may use a monoclonal or polyclonal antibody reagent that is directed against one epitope of the antigen being assayed. Alternatively, a combination of monoclonal or polyclonal antibodies may be used which are directed against more than one epitope. Protocols may be based, for example, upon competition where one may use competitive drug screening assays in which neutralizing antibodies capable of binding a polypeptide encoded by the polynucleotides of NSEQ, or a portion thereof, specifically compete with a test compound for binding the polypeptide. Alternatively one may use, direct antigen-antibody reactions or sandwich type assays and protocols may, for example, make use of solid supports or immunoprecipitation. Furthermore, antibodies may be labelled with a reporter molecule for easy detection. Assays that amplify the signal from a bound reagent are also known. Examples include immunoassays that utilize avidin and biotin, or which utilize enzyme-labelled antibody or antigen conjugates, such as ELISA assays.

Kits suitable for immunodiagnosis and containing the appropriate labelled reagents include antibodies directed against the polypeptide protein epitopes or antigenic regions, packaged appropriately with the remaining reagents and materials required for the conduct of the assay, as well as a suitable set of assay instructions.

The present invention therefore provides a kit for specifically assaying a polypeptide described herein, the kit may comprise, for example, an antibody or antibody fragment capable of binding specifically to the polypeptide described herein.

In accordance with the present invention, the kit may be a diagnostic kit, which may comprise:

a) one or more antibodies described herein; and b) a detection reagent which may comprise a reporter group.

In accordance with the present invention, the antibodies may be immobilized on a solid support. The detection reagent may comprise, for example, an anti-immunoglobulin, protein G, protein A or lectin etc. The reporter group may be selected, without limitation, from the group consisting of radioisotopes, fluorescent groups, luminescent groups, enzymes, biotin and dye particles.

In yet another aspect of the invention, an NSEQ, a portion thereof, or its complement, may be used therapeutically for the purpose of expressing mRNA and polypeptide, or conversely to block transcription or translation of the mRNA. Expression vectors may be constructed using elements from retroviruses, adenoviruses, herpes or vaccinia viruses, or bacterial plasmids, and the like. These vectors may be used for delivery of nucleotide sequences to a particular target organ, tissue, or cell population. Methods well known to those skilled in the art may be used to construct vectors to express nucleic acid sequences or their complements.

Alternatively, NSEQ, a portion thereof, or its complement, may be used for somatic cell or stem cell gene therapy. Vectors may be introduced in vivo, in vitro, and ex vivo. For ex vivo therapy, vectors are introduced into stem cells taken from the subject, and the resulting transgenic cells are clonally propagated for autologous transplant back into that same subject. Delivery of NSEQ by transfection, liposome injections, or polycationic amino polymers may be achieved using methods that are well known in the art. Additionally, endogenous NSEQ expression may be inactivated using homologous recombination methods that insert an inactive gene sequence into the coding region or other targeted region of NSEQ.

Vectors containing NSEQ may be transformed into a cell or tissue to express a missing polypeptide or to replace a nonfunctional polypeptide. Similarly a vector constructed to express the complement of NSEQ may be transformed into a cell to down-regulate the over-expression of a polypeptide encoded by the polynucleotides of NSEQ, or a portion thereof. Complementary or anti-sense sequences may consist of an oligonucleotide derived from the transcription initiation site; nucleotides between about positions −10 and +10 from the ATG are preferred. Similarly, inhibition may be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee et al. 1994)

Ribozymes, enzymatic RNA molecules, may also be used to catalyze the cleavage of mRNA and decrease the levels of particular mRNAs, such as those comprising the polynucleotide sequences of the invention. Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases, may be included.

One of skill in the art will readily appreciate that antibodies and antibody conjugates of the invention, where used in the human body for the purpose of the therapeutic applications discussed above, may be administered in the form of a composition. Such pharmaceutical compositions may consist of a polypeptide encoded by the polynucleotides of NSEQ, a portion thereof, or antibodies, mimetics, agonists, antagonists, or inhibitors of the polypeptide. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a subject alone or in combination with other agents, drugs, or hormones.

In addition to the active ingredients, these pharmaceutical compositions may contain pharmaceutically acceptable carriers comprising excipients and auxiliaries that facilitate processing of the active compounds into preparations that may be used pharmaceutically. Further details on techniques for formulation and administration may be found in the latest edition of Remington's Pharmaceutical Sciences (Maack Publishing Co., Easton Pa.).

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and most preferably, humans.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

The term "Treatment" for purposes of this disclosure refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

Use of NSEQ in General Research

The invention finally provides products, compositions, processes and methods that utilize an NSEQ, their open reading frame, or a polypeptide encoded by the polynucleotides of NSEQ or their open reading frame, or a portion thereof, their variants, analogs and derivatives for research, biological, clinical and therapeutic purposes. For example, to identify splice variants, mutations, and polymorphisms NSEQ may be extended utilizing a partial nucleotide sequence and employing various PCR-based methods known in the art to detect upstream sequences such as promoters and other regulatory elements. Additionally, one may use an XL-PCR kit (PE Biosystems, Foster City Calif.), nested primers, and commercially available cDNA libraries (Life Technologies, Rockville Md.) or genomic libraries (Clontech, Palo Alto Calif.) to extend the sequence.

The polynucleotides may also be used as targets in a micro-array. The micro-array may be used to monitor the expression patterns of large numbers of genes simultaneously and to identify splice variants, mutations, and polymorphisms. Information derived from analyses of the expression patterns may be used to determine gene function, to understand the genetic basis of a disease, to diagnose a disease, and to develop and monitor the activities of therapeutic agents used to treat a disease. Microarrays may also be used to detect genetic diversity, single nucleotide polymorphisms which may characterize a particular population, at the genomic level.

In yet another embodiment, polynucleotides may be used to generate hybridization probes useful in mapping the naturally occurring genomic sequence. Fluorescent in situ hybridization (FISH) may be correlated with other physical chromosome mapping techniques and genetic map data.

The present invention more particularly relates in one aspect thereof to a method of representatively identifying an endogeneously differentially expressed sequence involved in osteoclast differentiation. The sequence may be, for example, differentially expressed in a differentiated osteoclast cell compared to an undifferentiated osteoclast precursor cell.

The method of the present invention may comprise;

a) separately providing total messenger RNA from differentiated osteoclast cell and undifferentiated osteoclast precursor cell, the total messenger RNA may comprise, for example, at least one endogeneously differentially expressed sequence, b) generating (e.g., single copy of a) single-stranded cDNA from each messenger RNA of differentiated osteoclast cell and (e.g., randomly) tagging the 3'-end of the single-stranded cDNA with a RNA polymerase promoter sequence and a first sequence tag;

c) generating (e.g., single copy of a) single-stranded cDNA from each messenger RNA of undifferentiated osteoclast precursor cell and (e.g., randomly) tagging the 3'-end of the single-stranded cDNA with a RNA polymerase promoter sequence and a second sequence tag;

d) separately generating partially or completely double-stranded 5'-tagged-DNA from each of b) and c), the double-stranded 5'-tagged-DNA may thus comprise in a 5' to 3' direction, a double-stranded RNA polymerase promoter, a first or second sequence tag and an endogenously expressed sequence, e) separately linearly amplifying a first and second tagged sense RNA from each of d) with a RNA polymerase enzyme (which may be selected based on the promoter used for tagging), f) generating single-stranded complementary first or second tagged DNA from one of e), g) hybridizing the single-stranded complementary first or second tagged DNA of f) with the other linearly amplified sense RNA of e), h) recovering unhybridized RNA with the help of the first or second sequence tag (for example by PCR or hybridization), and;

i) identifying (determining) the nucleotide sequence of unhybridized RNA.

The method may further comprise the step of comparatively determining the presence of the identified endogeneously and differentially expressed sequence in a differentiated osteoclast cell relative to an undifferentiated osteoclast precursor cell.

A sequence which is substantially absent (e.g., totally absent or present in very low quantity) from one of differentiated osteoclast cell or an undifferentiated osteoclast precursor cell and present in the other of differentiated osteoclast cell or an undifferentiated osteoclast precursor cell may thus be selected.

In accordance with the present invention, the sequence may be further selected based on a reduced or substantially absent expression in other normal tissue, therefore representing a candidate sequence specifically involved in osteoclast differentiation and bone remodeling.

The method may also further comprise a step of determining the complete sequence of the nucleotide sequence and may also comprise determining the coding sequence of the nucleotide sequence.

The present invention also relates in a further aspect, to the isolated endogeneously and differentially expressed sequence (polynucleotide and polypeptide) identified by the method of the present invention.

More particularly, the present invention encompasses a polynucleotide which may comprise the identified polynucleotide sequence, a polynucleotide which may comprise the open reading frame of the identified polynucleotide sequence, a polynucleotide which may comprise a nucleotide sequence substantially identical to the polynucleotide identified by the method of the present invention, a polynucleotide which may comprise a nucleotide sequence substantially complementary to the polynucleotide identified by the method of the present invention, fragments and splice variant thereof, provided that the sequence does not consist in or comprise SEQ ID NO.:57.

In accordance with the present invention, the isolated endogeneously and differentially expressed sequence of the present invention may be a complete or partial RNA molecule.

Isolated DNA molecule able to be transcribed into the RNA molecule of the present invention are also encompassed herewith as well as vectors (including expression vectors) comprising the such DNA or RNA molecule.

The present invention also relates to libraries comprising at least one isolated endogeneously and differentially expressed sequence identified herein (e.g., partial or complete RNA or DNA, substantially identical sequences or substantially complementary sequences (e.g., probes) and fragments thereof (e.g., oligonucleotides)).

In accordance with the present invention, the isolated endogeneously and differentially expressed sequence may be selected, for example, from the group consisting of a polynucleotide which may consist in or comprise;

a) any one of SEQ ID NO.:1 to SEQ ID NO.56, SEQ ID NO.: 83, SEQ ID NO.:84 or SEQ ID NO.:87,
b) the open reading frame of any one of SEQ ID NO.:1 to SEQ ID NO.56, SEQ ID NO.: 83, SEQ ID NO.:84 or SEQ ID NO.:87,
c) a polynucleotide which may comprise a nucleotide sequence substantially identical to a) or b), and;
d) fragments of any one of a) to c).

Exemplary substantially identical sequence of a) or b) may comprise, for example, a sequence which may be selected from the group consisting of SEQ ID NO.:84, SEQ ID NO.: 85, SEQ ID NO.:88, SEQ ID NO.:89 and the open reading frame of the SEQ ID NO.:84, SEQ ID NO.:85, SEQ ID NO.:88, SEQ ID NO.:89.

In a further aspect the present invention relates to a polypeptide which may be encoded by the isolated endogeneously and differentially expressed sequence of the present invention.

Exemplary polypeptides may comprise a sequence selected from the group consisting of any one of SEQ ID NO.: 93 to 99, 101 to 155.

In accordance with the present invention, when the sequence is from a non-human mammal, the method further comprises identifying a corresponding human ortholog polynucleotide sequence using a method described herein or other methods known in the art.

The present invention therefore also relates to an isolated human ortholog polynucleotide sequence (involved in bone remodeling), the open reading frame of the human ortholog, substantially identical sequences, substantially complementary sequences, fragments and splice variants thereof.

The present invention as well relates to an isolated polypeptide encoded by the human ortholog polynucleotide as well as biologically active analogs and biologically active fragments thereof.

Exemplary embodiments of human ortholog polynucleotides encompassed herewith include, for example, a sequence selected form the group consisting of SEQ ID NO.: 84, SEQ ID NO.:85, SEQ ID NO.:88, SEQ ID NO.:89 and the open reading frame of the SEQ ID NO.:84, SEQ ID NO.:85, SEQ ID NO.:88, SEQ ID NO.:89.

Exemplary embodiments of isolated polypeptide encoded by some human orthologs identified herein include for example, a polypeptide selected from the group consisting of SEQ ID NO.:150, SEQ ID NO.:153, SEQ ID NO.:154 and SEQ ID NO.:155.

The present invention also more particularly relates, in an additional aspect thereof, to an isolated polynucleotide which may be differentially expressed in differentiated osteoclast cell compared to undifferentiated osteoclast precursor cell.

The isolated polynucleotide may comprise a member selected from the group consisting of;

a) a polynucleotide which may comprise any one of SEQ ID NO.:1 to SEQ ID NO.56, SEQ ID NO.: 83, SEQ ID NO.:86 or SEQ ID NO.:87,
b) a polynucleotide which may comprise the open reading frame of any one of SEQ ID NO.:1 to SEQ ID NO.56, SEQ ID NO.: 83, SEQ ID NO.:86 or SEQ ID NO.:87,
c) a polynucleotide which may comprise a sequence substantially identical (e.g., from about 50 to 100%, or about 60 to 100% or about 70 to 100% or about 80 to 100% or about 85, 90, 95 to 100% identical over the entire sequence or portion of sequences) to a) or b),
d) a polynucleotide which may comprise a sequence substantially complementary (e.g., from about 50 to 100%, or about 60 to 100% or about 70 to 100% or about 80 to 100% or about 85, 90, 95 to 100% complementarity over the entire sequence or portion of sequences) to a) or b), and;
e) a fragment of any one of a) to d)
f) including polynucleotides which consist in the above.

Exemplary polynucleotides which are substantially identical to those listed above, includes for example, polynucleotides selected from the group consisting of SEQ ID NO.:84, SEQ ID NO.:85, SEQ ID NO.:88, SEQ ID NO.:89 and the open reading frame of any one of SEQ ID NO.:84, SEQ ID NO.:85, SEQ ID NO.:88 or SEQ ID NO.:89.

Exemplary polynucleotides fragments of those listed above comprises polynucleotides of at least 10 nucleic acids which may be substantially complementary to the nucleic acid sequence of any one of SEQ ID NO.: 1 to 56 or SEQ ID NO.: 83 to SEQ ID NO.:89, such as, for example, fragments selected from the group consisting of any one of SEQ ID NO.: 64 to 80 or 90.

The present invention also relates to an isolated polynucleotide involved in osteoclast differentiation, the isolated polynucleotide may be selected, for example, from the group consisting of;

a) a polynucleotide comprising any one of SEQ ID NO.: 1 to 56 or 83 to 89,
b) a polynucleotide comprising the open reading frame of any one of SEQ ID NO.: 1 to 56 or 83 to 89, and;
c) a polynucleotide substantially identical to a) or b).

The present invention also further relates to an isolated polynucleotide which may be able to promote osteoclast differentiation (e.g., in a mammal or mammalian cell thereof). The polynucleotide may be selected, for example, from the group consisting of polynucleotides which may comprise;

a) any one of SEQ ID NO.:1 to 5, 8 to 56 or 83 to 89;
b) the open reading frame of any one of SEQ ID NO.:1 to 5, 8 to 56 or 83 to 89, and;
c) a sequence of at least 10 nucleic acids which may be complementary to the nucleic acid sequence of any one of SEQ ID NO.:6 or SEQ ID NO.:7.

In yet a further aspect, the present invention relates to an isolated polynucleotide which may be able to inhibit osteoclast differentiation (e.g., in a mammal or mammalian cell thereof). The polynucleotide may be selected, for example, from the group consisting of polynucleotides which may comprise;

a) any one of SEQ ID NO.:6 or SEQ ID NO.:7,
b) the open reading frame of any one of SEQ ID NO.:6 or SEQ ID NO.:7, and;
c) a sequence of at least 10 nucleic acids which is complementary to the nucleic acid sequence of any one of SEQ ID NO.:1 to 5 or 8 to 57 or 83 to 89.

Suitable polynucleotides include, for example, a polynucleotide having or comprising those which are selected from the group consisting of SEQ ID NO. 64 to 82 and 90.

Suitable polynucleotides may be those which may be able to inhibit osteoclast differentiation which has been induced by an inducer of osteoclast differentiation such as those listed herein.

In accordance with the present invention, the polynucleotide may be, for example, a RNA molecule, a DNA molecule, including those which are partial or complete, single-stranded or double-stranded, hybrids, etc.

The present invention also relates to a vector (e.g., an expression vector) comprising the polynucleotide of the present invention.

The present invention additionally relates in an aspect thereof to a library of polynucleotide sequences which may be differentially expressed in a differentiated osteoclast cell compared to an undifferentiated osteoclast precursor cell. The library may comprise, for example, at least one member selected from the group consisting of a) a polynucleotide which may comprise any one of SEQ ID NO.:1 to SEQ ID NO:57 and 83 to 89,
b) a polynucleotide which may comprise the open reading frame of any one of SEQ ID NO.:1 to SEQ ID NO.57 and 83 to 89,
c) a polynucleotide which may comprise a sequence substantially identical (e.g., from about 50 to 100%, or about 60 to 100% or about 70 to 100% or about 80 to 100% or about 85, 90, 95 to 100% identical over the entire sequence or portion of sequences) to a) or b),
d) a polynucleotide which may comprise a sequence substantially complementary (e.g., from about 50 to 100%, or about 60 to 100% or about 70 to 100% or about 80 to 100% or about 85, 90, 95 to 100% complementarity over the entire sequence or portion of sequences) to a) or b), and;
e) a fragment of any one of a) to d).

The present invention also relates to an expression library which may comprise a library of polynucleotides described herein. In accordance with the present invention, each of the polynucleotide may be contained within an expression vector.

Arrays and kits comprising a library of polynucleotide sequences (comprising at least one polynucleotide including complementary sequences) of the present invention are also encompassed herewith.

The present invention also provides in an additional aspect, a pharmaceutical composition for inhibiting osteoclast differentiation (bone resorption and bone resorption related diseases or disorders), the pharmaceutical composition may comprise, for example;

a) an isolated polynucleotide as defined herein (e.g., able to inhibit osteoclast differentiation) and;
b) a pharmaceutically acceptable carrier.

The present invention also provides in yet an additional aspect, a method for inhibiting osteoclast differentiation (e.g., for inhibiting bone resorption or for ameliorating bone resorption) in a mammal (individual) in need thereof (or in a mammalian cell), the method may comprise administering an isolated polynucleotide (e.g., able to inhibit osteoclast differentiation) or a suitable pharmaceutical composition.

In accordance with the present invention, the mammal in need may suffer, for example and without limitation, from a condition selected from the group consisting of osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes, etc.

In a further aspect, the present invention relates to the use of an isolated polynucleotide (e.g., able to inhibit osteoclast differentiation) for the preparation of a medicament for the treatment of a bone resorption disease.

The present invention in another aspect thereof, provides a pharmaceutical composition for promoting osteoclast differentiation in a mammal in need thereof. The pharmaceutical composition may comprise, for example;

a. an isolated polynucleotide (e.g., able to promote osteoclast differentiation) and;
b. a pharmaceutically acceptable carrier.

The present invention also further provides a method for promoting osteoclast differentiation in a mammal in need thereof (or in a mammalian cell), the method may comprise, for example, administering an isolated polynucleotide (e.g., able to promote osteoclast differentiation) or a suitable pharmaceutical composition as described above.

The present invention additionally relates to the use of an isolated polynucleotide (e.g., able to promote osteoclast differentiation) for the preparation of a medicament for the treatment of a disease associated with insufficient bone resorption (e.g., hyperostosis).

The present invention also relates to the use of at least one polynucleotide which may be selected from the group consisting of;

a) a polynucleotide comprising the any one of SEQ ID NO.:1 to SEQ ID NO.57 and 83 to 89, b) a polynucleotide comprising the open reading frame of any one of SEQ ID NO.:1 to SEQ ID NO.57 and 83 to 89, c) a polynucleotide comprising a sequence substantially identical (e.g., from about 50 to 100%, or about 60 to 100% or about 70 to 100% or about 80 to 100% or about 85, 90, 95 to 100% identical over the entire sequence or portion of sequences) to a) or b), d) a polynucleotide comprising a sequence substantially complementary (e.g., from about 50 to 100%, or about 60 to 100% or about 70 to 100% or about 80 to 100% or about 85, 90, 95 to 100% complementarity over the entire sequence or portion of sequences) to a) or b), e) a fragment of any one of a) to d) and;

f) a library comprising any one of a) to d)

in the diagnosis of a condition related to bone remodeling.

Also encompassed by the present invention are kits for the diagnosis of a condition related to bone remodeling. The kit may comprise, for example, at least one sequence substantially complementary to any one of SEQ ID NO.:1 to SEQ ID NO:57 or 83 to 89, the open reading frame of any one of SEQ ID NO.:1 to SEQ ID NO:57 or 83 to 89 and fragments thereof.

The present invention also provides in an additional aspect, an isolated polypeptide (polypeptide sequence) which may be able to promote osteoclast differentiation (in a mammal or a mammalian cell thereof). The polypeptide may comprise (or consist in) a sequence selected from the group consisting of;

a) any one of SEQ ID NO.: 93 to 97 or 101 to 155, b) a biologically active fragment of any one of a), c) a biologically active analog of any one of a).

In accordance with the present invention, the biologically active analog may comprise, for example, at least one conservative amino acid substitution compared to the original sequence.

In yet a further aspect, the present invention provides a pharmaceutical composition for promoting osteoclast differentiation (e.g., for promoting bone resorption). The pharmaceutical composition may comprise, for example a polypeptide (e.g., able to promote osteoclast differentiation) and a pharmaceutically acceptable carrier.

Methods for promoting osteoclast differentiation in a mammal in need thereof (or in a mammalian cell) are also provided by the present invention, which methods may comprise administering an isolated polypeptide (e.g., able to promote osteoclast differentiation) or suitable pharmaceutical composition described herein.

In additional aspects, the present invention relates to the use of an isolated polypeptide (e.g., able to promote osteoclast differentiation) for the preparation of a medicament for the treatment of a disease associated with insufficient bone resorption.

In a further aspect, the present invention relates to an isolated polypeptide able to inhibit osteoclast differentiation (in a mammal or mammalian cell thereof), the polypeptide may comprise, for example, a sequence selected from the group consisting of a) a sequence which may comprise or consist in any one of SEQ ID NO.:98 and SEQ ID NO.:99, b) a biologically active fragment of any one of a), c) a biologically active analog of any one of a).

In accordance with the present invention, the biologically active analog may comprise, for example, at least one conservative amino acid substitution in the amino acid sequence in comparison to another polypeptide The present invention further encompasses pharmaceutical compositions which may comprise the isolated polypeptide described herein.

Methods for ameliorating bone resorption in an individual in need thereof are also encompassed herewith, which method may comprise, for example, administering an isolated polypeptide (e.g., able to inhibit osteoclast differentiation) or suitable pharmaceutical compositions which may comprise such polypeptide.

In a further aspect the present invention provides a method for ameliorating bone resorption in an individual in need thereof which may comprise administering a compound capable of inhibiting (e.g., in an osteoclast precursor cell) the activity or expression of a polypeptide involved in (or able to promote) osteoclast differentiation such as for example, a polypeptide selected from the group consisting of SEQ ID NO.: 93 to 97 and 101 to 155.

In accordance with the present invention, the mammal may suffer, for example, from a condition selected from the group consisting of osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes, etc.

In yet a further aspect, the present invention relates to the use of a polypeptide able to inhibit osteoclast differentiation in the preparation of a medicament for the treatment of a bone resorption disease in an individual in need thereof.

The present invention also relates to the use of a compound able to inhibit (e.g., in an osteoclast precursor cell) the activity or expression of a polypeptide which may be selected, for example, from the group consisting of SEQ ID NO.: 93 to 97 and 101 to 155 in the preparation of a medicament for the treatment of a bone resorption disease in an individual in need thereof.

Antibodies and antigen-binding fragment thereof which are able to bind to any of the polypeptide described herein, including those which may be selected from the group consisting of SEQ ID NO.: 93 to 97 and 101 to 155 are also encompassed by the present invention.

In accordance with the present invention, the antibody may be able, for example, to inhibit osteoclast differentiation.

The present invention also relates to a composition (e.g., pharmaceutical composition) which may comprise;

a) an antibody able to bind to any of the polypeptide selected from the group consisting of SEQ ID NO.: 93 to 97 and 101 to 155, wherein said antibody is able to inhibit osteoclast differentiation and;

b) a pharmaceutically acceptable carrier.

The present invention relates in a further aspect to a method of inhibiting osteoclast differentiation which may comprise administering to a mammal in need thereof the antibody described herein or a pharmaceutical composition comprising such antibody.

The present invention relates in yet a further aspect to the use of an antibody as defined herein for the preparation of a medicament for the treatment of a bone resorption disease in an individual in need thereof.

In an additional aspect, the present invention relates to an immunizing composition which may comprise a polypeptide, such as a polypeptide selected from the group consisting of SEQ ID NO.: 93 to 155, analogs or fragments thereof or a nucleic acid (polynucleotide) selected, for example, from the group consisting of those comprising or consisting in (a) SEQ ID NO.: 1 to 56 and 83 to 89, (b) a polynucleotide which may comprise the open reading frame of SEQ ID NO.: 1 to 56 and 83 to 89, (c) substantially identical sequences of any one of (a) or (b) or fragments of any one of (a), (b) or (c) able to encode immunologically active polypeptides thereof.

In yet an additional aspect, the present invention relates to a method of diagnosing a condition related to a bone resorption disorder or disease in an individual in need thereof. The method may comprise, for example, quantifying a polynucleotide described herein, such as, for example, those selected from the group consisting of those comprising or consisting of (a) SEQ ID NO.:1 to 56 and 83 to 89 (b) a polynucleotide which may comprise the open reading frame of SEQ ID NO.: 1 to 56 and 83 to 89, (c) substantially identical sequences of any one of (a) or (b), or a polypeptide sequence which may be selected, for example, from the group consisting of 93 to 155 and analogs thereof in a sample from the individual compared to a standard or normal value.

In an additional aspect, the present invention provides a method for identifying an inhibitory compound (inhibitor, antagonist) which may be able to impair the function (activity) or expression of a polypeptide described herein, such as, for example, those which may be selected from the group consisting of SEQ ID NO.: 93 to 97 and 100 to 155 and analogs thereof. The method may comprise contacting the polypeptide or a cell expressing the polypeptide with a candidate compound and measuring the function (activity) or expression of the polypeptide. A reduction in the function or activity of the polypeptide (compared to the absence of the candidate compound) may positively identify a suitable inhibitory compound.

In accordance with the present invention, the impaired function or activity may be associated with a reduced ability of the polypeptide to promote osteoclast differentiation, such as osteoclast differentiation induced by an inducer described herein or known in the art.

In accordance with the present invention the cell may not naturally (endogenously) express (polypeptide may substantially be unexpressed in a cell) the polypeptide or analog or alternatively, the expression of a naturally expressed polypeptide analog may be repressed.

For example, suitable method of screening for an inhibitor of SEQ ID NO.:153, may comprise repressing the expression of SEQ ID NO.:93 in a mouse osteoclast cell and evaluating differentiation of the osteoclast cell in the presence or absence of a candidate inhibitor.

The impaired function or activity may also be associated with a reduced ability of the polypeptide to interact with a known partner.

For example, suitable method of screening for an inhibitor of SEQ ID NO.: 154 may comprise measuring (evaluating) the interaction of the polypeptide with the v-ATPase-a3 subunit in the presence or absence of a candidate inhibitor.

The present invention also provides a method for identifying an inhibitory compound (inhibitor, antagonist) able to impair the function (activity) or expression of a polypeptide such as, for example SEQ ID NO.: 98 or SEQ ID NO.:99. The method may comprise, for example, contacting the polypeptide or a cell expressing the polypeptide with a candidate compound and measuring the function (activity) or expression of the polypeptide. A reduction in the function or activity of the polypeptide (compared to the absence of the candidate compound) may thus positively identify a suitable inhibitory compound.

In accordance with the present invention, the impaired function or activity may be associated, for example, with a reduced ability of the polypeptide to inhibit osteoclast differentiation.

The cell used to carry the screening test may not naturally (endogenously) express the polypeptide or analogs, or alternatively the expression of a naturally expressed polypeptide analog may be repressed.

As used herein the term "sequence identity" relates to (consecutive) nucleotides of a nucleotide sequence which with reference to an original nucleotide sequence. The identity may be compared over a region or over the total sequence of a nucleic acid sequence.

Thus, "identity" may be compared, for example, over a region of 3, 4, 5, 10, 19, 20 nucleotides or more (and any number there between). It is to be understood herein that gaps of non-identical nucleotides may be found between identical nucleic acids. For example, a polynucleotide may have 100% identity with another polynucleotide over a portion thereof. However, when the entire sequence of both polynucleotide is compared, the two polynucleotides may have 50% of their overall (total) sequence identical to one another.

Polynucleotides of the present invention or portion thereof having from about 50 to about 100%, or about 60 to about 100% or about 70 to about 100% or about 80 to about 100% or about 85%, about 90%, about 95% to about 100% sequence identity with an original polynucleotide are encompassed herewith. It is known by those of skill in the art, that a polynucleotide having from about 50% to 100% identity may function (e.g., anneal to a substantially complementary sequence) in a manner similar to an original polynucleotide and therefore may be used in replacement of an original polynucleotide. For example a polynucleotide (a nucleic acid sequence) may comprise or have from about 50% to 100% identity with an original polynucleotide over a defined region and may still work as efficiently or sufficiently to achieve the present invention.

Percent identity may be determined, for example, with n algorithm GAP, BESTFIT, or FASTA in the Wisconsin Genetics Software Package Release 7.0, using default gap weights.

As used herein the terms "sequence complementarity" refers to (consecutive) nucleotides of a nucleotide sequence which are complementary to a reference (original) nucleotide sequence. The complementarity may be compared over a region or over the total sequence of a nucleic acid sequence.

Polynucleotides of the present invention or portion thereof having from about 50 to about 100%, or about 60 to about 100% or about 70 to about 100% or about 80 to about 100% or about 85%, about 90%, about 95% to about 100% sequence complementarity with an original polynucleotide are thus encompassed herewith. It is known by those of skill in the art, that an polynucleotide having from about 50% to 100% complementarity with an original sequence may anneal to that sequence in a manner sufficient to carry out the present invention (e.g., inhibit expression of the original polynucleotide).

An "analogue" is to be understood herein as a molecule having a biological activity and chemical structure similar to that of a polypeptide described herein. An "analogue" may have sequence similarity with that of an original sequence or a portion of an original sequence and may also have a modification of its structure as discussed herein. For example, an "analogue" may have at least 90% sequence similarity with an original sequence or a portion of an original sequence. An "analogue" may also have, for example; at least 70% or even 50% sequence similarity (or less, i.e., at least 40%) with an original sequence or a portion of an original sequence.

Also, an "analogue" may have, for example, at least 50% sequence similarity to an original sequence with a combination of one or more modification in a backbone or side-chain of an amino acid, or an addition of a group or another molecule, etc.

"Polynucleotide" generally refers to any polyribonucleotide or polydeoxyribonucleotide, which may be unmodified RNA or DNA, or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus "polynucleotide" embraces chemically, enzymatically or metabolically modified forms of polynucleotides as typically found in nature, as well as the chemical forms of DNA and RNA characteristic of viruses and cells. "Polynucleotide" includes but is not limited to linear and end-closed molecules. "Polynucleotide" also embraces relatively short polynucleotides, often referred to as oligonucleotides.

"Polypeptides" refers to any peptide or protein comprising two or more amino acids joined to each other by peptide bonds or modified peptide bonds (i.e., peptide isosteres). "Polypeptide" refers to both short chains, commonly referred as peptides, oligopeptides or oligomers, and to longer chains generally referred to as proteins. As described above, polypeptides may contain amino acids other than the 20 gene-encoded amino acids.

As used herein the term "polypeptide analog" relates to mutants, variants, chimeras, fusions, deletions, additions and any other type of modifications made relative to a given polypeptide.

As used herein the term "biologically active" refers to a variant or fragment which retains some or all of the biologicval activity of the natural polypeptide, i.e., to be able to promote or inhibit osteoclast differentiation.

Thus, biologically active polypeptides in the form of the original polypeptides, fragments (modified or not), analogues (modified or not), derivatives (modified or not), homologues, (modified or not) of the polypeptides described herein are encompassed by the present invention.

Therefore, any polypeptide having a modification compared to an original polypeptide which does not destroy significantly a desired biological activity is encompassed herein. It is well known in the art, that a number of modifications may be made to the polypeptides of the present invention without deleteriously affecting their biological activity. These modifications may, on the other hand, keep or increase the biological activity of the original polypeptide or may optimize one or more of the particularity (e.g. stability, bioavailability, etc.) of the polypeptides of the present invention which, in some instance might be desirable. Polypeptides of the present invention may comprise for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino- or carboxy-terminus. It will be appreciated that the same type of modification may be present in the same or varying degrees at several sites in a given polypeptide. Also, a given polypeptide may contain many types of modifications. It is to be understood herein that more than one modification to the polypeptides described herein are encompassed by the present invention to the extent that the biological activity is similar to the original (parent) polypeptide.

As discussed above, polypeptide modification may comprise, for example, amino acid insertion (i.e., addition), deletion and substitution (i.e., replacement), either conservative or non-conservative (e.g., D-amino acids, desamino acids) in the polypeptide sequence where such changes do not substantially alter the overall biological activity of the polypeptide.

Example of substitutions may be those, which are conservative (i.e., wherein a residue is replaced by another of the same general type or group) or when wanted, non-conservative (i.e., wherein a residue is replaced by an amino acid of another type). In addition, a non-naturally occurring amino acid may substitute for a naturally occurring amino acid (i.e., non-naturally occurring conservative amino acid substitution or a non-naturally occurring non-conservative amino acid substitution).

As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same type or group as that of the amino acid to be replaced. Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids, which are not naturally encoded by DNA (non-naturally occurring or unnatural amino acid) may also be made.

A non-naturally occurring amino acid is to be understood herein as an amino acid which is not naturally produced or found in a mammal. A non-naturally occurring amino acid comprises a D-amino acid, an amino acid having an acetylaminomethyl group attached to a sulfur atom of a cysteine, a pegylated amino acid, etc. The inclusion of a non-naturally occurring amino acid in a defined polypeptide sequence will therefore generate a derivative of the original polypeptide. Non-naturally occurring amino acids (residues) include also the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, norleucine, etc. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that analogues may be generated by substitutional mutagenesis and retain the biological activity of the polypeptides of the present invention. These analogues have at least one amino acid residue in the protein molecule removed and a different residue inserted in its place. For example, one site of interest for substitutional mutagenesis may include but are not restricted to sites identified as the active site(s), or immunological site(s). Other sites of interest may be those, for example, in which particular residues obtained from various species are identical. These positions may be important for biological activity. Examples of substitutions identified as "conservative substitutions" are shown in Table A. If such substitutions result in a change not desired, then other type of substitutions, denominated "exemplary substitutions" in Table A, or as further described herein in reference to amino acid classes, are introduced and the products screened.

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile)

(2) neutral hydrophilic: Cysteine (Cys), Serine (Ser), Threonine (Thr)

(3) acidic: Aspartic acid (Asp), Glutamic acid (Glu)

(4) basic: Asparagine (Asn), Glutamine (Gln), Histidine (His), Lysine (Lys), Arginine (Arg)

(5) residues that influence chain orientation: Glycine (Gly), Proline (Pro); and aromatic: Tryptophan (Trp), Tyrosine (Tyr), Phenylalanine (Phe)

Non-conservative substitutions will entail exchanging a member of one of these classes for another.

TABLE A

| Examplary amino acid substitution | | |
|---|---|---|
| Original residue | Exemplary substitution | Conservative substitution |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |

TABLE A-continued

| Examplary amino acid substitution | | |
|---|---|---|
| Original residue | Exemplary substitution | Conservative substitution |
| Tyr (Y) | Trp, Phe, Thr, Ser | Phe |
| Val (V) | Ile, Leu, Met, Phe, Ala, norleucine | Leu |

It is to be understood herein, that if a "range" or "group" of substances (e.g. amino acids), substituents" or the like is mentioned or if other types of a particular characteristic (e.g. temperature, pressure, chemical structure, time, etc.) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a percentage (%) of identity of from about 80 to 100%, it is to be understood as specifically incorporating herein each and every individual %, as well as sub-range, such as for example 80%, 81%, 84.78%, 93%, 99% etc.; and similarly with respect to other parameters such as, concentrations, elements, etc. . . .

It is in particular to be understood herein that the methods of the present invention each include each and every individual steps described thereby as well as those defined as positively including particular steps or excluding particular steps or a combination thereof; for example an exclusionary definition for a method of the present invention, may read as follows: "provided that said polynucleotide does not comprise or consist in SEQ ID NO.:57 or the open reading frame of SEQ ID NO.:57" or "provided that said polypeptide does not comprise or consist in SEQ ID NO.:100" or "provided that said polynucleotide fragment or said polypeptide fragment is less than X unit (e.g., nucleotides or amino acids) long or more than X unit (e.g., nucleotides or amino acids) long".

Other objects, features, advantages, and aspects of the present invention will become apparent to those skilled in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

In the appended drawings:

FIG. 6 are pictures illustrating the phenotypic effect on osteoclast differentiation in the presence of siRNAs specific for SEQ. ID. NO:2, panel a; control RAW-hU6 cells, panel b; RAW-hU6 treated with RANK ligand, panel c; RAW-hU6 treated with RANK ligand and siRNA specific for SEQ ID NO.:2 (RAW-0179.1), panel d; RAW-hU6 treated with RANK ligand and siRNA specific for SEQ ID NO.:2 (RAW-0179.2) and panel e; RAW-hU6 treated with RANK ligand and siRNA specific for SEQ ID NO.:2 (RAW-0179.3);

FIG. 8 are pictures illustrating the phenotypic effect on osteoclast differentiation in the presence of siRNAs specific for SEQ. ID. NO:3 panel a; control RAW-hU6 cells, panel b; RAW-hU6 treated with RANK ligand, panel c; RAW-hU6 treated with RANK ligand and siRNA specific for SEQ ID NO.:3 (RAW-0799.1), panel d; RAW-hU6 treated with RANK ligand and siRNA specific for SEQ ID NO.:3 (RAW-0799.2) and panel e; RAW-hU6 treated with RANK ligand and siRNA specific for SEQ ID NO.:3(RAW-0799.3);

FIG. 9 are pictures illustrating the phenotypic effect on osteoclast differentiation in the presence of siRNAs specific for SEQ. ID. NO:4 panel a; control RAW-hU6 cells, panel b; RAW-hU6 treated with RANK ligand, and panel c; RAW-hU6 treated with RANK ligand and siRNA specific for SEQ ID NO.:4 (RAW-0351.1);

FIG. 16A is a picture representing an examplary embodiment of a macroarray hybridization results of differential expression of some human orthologues in the different human tissues and human osteoclasts samples;

FIGS. 22 to 87 represents some polynucleotides and polypeptides identified using an examplary method of the present invention.

Figure 1:
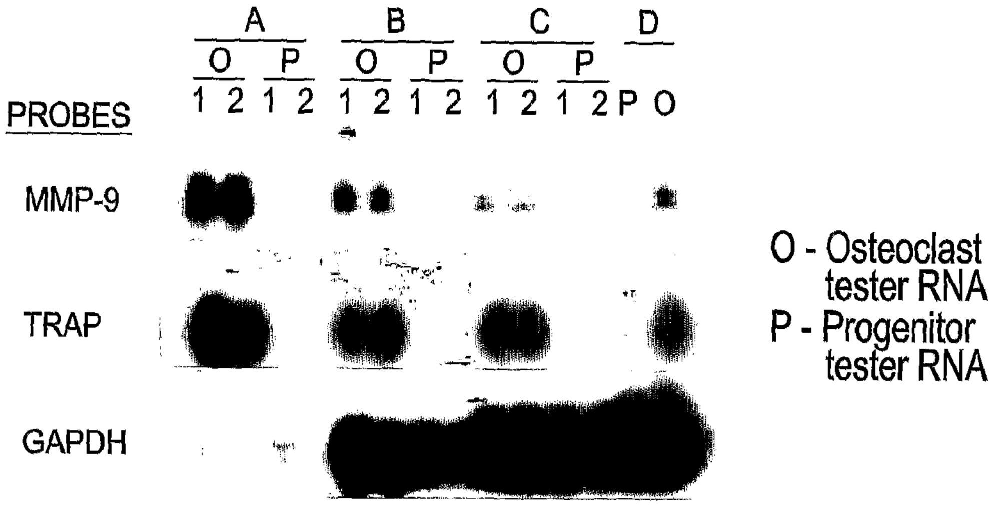
FIG. 1 is a picture of a Southern blot hybridization analysis of the "STAR" subtracted libraries with probes specific for MMP-9, TRAP and GAPDH demonstrating RNA subtraction using STAR.

SEQ ID NOs: 1-7, and 57 show differentially expressed sequences found in osteoclasts and demonstrated to have an effect on osteoclastogenesis following inhibition with specific siRNAs. SEQ ID NOs: 8-56 show differentially expressed sequences found in osteoclasts with putative roles in bone remodelling. SEQ ID NOs: 58-82 show the nucleotide sequences of plasmids, oligonucleotide primers and siRNAs used for experiments performed herein.

SEQ ID NOs: 83-87 show the mRNA sequence of spliced variants isolated from RNA prepared from osteoclasts for some of the osteoclast-specific sequences identified. SEQ ID NOs 83-87 thus show by way of examples that unique spliced variants exist and strongly suggest that others also exist for the model system under study and others. More specifically, SEQ ID NO: 83 is a variant of SEQ ID NO: 1; SEQ ID NO: 84 is a human sequence of the corresponding mouse variant #1 for SEQ ID NO: 2; SEQ ID NO: 85 is a human sequence of the corresponding mouse variant #2 for SEQ ID NO: 2; SEQ ID NO: 86 is a variant of SEQ ID NO: 3; and SEQ ID NO: 87 is a variant of SEQ ID NO: 3.

SEQ ID NO.: 88 and 89 shows the mRNA sequence of human orthologs of SEQ ID NO.:1 and 2 respectively.

SEQ ID NO.: 64 to 82 and 90 shows fragments which are complementary to a portion of a sequence of selected polynucleotides described herein.

SEQ ID NO.: 93 to 155 shows polypeptides encoded by the polynucleotides of the present invention.

Description of Illustrative Embodiments

The applicant employed a carefully planned strategy to identify and isolate genetic sequences involved in osteoclastogenesis and bone remodeling. The process involved the following steps: 1) preparation of highly representative cDNA libraries using mRNA isolated from precursors and osteoclasts; 2) isolation of sequences upregulated during osteoclastogenesis; 3) identification and characterization of upregulated sequences; 4) selection of upregulated sequences for tissue specificity; 5) determination of knock-down effects on osteoclastogenesis and 6) determination of knock-down effects on bone resorption.

The results discussed in this disclosure demonstrate the advantage of targeting osteoclast genes that are specific to this differentiated cell type and provide a more efficient screening method when studying the genetic basis of diseases and disorders. Genes that are known to have a role in other areas of biology have been shown to play a critical role in osteoclastogenesis and osteoclast function. Genes that are known but have not had a role assigned to them until the present disclosure have also been isolated and shown to have a critical role in osteoclastogenesis and osteoclast function. Finally, novel genes have been identified and play a role, however, applicant reserves their disclosure until further study has been completed.

The present invention is illustrated in further details below in a non-limiting fashion.

A—Material and Methods

Commercially available reagents referred to in the present disclosure were used according to supplier's instructions unless otherwise indicated. Throughout the present disclosure certain starting materials were prepared as follows:

B—Preparation of Osteoclast Differentiated Cells

The RAW 264.7 (RAW) osteoclast precursor cell line and human CD34+ progenitors are well known in the art as murine and human models of osteoclastogenesis. These murine and human osteoclasts are therefore excellent sources of materials for isolating and characterizing genes specialized for osteoclast function.

RAW cells were purchased from American Type Culture Collection and maintained in high glucose DMEM containing 10% fetal bovine serum and antibiotics. The cells were sub-cultured bi-weekly to a maximum of 10-12 passages. For osteoclast differentiation experiments, RAW cells were seeded in 96-well plates at a density of 4×103 cells/well and allowed to plate for 24 h. Differentiation was induced in high glucose DMEM, 10% charcoal-treated foetal bovine serum (Hyclone, Logan, Utah), 0.05% BSA, antibiotics, 10 ng/ml macrophage colony stimulating factor (M-CSF), and 100 ng/ml receptor activator of NF-kB (RANK) ligand. The plates were re-fed on day 3 and osteoclasts were clearly visible by day 4. Typically, the cells were stained for tartrate-resistant acid phosphatase (TRAP) on day 4 or 5 unless otherwise indicated. For TRAP staining, the cells were washed with PBS and fixed in 10% formaldehyde for 1 h. After two PBS washes, the cells were rendered lightly permeable in 0.2% Triton X-100 in PBS for 5 min before washing in PBS. Staining was conducted at 37° C. for 20-25 min in 0.01% Naphtol AS-MX phosphate, 0.06% Fast Red Violet, 50 mM sodium tartrate, 100 mM sodium acetate, pH 5.2. Cells were visualized microscopically.

Human osteoclasts were differentiated from G-CSF-mobilized peripheral blood mononuclear cells (Cambrex, East Rutherford, N.J.) as described by the supplier in the presence of 35 ng/ml M-CSF and 100 ng/ml RANK ligand. Multinucleated TRAP-staining osteoclasts were visible by 11-14 days. Osteoclasts from human cells were also derived from human osteoclasts precursor cells (Cambrex, East Rutherford, N.J.) and cultured as described by the supplier. In the latter case, osteoclasts are obtained after 7 days.

C—Method of Isolating Differentially Expressed mRNA

Key to the discovery of differentially expressed sequences unique to osteoclasts is the use of the applicant's patented STAR technology (Subtractive Transcription-based Amplification of mRNA; U.S. Pat. No. 5,712,127 Malek et al., Jan. 27, 1998). In this procedure, mRNA isolated from fully differentiated osteoclasts is used to prepare "tester RNA", which is hybridized to complementary single-stranded "driver DNA" prepared from osteoclast precursor mRNA and only the un-hybridized "tester RNA" is recovered, and used to create cloned cDNA libraries, termed "subtracted libraries". Thus, the "subtracted libraries" are enriched for differentially expressed sequences inclusive of rare and novel mRNAs often missed by micro array hybridization analysis, which are anticipated to be among the important gene targets for the development of better diagnostic and therapeutic strategies.

The clones contained in the enriched "subtracted libraries" are identified by DNA sequence analysis and their potential function assessed by database analysis. The non-redundant clones are then used to prepare DNA micro-arrays, which are used to quantify their relative differential expression patterns by hybridization to fluorescent cDNA probes. Two classes of cDNA probes are used, which are generated from either RNA transcripts prepared from the same subtracted libraries (subtracted probes) or mRNA isolated from different osteoclast samples (standard probes). The use of subtracted probes provides increased sensitivity for detecting the low abundance mRNA sequences that are preserved and enriched by STAR. Furthermore, the specificity of the differentially expressed sequences to osteoclast is measured by hybridizing radio-labeled probes prepared from each selected sequence to macroarrays containing RNA from different osteoclast samples and different murine and/or human tissues. Additionally, Northern blot analysis is performed so as to confirm the presence of one or more specific mRNA species in the osteoclast samples. Following this, the full-length cDNAs representative of the mRNA species and/or spliced variants are cloned in *E. coli* DH10B.

A major challenge in gene expression profiling is the limited quantities of RNA available for molecular analysis. The amount of RNA isolated from many osteoclast samples or human specimens (needle aspiration, laser capture micro-dissection (LCM) samples and transfected cultured cells) is often insufficient for preparing: 1) conventional tester and driver materials for STAR; 2) standard cDNA probes for DNA micro-array analysis; 3) RNA macroarrays for testing the specificity of expression; 4) Northern blots and; 5) full-length cDNA clones for further biological validation and characterization. Thus, the applicant has developed a proprietary technology called RAMP (RNA Amplification Procedure) (U.S. patent application Ser. No. 11/000,958 published under No. US 2005/0153333A1 on Jul. 14, 2005 and entitled "Selective Terminal Tagging of Nucleic Acids"), which linearly amplifies the mRNA contained in total RNA samples yielding microgram quantities of amplified RNA sufficient for the various analytical applications. The RAMP RNA produced is largely full-length mRNA-like sequences as a result of the proprietary method for adding a terminal sequence tag to the 3'-ends of single-stranded cDNA molecules, for use in linear transcription amplification. Greater than 99.5% of the sequences amplified in RAMP reactions show <2-fold variability and thus, RAMP provides unbiased RNA samples in quantities sufficient to enable the discovery of the unique mRNA sequences involved in osteoclastogenesis.

D—Preparation of Murine Osteoclasts Subtracted Library

RAW precursor cells and the corresponding fully differentiated (day 5) osteoclasts were prepared as described above. Isolation of cellular RNA followed by mRNA purification from each was performed using standard methods (Qiagen, Mississauga, ON). Following the teachings of Malek et al. (U.S. Pat. No. 5,712,127), 2 μg of poly A+ mRNA from each sample were used to prepare highly representative ($>2\times10^6$ CFU) cDNA libraries in specialized plasmid vectors necessary for preparing tester and driver materials. In each case, first-strand cDNA was synthesized using an oligo $dT_{11}$ primer with 3' locking nucleotides (e.g., A, G or C) and containing a Not I recognition site. Next, second-strand cDNA synthesis was performed according to the manufacturer's procedure for double-stranded cDNA synthesis (Invitrogen, Burlington, ON) and the resulting double-stranded cDNA ligated to linkers containing an Asc I recognition site (New England Biolabs, Pickering, ON). The double-stranded cDNAs were then digested with Asc I and Not I restriction enzymes (New England Biolabs, Pickering, ON), purified from the excess linkers using the cDNA fractionation column from Invitrogen (Burlington, ON) as specified by the manufacturer and each ligated into specialized plasmid vectors—p14 (SEQ. ID. NO:58) and p17+ (SEQ. ID. NO:59) used for preparing tester and driver materials respectively. Thereafter, the ligated cDNAs were transformed into *E. coli* DH10B resulting in the desired cDNA libraries (RAW 264.7-precursor-p14, RAW 264.7-precursor-p17+, RAW 264.7-osteoclasts-p14 and RAW 264.7-osteoclasts-p17+). The plasmid DNA pool for each cDNA library was purified and a 2-μg aliquot of each linearized with Not I restriction enzyme. In vitro transcription of the Not I digested p14 and p17+ plasmid libraries was then performed with T7 RNA polymerase and sp6 RNA polymerase respectively (Ambion, Austin, Tex.).

Next, in order to prepare 3'-represented tester and driver libraries, a 10-μg aliquot of each of the in vitro synthesized RNA was converted to double-stranded cDNA by performing first-strand cDNA synthesis as described above followed by primer-directed (primer OGS 77 for p14 (SEQ. ID. NO:62) and primer OGS 302 for p17+ (SEQ. ID. NO:63)) second-strand DNA synthesis using Advantage-2 Taq polymerase (BD Biosciences Clontech, Mississauga, ON). The sequences corresponding to OGS 77 and OGS 302 were introduced into the in vitro synthesized RNA by way of the specialized vectors used for preparing the cDNA libraries. Thereafter, 6×1-μg aliquots of each double-stranded cDNA was digested individually with one of the following 4-base recognition restriction enzymes Rsa I, Sau3A1, Mse I, Msp I, MinPI I and Bsh 1236I (MBI Fermentas, Burlington, ON), yielding up to six possible 3'-fragments for each RNA species contained in the cDNA library. Following digestion, the restriction enzymes were inactivated with phenol and the set of six reactions pooled. The restriction enzymes sites were then blunted with T4 DNA polymerase and ligated to linkers containing an Asc I recognition site. Each linker-adapted pooled DNA sample was digested with Asc I and Not I restriction enzymes, desalted and ligated to specialized plasmid vectors, p14 and p17 (p17 plasmid vector is similar to the p17+ plasmid vector except for the sequence corresponding to SEQ. ID. NO:63), and transformed into *E. coli* DH10B. The plasmid DNA pool for each p14 and p17 3'-represented library was purified (Qiagen, Mississauga, ON) and a 2-mg aliquot of each digested with Not I restriction enzyme, and transcribed in vitro with either T7 RNA polymerase or sp6 RNA polymerase (Ambion, Austin, Tex.). The resulting p14 3'-represented RNA was used directly as "tester RNA" whereas, the p17 3'-represented RNA was used to synthesize first-strand cDNA as described above, which then served as "driver DNA". Each "driver DNA" reaction was treated with RNase A and RNase H to remove the RNA, phenol extracted and desalted before use.

The following 3'-represented libraries were prepared:

Tester 1—RAW 264.7-osteoclast-3' in p14

Tester 2—RAW 264.7-precursor-3' in p14

Driver 1—RAW 264.7-precursor-3' in p17

Driver 2—RAW 264.7-osteoclast-3' in p17

The tester RNA samples were subtracted following the teachings of U.S. Pat. No. 5,712,127 with the corresponding driver DNA in a ratio of 1:100 for either 1- or 2-rounds following the teachings of Malek et al. (U.S. Pat. No. 5,712,127). Additionally, control reactions containing tester RNA and no driver DNA, and tester RNA plus driver DNA but no RNase H were prepared. The tester RNA remaining in each reaction after subtraction was converted to double-stranded DNA, and 5% removed and amplified in a standard PCR reaction for 30-cycles for analytical purposes. The remaining 95% of only the driver plus RNase H subtracted samples were amplified for 4-cycles in PCR, digested with Asc I and Not I restriction enzymes, and one half ligated into the pCATRMAN (SEQ. ID. NO:60) plasmid vector and the other half, into the p20 (SEQ. ID. NO:61) plasmid vector. The ligated materials were transformed into *E. coli* DH10B and individual clones contained in the pCATRMAN libraries were picked for further analysis (DNA sequencing and hybridization) whereas, clones contained in each p20 library were pooled for use as subtracted probes. Each 4-cycles amplified cloned subtracted library contained between 25,000 and 40,000 colonies.

The following cloned subtracted libraries were prepared:

T04-22—tester 1 (osteoclast) minus driver 1 (precursor) (1-round) in pCATRMAN

SL22—tester 1 (osteoclast) minus driver 1 (precursor) (2-rounds) in pCATRMAN

SL22—tester 1 (osteoclast) minus driver 1 (precursor) (2-rounds) in p20

SL27—tester 2 (precursor) minus driver 2 (osteoclast) (2-rounds) in pCATRMAN

SL27—tester 2 (precursor) minus driver 2 (osteoclast) (2-rounds) in p20

A 5-μL aliquot of the 30-cycles PCR amplified subtracted materials described above were visualized on a 1.5% agarose gel containing ethidium bromide and then transferred to Hybond N+ (Amersham Biosciences, Piscataway, N.J.) nylon membrane for Southern blot analysis. Three identical Southern transfers were prepared and were hybridized separately to radiolabeled probes specific to the MMP-9 (matrix metalloproteinase 9; NM_013599.2) and TRAP (tartrate resistant acid phosphatase; NM_007388.1) genes, which are known to be upregulated in osteoclasts, and GAPDH (glyceraldehyde-3-phosphate dehydrogenase; M32599.1), which is a non-differentially expressed house-keeping gene. The results of the hybridization analysis are shown in FIG. 1 where the following lanes contain the following materials:

AO 1—tester 1 RNA plus driver 1 DNA plus RNase H (1-round)

AO 2—tester 1 RNA plus driver 1 DNA plus RNase H (2-rounds)

AP 1—tester 2 RNA plus driver 2 DNA plus RNase H (1-round)

AP 2—tester 2 RNA plus driver 2 DNA plus RNase H (2-rounds)

BO 1—tester 1 RNA plus driver 1 DNA minus RNase H (1-round)

BO 2—tester 1 RNA plus driver 1 DNA minus RNase H (2-rounds)

BP 1—tester 2 RNA plus driver 2 DNA minus RNase H (1-round)

BP 2—tester 2 RNA plus driver 2 DNA minus RNase H (2-rounds)

CO 1—tester 1 RNA minus driver 1 DNA plus RNase H (1-round)

CO 2—tester 1 RNA minus driver 1 DNA plus RNase H (2-rounds)

CP 1—tester 2 RNA minus driver 2 DNA plus RNase H (1-round)

CP 2—tester 2 RNA minus driver 2 DNA plus RNase H (2-rounds)

DP—tester 2 RNA

DO—tester 1 RNA

These results clearly show reduction of the GAPDH mRNA levels, representative of a non-differentially expressed gene, when both driver DNA and RNase H were present in the reactions (complete) (GAPDH panel: Lanes AO 1, AO 2, AP 1 and AP 2) in comparison to the incomplete reactions (GAPDH panel: BO 1, BO 2, BP 1, BP 2, CO 1, CO 2, CP 1 and CP 2). Additionally, there was better subtraction of GAPDH after g-rounds (GAPDH panel: AO 2 and AP 2) compared to 1-round (GAPDH panel: AO 1 and AP 1). On the other hand, the differentially expressed upregulated genes (MMP-9 and TRAP) were enriched in the complete reactions (MMP-9 and TRAP panels: Lanes AO 1 and AO 2) in comparison to the incomplete reactions (MMP-9 and TRAP panels: BO 1, BO 2, CO 1 and CO 2), which showed amounts similar to the intact tester RNA (MMP-9 and TRAP panels: Lane DO).

Based on these results, it was anticipated that the subtracted libraries would be enriched for differentially expressed sequences. Thus, for T04-22 and SL22 libraries, genes up regulated in osteoclasts would be represented whereas, for SL27, the down-regulated genes would be represented.

E—Sequence Identification and Annotation of Clones Contained in the T04-22 and SL22 Subtracted Libraries:

Since GAPDH (see above) was most efficiently subtracted after 2-rounds (SL-22), it was anticipated that this library would be most enriched for differentially expressed osteoclast-related sequences. Thus, more exhaustive DNA sequence analysis was performed on clones contained in SL22 (1536 clones) compared to T04-22 (576 clones).

The individual colonies contained in the T04-22- and SL22-pCATRMAN libraries prepared as described previously were randomly picked using a Qbot (Genetix Inc., Boston, Mass.) into 60 μL of autoclaved water. Then, 42 μL of each was used in a 100-μL standard PCR reaction containing oligonucleotide primers, OGS 1 and OGS 142 and amplified for 40-cycles (94° C. for 10 minutes, 40×(94° C. for 40 seconds, 55° C. for 30 seconds and 72° C. for 2 minutes) followed by 72° C. for 7 minutes) in 96-wells microtitre plates using HotStart™ Taq polymerase (Qiagen, Mississauga, ON). The completed PCR reactions were desalted using the 96-well filter plates (Corning) and the amplicons recovered in 100 μL 10 mM Tris (pH 8.0). A 5-μL aliquot of each PCR reaction was visualized on a 1.5% agarose gel containing ethidium bromide and only those reactions containing a single amplified product were selected for DNA sequence analysis using standard DNA sequencing performed on an ABI 3100 instrument (Applied Biosystems, Foster City, Calif.). Each DNA sequence obtained was given a Sequence Identification Number and entered into a database for subsequent tracking and annotation.

Figure 2:
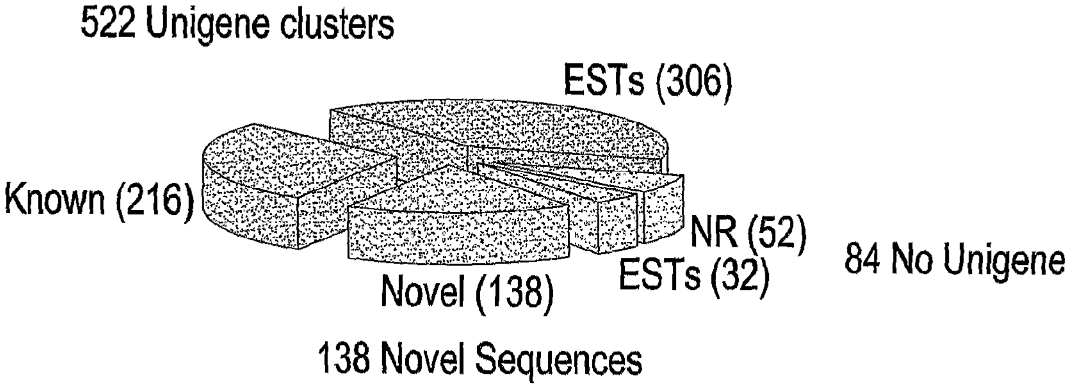
FIG. 2 shows a pie chart annotation of the clones isolated and sequenced from the SL22 subtracted library.

For the purpose of illustrating the ensuing strategies for identification of the clones, only the DNA sequences obtained for clones contained in SL22 will be discussed further. Of those sequences, 1408 were selected for BLAST analysis of public databases (e.g. NCBI), which yielded 744 unique sequences representing a redundancy of approximately 53% and thus, a sufficiently representative sampling of the subtracted library. Absent from these sequences were the standard housekeeping genes (GAPDH, actin, most ribosomal proteins etc.), which was a good indication that the subtracted library was depleted of at least the relatively abundant non-differentially expressed sequences. A limited survey of 96 clones from a corresponding un-subtracted library resulted in largely known and abundant housekeeping sequences such as GAPDH and beta-actin (data not shown). The 744 unique sequences were broadly classified into three categories shown in FIG. 2: 522 genes with Unigene clusters (70.2%), 84 genes with no Unigene cluster (11.3%) and 138 novel sequences (18.5%). Of the Unigene-clustered genes, only 114 were associated with GO (Gene Ontology) functional categories. Thus, it was evident from these results that the subtracted library (SL22) was enriched for known and novel sequences.

Once sequencing and annotation of the selected clones were completed, the next step involved identifying those sequences that were actually upregulated in osteoclasts compared to precursors.

F—Hybridization Analysis for Identifying Upregulated Sequences

The PCR amplicons representing the annotated sequences from the T04-22 and SL22 libraries were used to prepare DNA microarrays. The purified PCR amplicons from contained in 70 μL prepared in the previous section was lyophilized and each reconstituted in 20 μL of spotting solution comprising 3×SSC and 0.1% sarkosyl. DNA micro-arrays of each amplicon in triplicate were then prepared using CMT-GAP2 slides (Corning, Corning, N.Y.) and the GMS 417 spotter (Affymetrix, Santa Clara, Calif.).

The DNA micro-arrays were then hybridized with either standard or subtracted cy3 and cy5 labelled cDNA probes as recommended by the supplier (Amersham Biosciences, Piscataway, N.J.). The standard cDNA probes were synthesized using RAMP amplified RNA prepared from five different murine osteoclast samples and the corresponding precursors. It is well known to the skilled artisan that standard cDNA probes only provide limited sensitivity of detection and consequently, low abundance sequences contained in the cDNA probes are usually missed. Thus, the hybridization analysis was also performed using subtracted cDNA probes. These subtracted cDNA probes were synthesized from in vitro transcribed RNA prepared from the SL22-p20 and SL25-p20 subtracted libraries described above in D. These subtracted libraries may be enriched for low abundance sequences as a result of following the teachings of Malek et al., and therefore, may provide increased detection sensitivity.

All hybridization reactions were performed using the dye-swap procedure as recommended by the supplier (Amersham Biosciences, Piscataway, N.J.). Following analysis of the hybridization results obtained using the standard cDNA probes, 161 of the 744 unique sequences contained in SL22 appeared to be upregulated in the osteoclasts, showing >2-fold difference compared to the precursors. On the other hand, when the subtracted cDNA probes were used, 289 additional SL22-sequences appeared to be upregulated in the osteoclast samples as well.

Thus, it was evident from these results that the SL22 subtracted library was highly enriched for upregulated sequences (>60%), which were probably involved in osteoclastogenesis. A similar analysis was performed for the T04-22 clones, which showed a lower percentage of differentially expressed sequences likely due to insufficient subtraction after only 1-round of the STAR procedure.

G—Determining Osteoclast Specificity of the Differentially Expressed Sequences Identified:

The differentially expressed sequences identified in Section F for both SL22 and T04-22 libraries were tested for osteoclast specificity by hybridization to nylon membrane-based macroarrays. The macroarrays were prepared using RAMP amplified RNA from murine precursors and osteoclasts of five independent experiments, and various normal murine tissues (liver, brain, thymus, heart, lung, testicule, ovary, kidney and embryo) purchased commercially (Ambion, Austin, Tex.). Because of the limited quantities of mRNA available for many of these samples, it was necessary to first amplify the mRNA using the RAMP methodology. Each amplified RNA sample was reconstituted to a final concentration of 250 ng/μL in 3×SSC and 0.1% sarkosyl in a 96-well microtitre plate and 1 μL spotted onto Hybond N+ nylon membranes using the specialized MULTI-PRINT™ apparatus (VP Scientific, San Diego, Calif.), air dried and UV-cross linked. A total of 556 different sequences selected from SL22 and T04-22 were individually radiolabeled with $\alpha$-$^{32}$P-dCTP using the random priming procedure recommended by the supplier (Amersham, Piscataway, N.J.) and used as probes on the macroarrays. Hybridization and washing steps were performed following standard procedures well known to those skilled in the art.

Of the 556 sequences tested, approximately 80% were found to be upregulated in at least the primary osteoclast RNA sample that was used to prepare the subtracted libraries. However, many of these sequences were also readily detected in the different murine tissues. Based on these results, those sequences that appeared to be associated with experimental variability and those that were detected in many of the other murine tissues were eliminated. Consequently, only 73 sequences, which appeared to be highly osteoclast-specific, were selected for biological validation studies. This subset of 73 sequences included sequences present in two or less murine tissues relative to the precursor levels since it is entirely possible that the hybridization signals obtained for these tissues may be due to family members or spliced variants.

Figure 3:
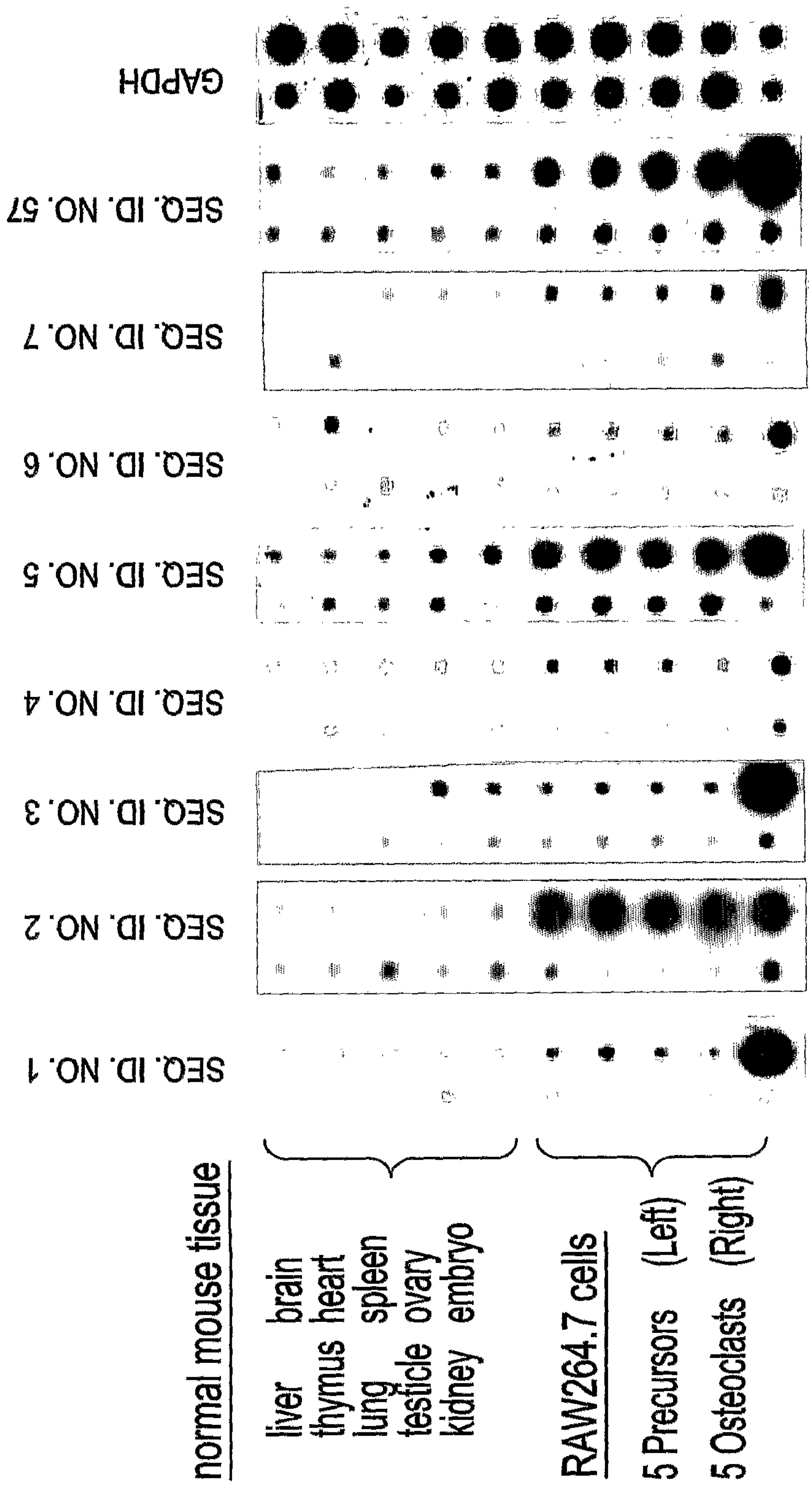
FIG. 3 is a picture illustrating the representative macroarray results of osteoclast specificity of the differentially expressed sequences selected for biological validation.

FIG. 3 shows examples of the macroarray patterns representative of the sequences selected for validation. Subsequently, RNA from 8 additional normal murine tissues (lymph node, eye, prostate, smooth muscle, spinal cord, stomach, uterus and bone marrow) were incorporated into secondary macroarrays and used to further test the specificity of many of the 73 selected sequences (data not shown). Amongst the 73 selected sequences were 41 genes with functional annotation of which, only two were previously linked to osteoclastogenesis (Unigene Clusters Mm.103560 and Mm.271689), 20 genes with no functional annotation and 12 novel sequences (data not disclosed). Representative sequences are characterized as follows:

SEQ. ID. NO:1:

The candidate protein encoded by SEQ. ID. NO:1 is a previously identified gene with the designation, testis-specific protease or Tsp50. The mouse polynucleotide contains an open reading frame of 1317 bp and encodes a polypeptide of 439 amino acids. The human polynucleotide contains an open reading frame of 1155 bp and encodes a polypeptide of 385 amino acids. It was originally described and cloned because of its expression in a hypomethylated region of genomic DNA in human breast cancer cells (Yuan et al., 1999). Analysis of the primary amino acid sequence suggests the presence of an amino-terminal signal peptide that will presumably target the protein to the plasma membrane, a carboxy-terminal transmembrane domain to anchor the protein in the plasma membrane, and a predicted catalytic domain homologous to serine proteases (Shan et al., 2002; Netzel-Arnett et al., 2003). The nature of the predicted catalytic activity and the exact cellular localization of Tsp50 have yet to be conclusively established. Applicant directs the reader's attention to U.S. Pat. No. 6,617,434 (Duffy, Sep. 9, 2003) and U.S. Pat. No. 6,451,555 (Duffy, Sep. 17, 2002) where Tsp50 is the subject matter. Despite all of the above information, no functional association with osteoclasts or bone remodeling disorders has been described prior to the present disclosure.

SEQ. ID. NO:2:

The candidate protein encoded by SEQ. ID. NO:2 is a previously identified gene that encodes the d2 subunit of the vacuolar (V-) ATPase multi-subunit complex. Although the d2 subunit does not span the membrane, it is part of the membrane-spanning complex and interacts directly with the larger a subunit that contains the transmembrane properties (Nishi and Forgac, 2002). The cDNA encoding the mouse V-ATPase d2 protein has recently been described but its function in bone physiology has yet to be established (Nishi et al., 2003). No functional association with osteoclasts or bone remodeling disorders has been described prior to the present disclosure.

SEQ. ID. NO:3:

The candidate protein encoded by SEQ. ID. NO:3 is a previously identified gene that encodes the cartilage-associated protein, Crtap (Morello et al., 1999; Tonachini et al., 1999). The gene was originally cloned from chick embryo and localized to cartilaginous tissues (Morello et al., 1999). No functional association with osteoclasts or bone remodeling disorders has been described prior to the present disclosure.

SEQ. ID. NO:4:

The candidate protein encoded by SEQ. ID. NO:4 is found in current databases and was cloned as part of the RIKEN Genome Exploration Research Group (Kawai et al., 2001). Although the mRNA contains a predicted open reading frame, no function has been assigned to this sequence prior to the present disclosure.

SEQ. ID. NO:5:

The candidate protein encoded by SEQ. ID. NO:5 is found in current databases and was cloned as part of the RIKEN Genome Exploration Research Group (Strausberg et al., 2002). Although the mRNA contains a predicted open reading frame, no function has been assigned to this sequence prior to the present disclosure.

SEQ. ID. NO:6:

The candidate protein encoded by SEQ. ID. NO:6 is found in current databases and was cloned as part of the RIKEN Genome Exploration Research Group (Strausberg et al., 2002). Although the mRNA contains a predicted open reading frame, no function has been assigned to this sequence prior to the present disclosure.

SEQ. ID. NO:7:

The candidate protein encoded by SEQ. ID. NO:7 is a previously identified gene that encodes the linker for activation of B cells. The gene has been reported as playing a role in thymocytes (Janssen et al., 2003). No functional association with osteoclasts or bone resorption disorders has been described prior to the present disclosure.

SEQ. ID. NO:57

The candidate protein encoded by SEQ. ID. NO:57 is a previously identified gene that encodes the jun dimerization protein 2. This gene has been shown to be involved in osteoclastogenesis using antisense technology (Kawaida et al., 2003). This example serves as further proof of concept of applicant's approach in identifying osteoclast-specific genes.

H—Cloning of Full-length cDNAs of Selected Sequences from Osteoclast mRNA:

It was necessary to obtain full-length cDNA sequences in order to perform functional studies of the expressed proteins. Spliced variants are increasingly being implicated in tissue specific functions and as such, it is critically necessary to work with cDNA clones from the system under study. Applicant also recognizes that spliced variants may not always be involved. Thus, the applicant's approach has been to isolate the relevant full-length cDNA sequences directly from osteoclasts in order to identify variants and their potential role with respect to specificity.

Coding cDNA clones were isolated using both a 5'-RACE strategy (Invitrogen, Burlington, ON) and a standard two-primer gene specific approach in PCR. The 5'-RACE strategy used cDNA prepared from cap-selected osteoclast RNA and/or RAMP amplified osteoclast RNA. For amplification using gene specific primers, either cDNA prepared from RAMP RNA or total RNA was used. All cDNAs were synthesized following standard reverse transcription procedures (Invitrogen, Burlington, ON). The cDNA sequences obtained were cloned in *E. coli* DH10B and the nucleotide sequences for multiple clones determined. Thereafter, the cDNA sequences for each set were aligned and the open reading frame(s) (ORF) identified using standard software (e.g. ORF Finder-NCBI). Table 3 shows examples of cDNA clones of spliced variants, which were obtained for some of the sequences under investigation.

I—RNA Interference Studies

RNA interference is a recently discovered gene regulation mechanism that involves the sequence-specific decrease in a gene's expression by targeting the mRNA for degradation and although originally described in plants, it has been discovered across many animal kingdoms from protozoans and invertebrates to higher eukaryotes (reviewed in Agrawal et al., 2003). In physiological settings, the mechanism of RNA interference is triggered by the presence of double-stranded RNA molecules that are cleaved by an RNAse III-like protein active in cells, called Dicer, which releases the 21-23 bp siRNAs. The siRNA, in a homology-driven manner, complexes into a RNA-protein amalgamation termed RISC (RNA-induced silencing complex) in the presence of mRNA to cause degradation resulting in attenuation of that mRNA's expression (Agrawal et al., 2003).

Current approaches to studying the function of genes, such as gene knockout mice and dominant negatives, are often inefficient, and generally expensive, and time-consuming. RNA interference is proving to be a method of choice for the analysis of a large number of genes in a quick and relatively inexpensive manner. Although transfection of synthetic siRNAs is an efficient method, the effects are often transient at best (Hannon G. J., 2002). Delivery of plasmids expressing short hairpin RNAs by stable transfection has been successful in allowing for the analysis of RNA interference in longer-term studies (Brummelkamp et al., 2002; Elbashir et al., 2001). In addition, more recent advances have permitted the expression of siRNA molecules, in the form of short hairpin RNAs, in primary human cells using viral delivery methods such as lentivirus (Lee et al., 2004; Rubinson et al., 2003).

J—Determination of Knockdown Effects on Osteoclastogenesis

The design and subcloning of individual siRNA expression cassettes and the procedure utilized for the characterization of each nucleotide sequence is described below. Selection of polynucleotides were chosen based on their RANK ligand-dependent upregulation in osteoclasts and the selective nature of their expression in osteoclasts compared to other tissues (see sections F and G above). The design of siRNA sequences was performed using web-based software that is freely available to those skilled in the art (Qiagen for example). These chosen sequences, usually 19-mers, were included in two complimentary oligonucleotides that form the template for the short hairpin RNAs, i.e. the 19-nt sense sequence, a 9-nt linker region (loop), the 19-nt antisense sequence followed by a 5-6 poly-T tract for termination of the RNA polymerase III. Appropriate restriction sites were inserted at the ends of these oligonucleotides to facilitate proper positioning of the inserts so that the transcriptional start point is at a precise location downstream of the hU6 promoter. For each sequence selected, at least two different siRNA expression vectors were constructed to increase the chance of observing RNA interference.

The transfection plasmids expressing the siRNAs under the control of the human U6 promoter were constructed as follows. Two primers containing an AseI site (forward) and a KpnI site (reverse) were used to PCR amplify a 330-bp fragment containing the human U6 promoter from 5 ng of human genomic DNA. This fragment was ligated in similarly digested pd2EGFP-N1 (BD Biosciences Clontech, Mississauga, ON) resulting in the replacement of the CMV E1 promoter of pd2EGFP-N1 by the human (h)U6 promoter sequence. Digesting with AgeI and NotI and religating the blunted ends to generate pd2-hU6 accomplished removal of the d2EGFP fragment. The template for the siRNA hairpin was designed by annealing two oligonucleotides yielding a 57-bp fragment blunt at the 5'-end and having a BamHI overhang at the 3'-end. The annealed oligonucleotides were ligated into pd2-hU6 that had been previously digested with KpnI (blunted) and BamHI resulting in pd2-hU6/siRNA. All plasmids were verified by sequencing to confirm presence of the siRNA hairpin sequence and proper positioning of the transcriptional start site following the hU6 promoter.

RAW cells were seeded in 6-well plates in high glucose DMEM containing 10% fetal bovine serum at a density of $6\times10^5$ cells/well, allowed to plate overnight and transfected with 1 μg of pd2-hU6/siRNA plasmid using the Fugene 6 reagent (Roche, Laval, QC). After 16 h of incubation, fresh medium was added containing 400 μg/ml G418 to select for stable transfectants. Control cells were transfected with pd2-hU6. After approximately 10 days, pools and/or individual clones of cells were isolated and analyzed for their ability to form osteoclasts in 96-well plates. The resulting phenotypes were observed microscopically by viewing cells assayed for TRAP staining. The efficacy of RNA interference was also assessed by conducting Northern blots on total RNA isolated from cells subjected to in vitro osteoclastogenesis.

K—Results of RNA Interference Studies

Figure 4A:
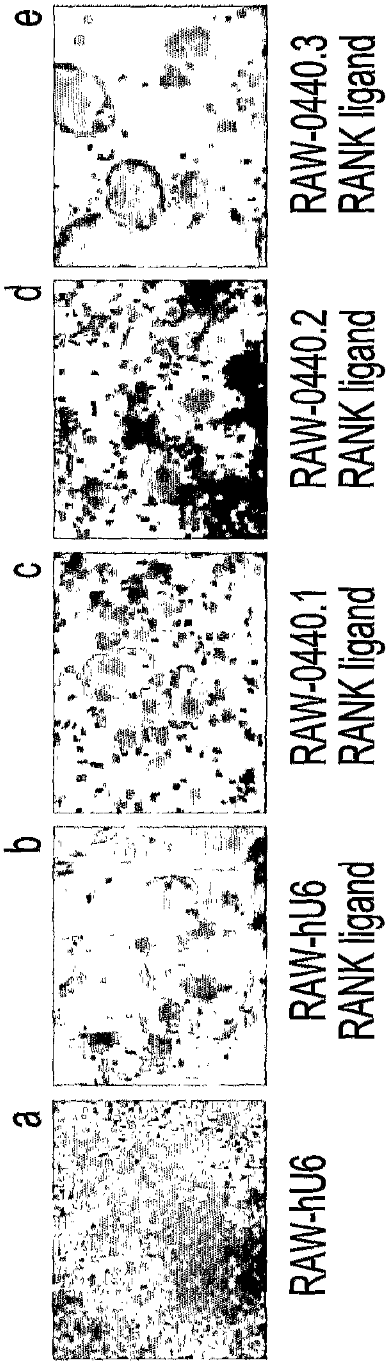
FIG. 4A is a picture showing the phenotypic effect on osteoclast differentiation in the presence of siRNAs specific for SEQ. ID. NO:1.
Figure 4B:
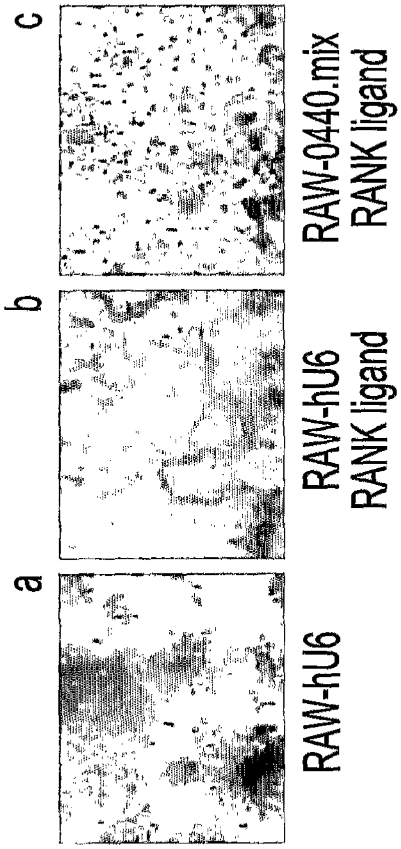
FIG. 4B is a picture showing the phenotypic effect on osteoclast differentiation in the presence of a mixture of siRNAs specific for SEQ. ID. NO:1.

SEQ. ID. NO:1:

The sequences used for RNA interference were derived from the polynucleotide SEQ. ID. NO:1 and have the SEQ. ID. NOs: 64, 65 and 66 (of course other sequences may be used). The cell lines derived from RAW cells transfected with plasmids encoding the three siRNAs pd2-hU6/0440.1, pd2-hU6/0440.2 and, pd2-hU6/0440.3 are designated hereafter as RAW-0440.1 (SEQ. ID. NO.:64), RAW-0440.2 (SEQ. ID. NO.:65), and RAW-0440.3 (SEQ. ID. NO.:66), respectively and collectively as RAW-0440. In addition, as a positive control for normal osteoclastogenesis, RAW cells were transfected with the empty vector (pd2-hU6) that does not contain a siRNA. Phenotypic analysis of all cell lines is shown in FIG. 4A. Panel a of FIG. 4A shows the control cell line, RAW-hU6, in the absence of RANK ligand where the presence of multinucleated osteoclasts is not observed and the undifferentiated RAW cells are completely devoid of TRAP staining. Upon treatment with RANK ligand, large, multinucleated, TRAP positive osteoclasts are seen demonstrating normal differentiation (panel b). The presence of the siRNA specific for SEQ. ID. NO:1 in RAW cells resulted in a greatly reduced ability of these cells to form large and mature osteoclasts in the presence of RANK ligand (panels c-e). In addition to a decreased number of osteoclasts per well, the RAW-0440 cells were smaller and most of exhibited a slight decrease in TRAP staining. Closer inspection revealed that these smaller osteoclasts were multinucleated suggesting normal cellular fusion of the RAW-0440 precursors. Analysis of another RAW cell line, RAW-0440.mix, transfected with an equivalent amount of all three siRNA expression vectors confirmed the previous phenotypic observations. As before, the control cell line transfected with the empty vector formed large multinucleated osteoclasts that stained for TRAP (FIG. 4B, panel b). As shown in panel c, the RAW-0440.mix osteoclasts were multinucleated but small and fewer in number.

Figure 5:
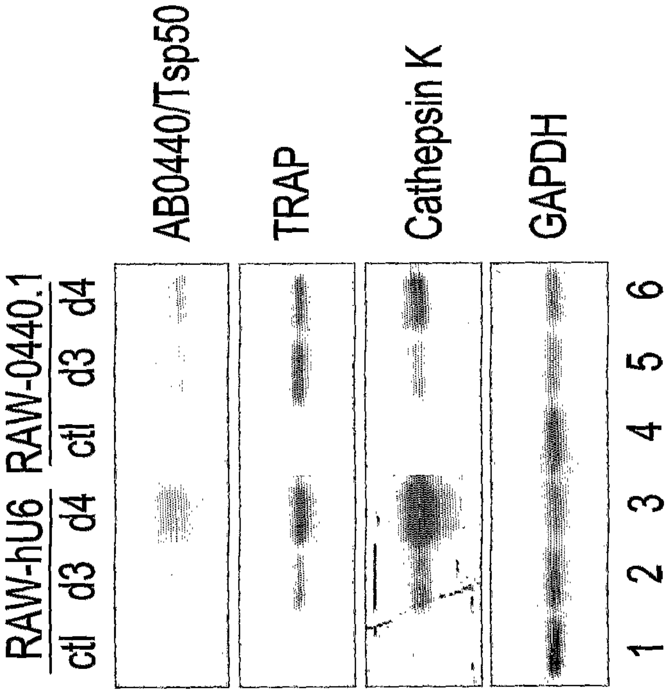
FIG. 5 is a picture of a Northern blot showing the attenuation of SEQ. ID. NO:1 gene expression in RAW cells in the presence of specific siRNAs compared to osteoclast-specific marker genes, TRAP and CTSK.
Figure 5:
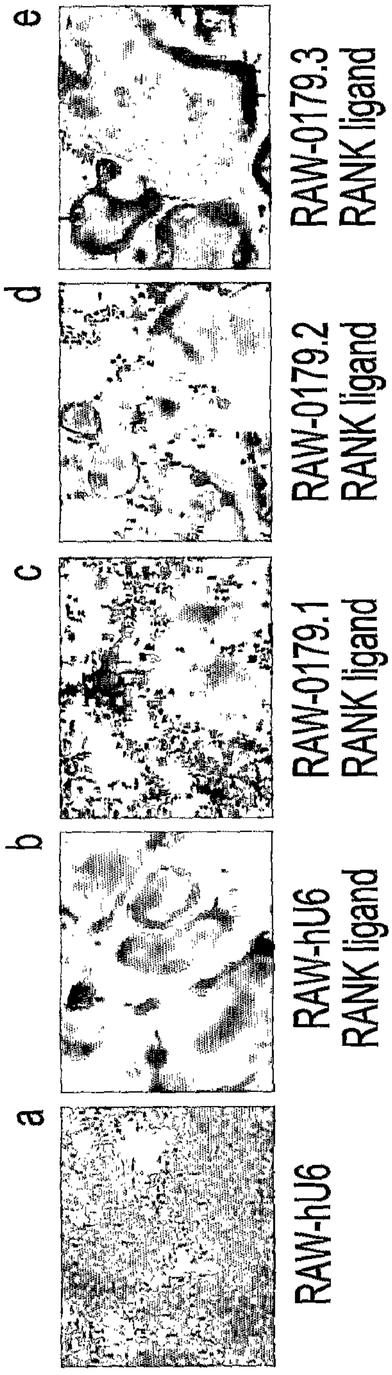

The effect of each siRNA was assessed by isolating total RNA from the mature osteoclasts after 3 and 4 days of RANK ligand treatment and probing with a fragment of the SEQ. ID. NO:1 cDNA to determine if knockdown of endogenous gene expression occurred. A representative experiment is shown in FIG. 5. When 10 μg of total RNA was probed with a fragment of the SEQ. ID. NO:1 cDNA, a single mRNA of 1.7 Kb was observed. A decrease, especially at day 4, in the amount of the SEQ. ID. NO1 mRNA was seen in the RNA isolated from the RAW-0440.1 cell line indicating RNA interference occurred in these cells (FIG. 5, top panel, compare lanes 3 and 6). Similarly, the expression of two known osteoclast marker genes, TRAP and Cathepsin K (Boyle et al., 2003), was significantly reduced in RAW-0440.1 cells (FIG. 5). The osteoclast-specific character of SEQ. ID. NO:1 was evident by the lack of expression in the precursor cells (see lanes 1 and 4). The difference in the expression of the SEQ. ID. NO:1 gene was not due to the difference in the amount of total RNA loaded on the gel as evidenced by the probing of the same membrane with a fragment of the housekeeping gene glyceraldehyde-3-phosphate dehydrogenase (GAPDH, FIG. 5).

These results demonstrate that the absence of physiological levels of SEQ. ID. NO:1 in RAW cells impairs their ability to differentiate into osteoclasts properly and implies an important role for this gene in these cells.

SEQ. ID. NO:2:

The sequences used for RNA interference were derived from the polynucleotide SEQ. ID. NO:2 and have the SEQ. ID. NOs:67, 68 and 69. The cell lines derived from RAW cells transfected with plasmids encoding the three siRNAs pd2-hU6/0179.1, pd2-hU6/0179.2 and, pd2-hU6/0179.3 are hereby-designated RAW-0179.1 (SEQ. ID. NO.:67), RAW-0179.2 (SEQ. ID. NO.:68), and RAW-0179.3 (SEQ. ID. NO.:69), respectively. In addition, as a positive control for normal osteoclastogenesis, RAW cells were transfected with the empty vector (pd2-hU6) that does not contain any siRNA. Phenotypic analysis of all cell lines is shown in FIG. 6. Panel a of FIG. 6 shows the control cell line, RAW-hU6, in the absence of RANK ligand where the presence of multinucleated osteoclasts is not observed and the undifferentiated RAW cells are completely devoid of TRAP staining. Upon treatment with RANK ligand, large and multinucleated, TRAP positive osteoclasts are seen demonstrating normal differentiation (panel b). Two of the siRNAs, namely those encoded by RAW-0179.1 and RAW-0179.2, resulted in a noticeable reduction in the ability of these cells to form large, mature osteoclasts in the presence of RANK ligand (panels c,d). A third siRNA sequence, RAW-0179.3, was not effective (see FIG. 6, panel e). In addition to a decreased number of osteoclasts per well, the RAW-0179.1 and RAW-0179.2 cells were generally smaller and contained less nuclei.

Figure 7:
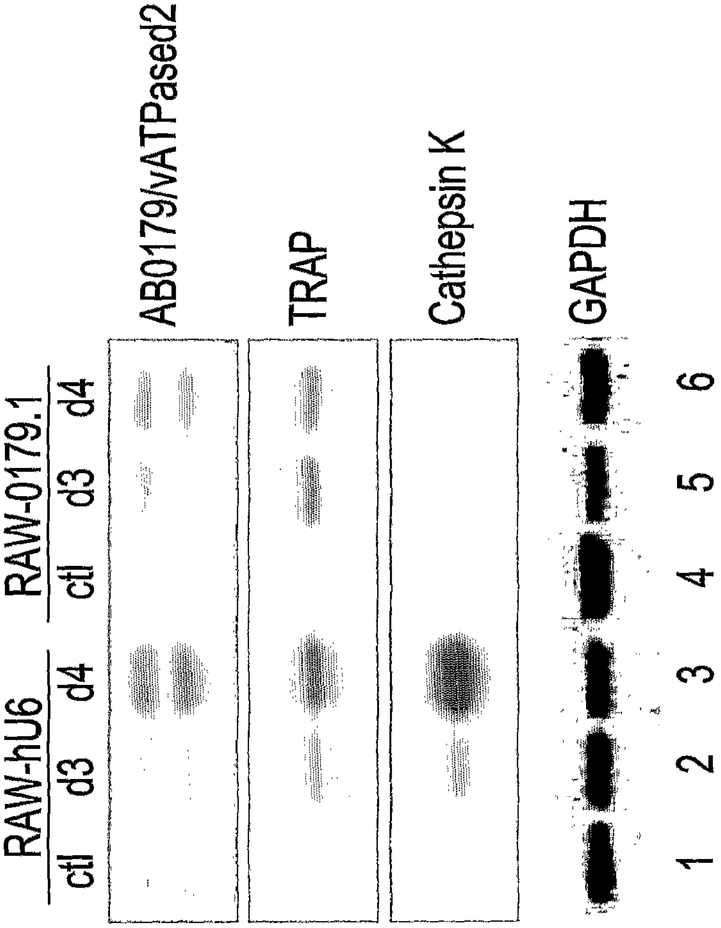
FIG. 7 is a picture of a Northern blot showing the attenuation of SEQ. ID. NO:2 gene expression in RAW cells in the presence of specific siRNAs. Also shown is the effect on the osteoclast-specific marker genes, TRAP and Cathepsin K.

Isolating total RNA from the mature osteoclasts after 3 and 4 days of RANK ligand treatment and probing with a fragment of the SEQ. ID. NO2 cDNA to determine if knockdown of endogenous gene expression occurred assessed the effect of each siRNA. A representative experiment is shown in FIG. 7. When 10 μg of total RNA was probed with a fragment of the SEQ. ID. NO2 cDNA, two mRNAs of 2.3 Kb and 1.6 Kb were observed. A decrease, especially at day 4, in the amount of the SEQ. ID. NO2 mRNA was seen in the RNA isolated from the RAW-0179.1 cell line indicating RNA interference occurred in these cells (FIG. 7, top panel, compare lanes 3 and 6). Furthermore, although the RAW-hU6 precursor cells expressed detectable levels of SEQ. ID. NO2 in the absence of RANK ligand, expression was not seen in RNA from the RAW-0179.1 cells under similar conditions (compare lanes 1 and 4 in FIG. 7, top). Taken together, these results show that effective RNA interference occurred. Two known osteoclast marker genes were also significantly reduced, especially Cathepsin K which was virtually undetectable in RAW-0179.1 cells compared to the control cell line. The difference in the expression of the SEQ. ID. NO2 gene was not due to the difference in the amount of total RNA loaded on the gel as evidenced by the probing of the same membrane with a fragment of the housekeeping gene glyceraldehyde-3-phosphate dehydrogenase (GAPDH, FIG. 7).

These results demonstrate that SEQ. ID. NO2 is required for proper osteoclast differentiation in RAW cells suggesting an important role for this gene in these cells.

SEQ. ID. NO:3:

The sequences used for RNA interference were derived from the polynucleotide SEQ. ID. NO:3 and have the SEQ. ID. NOs:70, 71 and 72. The use of RNA interference as described in the invention for SEQ. ID. NOs1 and 2 was applied to SEQ. ID. NO:3. The results obtained were similar showing that this gene is also required for proper differentiation of RAW osteoclasts. An illustration of this result is depicted in FIG. 8.

SEQ. ID. NO:4:

The sequences used for RNA interference were derived from the polynucleotide SEQ. ID. NO:4 and have the SEQ. ID. NOs:73 and 74. The use of RNA interference as described in the invention for SEQ. ID. NOs1 and 2 was applied to SEQ. ID. NO:4. The results obtained were similar showing that this gene is required for proper differentiation of RAW osteoclasts. An illustration of this result is depicted in FIG. 9.

Figure 10:
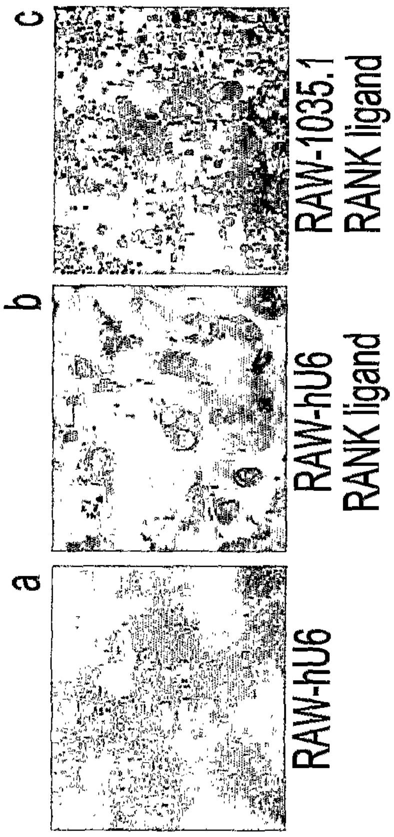
FIG. 10 are pictures illustrating the phenotypic effect on osteoclast differentiation in the presence of siRNAs specific for SEQ. ID. NO:5 panel a; control RAW-hU6 cells, panel b; RAW-hU6 treated with RANK ligand, and panel c; RAW-hU6 treated with RANK ligand and siRNA specific for SEQ ID NO.:5 (RAW-01035.1)

SEQ. ID. NO:5:

The sequences used for RNA interference were derived from the polynucleotide SEQ. ID. NO:5 and have the SEQ. ID. NOs:75 and 76. The use of RNA interference as described in the invention for SEQ. ID. NOs1 and 2 was applied to SEQ. ID. NO:5. The results obtained were similar showing that this gene is required for proper differentiation of RAW osteoclasts. An illustration of this result is depicted in FIG. 10.

Figure 11A:
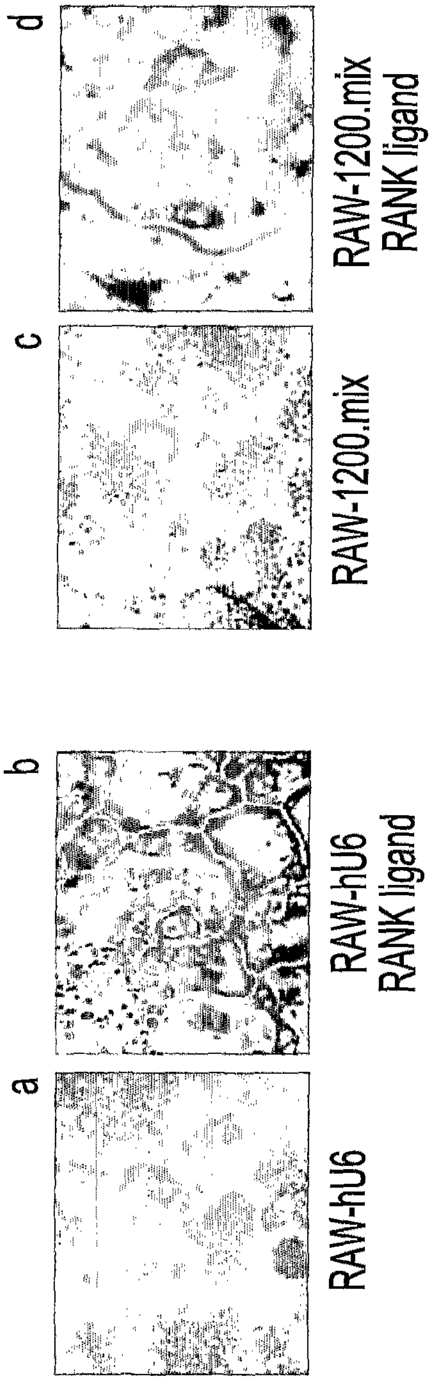
FIG. 11A are pictures illustrating the phenotypic effect on osteoclast differentiation in the presence of siRNAs specific for SEQ. ID. NO:6 panel a; control RAW-hU6 cells, panel b; RAW-hU6 treated with RANK ligand, panel c; RAW-hU6 treated with siRNA specific for SEQ ID NO.:6 (RAW-1200.mix) and panel d; RAW-hU6 treated with RANK ligand and siRNA specific for SEQ ID NO.:6 (RAW-1200.mix)

SEQ. ID. NO:6:

The sequences used for RNA interference were derived from the polynucleotide SEQ. ID. NO:6 and have the SEQ. ID. NOs:77 and 78. The same approach for RNA interference was applied for this sequence with the following modification. The siRNA expression plasmids pd2-hU6/1200.1 and pd2-hU6/1200.2 were transfected as a mixture where equivalent amounts were used. As was observed for SEQ. ID. NO:1, pooling the siRNA expression plasmids produces similar results to those obtained from individual plasmid transfections. Thus, the cell line that was obtained from this transfection was termed RAW-1200.mix (see FIG. 11).

Figure 11B:
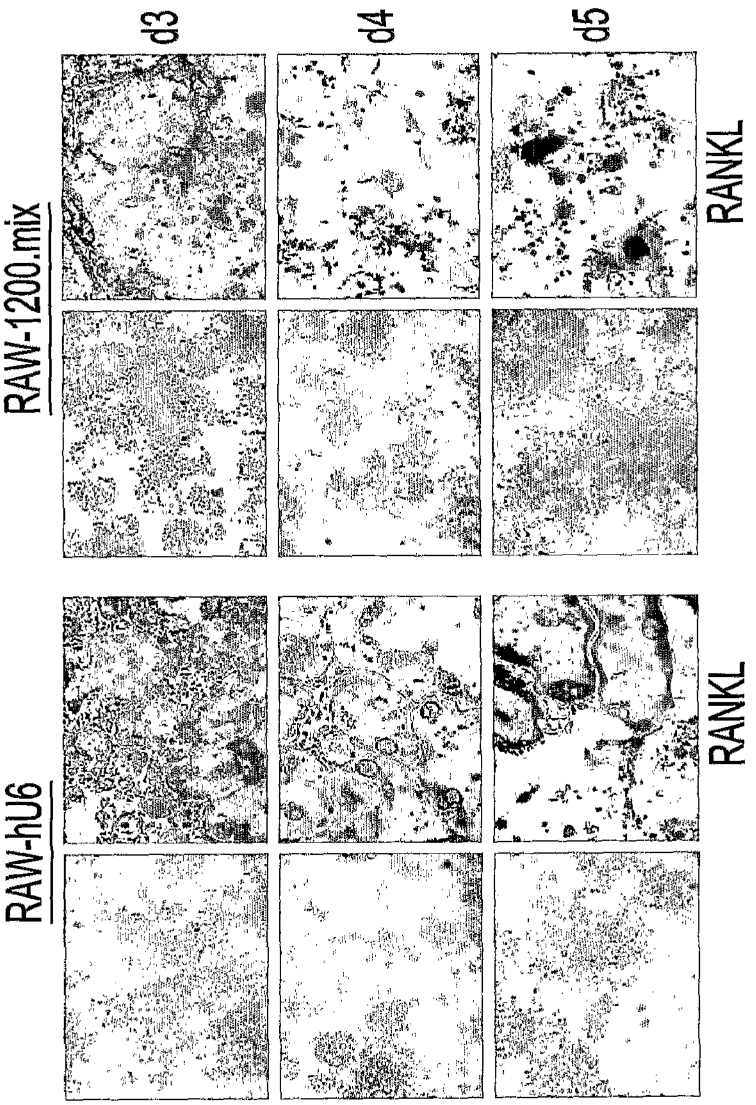
FIG. 11B are pictures illustrating a time-course of the phenotypic effect on osteoclast differentiation of RAW-hU6 observed in the presence or absence of RANK ligand and in the presence or absence siRNAs specific for SEQ. ID. NO:6 (RAW-1200.mix)

Treatment of this cell line with RANK ligand resulted in RAW cells that differentiated sooner than the control cell line, RAW-hU6. In addition, the osteoclasts were larger and contained more nuclei per cell (compare panels b and d in FIG. 11A). The experiment was repeated with TRAP staining conducted at days 3, 4 and 5 five to directly compare the RAW-1200.mix line with the control. As shown in FIG. 11B, the osteoclasts from the RAW-1200.mix cells appeared much sooner and were mature by day 3, a point at which the control RAW cells are just starting to form small multinucleated cells. Furthermore, osteoclasts derived from the RAW-1200.mix cell line seem to have a reduced survival as a decrease in the number of remaining osteoclasts is observed starting at day 4. The control cells are mature by day 4 and many osteoclasts are still present even on day 5.

This result demonstrates that RNA interference of osteoclast-specific genes using the approach of this invention not only identifies those genes that play a role in stimulating osteoclastogenesis, but also serves to validate those candidates that are negative regulators of this process.

Figure 12:
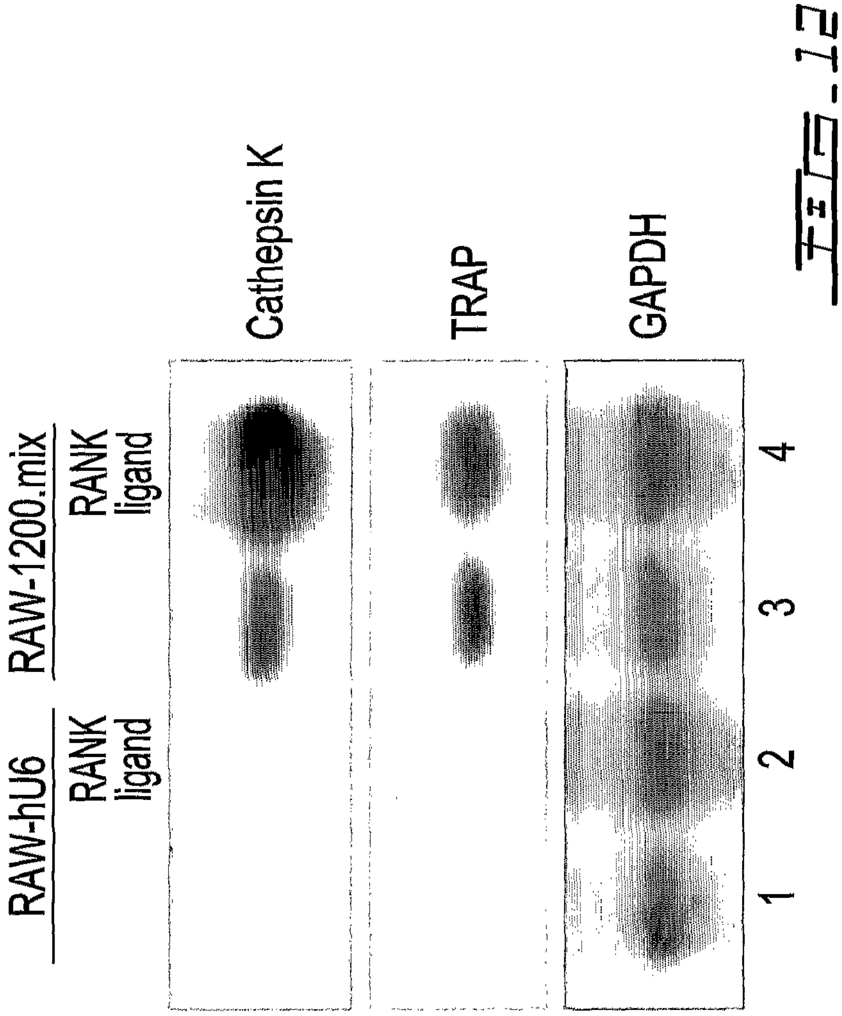
FIG. 12 are pictures illustrating the stimulation of the osteoclast-specific marker genes, TRAP and Cathepsin K, in RAW cells expressing specific siRNAs for SEQ. ID. NO:6 in the presence or absence of RANK ligand.

To further substantiate the observations described above, Northern blot analysis was conducted on the total RNA isolated from the RAW-1220.mix cell line and compared to the control RAW-hU6. The blot was initially probed with a fragment of the SEQ. ID. NO:6 cDNA but the message was almost undetectable by this method. The same blot was probed for the osteoclast marker genes, TRAP and Cathepsin K, as before. As shown in FIG. 12, the expression of TRAP was significantly increased in the RAW-1200.mix cells in agreement with the phenotypic observation. Cathepsin K was also upregulated albeit to a lesser extent. Again, GAPDH demonstrated that equal amounts of RNA were loaded in each lane. These results, like those from the osteoclastogenesis experiments, suggest that SEQ. ID. NO:6 is a negative regulator of osteoclast differentiation in RAW cells.

SEQ. ID. NO:7:

The sequences used for RNA interference were derived from the polynucleotide SEQ. ID. NO:7 and have the SEQ. ID. NOs:79 and 80. The use of RNA interference as described in the invention for SEQ. ID. NOs1 and 2 was applied to SEQ. ID. NO:7. The results obtained (data not shown) were similar to those of SEQ. ID. NO:6 showing that knock-down of this gene resulted in an increase in osteoclast differentiation suggesting that SEQ. ID. NO:7 is a negative regulator of this process in RAW cells.

Figure 13:
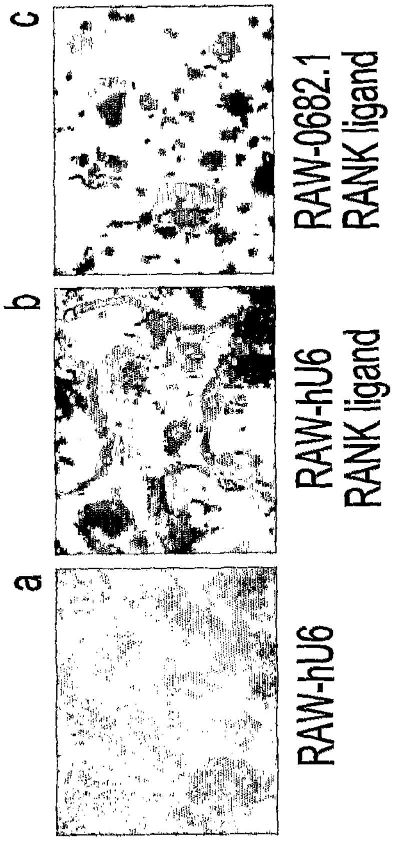
FIG. 13 are pictures illustrating the phenotypic effect on osteoclast differentiation in the presence of siRNAs specific for SEQ. ID. NO:8, panel a; control RAW-hU6 cells, panel b; RAW-hU6 treated with RANK ligand, and panel c; RAW-hU6 treated with RANK ligand and siRNA specific for SEQ ID NO.:8 (RAW-0682.1)

SEQ. ID. NO:57:

The sequences used for RNA interference were derived from the polynucleotide SEQ. ID. NO:57 and have the SEQ. ID. NOs:81 and 82. The use of RNA interference as described in the invention for SEQ. ID. NOs1 and 2 was applied to SEQ. ID. NO:57. The results obtained were similar showing that this gene is required for proper differentiation of RAW osteoclasts. An illustration of this result is depicted in FIG. 13.

L—Determination of Knockdown Effects on Bone Resorption

The functionality of the identified osteoclast-specific sequences was explored by seeding the cells on Osteologic™ (BD Biosciences, Mississauga, ON) discs to measure their bone resorptive activity. Osteologic™ discs are commercially available and contain a synthetic calcium phosphate substrate and are well known to the skilled artisan as a model for bone degradation.

RAW cells were seeded in 24-well plates containing a calcium phosphate-coated disc (Osteologic™) at a density of 35 000 cells/well. Treatment with differentiation medium containing 100 ng/ml RANK ligand was carried out for 5 days where after the osteoclasts were stained for TRAP expression as described above to determine the position and number of multinucleated cells. Osteoclasts were removed with bleach and stained with 5% silver nitrate according to manufacturer's modified von Kossa method. Resorbed pits were observed microscopically. The percentage of resorbed surface area is determined by scanning the negative image of the disc and using Photoshop™ (Adobe) to calculate the percentage of black pixels at maximum contrast. The control, RAW-hU6, was set to the value of 1 and the maximal amount of resorption that was observed with the RAW-hU6 cell line in the presence of RANK ligand was set to 100%.

Figure 14A:
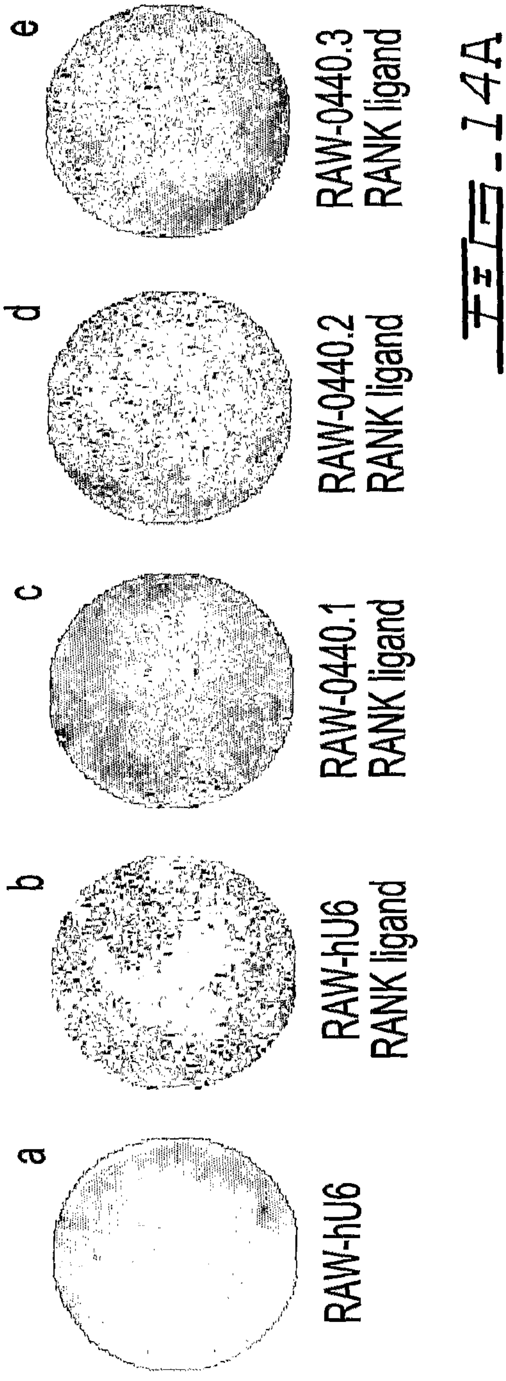
FIG. 14A are pictures illustrating the reduced resorptive activity of osteoclasts expressing specific siRNAs for SEQ. ID. NO:1 panel a; control RAW-hU6 cells, panel b; RAW-hU6 treated with RANK ligand, panel c; RAW-hU6 treated with RANK ligand and siRNA specific for SEQ ID NO.:1 (RAW-0440.1), panel d; RAW-hU6 treated with RANK ligand and siRNA specific for SEQ ID NO.:1 (RAW-0440.2) and panel e; RAW-hU6 treated with RANK ligand and siRNA specific for SEQ ID NO.:1 (RAW-0440.3)
Figure 14B:
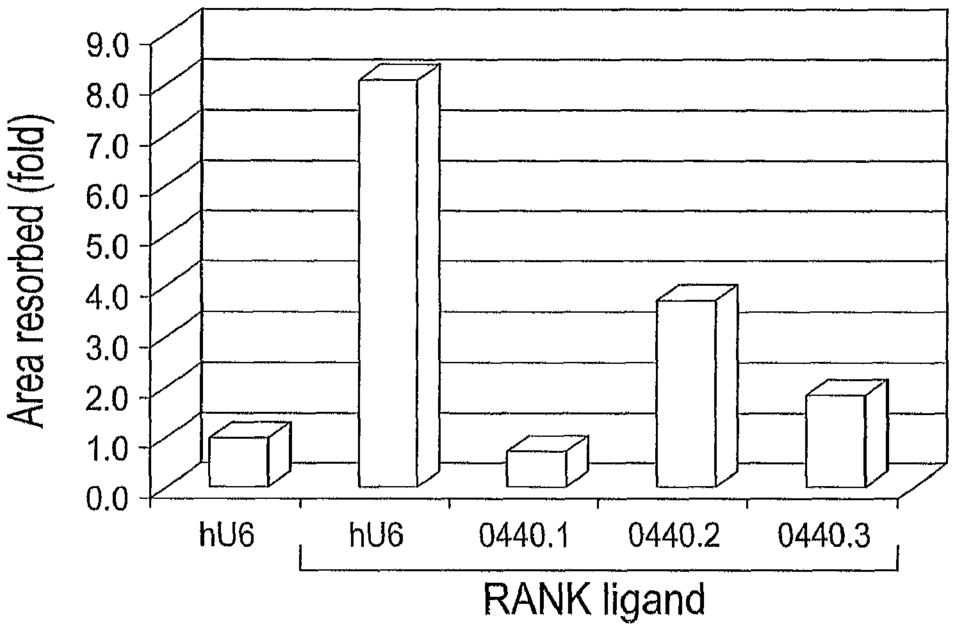
FIG. 14B is an histogram illustrating the results of FIG. 14A in a quantitative manner.

SEQ. ID. NO:1:

In order to determine if the function of the RAW-0440 cell lines were affected by knockdown of SEQ. ID. NO:1, the cells were cultured and differentiated on Osteologic™ discs. An equal number of RAW cells was seeded on each disc and treated with RANK ligand for a period of 4 days before being fixed and stained by the manufacturer's modified von Kossa method that stains the calcium phosphate substrate. White areas on the disc indicate osteoclast resorption. As shown in FIG. 14A, the control cell line, RAW-hU6, did not cause a large increase in the resorbed area on the disc (panel a) but treatment of RANK ligand to induce osteoclastogenesis resulted in a significant amount of substrate being degraded by the osteoclasts (panel b). All three RAW-0440 cell lines had a reduced ability to degrade the substrate and the discs had a larger area of unresorbed calcium phosphate substrate (panel c-e). The results are shown in FIG. 14B. The values (% black pixels) for the total resorbed area for osteoclasts from the RAW-0440.1, RAW-0440.2, and RAW-0440.3 cell lines were 8.7%, 45.9%, and 22.2%, respectively. These results indicate that targeting the SEQ. ID. NO:1 gene in osteoclasts has the effect of reducing their ability to resorb bone substrate.

Figure 15A:
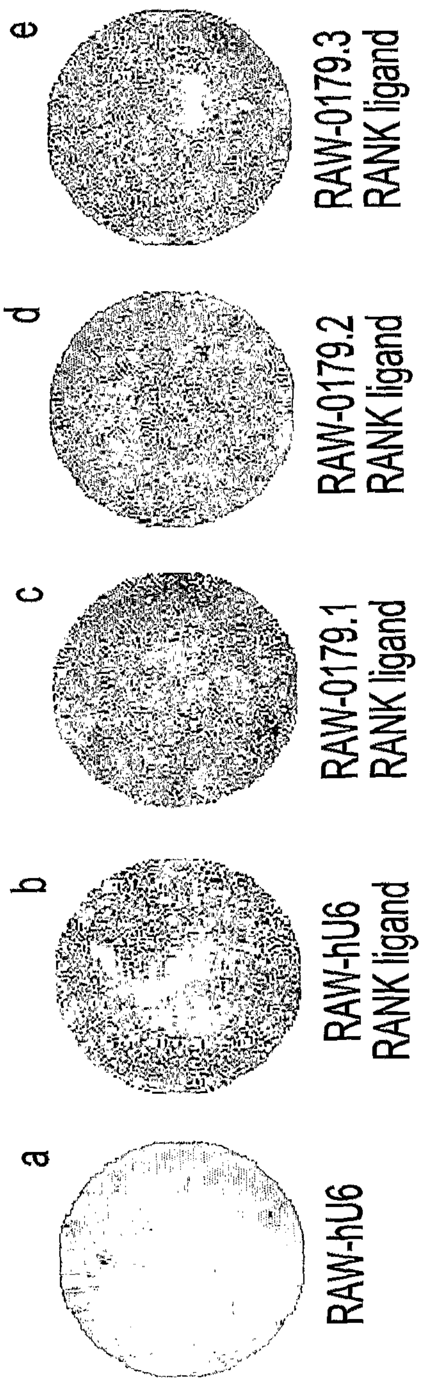
FIG. 15A shows the reduced resorptive activity of osteoclasts expressing specific siRNAs for SEQ. ID. NO:2 panel a; control RAW-hU6 cells, panel b; RAW-hU6 treated with RANK ligand, panel c; RAW-hU6 treated with RANK ligand and siRNA specific for SEQ ID NO.:2 (RAW-0179.1), panel d; RAW-hU6 treated with RANK ligand and siRNA specific for SEQ ID NO.:2 (RAW-0179.2) and panel e; RAW-hU6 treated with RANK ligand and siRNA specific for SEQ ID NO.:2 (RAW-0179.3)
Figure 15B:
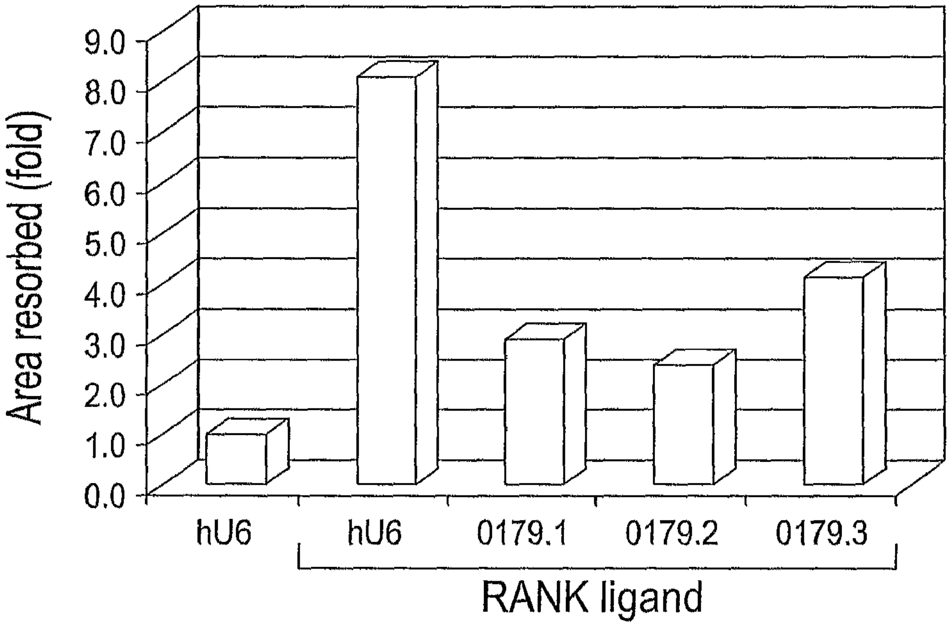
FIG. 15B is an histogram illustrating the results of FIG. 15A in a quantitative manner.

SEQ. ID. NO:2:

The approach used for SEQ. ID. NO:1 was used to analyze the RAW-0179 cell lines. As illustrated in FIG. 15, the osteoclasts exhibited a reduced ability to resorb the substrate (FIG. 15A). Quantitative analysis of the remaining material on the discs showed that total resorbed area was 36.1%, 29.4, and 51.2% for the RAW-0179.1, RAW-0179.2, and RAW-0179.3 cell lines, respectively (FIG. 15B). These results indicate that targeting the SEQ. ID. NO:2 gene in osteoclasts has the effect of reducing their ability to resorb bone substrate.

Figure 16B:
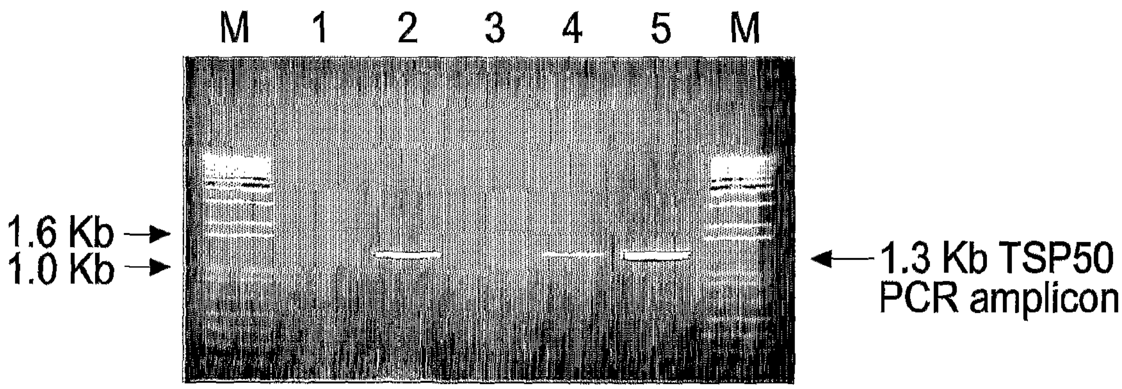
FIG. 16B is a picture of an agarose gel of RT-PCR-amplified SEQ ID NO.:1 in human precursor and osteoclast samples.

M—Differential Expression of Human Orthologues of Some of the Murine Osteoclast-specific Sequences:

The human orthologues for some of the murine osteoclast-specific genes have been isolated using gene specific primers for RT-PCR amplification and cloning of the corresponding double-stranded cDNA from mRNA of human osteoclasts and their differential expression pattern measured using RNA from human CD34+ precursor and osteoclasts. Also, their tissue specificity was determined using RNA from 30 different human tissues (adrenal, breast, jejunum, trachea, liver, placenta, aorta, brain, lung, adrenal cortex, esophagus, colon, ovary, kidney, prostate, thymus, skeletal muscle, vena cava, stomach, small intestine, heart, fallopian tube, spleen, bladder, cervix, pancreas, ileum, duodenum, thyroid and testicule) purchased from Ambion (Austin, Tex.). All RNA samples were amplified using RAMP and macroarrays were prepared as described in Section G. Each human orthologue cDNA was radiolabeled with $\alpha$-$^{32}$P-dCTP using a random priming procedure as specified by the supplier (Amersham, Piscataway, N.J.) and used as probe against the RNA present on the macroarrays. Hybridization and washing steps were performed following standard procedures well known in the art. FIG. 16A shows examples of the differential expression of human orthologues for SEQ. ID. NO:2 and SEQ. ID. NO:4 in the various tissues and osteoclasts samples represented on the macroarrays. However, in the case of SEQ. ID. NO:1, the hybridization signal on the macroarray was undetectable due to the relatively low abundance of this sequence. As such, standard RT-PCR with gene specific primers for human TSP50 was performed on human precursor and osteoclast samples in order to measure its expression (FIG. 16B). The 1.3 Kb TSP50 PCR amplicon was detected in the human osteoclast samples for both donor 1 and donor 4 (FIG. 16B, Lanes 2 and 4 respectively) but not the corresponding precursor samples (FIG. 16B, Lanes 1 and 3 respectively). The 1.3 Kb PCR amplicon was confirmed by sequence analysis as TSP50. It is evident from these results that the human orthologues of some of the murine selected osteoclast-specific sequences are similarly upregulated in the human CD34+ derived osteoclasts and are also highly specific. Thus, these results suggest that the use of the murine RAW264.7 model to identify osteoclast-specific genes involved in human osteoclastogenesis is a valid strategy.

N—Biological Validation of the Human Orthologue for SEQ. ID. NO. 1 (SEQ. ID. NO. 88) in Osteoclastogenesis.

In order to validate the biological significance of the human orthologue for SEQ. ID. NO. 1 (SEQ. ID. NO.88), it was important to demonstrate that the function observed in the mouse osteoclast model for SEQ. ID. NO. 1 was conserved in human osteoclasts. Unlike the mouse model where a cell line could be used for osteoclast differentiation, no equivalent model exists in humans. Thus, validation studies were conducted in human primary bone marrow cells using a commercial lentiviral short hairpin (sh) RNA delivery system as described by the manufacturer (Invitrogen, Burlington, ON) unless otherwise stated. The siRNA sequence, 5'-CTGCCTGATCTGGCGTGAT-3' (SEQ ID. NO. 90) was used to specifically target SEQ. ID. NO. 88, the coding sequence of which was cloned from a human osteoclast cDNA library in-house.

A template for the expression of the shRNA was cloned into the lentiviral expression vector and co-transfected in 293FT cells with expression vectors for the viral structural proteins. After two days, supernatants containing the lentivirus were collected and stored at −80° C. After titering, 20 MOIs (multiplicity of infection) were used to infect human osteoclast precursors purchased from Cambrex (East Rutherford, N.J.). The following day, the medium was replaced with fresh medium containing RANK ligand to initiate osteoclast differentiation. Approximately 7 days later, the cells were fixed and TRAP staining performed as described in section B—Preparation of osteoclast differentiated cells. In parallel, lentiviral particles containing a control shRNA against β-galactosidase were also used to infect the human osteoclast precursor cells.

Figure 17:
FIG. 17 is a picture illustrating the phenotypic effect on osteoclast differentiation in the presence of siRNAs specific for the human orthologue for SEQ ID NO.:1 (SEQ. ID. NO:88) right panel; control siRNA, left panel AB0440 siRNA.

FIG. 17 shows that infection of human bone marrow cells with lentiviruses expressing the specific shRNA for SEQ. ID. NO. 88 (AB0440 siRNA) resulted in a marked decrease of TRAP-positive multinucleated osteoclasts compared to human bone marrow cells infected with lentiviruses expressing the control shRNA (control siRNA) (see arrows in left panel of FIG. 17) in the presence of RANK ligand. These results were in agreement with the validation results obtained in the mouse model (section K-Results of RNA Interference studies) and thus, evidence that the human orthologue for SEQ. ID. NO. 1 (SEQ. ID. NO. 88) plays a similarly important role in differentiation of human osteoclasts.

O—A Functional Complementation Assay for SEQ. ID. NO. 88 to Screen for Inhibitors of Osteoclastogenesis.

A complementation assay was developed to test the function of SEQ. ID. NO. 88 in the differentiation of mouse osteoclasts from RAW264.7 cells devoid of the corresponding endogenous mouse protein. The RAW264.7 cell line containing the mouse-specific shRNA (RAW-AB0440si) for SEQ. ID. NO. 1, which showed greatly reduced ability to differentiate into mature osteoclasts, was transfected with an eukaryotic expression vector containing the entire coding sequence for SEQ. ID. NO. 88, termed Ip200-hAB0440. This Ip200 expression vector (SEQ. ID. NO. 91) was modified from a commercial vector, pd2-EGFP-N1 (Clontech, Mountain View, Calif.) where the NEO-KAN antibiotic cassette was replaced by a hygromycin resistance gene for selection in mammalian cells and an ampicillin resistance gene for propagation in prokaryotes. Expression of the inserted human gene sequence is under control of a strong CMV promoter in Ip200. Approximately $2.5\times10^5$ RAW-0440si cells/well were seeded in 6-well plates and transfected with either 1 μg Ip200 or Ip200-hAB0440 using Fugene 6 (Roche, Laval, QC), and stable transfectants selected for 5 days in the presence of 50 μg/ml hygromycin. Two RAW 264.7-0440si stable cell lines were selected—one that expressed SEQ. ID. NO. 88 (Ip200-hAB0440) and the other containing only the vector (Ip200). After expansion of these two cell lines, 4 000 cells/well for each were seeded in 96-well plates and left either untreated or treated for 4 days with 100 ng/ml RANK ligand. The cells were fixed and stained for TRAP expression in order to visualize mature osteoclasts.

Figure 18:
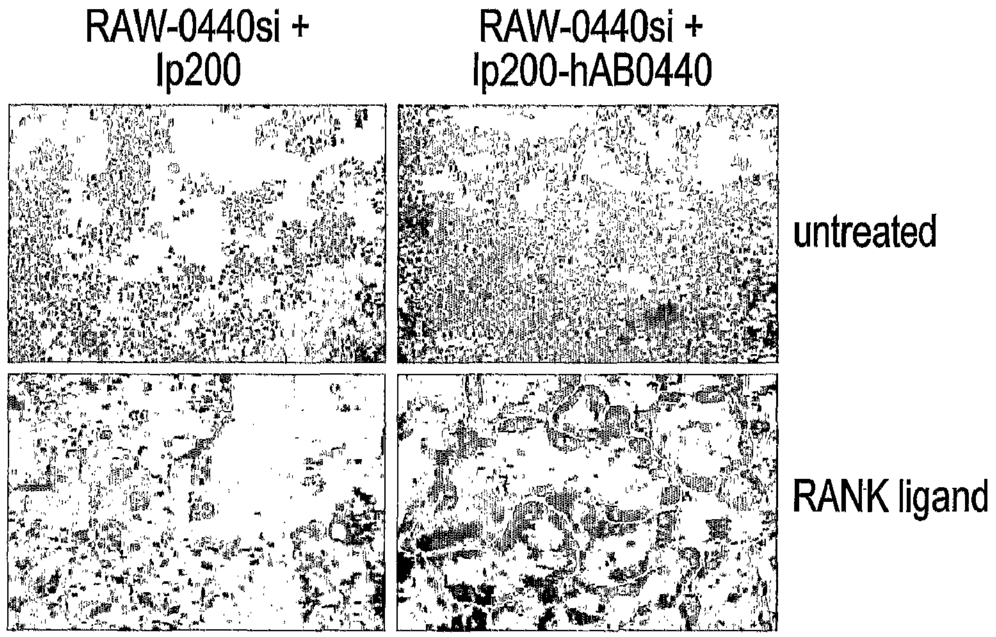
FIG. 18 are pictures illustrating the efficiency of the functional complementation assay for SEQ. ID. NO. 88 to screen for inhibitors of osteoclastogenesis.

FIG. 18 shows that the RAW-0440si cells transfected with only the empty Ip200 vector were unable to efficiently form osteoclasts (left panels). Conversely, the cells transfected with Ip200-hAB0440 (SEQ. ID. NO. 88) were rescued (complemented) and thus, differentiated in response to RANK ligand treatment into osteoclasts (right panels). These results confirm that the function for the mouse and human sequences corresponding to SEQ. ID. NO. 1 is conserved and essential for osteoclast differentiation.

Thus, it is anticipated that this type of complementation cell-based assay may serve as the basis for screening compounds capable of binding to and inhibiting the function of SEQ. ID. NO. 88. A compound library may be applied to this ‘rescued’ cell line in order to identify molecules (small molecule drugs, peptides, or antibodies) capable of inhibiting the complementation effect of SEQ. ID. NO. 88. Consequently, any measurable reduction in osteoclast differentiation would be indicative of compounds that attenuate the complementation activity of SEQ. ID. NO. 88 in the assay. It is further anticipated that this assay format may be applicable to any gene required for differentiation of RAW264.7 cells into osteoclast, which may be used for drug screening.

P—The Human Orthologue Protein of SEQ. ID. NO. 1 (SEQ. ID. NO. 88) is Membrane-Bound and Glycosylated.

It is contemplated in the literature that SEQ. ID. NO. 88 may encode a membrane-bound or secreted protease, termed Tsp50. In order to determine if the polypeptide for SEQ. ID. NO. 88 is truly membrane-bound or secreted, a plasmid (pCMX-HA-hAB0440) containing the entire coding sequence for SEQ. ID. NO. 88 was constructed. The expression vector, pCMX-HA (SEQ. ID. NO. 92) contains a strong CMV promoter for expression of the HA epitope and cDNA insert. Approximately, $2.5\times10^5$ Cos-7 cells/well were seeded in 6-well plates and transiently transfected with 1 mg of the pCMX-HA-hAB0440 expression plasmid using Fugene 6 (Roche, Laval, QC). Cells in some wells were not treated (−) while others were treated with either 2 mg/ml tunicamycin (T) for 24 hours or 0.5 units/ml phosphoinositol phospholipase C (P) for 1 hour. Tunicamycin blocks the reaction of UDP-GlcNAc and Dol-P in the first step of glycoprotein synthesis, thus inhibiting the synthesis of all N-linked glycoproteins. Phosphoinositol phospholipase C specifically cleaves glycosyl-phosphoinositol (GPI) linkages, which releases GPI anchored proteins into the surrounding medium. The expressed HA fused polypeptide for SEQ. ID. NO. 88 was detected by Western blot analysis with an anti-HA antibody (Sigma, St. Louis, Mo.). Following lysis of the pCMX-HA-hAB0440-Cos-7 cells, soluble fractions were prepared, separated on a SDS-polyacrylamide gel and transferred to a PVDF membrane. The protein blot was then incubated with anti-HA antibody for 1 hour and the bands visualized using the ECL kit from Roche (Laval, QC). The same Western blot was stripped and reacted with an anti-actin antibody to control for equal loading of protein samples.

Figure 19:
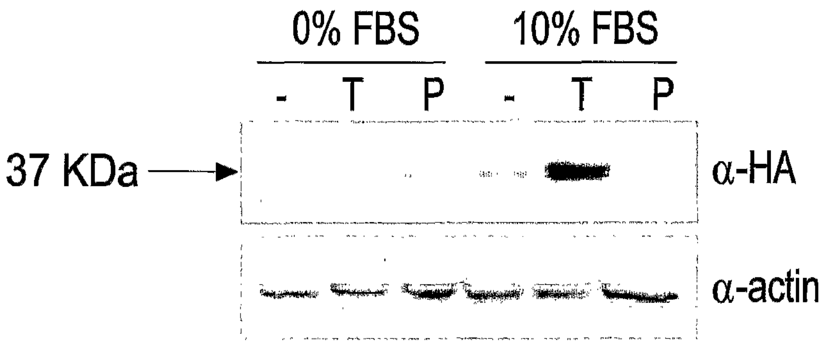
FIG. 19 is a picture of a Western blot from cell lysate obtained from cells expressing a SEQ ID NO.:88 fusion protein and treated or not with tunicamycin or phosphoinositol phospholipase C.

FIG. 19 shows a polypeptide with a predicted size of 37 KDa corresponding to the full-length polypeptide for SEQ. ID. NO. 88. Interestingly, expression of this polypeptide was only observed when the transiently transfected cells were treated with tunicamycin in the presence of 10% FBS in the culture media compared to serum-starved cells (0% FBS) (FIG. 19, Lanes T). This finding suggested that inhibition of N-linked glycosylation resulted in trapping of the SEQ. ID. NO. 88 polypeptide within the cells, which is evidence that the protein is glycosylated. Following treatment with phosphoinositol phospholipase C, the SEQ. ID. NO. 88 polypeptide was no longer detected in the soluble fraction (FIG. 19, Lanes P), which suggested that it was released into the media likely due to cleavage of the proposed GPI linkage. As a control for equal loading, the membrane was stripped and reacted with an antibody against the housekeeping protein, α-actin, which showed that the observed differences in expression of the SEQ. ID. NO. 88 polypeptide was not a result of unequal loading of the gel (FIG. 19, α-actin panel).

Q—Inhibition of RAW264.7 Differentiation into Osteoclast Using a Monoclonal Anti-Tsp50 (SEQ. ID. NO. 1) Antibody.

In light of the results demonstrating that of the polypeptide for SEQ. ID. NO. 88 (depicted in SEQ ID NO.:153) is essential for osteoclast differentiation (see Example N) and it is localized at the cell surface (see Example P), then this protein represents an excellent candidate for the development of an antibody therapeutic strategy for treating the symptoms of osteoporosis. A monoclonal antibody against mouse Tsp50 (R&D Systems, Minneapolis, Minn.) was purchased and used to test whether or not a specific antibody against the polypeptide for SEQ. ID. NO. 1 (depicted in SEQ ID NO.:93) would inhibit osteoclast differentiation in the RAW 264.7 model. Approximately, 4 000 RAW264.7 cells/well were seeded in 96-well plates and treated with 100 ng/ml RANK ligand in the presence of increasing concentrations of either the mouse monoclonal antibody against Tsp50 or a control anti-HA antibody (Sigma, St. Louis, Mo.). Three days later, the cells were fixed and stained for TRAP expression and the multinucleated cells were scored.

Figure 20A:
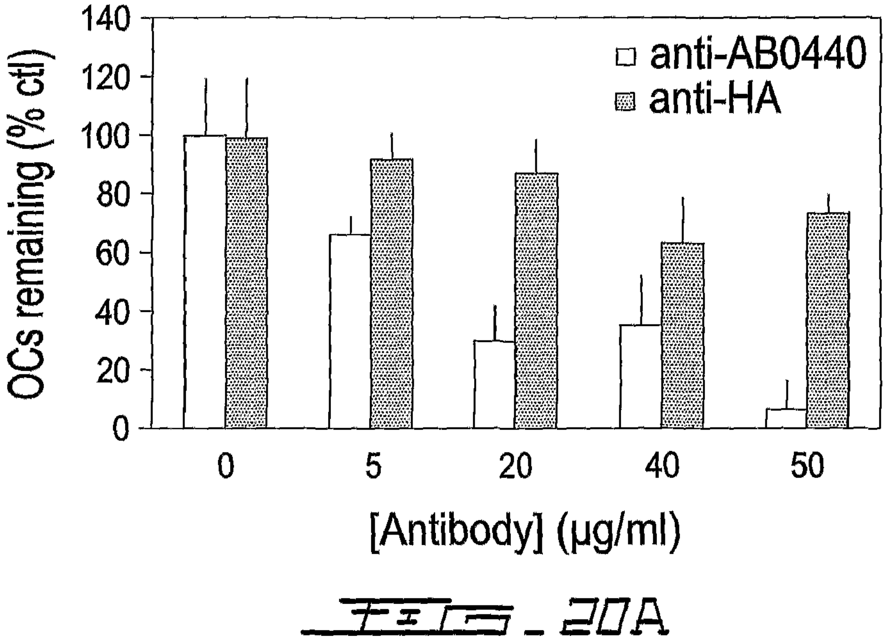
FIG. 20A is an histogram quantifying the inhibition of RAW264.7 differentiation into osteoclast using a monoclonal anti-Tsp50 (SEQ. ID. NO. 1) antibody.
Figure 20B:
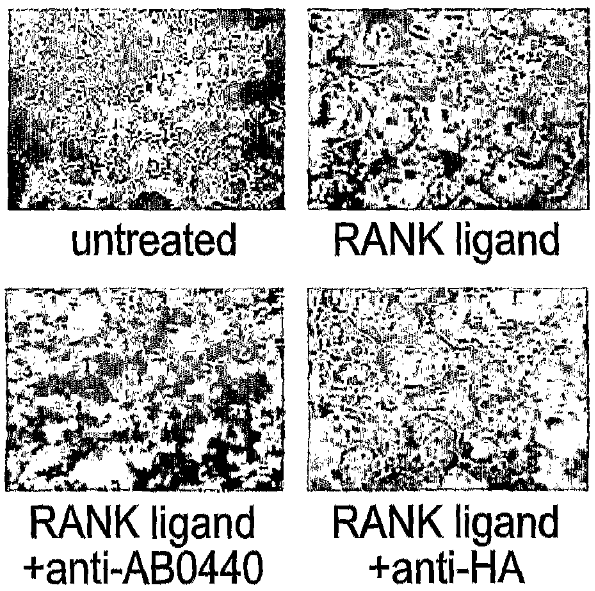
FIG. 20B are pictures representing the phenotypic inhibition of RAW264.7 differentiation into osteoclast using a monoclonal anti-Tsp50 (SEQ. ID. NO. 1) antibody

FIG. 20A is a histogram showing that increasing concentrations of anti-Tsp50 antibody (anti-AB0440) resulted in a dose-dependent decrease in the number of multinucleated osteoclasts with maximal inhibition seen at 50 mg/ml. Whereas, treatment of the RAW264.7 cells with equivalent concentrations of the anti-HA antibody resulted in no statistically significant effect. FIG. 20A represents an average of two experiments conducted in triplicate. Treatment with the anti-AB0440 did not result in death of the RAW264.7 cells but rather, inhibition of differentiation as measured by the loss in mature osteoclasts seen after TRAP staining and no significant reduction in precursor cell numbers (FIG. 20B). These results indicate that antibodies which specifically target osteoclast-specific cell surface or secreted proteins required for differentiation, as exemplified by anti-AB0440, have the potential to serve as therapeutic drugs for treating osteoporosis by reducing osteoclast numbers and consequently, bone resorption activity. It is contemplated that recombinant and/or monoclonal antibodies developed to the polypeptide for SEQ. ID. NO. 88 may function similarly to anti-AB0440 seen for the mouse model in this example.

R—Development of a Functional Interaction Assay to Screen for Inhibitors of Osteoclast Activity Using SEQ. ID. NO. 2 as a Model.

SEQ. ID. NO. 2 (AB0179) belongs to an osteoclast-specific vacuolar (v)-ATPase, a large protein complex containing several subunits. The v-ATPase a subunit comprises four isoforms (a1-a4), which constitutes the $V_0$ domain. This domain is important for the hydrolysis of ATP in order to provide the energy required for the secretion of protons across the plasma membrane into the pocket that is created between the ruffled membrane of the mature osteoclast and the bone surface. In osteoclasts, the a3 subunit interacts with the d subunit, which is important for the structural integrity of the ATPase complex (Nishi and Forgac, 2002). There are two d subunits in humans, d1 and d2, the latter found almost exclusively in osteoclasts and is coded for by the human orthologue of SEQ. ID. NO. 2 which corresponds to polynucleotide SEQ. ID. NO. 89 (encoding SEQ ID NO.:154). Validation studies using the RAW264.7 model have clearly demonstrated the importance of d2 in osteoclast function (section K—Results of RNA Interference studies) where in the presence of siRNAs against SEQ. ID. NO. 2, the bone resorbing activity of mature osteoclasts was markedly reduced. Additionally, it has been well documented that the a3 isoform is the major form of the v-ATPase a subunit in osteoclasts and bone in general (Smith et al., 2005). Thus, in order to identify molecules that are capable of inhibiting the function of the v-ATPase in osteoclasts, the specific interaction between the d2 and a3 subunits will be exploited.

The expression of the d isoforms in human osteoclast and precursor cells (HOPs) was measured by Northern blot analysis. Approximately, $1.5\times10^4$ precursor cells/well were seeded in 96-well plates and a portion was treated with 33 mg/ml M-CSF and 100 ng/ml RANK ligand for 7 days to form osteoclasts. Total RNA was prepared from the precursors and osteoclasts using Trizol™ (Invitrogen, Burlington, ON) and 10 mg/lane was electrophoresed in a 1% agarose/TAE gel.

The RNA was electrotransfered to a nylon membrane and hybridized sequentially to [$^{32}$P]dCTP labeled probes specific for the d2 (SEQ. ID. NO. 89) and d1 subunits, for the osteoclast-specific gene, Cathepsin K and for the housekeeping gene, b-actin. The washed membrane was exposed to film for the required amount of time to detect the corresponding mRNA bands.

Figure 21A:
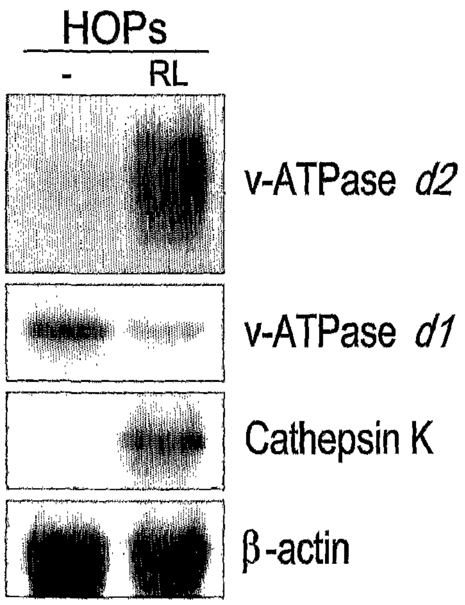
FIG. 21A is a picture of a Northern blot illustrating that SEQ. ID. NO. 89 (d2) expression is upregulated in osteoclasts compared to the d1 isoform, FIG. 21B are pictures of Western blots of a pull-down assay illustrating interaction of d2 with the v-ATPase a3 subunit but not the a4 subunit.

FIG. 21A shows that SEQ. ID. NO. 89 (d2) was upregulated in response to RANK ligand (Panel 1; Lane RL) compared to precursors (Panel 1; Lane -). With the probe specific for v-ATPase d1, the opposite expression pattern was observed indicating that this d isoform was downregulated in osteoclasts (Panel 2; Lane RL) compared to precursors (Panel 2; Lane -). As expected, the osteoclast-specific gene, Cathepsin K was highly upregulated in response to RANK ligand and not present in the precursors (Panel 3). Equal loading of the RNA samples was evident by the non-differential expression pattern of the housekeeping gene, b-actin (Panel 4). Since a3 is predominantly found in the v-ATPase a subunit of osteoclasts, these results then suggests that the d2 subunit would most likely be complexed with the a3 subunit in human osteoclasts v-ATPase. Thus, isolation of a specific inhibitor of this interaction would preferentially reduce the osteoclast-specific v-ATPase activity and thus, bone resorption.

Figure 21B:
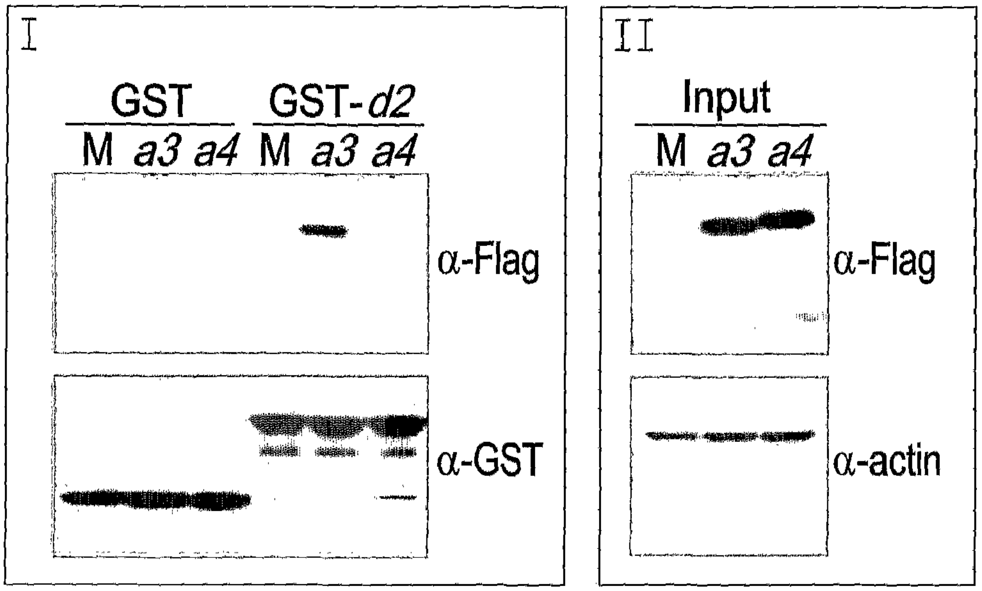

In order to experimentally demonstrate the interaction between d2 and a3, the coding sequence corresponding to SEQ. ID. NO. 89 (d2) (SEQ ID NO.:154) was cloned into the prokaryotic expression vector, pGEX-2T (Pharmacia, GE Healthcare), expressed as a GST fusion protein in *E. coli* and purified with glutathione beads. In parallel, cDNA fragments of mouse v-ATPase-a3 (amino acids 1-385) and v-ATPase a4 (amino acids 1-388) were cloned into the eukaryotic expression vector, pCMX-Flag in order to express a Flag-tagged a3 subunit or a4 subunit in mammalian cells. The pCMX-Flag/v-ATPase-a3 and pCMX-Flag/v-ATPase-a4 recombinant plasmids were transfected in 293FT cells and cell lysates were generated in which, the v-ATPase-a3 and v-ATPase-a4 FLAG-tagged polypeptides were readily detected with an anti-Flag antibody (FIG. 21B, II, upper panel).

In order to measure the interaction between d2 (SEQ. ID. NO. 89) and a3 or a4, equal amounts of 293FT lysates containing either Flag-tagged a3 or a4 were incubated with purified GST or GST-d2 at 4° C. for 90 minutes under mild agitation. After washing, the protein mixes were separated on a SDS-PAGE and transferred to PVDF membrane. The membrane was then incubated with anti-Flag antibody (Sigma, St. Louis, Mo.) and the bands visualized using the ECL kit from Roche (Laval, QC). Clearly, only the a3 fragment could be detected in the GST-d2 reactions compared to the GST reactions indicating a specific interaction between d2 and a3 (FIG. 21B, I-a3, upper panel) but not between d2 and a4 (FIG. 21B, I-a4, upper panel). The membrane was then re-probed with anti-GST antibody, which showed that equal amounts of GST fusion protein were used in each reaction (FIG. 21B, I, lower panel). Additionally, the use of an anti-Flag antibody showed that equal quantities of a3 and a4 were present in the binding reactions (FIG. 21B, II, upper panel) and the same membrane re-probed with an anti-actin antibody, demonstrated that equal amounts of the corresponding cell lysate was used (FIG. 21B, II, lower panel). Thus, this observed specific interaction between d2 and a3 forms the basis for developing a screening assay to interrogate compound libraries (small molecule drugs, peptides, or antibodies) in order to identify those compounds capable of inhibiting this interaction. Such a screening assay may be developed as a FRET (fluorescence resonance energy transfer) method or any similar methods, which are highly sensitive and easily upscalable for high throughput screening in multiwell plates. These compounds may be useful as therapeutics for modulating the bone resorption activity of osteoclasts by inhibiting the function of the osteoclast-specific v-ATPases.

v-ATPases present in other tissues, most notably the kidney (Nishi and Forgac, 2002) where the d2 gene is expressed at low levels as shown by us and others (Nishi et al., 2003; Smith et al., 2005) do not appear to contain the a3 subunit but rather, the a4 subunit (Stehberger et al., 2003; Smith et al., 2000). Therefore, an inhibitor of the interaction between d2 and a3 would preferentially be effective in human osteoclasts and would not interfere with v-ATPases in other tissues.

One of skill in the art will readily recognize that orthologues for all mammals may be identified and verified using well-established techniques in the art, and that this disclosure is in no way limited to one mammal. The term "mammal(s)" for purposes of this disclosure refers to any animal classified as a mammal, including humans, domestic and farm animals, and zoo, sports, or pet animals, such as dogs, cats, cattle, horses, sheep, pigs, goats, rabbits, etc. Preferably, the mammal is human.

The sequences in the experiments discussed above are representative of the NSEQ being claimed and in no way limit the scope of the invention. The disclosure of the roles of the NSEQs in osteoclastogenesis and osteoclast function satisfies a need in the art to better understand the bone remodeling process, providing new compositions that are useful for the diagnosis, prognosis, treatment, prevention and evaluation of therapies for bone remodeling and associated disorders.

The art of genetic manipulation, molecular biology and pharmaceutical target development have advanced considerably in the last two decades. It will be readily apparent to those skilled in the art that newly identified functions for genetic sequences and corresponding protein sequences allows those sequences, variants and derivatives to be used directly or indirectly in real world applications for the development of research tools, diagnostic tools, therapies and treatments for disorders or disease states in which the genetic sequences have been implicated.

Although the present invention has been described hereinabove by way of preferred embodiments thereof, it may be modified, without departing from the spirit and nature of the subject invention as defined in the appended claims.

TABLE 1

Differentially expressed sequences found in osteoclasts and demonstrated to have an effect on osteoclastogenesis following inhibition with specific siRNAs.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 1 | Mm.102265/ Tsp50/ 235631 | NM_146227 | 26-1345 encoding SEQ ID NO.: 93 | peptidase activity |

TABLE 1-continued

Differentially expressed sequences found in osteoclasts and demonstrated to have an effect on osteoclastogenesis following inhibition with specific siRNAs.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 2 | Mm.19298/ Atp6v0d2/ 242341 | NM_175406 | 70-1122 encoding SEQ ID NO.: 94 | hydrogen-transporting ATPase activity, rotational mechanism |
| SEQ ID NO. 3 | Mm.20904/ Crtap/ 56693 | NM_019922 | 72-1274 encoding SEQ ID NO.: 95 | extracellular space protein; function unknown |
| SEQ ID NO. 4 | Mm.12654/ A230106M15Rik/ 231717 | NM_175474 | 314-1114 encoding SEQ ID NO.: 96 | hypothetical protein LOC231717; function unknown |
| SEQ ID NO. 5 | Mm.181860/ Tubb6/ 67951 | NM_026473 | 28-1371 encoding SEQ ID NO.: 97 | GTPase activity; structural molecule activity |
| SEQ ID NO. 6 | Mm.323393/ Josd1/ 74158 | NM_028792 | 905-1513 encoding SEQ ID NO.: 98 | hypothetical protein LOC74158; function unknown |
| SEQ ID NO. 7 | Mm.332739/ Lat2/ 56743 | NM_022964 | 162-737 encoding SEQ ID NO.: 99 | extracellular space; function unknown |
| SEQ ID NO. 57 | Mm.103560/ Jundm2/ 81703 | NM_030887 | 232-723 encoding SEQ ID NO.: 100 | transcriptional repressor activity; shown to play a role in RANK-mediated signal transduction, especially in osteoclast differentiation |

TABLE 2

Differentially expressed sequences found in osteoclasts with putative roles in bone remodeling.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 8 | Mm.10154/ Tesk1/ 21754 | NM_011571 | 1497-3380 encoding SEQ ID NO.: 101 | Protein kinase activity |
| SEQ ID NO. 9 | Mm.142827/ Otud5/ 54644 | NM_138604 | 287-1987 encoding SEQ ID NO.: 102 | hypothetical protein LOC54644 |
| SEQ ID NO. 10 | Mm.146001/ Rassf8/ 71323 | BC004678 | 1-311 encoding SEQ ID NO.: 103 | Ras association possibly involved in signal transduction |
| SEQ ID NO. 11 | Mm.153014/ Gcn1l1/ 231659 | BC068244 | 251-1246 encoding SEQ ID NO.: 104 | possibly involved in amino acid biosynthesis with exact function unknown |
| SEQ ID NO. 12 | Mm.153159/ Cct6a/ 12466 | NM_009838 | 55-1650 encoding SEQ ID NO.: 105 | chaperonin containing TCP-1 possibly involved in protein folding and binding |
| SEQ ID NO. 13 | Mm.157103/ Hsd3b7/ 101502 | NM_133943 | 53-487 encoding SEQ ID NO.: 106 | involved in steroid biosynthesis |
| SEQ ID NO. 14 | Mm.169234/ 2310005O14Rik/ 67914 | NM_026452 | 6-947 encoding SEQ ID NO.: 107 | hypothetical protein LOC67914 |
| SEQ ID NO. 15 | Mm.266341/ Nrp2/ 18187 | NM_010939 | 537-3281 encoding SEQ ID NO.: 108 | receptor activity and cell adhesion |
| SEQ ID NO. 16 | Mm.17917/ Efhd2/ 27984 | NM_025994 | 55-777 encoding SEQ ID NO.: 109 | calcium ion binding |

TABLE 2-continued

Differentially expressed sequences found in osteoclasts with putative roles in bone remodeling.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 17 | Mm.200499/ Eif2ak1/ 15467 | NM_146165 | 116-958 encoding SEQ ID NO.: 110 | protein kinase or transferase activity |
| SEQ ID NO. 18 | Mm.20845/ Abcc5/ 27416 | NM_013790 | 200-4510 encoding SEQ ID NO.: 111 | ATPase activity, coupled to transmembrane movement of substances |
| SEQ ID NO. 19 | Mm.21880/ Htra2/ 64704 | NM_019752 | 146-1522 encoding SEQ ID NO.: 112 | proteolysis |
| SEQ ID NO. 20 | Mm.2271/ Ccl9/ 20308 | NM_011338 | 154-522 encoding SEQ ID NO.: 113 | chemokine activity |
| SEQ ID NO. 21 | Mm.24684/ Fosl2/ 14284 | NM_008037 | 171-1151 encoding SEQ ID NO.: 114 | regulation of transcription, DNA-dependent |
| SEQ ID NO. 22 | Mm.251199/ Arrdc4/ 66412 | NM_025549 | 139-1029 encoding SEQ ID NO.: 115 | molecular function unknown |
| SEQ ID NO. 23 | Mm.2534/ Pstpip1/ 19200 | NM_011193 | 242-1489 encoding SEQ ID NO.: 116 | cell adhesion |
| SEQ ID NO. 24 | Mm.266592/ C030034I22Rik/ 77533 | XM_488832 | 1-987 encoding SEQ ID NO.: 117 | molecular function unknown |
| SEQ ID NO. 25 | Mm.268165/ Cflar/ 12633 | BC029223 | 475-1920 encoding SEQ ID NO.: 118 | caspase activity |
| SEQ ID NO. 26 | Mm.272047/ Helz/ 78455 | BC060114 | 246-1286 encoding SEQ ID NO.: 119 | helicase activity |
| SEQ ID NO. 27 | Mm.278726/ Mak3/ 72117 | NM_028108 | 296-802 encoding SEQ ID NO.: 120 | N-acetyltransferase activity |
| SEQ ID NO. 28 | Mm.279861/ Polr2f/ 69833 | BC024419 | 49-432 encoding SEQ ID NO.: 121 | regulation of transcription |
| SEQ ID NO. 29 | Mm.280895/ Uck2; AI481316/ 80914; 98383 | BC0237897 AI481316 | 218-1003 encoding SEQ ID NO.: 122 | kinase activity/ hypothetical protein LOC98383 |
| SEQ ID NO. 30 | Mm.217216/ Magi1/ 14924 | BC095943 | 574-3920 encoding SEQ ID NO.: 123 | intracellular signaling cascade |
| SEQ ID NO. 31 | Mm.286536/ Fblim1/ 74202 | NM_133754 | 137-1264 encoding SEQ ID NO.: 124 | cell adhesion |
| SEQ ID NO. 32 | Mm.286753/ Rgs3/ 50780 | NM_019492 | 236-2068 encoding SEQ ID NO.: 125 | signal transducer activity |
| SEQ ID NO. 33 | Mm.298728/ Nisch/ 64652 | NM_022656 | 335-4399 encoding SEQ ID NO.: 126 | receptor activity; integrin binding |
| SEQ ID NO. 34 | Mm.129840/ 9430063L05Rik/ 229622 | BC050783 | 371-3727 encoding SEQ ID NO.: 127 | hypothetical protein LOC229622; function unknown |
| SEQ ID NO. 35 | Mm.31672/ Cdk6/ 12571 | NM_009873 | 56-1036 encoding SEQ ID NO.: 128 | cyclin-dependent protein kinase activity |
| SEQ ID NO. 36 | Mm.331198 Tdrkh/ 72634 | BC057030 | 94-1776 encoding SEQ ID NO.: 129 | transcription factor |
| SEQ ID NO. 37 | Mm.44901/ 2610510H03Rik/ 68215 | NM_026620 | 30-1319 encoding SEQ ID NO.: 130 | function unknown |

TABLE 2-continued

Differentially expressed sequences found in osteoclasts with putative roles in bone remodeling.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 38 | Mm.348047/ Usmg4/ 83679 | BC046620 | 329-610 encoding SEQ ID NO.: 131 | function unknown |
| SEQ ID NO. 39 | Mm.37803/ Specc1/ 432572 | BC030438 | | No significant predicted ORF at present/ function unknown |
| SEQ ID NO. 40 | Mm.295306/ BC025076/ 216829 | BC025076 | 123-494 encoding SEQ ID NO.: 132 | hypothetical protein LOC216829; function unknown |
| SEQ ID NO. 41 | Mm.45815/ Bcar3/ 29815 | BC023930 | 405-2867 encoding SEQ ID NO.: 133 | guanyl-nucleotide exchange factor activity |
| SEQ ID NO. 42 | Mm.4615/ Dlgh3/ 53310 | NM_016747 | 325-2874 encoding SEQ ID NO.: 134 | function unknown |
| SEQ ID NO. 43 | Mm.86572/ BC017612/ 170748 | BC017612 | 192-371 encoding SEQ ID NO.: 135 | function unknown |
| SEQ ID NO. 44 | Mm.354736/ Gas2I3/ 237436 | XM_137276 | 730-2781 encoding SEQ ID NO.: 136 | function unknown |
| SEQ ID NO. 45 | Mm.240265/ 5830415L20Rik/ 68152 | BC027051 | 81-428 encoding SEQ ID NO.: 137 | hypothetical protein LOC68152; function unknown |
| SEQ ID NO. 46 | Mm.27545/ Hrmt1I2/ 15469 | BC002249 | 25-1056 encoding SEQ ID NO.: 138 | S-adenosylmethionine-dependent methyltransferase activity |
| SEQ ID NO. 47 | Mm.28071/ 1810030N24Rik/ 66291 | BC027508 | 65-358 encoding SEQ ID NO.: 139 | integral to membrane; function unknown |
| SEQ ID NO. 48 | Mm.293761/ Pofut1/ 140484 | BC046295 | 56-1237 encoding SEQ ID NO.: 140 | transferase activity, transferring glycosyl groups |
| SEQ ID NO. 49 | Mm.341204/ Itsn2/ 20403 | NM_011365 | 258-5234 encoding SEQ ID NO.: 141 | calcium ion binding |
| SEQ ID NO. 50 | Mm.347964/ Fahd1/ 68636 | BC026949 | 189-872 encoding SEQ ID NO.: 142 | hydrolase activity; calcium ion binding activity |
| SEQ ID NO. 51 | Mm.46513/ 2610200G18Rik/ 67149 | NM_025998 | 87-710 encoding SEQ ID NO.: 143 | hypothetical protein LOC67149; integral to membrane; function unknown |
| SEQ ID NO. 52 | Mm.6743/ Nfe2I1/ 18023 | NM_008686 | 249-2474 encoding SEQ ID NO.: 144 | regulation of transcription, DNA-dependent |
| SEQ ID NO. 53 | Mm.78861/ Nolc1/ 70769 | NM_053086 | 30-1229 encoding SEQ ID NO.: 145 | nucleolus organization and biogenesis |
| SEQ ID NO. 54 | Mm.86437/ Spcs3/ 76687 | BC054817 | 59-601 encoding SEQ ID NO.: 146 | hydrolase activity; receptor activity |
| SEQ ID NO. 55 | Mm.296902/ Tapbpl/ 213233 | BC017613 | 264-1619 encoding SEQ ID NO.: 147 | function unknown |
| SEQ ID NO. 56 | Mm.159563/ Tm7sf4/ 75766 | XM_128030 | 50-1294 encoding SEQ ID NO.: 148 | transmembrane 7 superfamily member 4; function unknown |

TABLE 3

List of mRNA spliced variants for some Sequence IDs isolated thus far from mouse and human osteoclast RNA samples

| Nucleotide Sequence No. | Spliced Variant Identification | ORF Nucleotide Postitions | Polypeptide sequence No. |
|---|---|---|---|
| SEQ ID NO. 83 | 0440-TO4-22-mFL_15 | 21-1259 | SEQ ID NO.: 149 |
| SEQ ID NO. 84 | 0179-SL22-hFL_36 (human orthologue variant #1) | 40-1092 | SEQ ID NO.: 150 |
| SEQ ID NO. 85 | 0179-SL22-hFL_1 (human orthologue variant #2) | 40-978 | SEQ ID NO.: 155 |
| SEQ ID NO. 86 | 0799-SL22-mFL_3_(TAG1-3'UTR) | 40-978 | SEQ ID NO.: 151 |
| SEQ ID NO. 87 | 0799-SL22-mFL_4_(TAG1-3'UTR) | 124-750 | SEQ ID NO.: 152 |

TABLE 4

List of some human orthologue

| Sequence Identification | NCBI Unigene Cluster | Accession Number | ORF Nucleotide Positions | Polypeptide sequence No. |
|---|---|---|---|---|
| SEQ ID NO. 88 | Hs.120365 | NM_013270 | 51-1208 | SEQ ID NO.: 153 |
| SEQ ID NO. 89 | Hs.436360 | NM_152565 | 70-1122 | SEQ ID NO.: 154 |

TABLE 5 list of additional sequences identification of plasmids and siRNA oligonucleotides

| Sequence Identification | name | Description |
|---|---|---|
| SEQ. ID. NO. 58 | p14 | Vector for STAR |
| SEQ. ID. NO. 59 | p17+ | Vector for STAR |
| SEQ. ID. NO. 60 | pCATRMAN | Vector for STAR |
| SEQ. ID. NO. 61 | p20 | Vector for STAR |
| SEQ. ID. NO. 62 | OGS 77 | Primer used for STAR p14 vector |
| SEQ. ID. NO. 63 | OGS 302 | Primer used for STAR p17+ vector |
| SEQ. ID. NO: 64 | 0440.1 | siRNA sequence for SEQ. ID. NO. 1 |
| SEQ. ID. NO: 65 | 0440.2 | siRNA sequence for SEQ. ID. NO. 1 |
| SEQ. ID. NO: 66 | 0440.3 | siRNA sequence for SEQ. ID. NO. 1 |
| SEQ. ID. NO: 67 | 0.179.1 | siRNA sequence for SEQ ID NO.: 2 |
| SEQ. ID. NO: 68 | 0.179.2 | siRNA sequence for SEQ ID NO.: 2 |
| SEQ. ID. NO: 69 | 0.179.3 | siRNA sequence for SEQ ID NO.: 2 |
| SEQ. ID. NO: 70 | 0799.1 | siRNA sequence for SEQ ID NO.: 3 |
| SEQ. ID. NO: 71 | 0799.2 | siRNA sequence for SEQ ID NO.: 3 |
| SEQ. ID. NO: 72 | 0799.3 | siRNA sequence for SEQ ID NO.: 3 |
| SEQ. ID. NO: 73 | 0351.1 | siRNA sequence for SEQ ID NO.: 4 |
| SEQ. ID. NO: 74 | 0351.2 | siRNA sequence for SEQ ID NO.: 4 |
| SEQ. ID. NO: 75 | 1035.1 | siRNA sequence for SEQ ID NO.: 5 |

TABLE 5-continued list of additional sequences identification of plasmids and siRNA oligonucleotides

| Sequence Identification | name | Description |
|---|---|---|
| SEQ. ID. NO: 76 | 1035.2 | siRNA sequence for SEQ ID NO.: 5 |
| SEQ. ID. NO: 77 | 1200.1 | siRNA sequence for SEQ ID NO.: 6 |
| SEQ. ID. NO: 78 | 1200.2 | siRNA sequence for SEQ ID NO.: 6 |
| SEQ. ID. NO: 79 | 0233A.1 | siRNA sequence for SEQ ID NO.: 7 |
| SEQ. ID. NO: 80 | 0233A.2 | siRNA sequence for SEQ ID NO.: 7 |
| SEQ. ID. NO: 81 | 0682.1 | siRNA sequence for SEQ ID NO.: 57 |
| SEQ. ID. NO: 82 | 0682.2 | siRNA sequence for SEQ ID NO.: 57 |
| SEQ. ID. NO. 90 | | siRNA sequence for SEQ. ID. NO. 88 |
| SEQ. ID. NO. 91 | | Ip200 expression vector |
| SEQ. ID. NO. 92 | | pCMX-HA expression vector |

REFERENCES

Patents

U.S. Pat. No. 5,712,127 Malek et al., Jan. 27, 1998

U.S. Pat. No. 6,498,024, Malek et al., Dec. 24, 2002

(U.S. patent application Ser. No. 11/000,958 field on Dec. 2, 2003 published under No. US 2005/0153333A1 on Jul. 14, 2005 and entitled “Selective Terminal Tagging of Nucleic Acids”

U.S. Pat. No. 6,617,434 Duffy, Sep. 9, 2003

U.S. Pat. No. 6,451,555 Duffy, Sep. 17, 2002

OTHER REFERENCES

1. Frost H. M., 1964 Dymanics of Bone Remodeling. In: Bone Biodynamics, Little and Brown, Boston, Mass., USA pp. 315;
2. Baron, R., Anatomy and Biology of Bone Matrix and Cellular Elements, In: Primer on the Metabolic Bone Diseases and Disorders of Mineral Metabolism, Fifth Edition 2003, American Society for Bone and Mineral Research, Washington D.C., pp. 1-8;
3. Jilka, R. L. et al., “Increased Osteoclast Development After Esgtrogen Loss: Mediation by Interleukin-6”, Science 257: 88-91 (1992).
4. Poli, V. et al., “Interleukin-6 deficient mice are protected from bone loss caused by estrogen depletion”, EMBO J 13: 1189-1196 (1994).
5. Srivastava, S. et al., “Estrogen Blocks M-CSF Gene Expression and Osteoclast Formation by Regulating Phosphorylation of Egr-1 and Its Interaction with Sp-1”, J Clin Invest 102: 1850-1859 (1998).
6. de Vernejoul, M. C., “Dynamics of Bone Remodeling: Biochemical and Pathophysiological Basis”, Eur J Clin Chem Clin Biochem 34: 729-734 (1996).
7. Netzel-Arnett, S., J. D. Hooper, et al. (2003). “Membrane anchored serine proteases: a rapidly expanding group of cell surface proteolytic enzymes with potential roles in cancer.” Cancer Metastasis Rev 22(2-3): 237-58.
8. Shan, J., L. Yuan, et al. (2002). “TSP50, a possible protease in human testes, is activated in breast cancer epithelial cells.” CancerRes 62(1): 290-4.

9. Yuan, L., J. Shan, et al. (1999). "Isolation of a novel gene, TSP50, by a hypomethylated DNA fragment in human breast cancer." Cancer Res 59(13): 3215-21.
10. Nishi, T. and M. Forgac (2002). "The vacuolar (H+)-ATPases—nature's most versatile proton pumps." Nat Rev Mol Cell Biol 3(2): 94-103.
11. Nishi, T., S. Kawasaki-Nishi, et al. (2003). "Expression and function of the mouse V-ATPase d subunit isoforms." J Biol Chem 278(47): 46396-402.
12. Morello, R., L. Tonachini, et al. (1999). "cDNA cloning, characterization and chromosome mapping of Crtap encoding the mouse cartilage associated protein." Matrix Biol 18(3): 319-24.
13. Tonachini, L., R. Morello, et al. (1999). "cDNA cloning, characterization and chromosome mapping of the gene encoding human cartilage associated protein (CRTAP)." Cytogenet Cell Genet 87(3-4): 191-4.
14. Kawai, J., A. Shinagawa, et al. (2001). "Functional annotation of a full-length mouse cDNA collection." Nature 409(6821): 685-90.
15. Strausberg, R. L., E. A. Feingold, et al. (2002). "Generation and initial analysis of more than 15,000 full-length human and mouse cDNA sequences." Proc Natl Acad Sci USA 99(26): 16899-903.
16. Janssen, E., M. Zhu, et al. (2003). "LAB: a new membrane-associated adaptor molecule in B cell activation." Nat Immunol 4(2): 117-23.
17. Kawaida, R., T. Ohtsuka, et al. (2003). "Jun dimerization protein 2 (JDP2), a member of the AP-1 family of transcription factor, mediates osteoclast differentiation induced by RANKL." J Exp Med 197(8): 1029-35.
18. Agrawal, N., P. V. Dasaradhi, et al. (2003). "RNA interference: biology, mechanism, and applications." Microbiol Mol Biol Rev 67(4): 657-85.
19. Hannon, G. J. (2002). "RNA interference." Nature 418 (6894): 244-51.
20. Brummelkamp, T. R., R. Bernards, et al. (2002). "A system for stable expression of short interfering RNAs in mammalian cells." Science 296(5567): 550-3.
21. Elbashir, et al. (2001). "Duplexes of 21-nucleotide RNAs mediate RNA interference in cultured mammalian cells." Nature 411(6836): 494-8.
22. Lee, J. S., Z. Hmama, et al. (2004). "Stable gene silencing in human monocytic cell lines using lentiviral-delivered small interference RNA. Silencing of the p110alpha isoform of phosphoinositide 3-kinase reveals differential regulation of adherence induced by 1alpha,25-dihydroxycholecalciferol and bacterial lipopolysaccharide." J Biol Chem 279(10): 9379-88.
23. Rubinson, D. A., C. P. Dillon, et al. (2003). "A lentivirus-based system to functionally silence genes in primary mammalian cells, stem cells and transgenic mice by RNA interference." Nat Genet 33(3): 401-6.
24. Boyle, W. J., W. S. Simonet, et al. (2003). "Osteoclast differentiation and activation." Nature 423(6937): 337-42.
25. Gee et al. In: Huber and Carr (1994) Molecular and Immunologic Approaches, Futura Publishing Co., Mt. Kisco N.Y., pp. 163-177.
26. Smith, A. N., F. Jouret, et al. (2005). "Vacuolar H+-ATPase d2 subunit: molecular characterization, developmental regulation, and localization to specialized proton pumps in kidney and bone." J Am Soc Nephrol 16(5): 1245-56
27. Smith, A. N., J. Skaug, et al. (2000). "Mutations in ATP6N1B, encoding a new kidney vacuolar proton pump 116-kD subunit, cause recessive distal renal tubular acidosis with preserved hearing." Nat Genet 26(1): 71-5.
28. Stehberger, P. A., N. Schulz, et al. (2003). "Localization and regulation of the ATP6V0A4 (a4) vacuolar H+-ATPase subunit defective in an inherited form of distal renal tubular acidosis." J Am Soc Nephrol 14(12): 3027-38.

What is claimed is:

1. A method for inhibiting bone resorption comprising administering to a subject suffering from a bone remodelling disorder, an antibody or an antigen binding fragment capable of specific binding to a polypeptide consisting of SEQ ID NO.:153 or to a polypeptide consisting of SEQ ID NO.:93.

2. The method of claim 1, wherein the antibody or antigen binding fragment inhibits osteoclast differentiation or osteoclast function.

3. The method of claim 1, wherein the antibody is selected from the group consisting of a polyclonal antibody, a monoclonal antibody, a chimeric antibody, a humanized antibody and a human antibody.

4. The method of claim 1, wherein the antigen binding fragment is a FV, a Fab, a Fab' or a $(Fab')_2$.

5. The method of claim 1, wherein the antibody or antigen binding fragment is administered in combination with a drug or an hormone.

6. The method of claim 1, wherein the antibody or antigen binding fragment is conjugated with a therapeutic agent.

7. The method of claim 1, wherein the bone remodelling disorder is associated with a decrease in bone mass.

8. A method for impairing osteoclast differentiation in a subject suffering from a bone remodelling disorder, the method comprising administering an antibody or an antigen binding fragment capable of specific binding to a polypeptide consisting of SEQ ID NO.:153 or to a polypeptide consisting of SEQ ID NO.:93.

9. The method of claim 8, wherein the antibody or antigen binding fragment inhibits osteoclast differentiation or osteoclast function.

10. The method of claim 8, wherein the antibody is selected from the group consisting of a polyclonal antibody, a monoclonal antibody, a chimeric antibody, a humanized antibody and a human antibody.

11. The method of claim 8, wherein the antigen binding fragment is a FV, a Fab, a Fab' or a $(Fab')_2$.

12. The method of claim 8, wherein the antibody or antigen binding fragment is administered in combination with a drug or an hormone.

13. The method of claim 8, wherein the antibody or antigen binding fragment is conjugated with a therapeutic agent.

14. The method of claim 8, wherein the bone remodelling disorder is associated with a decrease in bone mass.

15. The method of claim 1, wherein the bone remodeling disorder is associated with a condition selected from the group consisting of:

osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets, fibrogenesis imperfecta ossium, osteosclerotic disorders and damage caused by macrophage-mediated inflammatory processes.

16. The method of claim 8, wherein the bone remodeling disorder is associated with a condition selected from the group consisting of:

osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets, fibrogenesis imperfecta ossium, osteosclerotic disorders and damage caused by macrophage-mediated inflammatory processes.

* * * * *